United States Patent
Eckhardt et al.

(10) Patent No.: US 8,642,585 B2
(45) Date of Patent: Feb. 4, 2014

(54) INDANYLOXYDIHYDROBENZOFURANYL ACETIC ACIDS

(71) Applicants: Matthias Eckhardt, Biberach an der Riss (DE); Sara Frattini, Castelleone (IT); Dieter Hamprecht, Pozzolengo (IT); Frank Himmelsbach, Mittelbiberach (DE); Elke Langkopf, Biberach an der Riss (DE); Iain Lingard, Monza (IT); Stefan Peters, Biberach an der Riss (DE); Holger Wagner, Mettenberg (DE)

(72) Inventors: Matthias Eckhardt, Biberach an der Riss (DE); Sara Frattini, Castelleone (IT); Dieter Hamprecht, Pozzolengo (IT); Frank Himmelsbach, Mittelbiberach (DE); Elke Langkopf, Biberach an der Riss (DE); Iain Lingard, Monza (IT); Stefan Peters, Biberach an der Riss (DE); Holger Wagner, Mettenberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/803,237

(22) Filed: Mar. 14, 2013

(65) Prior Publication Data

US 2013/0252937 A1 Sep. 26, 2013

(30) Foreign Application Priority Data

Mar. 26, 2012 (EP) .................... 12161240

(51) Int. Cl.
| | | |
|---|---|---|
| A61K 31/553 | (2006.01) | |
| C07D 267/10 | (2006.01) | |
| A61K 31/443 | (2006.01) | |
| C07D 405/02 | (2006.01) | |
| A61K 31/4155 | (2006.01) | |
| C07D 231/10 | (2006.01) | |
| A61K 31/422 | (2006.01) | |
| C07D 263/30 | (2006.01) | |
| A61K 31/4178 | (2006.01) | |
| C07D 233/54 | (2006.01) | |
| A61K 31/4245 | (2006.01) | |
| C07D 271/06 | (2006.01) | |
| A61K 31/427 | (2006.01) | |
| C07D 277/20 | (2006.01) | |
| A61K 31/501 | (2006.01) | |
| C07D 403/02 | (2006.01) | |
| A61K 31/5377 | (2006.01) | |
| C07D 413/14 | (2006.01) | |
| A61K 31/497 | (2006.01) | |
| C07D 307/77 | (2006.01) | |
| A61K 31/343 | (2006.01) | |
| C07D 257/02 | (2006.01) | |
| A61K 31/506 | (2006.01) | |
| A61K 31/41 | (2006.01) | |
| C07D 249/08 | (2006.01) | |
| A61K 31/4196 | (2006.01) | |
| A61K 31/4025 | (2006.01) | |
| C07D 409/02 | (2006.01) | |
| A61K 31/382 | (2006.01) | |
| C07D 413/02 | (2006.01) | |

(52) U.S. Cl.
USPC ........... 514/211.01; 514/233.5; 514/252.01; 514/255.05; 514/256; 514/337; 514/364; 514/365; 514/374; 514/382; 514/383; 514/385; 514/406; 514/422; 514/432; 514/469; 540/544; 544/124; 544/153; 544/238; 544/242; 544/336; 546/284.1; 548/131; 548/202; 548/235; 548/262.2; 548/315.4; 548/364.4; 548/525; 549/13; 549/462

(58) Field of Classification Search
USPC ........... 514/211.01, 233.5, 252.01, 255.05, 514/256, 337, 364, 365, 374, 382, 383, 385, 514/406, 422, 432, 469; 540/544; 544/124, 544/153, 238, 242, 336; 546/284.1; 548/131, 202, 235, 262.2, 315.4, 548/364.4, 525; 549/13, 462
See application file for complete search history.

(56) References Cited

U.S. PATENT DOCUMENTS

| 2006/0258722 A1 | 11/2006 | Yasuma et al. |
| 2012/0302566 A1 | 11/2012 | Himmelsbach et al. |
| 2013/0196998 A1* | 8/2013 | Stoit et al. ................ 514/238.8 |

FOREIGN PATENT DOCUMENTS

EP 1559422 A1 8/2005
(Continued)

OTHER PUBLICATIONS

Itoh, et al., Free fatty acids regulate insulin secretion from pancreatic b cells through GPR40, Letters to Nature, 2003, vol. 422, p. 173-176.

(Continued)

Primary Examiner — Samantha Shterengarts
(74) Attorney, Agent, or Firm — Michael P. Morris; Timothy X. Witkowski

(57) ABSTRACT

The present invention relates to compounds of general formula I,

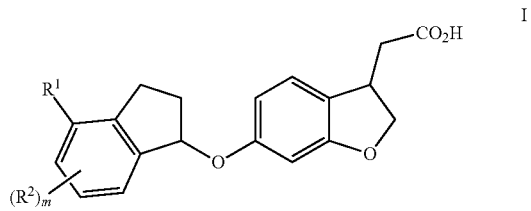

wherein the groups $R^1$, $R^2$ and m are defined as in claim 1, which have valuable pharmacological properties, in particular bind to the GPR40 receptor and modulate its activity. The compounds are suitable for treatment and prevention of diseases which can be influenced by this receptor, such as metabolic diseases, in particular diabetes type 2.

32 Claims, No Drawings

(56) References Cited

FOREIGN PATENT DOCUMENTS

| EP | 1630152 | A1 | 3/2006 |
|---|---|---|---|
| EP | 2006271 | A2 | 12/2008 |
| EP | 2289868 | A1 | 3/2011 |
| WO | 2008001931 | A2 | 1/2008 |
| WO | 2009157418 | A1 | 12/2009 |
| WO | 201045258 | A2 | 4/2010 |
| WO | 2010143733 | A1 | 12/2010 |
| WO | 2012072691 | A1 | 6/2012 |

OTHER PUBLICATIONS

Briscoe, et al., "The Orphan G Protein-coupled Receptor GPR40 is activated by Medium and Long Chain Fatty Acids", Journal of Biological Chemistry, vol. 278, No. 13, 2003, p. 11303-11311.

Kotarsky, et al., "A human cell surface receptor activated by free fatty acids and thiazolidine drugs'", Biochemical and Biophysical Research Communications, vol. 301, No. 2, 2003, p. 406-410.

Song et al., "Synthesis and Biological Evaluation of 3-Aryl-3-(4-phenoxy)-propionic Acid as a Novel Series of G Protein-Coupled Receptor 40 Agonists", Journal of Medicinal Chemistry, vol. 50, 2007, p. 2807-2817.

Tan, et al., "Selective Small-Molecule Agonists of G Protein-coupled Receptor 40 Promote Glucose-Dependent Insulin Secretion and Reduce Blood Glucose in Mice", Diabetes, vol. 57, 2008, p. 2211.

Mikami, Satoshi et al. "Discovery of Phenylpropanoic Acid Derivatives Containing Polar Functionalities as Potent and Orally Bioavailable G Protein-Coupled Receptor 40 Agonists for the Treatment of Type 2 Diabetes" Journal of Medicinal Chemistry (2012) 55, 3756-3776.

Negoro, Nobuyuki et al. "Identification of Fused-Ring Alkanoic Acids with Improved Pharmacokinetic Profiles that Act as G Protein-Coupled Receptor 40/ Free Fatty Acid Receptor 1 Agonists" Journal of Medicinal Chemistry, (2012) 55, pgs. 1538-1552.

International Search Report for PCT/EP2013/056312 mailed on May 27, 2013.

Mikami, et al., "Discovery of Phenylpropanoic Acid Derivatives Containing Polar Functionalities as Potent and Orally Bioavailable G Protein-Coupled Receptor 40 Agonists for the Treatment of Type 2 Diabetes", Journal of Medicinal Chemistry, 2012, V. 55, No. 8, p. 3756-3776.

International Search Report and written opinion for PCT/EP 2013/058840 mailed Aug. 22, 2013.

\* cited by examiner

INDANYLOXYDIHYDROBENZOFURANYL ACETIC ACIDS

This application claims priority to European Patent Application No. 12 161 240.2, filed Mar. 26, 2012, the contents of which are hereby incorporated by reference in its entirety.

FIELD OF THE INVENTION

The present invention relates to novel indanyloxydihydrobenzofuranylacetic acids, that are agonists of the G-protein coupled receptor 40 (GPR40, also known as free fatty acid receptor FFAR 1), to processes for their preparation, to pharmaceutical compositions containing these compounds and to their medical use for the prophylaxis and/or treatment of diseases which can be influenced by the modulation of the function of GPR40. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

The free fatty acid receptor GPR40 (also referred to as either FFAR, FFAR1, or FFA1) is a cell-surface receptor and a member of the gene superfamily of G-protein coupled receptors, which was first identified as a so-called orphan receptor, i.e. a receptor without a known ligand, based on the predicted presence of seven putative transmembrane regions in the corresponding protein (Sawzdargo et al. (1997) Biochem. Biophys. Res. Commun. 239: 543-547). GPR40 is found to be highly expressed in several particular cell types: the pancreatic β cells and insulin-secreting cell lines, as well as in enteroendocrine cells, taste cells, and is reported to be expressed in immune cells, splenocytes, and in the human and monkey brain. Meanwhile, fatty acids of varying chain lengths are thought to represent the endogenous ligands for GPR40, activation of which is linked primarily to the modulation of the Gq family of intra-cellular signaling G proteins and concomitant induction of elevated calcium levels, although activation of Gs- and Gi-proteins to modulate intra-cellular levels of cAMP have also been reported. GPR40 is activated especially by long-chain FFA, particularly oleate, as well as the PPAR-gamma agonist rosiglitazone.

It has been recognized that the fatty acids that serve as activators for GPR40 augment the elevated plasma glucose-induced secretion of insulin through GPR40 receptors that are expressed in the insulin secreting cells (Itoh et al. (2003) Nature 422: 173-176; Briscoe et al. (2003) J. Biol. Chem. 278: 11303-11311; Kotarsky et al. (2003) Biochem. Biophys. Res. Commun. 301: 406-410). Despite initial controversy, the use of GPR40 agonist appears to be the appropriate for increasing insulin release for the treatment of diabetes (see e.g. Diabetes 2008, 57, 2211; J. Med. Chem. 2007, 50, 2807). Typically, long term diabetes therapy leads to the gradual diminution of islet activity, so that after extended periods of treatment Type 2 diabetic patients need treatment with daily insulin injections instead. GPR40 agonists may have the potential to restore or preserve islet function, therefore, GPR40 agonists may be beneficial also in that that they may delay or prevent the diminution and loss of islet function in a Type 2 diabetic patient.

It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Further studies indicating that the GPR40 modulatory role on the release of incretins from the enteroendocrine cells, including CCK, GLP-1, GIP, PYY, and possibly others, suggest that GPR40 modulators may contribute to enhanced insulin release from the pancreatic beta cells also indirectly by e.g. a synergistic effect of GLP-1 and possibly GIP on the insulin release, and the other release incretins may also contribute to an overall beneficial contribution of GPR40 modulation on metabolic diseases. The indirect contributions of GPR40 modulation on insulin release through the elevation of plasma levels of incretins may be further augmented by the coadministration of inhibitors of the enzymes responsible for the incretin degradation, such as inhibitors of DPP-4.

Insulin imbalances lead to conditions such as type II diabetes mellitus, a serious metabolic disease. The modulation of the function of GPR40 in modulating insulin secretion indicates the therapeutic agents capable of modulating GPR40 function could be useful for the treatment of disorders such as diabetes and conditions associated with the disease, including insulin resistance, obesity, cardiovascular disease and dyslipidemia.

OBJECT OF THE PRESENT INVENTION

The object of the present invention is to provide new compounds, hereinafter described as compounds of formula (I), in particular new 2,3-indanyloxydihydrobenzofuranylacetic acids, which are active with regard to the G-protein-coupled receptor GPR40, notably are agonists of the G-protein-coupled receptor GPR40.

A further object of the present invention is to provide new compounds, in particular new indanyloxydihydrobenzofuranylacetic acids, which have an activating effect on the G-protein-coupled receptor GPR40 in vitro and/or in vivo and possess suitable pharmacological and pharmacokinetic properties to use them as medicaments.

A further object of the present invention is to provide effective GPR40 agonists, in particular for the treatment of metabolic disorders, for example diabetes, dyslipidemia and/or obesity.

A further object of the present invention is to provide methods for treating a disease or condition mediated by the activation of the G-protein-coupled receptor GPR40 in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

GPR40 modulators are known in the art, for example, the compounds disclosed in WO 2004041266 (EP 1559422), WO 2007033002 and WO 2009157418. The indanyloxydihydrobenzofuranylacetic acids of the present invention may provide several advantages, such as enhanced potency, high metabolic and/or chemical stability, high selectivity and tolerability, enhanced solubility, and the possibility to form stable salts.

SUMMARY OF THE INVENTION

In a first aspect the invention relates to a compound of formula I

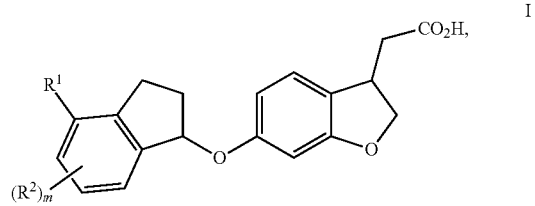

wherein
$R^1$ is selected from the group $R^1$-G1 consisting of a phenyl ring, a tetrazolyl ring, and a 5- or 6-membered heteroaromatic ring which contains 1, 2, or 3 heteroatoms independently of each other selected from =N—, —NH—, —O— and —S—;
wherein optionally a second ring is annulated to said phenyl or heteroaromatic ring,
wherein said second ring is 5- or 6-membered, partially unsaturated or aromatic and may contain 1, 2, or 3 heteroatoms independently of each other selected from =N—, —NH—, —O— and —S— with the proviso that only up to two of the heteroatoms are O and S and no O—O, S—S, and S—O bond is formed, and
wherein in said second ring independently of the presence of heteroatoms 1 or 2 $CH_2$ groups may be replaced by —C(=O)—, —S(=O)— or —S(=O)$_2$—, and
wherein said phenyl ring, tetrazolyl ring, heteroaromatic ring, annulated phenyl ring, and annulated heteroaromatic ring are substituted with one group $R^3$; and
wherein each of the phenyl ring, tetrazolyl ring, heteroaromatic ring, annulated phenyl ring, and annulated heteroaromatic ring is optionally additionally substituted with 1 to 4 groups independently selected from $R^4$; and
wherein in said heteroaromatic ring and/or said second ring the H-atom in one or more NH groups, if present, is replaced by $R^N$ or $R^3$;
$R^2$ is selected from the group $R^2$-G1 consisting of F, Cl, Br, I, $C_{1-4}$-alkyl, $C_{3-6}$-cycloalkyl, NC—, $H_2$N—C(=O)—, $C_{1-4}$-alkyl-NR$^N$—C(=O)—, HO—O(=O)—, $C_{1-4}$-alkyl-O—C(=O)—, $C_{1-4}$-alkyloxy, and $C_{1-4}$-alkyl-S(=O)$_2$—,
wherein any alkyl and cycloalkyl group or sub-group within the groups mentioned is optionally substituted with one or more F atoms, and wherein multiple $R^2$ may be identical or different, if m is 2 or 3;
$R^3$ is selected from the group $R^3$-G1 consisting of
$C_{1-6}$-alkyl, $C_{2-6}$-alkenyl, $C_{2-6}$-alkinyl, $C_{3-6}$-cycloalkyl, $C_{1-4}$-alkyl-NH—, ($C_{1-4}$-alkyl)$_2$N—, $C_{1-6}$-alkyl-O—, $C_{3-6}$-cycloalkyl-O—, $C_{1-4}$-alkyl-S—, $C_{1-4}$-alkyl-S(=O)—, and $C_{1-4}$-alkyl-S(=O)$_2$,
wherein each alkyl and cycloalkyl group and each alkyl and cycloalkyl sub-group within the groups mentioned is substituted with 1 to 3 groups independently selected from $R^5$ and optionally substituted with 1 or more F atoms;
or from $C_{1-4}$-alkyl-C(=O)—, heterocyclyl-O(=O)—, HNR$^N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO$_2$O—, $C_{1-4}$-alkyl-O—O(=O)—, $C_{3-6}$-cycloalkyl-O—C(=O)—, heterocyclyl-O—O(=O)—, —NHR$^N$, $C_{1-4}$-alkyl-C(=O)NR$^N$—, $C_{3-6}$-cycloalkyl-C(=O)NR$^N$—, heterocyclyl-O(=O)NR$^N$—, phenyl-O(=O)NR$^N$—, heteroaryl-O(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, heterocyclyl-O—, phenyl-O—, heteroaryl-O—, C$_{3-6}$-cycloalkyl-S—, heterocyclyl-S—, phenyl-S—, heteroaryl-S—, C$_{3-6}$-cycloalkyl-S(=O)—, heterocyclyl-S(=O)—, phenyl-S(=O)—, heteroaryl-S(=O)—, C$_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, C$_{1-4}$-alkyl-NR$^N$—S(=O)$_2$—, heterocyclyl, phenyl, and heteroaryl, wherein each alkyl, cycloalkyl, and heterocyclyl group or sub-group within the groups mentioned is optionally substituted with 1 to 3 groups independently selected from R$^5$ and optionally substituted with 1 or more F atoms; and wherein each phenyl and heteroaryl group is optionally substituted with 1 to 5 substituents independently selected from R$^6$;

wherein heterocyclyl is selected from
- a cyclobutyl group wherein 1 CH$_2$ group is replaced by —NH— or —O—,
- a saturated or partially unsaturated C$_{5-7}$-cycloalkyl group wherein 1 CH$_2$ group is replaced by —O(=O)—, —NH—, —O—, —S(=O)— or —S(=O)$_2$— and/or 1 CH group by N;
- a saturated or partially unsaturated C$_{5-7}$-cycloalkyl group wherein 1 CH$_2$ group is replaced by —NH— or —O—, a second CH$_2$ group is replaced by —NH—, —C(=O)—, —S(=O)— or —S(=O)$_2$— and/or 1 CH group is replaced by N; and
- a saturated or partially unsaturated C$_{5-7}$-cycloalkyl group wherein 2 CH$_2$ groups are replaced by —NH— or 1 CH$_2$ group by —NH— and the other by —O— and a third CH$_2$ group is replaced by —O(=O)—, —S(=O)— or —S(=O)$_2$— and/or 1 CH group by N;

wherein heteroaryl is selected from
- a tetrazolyl ring, and a 5- or 6-membered heteroaromatic ring which contains 1, 2, or 3 heteroatoms independently of each other selected from =N—, —NH—, —O—, and —S—, wherein in heteroaromatic groups containing a —HC=N— unit this group is optionally replaced by —NH—C(=O)—;

wherein in heteroaryl and heterocyclyl rings with one or more NH groups each of them is replaced by NR$^N$ or NR$^5$, with the proviso that R$^3$ in total cannot be C$_{1-4}$-alkyl-, C$_{1-4}$-alkyl-O—C$_{1-4}$-alkyl, HO—C$_{1-4}$-alkyl, C$_{3-4}$-alkenyl, C$_{3-4}$-alkinyl, H$_2$N—, (C$_{1-4}$-alkyl)$_2$N—, C$_{1-4}$-alkyl-O—, C$_{1-4}$-alkyl-S—, C$_{1-4}$-alkyl-S(=O)—, and C$_{1-4}$-alkyl-S(=O)$_2$—;

R$^4$ is selected from the group R$^4$-G1 consisting of F, Cl, Br, I, CN, —OH, C$_{1-4}$-alkyl, C$_{3-6}$-cycloalkyl, HO—C$_{1-4}$-alkyl, C$_{1-4}$-alkyl-O—C$_{1-4}$-alkyl, —NR$^N$H, C$_{1-4}$-alkyl-NR$^N$—, C$_{1-4}$-alkyl-O—, C$_{3-6}$-cycloalkyl-O—, C$_{1-4}$-alkyl-O—C$_{1-4}$-alkyl-O—, C$_{1-4}$-alkyl-S—, C$_{1-4}$-alkyl-S(=O)—, and C$_{1-4}$-alkyl-S(=O)$_2$—, wherein any alkyl and cycloalkyl group or sub-group within the groups mentioned is optionally substituted with 1 or more F atoms;

R$^5$ is selected from the group R$^5$-G1 consisting of Cl, Br, I, C$_{1-4}$-alkyl-, CN, C$_{3-6}$-cycloalkyl, heterocyclyl-C(=O)—, H$_2$N—C(=O)—, C$_{1-4}$-alkyl-NR$^N$—C(=O)—, C$_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO—C(=O)—, C$_{1-4}$-alkyl-O—C(=O)—, —NHR$^N$, C$_{1-4}$-alkyl-NR$^N$—, C$_{1-4}$-alkyl-C(=O)NR$^N$—, C$_{3-6}$-cycloalkyl-C(=O)NR$^N$—, heterocyclyl-C(=O) NR$^N$—, phenyl-C(=O)NR$^N$—, heteroaryl-C(=O) NR$^N$—, C$_{1-4}$-alkyl-S(=O)$_2$NR$^N$—, C$_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, —OH, C$_{1-4}$-alkyl-O—, C$_{1-4}$-alkyl-O—C$_{1-4}$-alkyl-O—, C$_{3-6}$-cycloalkyl-O—, heterocyclyl-O—, phenyl-O—, heteroaryl-O—, C$_{1-4}$-alkyl-S—, C$_{3-6}$-cycloalkyl-S—, heterocyclyl-S—, phenyl-S—, heteroaryl-S—, C$_{1-4}$-alkyl-S(=O)—, C$_{3-6}$-cycloalkyl-S(=O)—, heterocyclyl-S(=O)—, phenyl-S(=O)—, heteroaryl-S(=O)—, C$_{1-4}$-alkyl-S(=O)$_2$—, C$_{3-6}$-cycloalkyl-S(=O)$_2$—, heterocyclyl-S(=O)$_2$—, phenyl-S(=O)$_2$—, heteroaryl-S(=O)$_2$—, H$_2$N—S(=O)$_2$—, C$_{1-4}$-alkyl-NR$^N$—S(=O)$_2$—, heterocyclyl, phenyl, and heteroaryl, wherein any alkyl, cycloalkyl and heterocyclyl group or sub-group within the groups mentioned is optionally substituted with 1 or more F atoms and optionally substituted with 1 or 2 groups independently selected from H$_3$C—, HO—, H$_3$C—O—, and —CN;

wherein heterocyclyl is selected from
- a cyclobutyl group wherein 1 CH$_2$ group is replaced by —NR$^N$— or —O—,
- a saturated or partially unsaturated C$_{5-7}$-cycloalkyl group wherein 1 CH$_2$ group is replaced by —C(=O)—, —NR$^N$—, —O—, —S(=O)— or —S(=O)$_2$— and/or 1 CH group by N;
- a saturated or partially unsaturated C$_{5-7}$-cycloalkyl group wherein 1 CH$_2$ group is replaced by —NR$^N$— or —O—, a second CH$_2$ group is replaced by —NR$^N$—, —C(=O)—, —S(=O)— or —S(=O)$_2$— and/or 1 CH group is replaced by N; and
- a saturated or partially unsaturated C$_{5-7}$-cycloalkyl group wherein 2 CH$_2$ groups are replaced by —NR$^N$— or 1 CH$_2$ group by —NR$^N$— and the other by —O—, and a third CH$_2$ group is replaced by —O(=O)—, —S(=O)— or —S(=O)$_2$— and/or 1 CH group by N;

and wherein heteroaryl is selected from
- a tetrazolyl ring, and a 5- or 6-membered heteroaromatic ring which contains 1, 2, or 3 heteroatoms independently of each other selected from =N—, —NH—, —O—, and —S—, wherein in heteroaromatic groups containing a —HC=N— unit this group is optionally replaced by —NR$^N$—C(=O)—, and wherein in heteroaromatic rings with one ore more NH groups each of them is replaced by NR$^N$, and each heteroaryl group is optionally substituted with 1 to 3 substituents independently selected from F, Cl, —CH$_3$, —CN, and —O—CH$_3$;

R$^6$ is selected from the group R$^6$-G1 consisting of F, Cl, Br, I, CN, C$_{1-4}$-alkyl, C$_{3-6}$-cycloalkyl-, HO—C$_{1-4}$-alkyl-, C$_{1-4}$-alkyl-O—C$_{1-4}$-alkyl-, R$^N$HN—, C$_{1-4}$-alkyl-O—, —S(=O)—C$_{1-4}$-alkyl, and S(=O)$_2$—C$_{1-4}$-alkyl, wherein any alkyl and cycloalkyl group or sub-group within the groups mentioned is optionally substituted with one or more F atoms;

R$^N$ is independently of each other selected from the group R$^N$-G1 consisting of H, C$_{1-4}$-alkyl, C$_{1-4}$-alkyl-C(=O)—, C$_{1-4}$-alkyl-NH—C(=O)—, C$_{1-4}$-alkyl-N(C$_{1-4}$-alkyl)-O(=O)—, C$_{1-4}$-alkyl-O—O(=O)—, and C$_{1-4}$-alkyl-S(=O)$_2$—; and m is an integer selected from 0, 1, 2, and 3;

wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

In a particular embodiment the invention relates to a compound of formula I.I, as a substructure of formula I,

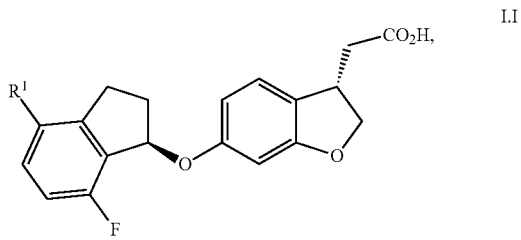

I.I wherein $R^1$ is defined as mentioned hereinbefore under formula I, the isoforms, tautomers, stereoisomers, metabolites, prodrugs, solvates, hydrates, and the salts thereof, particularly the physiologically acceptable salts thereof with inorganic or organic acids or bases, or the combinations thereof.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or I.I, or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR40 in a patient in need thereof characterized in that a compound of general formula I or I.I, or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or I.I, or a pharmaceutically acceptable salt thereof is administered to the patient.

According to another aspect of the invention, there is provided the use of a compound of the general formula I or I.I, or a pharmaceutically acceptable salt thereof for the manufacture of a medicament for a therapeutic method as described hereinbefore and hereinafter.

According to another aspect of the invention, there is provided a compound of the general formula I or I.I, or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR40 in a patient that includes the step of administering to the patient in need of such treatment a therapeutically effective amount of a compound of the general formula I or I.I, or a pharmaceutically acceptable salt thereof in combination with a therapeutically effective amount of one or more additional therapeutic agents.

In a further aspect this invention relates to the use of a compound of the general formula I or I.I, or a pharmaceutically acceptable salt thereof in combination with one or more additional therapeutic agents for the treatment of diseases or conditions which are mediated by the activation of the G-protein-coupled receptor GPR40.

In a further aspect this invention relates to a pharmaceutical composition which comprises a compound according to general formula I or I.I, or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

The following definitions refer to the particular substructure of formula I.I. Unless otherwise stated, the groups, residues, and substituents, particularly $R^1$, $R^3$, $R^4$, $R^5$, $R^6$ and $R^N$ are defined as above and hereinafter. If residues, substituents, or groups occur several times in a compound, as for example $R^N$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of a phenyl ring, a 5-membered heteroaromatic ring which contains 2 or 3 heteroatoms independently of each other selected from =N—, —NH—, —O— and —S— with the proviso that not more than one heteroatom is —O— or —S—, and a 6-membered heteroaromatic ring which contains 1 or 2 =N— atoms;

wherein optionally a second ring is annulated to said phenyl ring and 5- and 6-membered heteroaromatic rings, wherein said second ring is 5- or 6-membered, partially unsaturated or aromatic and may contain 1 or 2 heteroatoms independently of each other selected from =N—, —NH—, —O— and —S— with the proviso that no O—O, S—S, and S—O bond is formed, and wherein in said second ring independently of the presence of heteroatoms 1 or 2 —CH$_2$— groups may be replaced by —C(=O)— or —S(=O)$_2$—, and wherein in said heteroaromatic ring and/or said second ring
    the H-atom in one or more NH groups, if present, is replaced by $R^N$ or $R^3$, and wherein each of said phenyl ring, heteroaromatic rings, annulated phenyl ring, and annulated heteroaromatic rings is
    substituted with one group $R^3$ and optionally additionally substituted with 1 or 2 substituents independently selected from $R^4$.

$R^1$-G2a:

According to one embodiment the group $R^1$ is selected from the group $R^1$-G2a consisting of a phenyl ring, a 5-membered heteroaromatic ring which contains 2 or 3 heteroatoms independently of each other selected from =N—, —NH—, —O— and —S—, and a 6-membered heteroaromatic ring which contains 1 or 2 =N— atoms;

wherein in said 5-membered heteroaromatic ring the H-atom in one or more NH groups is replaced with $R^N$ or $R^3$, and wherein each of said phenyl ring and heteroaromatic rings is substituted with one group R³ and optionally additionally substituted with 1 or 2 substituents independently selected from R⁴.

R¹-G2b:

According to one embodiment the group R¹ is selected from the group R¹-G2b consisting of a phenyl ring, a 5-membered heteroaromatic ring which contains 2 or 3 heteroatoms independently of each other selected from =N—, —NH—, —O— and —S—, and a 6-membered heteroaromatic ring which contains 1 or 2 =N— atoms, wherein a second 5- or 6-membered, partially unsaturated or aromatic ring is annulated to said phenyl ring and 5- and 6-membered heteroaromatic rings, which may contain 1 or 2 heteroatoms independently of each other selected from =N—, —NH—, —O— and —S— with the proviso that no O—O, S—S, and S—O bond is formed, and wherein in said second ring 1 or 2 —CH₂— groups may be replaced by —C(=O)— or —S(=O)₂—, and wherein in said heteroaromatic rings and said second rings the H-atom in one or more NH groups, if present, is replaced by $R^N$ or R³, and wherein each annulated phenyl ring and annulated heteroaromatic ring is substituted with one group R³ and optionally additionally substituted with 1 or 2 substituents independently selected from R⁴.

R¹-G3:

According to one embodiment the group R¹ is selected from the group R¹-G3 consisting of:

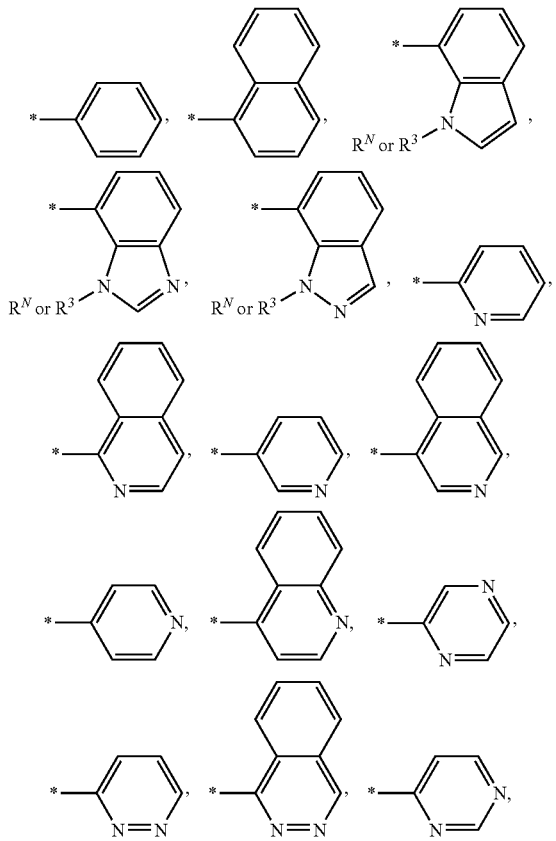

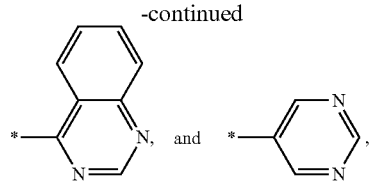

wherein each group is substituted with one group R³ and optionally additionally substituted with 1 or 2 groups independently selected from R⁴.

R¹-G4:

In another embodiment the group R¹ is selected from the group R¹-G4 consisting of

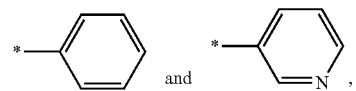

wherein each group is substituted with one group R³ and optionally additionally substituted with 1 or 2 groups independently selected from R⁴.

R¹-G4a:

In another embodiment the group R¹ is selected from the group R¹-G4a consisting of

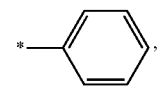

which is substituted with one group R³ and optionally additionally substituted with 1 or 2 groups independently selected from R⁴.

R¹-G5:

In another embodiment the group R¹ is selected from the group R¹-G5 consisting of

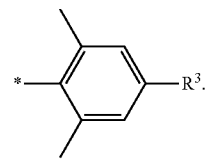

R³:

R³-G1:

The group R³ is preferably selected from the group R³-G1 as defined hereinbefore.

R³-G2:

In another embodiment the group R³ is selected from the group R³-G2 consisting of $C_{1-4}$-alkyl, $C_{3-6}$-cycloalkyl-, $C_{1-4}$-alkyl-O—, $C_{3-6}$-cycloalkyl-O—, $C_{1-4}$-alkyl-S(=O)—, and $C_{1-4}$-alkyl-S(=O)₂—, wherein each alkyl and cycloalkyl group and each alkyl and cycloalkyl sub-group within the groups mentioned is substituted with 1 to 3 groups independently selected from R⁵ and optionally substituted with 1 or more F atoms;

or from heterocyclyl-C(=O)—, HNR$^N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, $C_{1-4}$-alkyl-C(=O)NR$^N$—, $C_{3-6}$-cycloalkyl-C(=O)NR$^N$—, heterocyclyl-C(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, heterocyclyl-O—, phenyl-O—, heteroaryl-O—, $C_{3-6}$-cycloalkyl-S(=O)—, heterocyclyl-S(=O)—, phenyl-S(=O)—, heteroaryl-S(=O)—, $C_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, $C_{1-4}$-alkyl-NR$^N$—S(=O)$_2$—, heterocyclyl, phenyl, and heteroaryl, wherein each alkyl, cycloalkyl, and heterocyclyl group or sub-group within the groups mentioned is optionally substituted with 1 to 3 groups independently selected from R$^5$ and optionally substituted with 1 or more F atoms; and wherein each phenyl and heteroaryl group is optionally substituted with 1 to 3 substituents independently selected from R$^6$;

wherein heterocyclyl is selected from
a cyclobutyl group wherein 1 CH$_2$ group is replaced by —NH— or —O—,
a saturated or mono-unsaturated $C_{5-7}$-cycloalkyl group wherein 1 CH$_2$ group is replaced by —C(=O)—, —NH—, —O—, —S(=O)— or —S(=O)$_2$— and/or 1 CH group by N;
a saturated or mono-unsaturated $C_{5-6}$-cycloalkyl group wherein 1 CH$_2$ group is replaced by —NH— or —O—, a second CH$_2$ group is replaced by —NH—, —C(=O)—, —S(=O)— or —S(=O)$_2$— and/or 1 CH group is replaced by N; and
a saturated or mono-unsaturated $C_{5-6}$-cycloalkyl group wherein 2 CH$_2$ groups are replaced by —NH— or 1 CH$_2$ group by —NH— and the other by —O— and a third CH$_2$ group is replaced by —O(=O)—, —S(=O)— or —S(=O)$_2$— and/or 1 CH group by N;

wherein heteroaryl is selected from
a tetrazolyl ring, a 5-membered heteroaromatic ring which contains 1, 2, or 3 heteroatoms independently of each other selected from =N—, —NH—, O, and S, and a 6-membered heteroaromatic ring which contains 1 or 2 =N— atom, wherein a —HC=N— unit is optionally replaced by —NH—C(=O)—;

and wherein in heteroaryl and heterocyclyl rings with one ore more NH groups each of them is replaced by NR$^N$ or NR$^5$, with the proviso that R$^3$ in total cannot be $C_{1-4}$-alkyl-, $C_{1-4}$-alkyl-O—$C_{1-4}$-alkyl, HO—$C_{1-4}$-alkyl, $C_{1-4}$-alkyl-O—, $C_{1-4}$-alkyl-S(=O)—, and $C_{1-4}$-alkyl-S(=O)$_2$.

R$^3$-G3:
In another embodiment the group R$^3$ is selected from the group R$^3$-G3 consisting of $C_{1-4}$-alkyl, $C_{1-4}$-alkyl-O—, and $C_{3-6}$-cycloalkyl-O—, wherein each alkyl and cycloalkyl group and each alkyl and cycloalkyl sub-group within the groups mentioned is substituted with 1 to 3 groups independently selected from R$^5$ and optionally substituted with 1 to 3 F atoms;
or from
$C_3$-alkyl-S(=O)$_2$— substituted with 1 HO— or H$_3$C—O— group; and
heterocyclyl-O(=O)—, H$_2$N—C(=O)—, HO—(H$_3$C)$_2$C—CH$_2$—NH—C(=O)—, $C_{1-3}$-alkyl-NR$^N$—C(=O)—, $C_{1-4}$-alkyl-C(=O)NR$^N$—, $C_{3-6}$-cycloalkyl-C(=O)NR$^N$—, heterocyclyl-O(=O)NR$^N$—, $C_{1-4}$-alkyl-S(=O)$_2$NR$^N$—, heterocyclyl-O—, phenyl-O—, heteroaryl-O—, heterocyclyl-S(=O)$_2$—, heterocyclyl, phenyl, and heteroaryl, wherein each alkyl, cycloalkyl, and heterocyclyl group or sub-group within the groups mentioned is optionally substituted with 1 or 2 groups independently selected from R$^5$ and optionally substituted with 1 or more F atoms; and wherein each phenyl and heteroaryl group is optionally substituted with 1 to 3 substituents independently selected from R$^6$;

wherein heterocyclyl is selected from
a cyclobutyl group wherein 1 CH$_2$ group is replaced by —NH— or —O—,
a saturated or mono-unsaturated $C_{5-7}$-cycloalkyl group wherein 1 CH$_2$ group is replaced by —C(=O)—, —NH—, —O— or —S(=O)$_2$— and/or 1 CH group by N;
a saturated or mono-unsaturated $C_{5-6}$-cycloalkyl group wherein 1 CH$_2$ group is replaced by —NH— or —O—, a second CH$_2$ group is replaced by —C(=O)— or —S(=O)$_2$— and/or 1 CH group is replaced by N; and wherein heteroaryl is selected from
tetrazolyl, a 5-membered heteroaromatic ring which contains 1, 2, or 3 heteroatoms independently of each other selected from =N—, —NH—, O, and S, and a 6-membered heteroaromatic ring which contains 1 or 2 =N— atoms, wherein a —HC=N— unit is optionally replaced by —NH—C(=O)—;

and wherein in heteroaryl and heterocyclyl rings with one ore more NH groups each of them is replaced by NR$^N$ or NR$^5$; with the proviso that R$^3$ in total cannot be $C_{1-4}$-alkyl-, $C_{1-4}$-alkyl-O—$C_{1-4}$-alkyl, HO—$C_{1-4}$-alkyl, and $C_{1-4}$-alkyl-O—.

R$^3$-G3a:
In another embodiment the group R$^3$ is selected from the group R$^3$-G3a consisting of $C_{1-4}$-alkyl-O—, wherein the alkyl group is substituted with 1 to 3 groups independently selected from R$^5$ and optionally substituted with 1 to 3 F atoms; and
heteroaryl, wherein the heteroaryl group is optionally substituted with 1 to 3 substituents independently selected from R$^6$;

wherein heteroaryl is selected from
tetrazolyl, a 5-membered heteroaromatic ring which contains 1, 2, or 3 heteroatoms independently of each other selected from =N—, —NH—, O, and S, and a 6-membered heteroaromatic ring which contains 1 or 2 =N— atoms, wherein a —HC=N— unit is optionally replaced by —NH—C(=O)—;

and wherein in heteroaryl and heterocyclyl rings with one ore more NH groups each of them is replaced by NR$^N$ or NR$^5$; with the proviso that R$^3$ in total cannot be $C_{1-4}$-alkyl-O—.

R$^3$-G4:
In another embodiment the group R$^3$ is selected from the group R$^3$-G4 consisting of $C_{1-4}$-alkyl, $C_{1-4}$-alkyl-O—, and $C_{3-6}$-cycloalkyl-O—, wherein each alkyl and cycloalkyl group and each alkyl and cycloalkyl sub-group within the groups mentioned is substituted with 1 group selected from R$^5$ and optionally substituted with 1 or 2 H$_3$C— group;
or from
$C_3$-alkyl-S(=O)$_2$— substituted with 1 HO— or H$_3$C—O— group; and
heterocyclyl-C(=O)—, H$_2$N—C(=O)—, HO—(H$_3$C)$_2$C—CH$_2$—NH—C(=O)—, H$_3$C—NR$^N$—C(=O)—, heterocyclyl-O—, heterocyclyl, phenyl, and heteroaryl, wherein each heterocyclyl group or sub-group within the groups mentioned is optionally substituted with 1 or 2 groups independently selected from R$^5$ and optionally substituted with 1 or more F atoms; and wherein each phenyl and heteroaryl group is optionally substituted with 1 or 2 substituents independently selected from $R^6$;

wherein heterocyclyl is selected from
  a cyclobutyl group wherein 1 $CH_2$ group is replaced by —NH— or —O—;
  a saturated or mono-unsaturated $C_{5-7}$-cycloalkyl group wherein 1 $CH_2$ group is replaced by —O(=O)—, —NH—, —O— or —S(=O)_2— and/or 1 CH group by N;
  a saturated or mono-unsaturated $C_{5-6}$-cycloalkyl group wherein 1 $CH_2$ group is replaced by —NH— or —O—, a second $CH_2$ group is replaced by —NH—, —O(=O)— or —S(=O)_2— and/or 1 CH group is replaced by N; and wherein heteroaryl is selected from
  tetrazolyl, a 5-membered heteroaromatic ring which contains 1 to 3 heteroatoms independently of each other selected from =N—, —NH—, —O—, and —S—, and a 6-membered heteroaromatic ring which contains 1 or 2 =N— atoms, wherein a —HC=N— unit is optionally replaced by —NH—C(=O)—;

wherein in heteroaryl and heterocyclyl rings with one ore more NH groups each of them is replaced by $NR^N$ or $NR^5$;
with the proviso that $R^3$ in total cannot be $C_{1-4}$-alkyl-, $C_{1-4}$-alkyl-O—$C_{1-4}$-alkyl, HO—$C_{1-4}$-alkyl, and $C_{1-4}$-alkyl-O—.

$R^3$-G5:

According to another embodiment the group $R^3$ is selected from the group $R^3$-G5 consisting of
  $C_4$-alkyl substituted with 1 HO— and $H_3C$— group;
  $C_{2-3}$-alkyl substituted with 1 group selected from $H_3C$—C(=O)—NH—, $H_3C$—S(=O)_2—NH— and $H_3C$—S(=O)_2—;
  $(H_3C)_3C$—$CH_2$—O—;
  cyclopropyl-$CH_2$—O— substituted with 1 HO— group;
  $C_{1-4}$-alkyl-O— optionally substituted with 1 or 2 $H_3C$— groups but necessarily substituted with 1 group selected from NC—, $H_2N$—C(=O)—, $H_3CNH$—C(=O)—, $(H_3C)_2N$—C(=O)—, $(H_3C)_2N$—, $H_3C$—C(=O)—NH—, $(H_3C)_3C$—O—C(=O)—NH—, $H_3C$—S(=O)_2—NH—, HO—, $C_{1-2}$-alkyl-O—, $H_3C$—S(=O)—, $H_3C$—S(=O)_2—, heterocyclyl, and heteroaryl;

wherein each heterocyclyl group and subgroup is selected from the group consisting of azetidinyl, oxetanyl, pyrrolidin-2-onyl, tetrahydrofuranyl, sulfolanyl, 1,1-dioxo-isothiazolidinyl, piperidinyl, tetrahydropyranyl, tetrahydrothiopyranyl, and 1,1-dioxo-tetrahydrothiopyranyl, each of which is optionally substituted with 1 group selected from $H_3C$— and HO—, and wherein a NH group, if present, optionally is replaced by $C_{1-3}$-alkyl-S(=O)_2—N; and wherein heteroaryl is selected from the group consisting of imidazolyl, pyrazolyl, oxazolyl, pyridinyl, and pyridin-2-onyl, wherein a NH group, if present, optionally is replaced by N—$CH_3$ and each heteroaryl is optionally substituted with 1 $H_3C$— or $H_3C$—O— group;

$C_{4-5}$-cycloalkyl-O— which is substituted with 1 group selected from —$N(CH_3)S(=O)_2CH_3$ and —OH, and is optionally additionally substituted with 1 $H_3C$— group;

azetidinyloxy, pyrrolidinyloxy, pyrrolidin-2-onyloxy, piperidinyloxy and 1,1-dioxo-[1,2]thiazinanyloxy, in each of which the NH group is optionally replaced by N—$CH_3$ or N—S(=O)_2—$CH_3$;

tetrahydrofuranyloxy, tetrahydropyranyloxy, and 1,1-dioxo-tetrahydrothiopyranyloxy;

$H_2N$—C(=O)—, $H_3C$—NH—C(=O)—, HO—$(H_3C)_2$C—$CH_2$—NH—C(=O)—, $(H_3C)_2N$—C(=O)—, morpholin-4-yl-C(=O)—, tetrahydrofuranyl, 3,6-dihydropyranyl, 1-methanesulfonyl-1,2,3,6-tetrahydropyridinyl, morpholin-4-yl, [1,4]oxazepan-4-yl, 6-oxo-3,6-dihydro-pyran-4-yl;

$C_3$-alkyl-S(=O)_2— substituted with 1 HO— or $H_3C$—O— group;

and phenyl, furanyl, imidazolyl, pyrazolyl, oxazolyl, thiazolyl, triazolyl, oxadiazolyl, tetrazolyl, pyridinyl, pyrimidinyl, pyridazinyl, pyrazinyl, pyridin-2-onyl, pyrimidin-2-onyl, pyrimidin-4-onyl and pyridazin-3-onyl, wherein a NH group, if present, optionally is replaced by N—$CH_3$, N—$CH_2$—C$(CH_3)_2$—OH or N—C$(CH_3)_2$—$CH_2$—OH, and which are optionally substituted with 1 $H_3C$— group and optionally substituted with 1 group selected from —$CH_3$, —$CH_2$—$CH_3$, cyclopropyl, —C$(CH_3)_2$—OH, and —O—$CH_3$.

$R^3$-G6:

According to another embodiment the group $R^3$ is selected from the group $R^3$-G6 consisting of

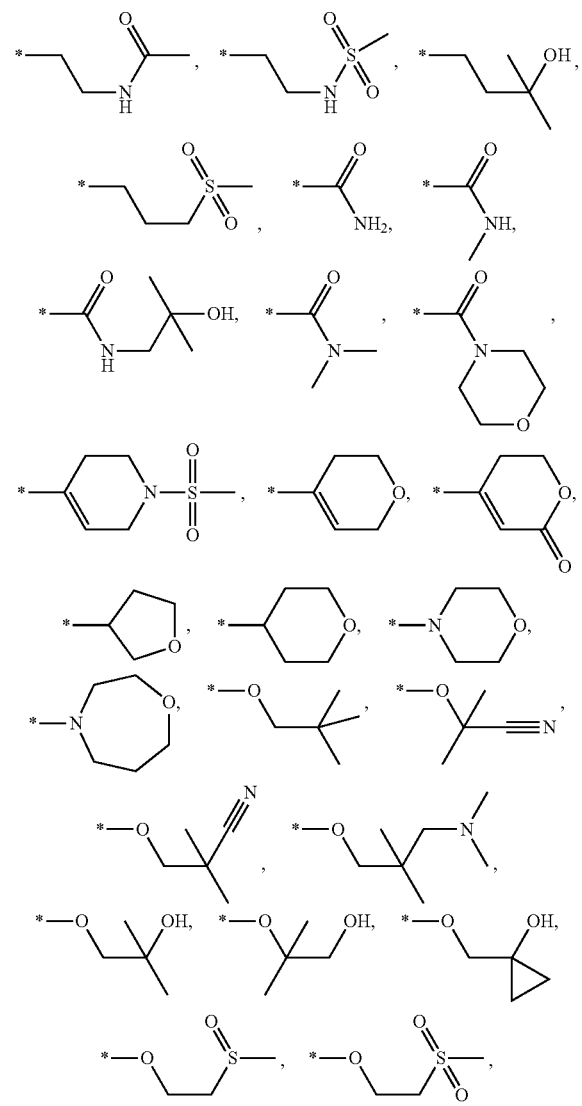

-continued
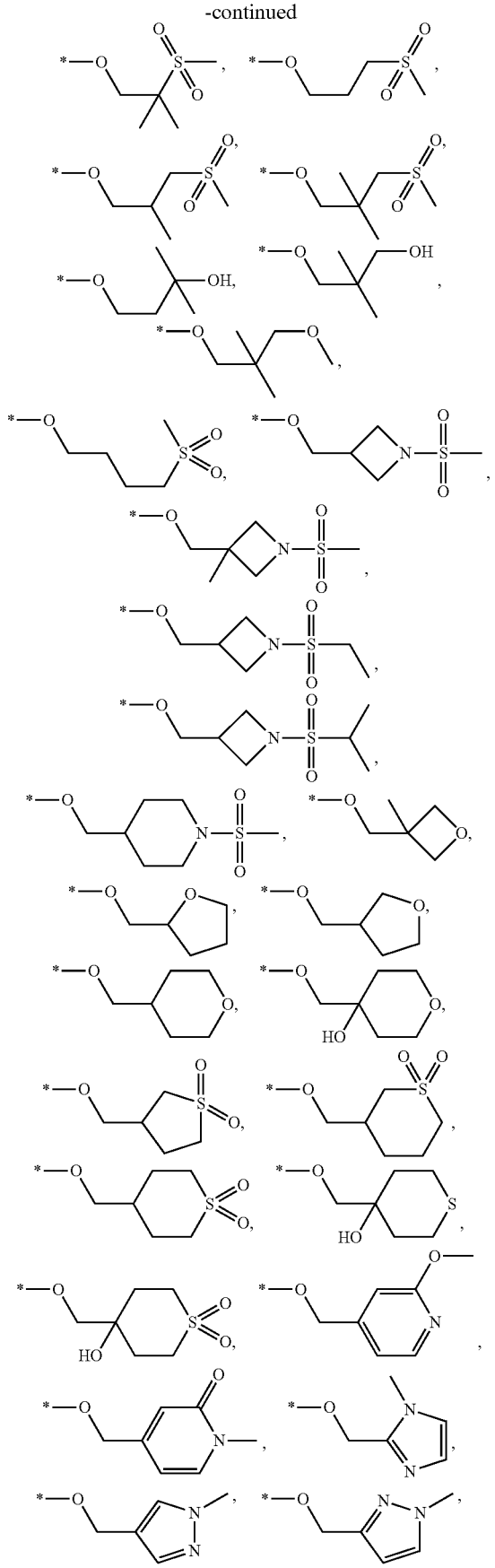
-continued
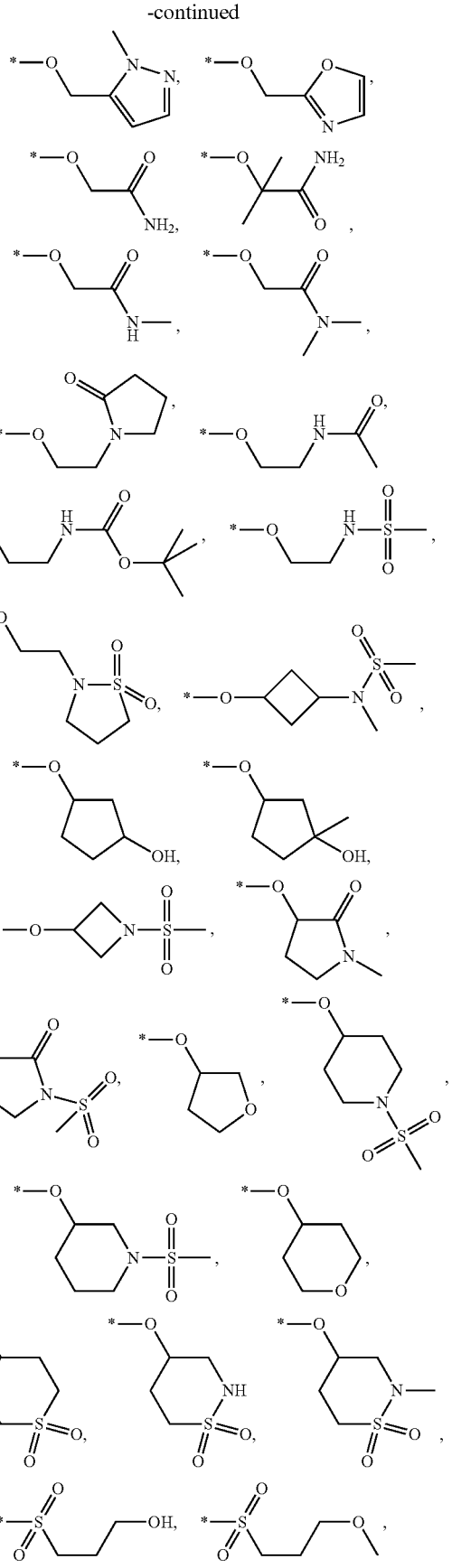

-continued

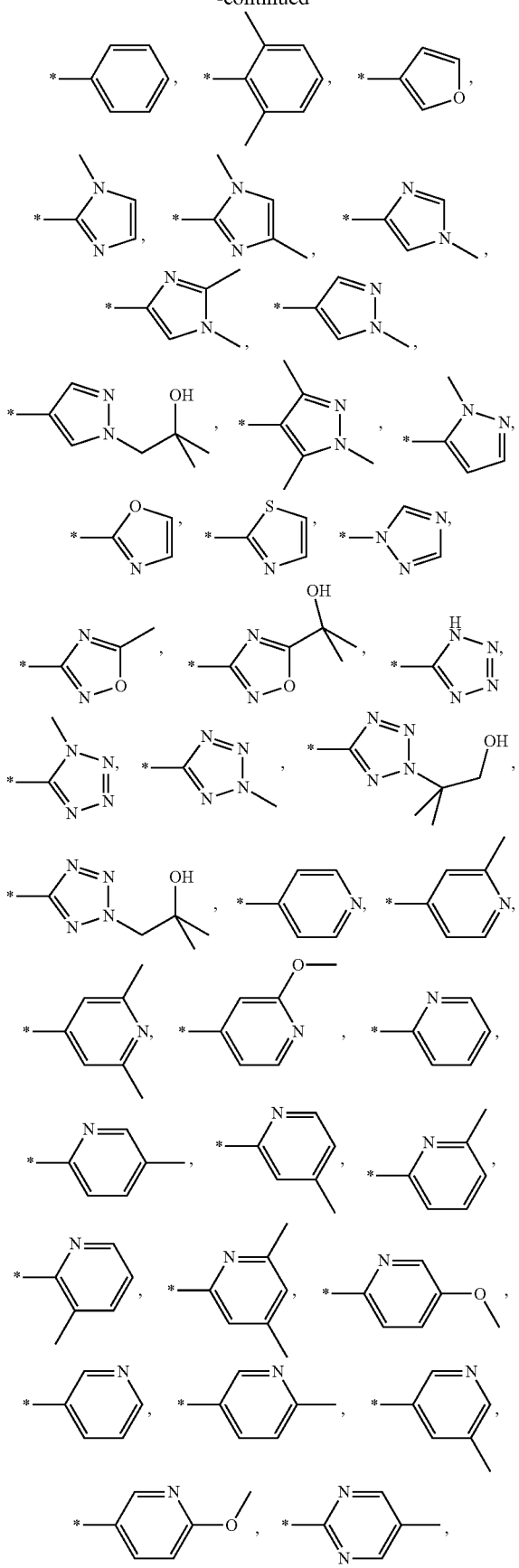

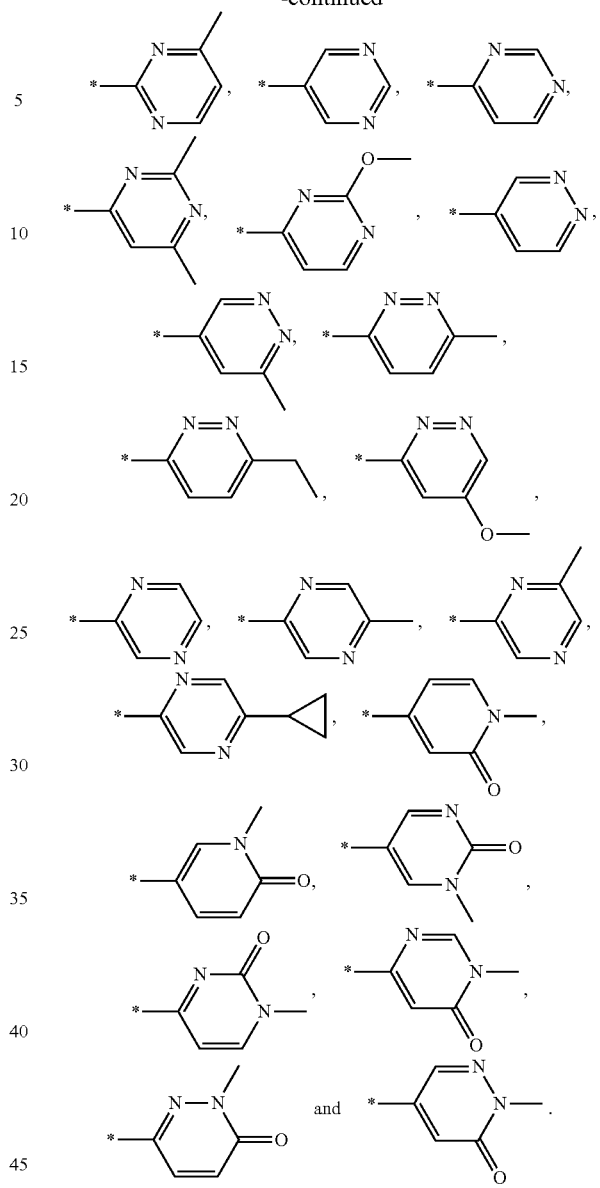

R⁴
R⁴-G1:
The group $R^4$ is preferably selected from the group $R^4$-G1 as defined hereinbefore.

R⁴-G2:
In another embodiment the group $R^4$ is selected from the group $R^4$-G2 consisting of F, Cl, Br, CN, $C_{1-3}$-alkyl, $C_{3-4}$-cycloalkyl-, HO—$C_{1-3}$-alkyl, $C_{1-3}$-alkyl-O—$C_{1-3}$-alkyl, —NR$^N$H, $C_{1-4}$-alkyl-O—, $C_{3-5}$-cycloalkyl-O—, $H_3C$—S(=O)—, $H_3C$—S(=O)$_2$—, wherein any alkyl and cycloalkyl group is optionally substituted with 1 or more F atoms.

R⁴-G3:
In another embodiment the group $R^4$ is selected from the group $R^4$-G3 consisting of F, Cl, CN, —$CH_3$, —$CF_3$, isopropyl, cyclopropyl, $H_3C$—O—$CH_2$—, $H_3C$—O—, and $F_3C$—O—.

R⁴-G4:
In another embodiment the group $R^4$ is selected from the group $R^4$-G4 consisting of $CH_3$.

$R^5$ $R^5$-G1:

The group $R^5$ is preferably selected from the group $R^5$-G1 as defined hereinbefore.

$R^5$-G2:

In one embodiment the group $R^5$ is selected from the group $R^5$-G2 consisting of $C_1$, $C_{1-4}$-alkyl-, —CN, $C_{3-6}$-cycloalkyl-, heterocyclyl-C(=O)—, $H_2N$—C(=O)—, $C_{1-4}$-alkyl-$NR^N$—C(=O)—, $C_{3-6}$-cycloalkyl-$NR^N$—C(=O)—, heterocyclyl-$NR^N$—C(=O)—, heteroaryl-$NR^N$—C(=O)—, —$NH_2$, $C_{1-4}$-alkyl-$NR^N$—, $C_{1-4}$-alkyl-C(=O)$NR^N$—, $C_{3-6}$-cycloalkyl-C(=O)$NR^N$—, heterocyclyl-C(=O)$NR^N$—, heteroaryl-C(=O)$NR^N$—, $C_{1-4}$-alkyl-S(=O)$_2NR^N$—, —OH, $C_{1-4}$-alkyl-O—, $C_{1-4}$-alkyl-O—$C_{1-4}$-alkyl-O—, $C_{3-6}$-cycloalkyl-O—, heterocyclyl-O—, phenyl-O—, heteroaryl-O—, $C_{1-4}$-alkyl-S(=O)—, $C_{3-6}$-cycloalkyl-S(=O)—, $C_{1-4}$-alkyl-S(=O)$_2$—, $C_{3-6}$-cycloalkyl-S(=O)$_2$—, heterocyclyl, and heteroaryl, wherein any alkyl, cycloalkyl, and heterocyclyl group or subgroup within the groups mentioned is optionally substituted with 1 or more F atoms and optionally substituted with 1 or 2 groups independently selected from $H_3C$—, HO—, $H_3C$—O—, and —CN, wherein heterocyclyl is selected from a cyclobutyl group wherein 1 $CH_2$ group is replaced by —$NR^N$— or —O—;

a saturated or partially unsaturated $C_{5-6}$-cycloalkyl group wherein 1 $CH_2$ group is replaced by —C(=O)—, —$NR^N$—, —O—, —S(=O)— or —S(=O)$_2$— and/or 1 CH group by N;

a saturated or partially unsaturated $C_{5-6}$-cycloalkyl group wherein 1 $CH_2$ group is replaced by —$NR^N$—, or —O—, a second $CH_2$ group is replaced by —$NR^N$—, —C(=O)—, —S(=O)— or —S(=O)$_2$— and/or 1 CH group is replaced by N; and a saturated or partially unsaturated $C_{5-6}$-cycloalkyl group wherein 2 $CH_2$ group are replaced by —$NR^N$— or 1 $CH_2$ group by —$NR^N$— and the other by —O—, and a third $CH_2$ group is replaced by —C(=O)—, —S(=O)— or —S(=O)$_2$— and/or 1 CH group by N;

and wherein heteroaryl is selected from a tetrazolyl ring, a pyridin-2-onyl ring, a 5-membered heteroaromatic ring which contains 1, 2, or 3 heteroatoms independently of each other selected from =N—, —NH—, —O—, and —S—, and a 6-membered heteroaromatic ring which contains 1 or 2 =N— atoms, and wherein in heteroaromatic rings with one ore more NH groups each of them is replaced by $NR^N$, and each heteroaryl group is optionally substituted with 1 to 3 substituents independently selected from F, Cl, —$CH_3$, —CN, and —O—$CH_3$.

$R^5$-G3:

In another embodiment the group $R^5$ is selected from the group $R^5$-G3 consisting of $C_{1-4}$-alkyl-, —CN, $C_{3-6}$-cycloalkyl-, $H_2N$—C(=O)—, $C_{1-4}$-alkyl-$NR^N$—C(=O)—, $C_{1-4}$-alkyl-$NR^N$—, $C_{1-4}$-alkyl-C(=O)$NR^N$—, —NHC(=O)—O—C(CH$_3$)$_3$, $C_{1-4}$-alkyl-S(=O)$_2NR^N$—, —OH, $C_{1-4}$-alkyl-O—, $C_{1-4}$-alkyl-S(=O)—, $C_{1-4}$-alkyl-S(=O)$_2$—, heterocyclyl, and heteroaryl, wherein any alkyl, cycloalkyl, and heterocyclyl group or subgroup within the groups mentioned is optionally substituted with 1 to 3 F atoms and optionally substituted with 1 or 2 groups independently selected from $H_3C$—, HO—, $H_3C$—O—, and —CN, wherein heterocyclyl is selected from a cyclobutyl group wherein 1 $CH_2$ group is replaced by —$NR^N$— or —O—, a saturated or partially unsaturated $C_{5-6}$-cycloalkyl group wherein 1 $CH_2$ group is replaced by —C(=O)—, —$NR^N$—, —O—, —S(=O)— or —S(=O)$_2$— and/or 1 CH group by N;

a saturated or partially unsaturated $C_{5-6}$-cycloalkyl group wherein 1 $CH_2$ group is replaced by —$NR^N$— or —O—, a second $CH_2$ group is replaced by —$NR^N$—, —C(=O)—, —S(=O)— or —S(=O)$_2$— and/or 1 CH group is replaced by N; and a saturated or partially unsaturated $C_{5-6}$-cycloalkyl group wherein 2 $CH_2$ groups are replaced by —$NR^N$— or 1 $CH_2$ group by —$NR^N$— and the other by —O—, and a third $CH_2$ group is replaced by —C(=O)—, —S(=O)— or —S(=O)$_2$— and/or 1 CH group by N;

and wherein heteroaryl is selected from a pyridin-2-onyl ring, a 5-membered heteroaromatic ring which contains 1 or 2 heteroatoms independently of each other selected from =N—, —NH—, —O—, and —S—, and a 6-membered heteroaromatic ring which contains 1 or 2 =N— atoms, and wherein in heteroaromatic rings with one ore more NH groups each of them is replaced by $NR^N$, and each heteroaryl group is optionally substituted with 1 or 2 substituents independently selected from F, Cl, —$CH_3$, —CN, and —O—$CH_3$.

$R^5$-G4:

In another embodiment the group $R^5$ is selected from the group $R^5$-G4 consisting of —$CH_3$, —CN, 1-hydroxycyclopropyl, $H_2N$—C(=O)—, —C(=O)NHCH$_3$, —C(=O)N(CH$_3$)$_2$, —N(CH$_3$)$_2$, $H_3C$—C(=O)NH—, —NHC(=O)—O—C(CH$_3$)$_3$, $H_3C$—S(=O)$_2NH$—, $H_3C$—S(=O)$_2$N(CH$_3$)—, —OH, $C_{1-3}$-alkyl-O—, $H_3C$—S(=O)—, $H_3C$—S(=O)$_2$—, heterocyclyl, and heteroaryl, wherein heterocyclyl is selected from an azetidinyl, oxetanyl, a pyrrolidin-2-onyl, tetrahydrofuranyl, sulfolanyl, 1,1-dioxo-isothiazolidinyl, piperidinyl, tetrahydropyranyl, tetrahydrothiopyranyl, 1,1-dioxo-tetrahydrothiopyranyl ring, wherein each of these rings optionally is substituted with 1 $CH_3$ or 1OH group and wherein an NH group, if present, optionally is replaced with NS(=O)$_2$—$C_{1-3}$-alkyl;

and wherein heteroaryl is selected from a 2-methoxy-pyridinyl, pyridin-2-onyl, imidazolyl, pyrazolyl, and oxazolyl ring, wherein in a heteroaryl group with a NH group this unit optionally is replaced by a N—$CH_3$ group.

$R^5$-G5:

According to another embodiment the group $R^5$ is selected from the group $R^5$-G5 consisting of —$CH_3$, —CN, —C(=O)NH$_2$, —C(=O)NHCH$_3$, —C(=O)N(CH$_3$)$_2$, —N(CH$_3$)$_2$, —NHC(=O)CH$_3$, —NHC(=O)—O—C(CH$_3$)$_3$, —NHS(=O)$_2$CH$_3$, —N(CH$_3$)S(=O)$_2$CH$_3$, —OH, —O—CH$_3$, —S(=O)CH$_3$, —S(=O)$_2$CH$_3$,

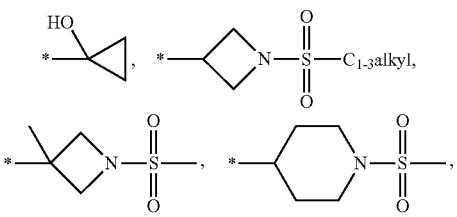

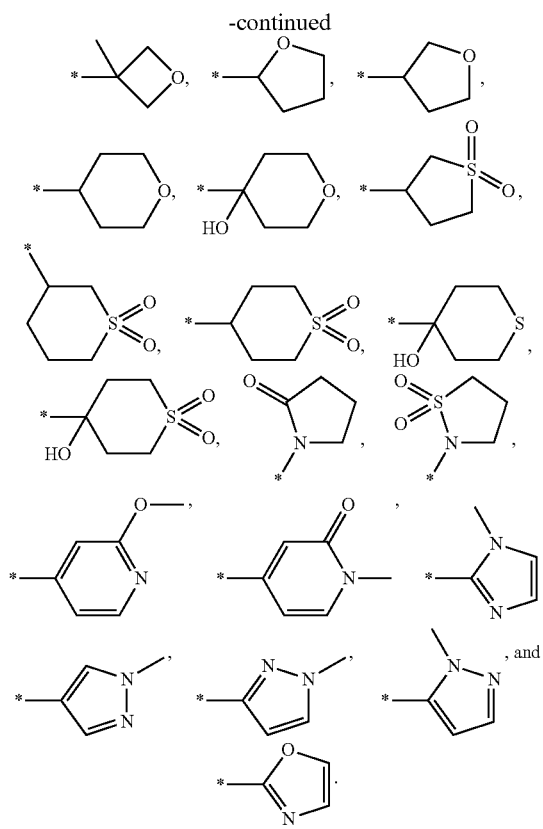

R⁶

R⁶-G1:
The group R⁶ is preferably selected from the group R⁶-G1 as defined hereinbefore.

R⁶-G2:
In one embodiment the group R⁶ is selected from the group R⁶-G2 consisting of F, Cl, —CN, $C_{1-3}$-alkyl, cyclopropyl, HO—$C_{1-3}$-alkyl-, $H_3C$—O—$C_{1-3}$-alkyl-, $H_3C$—O—, —S(=O)CH₃, and —S(=O)₂—CH₃, wherein any alkyl and cycloalkyl group or sub-group within the groups mentioned is optionally substituted with 1 to 3 F atoms.

R⁶-G3:
In another embodiment the group R⁶ is selected from the group R⁶-G3 consisting of F, Cl, —CN, —CH₃, —CH₂—CH₃, cyclopropyl, HO—C(CH₃)₂—, —CF₃, —OCH₃, —OCF₃, —S(=O)CH₃, and —S(=O)₂—CH₃.

R⁶-G4:
In another embodiment the group R⁶ is selected from the group R⁶-G4 consisting of F, —CH₃, —CH₂—CH₃, cyclopropyl, HO—C(CH₃)₂—, and —OCH₃.

R⁶-G5:
In another embodiment the group R⁶ is selected from the group R⁶-G5 consisting of —CH₃ and —OCH₃.

R^N

R^N-G1:
The group R^N is preferably selected from the group R^N-G1 as defined hereinbefore.

R^N-G2:
In another embodiment the group R^N is selected from the group R^N-G2 consisting of H, $C_{1-3}$-alkyl, $C_{1-3}$-alkyl-C(=O)—, and $C_{1-3}$-alkyl-S(=O)₂—.

RN-G3:
In another embodiment the group R^N is selected from the group R^N-G3 consisting of H, H₃C—, H₃C—C(=O)—, and $C_{1-3}$-alkyl-S(=O)₂—.

Examples of preferred subgeneric embodiments (E) according to the present invention are set forth in the following table, wherein each substituent group of each embodiment is defined according to the definitions set forth hereinbefore and wherein all other substituents of the formula I.I are defined according to the definitions set forth hereinbefore:

| E | R¹- | R³- | R⁴- | R⁵- | R⁶- | R^N- |
|---|---|---|---|---|---|---|
| E-1 | R¹-G1 | R³-G1 | R⁴-G1 | R⁵-G1 | R⁶-G1 | R^N-G1 |
| E-2 | R¹-G2 | R³-G2 | R⁴-G2 | R⁵-G2 | R⁶-G2 | R^N-G2 |
| E-3 | R¹-G2a | R³-G2 | R⁴-G2 | R⁵-G2 | R⁶-G2 | R^N-G2 |
| E-4 | R¹-G2b | R³-G2 | R⁴-G2 | R⁵-G2 | R⁶-G2 | R^N-G2 |
| E-5 | R¹-G3 | R³-G3 | R⁴-G3 | R⁵-G3 | R⁶-G3 | R^N-G3 |
| E-6 | R¹-G4 | R³-G3 | R⁴-G3 | R⁵-G3 | R⁶-G3 | R^N-G3 |
| E-7 | R¹-G4a | R³-G2 | R⁴-G3 | R⁵-G3 | R⁶-G3 | R^N-G3 |
| E-8 | R¹-G4a | R³-G3 | R⁴-G3 | R⁵-G3 | R⁶-G3 | R^N-G3 |
| E-9 | R¹-G4a | R³-G4 | R⁴-G3 | R⁵-G3 | R⁶-G3 | R^N-G3 |
| E-10 | R¹-G4a | R³-G4 | R⁴-G3 | R⁵-G3 | R⁶-G4 | R^N-G3 |
| E-11 | R¹-G4a | R³-G4 | R⁴-G3 | R⁵-G4 | R⁶-G4 | R^N-G3 |
| E-12 | R¹-G4a | R³-G4 | R⁴-G3 | R⁵-G5 | R⁶-G4 | R^N-G3 |
| E-13 | R¹-G5 | R³-G1 | — | R⁵-G1 | R⁶-G1 | R^N-G1 |
| E-14 | R¹-G5 | R³-G2 | — | R⁵-G2 | R⁶-G2 | R^N-G2 |
| E-15 | R¹-G5 | R³-G3 | — | R⁵-G3 | R⁶-G3 | R^N-G3 |
| E-16 | R¹-G5 | R³-G3a | — | R⁵-G3 | R⁶-G3 | R^N-G3 |
| E-17 | R¹-G5 | R³-G3a | — | R⁵-G4 | R⁶-G4 | R^N-G3 |
| E-18 | R¹-G5 | R³-G4 | — | R⁵-G3 | R⁶-G3 | R^N-G3 |
| E-19 | R¹-G5 | R³-G4 | — | R⁵-G3 | R⁶-G4 | R^N-G3 |
| E-20 | R¹-G5 | R³-G4 | — | R⁵-G4 | R⁶-G4 | R^N-G3 |
| E-21 | R¹-G5 | R³-G3 | — | R⁵-G5 | R⁶-G4 | R^N-G3 |
| E-22 | R¹-G5 | R³-G4 | — | R⁵-G5 | R⁶-G4 | R^N-G3 |
| E-23 | R¹-G5 | R³-G5 | — | — | — | — |
| E-24 | R¹-G5 | R³-G6 | — | — | — | — |

The following preferred embodiment of compounds of the formula I.I is described using generic formula (I.1), wherein any tautomers, stereoisomers, solvates, hydrates and salts thereof, in particular the pharmaceutically acceptable salts thereof, are encompassed.

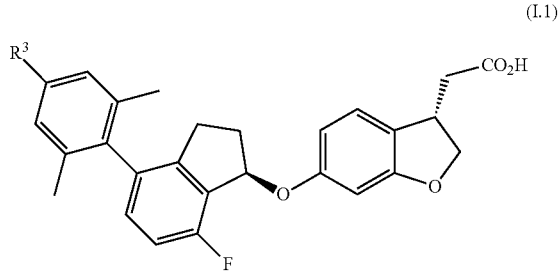

(I.1)

Preferred are those compounds of formula (I.1), wherein
R³ is selected from the group consisting of $C_{1-4}$-alkyl, $C_{1-4}$-alkyl-O—, and $C_{3-6}$-cycloalkyl-O—,
wherein each alkyl and cycloalkyl group and each alkyl and cycloalkyl sub-group within the groups mentioned is substituted with 1 to 3 groups independently selected from R⁵ and optionally substituted with 1 to 3 F atoms;
or
R³ is selected from
C₃-alkyl-S(=O)₂— substituted with 1 HO— or H₃C—O— group; and
heterocyclyl-C(=O)—, H₂N—C(=O)—, HO—(H₃C)₂C—CH₂—NH—C(=O)—, $C_{1-3}$-alkyl-NR^N—C(=O)—, $C_{1-4}$-alkyl-C(=O)NR^N—, $C_{3-6}$-cycloalkyl-C(=O)NR^N—, heterocyclyl-C(=O)NR^N—, $C_{1-4}$-alkyl-S(=O)₂NR^N—, heterocyclyl-O—, phenyl-O—, heteroaryl-O—, heterocyclyl-S(=O)₂—, heterocyclyl, phenyl, and heteroaryl, wherein each alkyl, cycloalkyl, and heterocyclyl group or sub-group within the groups mentioned is optionally substituted with 1 or 2 groups independently selected from $R^5$ and optionally substituted with 1 or more F atoms; and wherein each phenyl and heteroaryl group is optionally substituted with 1 to 3 substituents independently selected from $R^6$;

wherein heterocyclyl is selected from
  a cyclobutyl group wherein 1 $CH_2$ group is replaced by —NH— or —O—,
  a saturated or mono-unsaturated $C_{5-7}$-cycloalkyl group wherein 1 $CH_2$ group is replaced by —C(=O)—, —NH—, —O— or —S(=O)$_2$— and/or 1 CH group by N;
  a saturated or mono-unsaturated $C_{5-6}$-cycloalkyl group wherein 1 $CH_2$ group is replaced by —NH— or —O—, a second $CH_2$ group is replaced by —C(=O)— or —S(=O)$_2$— and/or 1 CH group is replaced by N; and wherein heteroaryl is selected from
  tetrazolyl, a 5-membered heteroaromatic ring which contains 1, 2, or 3 heteroatoms independently of each other selected from =N—, —NH—, O, and S, and a 6-membered heteroaromatic ring which contains 1 or 2 =N— atoms, wherein a —HC=N— unit is optionally replaced by —NH—C(=O)—;

and wherein in heteroaryl and heterocyclyl rings with one ore more NH groups each of them is replaced by $NR^N$ or $NR^5$;

with the proviso that $R^3$ in total cannot be $C_{1-4}$-alkyl-, $C_{1-4}$-alkyl-O—$C_{1-4}$-alkyl, HO—$C_{1-4}$-alkyl, and $C_{1-4}$-alkyl-O—;

$R^5$ is selected from the group consisting of $C_{1-4}$-alkyl-, —CN, $C_{3-6}$-cycloalkyl-, $H_2N$—C(=O)—, $C_{1-4}$-alkyl-$NR^N$—C(=O)—, $C_{1-4}$-alkyl-$NR^N$—, $C_{1-4}$-alkyl-C(=O)$NR^N$—, —NHC(=O)—O—C(CH$_3$)$_3$, $C_{1-4}$-alkyl-S(=O)$_2$$NR^N$—, —OH, $C_{1-4}$-alkyl-O—, $C_{1-4}$-alkyl-S(=O)—, $C_{1-4}$-alkyl-S(=O)$_2$—, heterocyclyl, and heteroaryl, wherein any alkyl, cycloalkyl, and heterocyclyl group or sub-group within the groups mentioned is optionally substituted with 1 to 3 F atoms and optionally substituted with 1 or 2 groups independently selected from $H_3C$—, HO—, $H_3C$—O—, and —CN, wherein heterocyclyl is selected from
  a cyclobutyl group wherein 1 $CH_2$ group is replaced by —$NR^N$— or —O—,
  a saturated or partially unsaturated $C_{5-6}$-cycloalkyl group wherein 1 $CH_2$ group is replaced by —C(=O)—, —$NR^N$—, —O—, —S(=O)— or —S(=O)$_2$— and/or 1 CH group by N;
  a saturated or partially unsaturated $C_{5-6}$-cycloalkyl group wherein 1 $CH_2$ group is replaced by —$NR^N$— or —O—, a second $CH_2$ group is replaced by —$NR^N$—, —C(=O)—, —S(=O)— or —S(=O)$_2$— and/or 1 CH group is replaced by N; and
  a saturated or partially unsaturated $C_{5-6}$-cycloalkyl group wherein 2 $CH_2$ groups are replaced by —$NR^N$— or 1 $CH_2$ group by —$NR^N$— and the other by —O—, and a third $CH_2$ group is replaced by —C(=O)—, —S(=O)— or —S(=O)$_2$— and/or 1 CH group by N;

and wherein heteroaryl is selected from
a pyridin-2-onyl ring, a 5-membered heteroaromatic ring which contains 1 or 2 heteroatoms independently of each other selected from =N—, —NH—, —O—, and —S—, and a 6-membered heteroaromatic ring which contains 1 or 2 =N— atoms, and wherein in heteroaromatic rings with one ore more NH groups each of them is replaced by $NR^N$, and each heteroaryl group is optionally substituted with 1 or 2 substituents independently selected from F, Cl, —$CH_3$, —CN, and —O—$CH_3$;

$R^6$ is selected from the group F, Cl, —CN, —$CH_3$, —$CH_2$—$CH_3$, cyclopropyl, HO—C(CH$_3$)$_2$—, —$CF_3$, —$OCH_3$, —$OCF_3$, —S(=O)$CH_3$, and —S(=O)$_2$—$CH_3$;

$R^N$ is selected from the group consisting of H, $H_3C$—, $H_3C$—C(=O)—, and $C_{1-3}$-alkyl-S(=O)$_2$—;

and the pharmaceutically acceptable salts thereof.

More preferred are those compounds of formula (I.1), wherein $R^3$ is selected from the group consisting of $C_{1-4}$-alkyl, $C_{1-4}$-alkyl-O—, and $C_{3-6}$-cycloalkyl-O—, wherein each alkyl and cycloalkyl group and each alkyl and cycloalkyl sub-group within the groups mentioned is substituted with 1 group selected from $R^5$ and optionally substituted with 1 or 2 $H_3C$— group;

or from
$C_3$-alkyl-S(=O)$_2$— substituted with 1 HO— or $H_3C$—O— group; and heterocyclyl-C(=O)—, $H_2N$—C(=O)—, HO—(H$_3$C)$_2$C—$CH_2$—NH—C(=O)—, $H_3C$—$NR^N$—C(=O)—, heterocyclyl-O—, heterocyclyl, phenyl, and heteroaryl, wherein each heterocyclyl group or sub-group within the groups mentioned is optionally substituted with 1 or 2 groups independently selected from $R^5$ and optionally substituted with 1 or more F atoms; and wherein each phenyl and heteroaryl group is optionally substituted with 1 or 2 substituents independently selected from $R^6$;

wherein heterocyclyl is selected from
  a cyclobutyl group wherein 1 $CH_2$ group is replaced by —NH— or —O—;
  a saturated or mono-unsaturated $C_{5-7}$-cycloalkyl group wherein 1 $CH_2$ group is replaced by —C(=O)—, —NH—, —O— or —S(=O)$_2$— and/or 1 CH group by N;
  a saturated or mono-unsaturated $C_{5-6}$-cycloalkyl group wherein 1 $CH_2$ group is replaced by —NH— or —O—, a second $CH_2$ group is replaced by —NH—, —C(=O)— or —S(=O)$_2$— and/or 1 CH group is replaced by N; and wherein heteroaryl is selected from
  tetrazolyl, a 5-membered heteroaromatic ring which contains 1 to 3 heteroatoms independently of each other selected from =N—, —NH—, —O—, and —S—, and a 6-membered heteroaromatic ring which contains 1 or 2 =N— atoms, wherein a —HC=N— unit is optionally replaced by —NH—C(=O)—;

wherein in heteroaryl and heterocyclyl rings with one ore more NH groups each of them is replaced by $NR^N$ or $NR^5$;

with the proviso that $R^3$ in total cannot be $C_{1-4}$-alkyl-, $C_{1-4}$-alkyl-O—$C_{1-4}$-alkyl, HO—$C_{1-4}$-alkyl, and $C_{1-4}$-alkyl-O—;

$R^5$ is selected from the group consisting of —$CH_3$, —CN, 1-hydroxycyclopropyl, $H_2N$—C(=O)—, —C(=O)$NHCH_3$, —C(=O)N(CH$_3$)$_2$, —N(CH$_3$)$_2$, $H_3C$—C(=O)NH—, —NHC(=O)—O—C(CH$_3$)$_3$, $H_3C$—S(=O)$_2$NH—, $H_3C$—S(=O)$_2$N(CH$_3$)—, —OH, $C_{1-3}$-alkyl-O—, $H_3C$—S(=O)—, $H_3O$—S(=O)$_2$—, heterocyclyl, and heteroaryl, wherein heterocyclyl is selected from
  an azetidinyl, oxetanyl, a pyrrolidin-2-onyl, tetrahydrofuranyl, sulfolanyl, 1,1-dioxo-isothiazolidinyl, piperidinyl, tetrahydropyranyl, tetrahydrothiopyranyl, 1,1-dioxo-tetrahydrothiopyranyl ring, wherein each of these rings optionally is substituted with 1 $CH_3$ or 1OH group and wherein an NH group, if present, optionally is replaced with NS(=O)$_2$—$C_{1-3}$-alkyl;

and wherein heteroaryl is selected from
a 2-methoxy-pyridinyl, pyridin-2-onyl, imidazolyl, pyrazolyl, and oxazolyl ring, wherein in a heteroaryl group with a NH group this unit optionally is replaced by a N—$CH_3$ group;

$R^6$ is selected from the group F, Cl, —CN, —$CH_3$, —$CH_2$—$CH_3$, cyclopropyl, HO—C($CH_3$)$_2$—, —$CF_3$, —$OCH_3$, —$OCF_3$, —S(=O)$CH_3$, and —S(=O)$_2$—$CH_3$;

$R^N$ is selected from the group consisting of H, $H_3$C—, $H_3$C—C(=O)—, and $C_{1-3}$-alkyl-S(=O)$_2$—;

and the pharmaceutically acceptable salts thereof.

Particularly preferred are those compounds of formula (I.1), wherein
$R^3$ is selected from the group consisting of
$C_4$-alkyl substituted with 1 HO— and 1 $H_3$C— group;
$C_{2-3}$-alkyl substituted with 1 group selected from $H_3$C—C(=O)—NH—, $H_3$C—S(=O)$_2$—NH— and
$H_3$C—S(=O)$_2$—;
($H_3$C)$_3$C—$CH_2$—O—;
cyclopropyl-$CH_2$—O— substituted with 1 HO— group;
$C_{1-4}$-alkyl-O— optionally substituted with 1 or 2 $H_3$C— groups but necessarily substituted with 1 group selected from NC—, $H_2$N—C(=O)—, $H_3$CNH—C(=O)—, ($H_3$C)$_2$N—C(=O)—, ($H_3$C)$_2$N—, $H_3$C—C(=O)—NH—, ($H_3$C)$_3$C—O—C(=O)—NH—, $H_3$C—S(=O)$_2$—NH—, HO—, $C_{1-2}$-alkyl-O—, $H_3$C—S(=O)—, $H_3$C—S(=O)$_2$—, heterocyclyl, and heteroaryl;
wherein each heterocyclyl group and subgroup is selected from the group consisting of azetidinyl, oxetanyl, pyrrolidin-2-onyl, tetrahydrofuranyl, sulfolanyl, 1,1-dioxo-isothiazolidinyl, piperidinyl, tetrahydropyranyl, tetrahydrothiopyranyl, and 1,1-dioxo-tetrahydrothiopyranyl, each of which is optionally substituted with 1 group selected from $H_3$C— and HO—, and wherein a NH group, if present, optionally is replaced by $C_{1-3}$-alkyl-S(=O)$_2$—N; and
wherein heteroaryl is selected from the group consisting of imidazolyl, pyrazolyl, oxazolyl, pyridinyl, and pyridin-2-onyl, wherein a NH group, if present, optionally is replaced by N—$CH_3$ and each heteroaryl is optionally substituted with 1 $H_3$C— or $H_3$C—O— group;
$C_{4-5}$-cycloalkyl-O— which is substituted with 1 group selected from —N($CH_3$)S(=O)$_2$$CH_3$ and —OH, and is optionally additionally substituted with 1 $H_3$C— group;
azetidinyloxy, pyrrolidinyloxy, pyrrolidin-2-onyloxy, piperidinyloxy and 1,1-dioxo-[1,2]thiazinanyloxy, in each of which the NH group is optionally replaced by N—$CH_3$ or N—S(=O)$_2$—$CH_3$;
tetrahydrofuranyloxy, tetrahydropyranyloxy, and 1,1-dioxo-tetrahydrothiopyranyloxy;
$H_2$N—C(=O)—, $H_3$C—NH—C(=O)—, HO—($H_3$C)$_2$C—$CH_2$—NH—C(=O)—, ($H_3$C)$_2$N—C(=O)—, morpholin-4-yl-C(=O)—, tetrahydrofuranyl, 3,6-dihydropyranyl, 1-methanesulfonyl-1,2,3,6-tetrahydropyridinyl, morpholin-4-yl, [1,4]oxazepan-4-yl, 6-oxo-3,6-dihydro-pyran-4-yl;
$C_3$-alkyl-S(=O)$_2$— substituted with 1 HO— or $H_3$C—O— group;
and
phenyl, furanyl, imidazolyl, pyrazolyl, oxazolyl, thiazolyl, triazolyl, oxadiazolyl, tetrazolyl, pyridinyl, pyrimidinyl, pyridazinyl, pyrazinyl, pyridin-2-onyl, pyrimidin-2-onyl, pyrimidin-4-onyl and pyridazin-3-onyl, wherein a NH group, if present, optionally is replaced by N—$CH_3$, N—$CH_2$—C($CH_3$)$_2$—OH or N—C($CH_3$)$_2$—$CH_2$—OH, and which are optionally substituted with 1 $H_3$C— group and optionally substituted with 1 group selected from —$CH_3$, —$CH_2$—$CH_3$, cyclopropyl, —C($CH_3$)$_2$—OH, and —O—$CH_3$;
and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of formula I.I are preferably accessed from a precursor 1 that bears the carboxylic acid group protected as ester (Scheme 1); $R^1$ has the meaning as defined hereinbefore and hereinafter. The ester group may be hydrolysed in the presence of an acid, such as hydrochloric acid or sulfuric acid, or preferably an alkali metal hydroxide, such as lithium hydroxide, sodium hydroxide, or potassium hydroxide, to yield the carboxylic acid. The hydrolysis is preferably conducted in aqueous solvents, such as water combined with tetrahydrofuran, 1,4-dioxane, alcohol, e.g. methanol, ethanol and isopropanol, or dimethyl sulfoxide, at 0 to 80° C. A tert-butyl ester is preferably cleaved under acidic conditions, e.g. trifluoroacetic acid or hydrochloric acid, in a solvent, such as dichloromethane, 1,4-dioxane, isopropanol or ethyl acetate. A benzyl ester is advantageously cleaved using hydrogen in the presence of a transition metal, preferably palladium on carbon. Benzyl esters bearing electron donating groups on the phenyl ring, such as methoxy, may also be cleaved under oxidative conditions; ceric ammonium nitrate (CAN) or 2,3-dichloro-5,6-dicyanoquinone (DDQ) are two commonly used reagents for this approach.

Scheme 1

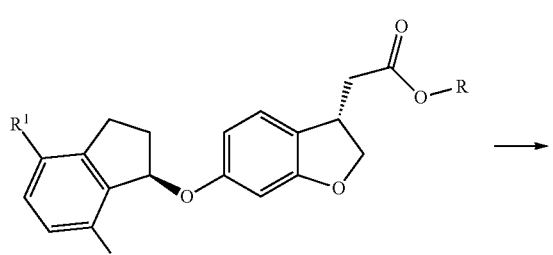

-continued

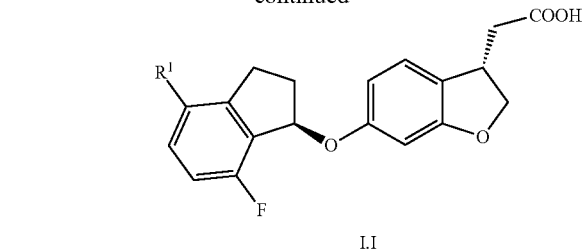

I.I

R = $C_{1-4}$-alkyl, optionally substituted with one or more F atoms;
$CH_2$-phenyl, wherein phenyl is optionally substituted with one or more F atoms and/or one or two groups independently selected from Cl, Br, $CH_3$, $OCH_3$, and $NO_2$; allyl Compound 1 may be assembled using building blocks 2, 3 and 4 (Scheme 2); $R^1$ has the meaning as defined hereinbefore and hereinafter.

Scheme 2

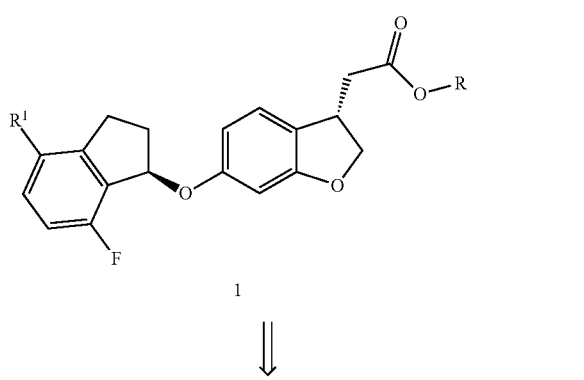

1

⇓

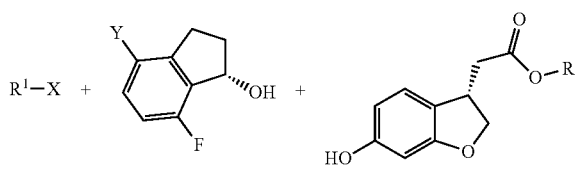

2   3   4

X, Y = e.g., $B(OH)_2$, $B(OCMe_2CMe_2O)$, $BF_3K$, ZnHal, MgHal (Hal = Cl, Br, I) or e.g., Cl, Br, I, $OSO_2CF_3$, $OSO_2Me$;
R = as defined in Scheme 1

Building blocks 3 and 4 may be combined in a stereoselective fashion employing the conditions of the Mitsunobu reaction or variations thereof (Scheme 3); $R^1$ has the meaning as defined hereinbefore and hereinafter. The reaction is usually conducted with a phosphine and an azodicarboxylic ester or amide in tetrahydrofuran, 1,4-dioxane, diethyl ether, toluene, benzene, dichloromethane, or mixtures thereof, at −30 to 100° C. Phosphines often used are triphenylphosphine and tributylphosphine, which are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

Scheme 3

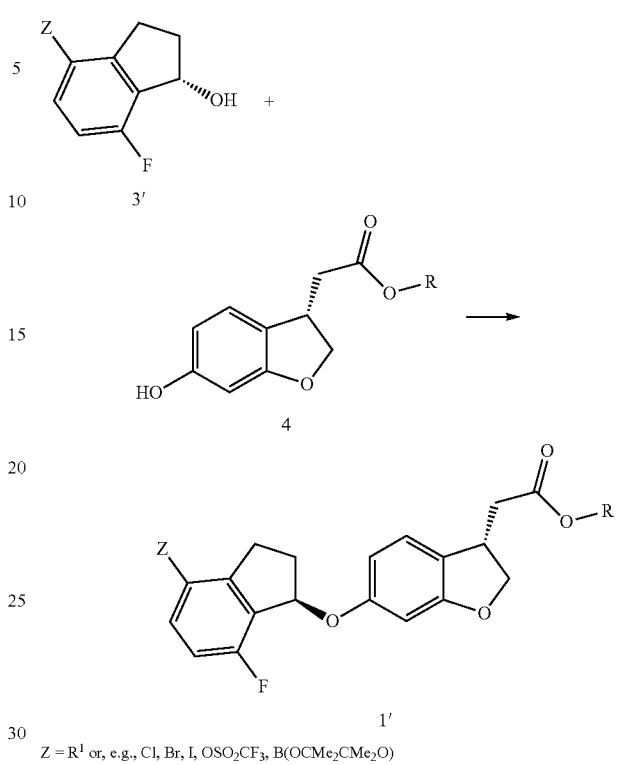

3'

4

1'

Z = $R^1$ or, e.g., Cl, Br, I, $OSO_2CF_3$, $B(OCMe_2CMe_2O)$
R is as defined in Scheme 1

Residue $R^1$ is attached to the indane moiety of the compounds of the invention preferably via a transition metal catalyzed coupling reaction (Scheme 3); $R^1$ is defined as hereinbefore and hereinafter. The coupling is preferably conducted with $R^1$ as the electrophilic component, bearing a leaving group such as Cl, Br or I at the carbon to be coupled. The indane residue is then employed as the nucleophilic partner, bearing a metal or pseudo-metal group such as $B(OH)_2$, $B(OCMe_2CMe_2O)$ or $BF_3K$ at the carbon to be coupled. Nevertheless, the coupling partners may also be combined with their reversed reactivity, i.e. $R^1$ is used as the nucleophilic partner bearing the metal or pseudo-metal group and the indane residue as the electrophilic partner bearing the leaving group. The reaction is preferably mediated by a transition metal complex derived from palladium. The catalyst may be a preformed complex, such as $Pd(PPh_3)_4$, $PdCl_2[1,1'$-bis(diphenylphosphino)ferrocene], dichloro[1,3-bis(2,6-di-isopropylphenyl)-imidazol-2-ylidene]-(3-chloropyridyl)-palladium(II) (PEPPSI-IPr) or dichloro[1,3-bis(2,6-dipent-3-yl-phenyl)imidazol-2-ylidene](3-chloropyridyl)-palladium (II) (PEPPSI-(Pent), or formed in situ from a salt of the transition metal, such as fluoride, chloride, bromide, iodide, acetate, triflate or trifluoroacetate, and a ligand, such as phosphines, e.g. tri-tert-butylphosphine, tricyclohexylphosphine, optionally substituted biphenyl-dicyclohexyl-phosphines (e.g., S-Phos, Ru-Phos, X-Phos), optionally substituted biphenyl-di-tert-butyl-phosphines, 1,1'-bis(diphenylphosphino)-ferrocene, or triphenylphosphine. The reaction using boronic acids or esters or trifluoroborates is preferably carried out in the presence of water and a base, e.g. NaOH, KOH, KF, $Na_2CO_3$, $K_2CO_3$, $Cs_2CO_3$ or $K_3PO_4$, in toluene, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at 10 to 180° C.

Scheme 4

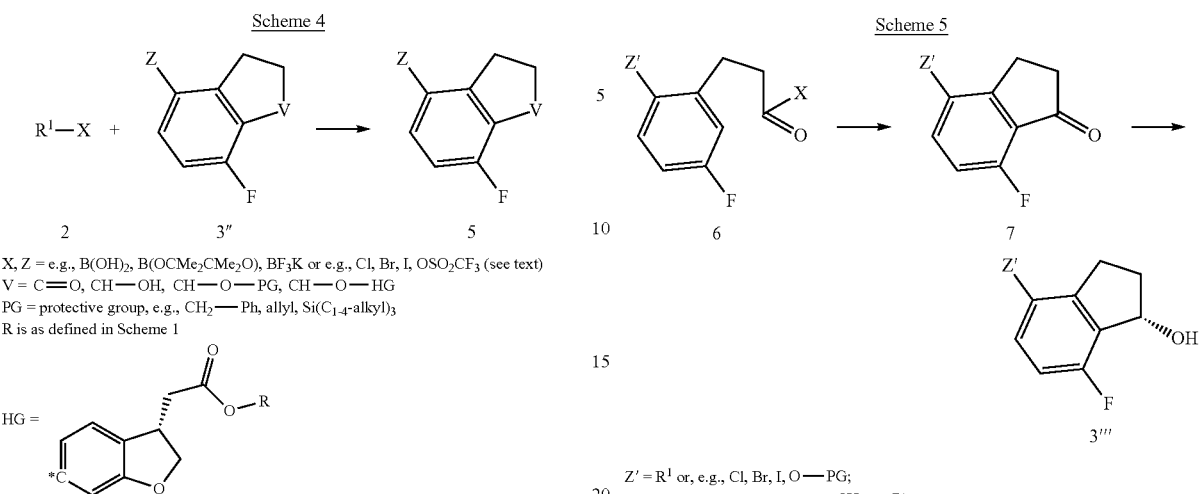

X, Z = e.g., B(OH)$_2$, B(OCMe$_2$CMe$_2$O), BF$_3$K or e.g., Cl, Br, I, OSO$_2$CF$_3$ (see text)
V = C=O, CH—OH, CH—O—PG, CH—O—HG
PG = protective group, e.g., CH$_2$—Ph, allyl, Si(C$_{1-4}$-alkyl)$_3$
R is as defined in Scheme 1

Intermediate 3 or derivatives thereof, as 3''', may be obtained from indanone 7, which, in turn, may be prepared from phenylpropionic acid derivative 6 (Scheme 5); R$^1$ has the meaning as defined hereinbefore and hereinafter. For the intramolecular acylation (Friedel-Crafts acylation), 6→7, a considerable number of approaches has been reported. The reaction may be performed starting with a carboxylic acid, carboxylic ester, carboxylic anhydride, carboxylic chloride or fluoride, or a nitrile using a Lewis acid as catalyst. The following Lewis acids are some of the more often used ones: hydrobromic acid, hydroiodic acid, hydrochloric acid, sulfuric acid, phosphoric acid, P$_4$O$_{10}$, trifluoroacetic acid, methanesulfonic acid, toluenesulfonic acid, trifluoromethanesulfonic acid, ClSO$_3$H, Sc(OSO$_2$CF$_3$)$_3$, Tb(OSO$_2$CF$_3$)$_3$, SnCl$_4$, FeCl$_3$, AlBr$_3$, AlCl$_3$, SbCl$_5$, BCl$_3$, BF$_3$, ZnCl$_2$, montmorillonites, POCl$_3$, and PCl$_5$. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid or trifluoroacetic acid at 0 to 120° C., while carboxylic chlorides are preferably reacted with AlCl$_3$ in dichloromethane or 1,2-dichloroethane at 0 to 80° C.

The subsequent reduction of the carbonyl group in compound 7 providing the alcohol 3''' in enantiomerically enriched or pure form may be accomplished using hydrogen or a hydrogen source, such as formate or silane, and a transition metal catalyst derived from, e.g., Ir, Rh, Ru or Fe and a chiral auxiliary. For instance, a ruthenium complex, such as chloro{[(1S,2S)-(−)-2-amino-1,2-diphenylethyl](4-toluenesulfonyl)-amido}-(mesitylene)ruthenium(II), may deliver the hydroxy compound 3''' with high enantiomeric excess using, e.g., formic acid in the presence of a base, e.g. triethylamine, in dichloromethane, at −20 to 60° C. Alternatively, boranes combined with an enantiomerically pure [1,3,2]oxazaborol may be used as reducing agent (Corey-Bakshi-Shibata reaction or Corey-Itsuno reaction). Typical reaction conditions for this approach employ borane (complexed with, e.g., dimethyl sulfide) and (R)- or (S)-3,3-diphenyl-1-methyltetrahydro-1H,3H-pyrrolo[1,2-c][1,3,2]oxazaborolin, e.g., dichloromethane, toluene, methanol, tetrahydrofuran, or mixtures thereof, at 0 to 60° C.

Z' = R$^1$ or, e.g., Cl, Br, I, O—PG;
PG = protective group, e.g., Me, CH$_2$—Ph The compounds of formula I are preferably accessed from a precursor 1a that bears the carboxylic acid function in a protected or masked form as sketched in Scheme 1a; R$^1$, R$^2$, and m have the meanings as defined hereinbefore and hereinafter. Suited precursor groups for the carboxylic acid may be, e.g., a carboxylic ester, a carboxylic amide, cyano, an olefin, oxazole, or a thiazole. All these groups have been transformed into the carboxylic acid function by different means which are described in the organic chemistry literature and are known to the one skilled in the art. The preferred precursor group is a C$_{1-4}$-alkyl or benzyl carboxylate, each of which may be additionally mono- or polysubstituted with fluorine, methyl, and/or methoxy. These ester groups may be hydrolysed with an acid, such as hydrochloric acid or sulfuric acid, or an alkali metal hydroxide, such as lithium hydroxide, sodium hydroxide, or potassium hydroxide, to yield the carboxylic acid function; the hydrolysis is preferably conducted in aqueous solvents, such as water and tetrahydrofuran, 1,4-dioxane, alcohol, e.g. methanol, ethanol, and isopropanol, or dimethyl sulfoxide, at 0 to 120° C. A tert-butyl ester is preferably cleaved under acidic conditions, e.g. trifluoroacetic acid or hydrochloric acid, in a solvent such as dichloromethane, 1,4-dioxane, isopropanol, or ethyl acetate. A benzyl ester is advantageously cleaved using hydrogen in the presence of a transition metal, preferably palladium on carbon. Benzyl esters bearing electron donating groups, such as methoxy groups, on the aromatic ring may also be removed under oxidative conditions; ceric ammonium nitrate (CAN) or 2,3-dichloro-5,6-dicyanoquinone (DDQ) are two commonly used reagents for this approach.

Scheme 1a: Liberation of Carboxylic Acid Function to Access Compounds of the Invention

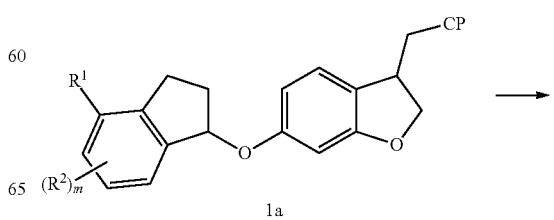

-continued

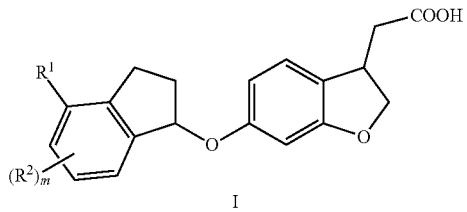

I

CP = masked or protected form of COOH, e.g., CO$_2$C$_{1-4}$-alkyl, CO$_2$CH$_2$aryl, CON(C$_{1-4}$-alkyl)$_2$, CN, CH═CH$_2$, thiazol-2-yl, oxazol-2-yl Compound 1a, in turn, may be obtained from indane 2a, which bears a leaving group, and phenol 3a, which is decorated with the carboxylic acid precursor group (Scheme 2); R$^1$, R$^2$, and m in Scheme 2 have the meanings as defined hereinbefore and hereinafter. The leaving group LG in 2a is replaced with the O in 3a via a nucleophilic substitution; suited LG may be Cl, Br, I, methylsulfonyloxy, phenylsulfonyloxy, p-tolylsulfonyloxy, and trifluoromethylsulfonyloxy. The reaction is usually carried out in the presence of a base, such as triethylamine, ethyldiisopropylamine, 1,8-diazabicyclo[5.4.0]undecene, carbonates, e.g. Li$_2$CO$_3$, Na$_2$CO$_3$, K$_2$CO$_3$, and Cs$_2$CO$_3$, hydroxides, e.g. LiOH, NaOH, and KOH, alcoholates, e.g. NaOMe, NaOEt, and KOtBu, hydrides, e.g. NaH and KH, amides, e.g. NaNH$_2$, KN(SiMe$_3$)$_2$, and LiN(iPr)$_2$, and oxides, e.g. CaO and Ag$_2$O. Additives, such as silver salts, e.g. AgNO$_3$, AgOSO$_2$CF$_3$, and Ag$_2$CO$_3$, crown ethers, e.g. 12-crown-4, 15-crown-5, and 18-crown-6, hexamethylphosphorus triamide (HMPT), and 1,3-dimethyl-3,4,5,6-dihydro-2-pyrimidinone (DMPU), may be beneficial or even essential for the reaction to proceed. Preferred solvents are dimethylsulfoxide, N,N-dimethylformamide, N,N-dimethylacetamide, N-methylpyrrolidinone, acetonitrile, acetone, 1,4-dioxane, tetrahydrofuran, alcohol, e.g. ethanol or isopropanol, water, or mixtures thereof, while not all of the solvents can be combined with each additive and base mentioned above. Suited reaction temperatures range from −20 to 140° C.

Scheme 2a: Preparation of Precursor 1a

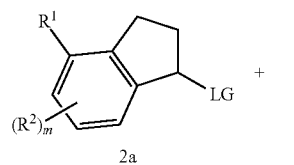

2a

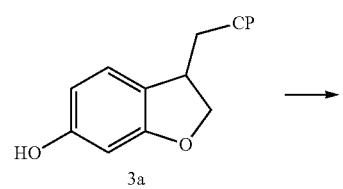

3a

-continued

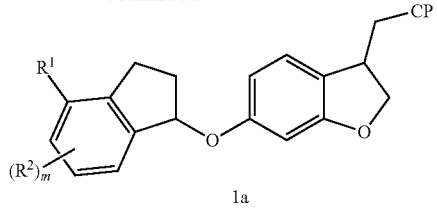

1a

LG = leaving group, e.g., Cl, Br, I, OSO$_2$Me, OSO$_2$Ph, OSO$_2$Tol, OSO$_2$CF$_3$
CP = masked or protected form of COOH, e.g., CO$_2$C$_{1-4}$-alkyl, CO$_2$CH$_2$aryl, CON(C$_{1-4}$-alkyl)$_2$, CN, CH═CH$_2$, thiazol-2-yl, oxazol-2-yl An alternative reaction to combine building blocks 2a and 3a is the Mitsunobu reaction or variations thereof (Scheme 3a); R$^1$, R$^2$, and m in Scheme 3a have the meanings as defined hereinbefore and hereinafter. The reaction is usually conducted with a phosphine and an azodicarboxylic ester or amide in tetrahydrofuran, 1,4-dioxane, diethyl ether, toluene, benzene, dichloromethane, or mixtures thereof, at −30 to 100° C. Phosphines often used are triphenylphosphine and tributylphosphine which are commonly combined with dimethyl azodicarboxylate, diethyl azodicarboxylate, diisopropyl azodicarboxylate, di-(4-chlorobenzyl)azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

Scheme 3a: Mitsunobu Reaction to Access Precursor 1a

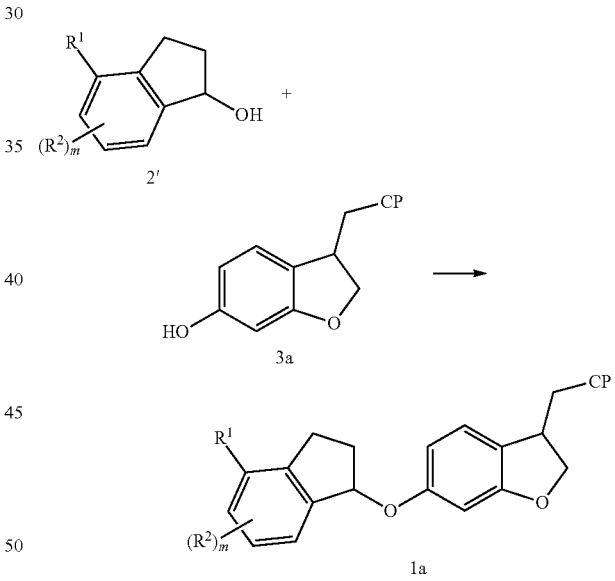

1a

CP = masked or protected form of COOH, e.g., CO$_2$C$_{1-4}$-alkyl, CO$_2$CH$_2$aryl, CON(C$_{1-4}$-alkyl)$_2$, CN, CH═CH$_2$, thiazol-2-yl, oxazol-2-yl Intermediate 2' is conveniently obtained from indanone 4a which, in turn, may be prepared from phenylpropionic acid derivative 5a (Scheme 4a); R$^1$, R$^2$, and m in Scheme 4a have the meanings as defined hereinbefore and hereinafter. For the intramolecular acylation (Friedel-Crafts acylation), 5a→4a, a considerable number of approaches has been reported. The reaction may be performed starting with a carboxylic acid, carboxylic ester, carboxylic anhydride, carboxylic chloride or fluoride, or a nitrile using a Lewis acid as catalyst. The following Lewis acids are some of the more often used ones: hydrobromic acid, hydroiodic acid, hydrochloric acid, sulfuric acid, phosphoric acid, P$_4$O$_{10}$, trifluoroacetic acid, methanesulfonic acid, toluenesulfonic acid, trifluoromethanesulfonic acid, $ClSO_3H$, $Sc(OSO_2CF_3)_3$, $Tb(OSO_2CF_3)_3$, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid at 0 to 120° C., while carboxylic chlorides are preferably reacted with $AlCl_3$ in dichloromethane or 1,2-dichloroethane at 0 to 80° C.

The subsequent reduction of the keto group in Scheme 4a is a standard transformation in organic synthesis, which may be accomplished with lithium borohydride, sodium borohydride, lithium aluminum hydride, or diisobutylaluminum hydride. While sodium borohydride is employed in aqueous or alcoholic solution at 0 to 60° C., the other reducing agents mentioned are preferably used in inert solvents, such as tetrahydrofuran, diethyl ether, dichloromethane, and toluene, at −80 to 60° C. The reduction of the keto group may also be conducted in a stereoselective fashion providing the alcohol in enantiomerically enriched or pure form. Suited chiral reducing agents are boranes combined with an enantiomerically pure [1,3,2]oxazaborol (Corey-Bakshi-Shibata reaction or Corey-Itsuno reaction) or formic acid, formates, hydrogen, or silanes in the presence of an enantiomerically pure transition metal catalyst. Typical reaction conditions for the former approach are borane (complexed with, e.g., dimethyl sulfide) and (R)- or (S)-3,3-diphenyl-1-methyltetrahydro-1H,3H-pyrrolo[1,2-c][1,3,2]oxazaborol in, e.g., dichloromethane, toluene, methanol, tetrahydrofuran, or mixtures thereof, at 0 to 60° C. Using a chiral transition metal catalyst, such as a ruthenium complex, e.g. chloro{[(1S,2S)-(+2-amino-1,2-diphenylethyl](4-toluenesulfonyl)-amido}-mesitylene)ruthenium(II), may deliver the hydroxy compound with high enantiomeric excess using, e.g., formic acid in the presence of a base, e.g. triethylamine, in dichloromethane, at −20 to 60° C.

Scheme 4a: Preparation of Intermediate 2'

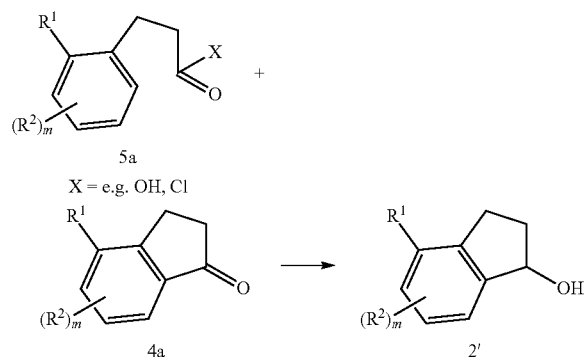

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I or I.I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I or I.I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I or I.I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

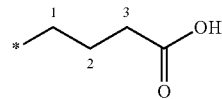

wherein the carboxy group is attached to the third carbon atom of the propyl group. The terms "1-methylpropyl-", "2,2-dimethylpropyl-" or "cyclopropylmethyl-" group represent the following groups:

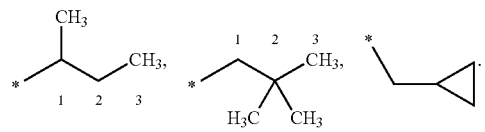

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo-, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making pharmaceutically acceptable acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)- and —C(CH$_3$)(CH$_2$CH$_3$)—.

The term "C$_{2-n}$-alkenyl", is used for a group as defined in the definition for "C$_{1-n}$-alkyl" with at least two carbon atoms, if at least two of those carbon atoms of said group are bonded to each other by a double bond. For example the term C$_{2-3}$-alkenyl includes —CH═CH$_2$, —CH═CH—CH$_3$, —CH$_2$—CH═CH$_2$.

The term "C$_{2-n}$-alkenylene" is used for a group as defined in the definition for "C$_{1-n}$-alkylene" with at least two carbon atoms, if at least two of those carbon atoms of said group are bonded to each other by a double bond. For example the term C$_{2-3}$-alkenylene includes —CH═CH—, —CH═CH—CH$_2$—, —CH$_2$—CH═CH—.

The term "C$_{2-n}$-alkynyl", is used for a group as defined in the definition for "C$_{1-n}$-alkyl" with at least two carbon atoms, if at least two of those carbon atoms of said group are bonded to each other by a triple bond. For example the term C$_{2-3}$-alkynyl includes —C≡CH, —C≡C—CH$_3$, —CH$_2$—C≡CH.

The term "C$_{2-n}$-alkynylene" is used for a group as defined in the definition for "C$_{1-n}$-alkynylene" with at least two carbon atoms, if at least two of those carbon atoms of said group are bonded to each other by a triple bond. For example the term C$_{2-3}$-alkynylene includes —C≡C—, —C≡C—CH$_2$—, —CH$_2$—C≡C—.

The term "C$_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term C$_{3-10}$-carbocyclyl includes C$_{3-10}$-cycloalkyl, C$_{3-10}$-cycloalkenyl, octahydropentalenyl, octahydroindenyl, decahydronaphthyl, indanyl, tetrahydronaphthyl. Most preferably the term C$_{3-n}$-carbocyclyl denotes C$_{3-n}$-cycloalkyl, in particular C$_{3-7}$-cycloalkyl.

The term "C$_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "C$_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term C$_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, unless specified otherwise, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl", unless specified otherwise, means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

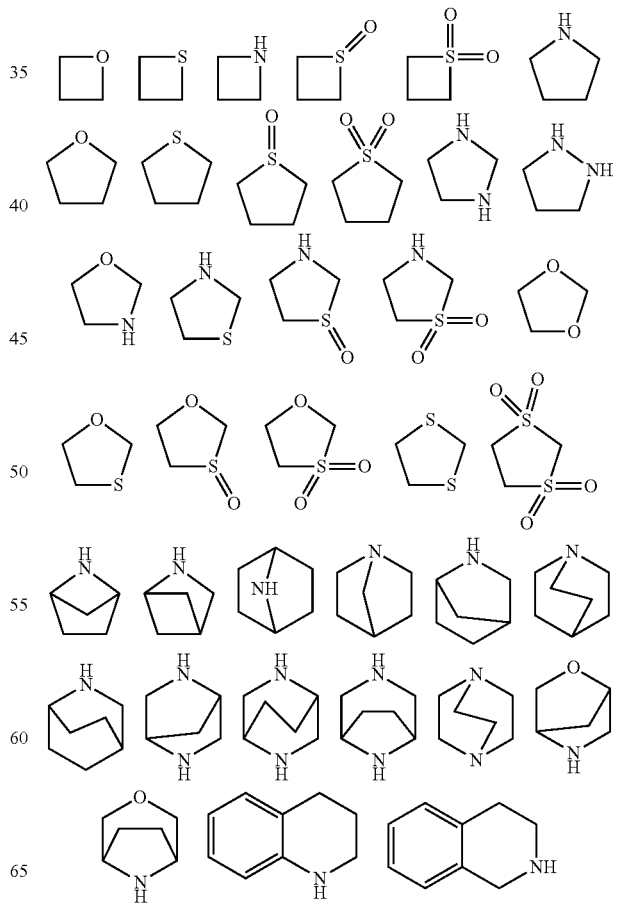

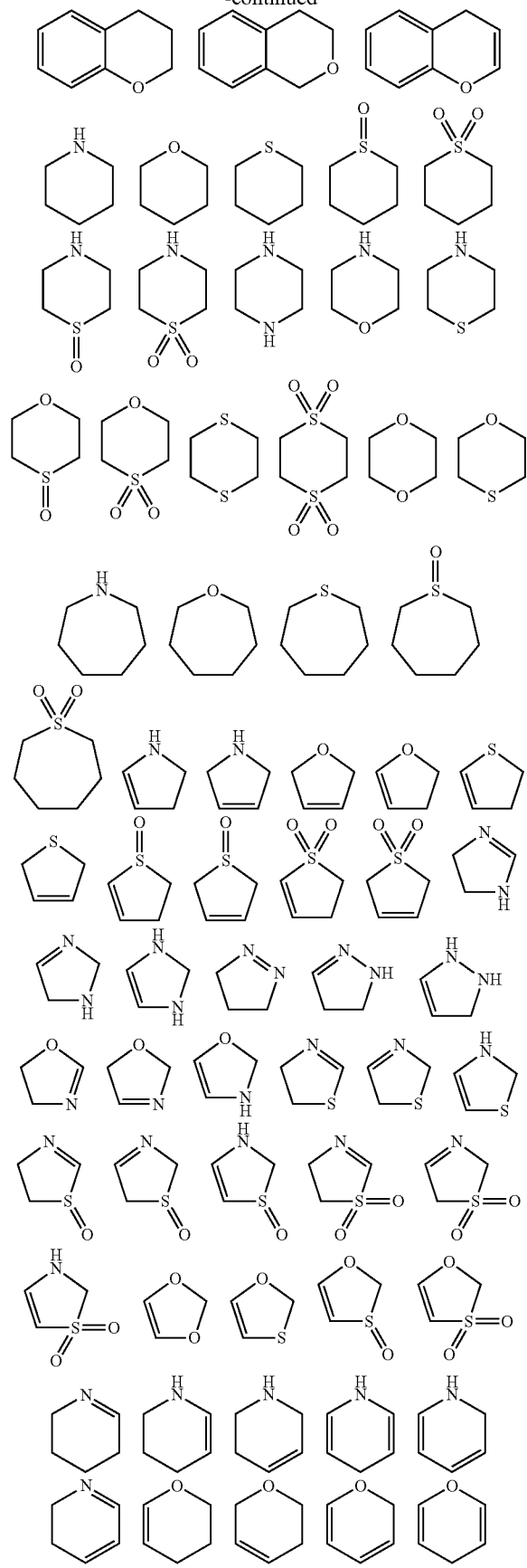
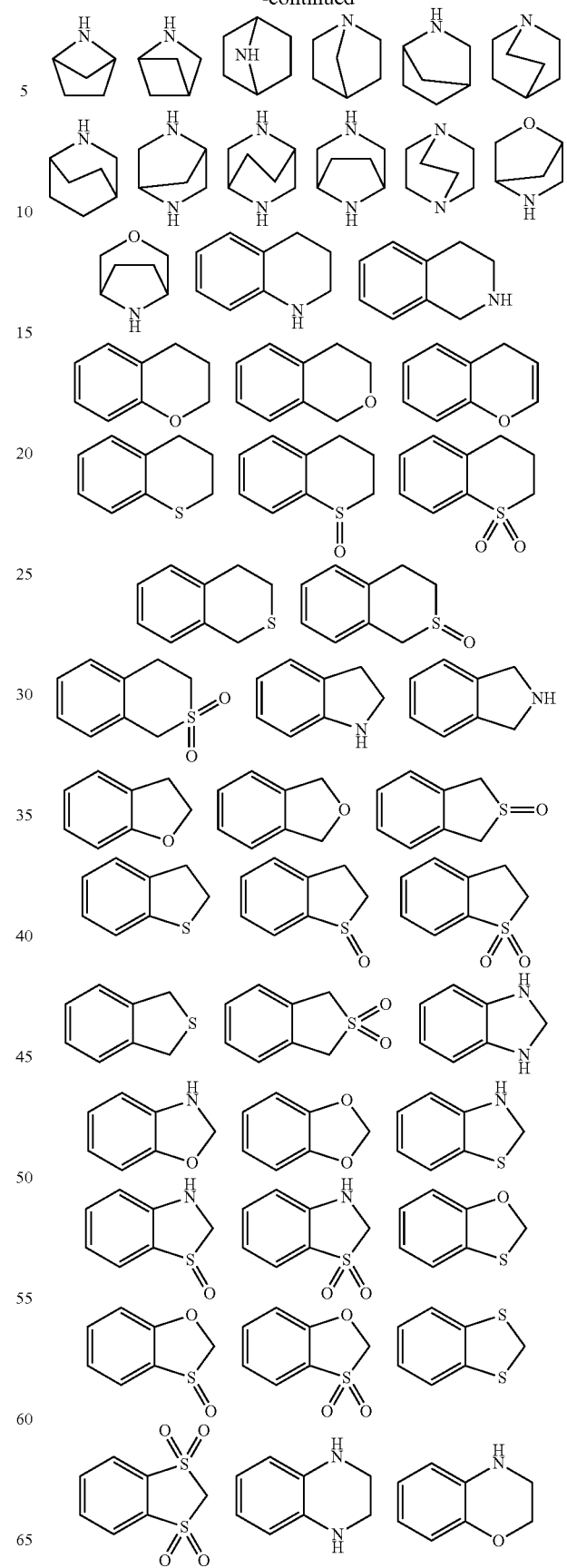

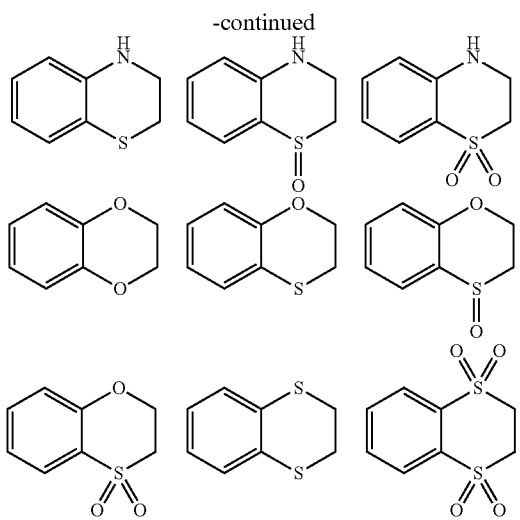

The term "heteroaryl", unless specified otherwise, means a mono- or polycyclic, preferably mono- or bicyclic-ring system containing one or more heteroatoms selected from N, O or $S(O)_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or $S(O)_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

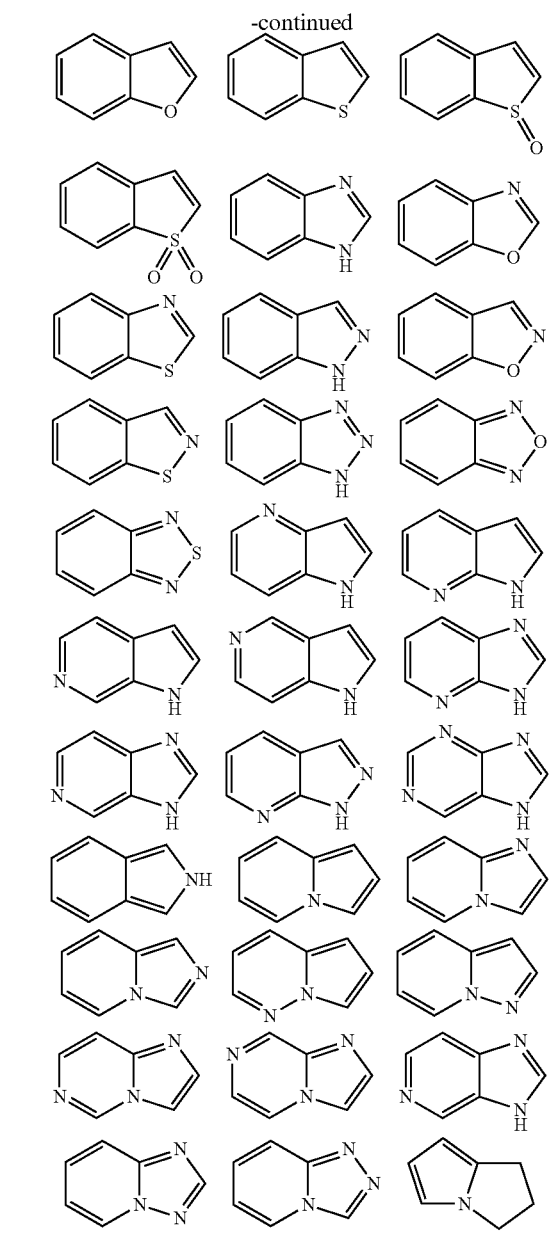

Many of the terms given above may be used repeatedly in the definition of a formula or group and in each case have one of the meanings given above, independently of one another.

Pharmacological Activity

The activity of the compounds of the invention may be demonstrated using the following assays:

Assay I:

$IP_1$ accumulation measurements using the IPOne assay system—1321N1 cells stably expressing human GPR40 receptor (Euroscreen, Belgium) are seeded 24 h before the assay in black clear-bottom collagen-coated 384-well plates in culture medium containing 10% FCS, 1% Na-Pyruvate and 400 μg/mL G418. $IP_1$ is assayed according to the Manufacturers description (Cisbio Bioassays, France). In brief, the assay is started by substitution of the culture medium by stimulation buffer (Hepes 10 mM, $CaCl_2$ 1 mM, $MgCl_2$ 0.5 mM, KCl 4.2 mM, NaCl 146 mM and glucose 5.5 mM, pH 7.4) without LiCl. Cells are stimulated for 1 hour at 37° C., 10% $CO_2$ by addition of the compounds that are diluted in stimulation buffer containing LiCl yielding a final LiCl concentration of 50 mM. Assays are stopped by adding HTRF-conjugates (IP1-d2 and Anti-IP1 cryptate Tb) and lysis buffer, provided by the manufacturer. After an incubation time of 1 hour at room temperature plates are measured using an EnVision™, Perkin Elmer. The obtained fluorescence ratios at 665/615 nM are then used to calculate the pEC$_{50}$ values using GraphPad Prism 5 (Graphpad Software Inc, USA) by interpolation using an IP$_1$ reference curve and subsequent sigmoidal curve fitting allowing for a variable hill slope.

The compounds according to the invention typically have EC$_{50}$ values in the range from about 1 nM to about 10 μM, preferably less than 1 μM, more preferably less than 100 nM.

EC$_{50}$ values for compounds according to the invention determined in Assay I are shown in the following table. The number of the compound corresponds to the number of the Example in the experimental section.

| Example | EC$_{50}$ [nM] | Example | EC$_{50}$ [nM] | Example | EC$_{50}$ [nM] | Example | EC$_{50}$ [nM] |
|---|---|---|---|---|---|---|---|
| 1 | 4 | 2 | 5 | 3 | 6 | 4 | 5 |
| 5 | 19 | 6 | 22 | 7 | 6 | 8 | 4 |
| 9 | 9 | 10 | 9 | 11 | 5 | 12 | 12 |
| 13 | 63 | 14 | 14 | 15 | 5 | 16 | 5 |
| 17 | 4 | 18 | 4 | 19 | 3 | 20 | 9 |
| 21 | 9 | 22 | 17 | 23 | 10 | 24 | 3 |
| 25 | 35 | 26 | 17 | 27 | 9 | 28 | 6 |
| 29 | 11 | 30 | 7 | 31 | 17 | 32 | 26 |
| 33 | 12 | 34 | 11 | 35 | 57 | 38 | 76 |
| 39 | 8 | 53 | 1223 | 57 | 26 | 58 | 58 |
| 59 | 117 | 60 | 26 | 61 | 51 | 62 | 11 |
| 63 | 38 | 65 | 34 | 147 | 2 | 151 | 3 |

Assay II:

IP$_1$ accumulation measurements using the IPOne assay system—1321N1 cells stably expressing human GPR40 receptor (Euroscreen, Belgium) are seeded 24 h before the assay in white 384-well plates in culture medium containing 10% FCS, 1% Na-Pyruvate and 400 μg/mL G418. IP$_1$ is assayed according to the manufacturers description (Cisbio Bioassays, France). In brief, the assay is started by substitution of the culture medium by stimulation buffer (Hepes 10 mM, CaCl$_2$ 1 mM, MgCl$_2$ 0.5 mM, KCl 4.2 mM, NaCl 146 mM, glucose 5.5 mM and LiCl 50 mM, pH 7.4). Cells are stimulated for 1 h at 37° C., 5% CO$_2$ by addition of the compounds that are diluted in stimulation buffer containing LiCl. Assays are stopped by adding HTRF-conjugates (IP1-d2 and Anti-IP1 cryptate Tb) and lysis buffer, provided by the manufacturer. After an incubation time of 1 h at room temperature plates are measured using an EnVision™, Perkin Elmer. The obtained fluorescence ratios at 665/615 nM are then used to calculate the pEC$_{50}$ values using Assay Explorer 3.3 Software (Accelrys, Inc.) by interpolation using an IP$_1$ reference curve and subsequent sigmoidal curve fitting allowing for a variable hill slope.

The compounds according to the invention typically have EC$_{50}$ values in the range from about 1 nM to about 10 μM, preferably less than 1 μM, more preferably less than 100 nM.

EC$_{50}$ values for compounds according to the invention determined in Assay II are shown in the following table. The number of the compound corresponds to the number of the Example in the experimental section.

| Example | EC$_{50}$ [nM] | Example | EC$_{50}$ [nM] | Example | EC$_{50}$ [nM] | Example | EC$_{50}$ [nM] |
|---|---|---|---|---|---|---|---|
| 36 | 8 | 37 | 6 | 40 | 13 | 41 | 18 |
| 42 | 11 | 43 | 22 | 44 | 17 | 45 | 9 |
| 46 | 7 | 47 | 8 | 48 | 14 | 49 | 10 |
| 50 | 20 | 51 | 7 | 54 | 13 | 55 | 25 |
| 56 | 43 | 64 | 8 | 66 | 5 | 67 | 7 |
| 68 | 10 | 69 | 8 | 70 | 60 | 71 | 28 |
| 72 | 23 | 73 | 13 | 74 | 40 | 75 | 17 |
| 76 | 27 | 77 | 10 | 78 | 4 | 79 | 5 |
| 80 | 11 | 81 | 8 | 82 | 14 | 83 | 6 |
| 84 | 9 | 85 | 7 | 86 | 8 | 87 | 24 |
| 88 | 3 | 89 | 9 | 90 | 5 | 91 | 3 |
| 92 | 5 | 93 | 4 | 94 | 82 | 95 | 3 |
| 96 | 20 | 97 | 5 | 98 | 3 | 99 | 4 |
| 100 | 58 | 101 | 3 | 102 | 2239 | 103 | 1429 |
| 104 | 7 | 105 | 582 | 106 | 59 | 107 | 4 |
| 108 | >10000 | 109 | 8 | 110 | 351 | 111 | 4 |
| 112 | 5 | 113 | 1 | 114 | 2 | 115 | 2 |
| 116 | 3 | 117 | 2 | 118 | 2 | 119 | 1 |
| 120 | 2 | 121 | 2 | 122 | 2 | 123 | 7 |
| 124 | 339 | 125 | 4 | 126 | 6 | 127 | 48 |
| 128 | 288 | 129 | 4 | 130 | 5 | 131 | 2 |
| 132 | 2 | 133 | 2 | 134 | 3 | 135 | 7 |
| 136 | 3 | 137 | 2 | 138 | 9 | 139 | 2 |
| 140 | 2 | 141 | 3 | 142 | 16 | 143 | 3 |
| 144 | 17 | 145 | 15 | 146 | 7 | 148 | 13 |
| 149 | 12 | 150 | 6 | 152 | 19 | | |

In view of their ability to modulate the activity of the G-protein-coupled receptor GPR40, in particular an agonistic activity, the compounds of general formula I and I.I according to the invention, including the corresponding salts thereof, are theoretically suitable for the treatment of all those diseases or conditions which may be affected or which are mediated by the activation of the G-protein-coupled receptor GPR40.

Accordingly, the present invention relates to a compound of general formula I or I.I as a medicament.

Furthermore, the present invention relates to the use of a compound of general formula I or I.I or a pharmaceutical composition according to this invention for the treatment and/or prevention of diseases or conditions which are mediated by the activation of the G-protein-coupled receptor GPR40 in a patient, preferably in a human.

In yet another aspect the present invention relates to a method for treating a disease or condition mediated by the activation of the G-protein-coupled receptor GPR40 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR40 embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and I.I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and I.I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

- for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);
- for improving glycaemic control and/or reducing fasting plasma glucose, postprandial plasma glucose and/or the glycosylated haemoglobin HbA1c;
- for preventing, delaying, slowing or reversing the progression of disrupted glucose tolerance, insulin resistance and/or metabolic syndrome to type 2 diabetes;
- for preventing, delaying, slowing the progression of or treating a condition or a disease selected from among the complications of diabetes, such as for example retinopathy, nephropathy or neuropathies, diabetic foot, ulcers or macroangiopathies;
- for reducing weight or preventing weight gain or assisting weight loss;
- for preventing or treating the degradation of pancreatic beta cells and/or improving and/or restoring the functionality of pancreatic beta cells and/or restoring the functionality of pancreatic insulin secretion;
- for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I or I.I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I or I.I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I or I.I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I or I.I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g.

inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR40, in particular diseases or conditions as described hereinbefore and hereinafter.

In yet another aspect the present invention relates a method for treating a disease or condition mediated by the activation of the G-protein-coupled receptor GPR40 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The terms "ambient temperature" and "room temperature" are used interchangeably and designate a temperature of about 20° C.

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

Analytical HPLC Parameters Employed for Characterization of Products (TFA Denotes Trifluoroacetic Acid):

| Method: | 1 |
|---|---|
| Device: | Agilent 1200 with DA and MS detector |
| Column: | XBridgeC18, 3 × 30 mm, 2.5 μm |
| Column Supplier: | Waters |

| Gradient/Solvent Time [min] | % Solvent [H$_2$O, 0.1% TFA] | % Solvent [Methanol] | Flow [mL/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method: | 4 |
|---|---|
| Device: | Agilent 1100 with DA and MS detector |
| Column: | XBridge C18, 4.6 × 30 mm, 3.5 μm |
| Column Supplier: | Waters |

| Gradient/Solvent Time [min] | % Solvent [H$_2$O, 0.1% HCOOH] | % Solvent [Methanol] | Flow [mL/min] | Temperature [° C.] |
|---|---|---|---|---|
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

-continued

|  | Method: | 7 |  |  |
|---|---|---|---|---|
|  | Device: | Agilent 1200 with DA and MS detector |  |  |
|  | Column: | XBridge C18, 3 × 30 mm, 2.5 μm |  |  |
|  | Column Supplier: | Waters |  |  |

| Gradient/Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

|  | Method: | 8 |  |  |
|---|---|---|---|---|
|  | Device: | Agilent 1200 with DA and MS detector |  |  |
|  | Column: | XBridge C18, 3 × 30 mm, 2.5 μm |  |  |
|  | Column Supplier: | Waters |  |  |

| Gradient/Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

|  | Method: | 9 |  |  |
|---|---|---|---|---|
|  | Device: | Agilent 1200 with DA and MS detector |  |  |
|  | Column: | XBridge C18, 3 × 30 mm, 2.5 μm |  |  |
|  | Column Supplier: | Waters |  |  |

| Gradient/Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

|  | Method: | 11 |  |  |
|---|---|---|---|---|
|  | Device: | Agilent 1200 with DA and MS detector |  |  |
|  | Column: | Sunfire, 3 × 30 mm, 2.5 μm |  |  |
|  | Column Supplier: | Waters |  |  |

| Gradient/Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

|  | Method: | 12 |  |  |
|---|---|---|---|---|
|  | Device: | Agilent 1200 with DA and MS detector |  |  |
|  | Column: | Stable Bond, 3 × 30 mm, 1.8 μm |  |  |
|  | Column Supplier: | Agilent |  |  |

| Gradient/Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

|  | Method: | 13 |  |  |
|---|---|---|---|---|
|  | Device: | Agilent 1200 with DA and MS detector |  |  |
|  | Column: | XBridge C18, 3 × 30 mm, 2.5 μm |  |  |
|  | Column Supplier: | Waters |  |  |

| Gradient/Solvent Time [min] | % Solvent [H$_2$O, 0.1% NH$_3$] | % Solvent [CH$_3$CN] | Flow [mL/min] | Temperature [° C.] |
|---|---|---|---|---|
| 0.00 | 50 | 50 | 2.2 | 60 |
| 0.20 | 50 | 50 | 2.2 | 60 |

-continued

| Gradient/Solvent Time [min] | % Solvent | % Solvent | Flow [mL/min] | Temperature [° C.] |
|---|---|---|---|---|
| 1.20 | 0 | 100 | 2.2 | 60 |
| 1.25 | 0 | 100 | 3 | 60 |
| 1.40 | 0 | 100 | 3 | 60 |

| | Method: | 14 | | |
|---|---|---|---|---|
| | Device: | Agilent 1200 with DA and MS detector | | |
| | Column: | XBridge C18, 3 × 30 mm, 2.5 μm | | |
| | Column Supplier: | Waters | | |

| Gradient/Solvent Time [min] | % Solvent [H$_2$O, 0.1% NH$_3$] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| | Method: | 15 | | |
|---|---|---|---|---|
| | Device: | Agilent 1200 with DA and MS detector | | |
| | Column: | Sunfire C18, 3 × 30 mm, 2.5 μm | | |
| | Column Supplier: | Waters | | |

| Gradient/Solvent Time [min] | % Solvent [H$_2$O, 0.1% TFA] | % Solvent [CH$_3$CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| | Method: | 17 | | |
|---|---|---|---|---|
| | Device: | LC/MS Waters Acquity UPLC System DAD, SQD single quadrupole | | |
| | Column: | BEH C18, 1.7 μm, 2.1 × 50 mm | | |

| Gradient/Solvent Time [min] | % Solvent [H$_2$O/CH$_3$CN 90:10, 5 mM NH$_4$COOH] | % Solvent [CH$_3$CN/H$_2$O 90:10] | Flow [mL/min] | Temperature [° C.] |
|---|---|---|---|---|
| 0.00 | 100 | 0 | 0.70 | 35 |
| 1.20 | 0 | 100 | 0.70 | 35 |
| 1.45 | 0 | 100 | 0.70 | 35 |
| 1.55 | 100 | 0 | 0.70 | 35 |
| 1.75 | 100 | 0 | 0.70 | 35 |

| | Method: | 19 | | |
|---|---|---|---|---|
| | Device: | LC/MS Waters Acquity UPLC System DAD, SQD single quadrupole | | |
| | Column: | BEH C18, 1.7 μm, 2.1 × 50 mm | | |

| Gradient/Solvent Time [min] | % Solvent [H$_2$O/CH$_3$CN 90:10, 5 mM NH$_4$COOH] | % Solvent [CH$_3$CN/H$_2$O 90:10] | Flow [mL/min] | Temperature [° C.] |
|---|---|---|---|---|
| 0.00 | 100 | 0 | 0.70 | 35 |
| 1.20 | 0 | 100 | 0.70 | 35 |
| 1.45 | 0 | 100 | 0.70 | 35 |
| 1.55 | 100 | 0 | 0.70 | 35 |
| 1.75 | 100 | 0 | 0.70 | 35 |

| | Method: | 20 | |
|---|---|---|---|
| | Device: | LC/MS ThermoFinnigan HPLC Surveyor DAD, MSQ single quadrupole | |
| | Column: | Synergi Hydro RP100A, 2.5 μm, 3 × 50 mm | |

| Gradient/Solvent Time [min] | % Solvent [H$_2$O/CH$_3$CN 90:10, 10 mM NH$_4$COOH] | % Solvent [CH$_3$CN/H$_2$O 90:10 10 mM NH$_4$COOH] | Flow [mL/min] |
|---|---|---|---|
| 0.00 | 100 | 0 | 0.7 |
| 1.50 | 100 | 0 | 0.7 |
| 8.00 | 0 | 100 | 0.7 |
| 10.00 | 0 | 100 | 0.7 |
| 11.00 | 100 | 0 | 0.7 |
| 12.00 | 100 | 0 | 0.7 |

-continued

| | Method: | 20A | | |
|---|---|---|---|---|
| | Device: | LC/MS ThermoFinnigan HPLC Surveyor DAD, LCQFleet Ion Trap | | |
| | Column: | Simmetry Shield RP8, 5 μm, 4.6 × 150 mm | | |

| Gradient/Solvent Time [min] | % Solvent [$H_2O/CH_3CN$ 90:10, 10 mM HCOOH] | % Solvent [$CH_3CN/H_2O$ 90:10, 10 mM HCOOH] | Flow [mL/min] |
|---|---|---|---|
| 0.00 | 70 | 30 | 8.50 |
| 1.50 | 50 | 50 | 8.50 |
| 8.50 | 0 | 100 | 8.50 |
| 13.05 | 0 | 100 | 8.50 |
| 14.00 | 70 | 30 | 8.50 |
| 15 | 70 | 30 | 8.50 |

| | Method: | 21 | | |
|---|---|---|---|---|
| | Device: | LC/MS ThermoFinnigan HPLC Surveyor DAD, LCQFleet Ion Trap | | |
| | Column: | Symmetry Shield RP8, 5 μm, 4.6 × 150 mm | | |

| Gradient/Solvent Time [min] | % Solvent [$H_2O/CH_3CN$ 90:10, 0.1% HCOOH] | % Solvent [$CH_3CN/H_2O$ 90:10, 0.1% HCOOH] | Flow [mL/min] |
|---|---|---|---|
| 0.00 | 95 | 5 | 1 |
| 1.50 | 95 | 5 | 1 |
| 11.05 | 5 | 95 | 1 |
| 13 | 5 | 95 | 1 |
| 13.03 | 95 | 5 | 1 |
| 15 | 95 | 5 | 1 |

| | Method: | 23 | | |
|---|---|---|---|---|
| | Device: | Waters 1525 with DA and MS Detector | | |
| | Column: | Sunfire C18, 4.6 × 30 mm, 2.5 μm | | |
| | Column Supplier: | Waters | | |

| Gradient/Solvent Time [min] | % Solvent [$H_2O$, 0.1% TFA] | % Solvent [$CH_3CN$] | Flow [ml/min] | Temperature [° C.] |
|---|---|---|---|---|
| 0.0 | 97 | 3 | 4 | 60 |
| 0.15 | 97 | 3 | 3 | 60 |
| 2.15 | 0 | 100 | 3.0 | 60 |
| 2.20 | 0 | 100 | 4.5 | 60 |
| 2.40 | 0 | 100 | 4.5 | 60 |

| | Method: | 25 | | |
|---|---|---|---|---|
| | Device: | LC/MS Waters Acquity UPLC System DAD, SQD single quadrupole | | |
| | Column: | HSS C18, 1.8 μm, 2.1 × 50 mm | | |

| Gradient/Solvent Time [min] | % Solvent [$H_2O/CH_3CN$ 90:10, 0.1% TFA] | % Solvent [$CH_3CN/H_2O$ 90:10] | Flow [ml/min] | Temperature [° C.] |
|---|---|---|---|---|
| 0.00 | 100 | 0 | 0.70 | 35 |
| 1.20 | 0 | 100 | 0.70 | 35 |
| 1.45 | 0 | 100 | 0.70 | 35 |
| 1.55 | 100 | 0 | 0.70 | 35 |
| 1.75 | 100 | 0 | 0.70 | 35 |

| | Method: | 26 | | |
|---|---|---|---|---|
| | Device: | Agilent 1200 with DA and MS detector | | |
| | Column: | XBridge C18, 3 × 30 mm, 2.5 μm | | |
| | Column Supplier: | Waters | | |

| Gradient/Solvent Time [min] | % Solvent [$H_2O$, 0.1% TFA] | % Solvent [$CH_3CN$] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

Analytical Chiral HPLC Parameters Employed for Characterization of Products

| Method: | 1a | | | |
|---|---|---|---|---|
| Device: | Agilent 1100 with DAD | | | |
| Column: | Daicel Chiralcel OJ-H | | | |
| Solvent Time[min] | % Solvent [Hexane] | % Solvent [Ethanol] | Flow [mL/min] | Temperature [° C.] |
| isocratic | 70 | 30 | 1.0 | 25 |

The Examples that follow are intended to illustrate the present invention without restricting it:

Intermediate 1

Methyl 2-((S)-6-((R)-4-(2,6-dimethyl-4-((3-methyloxetan-3-yl)methoxy)phenyl)-7-fluoro-2,3-dihydro-1H-inden-1-yloxy)-2,3-dihydrobenzofuran-3-yl)acetate

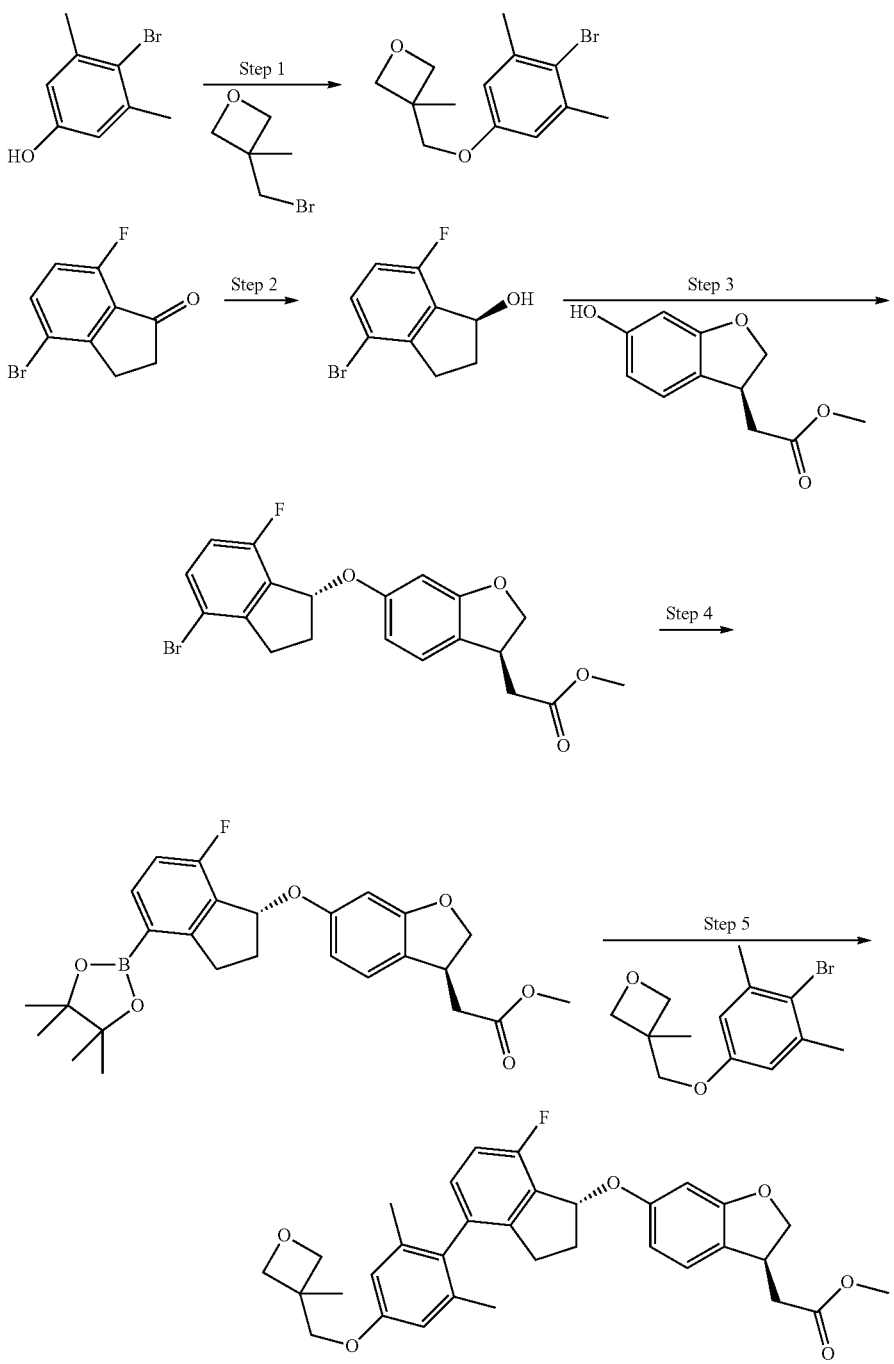

Step 1: 3-((4-Bromo-3,5-dimethylphenoxy)methyl)-3-methyloxetane

To a solution of 4-bromo-3,5-dimethylphenol (3.0 g) and K₂CO₃ (5.5 g) in N,N-dimethylformamide (10 mL) is added 3-(bromomethyl)-3-methyloxetane (2.95 g). The mixture is stirred for 12 hours at room temperature and then partitioned between saturated aqueous NaHCO₃ solution and ethyl acetate. The aqueous phase is extracted with ethyl acetate and the combined organic phases are dried (MgSO₄). The solvent is evaporated and the residue is chromatographed on silica gel (cyclohexane/ethyl acetate 100:0→70:30) to give the title compound. Yield: 3.5 g; LC (method 4): t_R=1.81 min; Mass spectrum (ESI⁺): m/z=285 [M+H]⁺.

Step 2: (S)-4-Bromo-7-fluoro-2,3-dihydro-1H-inden-1-ol

Formic acid (8 mL) is added to a solution of triethylamine (25.6 mL) in dichloromethane (150 mL) chilled in an ice bath. 4-Bromo-7-fluoro-2,3-dihydro-1H-inden-1-one (14 g) is added and the flask is purged with argon for 5 minutes. Chloro{[(1S,2S)-(+2-amino-1,2-diphenylethyl](4-toluenesulfonyl)amido}-(mesitylene)ruthenium(II) (850 mg; alternatively, the catalyst is formed in situ from N-[(1S,2S)-2-amino-1,2-diphenylethyl]-4-methylbenzenesulfonamide and dichloro(p-cymene)-ruthenium(II) dimer) is added and the mixture is stirred at room temperature for 16 hours. Water is added and the resulting mixture is extracted with dichloromethane. The combined extract is washed with saturated aqueous NaHCO₃ solution and dried (MgSO₄). The solvent is evaporated and the residue is chromatographed on silica gel (cyclohexane/ethyl acetate 90:10→60:40) to give the title compound. Yield: 11.95 g; LC (method 1): t_R=1.04 min; Mass spectrum (ESI⁺): m/z=213 [M+H—H₂O]⁺.

Step 3: Methyl 2-((S)-6-((R)-4-bromo-7-fluoro-2,3-dihydro-1H-inden-1-yloxy)-2,3-dihydrobenzofuran-3-yl)acetate A solution of di-tert.-butyl azodicarboxylate (18 g) in tetrahydrofuran (80 mL) is added dropwise over 45 minutes to a solution of (S)-methyl 2-(6-hydroxy-2,3-dihydrobenzofuran-3-yl)acetate (11 g), (S)-4-bromo-7-fluoro-2,3-dihydro-1H-inden-1-ol (11.95 g) and tributylphosphine (19.3 mL) in tetrahydrofuran (320 mL) at −10° C. The resulting solution is stirred for 30 minutes and then partitioned between saturated aqueous NaHCO₃ solution and dichloromethane. The aqueous phase is extracted with dichloromethane. The combined organic phases are dried (MgSO₄) and concentrated. The residue is chromatographed on silica gel (cyclohexane/ethyl acetate 90:10→70:30) to give the title compound. Yield: 10.35 g; LC (method 1): t_R=1.41 min; Mass spectrum (ESI⁺): m/z=421 [M+H]⁺.

Step 4: Methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate In a microwave vial methyl 2-((S)-6-((R)-4-bromo-7-fluoro-2,3-dihydro-1H-inden-1-yloxy)-2,3-dihydrobenzofuran-3-yl)acetate (7.0 g), bis-(pinacolato)-diboron (5.6 g) and potassium acetate (4.2 g) are suspended in 1,4-dioxane and purged for 10 minutes with argon. [1,1'-Bis(diphenylphosphino)-ferrocene]-dichloropalladium-(II) (600 mg) is added, the vial is sealed and the mixture is stirred at 100° C. for 4 hours. After cooling to room temperature the mixture is partitioned between diethylether and saturated aqueous NH₄Cl solution. The organic phase is dried (MgSO₄) and concentrated. The residue is chromatographed on silica gel (cyclohexane/ethyl acetate 99:1→70:30) to give the title compound. Yield: 5.85 g; LC (method 1): t_R=1.48 min; Mass spectrum (ESI⁺): m/z=469 [M+H]⁺.

Step 5: Methyl 2-((S)-6-((R)-4-(2,6-dimethyl-4-((3-methyloxetan-3-yl)methoxy)phenyl)-7-fluoro-2,3-dihydro-1H-inden-1-yloxy)-2,3-dihydrobenzofuran-3-yl)acetate In a microwave vial methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (500 mg), 3-((4-bromo-3,5-dimethylphenoxy)methyl)-3-methyloxetane (450 mg), K₃PO₄ (450 mg) are suspended in toluene (2.5 mL) and water (250 μL) and purged for 10 minutes with argon. Palladium-(II)-acetate (12 mg) and dicyclohexyl(2',6'-dimethoxybiphenyl-2-yl)phosphine (S-Phos) (44 mg) are added, the vial is sealed and the mixture is stirred at 100° C. for 4 hours. After cooling to room temperature the mixture is partitioned between diethylether and saturated aqueous NH₄Cl solution. The organic phase is dried (MgSO₄) and concentrated. The residue is chromatographed on silica gel (cyclohexane/ethyl acetate 90:10→60:40) to give the title compound. Yield: 420 mg; LC (method 4): t_R=1.93 min; Mass spectrum (ESI⁺): m/z=569 [M+Na]⁺.

Intermediate 2

Methyl 2-((3S)-6-((1R)-4-(2,6-dimethyl-4-((tetrahydrofuran-3-yl)methoxy)phenyl)-7-fluoro-2,3-dihydro-1H-inden-1-yloxy)-2,3-dihydrobenzofuran-3-yl)acetate

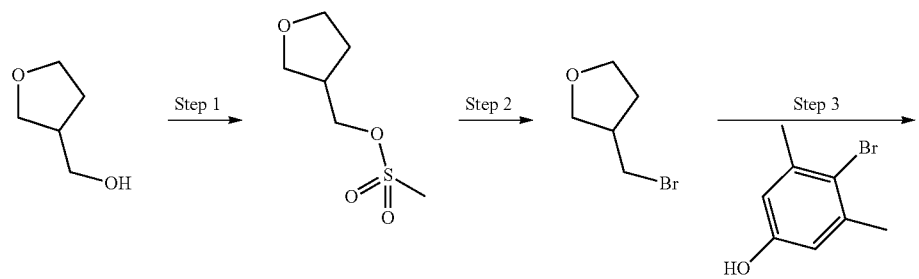

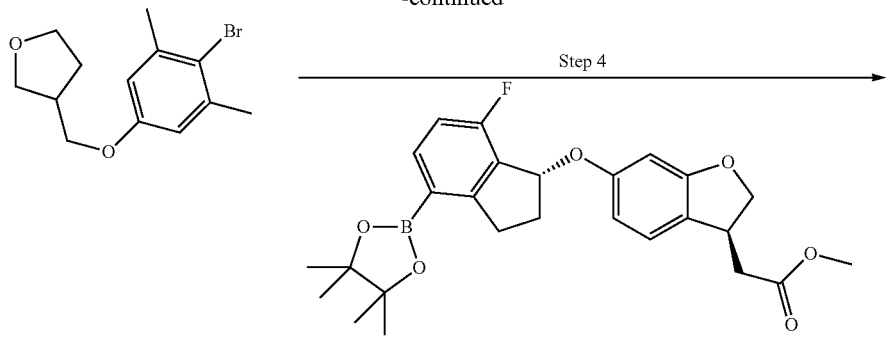

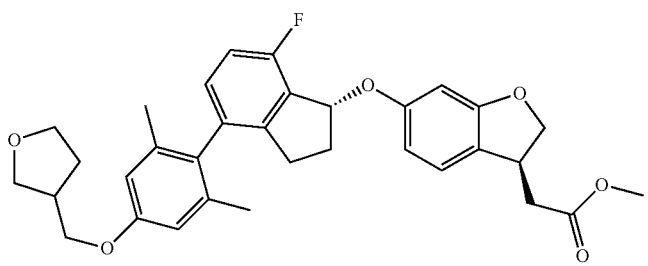

Step 1: (Tetrahydrofuran-3-yl)methyl methanesulfonate

To a cooled (0° C.) solution of (tetrahydrofuran-3-yl) methanol (3.0 mL) and triethylamine (5.7 mL) in dichloromethane (30 mL) is added methanesulfonyl chloride (3.1 mL). The mixture is stirred for 12 hours at room temperature. After cooling to 0° C. triethylamine (1.3 mL) and methanesulfonyl chloride (0.7 mL) are added and the mixture is stirred for 12 hours at room temperature. The mixture is partitioned between dichloromethane and saturated aqueous $NaHCO_3$ solution and stirred vigorously for 30 minutes. The organic phase is separated, washed with brine and dried ($MgSO_4$). The solvent is evaporated to give the title compound. Yield: 5.6 g; TLC: $r_f$=0.35 (silicagel, cyclohexane/ethyl acetate 1:1); Mass spectrum ($ESI^+$): m/z=181 $[M+H]^+$.

Step 2: 3-(Bromomethyl)tetrahydrofuran

To solution of (tetrahydrofuran-3-yl)methyl methanesulfonate (5.6 g) in acetone (80 mL) is added lithium bromide (13.6 g). The mixture is heated to reflux for 4 hours. Then the solvent is evaporated in vacuo and the residue is partitioned between dichloromethane and water. The organic phase is separated and dried ($MgSO_4$). The solvents are evaporated. The residue is dissolved in dichloromethane and filtered over a small plug of silica gel. Concentration gives the title compound. Yield: 3.9 g; TLC: $r_f$=0.80 (silicagel, cyclohexane/ethyl acetate 1:1).

Step 3: 3-((4-Bromo-3,5-dimethylphenoxy)methyl) tetrahydrofuran

To a solution of 4-bromo-3,5-dimethylphenol (1.5 g) and $K_2CO_3$ (3.2 g) in N,N-dimethylformamide (12 mL) is added 3-(bromomethyl)tetrahydrofuran (3.6 g). The mixture is stirred for 16 hours at 80° C. and then partitioned between water and ethyl acetate. The organic phase is washed with brine and dried ($MgSO_4$). The solvent is evaporated and the residue is chromatographed on silica gel (cyclohexane/ethyl acetate 99:1→70:30) to give the title compound. Yield: 1.72 g; LC (method 1): $t_R$=1.37 min; Mass spectrum ($ESI^+$): m/z=285 $[M+H]^+$.

Step 4: Methyl 2-((3S)-6-((1R)-4-(2,6-dimethyl-4-((tetrahydrofuran-3-yl)methoxy)phenyl)-7-fluoro-2,3-dihydro-1H-inden-1-yloxy)-2,3-dihydrobenzofuran-3-yl)acetate In a microwave vial methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (170 mg) and 3-((4-bromo-3,5-dimethylphenoxy)methyl)tetrahydrofuran (170 mg) and $K_3PO_4$ (290 mg) are suspended in tetrahydrofuran (10 mL). The mixture is purged for 5 minutes with argon. [1,1'-Bis(diphenylphosphino)-ferrocene]-dichloropalladium (27 mg) is added, the vial is sealed and the mixture is stirred at 100° C. for 12 hours. After cooling to room temperature the mixture is diluted with diethylether and washed with saturated aqueous $NH_4Cl$ solution. The organic phase is dried ($MgSO_4$) and concentrated. The residue is chromatographed on silica gel (cyclohexane/ethyl acetate 90:10→50:50) to give the title compound. Yield: 47 mg; LC (method 1): $t_R$=1.48 min; Mass spectrum ($ESI^+$): m/z=569 $[M+Na]^+$.

Intermediate 3

Methyl 2-((3S)-6-((1R)-4-(2,6-dimethyl-4-((tetrahydrofuran-2-yl)methoxy)phenyl)-7-fluoro-2,3-dihydro-1H-inden-1-yloxy)-2,3-dihydrobenzofuran-3-yl)acetate

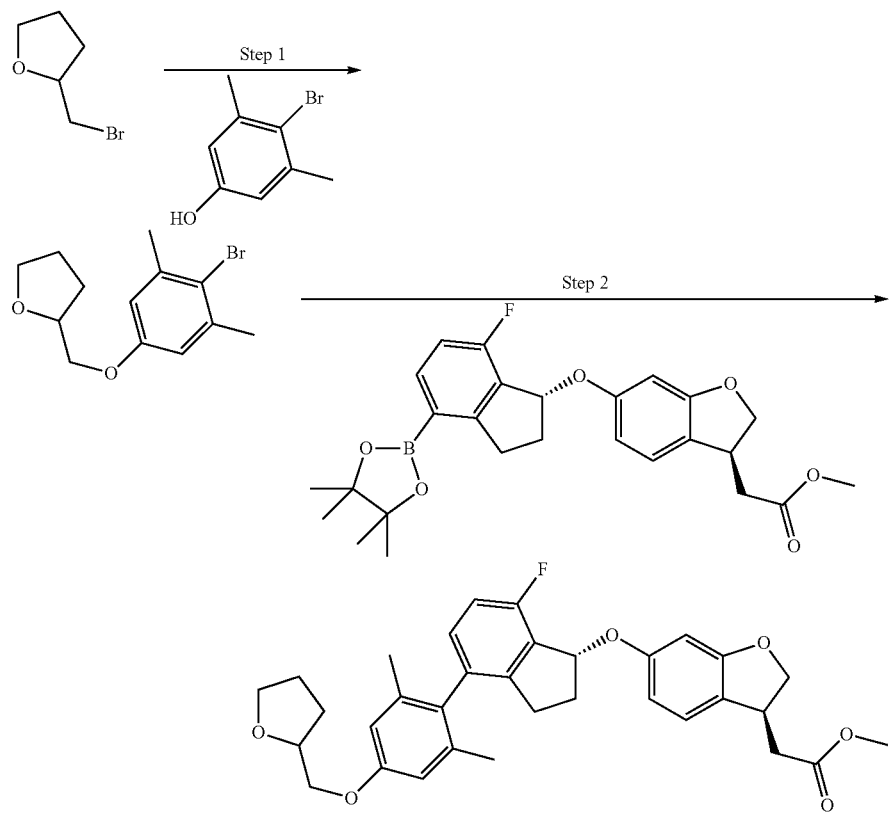

Step 1: 2-((4-Bromo-3,5-dimethylphenoxy)methyl)tetrahydrofuran

The title compound is prepared from 4-bromo-3,5-dimethylphenol and 2-(bromomethyl)tetrahydrofuran following a procedure analogous to that described in Step 3 of Intermediate 2. LC (method 1): $t_R$=1.37 min; Mass spectrum (ESI$^+$): m/z=285 [M+H]$^+$.

Step 2: Methyl 2-((3S)-6-((1R)-4-(2,6-dimethyl-4-((tetrahydrofuran-2-yl)methoxy)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 2-((4-bromo-3,5-dimethylphenoxy)methyl)tetrahydrofuran following a procedure analogous to that described in Step 5 of Intermediate 1. LC (method 1): $t_R$=1.48 min; Mass spectrum (ESI$^+$): m/z=569 [M+Na]$^+$.

Intermediate 4

4-(4-Bromo-3,5-dimethylphenoxy)-2-methylbutan-2-ol

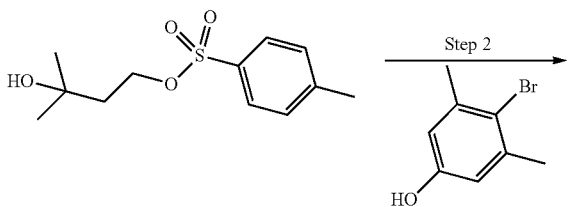

Step 1: 3-Hydroxy-3-methylbutyl 4-methylbenzenesulfonate

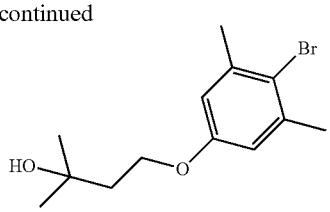

To a solution of 3-methylbutane-1,3-diol (2.5 mL) in dichloromethane (30 mL) and pyridine (2.1 mL) is added at 0° C. p-toluene-sulfonylchloride (4.6 g) in portions. The mixture is stirred for 12 hours at room temperature, diluted with dichloromethane and washed with 1 M aqueous HCl solution and brine. After drying (MgSO$_4$) the solvent is evaporated and the product is purified by chromatography on silica gel (cyclohexane/ethyl acetate 90:10→70:30) to give the title compound. Yield: 3.2 g; Mass spectrum (ESI$^+$): m/z=276 [M+NH$_4$]$^+$.

Step 2: 4-(4-Bromo-3,5-dimethylphenoxy)-2-methylbutan-2-ol

The title compound is prepared from 4-bromo-3,5-dimethylphenol and 3-hydroxy-3-methylbutyl 4-methylbenzenesulfonate following a procedure analogous to that described in Step 3 of Intermediate 2. LC (method 1): t$_R$=1.35 min; Mass spectrum (ESI$^+$): m/z=269 [M+H—H$_2$O]$^+$.

Intermediate 5

Methyl 2-((S)-6-((R)-7-fluoro-4-(4-(3-hydroxy-3-methylbutoxy)-2,6-dimethylphenyl)-2,3-dihydro-1H-inden-1-yloxy)-2,3-dihydrobenzofuran-3-yl)acetate

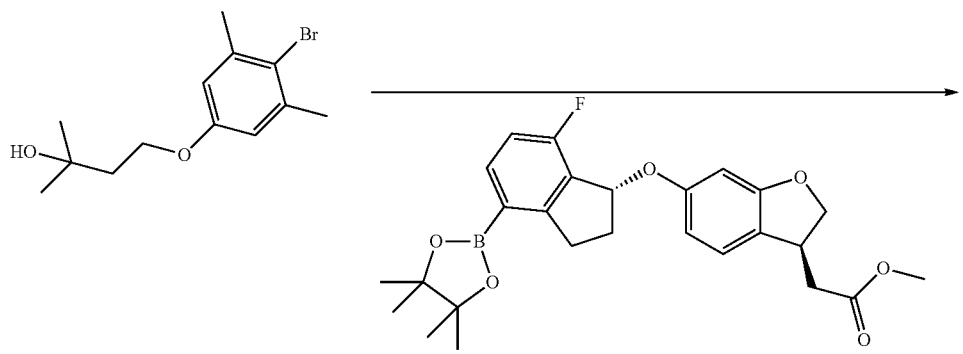

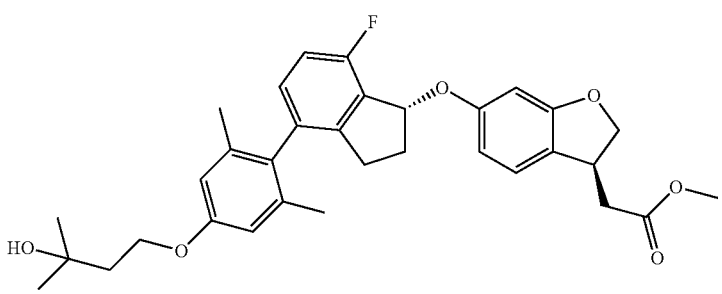

The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and 4-(4-bromo-3,5-dimethylphenoxy)-2-methylbutan-2-ol following a procedure analogous to that described in Step 5 of Intermediate 1. LC (method 4): t$_R$=1.90 min; Mass spectrum (ESI$^+$): m/z=571 [M+Na]$^+$.

Intermediate 6
Methyl 2-((3S)-6-(((1R)-4-(2,6-dimethyl-4-(2-(methylsulfinyl)ethoxy)phenyl)-7-fluoro-2,3-dihydro-1H-inden-1-yloxy)-2,3-dihydrobenzofuran-3-yl)acetate
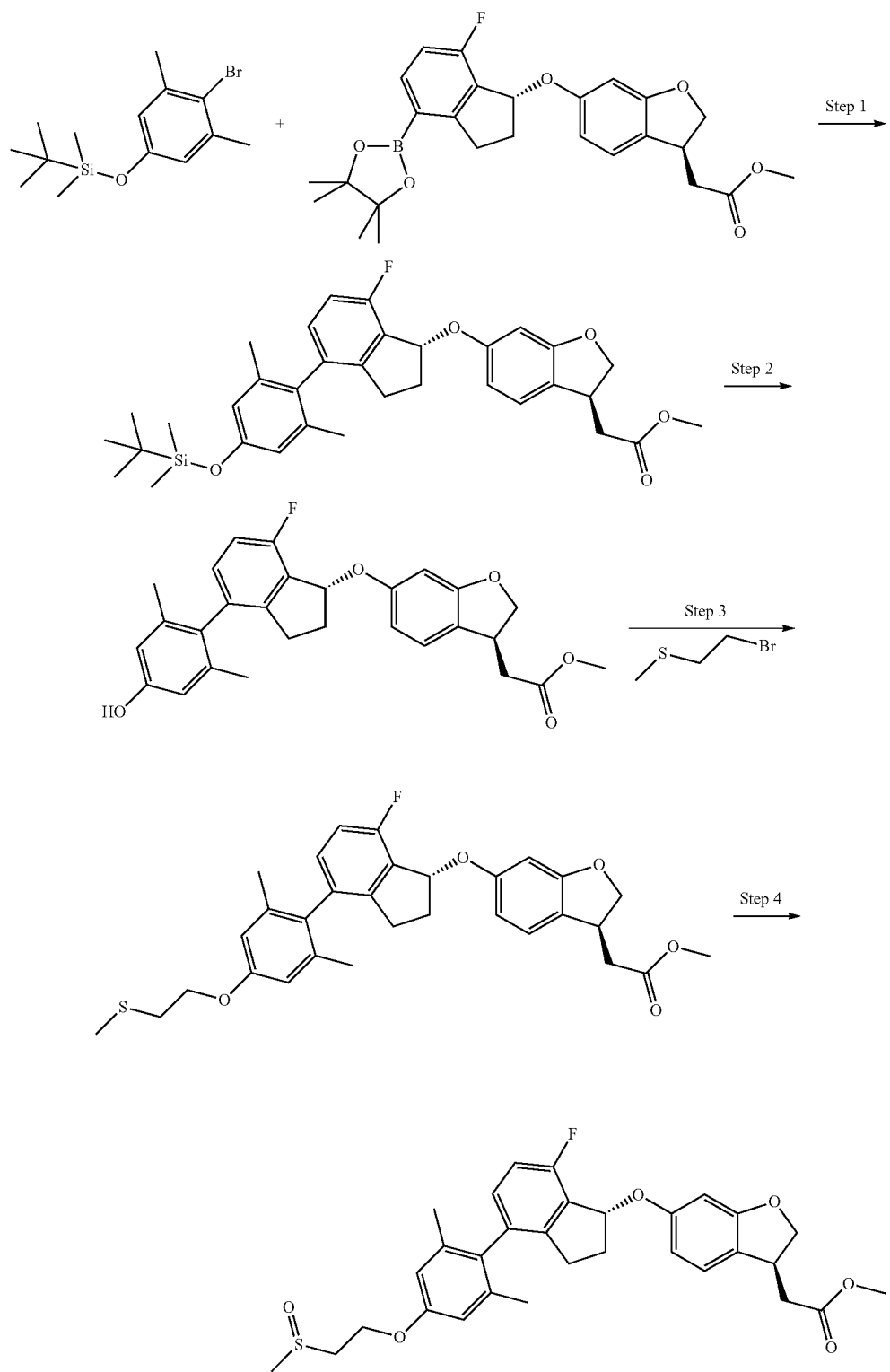

Step 1: Methyl 2-((S)-6-((R)-4-(4-(tert-butyldimethylsilyloxy)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzo-furan-3-yl)acetate and (4-bromo-3,5-dimethylphenoxy)(tert-butyl)dimethylsilane following a procedure analogous to that described in Step 5 of Intermediate 1. LC (method 4): $t_R$=2.09 min; Mass spectrum (ESI$^+$): m/z=599 [M+Na]$^+$.

Step 2: Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate To a solution of methyl 2-((S)-6-((R)-4-(4-(tert-butyldimethylsilyloxy)-2,6-dimethylphenyl)-7-fluoro-2,3-dihydro-1H-inden-1-yloxy)-2,3-dihydrobenzofuran-3-yl)acetate (440 mg) in tetrahydrofuran (5 mL) is added at 0° C. tetrabutylammonium fluoride (3.1 mL of a 1 M solution in tetrahydrofuran). The mixture is stirred for 2 hours at room temperature, diluted with diethylether and washed with water and brine. After drying (MgSO$_4$) the solvents are evaporated and the residue is chromatographed on silica gel (cyclohexane/ethyl acetate 90:10→60:40) to give the title compound. Yield: 280 mg; LC (method 4): $t_R$=1.79 min; Mass spectrum (ESI$^+$): m/z=485 [M+Na].

Step 3: Methyl 2-((S)-6-((R)-4-(2,6-dimethyl-4-(2-(methylthio)ethoxy)phenyl)-7-fluoro-2,3-dihydro-1H-inden-1-yloxy)-2,3-dihydrobenzofuran-3-yl)acetate To a solution of methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (280 mg) and 2-(methylthio)-ethanol (54 μL) in toluene (8 mL) are successively added 1,1'-(azodicarbonyl)-dipiperidine (240 mg) and tributylphosphine (240 mL). The mixture is stirred for 12 hours at room temperature, partitioned between saturated aqueous NaHCO$_3$ solution and dichloromethane and stirred for 30 minutes. The phases are separated and the organic phase is dried (MgSO$_4$). The solvents are evaporated and the residue is chromatographed on silica gel (cyclohexane/ethyl acetate 90:10→70:30) to give the title compound. Yield: 235 mg; LC (method 4): $t_R$=1.97 min; Mass spectrum (ESI$^+$): m/z=537 [M+H]$^+$.

Step 4: Methyl 2-((3S)-6-((1R)-4-(2,6-dimethyl-4-(2-(methylsulfinyl)ethoxy)phenyl)-7-fluoro-2,3-dihydro-1H-inden-1-yloxy)-2,3-dihydrobenzofuran-3-yl)acetate To a solution of methyl 2-((S)-6-((R)-4-(2,6-dimethyl-4-(2-(methylthio)ethoxy)phenyl)-7-fluoro-2,3-dihydro-1H-inden-1-yloxy)-2,3-dihydrobenzofuran-3-yl)acetate (230 mg) in methanol (4 mL) and water (2 mL) is added potassium peroxomonoslufate (Oxone®) (490 mg). The mixture is stirred for 1 hour at room temperature and then partitioned between dichloromethane and water. The organic phase is dried (MgSO$_4$) and concentrated to give the crude product, which is directly in the next step. Yield: 220 mg; LC (method 4): $t_R$=1.79 min; Mass spectrum (ESI$^+$): m/z=553 [M+H]$^+$.

Intermediate 7

Methyl 2-((S)-6-((R)-4-(2,6-dimethyl-4-(tetrahydro-2H-pyran-4-yloxy)phenyl)-7-fluoro-2,3-dihydro-1H-inden-1-yloxy)-2,3-dihydrobenzofuran-3-yl)acetate

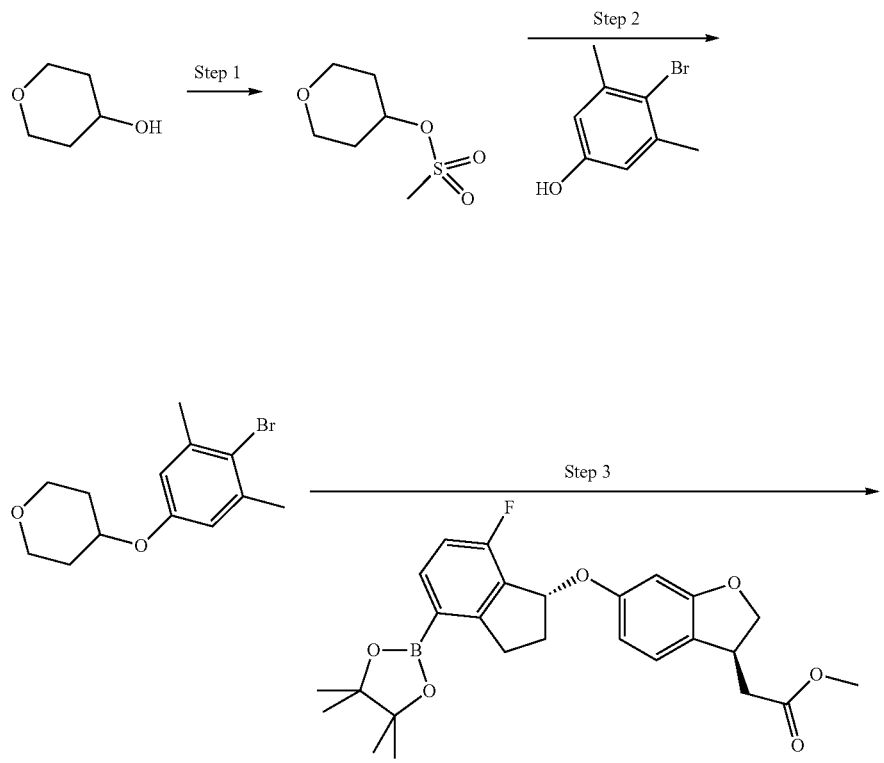

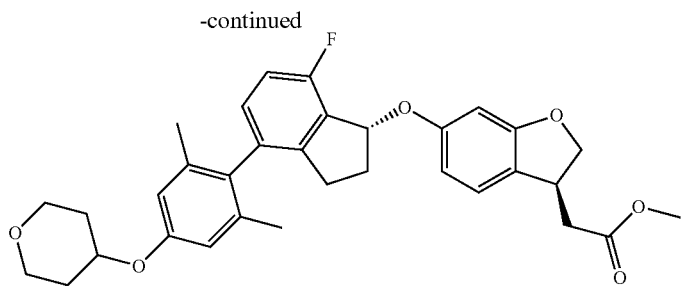

Step 1: Tetrahydro-2H-pyran-4-yl methanesulfonate

To a solution of tetrahydro-2H-pyran-4-ol (20 g) in tetrahydrofuran (150 mL) and triethylamine (28.5 mL) is slowly added methanesulfonyl chloride (15.5 mL), while keeping the temperature below 30° C. The mixture is stirred for 12 hours at room temperature. The precipitate is filtered off and washed twice with tetrahydrofuran. The combined organic phases are concentrated and partitioned between ethyl acetate and water. The organic phase is dried (Na$_2$SO$_4$) and concentrated to give the title compound. Yield: 29.4 g; TLC: r$_f$=0.36 (silicagel, petrole ether/ethyl acetate 1:1); Mass spectrum (ESI$^+$): m/z=198 [M+NH$_4$]$^+$.

Step 2: 4-(4-Bromo-3,5-dimethylphenoxy)tetrahydro-2H-pyran

To a solution of 4-bromo-3,5-dimethylphenol (3 g) in N-methyl-pyrrolidone (10 mL) is slowly added Cs$_2$CO$_3$ (9.7 g) and tetrahydro-2H-pyran-4-yl methanesulfonate (5.4 g). The mixture is heated for 3 hours at 140° C. After cooling to room temperature the mixture is partitioned between saturated aqueous Na$_2$CO$_3$ solution and ethyl acetate. The aqueous phase is extracted with ethyl acetate and the combined organic phases are dried (MgSO$_4$). The solvents are evaporated and the residue is purified by HPLC on reversed phase to give the title compound. Yield: 1.2 g; LC (method 4): t$_R$=1.83 min.

Step 3 Methyl 2-((S)-6-((R)-4-(2,6-dimethyl-4-(tetrahydro-2H-pyran-4-yloxy)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 4-(4-bromo-3,5-dimethylphenoxy)tetrahydro-2H-pyran following a procedure analogous to that described in Step 5 of Intermediate 1. LC (method 4): t$_R$=1.92 min; Mass spectrum (ESI$^+$): m/z=569 [M+Na]$^+$.

Intermediate 8

(S)-3-(4-Bromo-3,5-dimethylphenoxy)tetrahydrofuran

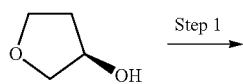

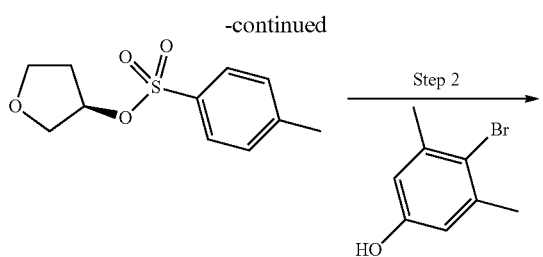

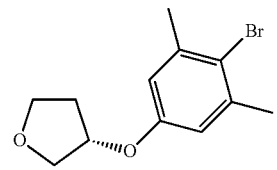

Step 1: (R)-Tetrahydrofuran-3-yl-4-methylbenzenesulfonate

To a solution of (R)-tetrahydrofuran-3-ol (25.4 g) in dichloromethane (250 mL) and pyridine (60 mL) is added at 0° C. N,N-dimethylaminopyridine (DMAP; 1 g) and p-toluene-sulfonylchloride (73 g) in portions. The mixture is stirred for 12 hours at room temperature, diluted with dichloromethane and washed with 1 M aqueous HCl solution and brine. After drying (MgSO$_4$) the solvent is evaporated and the residue is chromatographed on silica gel (dichloromethane/methanol 100:0→95:5) to give the title compound. Yield: 59.5 g; Mass spectrum (ESI$^+$): m/z=243 [M+H]$^+$.

Step 2: (S)-3-(4-Bromo-3,5-dimethylphenoxy)tetrahydrofuran

The title compound is prepared from (R)-tetrahydrofuran-3-yl 4-methylbenzenesulfonate following a procedure analogous to that described in Step 3 of Intermediate 2. LC (method 1): $t_R$=1.30 min; Mass spectrum (ESI⁺): m/z=271 [M+H]⁺.

Intermediate 9

Methyl 2-((S)-6-((R)-4-(2,6-dimethyl-4-((S)-tetrahydrofuran-3-yloxy)phenyl)-7-fluoro-2,3-dihydro-1H-inden-1-yloxy)-2,3-dihydrobenzofuran-3-yl)acetate

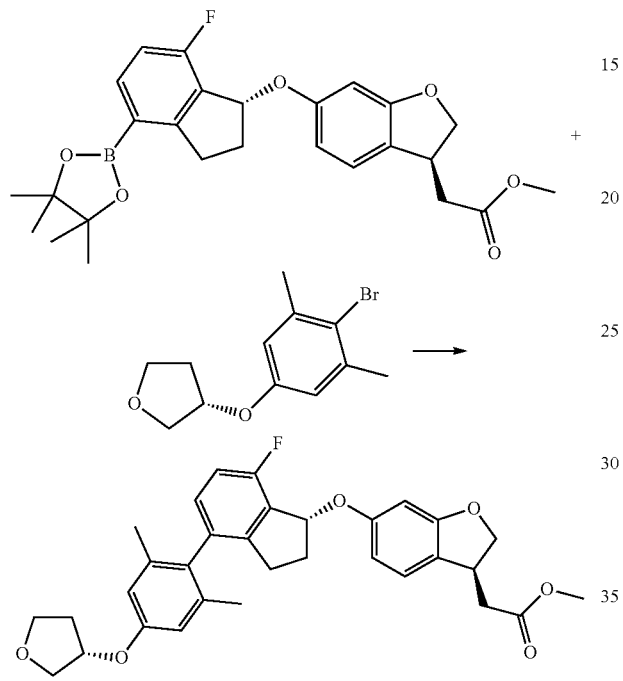

The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and (S)-3-(4-bromo-3,5-dimethylphenoxy)tetrahydrofuran following a procedure analogous to that described in Step 5 of Intermediate 1. LC (method 4): $t_R$=1.89 min; Mass spectrum (ESI⁺): m/z=555 [M+Na]⁺.

Intermediate 10

(R)-3-(4-Bromo-3,5-dimethylphenoxy)tetrahydrofuran

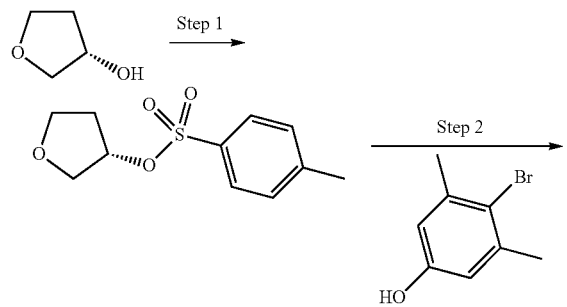

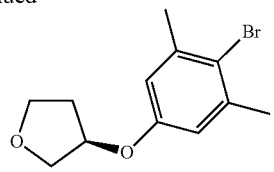

Step 1: (S)-Tetrahydrofuran-3-yl 4-methylbenzenesulfonate

The title compound is prepared from (S)-tetrahydrofuran-3-ol following a procedure analogous to that described in Step 1 of Intermediate 8. Mass spectrum (ESI⁺): m/z=243 [M+H]⁺.

Step 2: (R)-3-(4-Bromo-3,5-dimethylphenoxy)tetrahydrofuran

The title compound is prepared from (S)-tetrahydrofuran-3-yl 4-methylbenzenesulfonate following a procedure analogous to that described in Step 3 of Intermediate 2. LC (method 1): $t_R$=1.40 min; Mass spectrum (ESI⁺): m/z=271 [M+H]⁺.

Intermediate 11

Methyl 2-((S)-6-((R)-4-(2,6-dimethyl-4-((R)-tetrahydrofuran-3-yloxy)phenyl)-7-fluoro-2,3-dihydro-1H-inden-1-yloxy)-2,3-dihydrobenzofuran-3-yl)acetate

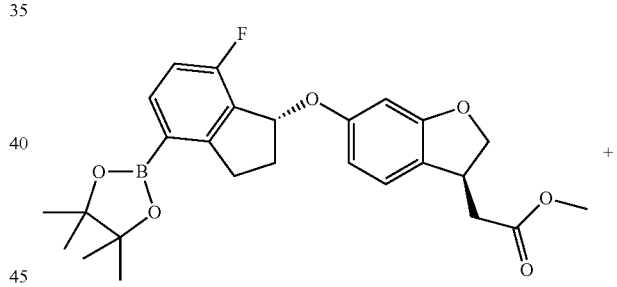

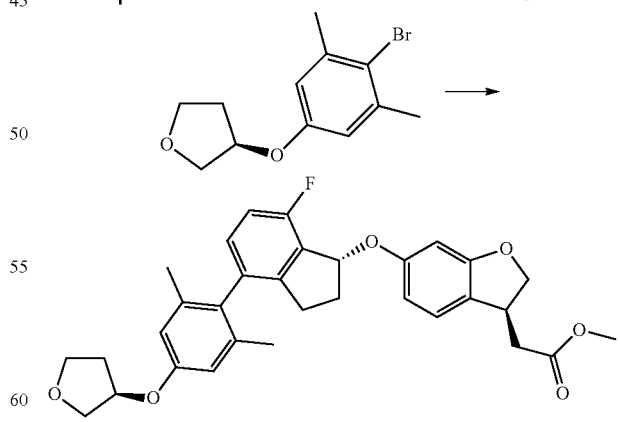

The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and (R)-3-(4-bromo-3,5-dimethylphenoxy)tetrahydrofuran following a procedure analogous to that described in Step 5 of Intermediate 1. LC (method 4): $t_R$=1.89 min; Mass spectrum (ESI⁺): m/z=555 [M+Na]⁺.

Intermediate 12

Methyl 2-((S)-6-((R)-7-fluoro-4-(4-(2-hydroxy-2-methylpropoxy)-2,6-dimethylphenyl)-2,3-dihydro-1H-inden-1-yloxy)-2,3-dihydrobenzofuran-3-yl)acetate

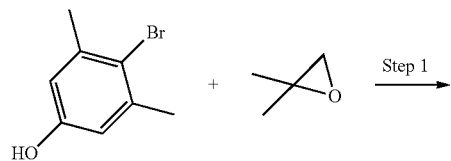

rated aqueous Na₂CO₃ solution and ethyl acetate. The aqueous phase is extracted twice with ethyl acetate and the combined organic phases are dried (MgSO₄) and concentrated. The residue is chromatographed on silica gel (cyclohexane/ethyl acetate 100:0→50:50) to give the title compound. Yield: 2.9 g; LC (method 4): $t_R$=1.76 min; Mass spectrum (ESI⁺): m/z=273 [M+H]⁺.

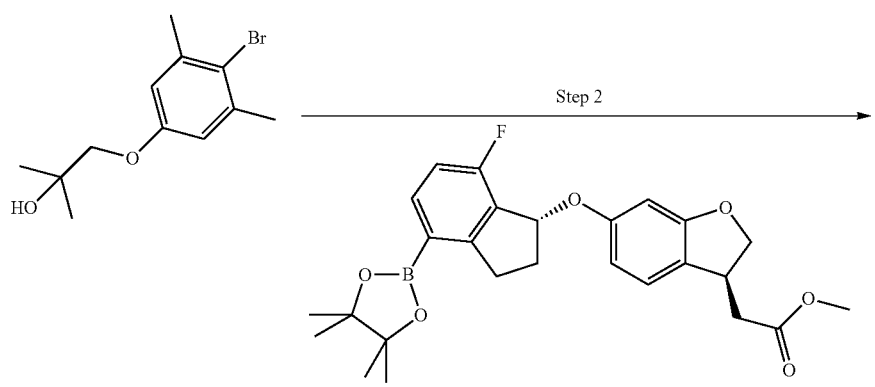

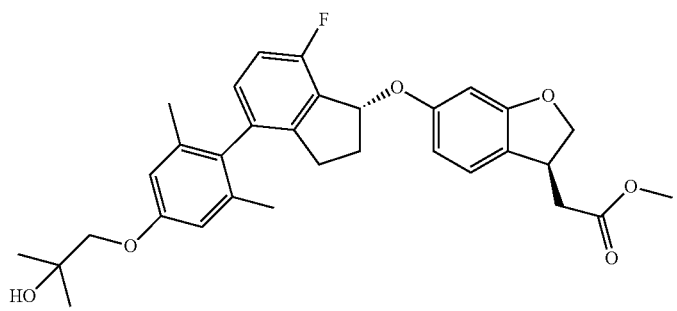

Step 1: 1-(4-Bromo-3,5-dimethylphenoxy)-2-methylpropan-2-ol

In a microwave vial 2,2-dimethyloxirane (2.2 g) is added to a suspension of 4-bromo-3,5-dimethylphenol and K₂CO₃ (11 g) in N,N-dimethylformamide (6 mL). The vial is sealed and the mixture is heated for 48 hours to 120° C. After cooling to room temperature the mixture is partitioned between satu- Step 2: Methyl 2-((S)-6-((R)-7-fluoro-4-(4-(2-hydroxy-2-methylpropoxy)-2,6-dimethylphenyl)-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)

acetate and 1-(4-bromo-3,5-dimethylphenoxy)-2-methylpropan-2-ol following a procedure analogous to that described in Step 5 of Intermediate 1. LC (method 8): $t_R$=0.77 min; Mass spectrum (ESI⁺): m/z=535 [M+H]⁺.

Intermediate 13

Methyl 2-((3S)-6-((1R)-7-fluoro-4-(4-(3-hydroxycyclopentyloxy)-2,6-dimethylphenyl)-2,3-dihydro-1H-inden-1-yloxy)-2,3-dihydrobenzofuran-3-yl)acetate

Step 2: 3-(4-Bromo-3,5-dimethylphenoxy)cyclopentanol

The title compound is prepared from 3-hydroxycyclopentyl 4-methylbenzenesulfonate and 4-bromo-3,5-dimethylphenol following a procedure analogous to that described in Step 3 of Intermediate 2. LC (method 7): $t_R$=1.07 min; Mass spectrum (ESI⁺): m/z=285 [M+H]⁺.

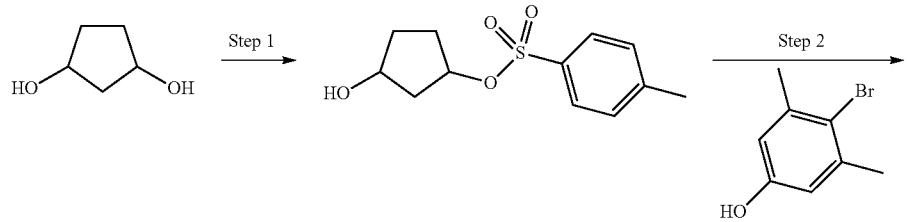

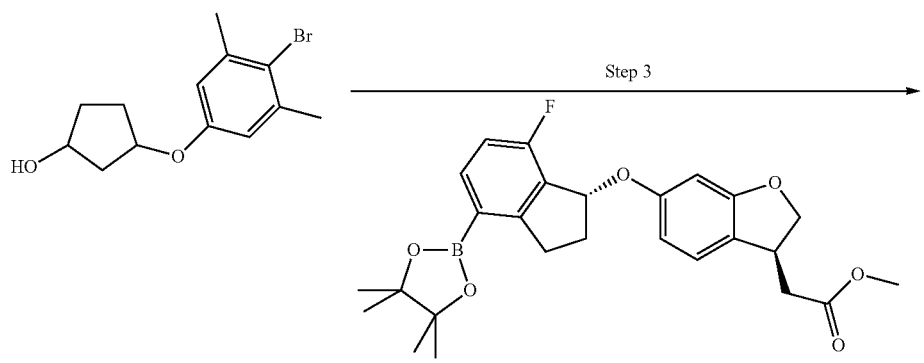

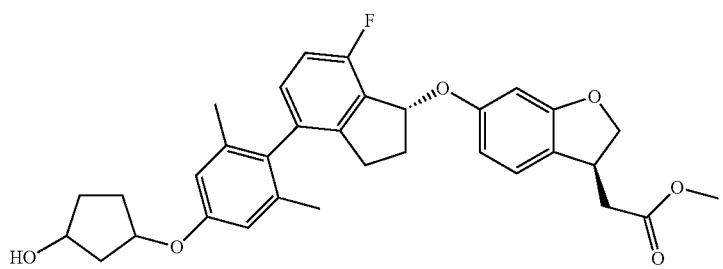

Step 1: 3-Hydroxycyclopentyl 4-methylbenzenesulfonate

The title compound is prepared from cyclopentane-1,3-diol following a procedure analogous to that described in Step 1 of Intermediate 8. The product is purified by chromatography on silica gel (petrole ether/ethyl acetate 90:10→10:90) to give the title compound. LC (method 7): $t_R$=0.86 min; Mass spectrum (ESI⁺): m/z=257 [M+H]⁺.

Step 3: Methyl 2-((3S)-6-((1R)-7-fluoro-4-(4-(3-hydroxycyclopentyloxy)-2,6-dimethylphenyl)-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 3-(4-bromo-3,5-dimethylphenoxy)cyclopentanol following a procedure analogous to that described in Step 5 of Intermediate 1. Mass spectrum (ESI⁺): m/z=547 [M+H]⁺.

Intermediate 14

2-((S)-6-((R)-7-Fluoro-4-(4-(2-methoxy-2-oxoethoxy)-2,6-dimethylphenyl)-2,3-dihydro-1H-inden-1-yloxy)-2,3-dihydrobenzofuran-3-yl)acetic acid Step 2: Methyl 2-((S)-6-((R)-4-(4-(cyanomethoxy)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 2-(4-bromo-3,5-dimethylphenoxy)acetonitrile

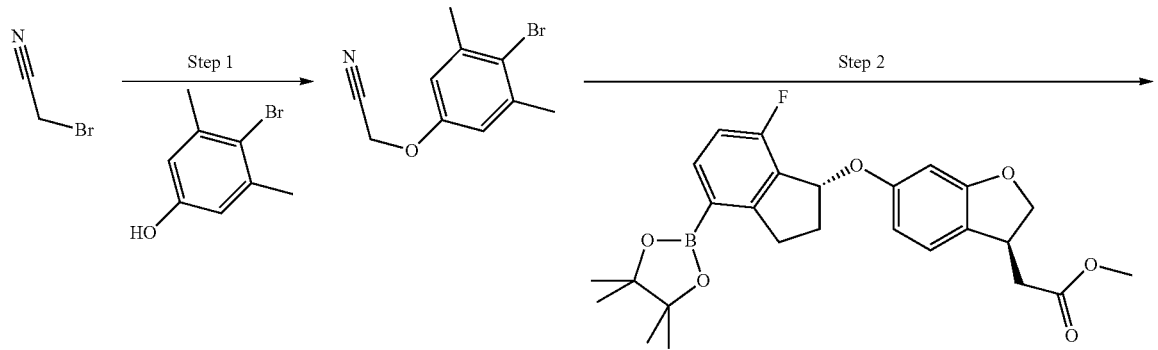

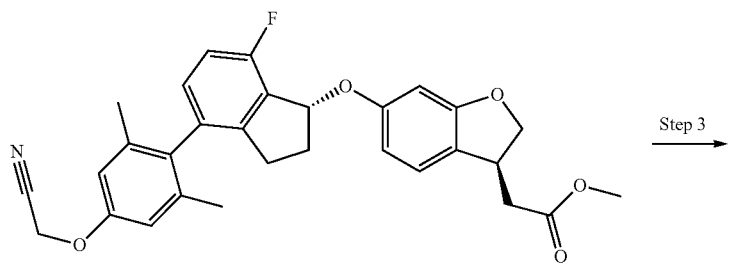

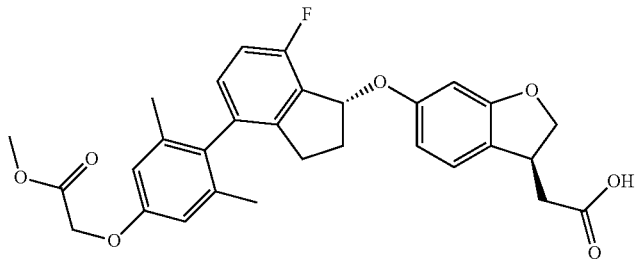

Step 1:
2-(4-Bromo-3,5-dimethylphenoxy)acetonitrile

To a solution of 4-bromo-3,5-dimethylphenol (500 mg) and Cs₂CO₃ (1.3 g) in N,N-dimethylformamide (5 mL) is added 2-bromoacetonitrile (290 µL) and the mixture is stirred for 2 hours at 35° C. The mixture is poured on water and stirred for 15 minutes. The precipitate is foltered off and dried to give the title compound. Yield: 535 mg; Mass spectrum (EI): m/z=239 [M]⁺.

following a procedure analogous to that described in Step 5 of Intermediate 1. LC (method 8): t$_R$=0.71 min; Mass spectrum (ESI⁺): m/z=502 [M+H]⁺.

Step 3: 2-((S)-6-((R)-7-Fluoro-4-(4-(2-methoxy-2-oxoethoxy)-2,6-dimethylphenyl)-2,3-dihydro-1H-inden-1-yloxy)-2,3-dihydrobenzofuran-3-yl)acetic acid A 1 M aqueous NaOH solution (400 µL) is added to a solution of methyl 2-((S)-6-((R)-4-(4-(cyanomethoxy)-2,6-dimethylphenyl)-7-fluoro-2,3-dihydro-1H-inden-1-yloxy)-2,3-dihydrobenzofuran-3-yl)acetate (120 mg) in methanol (4 mL). The mixture is stirred for 12 hours at room temperature. Methanol is evaporated off in vacuo and the residue is diluted with water. 1 M hydrochloric acid (400 µL) is added and the aqueous phase is extracted twice with dichloromethane The combined organic phases are dried (MgSO$_4$) and concentrated. The residue is chromatographed on silica gel (petrole ether/ethyl acetate 60:40→0:100). The product thus obtained is crystallized from n-hexane to give the title compound. Yield: 75 mg; LC (method 7): t$_R$=0.99 min; Mass spectrum (ESI$^+$): m/z=521 [M+H]$^+$.

Intermediate 15

Methyl 2-((S)-6-((R)-7-fluoro-4-(4-(3-hydroxy-2,2-dimethylpropoxy)-2,6-dimethylphenyl)-2,3-dihydro-1H-inden-1-yloxy)-2,3-dihydrobenzofuran-3-yl)acetate chilled in an ice bath. The mixture is heated to 40° C. for 3 hours and partitioned between saturated aqueous NaHCO$_3$ solution and dichloromethane. The organic phase is washed with brine, dried (MgSO$_4$) and concentrated to give the title compound. Yield: 535 mg; TLC: r$_f$=0.65 (silicagel, cyclohexane/ethyl acetate 3:1).

Step 2: 3-(4-Bromo-3,5-dimethylphenoxy)-2,2-dimethylpropan-1-ol

In a microwave vial Cs$_2$CO$_3$ (5.4 g) is added to a solution of 5,5-dimethyl-[1,3,2]dioxathiane 2-oxide (500 mg) and 4-bromo-3,5-dimethylphenol (670 mg) in N,N-dimethylformamide (5 mL). The vial is sealed and the mixture is heated to 120° C. for 12 hours. The mixture is partitioned between ethyl acetate and water. The organic phase is washed three times with 2 M aqueous NaOH and with brine. After drying

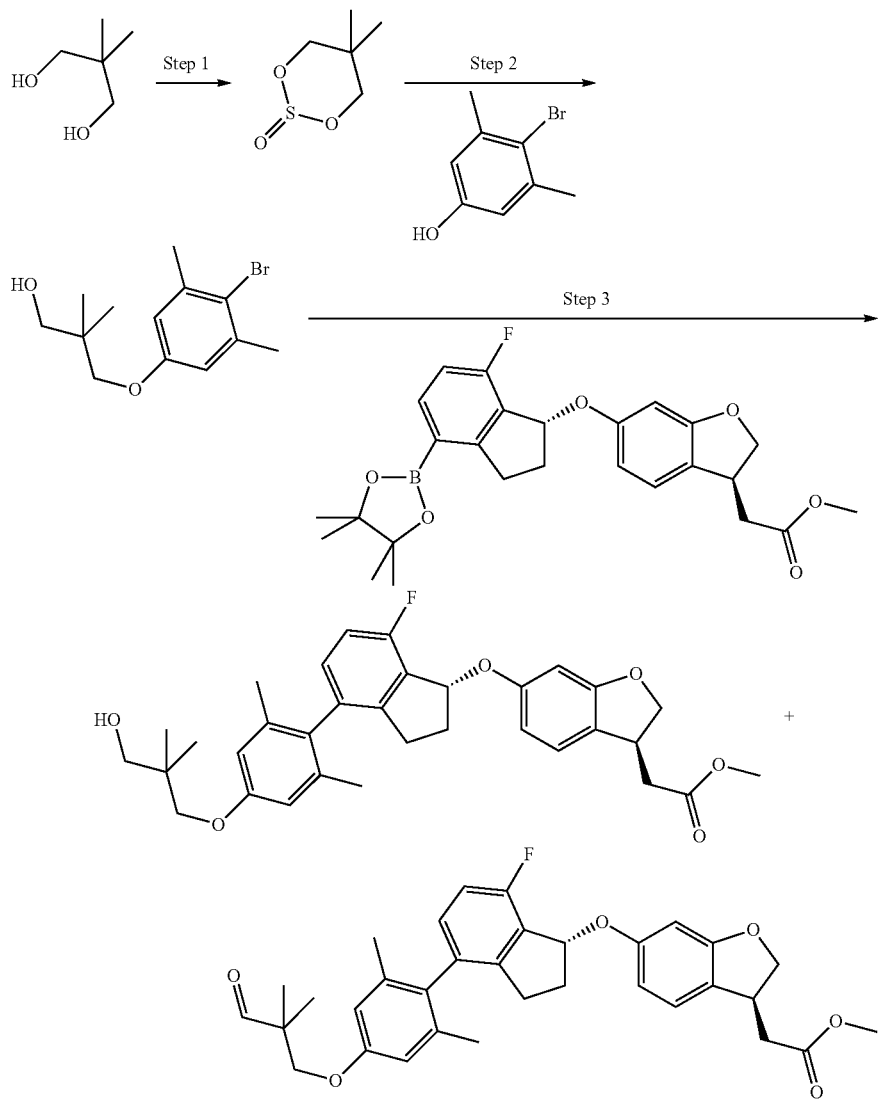

Step 1: 5,5-Dimethyl-[1,3,2]dioxathiane 2-oxide

Thionylchloride (735 mL) is added to a solution of 2,2-dimethylpropane-1,3-diol (1 g) in dichloromethane (10 mL)

(MgSO$_4$) and concentration the residue is chromatographed on silica gel (cyclohexane/ethyl acetate 99:1→50:50) to give the title compound. Yield: 372 mg; LC (method 7): t$_R$=1.17 min; Mass spectrum (ESI$^+$): m/z=287 [M+H]$^+$.

Step 3: Methyl 2-((S)-6-((R)-7-fluoro-4-(4-(3-hydroxy-2,2-dimethylpropoxy)-2,6-dimethylphenyl)-2,3-dihydro-1H-inden-1-yloxy)-2,3-dihydrobenzofuran-3-yl)acetate In a microwave vial methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (250 mg), 3-(4-bromo-3,5-dimethylphenoxy)-2,2-dimethylpropan-1-ol (226 mg), K₃PO₄ (230 mg) are suspended in toluene (2 mL) and water (200 μL) and purged for 10 minutes with argon. Palladium-(II)-acetate (12 mg) and dicyclohexyl(2',6'-dimethoxybiphenyl-2-yl)phosphine (S-Phos) (44 mg) are added, the vial is sealed and the mixture is stirred at 100° C. for 12 hours. After cooling to room temperature the mixture is partitioned between ethyl acetate and water. The organic phase is washed with brine, dried (MgSO₄) and concentrated. The residue is chromatographed on silica gel (cyclohexane/ethyl acetate 99:1→60:40) to give the title compound. Yield: 99 mg; LC (method 8): $t_R$=0.87 min; Mass spectrum (ESI⁺): m/z=549 [M+H]⁺.

Additionally methyl 2-((S)-6-((R)-4-(4-(2,2-dimethyl-3-oxopropoxy)-2,6-dimethylphenyl)-7-fluoro-2,3-dihydro-1H-inden-1-yloxy)-2,3-dihydrobenzofuran-3-yl)acetate is isolated. Yield: 83 mg; LC (method 8): $t_R$=0.95 min; Mass spectrum (ESI⁺): m/z=547 [M+H]⁺.

Intermediate 16

Methyl 2-((S)-6-((R)-7-fluoro-4-(4-(3-methoxy-2,2-dimethylpropoxy)-2,6-dimethylphenyl)-2,3-dihydro-1H-inden-1-yloxy)-2,3-dihydrobenzofuran-3-yl)acetate

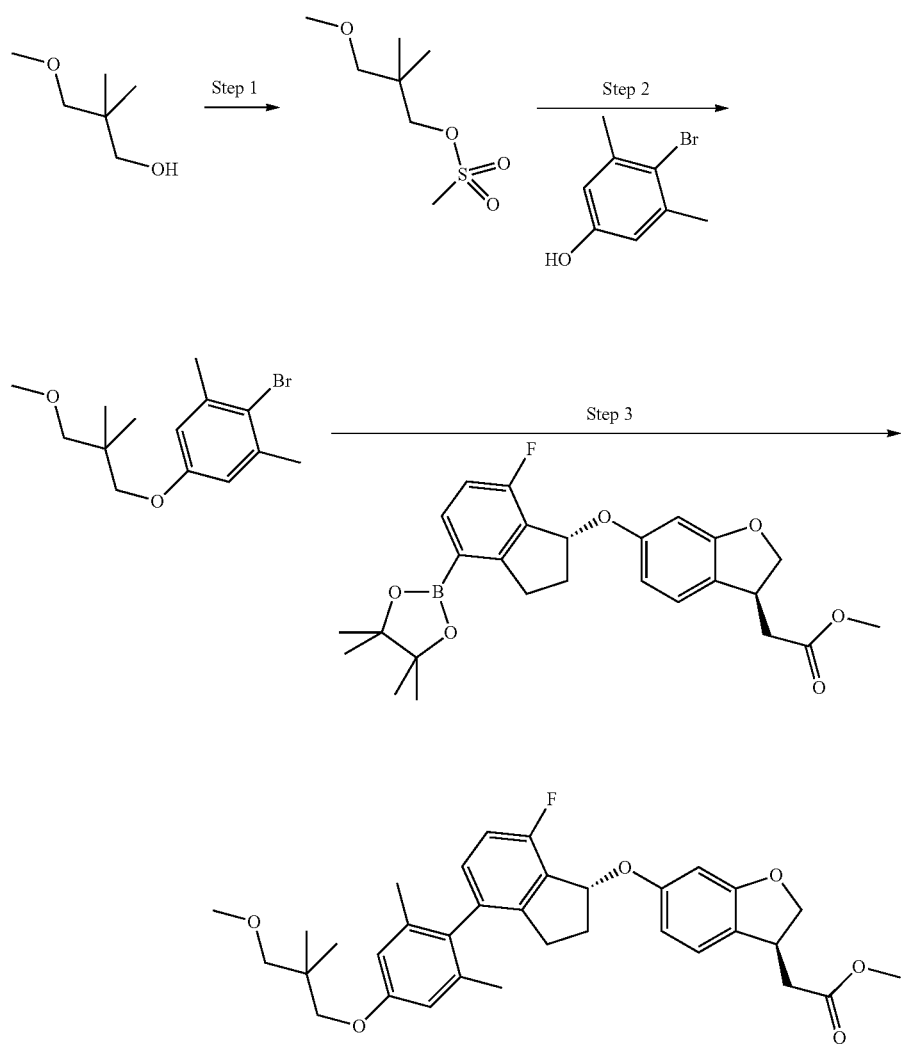

Step 1: 3-Methoxy-2,2-dimethylpropyl methanesulfonate

Methanesulfonyl chloride (330 mL) is added dropwise to a solution of 3-methoxy-2,2-dimethylpropan-1-ol (250 mg) and N,N-diisopropylethylamine (1.1 mL) in dichloromethane (3 mL) chilled in an ice bath. The mixture is stirred at room temperature for 12 hours and partitioned between saturated aqueous NaHCO₃ solution and dichloromethane. The organic phase is washed with twice with 1 N hydrochloric acid, saturated aqueous NaHCO₃ solution and brine. Then the organic phase is dried (MgSO₄) and concentrated to give the title compound. Yield: 407 mg; TLC: $r_f$=0.75 (silicagel, cyclohexane/ethyl acetate 3:1).

Step 2: 2-Bromo-5-(3-methoxy-2,2-dimethylpropoxy)-1,3-dimethylbenzene

In a microwave vial $Cs_2CO_3$ (3.3 g) and KI (50 mg) are added to a solution of 3-methoxy-2,2-dimethylpropyl methanesulfonate (407 mg) and 4-bromo-3,5-dimethylphenol (415 mg) in N,N-dimethylformamide (5 mL). The vial is sealed and the mixture is heated to 120° C. for 12 hours. The mixture is partitioned between ethyl acetate and water. The organic phase is washed with water and brine and is dried ($MgSO_4$). The solvents are evaporated and the residue is chromatographed on silica gel (cyclohexane/ethyl acetate 99:1→80:20). The product thus obtained is purified by HPLC on reversed phase to give the title compound. Yield: 171 mg; LC (method 8): $t_R$=1.02 min; Mass spectrum (ESI⁺): m/z=301 [M+H]⁺.

Step 3: Methyl 2-((S)-6-((R)-7-fluoro-4-(4-(3-methoxy-2,2-dimethylpropoxy)-2,6-dimethylphenyl)-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and 2-bromo-5-(3-methoxy-2,2-dimethylpropoxy)-1,3-dimethylbenzene following a procedure analogous to that described in Step 5 of Intermediate 1. LC (method 8): $t_R$=1.12 min; Mass spectrum (ESI⁺): m/z=563 [M+H]⁺.

Intermediate 17

Methyl 2-((S)-6-((R)-4-(2,6-dimethyl-4-(pyrimidin-5-yl)phenyl)-7-fluoro-2,3-dihydro-1H-inden-1-yloxy)-2,3-dihydrobenzofuran-3-yl)acetate

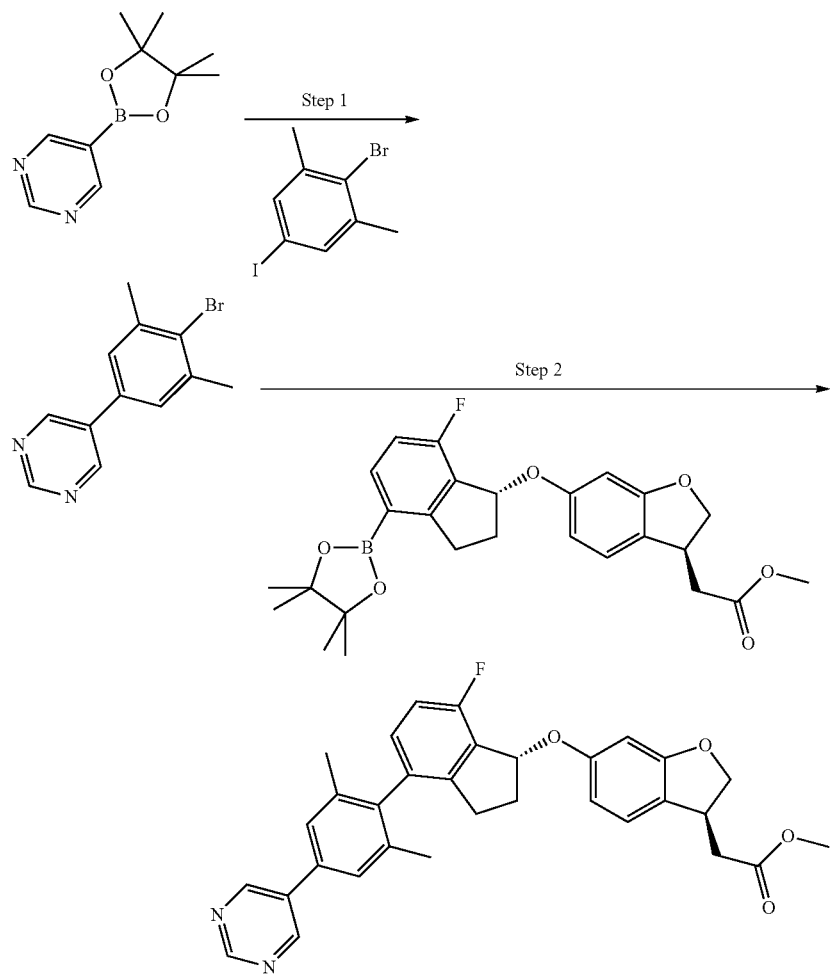

Step 1: 5-(4-Bromo-3,5-dimethylphenyl)pyrimidine

In a microwave vial 2-bromo-5-iodo-1,3-dimethylbenzene (1 g) and 5-(4,4,5,5-tetramethyl-1,3,2-dioxaborolan-2-yl)pyrimidine (665 mg) are suspended in N,N-dimethylformamide (15 mL) and $Na_2CO_3$ (4 mL of a 2 M aqueous solution). The mixture is purged for 5 minutes with argon. [1,1'-Bis(diphenylphosphino)-ferrocene]-dichloropalladium dichloromethane complex (85 mg) is added, the vial is sealed and the mixture is stirred at 60° C. for 3 hours. After cooling to room temperature the mixture is Partitioned between water and ethyl acetate. The aqueous phase is extracted with ethyl acetate and the combined organic phases are washed with brine. Then the organic phase is dried (MgSO$_4$) and concentrated. The residue is chromatographed on silica gel (cyclohexane/ethyl acetate 80:20→50:50) to give the title compound. Yield: 446 mg; LC (method 9): t$_R$=1.05 min; Mass spectrum (ESI$^+$): m/z=263 [M+H]$^+$.

Intermediate 18

Methyl 2-((S)-6-((R)-4-(2,6-dimethyl-4-(oxazol-2-yl)phenyl)-7-fluoro-2,3-dihydro-1H-inden-1-yloxy)-2,3-dihydrobenzofuran-3-yl)acetate

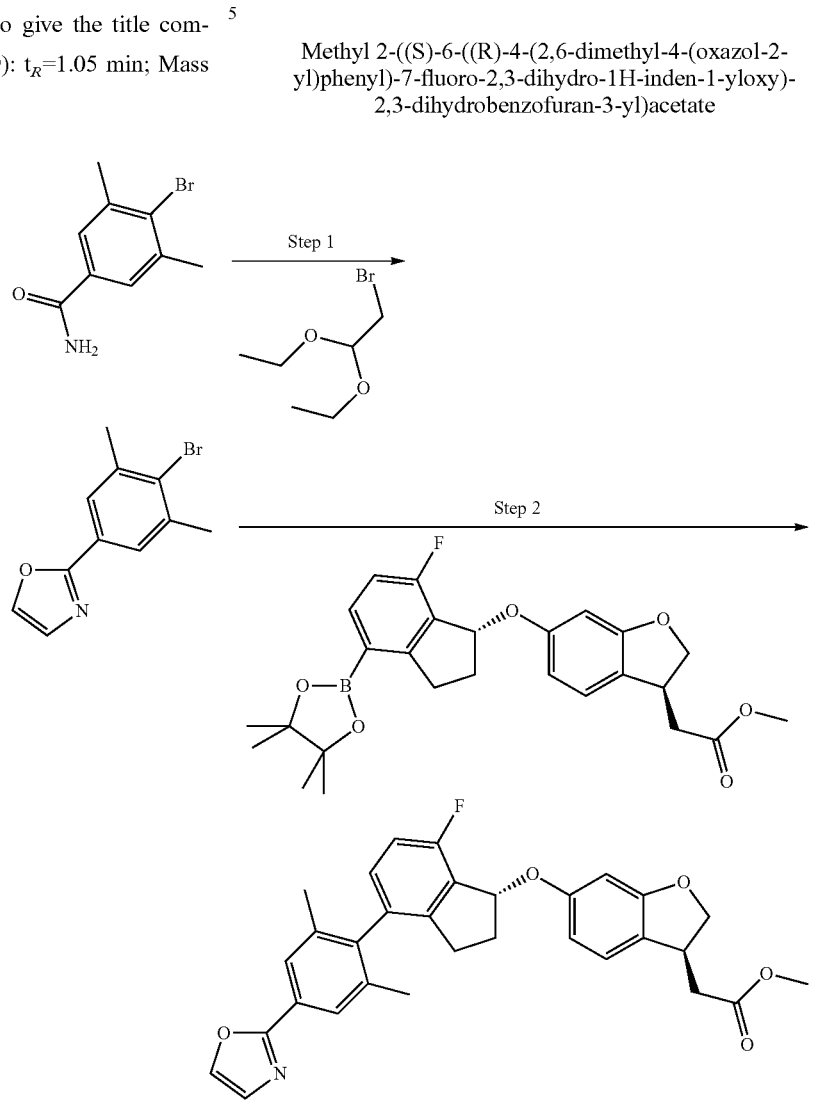

Step 1: 2-(4-Bromo-3,5-dimethylphenyl)oxazole

In a microwave vial 4-bromo-3,5-dimethylbenzamide (200 mg) is mixed with 2-bromo-1,1-diethoxyethane (1 mL), the vial is sealed and the mixture is heated to 150° C. for 30 minutes. The mixture is diluted with acetonitrile (2 mL) and purified by HPLC on reversed phase to give the title compound. Yield: 125 mg; LC (method 7): t$_R$=1.13 min; Mass spectrum (ESI$^+$): m/z=252 [M+H]$^+$.

Step 2: Methyl 2-((S)-6-((R)-4-(2,6-dimethyl-4-(oxazol-2-yl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 2-(4-bromo-3,5-dimethylphenyl)oxazole following a procedure analogous to that described in Step 2 of Intermediate 17. LC (method 11): t$_R$=1.27 min; Mass spectrum (ESI$^+$): m/z=514 [M+H]$^+$.

Step 2: Methyl 2-((S)-6-((R)-4-(2,6-dimethyl-4-(pyrimidin-5-yl)phenyl)-7-fluoro-2,3-dihydro-1H-inden-1-yloxy)-2,3-dihydrobenzofuran-3-yl)acetate In a microwave vial methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (100 mg), 5-(4-bromo-3,5-dimethylphenyl)pyrimidine (85 mg), K$_3$PO$_4$ (90 mg) are suspended in toluene (1 mL) and water (100 µL) and purged for 10 minutes with argon. Palladium(II)-acetate (2.4 mg) and dicyclohexyl(2',6'-dimethoxybiphenyl-2-yl)phosphine (S-Phos) (8.8 mg) are added, the vial is sealed and the mixture is stirred at 100° C. for 12 hours. The mixture is diluted with tetrahydrofuran and purified by HPLC on reversed phase to give the title compound. Yield: 40 mg; Mass spectrum (ESI$^+$): m/z=525 [M+H]$^+$.

Intermediate 19

Methyl 2-((S)-6-((R)-4-(2,6-dimethyl-4-(1-methyl-1H-pyrazol-4-yl)phenyl)-7-fluoro-2,3-dihydro-1H-inden-1-yloxy)-2,3-dihydrobenzofuran-3-yl)acetate

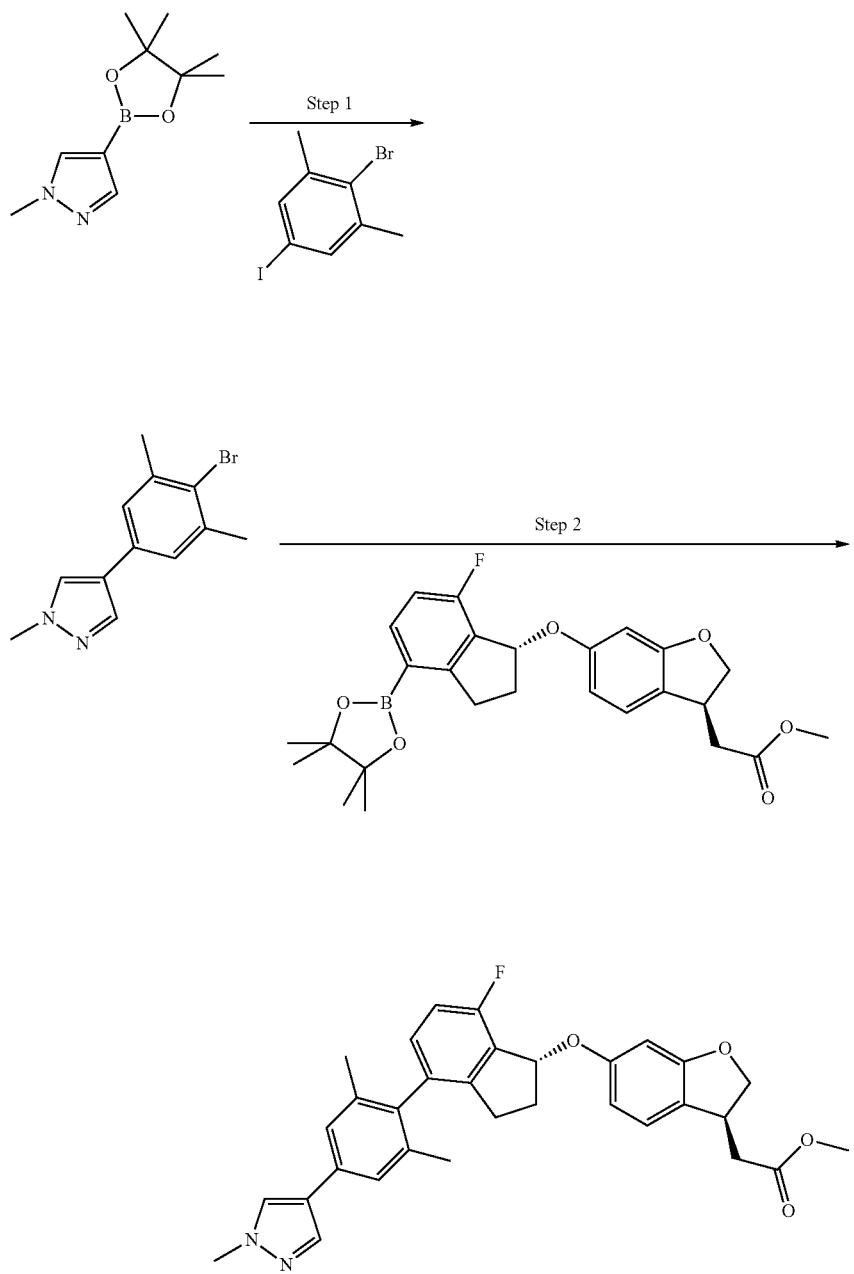

Step 1: 4-(4-Bromo-3,5-dimethylphenyl)-1-methyl-1H-pyrazole

The title compound is prepared from 2-bromo-5-iodo-1,3-dimethylbenzene and 1-methyl-4-(4,4,5,5-tetramethyl-1,3,2-dioxaborolan-2-yl)-1H-pyrazole following a procedure analogous to that described in Step 1 of Intermediate 17. LC (method 9): $t_R$=1.09 min; Mass spectrum (ESI$^+$): m/z=265 [M+H]$^+$.

Step 2: Methyl 2-((S)-6-((R)-4-(2,6-dimethyl-4-(1-methyl-1H-pyrazol-4-yl)phenyl)-7-fluoro-2,3-dihydro-1H-inden-1-yloxy)-2,3-dihydrobenzofuran-3-yl) acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and 4-(4-bromo-3,5-dimethylphenyl)-1-methyl-1H- pyrazole following a procedure analogous to that described in Step 2 of Intermediate 17. Mass spectrum (ESI+): m/z=527 [M+H]+.

Intermediate 20

Methyl 2-((S)-6-((R)-4-(2,6-dimethyl-4-(1-methyl-1H-pyrazol-5-yl)phenyl)-7-fluoro-2,3-dihydro-1H-inden-1-yloxy)-2,3-dihydrobenzofuran-3-yl)acetate Step 1: 5-(4-Bromo-3,5-dimethylphenyl)-1-methyl-1H-pyrazole The title compound is prepared from 2-bromo-5-iodo-1,3-dimethylbenzene and 1-methyl-5-(4,4,5,5-tetramethyl-1,3,2-dioxaborolan-2-yl)-1H-pyrazole following a procedure analogous to that described in Step 1 of Intermediate 17. LC (method 9): $t_R$=1.11 min; Mass spectrum (ESI+): m/z=265 [M+H]+.

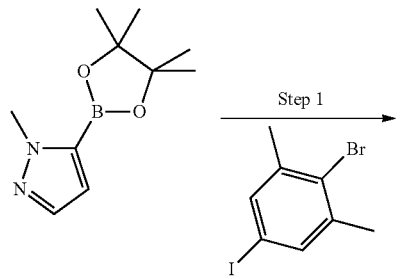

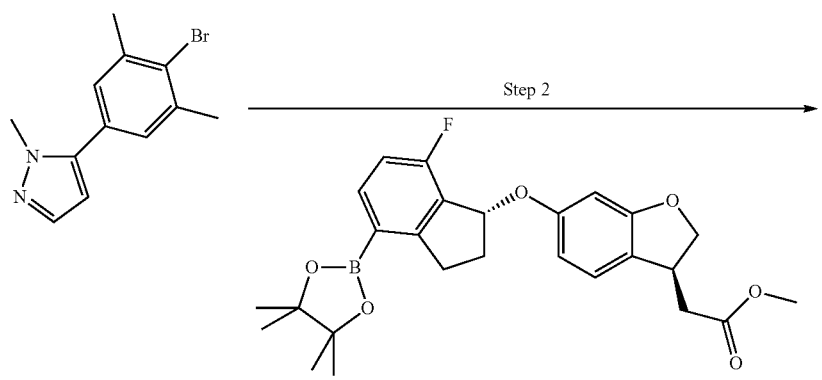

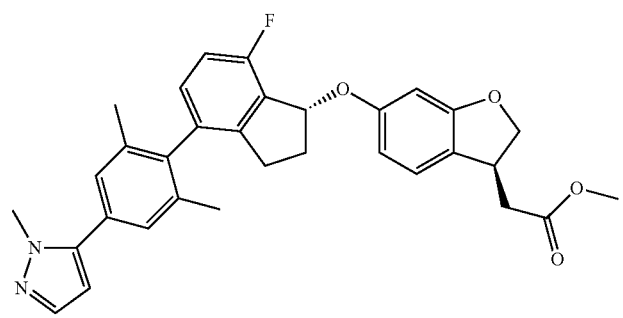

Step 2: Methyl 2-((S)-6-((R)-4-(2,6-dimethyl-4-(1-methyl-1H-pyrazol-5-yl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 5-(4-bromo-3,5-dimethylphenyl)-1-methyl-1H-pyrazole following a procedure analogous to that described in Step 2 of Intermediate 17. Mass spectrum (ESI$^+$): m/z=527 [M+H]$^+$.

Intermediate 21

Methyl 2-((S)-6-((R)-4-(4-(2-cyanopropan-2-yloxy)-2,6-dimethylphenyl)-7-fluoro-2,3-dihydro-1H-inden-1-yloxy)-2,3-dihydrobenzofuran-3-yl)acetate

Step 1: 2-(4-Bromo-3,5-dimethylphenoxy)-2-methylpropanenitrile

Under argon diisopropylamin (650 μL) is dissolved in tetrahydrofuran (6 mL), cooled to −30° C. and treated dropwise with n-butyllithium (2.75 mL of a 1.6 M solution in n-hexane). The mixture is stirred for 30 minutes, cooled to −78° C. and then treated dropwise with a solution of 2-(4-bromo-3,5-dimethylphenoxy)acetonitrile (350 mg) and methyliodide (549 μL) in tetrahydrofuran (6 mL). The mixture is stirred for 2 hours warmed to 0° C. and stirred for 1 hour. The reaction is quenched by addition of saturated aqueous NH$_4$Cl solution, the aqueous phase is extracted with diethylether and the organic phase is dried (MgSO$_4$). The solvents are evaporated and the residue is chromatographed on silica gel (petrole ether/ethyl acetate 95:5→60:40) to give the title compound. Yield: 120 mg; Mass spectrum (EI): m/z=267 [M]$^+$.

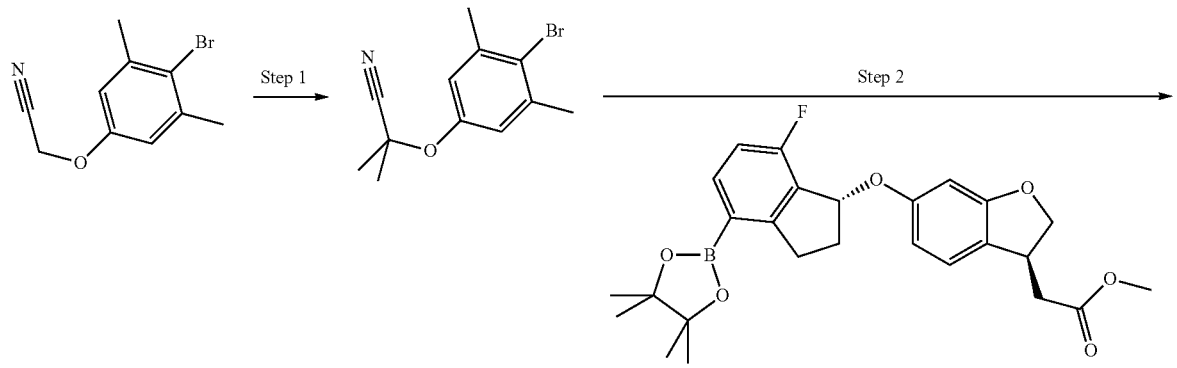

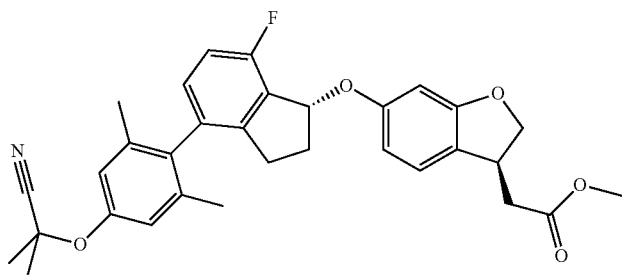

Step 2: Methyl 2-((S)-6-((R)-4-(4-(2-cyanopropan-2-yloxy)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 2-(4-bromo-3,5-dimethylphenoxy)-2-methylpropanenitrile following a procedure analogous to that described in Step 5 of Intermediate 1. LC (method 7): $t_R$=1.25 min; Mass spectrum (ESI⁺): m/z=530 [M+H]⁺.

Intermediate 22

Methyl 2-((S)-6-((R)-4-(4-(3-(dimethylamino)-2,2-dimethylpropoxy)-2,6-dimethylphenyl)-7-fluoro-2,3-dihydro-1H-inden-1-yloxy)-2,3-dihydrobenzofuran-3-yl)acetate

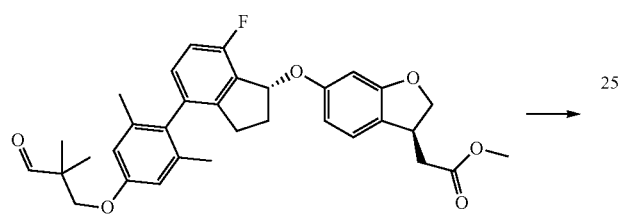

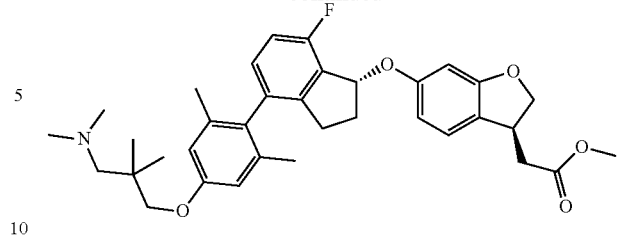

Dimethylamine (95 μL of a 2 M solution in tetrahydrofuran) is added to a solution of methyl 2-((S)-6-((R)-4-(4-(2,2-dimethyl-3-oxopropoxy)-2,6-dimethylphenyl)-7-fluoro-2,3-dihydro-1H-inden-1-yloxy)-2,3-dihydrobenzofuran-3-yl)acetate (83 mg) and acetic acid (13 μL) in 1,2-dichloroethane (2 mL). The mixture is stirred for 20 minutes and then treated with sodium triacetoxyborohydride (130 mg). After stirring for 12 hours the mixture is diluted with dichloromethane, washed with water and brine, dried (MgSO₄) and concentrated. The residue is purified by HPLC on reversed phase to give the title compound. Yield: 20 mg; LC (method 13): $t_R$=1.18 min; Mass spectrum (ESI⁺): m/z=576 [M+H]⁺.

Intermediate 23

Methyl 2-((S)-6-((R)-4-(2,6-dimethyl-4-(2-(2-oxopyrrolidin-1-yl)ethoxy)phenyl)-7-fluoro-2,3-dihydro-1H-inden-1-yloxy)-2,3-dihydrobenzofuran-3-yl)acetate

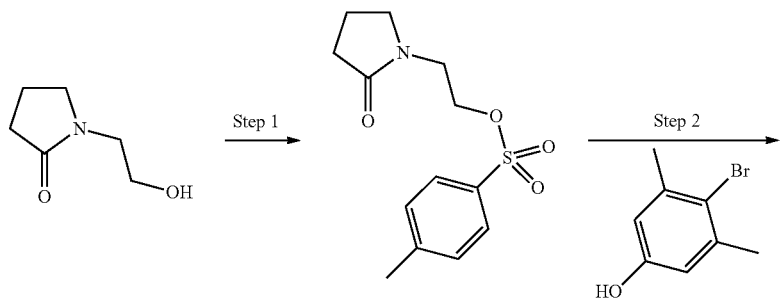

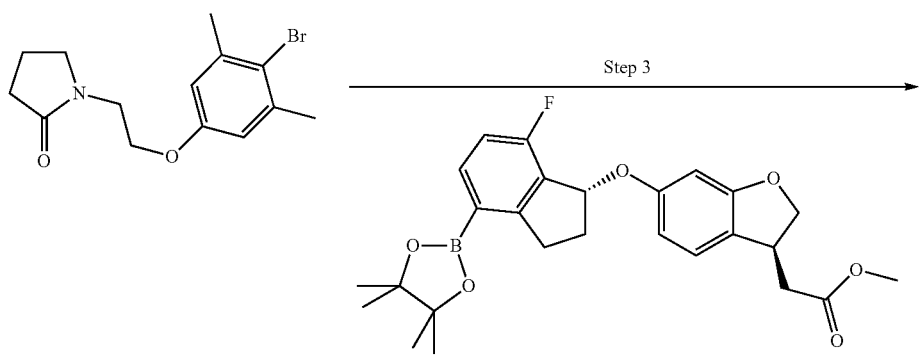

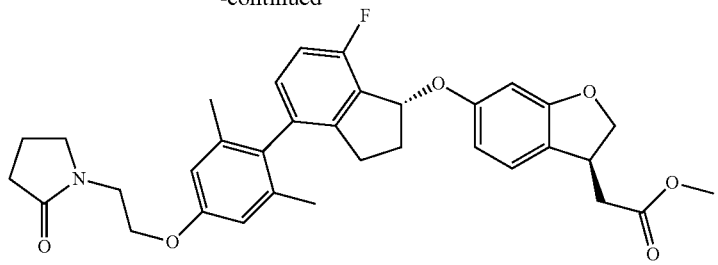

Step 1: 2-(2-oxopyrrolidin-1-yl)ethyl 4-methylbenzenesulfonate p-Toluenesulfonylchloride (1 g) is added portionwise to a solution of 1-(2-hydroxyethyl)pyrrolidin-2-one (500 µL) and pyridine (1.5 mL) in dichloromethane (8 mL) chilled in an ice bath. The mixture is stirred at room temperature for 12 hours and partitioned between 1 M hydrochloric acid and diethylether. The organic phase is dried (MgSO$_4$) and concentrated. The residue is chromatographed on silica gel (ethyl acetate) to give the title compound. Yield: 390 mg; Mass spectrum (ESI$^+$): m/z=284 [M+H]$^+$.

Step 2: 1-(2-(4-Bromo-3,5-dimethylphenoxy)ethyl)pyrrolidin-2-one

Cs$_2$CO$_3$ (850 mg) is added to a solution of 2-(2-oxopyrrolidin-1-yl)ethyl 4-methylbenzenesulfonate (390 mg) and 4-bromo-3,5-dimethylphenol (200 mg) in N,N-dimethylformamide (4 mL). The mixture is heated to 50° C. for 12 hours and partitioned between diethylether and saturated aqueous NH$_4$Cl solution. The organic phase is dried (MgSO$_4$) and concentrated. The residue is chromatographed on silica gel (ethyl acetate) to give the title compound. Yield: 210 mg; Mass spectrum (ESI$^+$): m/z=312 [M+H]$^+$.

Step 3: Methyl 2-((S)-6-((R)-4-(2,6-dimethyl-4-(2-(2-oxopyrrolidin-1-yl)ethoxy)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 1-(2-(4-bromo-3,5-dimethylphenoxy)ethyl)pyrrolidin-2-one following a procedure analogous to that described in Step 5 of Intermediate 1. The product is purified by HPLC on reversed phase. LC (method 8): t$_R$=0.68 min; Mass spectrum (ESI$^+$): m/z=574 [M+H]$^+$.

Intermediate 24

Methyl 2-((S)-6-((R)-4-(4-(3,6-dihydro-2H-pyran-4-yl)-2,6-dimethylphenyl)-7-fluoro-2,3-dihydro-1H-inden-1-yloxy)-2,3-dihydrobenzofuran-3-yl)acetate

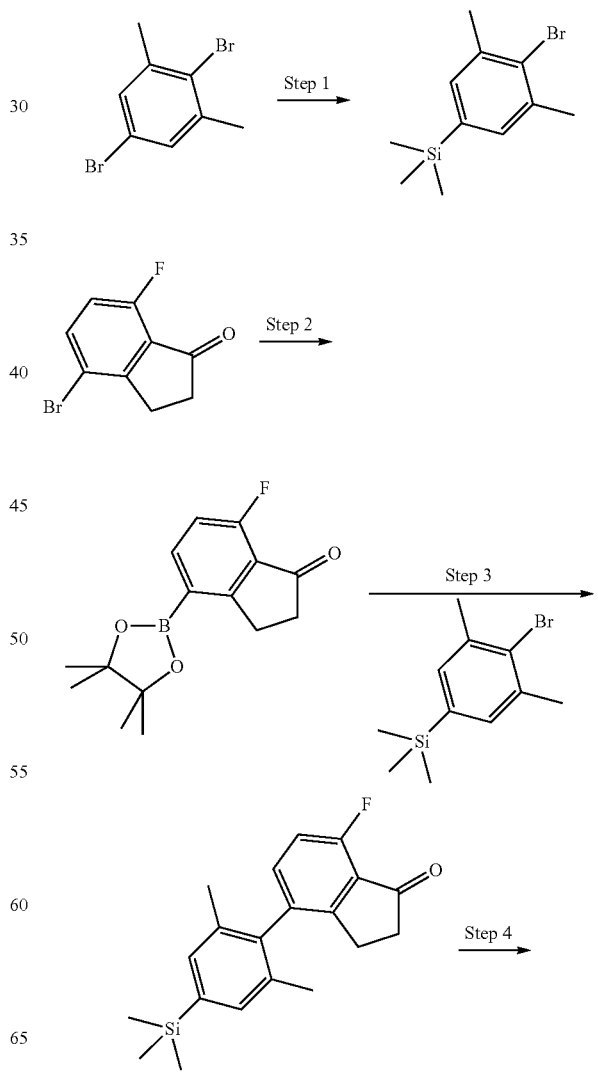

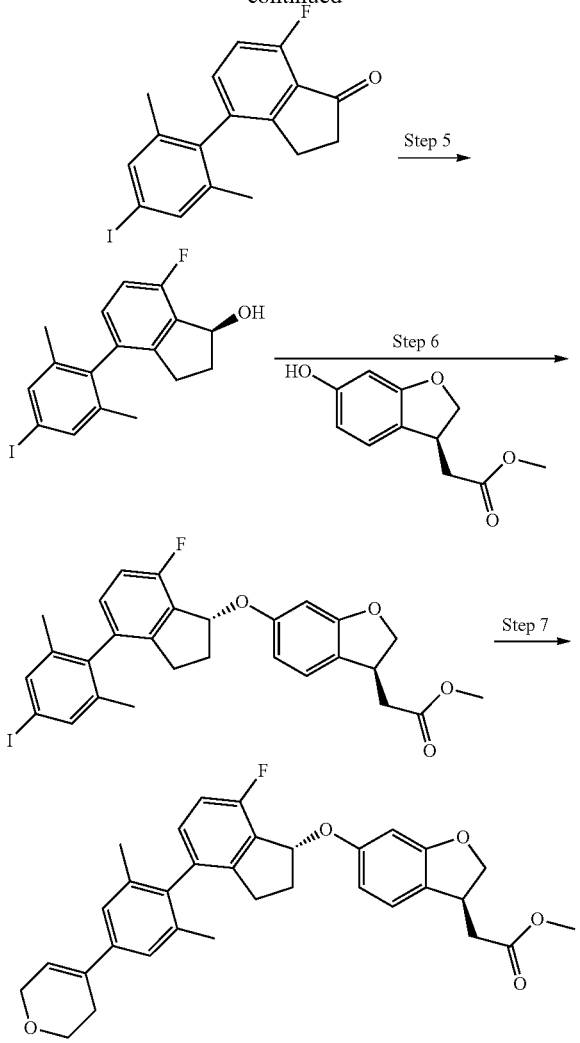

Step 1: (4-Bromo-3,5-dimethylphenyl)trimethylsilane

A solution of 2,5-dibromo-1,3-dimethylbenzene (500 mg) in diethylether (3 mL) and tetrahydrofuran (2.5 mL) is cooled to −78° C. and treated dropwise with n-butyllithium (200 μL of a 10 M solution in n-hexane). The mixture is stirred for 1 hour and treated dropwise with chloro-trimethyl-silane (275 μL). After stirring for 2 hours the reaction is quenched by addition of saturated aqueous NH$_4$Cl solution. The mixture is extracted with diethylether. The organic phase is dried (MgSO$_4$) and concentrated. The residue is chromatographed on silica gel (cyclohexane/ethyl acetate 99:1→90:10) to give the title compound. Yield: 260 mg; Mass spectrum (ESI$^+$): m/z=279 [M+Na]$^+$.

Step 2: 7-Fluoro-4-(4,4,5,5-tetramethyl-1,3,2-dioxaborolan-2-yl)-2,3-dihydro-1H-inden-1-one The title compound is prepared from 4-bromo-7-fluoro-2,3-dihydro-1H-inden-1-one following a procedure analogous to that described in Step 4 of Intermediate 1. LC (method 8): t$_R$=0.36 min; Mass spectrum (ESI$^+$): m/z=277 [M+H]$^+$.

Step 3: 4-(2,6-Dimethyl-4-(trimethylsilyl)phenyl)-7-fluoro-2,3-dihydro-1H-inden-1-one The title compound is prepared from 7-fluoro-4-(4,4,5,5-tetramethyl-1,3,2-dioxaborolan-2-yl)-2,3-dihydro-1H-inden-1-one and (4-bromo-3,5-dimethylphenyl)trimethylsilane following a procedure analogous to that described in Step 5 of Intermediate 1. LC (method 8): t$_R$=0.89 min; Mass spectrum (ESI$^+$): m/z=327 [M+H]$^+$.

Step 4: 7-Fluoro-4-(4-iodo-2,6-dimethylphenyl)-2,3-dihydro-1H-inden-1-one 4-(2,6-Dimethyl-4-(trimethylsilyl)phenyl)-7-fluoro-2,3-dihydro-1H-inden-1-one (110 mg) is dissolved in dichloromethane (2 mL), cooled to −30° C. and treated dropwise with ICl (355 μL of a 1 M solution in dichloromethane). The mixture is stirred for 1 hour and then partitioned between saturated aqueous NaHCO$_3$ solution and dichloromethane. The organic phase is washed with a 10% aqueous solution of Na$_2$S$_2$O$_3$ and brine. After drying (MgSO$_4$) the solvents are evaporated off to give the title compound. Yield: 160 mg; LC (method 8): t$_R$=0.66 min; Mass spectrum (ESI$^+$): m/z=381 [M+H]$^+$.

Step 5: (S)-7-Fluoro-4-(4-iodo-2,6-dimethylphenyl)-2,3-dihydro-1H-inden-1-ol The title compound is prepared from 7-fluoro-4-(4-iodo-2,6-dimethylphenyl)-2,3-dihydro-1H-inden-1-one following a procedure analogous to that described in Step 2 of Intermediate 1. LC (method 8): t$_R$=0.65 min; Mass spectrum (ESI$^-$): m/z=381 [M−H]$^-$.

Step 6: Methyl 2-((S)-6-((R)-7-fluoro-4-(4-iodo-2,6-dimethylphenyl)-2,3-dihydro-1H-inden-1-yloxy)-2,3-dihydrobenzofuran-3-yl)acetate The title compound is prepared from (S)-7-fluoro-4-(4-iodo-2,6-dimethylphenyl)-2,3-dihydro-1H-inden-1-ol and (S)-methyl 2-(6-hydroxy-2,3-dihydrobenzofuran-3-yl)acetate following a procedure analogous to that described in Step 3 of Intermediate 1. LC (method 8): t$_R$=1.08 min; Mass spectrum (ESI$^+$): m/z=595 [M+Na]$^+$.

Step 7: Methyl 2-((S)-6-((R)-4-(4-(3,6-dihydro-2H-pyran-4-yl)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4-iodo-2,6-dimethylphenyl)-2,3-dihydro-1H-inden-1-yloxy)-2,3-dihydrobenzofuran-3-yl)acetate and 2-(3,6-dihydro-2H-pyran-4-yl)-4,4,5,5-tetramethyl-1,3,2-dioxaborolane following a procedure analogous to that described in Step 4 of Intermediate 2. LC (method 8): t$_R$=0.92 min; Mass spectrum (ESI$^+$): m/z=551 [M+Na]$^+$.

Intermediate 25

Methyl 2-((S)-6-((R)-4-(2,6-dimethyl-4-(1-(methyl-sulfonyl)-1,2,3,6-tetrahydropyridin-4-yl)phenyl)-7-fluoro-2,3-dihydro-1H-inden-1-yloxy)-2,3-dihydrobenzofuran-3-yl)acetate

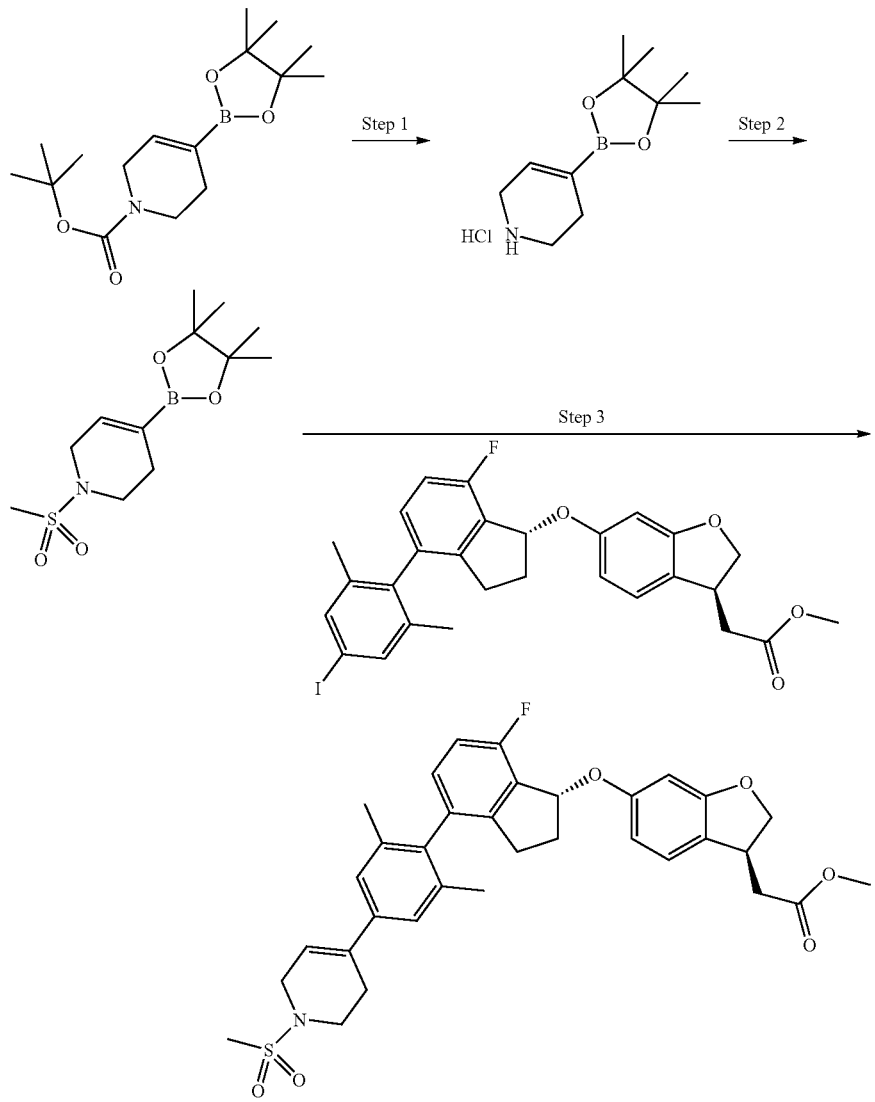

Step 1: 4-(4,4,5,5-Tetramethyl-1,3,2-dioxaborolan-2-yl)-1,2,3,6-tetrahydropyridinium chloride Tert-butyl 4-(4,4,5,5-tetramethyl-1,3,2-dioxaborolan-2-yl)-5,6-dihydropyridine-1(2H)-carboxylate (10 g) is dissolved in dichloromethane (100 mL) and 5 M HCl in isopropanol (120 mL) and stirred for 12 hours. The solvents are evaporated, the residue is redissolved in toluene and the solvent is again evaporated to give the title compound. Yield: 8 g; LC (method 11): $t_R$=0.68 min; Mass spectrum (ESI$^+$): m/z=210 [M+H]$^+$.

Step 2: 1-(Methylsulfonyl)-4-(4,4,5,5-tetramethyl-1,3,2-dioxaborolan-2-yl)-1,2,3,6-tetrahydropyridine To a cooled (0° C.) solution of 4-(4,4,5,5-tetramethyl-1,3,2-dioxaborolan-2-yl)-1,2,3,6-tetrahydropyridinium chloride (8 g) and N-ethyldiisopropylamine (12 mL) in dichloromethane (100 mL) is added dropwise methanesulfonyl chloride (3 mL). The mixture is stirred for 12 hours at room temperature. The mixture is partitioned between dichloromethane and 0.1 M hydrochloric acid. The organic phase is separated, washed with brine and dried (MgSO$_4$). The solvent is evaporated and the residue is crystallized from diethylether to give the title compound. Yield: 7.4 g; LC (method 15): $t_R$=0.98 min; Mass spectrum (ESI$^+$): m/z=288 [M+H]$^+$.

Step 3: Methyl 2-((S)-6-((R)-4-(2,6-dimethyl-4-(1-(methylsulfonyl)-1,2,3,6-tetrahydropyridin-4-yl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4-iodo-2,6-dimethylphenyl)-2,3-dihydro-1H-inden-1-yloxy)-2,3-dihydrobenzofuran-3-yl)acetate and 1-(methylsulfonyl)-4-(4,4,5,5-tetramethyl-1,3,2-dioxaborolan-2-yl)-1,2,3,6-tetrahydropyridine following a procedure analogous to that described in Step 4 of Intermediate 2. LC (method 8): $t_R$=0.79 min; Mass spectrum (ESI$^+$): m/z=628 [M+Na]$^+$.

Intermediate 26-1

(1,1-Dioxo-tetrahydrothiophen-3-yl)methanol

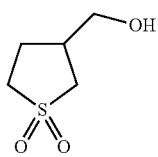

1,1-Dioxo-tetrahydrothiophene-3-carboxylic acid (300 mg) is dissolved in dry tetrahydrofuran (10 mL). The reaction mixture is cooled to 0° C. and borane tetrahydrofuran complex (2 mL) is added dropwise. After stirring for 1 hour at 0° C., the mixture is concentrated under vacuum, partitioned between dichloromethane and water. The organic phase is dried (MgSO$_4$) and concentrated to give the title compound. Yield: 250 mg.

Intermediate 26-2

(1,1-Dioxo-tetrahydro-2H-thiopyran-4-yl)methanol

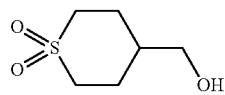

The title compound is prepared in analogy to Intermediate 26-1 starting from 1,1-dioxo-tetrahydro-2H-thiopyran-4-carboxylic acid.

Intermediate 26-3 tert-Butyl 3-(hydroxymethyl)azetidine-1-carboxylate

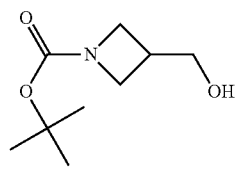

The title compound is prepared in analogy to Intermediate 26-1 starting from 1-(tert-butoxycarbonyl)azetidine-3-carboxylic acid.

Intermediate 26-4

1-(Methylsulfonyl)azetidin-3-yl methanesulfonate

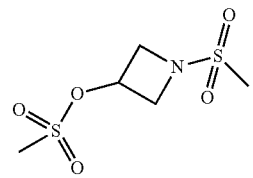

Azetidin-3-ol (3.3 g) and DIPEA (20 mL) are dissolved in dry tetrahydrofuran (40 mL). After 30 min the reaction mixture is cooled to 0° C. and methanesulfonyl chloride (10.9 g) is added dropwise. After stirring for 2 hours at ambient temperature, the mixture is concentrated under vacuum, partitioned between ethyl acetate and water. The organic phase is dried (MgSO$_4$) and concentrated. Chromatography of the residue on silica gel (cyclohexane/ethyl acetate 70:30) gives the title compound. Yield: 5 g.

The intermediates in the following table are prepared following a procedure analogous to that described for Intermediate 26-4.

| starting amino-alcohol | Intermediate | Molecular structure and name |
|---|---|---|
| (R)-(+)-3-pyrrolidinol | 26-5 | (R)-1-(Methylsulfonyl)pyrrolidin-3-yl methanesulfonate |
| (S)-(+)-3-pyrrolidinol | 26-5a | (S)-1-(Methylsulfonyl)pyrrolidin-3-yl methanesulfonate |
| Piperidin-4-yl-methanol | 26-6 | (1-(Methylsulfonyl)piperidin-4-yl)methyl methanesulfonate |

-continued

| starting amino-alcohol | Intermediate | Molecular structure and name |
|---|---|---|
| Piperidin-4-ol | 26-6a | Methanesulfonic acid methanesulfonyl-piperidin-4-yl ester |
| (structure with OH) | 26-6b | (S)-3-Methanesulfonyloxy-piperidine-1-carboxylic acid tert-butyl ester |
| (structure with OH) | 26-6c | (R)-3-Methanesulfonyloxy-piperidine-1-carboxylic acid tert-butyl ester |

Intermediate 26-7

1,1-Dioxo-tetrahydro-2H-thiopyran-4-yl methanesulfonate

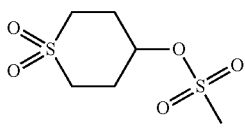

Methanesulfonyl chloride (0.15 mL), (1,1-dioxo-tetrahydro-2H-thiopyran-4-yl)methanol (150 mg) and triethylamine (0.3 mL) are stirred at 0° C. in dry dichloromethane (2 mL). After 30 min, the reaction mixture is warmed to ambient temperature. After stirring for 3 hours, the mixture is diluted with dichloromethane, washed with 10% aqueous solution of KHSO$_4$, then with 10% aqueous solution of K$_2$CO$_3$. The organic phase is collected by passing through a phase separator cartridge and concentrated. The residue is chromatographed on silica gel (dichloromethane/methanol 100:0→95:5) to give the title compound. Yield: 197 mg.

Intermediate 26-8

Trans-3-(tert-butoxycarbonylamino)cyclobutyl 4-methylbenzenesulfonate

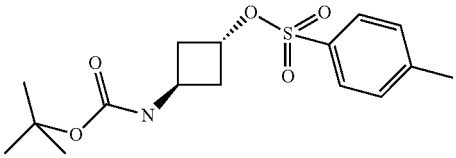 [SMILES: Cc1ccc(S(=O)(=O)O[C@H]2C[C@H](NC(=O)OC(C)(C)C)C2)cc1]

Trans-tert-butyl-3-hydroxycyclobutylcarbamate (440 mg), p-toluenesulfonyl chloride (498 mg) and pyridine (0.74 mL) are dissolved in dichloromethane (7 mL) and a catalytic amount of 4-(dimethylamino)pyridine is added. The reaction mixture is stirred at ambient temperature overnight, concentrated, partitioned between ethyl acetate and water. The organic phase is washed with a 20% aqueous solution of citric acid, dried (MgSO$_4$) and concentrated to give the title compound. Yield: 806 mg.

Intermediate 26-9

Methanesulfonic acid 1-methanesulfonyl-3-methyl-azetidin-3-ylmethyl ester

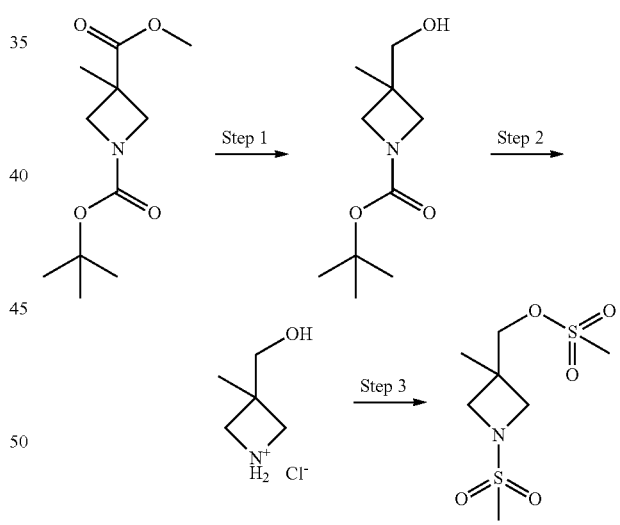

Step 1:
3-Hydroxymethyl-3-methyl-azetidine-1-carboxylic acid tert-butyl ester

3-Methyl-azetidine-1,3-dicarboxylic acid 1-tert-butyl ester 3-methyl ester (WO2006/73361 A1, 2006) (1.1 g) is dissolved in 20 mL of tetrahydrofurane. Lithiumborohydride (16.8 mL of a 2 M solution in tetrahydrofurane) is added dropwise and the reaction mixture is stirred at room temperature overnight. The reaction mixture is diluted with water, washed with a saturated ammonium chloride water solution and the organic phase is separated, dried over sodium sulfate and concentrated under vacuum. The residue is chromatographed on silica gel (hexane/ethyl acetate 100:0→50:50) to give the title compound. Yield: 970 mg.

Step 2: 3-Hydroxymethyl-3-methyl-azetidine hydrochloride

3-Hydroxymethyl-3-methyl-azetidine-1-carboxylic acid tert-butyl ester (1 g) is dissolved in 5 mL of ethyl ether. A 2 M aqueous solution of hydrochloric acid (4 mL) is added, the reaction mixture is stirred overnight and then concentrated under vacuum to give the title compound. Yield: 600 mg.

Step 3: Methanesulfonic acid 1-methanesulfonyl-3-methyl-azetidin-3-ylmethyl ester The title compound is prepared following a procedure analogous to that described for Intermediate 26-4.

Intermediate 26-10

Methanesulfonic acid 2-methanesulfonyl-2-methyl-propyl ester

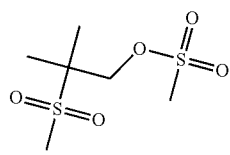

The title compound is prepared following a procedure analogous to that described for Intermediate 26-7 starting from 2-methanesulfonyl-2-methyl-propan-1-ol (Rouchard, Jean; Moons, Chantal; Meyer, Joseph Bulletin de la Societe Chimique de France, 1980, vol. 2, #9-10 p. 441-443).

Intermediate 27-1

1,1-Dioxo-3-((4-bromo-3,5-dimethylphenoxy)methyl)tetrahydrothiophene

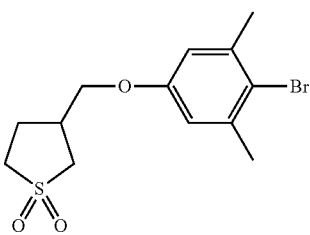 [SMILES: Cc1cc(OCC2CCS(=O)(=O)C2)cc(C)c1Br]

Intermediate 26-1 (235 mg), 4-bromo-3,5-dimethylphenol (318 mg), di-tert-butyl azodicarboxylate (396 mg) and triphenylphosphine (451 mg) are dissolved in dichloromethane (100 mL). The mixture is stirred at ambient temperature for 2 hours, diluted with dichloromethane and washed with water and brine. The organic phase is dried (MgSO$_4$) and concentrated. The residue is chromatographed on silica gel (cyclohexane/ethyl acetate 100:0→50:50) to give the title compound. Yield: 260 mg.

Intermediate 27-1a (S)-3-(4-Bromo-3,5-dimethyl-phenoxymethyl)-tetrahydro-thiophene 1,1-dioxide

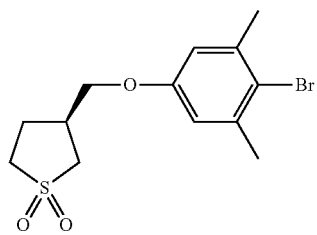 [SMILES: Cc1cc(OC[C@@H]2CCS(=O)(=O)C2)cc(C)c1Br]

The title compound is obtained by chiral HPLC chromatographic separation of the racemate 1,1-dioxo-3-((4-bromo-3,5-dimethylphenoxy)methyl)tetrahydrothiophene.
Chiral HPLC (method 1a): t$_R$=18.85 min.
Absolute configuration unknown.

Intermediate 27-1b (R)-3-(4-Bromo-3,5-dimethyl-phenoxymethyl)-tetrahydro-thiophene 1,1-dioxide

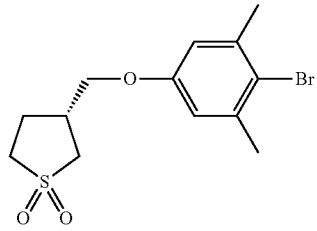 [SMILES: Cc1cc(OC[C@H]2CCS(=O)(=O)C2)cc(C)c1Br]

Further elution from the chiral column gives the title compound.
Chiral HPLC (method 1a): t$_R$=23, 57 min
Absolute configuration unknown.

Intermediate 27-2

1,1-Dioxo-4-((4-bromo-3,5-dimethylphenoxy)methyl)tetrahydro-2H-thiopyran

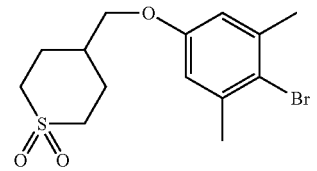 [SMILES: Cc1cc(OCC2CCS(=O)(=O)CC2)cc(C)c1Br]

The title compound is prepared in analogy to Intermediate 27-1, starting from Intermediate 26-2.

Intermediate 27-2a 3-(4-Bromo-3,5-dimethyl-phenoxymethyl)-tetrahydro-thiopyran 1,1-dioxide

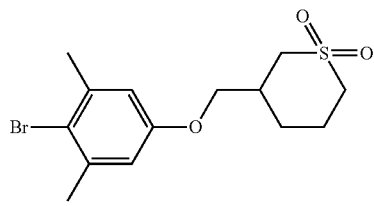 [SMILES: Cc1cc(OCC2CCCS(=O)(=O)C2)cc(C)c1Br]

3-(Bromomethyl)tetrahydro-2H-thiopyrane 1,1-dioxide (1 g) is dissolved in 40 mL of N,N-dimethylformamide. 4-Bromo-3,5-dimethylphenol (885 mg) and cesium carbonate (2.85 g) are added and the reaction mixture is stirred at 130° C. overnight. The reaction mixture is concentrated under vacuum. Water is added and the mixture is extracted with ethyl acetate, The organic phase is separated, dried over sodium sulfate and concentrated under vacuum. The residue is chromatographed on silica gel (cyclohexane/ethyl acetate 100:0→80:20) to give the title compound. Yield: 800 mg.

Intermediate 27-3

3-((4-Bromo-3,5-dimethylphenoxy)methyl)azetidine

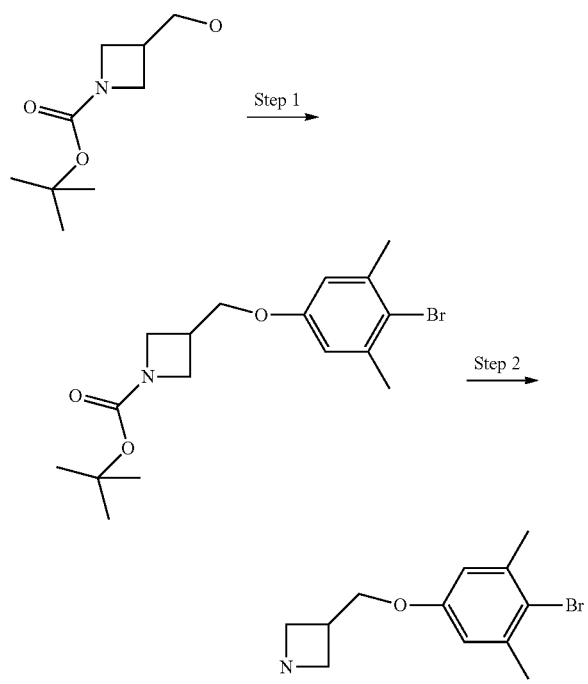

Step 1: tert-Butyl 3-((4-bromo-3,5-dimethylphenoxy)methyl)azetidine-1-carboxylate the title compound is prepared starting from Intermediate 26-3 and 4-bromo-3,5-dimethylphenol as described in the preparation of Intermediate 27-1.

Step 2: 3-((4-Bromo-3,5-dimethylphenoxy)methyl)azetidine tert-Butyl 3-((4-bromo-3,5-dimethylphenoxy)methyl)azetidine-1-carboxylate (900 mg) and trifluoroacetic acid (0.3 mL) are dissolved in dichloromethane (40 mL). The reaction mixture is stirred at 0° C. for 6 hours, diluted with a saturated aqueous solution of NaHCO$_3$, dried (MgSO$_4$) and concentrated to give the title compound. Yield: 400 mg.

Intermediate 27-4

3-((4-Bromo-3,5-dimethylphenoxy)methyl)-1-(methylsulfonyl)azetidine

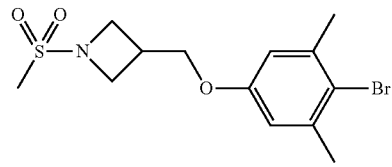 [SMILES: Cc1cc(OCC2CN(S(C)(=O)=O)C2)cc(C)c1Br]

Intermediate 27-3 (400 mg) and N-ethyldiisopropylamine (0.48 mL) are dissolved in dry dichloromethane (26 mL). The reaction mixture is cooled to 0° C. and methanesulfonyl chloride (0.1 mL) is added dropwise. After stirring for 0.5 hours at ambient temperature, the mixture is partitioned between dichloromethane and water. The organic phase is dried (MgSO$_4$) and concentrated. The residue is chromatographed on silica gel (cyclohexane/ethyl acetate 100:0→50:50) to give the title compound. Yield: 330 mg.

The bromo-aryl intermediates in the following table are prepared starting from Intermediate 27-3 and the corresponding sulfonyl chlorides following a procedure analogous to that described for Intermediate 27-4.

| Sulfonyl chloride | Intermediate | Molecular structure and name |
|---|---|---|
| Ethanesulfonyl chloride | 27-5 | 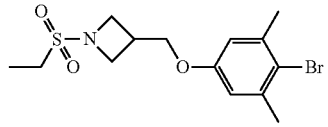<br>3-((4-bromo-3,5-dimethylphenoxy)methyl)-1-(ethylsulfonyl)azetidine |
| Isopropylsulfonyl chloride | 27-6 | 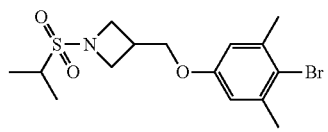<br>3-((4-bromo-3,5-dimethylphenoxy)methyl)-1-(isopropylsulfonyl)azetidine |

Intermediate 27-7

3-(4-Bromo-3,5-dimethylphenoxy)-1-(methylsulfonyl)azetidine

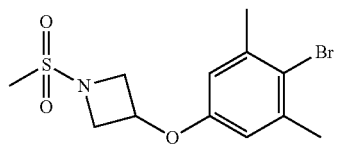

In a microwave vial 4-bromo-3,5-dimethylphenol (1 g) and sodium hydride (100 mg) are stirred in dry N,N-dimethylacetamide (25 mL) for 30 minutes. Intermediate 26-4 (1 g) is added, the vial is sealed and the mixture is stirred at 140° C. for 1.5 hours (100 W). After cooling to ambient temperature, the mixture is concentrated, partitioned between ethyl acetate and water. The organic phase is dried (MgSO$_4$) and concentrated. The residue is chromatographed on silica gel (cyclohexane/ethyl acetate 100:0→70:30) to give the title compound. Yield: 500 mg.

Intermediate 27-7a 4-(4-Bromo-3,5-dimethyl-phenoxy)-1-methanesulfonyl-piperidine

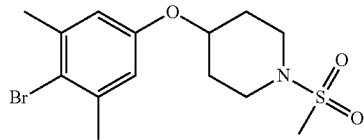 [SMILES: Cc1cc(OC2CCN(S(C)(=O)=O)CC2)cc(C)c1Br]

The title compound is prepared in analogy to Intermediate 27-7, starting from Intermediate 26-6a.

Intermediate 27-7b 3-(4-Bromo-3,5-dimethyl-phenoxymethyl)-1-methanesulfonyl-3-methyl-azetidine

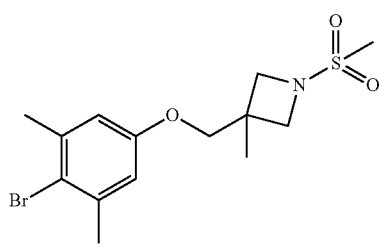

The title compound is prepared in analogy to Intermediate 27-7, starting from Intermediate 26-9.

Intermediate 27-7c (R)-3-(4-Bromo-3,5-dimethyl-phenoxy)-1-methanesulfonyl-pyrrolidine

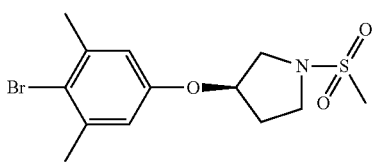 [SMILES: Cc1cc(O[C@@H]2CCN(S(C)(=O)=O)C2)cc(C)c1Br]

The title compound is prepared in analogy to Intermediate 27-7, starting from intermediate 26-5a.

Intermediate 27-7d (R)-3-(4-Bromo-3,5-dimethyl-phenoxy)-1-methanesulfonyl-piperidine

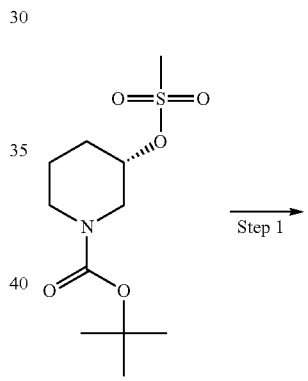

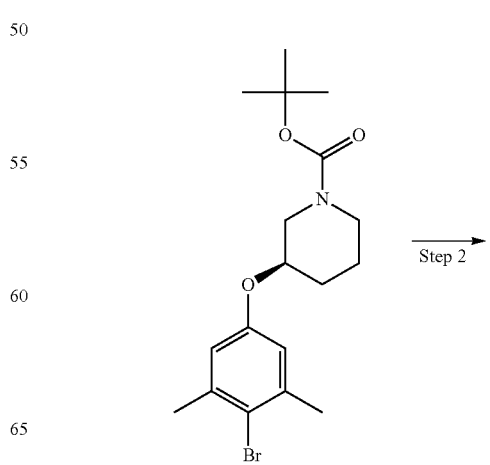

-continued

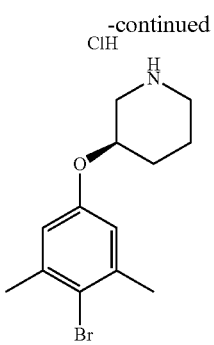

Step 1: (R)-3-(4-Bromo-3,5-dimethyl-phenoxy)-piperidine-1-carboxylic acid tert-butyl ester The title compound is prepared in analogy to Intermediate 27-7, starting from intermediate 26-6b.

Step 2: (R)-3-(4-Bromo-3,5-dimethyl-phenoxy)-piperidine hydrochloride

The title compound is prepared in analogy to Step 2 in the preparation of Intermediate 26-9, starting from (R)-3-(4-Bromo-3,5-dimethyl-phenoxy)-piperidine-1-carboxylic acid tert-butyl ester Step 3: (R)-3-(4-Bromo-3,5-dimethyl-phenoxy)-1-methanesulfonyl-piperidine The title compound is prepared in analogy to Intermediate 27-4 starting from (R)-3-(4-bromo-3,5-dimethyl-phenoxy)-piperidine hydrochloride.

Intermediate 27-7e (S)-3-(4-Bromo-3,5-dimethyl-phenoxy)-1-methanesulfonyl-piperidine

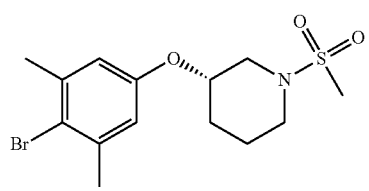 [SMILES: Cc1cc(O[C@H]2CCCN(S(C)(=O)=O)C2)cc(C)c1Br]

The title compound is prepared in analogy to Intermediate 27-7d, starting from intermediate 26-6c.

Intermediate 27-8

1,1-Dioxo-4-(4-bromo-3,5-dimethylphenoxy)tetrahydro-2H-thiopyran

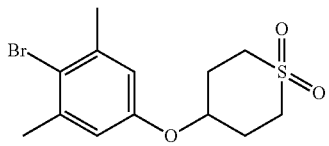 [SMILES: Cc1cc(OC2CCS(=O)(=O)CC2)cc(C)c1Br]

The title compound is prepared in analogy to Intermediate 27-7, starting from Intermediate 26-7.

Intermediate 27-8a

2-Bromo-5-(2-methanesulfonyl-2-methyl-propoxy)-1,3-dimethyl-benzene

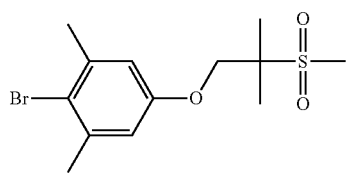 [SMILES: Cc1cc(OCC(C)(C)S(C)(=O)=O)cc(C)c1Br]

The title compound is prepared in analogy to Intermediate 27-7, starting from Intermediate 26-10.

Intermediate 27-9

N-((1s,3s)-3-(4-Bromo-3,5-dimethylphenoxy)cyclobutyl)-N-methylmethanesulfonamide

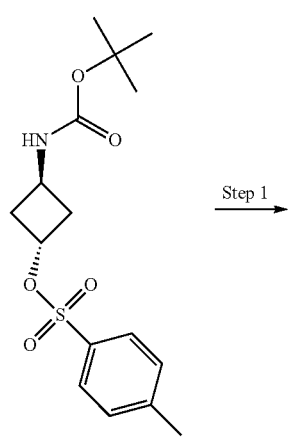

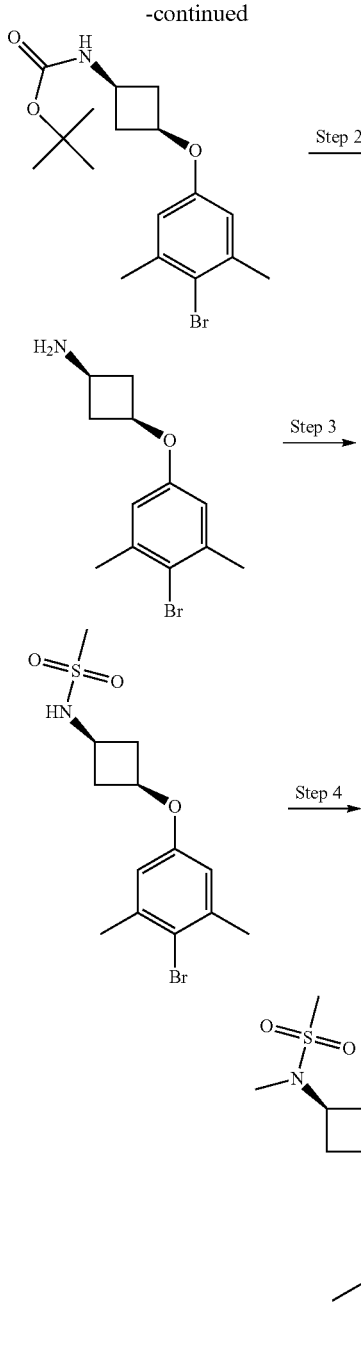

Step 1: tert-Butyl cis-3-(4-bromo-3,5-dimethylphenoxy)cyclobutylcarbamate 4-bromo-3,5-dimethylphenol (450 mg) and sodium hydride (60 mg) are stirred in N,N-dimethylacetamide (15 mL) for 30 minutes. Intermediate 26-8 (300 mg) is added and the mixture is stirred at 80° C. for 3 hours. After cooling to ambient temperature, the mixture is concentrated, partitioned between ethyl acetate and water. The organic phase is dried (MgSO$_4$) and concentrated. The residue is chromatographed on silica gel (cyclohexane/ethyl acetate 90:10→40:60) to give the title compound. Yield: 200 mg.

Step 2: cis-3-(4-Bromo-3,5-dimethylphenoxy)cyclobutanamine tert-Butyl cis-3-(4-bromo-3,5-dimethylphenoxy)cyclobutylcarbamate (200 mg) and trifluoroacetic acid (0.13 mL) are dissolved in dichloromethane (6 mL). The reaction mixture is stirred at 0° C. for 5 hours, diluted with a saturated aqueous solution of NaHCO$_3$, dried (MgSO$_4$) and concentrated to give the title compound. Yield: 400 mg.

Step 3: N-(cis-3-(4-bromo-3,5-dimethylphenoxy)cyclobutyl)methanesulfonamide

Methanesulfonyl chloride (0.16 mL), cis-3-(4-Bromo-3,5-dimethylphenoxy)cyclobutanamine (300 mg) and triethylamine (0.3 mL) are stirred at 0° C. in dry dichloromethane (25 mL). After 10 min, the reaction mixture is warmed to ambient temperature. After stirring for 3 hours, the mixture is diluted with dichloromethane, washed with 10% aqueous solution of KHSO$_4$, then with 10% aqueous solution of K$_2$CO$_3$. The organic phase was passed through a phase separator and concentrated. The residue is chromatographed on silica gel (cyclohexane/ethyl acetate 90:10→50:50) to give the title compound. Yield: 200 mg.

Step 4: N-(cis-3-(4-bromo-3,5-dimethylphenoxy)cyclobutyl)-N-methylmethanesulfonamide N-(cis-3-(4-bromo-3,5-dimethylphenoxy)cyclobutyl)methanesulfonamide (130 mg) and sodium hydride (16 mg) are stirred in N,N-dimethylacetamide (2 mL) for 10 minutes. Iodomethane (0.1 mL) is added and the mixture is stirred at ambient temperature overnight. After cooling to ambient temperature, the mixture is concentrated, partitioned between ethyl acetate and water. The organic phase is dried (MgSO$_4$) and concentrated. The residue is chromatographed on silica gel (cyclohexane/ethyl acetate gradient of increasing polarity) to give the title compound. Yield: 110 mg.

Intermediate 27-10

(4-Bromo-3,5-dimethylphenoxy)(tert-butyl)dimethylsilane

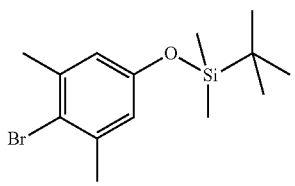 [SMILES: Cc1cc(O[Si](C)(C)C(C)(C)C)cc(C)c1Br]

4-Bromo-3,5-dimethylphenol (3.5 g), 4-(dimethylamino)pyridine (212 mg) and triethylamine (2.7 mL) are stirred in dichloromethane (25 mL) at 0° C., then tert-butyldimethylchlorosilane (19 mL) is added dropwise. The reaction mixture is warmed to ambient temperature and stirred overnight. The reaction mixture is diluted with dichloromethane, washed with aqueous HCl (1 M, 25 mL) and then with saturated aqueous NaHCO₃ (25 mL). The organic phase is dried (MgSO₄) and concentrated to give the title compound. Yield: 5.4 g

Intermediate 27-11

1-Bromo-2-methyl-3-(3-(methylsulfonyl)propoxy)benzene

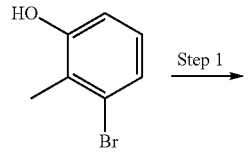

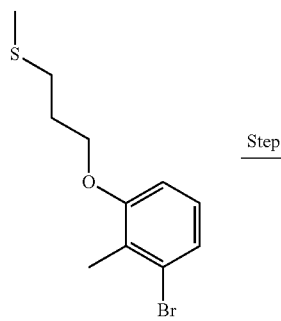 → 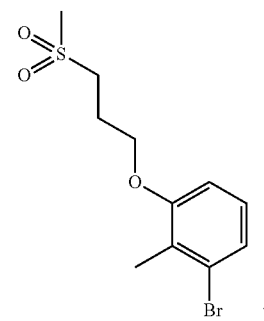

Step 1:
(3-(3-Bromo-2-methylphenoxy)propyl)(methyl)sulfane

3-Bromo-2-methylphenol (0.10 g), 3-(methylthio)propanol (0.055 mL), tri-n-butyl phosphine (0.12 g) and 1,1'-(azodicarbonyl)dipiperidine (0.15 g) are stirred in tetrahydrofurane for 16 hours. Water is added and the mixture extracted with diethyl ether. The organic layer is washed with brine, dried (Na₂SO₄) and volatiles removed under reduced pressure. The product (80 mg) is obtained after column chromatography (silica gel, n-hexane/ethyl acetate gradient 100:0 to 50:50).

Step 2: 1-Bromo-2-methyl-3-(3-(methylsulfonyl)propoxy)benzene (3-(3-Bromo-2-methylphenoxy)propyl)(methyl)sulfane (0.90 g) and 3-chloroperbenzoic acid (1.7 g) are allowed to react in dichloromethane (15 mL) for 16 h. A saturated solution of K₂CO₃ is added with vigorous stirring, the organic layer collected, washed (brine), dried (Na₂SO₄) and volatiles removed under reduced pressure. The product (0.91 g) is obtained after column chromatography (silica gel, n-hexane/ethyl acetate gradient 100:0 to 70:30).

Intermediate 27-11a

2-Bromo-5-(4-methanesulfonyl-butoxy)-1,3-dimethyl-benzene

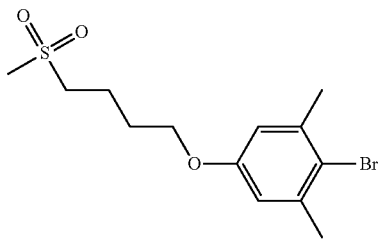 [SMILES: Cc1cc(OCCCCS(C)(=O)=O)cc(C)c1Br]

The title compound is prepared in analogy to Intermediate 27-11, starting from 4-methylsulfanyl-butan-1-ol and from 4-bromo-3,5-dimethyl-phenol.

Intermediate 27-12

4-(3-Bromo-2-methyl-phenoxy)-tetrahydro-thiopyran 1,1-dioxide

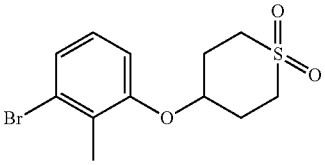 [SMILES: Cc1c(Br)cccc1OC1CCS(=O)(=O)CC1]

The title compound is prepared in analogy to Intermediate 27-7, starting from Intermediate 26-7 and from 3-bromo-2-methyl-phenol.

Intermediate 27-13

2-Bromo-5-((R)-3-methanesulfonyl-2-methyl-propoxy)-1,3-dimethyl-benzene

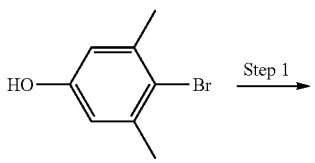

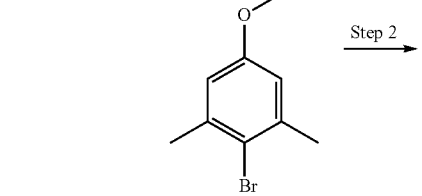

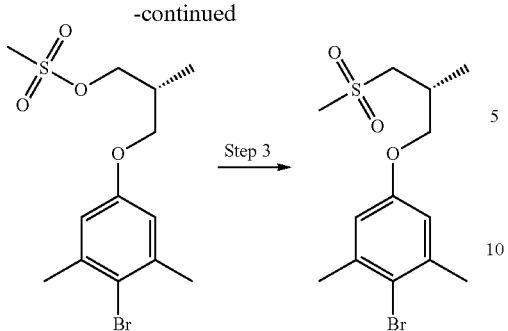

Step 1: (S)-3-(4-Bromo-3,5-dimethyl-phenoxy)-2-methyl-propan-1-ol (S)-3-Bromo-2-methyl-1-propanol (150 mg), 4-bromo-3,5-dimethylphenol (98.5 mg) and potassium carbonate are stirred in 5 mL of acetonitrile at 80° C. for 4 h. The reaction mixture is cooled to room temperature, water is added and the reaction mixture is extracted with diethyl ether. The organic phase is separated, dried over sodium sulfate and concentrated under vacuum to give a solid, used in the next step without further purification. Yield: 130 mg.

Step 2: Methanesulfonic acid (R)-3-(4-bromo-3,5-dimethyl-phenoxy)-2-methyl-propyl ester (S)-3-(4-Bromo-3,5-dimethyl-phenoxy)-2-methyl-propan-1-ol (130 mg), methanesulfonyl chloride (0.073 mL) and triethylamine (0.264 mL) are stirred in 5 mL of dichloromethane at room temperature overnight. The reaction mixture is washed with citric acid saturated aqueous solution and with brine. The organic phase is separated, dried over sodium sulfate and concentrated under vacuum to give the title compound, used in the next step without further purification. Yield: 148 mg.

Step 3: 2-Bromo-5-((R)-3-methanesulfonyl-2-methyl-propoxy)-1,3-dimethyl-benzene

Methanesulfonic acid (R)-3-(4-bromo-3,5-dimethyl-phenoxy)-2-methyl-propyl ester (148 mg) and sodium methanesulfinate (215 mg) are stirred in 3 mL of N,N-dimethylformamide at 80° C. for 4 h. The reaction mixture is cooled to room temperature, water is added and the reaction mixture is extracted with diethyl ether. The organic phase is separated, dried over sodium sulfate and concentrated under vacuum to give the title compound. Yield: 118 mg.

Intermediate 27-14

2-Bromo-5-((S)-3-methanesulfonyl-2-methyl-propoxy)-1,3-dimethyl-benzene

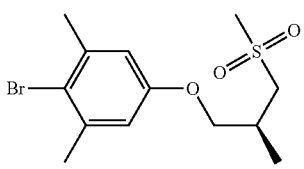 [SMILES: Cc1cc(OC[C@H](C)CS(C)(=O)=O)cc(C)c1Br]

The title compound is prepared in analogy to Intermediate 27-13, starting from (R)-3-bromo-2-methyl-1-propanol.

Intermediate 27-15

2-[2-(4-Bromo-3,5-dimethyl-phenoxy)-ethyl]-isothiazolidine 1,1-dioxide

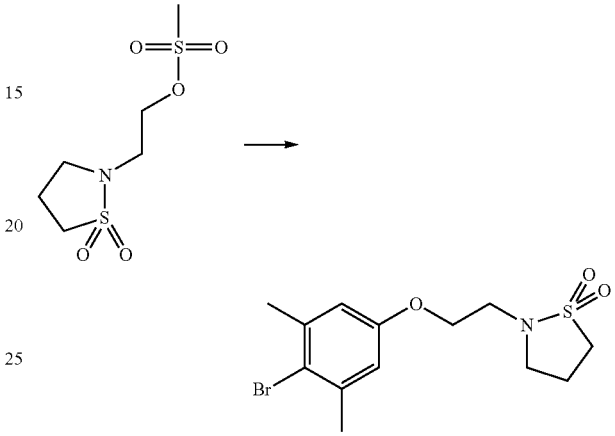

The title compound is prepared in analogy to Intermediate 27-7, starting from methanesulfonic acid 2-(1,1-dioxo-1-isothiazolidin-2-yl)-ethyl ester (EP1479684 A1, 2004).

Intermediate 27-16

4-(4-Bromo-3,5-dimethyl-phenoxy)-[1,2]thiazinane 1,1-dioxide

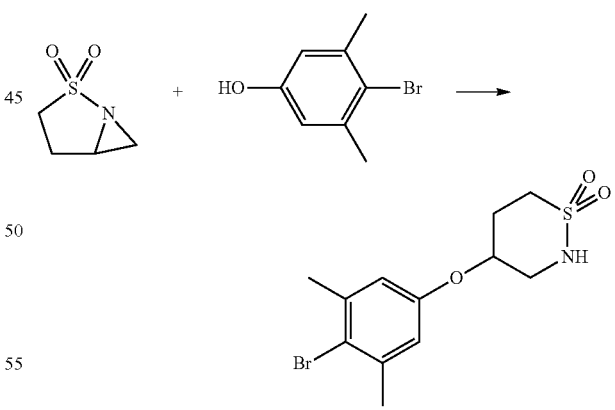

2-Thia-1-aza-bicyclo[3.1.0]hexane 2,2-dioxide (Liang, Jiang-Lin et al., Organic Letters, 2002, vol. 4, #25 p. 4507-4510) (300 mg) is added to a suspension of 4-bromo-3,5-dimethylphenol (1.14 g) and sodium hydride (140 mg of a 60% mineral oil suspension) in 25 mL of N,N-dimethylacetamide. The reaction mixture is stirred at 130° C. for 5 h. Water is added and the reaction mixture is extracted with ethyl acetate. The organic phase is separated, dried over sodium sulfate and concentrated under vacuum. The residue is chromatographed on silica gel (cyclohexane/ethyl acetate 100:0→30:70) to give the title compound. Yield: 220 mg.

Intermediate 27-17

4-(4-Bromo-3,5-dimethyl-phenoxy)-2-methyl-[1,2]thiazinane 1,1-dioxide

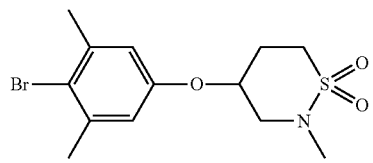 [SMILES: Cc1cc(OC2CCS(=O)(=O)N(C)C2)cc(C)c1Br]

4-(4-Bromo-3,5-dimethyl-phenoxy)-[1,2]thiazinane 1,1-dioxide (110 mg) and sodium hydride (14.5 mg of a 60% mineral oil suspension) are suspended in 2 mL of N,N-dimethylformamide. Iodomethane (0.02 mL) is added and the reaction mixture is stirred at room temperature for 3 h. The solvent is removed, water is added and the reaction mixture is extracted with ethyl acetate. The organic phase is separated, dried over sodium sulfate and concentrated under vacuum. The residue is chromatographed on silica gel (cyclohexane/ethyl acetate 90:10→60:40) to give the title compound. Yield: 110 mg.

Intermediate 27-18

2-(4-Bromo-3,5-dimethyl-phenoxy)-2-methyl-propan-1-ol

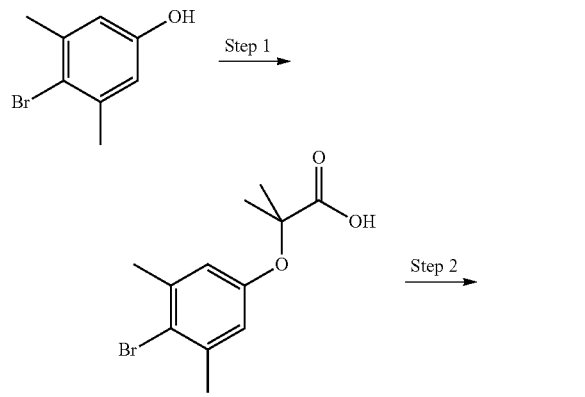

Step 1: 2-(4-Bromo-3,5-dimethyl-phenoxy)-2-methyl-propionic acid

To a solution of 4-bromo-3,5-dimethylphenol (5 g) in 100 mL of acetone stirred at −30° C., sodium hydroxide (31 g) and trichloromethane (6 mL) are added and the reaction mixture is allowed to reach room temperature in 30 min, then warmed to reflux for 3 h. The reaction mixture is concentrated under vacuum, iced-water is added and a 6 M solution of HCl is added up to acidic pH. The reaction mixture is extracted with ethyl acetate. The organic phase is separated, dried over sodium sulfate and concentrated under vacuum. The residue is chromatographed on silica gel (hexane/ethyl acetate: 50/50) to give the title compound. Yield: 8 g.

Step 2: 2-(4-Bromo-3,5-dimethyl-phenoxy)-2-methyl-propan-1-ol 2-(4-Bromo-3,5-dimethyl-phenoxy)-2-methyl-propionic acid (4.45 g) is dissolved in 50 mL of tetrahydrofurane, borane methylsulfide complex (2.6 mL) is added and the reaction mixture is stirred at room temperature for 5 h. The reaction mixture is cooled to 0° C., 10% HCl water solution is added dropwise and the reaction mixture is extracted with dichloromethane. The organic phase is separated, dried over sodium sulfate and concentrated under vacuum. The residue is chromatographed on silica gel (hexane/ethyl acetate 100:0→50:50) to give the title compound. Yield: 2.6 g.

Intermediate 27-19

2-(4-Bromo-3,5-dimethyl-phenoxy)-2-methyl-propionamide

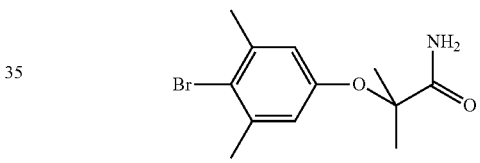

2-(4-Bromo-3,5-dimethyl-phenoxy)-2-methyl-propionic acid (500 mg) is dissolved in 10 mL of tetrahydrofurane, 1,1'-carbonyldimidazole (217 mg) and 30% ammonium hydroxide water solution are added and the reaction mixture is stirred at room temperature for 3 h. The reaction mixture is concentrated under vacuum, ethyl acetate is added and the organic solution is washed with a 10% HCl water solution. The organic phase is separated, dried over sodium sulfate and concentrated under vacuum to give the title compound. Yield: 300 mg.

Intermediate 27-20

3-(4-Bromo-3,5-dimethyl-benzenesulfonyl)-propan-1-ol

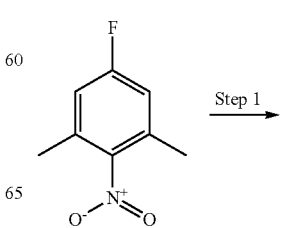

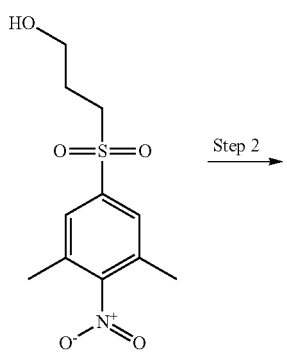

Step 2: 3-(4-Amino-3,5-dimethyl-benzenesulfonyl)-propan-1-ol 3-(3,5-Dimethyl-4-nitro-benzenesulfonyl)-propan-1-ol is dissolved in 15 mL of ethanol, Pd/C(5%) (55 mg) is added and the reaction mixture is stirred under hydrogen atmosphere (3 bar) for 3 h. The reaction mixture is filtered on a celite pad, the solvent is concentrated under vacuum to give the title compound. Yield: 1 g.

Step 3: 3-(4-Bromo-3,5-dimethyl-benzenesulfonyl)-propan-1-ol

The title compound is prepared following a procedure analogous to Step 3 in the preparation of Intermediate 27-21, starting from 3-(4-Amino-3,5-dimethyl-benzenesulfonyl)-propan-1-ol. Yield: 740 mg.

Intermediate 27-21

2-Bromo-5-(3-methoxy-propane-1-sulfonyl)-1,3-dimethyl-benzene

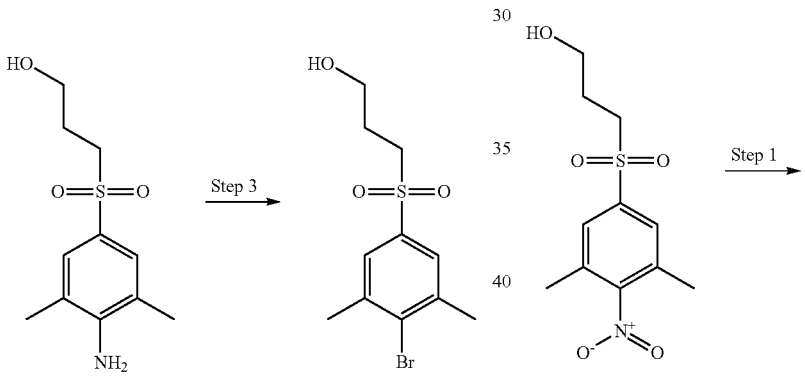

Step 1: 3-(3,5-Dimethyl-4-nitro-benzenesulfonyl)-propan-1-ol

5-Fluoro-1,3-dimethyl-2-nitrobenzene (2 g), 3-mercapto-1-propanol (1.5 mL) and potassium carbonate (2.4 g) are stirred in 20 mL of N,N-dimethylformamide at 60° C. for 4 h. The reaction mixture is cooled to 0° C. and 3-chloroperbenzoic acid (10 g) is added. The reaction mixture is stirred at room temperature for 1 h, water is added and the reaction mixture is extracted with ethyl acetate. The organic phase is washed with a bicarbonate saturated aqueous solution, with a 5% sodium sulfite water solution and with brine. The solvent is remove to give the title compound, used in the next step without further purification. Yield: 2.8 g.

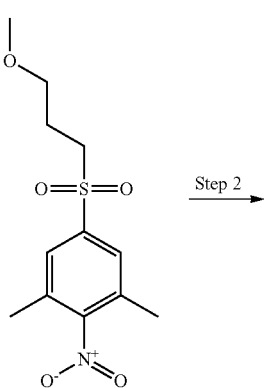

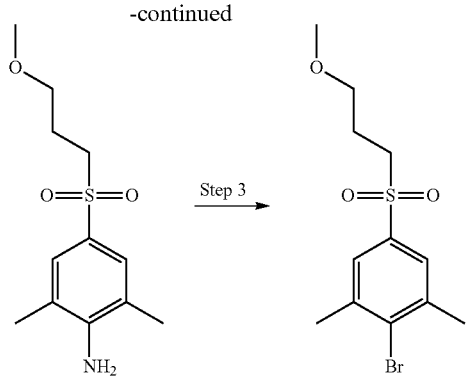

Step 1: 5-(3-Methoxy-propane-1-sulfonyl)-1,3-dimethyl-2-nitro-benzene 3-(3,5-Dimethyl-4-nitro-benzenesulfonyl)-propan-1-ol (1.4 g) is dissolved in 20 mL of acetonitrile, cesium carbonate (3.34 g) and iodomethane (638 mL) are added and the reaction mixture is stirred at room temperature overnight. Water is added and the reaction mixture is extracted with ethyl ether. The organic phase is separated, dried over sodium sulfate and concentrated under vacuum. The residue is chromatographed on silica gel (hexane/ethyl acetate 100:0→50.50) to give the title compound. Yield: 1 g.

Step 2: 4-(3-Methoxy-propane-1-sulfonyl)-2,6-dimethyl-phenylamine

The title compound is prepared following a procedure analogous to Step 2 in the preparation of Intermediate 27-20, starting from 5-(3-Methoxy-propane-1-sulfonyl)-1,3-dimethyl-2-nitro-benzene

Step 3: 2-Bromo-5-(3-methoxy-propane-1-sulfonyl)-1,3-dimethyl-benzene

Copper bromide (730 mg) and tert-butylnitrite (899 µL) are stirred in 15 mL of acetonitrile at 65° C. for 10 minutes, A solution of 4-(3-methoxy-propane-1-sulfonyl)-2,6-dimethyl-phenylamine (700 mg) in acetonitrile (15 mL) is added and the reaction mixture is stirred at 65° C. for 4 h. The reaction mixture is concentrated under vacuum, The residue is chromatographed on silica gel (cyclohexane/ethyl acetate 100:0→50:50) to give the title compound. Yield: 550 mg.

Intermediate 28-1

Methyl 2-((S)-6-((R)-4-(2,6-dimethyl-4-(1-(methylsulfonyl)azetidin-3-yloxy)phenyl)-7-fluoro-2,3-dihydro-1H-inden-1-yloxy)-2,3-dihydrobenzofuran-3-yl)acetate

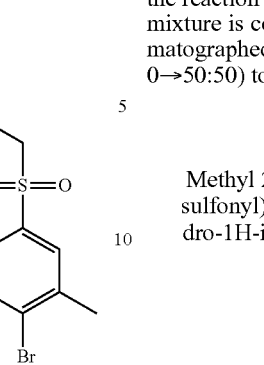

In a microwave vial, methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (130 mg), intermediate 27-7 (104 mg), $K_3PO_4$ (133 mg) are suspended in toluene (2 mL) and water (200 µL) and purged for 10 minutes with nitrogen. Palladium-(II)-acetate (5 mg) and dicyclohexyl(2',6'-dimethoxybiphenyl-2-yl)phosphine (S-Phos) (8.5 mg) are added, the vial is sealed and the mixture is stirred at 120° C. for 1 hours (100 W). After cooling to ambient temperature the mixture is partitioned between diethylether and saturated aqueous $NH_4Cl$ solution. The organic phase is dried ($MgSO_4$) and concentrated. The residue is chromatographed on silica gel (cyclohexane/ethyl acetate 100:0→50:50) to give the title compound. Yield: 55 mg.

The intermediates in the following table are prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and the corresponding starting bromo-aryl intermediates following a procedure analogous to that described for Intermediate 28-1.

| Starting bromoaryl Intermediate | Intermediate | Molecular structure and name |
|---|---|---|
| 27-1 | 28-2 | 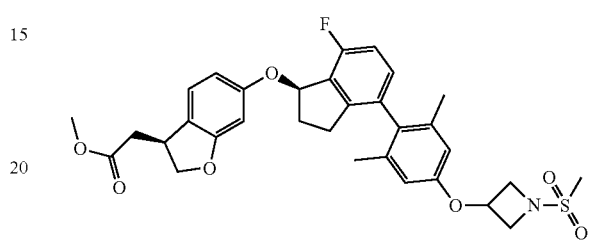<br>Methyl 2-((3S)-6-((1R)-4-(2,6-dimethyl-4-((1,1-dioxo-tetrahydrothiophen-3-yl)methoxy)phenyl)-7-fluoro-2,3-dihydro-1H-inden-1-yloxy)-2,3-dihydrobenzofuran-3-yl)acetate |

| Starting bromoaryl Intermediate | Intermediate | Molecular structure and name |
|---|---|---|
| 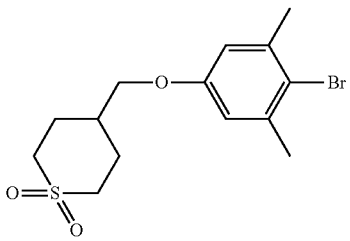<br>27-2 | 28-3 | 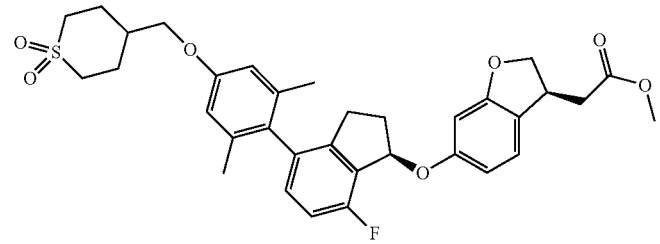<br>Methyl 2-((S)-6-((R)-4-(2,6-dimethyl-4-((1,1-dioxo-tetrahydro-2H-thiopyran-4-yl)methoxy)phenyl)-7-fluoro-2,3-dihydro-1H-inden-1-yloxy)-2,3-dihydrobenzofuran-3-yl)acetate |
| 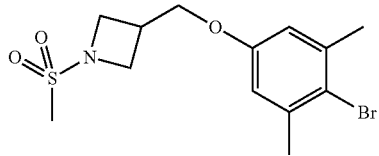<br>27-4 | 28-4 | 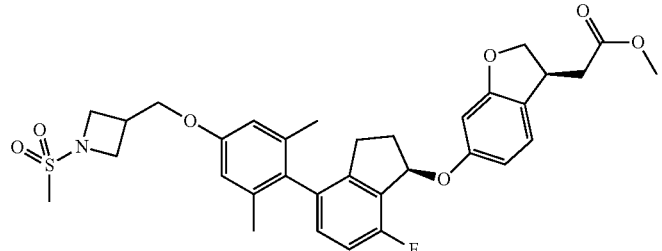<br>Methyl 2-((S)-6-((R)-4-(2,6-dimethyl-4-((1-(methylsulfonyl)azetidin-3-yl)methoxy)phenyl)-7-fluoro-2,3-dihydro-1H-inden-1-yloxy)-2,3-dihydrobenzofuran-3-yl)acetate |
| 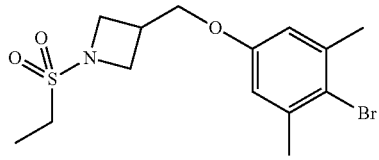<br>27-5 | 28-5 | 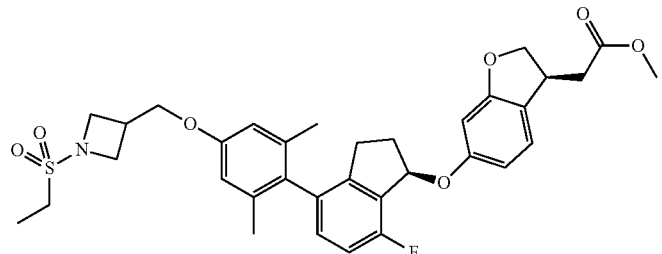<br>Methyl 2-((S)-6-((R)-4-(4-((1-(ethylsulfonyl)azetidin-3-yl)methoxy)-2,6-dimethylphenyl)-7-fluoro-2,3-dihydro-1H-inden-1-yloxy)-2,3-dihydrobenzofuran-3-yl)acetate |
| 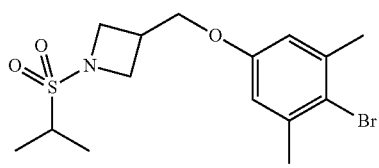<br>27-6 | 28-6 | 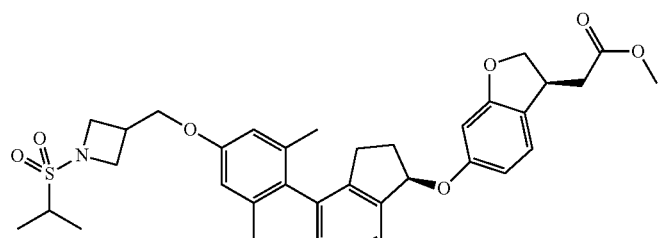<br>Methyl 2-((S)-6-((R)-7-fluoro-4-(4-((1-(isopropylsulfonyl)azetidin-3-yl)methoxy)-2,6-dimethylphenyl)-2,3-dihydro-1H-inden-1-yloxy)-2,3-dihydrobenzofuran-3-yl)acetate |

| Starting bromoaryl Intermediate | Intermediate | Molecular structure and name |
|---|---|---|
| 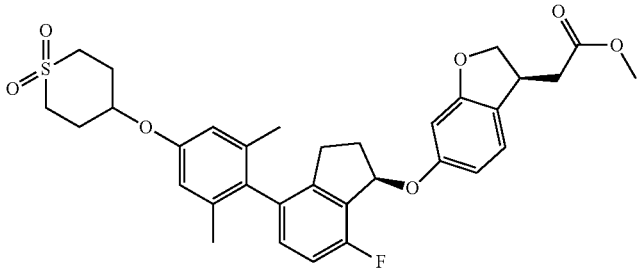 27-8 | 28-7 | Methyl 2-((S)-6-((R)-4-(2,6-dimethyl-4-(1,1-dioxo-tetrahydro-2H-thiopyran-4-yloxy)phenyl)-7-fluoro-2,3-dihydro-1H-inden-1-yloxy)-2,3-dihydrobenzofuran-3-yl)acetate |
| 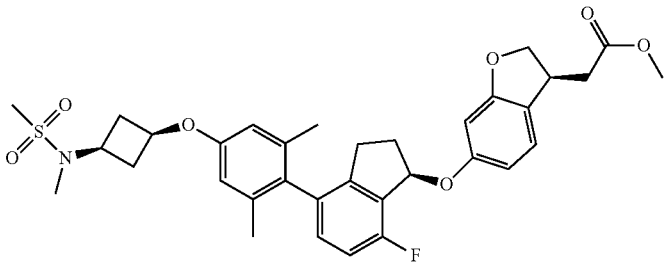 27-9 | 28-8 | Methyl 2-((S)-6-((R)-4-(2,6-dimethyl-4-((1s,3S)-3-(N-methylmethylsulfonamido)cyclobutoxy)phenyl)-7-fluoro-2,3-dihydro-1H-inden-1-yloxy)-2,3-dihydrobenzofuran-3-yl)acetate |
| 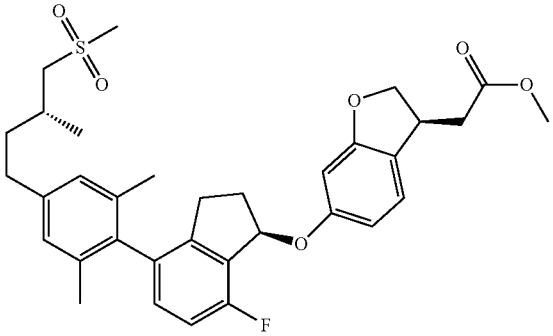 27-13 | 28-9 | ((S)-6-{(R)-7-Fluoro-4-[4-((R)-3-methanesulfonyl-2-methyl-propoxy)-2,6-dimethyl-phenyl]-indan-1-yloxy}-2,3-dihydro-benzofuran-3-yl)-acetic acid methyl ester |

| Starting bromoaryl Intermediate | Intermediate | Molecular structure and name |
| --- | --- | --- |
| 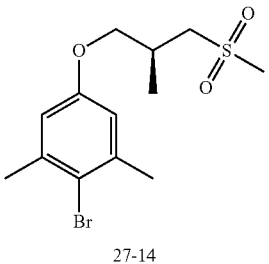<br>27-14 | 28-10 | 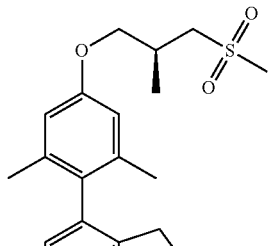<br>((S)-6-{(R)-7-Fluoro-4-[4-((S)-3-methanesulfonyl-2-methyl-propoxy)-2,6-dimethyl-phenyl]-indan-1-yloxy}-2,3-dihydro-benzofuran-3-yl)-acetic acid methyl ester |
| 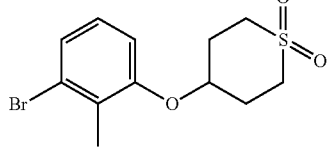<br>27-12 | 28-11 | 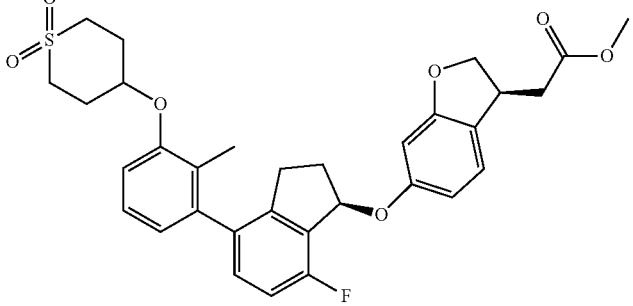<br>((S)-6-{(R)-4-[3-(1,1-Dioxo-hexahydro-1-thiopyran-4-yloxy)-2-methyl-phenyl]-7-fluoro-indan-1-yloxy}-2,3-dihydro-benzofuran-3-yl)-acetic acid methyl ester |
| 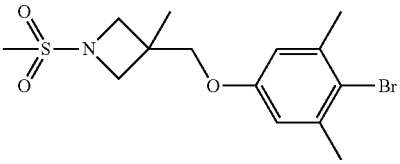<br>27-7b | 28-12 | 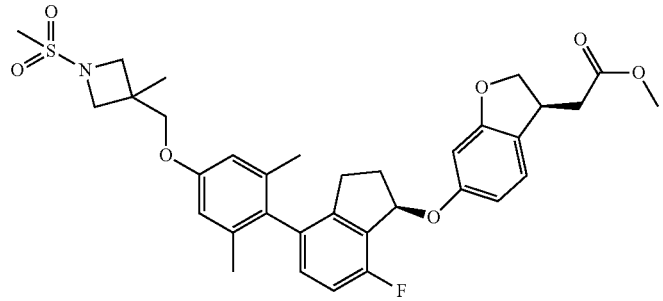<br>((S)-6-{(R)-7-Fluoro-4-[4-(1-methanesulfonyl-3-methyl-azetidin-3-ylmethoxy)-2,6-dimethyl-phenyl]-indan-1-yloxy}-2,3-dihydro-benzofuran-3-yl)-acetic acid methyl ester |

-continued

| Starting bromoaryl Intermediate | Intermediate | Molecular structure and name |
|---|---|---|
| 27-15 | 28-13 | [(S)-6-((R)-4-{4-[2-(1,1-Dioxo-1-isothiazolidin-2-yl)-ethoxy]-2,6-dimethyl-phenyl}-7-fluoro-indan-1-yloxy)-2,3-dihydro-benzofuran-3-yl]-acetic acid methyl ester |
| 27-16 | 28-14 | ((S)-6-{(R)-4-[4-(1,1-Dioxo-1-[1,2]thiazinan-4-yloxy)-2,6-dimethyl-phenyl]-7-fluoro-indan-1-yloxy}-2,3-dihydro-benzofuran-3-yl)-acetic acid methyl ester |
| 27-17 | 28-15 | ((S)-6-{(R)-4-[2,6-Dimethyl-4-(2-methyl-1,1-dioxo-1-1,2]thiazinan-4-yloxy)-phenyl]-7-fluoro-indan-1-yloxy}-2,3-dihydro-benzofuran-3-yl)-aceticacid methyl ester |

-continued

| Starting bromoaryl Intermediate | Intermediate | Molecular structure and name |
|---|---|---|
| 27-11a | 28-16 | ((S)-6-{(R)-7-Fluoro-4-[4-(4-methanesulfonyl-butoxy)-2,6-dimethyl-phenyl]-indan-1-yloxy}-2,3-dihydro-benzofuran-3-yl)-acetic acid methyl ester |
| 27-7c | 28-17 | ((S)-6-{(R)-7-Fluoro-4-[4-((R)-1-methanesulfonyl-pyrrolidin-3-yloxy)-2,6-dimethyl-phenyl]-indan-1-yloxy}-2,3-dihydro-benzofuran-3-yl)-acetic acid methyl ester |
| 27-8a | 28-18 | ((S)-6-{(R)-7-Fluoro-4-[4-(2-methanesulfonyl-2-methyl-propoxy)-2,6-dimethyl-phenyl]-indan-1-yloxy}-2,3-dihydro-benzofuran-3-yl)-acetic acid methyl ester |

-continued

| Starting bromoaryl Intermediate | Intermediate | Molecular structure and name |
|---|---|---|
| 27-1a | 28-19 | ((S)-6-{(R)-4-[4-((S)-1,1-Dioxo-tetrahydro-1-thiophen-3-ylmethoxy)-2,6-dimethyl-phenyl]-7-fluoro-indan-1-yloxy}-2,3-dihydro-benzofuran-3-yl)-acetic acid methyl ester Absolute configuration unknown. |
| 27-1b | 28-20 | ((S)-6-{(R)-4-[4-((R)-1,1-Dioxo-tetrahydro-1-thiophen-3-ylmethoxy)-2,6-dimethyl-phenyl]-7-fluoro-indan-1-yloxy}-2,3-dihydro-benzofuran-3-yl)-acetic acid methyl ester. Absolute configuration unknown. |
| 27-7a | 28-21 | ((S)-6-{(R)-7-Fluoro-4-[4-(1-methanesulfony-piperidin-4-yloxy)-2,6-dimethyl-phenyl]-indan-1-yloxy}-2,3-dihydro-benzofuran-3-yl)-acetic acid methyl ester |
| 27-7d | 28-22 | ((S)-6-{(R)-7-Fluoro-4-[4-((R)-1-methanesulfonyl-piperidin-3-yloxy)-2,6-dimethyl-phenyl]-indan-1-yloxy}-2,3-dihydro-benzofuran-3-yl)-acetic acid methyl ester |

| Starting bromoaryl Intermediate | Intermediate | Molecular structure and name |
|---|---|---|
| 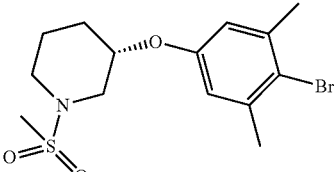<br>27-7e | 28-23 | 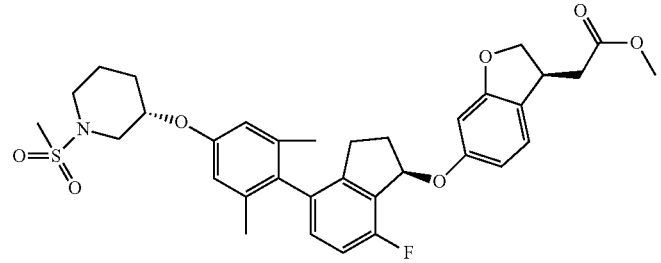<br>((S)-6-{(R)-7-Fluoro-4-[4-((S)-1-methanesulfonyl-piperidin-3-yloxy)-2,6-dimethyl-phenyl]-indan-1-yloxy}-2,3-dihydro-benzofuran-3-yl)-acetic acid methyl ester |
| 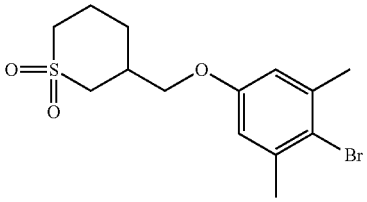<br>27-2a | 28-24 | 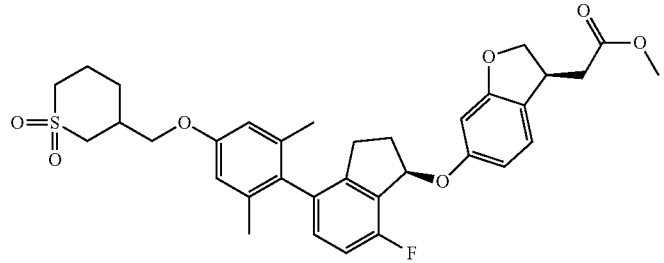<br>((S)-6-{(R)-4-[4-(1,1-Dioxo-hexahydro-1-thiopyran-3-ylmethoxy)-2,6-dimethyl-phenyl]-7-fluoro-indan-1-yloxy}-2,3-dihydro-benzofuran-3-yl)-acetic acid methyl ester |
| 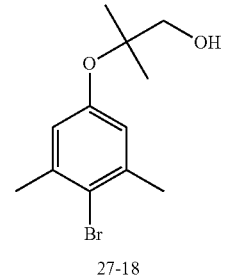<br>27-18 | 28-25 | 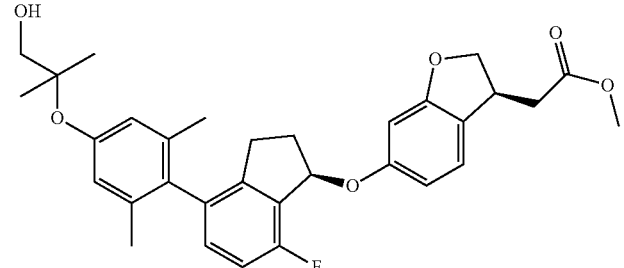<br>((S)-6-{(R)-7-Fluoro-4-[4-(2-hydroxy-1,1-dimethyl-ethoxy)-2,6-dimethyl-phenyl]-indan-1-yloxy}-2,3-dihydro-benzofuran-3-yl)-acetic acid methyl ester |
| 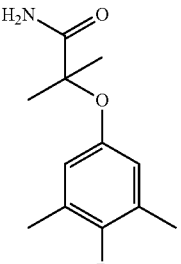<br>27-19 | 28-26 | 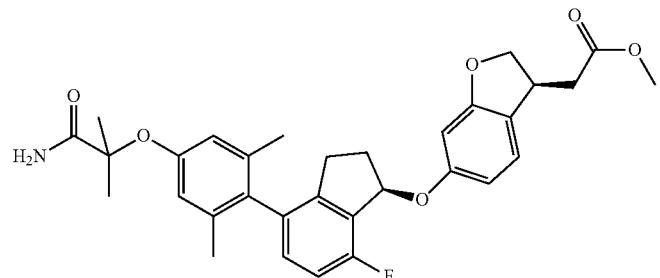<br>((S)-6-{(R)-4-[4-(1-Carbamoyl-1-methyl-ethoxy)-2,6-dimethyl-phenyl]-7-fluoro-indan-1-yloxy}-2,3-dihydro-benzofuran-3-yl)-acetic acid methyl ester |

-continued

| Starting bromoaryl Intermediate | Intermediate | Molecular structure and name |
|---|---|---|
| 27-20 | 28-27 | ((S)-6-{(R)-7-Fluoro-4-[4-(3-hydroxy-propane-1-sulfonyl)-2,6-dimethyl-phenyl]-indan-1-yloxy}-2,3-dihydro-benzofuran-3-yl)-acetic acid methyl ester |
| 27-21 | 28-28 | (6-{7-Fluoro-4-[4-(3-methoxy-propane-1-sulfonyl)-2,6-dimethyl-phenyl]-indan-1-yloxy}-2,3-dihydro-benzofuran-3-yl)-acetic acid methyl ester |

Intermediate 28-29

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate

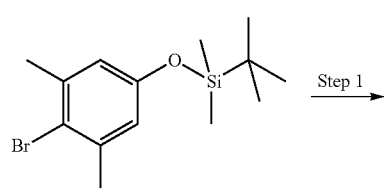

Step 1 →

-continued

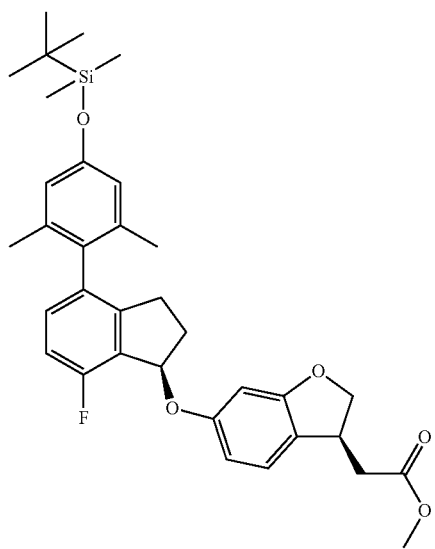

Step 2 →

-continued

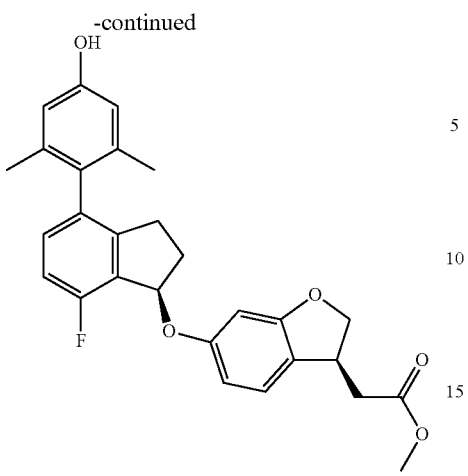

Step 1: Methyl 2-((S)-6-((R)-4-(4-(tert-butyldimethylsilyloxy)-2,6-dimethylphenyl)-7-fluoro-2,3-dihydro-1H-inden-1-yloxy)-2,3-dihydrobenzofuran-3-yl)acetate Methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (500 mg), Intermediate 27-10 (500 mg), $K_3PO_4$ (450 mg) are suspended in toluene (2.5 mL) and water (0.2 mL) and purged for 10 minutes with argon. Palladium-(II)-acetate (12 mg) and dicyclohexyl(2',6'-dimethoxybiphenyl-2-yl)phosphine (S-Phos) (44 mg) are added and the mixture is stirred at 100° C. overnight. After cooling to ambient temperature the mixture is partitioned between diethylether and saturated aqueous $NH_4Cl$ solution. The organic phase is dried ($MgSO_4$) and concentrated. The residue is chromatographed on silica gel (cyclohexane/ethyl acetate 99:1→70:30) to give the title compound. Yield: 440 mg.

Step 2: Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate Methyl 2-((S)-6-((R)-4-(4-(tert-butyldimethylsilyloxy)-2,6-dimethylphenyl)-7-fluoro-2,3-dihydro-1H-inden-1-yloxy)-2,3-dihydrobenzofuran-3-yl)acetate (440 mg) and tetrabutylammonium fluoride in tetrahydrofuran (1 M; 3.1 mL) are stirred in tetrahydrofuran (5 mL) at ambient temperature overnight. The reaction mixture is partitioned between diethylether and saturated aqueous $NH_4Cl$ solution. The organic phase is dried ($MgSO_4$) and concentrated. The residue is chromatographed on silica gel (cyclohexane/ethyl acetate 90:10→60:40) to give the title compound. Yield: 280 mg.

Intermediate 28-30

Methyl 2-((S)-6-((R)-4-(2,6-dimethyl-4-((S)-1-(methylsulfonyl)pyrrolidin-3-yloxy)phenyl)-7-fluoro-2,3-dihydro-1H-inden-1-yloxy)-2,3-dihydrobenzofuran-3-yl)acetate

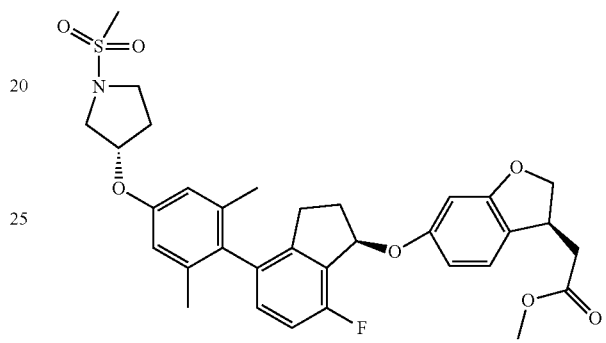

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (60 mg), Intermediate 26-5 and $K_2CO_3$ (34 mg) are suspended in N,N-dimethylformamide (5 mL) and stirred at 95° C. for 72 hours. The reaction mixture is concentrated under vacuum, partitioned between ethyl acetate and water. The organic phase is dried ($MgSO_4$) and concentrated. The residue is chromatographed on silica gel (cyclohexane/ethyl acetate 100:0→75:25) to give the title compound. Yield: 29 mg.

Intermediate 28-31

Methyl 2-((S)-6-((R)-4-(2,6-dimethyl-4-((1-(methylsulfonyl)piperidin-4-yl)methoxy)phenyl)-7-fluoro-2,3-dihydro-1H-inden-1-yloxy)-2,3-dihydrobenzofuran-3-yl)acetate

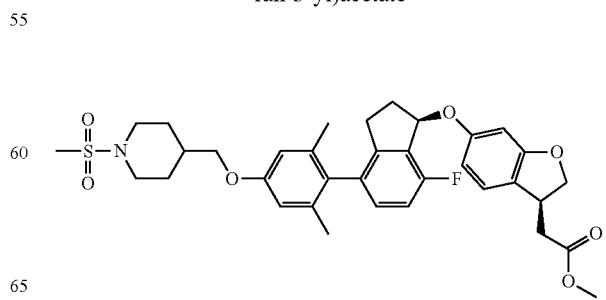

143

The title compound is prepared in analogy to Intermediate 28-30 starting from Intermediate 26-6 and Intermediate 29-29.

Intermediate 28-32

Methyl 2-((3S)-6-((1R)-7-fluoro-4-(2-methyl-3-(3-(methylsulfonyl)propoxy)phenyl)-2,3-dihydro-1H-inden-1-yloxy)-2,3-dihydrobenzofuran-3-yl)acetate

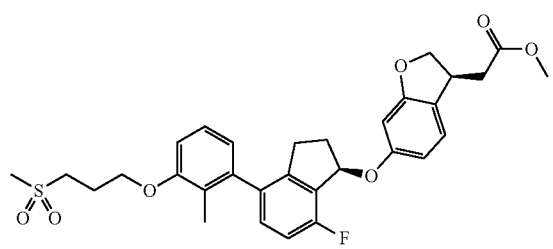

The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and Intermediate 27-11 following a procedure analogous to that described for Intermediate 28-1.

LC (method 17): $t_R$=1.38 min.

Intermediate 29

Methyl 2-((S)-6-((R)-4-(2,6-dimethyl-4-(3-(methylsulfonyl)propoxy)phenyl)-7-fluoro-2,3-dihydro-1H-inden-1-yloxy)-2,3-dihydrobenzofuran-3-yl)acetate

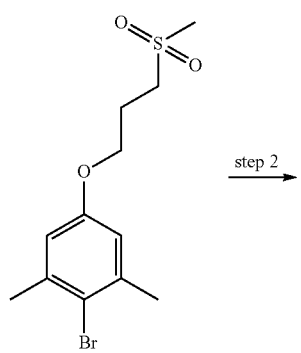

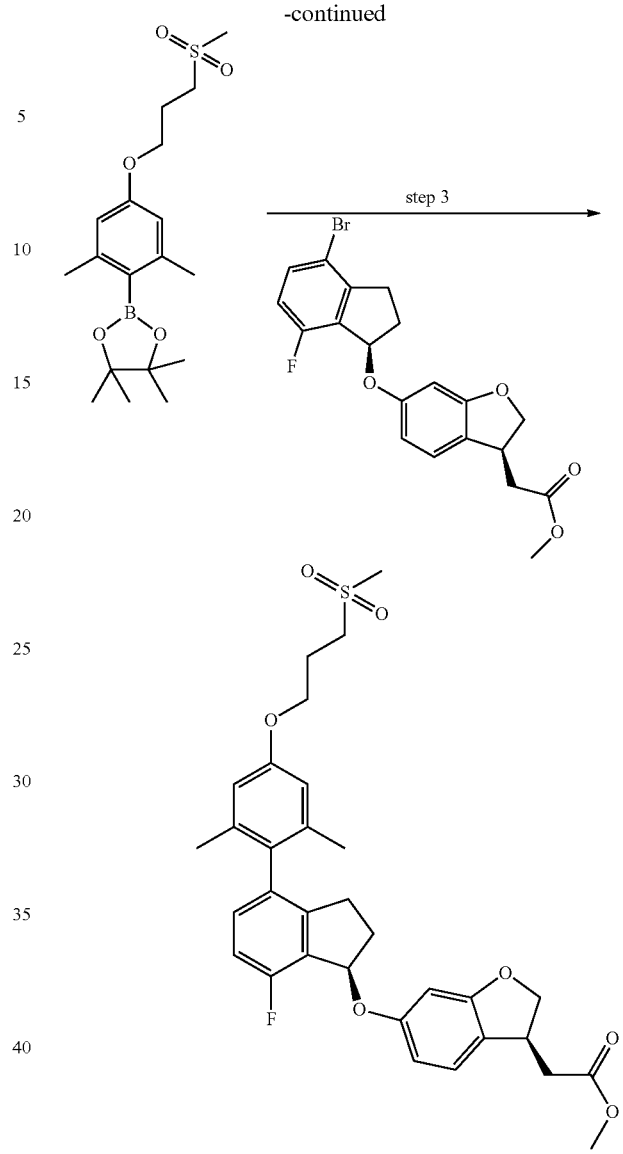

Step 1: 2-Bromo-1,3-dimethyl-5-(3-(methylsulfonyl)propoxy)benzene

4-Bromo-3,5-dimethylphenol (0.5 g), 3-methylthiopropanol (0.25 mL), triphenyl phosphine (710 mg) and di-tert-butyl azodicarboxylate (624 mg) are dissolved in dichloromethane (10 mL) and stirred for 2 hours. 3-Chloroperbenzoic acid (1.3 g) is added and the mixture is stirred overnight. The mixture is washed with saturated sodium carbonate solution, the organic phase collected by passing through a phase separator cartridge and the solvent removed under vacuum. The residue is purified by chromatography on silica gel (cyclohexane/ethyl acetate 100:0→0:100) to give the title compound (480 mg).

Step 2: 2-(2,6-Dimethyl-4-(3-(methylsulfonyl)propoxy)phenyl)-4,4,5,5-tetramethyl-1,3,2-dioxaborolane 2-Bromo-1,3-dimethyl-5-(3-(methylsulfonyl)propoxy)benzene (100 mg), bis(pinacolato)diboron (158 mg), [1,1'-bis (diphenylphosphino)-ferrocene]-dichloropalladium-(II) (23 mg) and potassium acetate (92 mg) are suspended in dry 1,4-dioxane (3 mL) in a microwave vial and degassed for 5 minutes with a flow of nitrogen. The mixture is heated under microwave irradiation for 60 minutes at 110° C. The mixture is diluted with ethyl acetate, washed with water, the organic phase dried and the solvent removed under vacuum. The residue is purified by chromatography on silica gel (cyclohexane/ethyl acetate 100:0→0:100) to give the title compound (110 mg).

vacuum. The residue is purified by chromatography on silica gel (cyclohexane/ethyl acetate 100:0→50:50) to give the title compound (9 mg). LC (method 19): $t_R$=1.38 min; Mass spectrum: m/z=583 [M+H]$^+$.

Intermediate 30

2-((3S)-6-((1R)-4-(3-Cyano-2-methylphenyl)-7-fluoro-2,3-dihydro-1H-inden-1-yloxy)-2,3-dihydrobenzofuran-3-yl)acetic acid

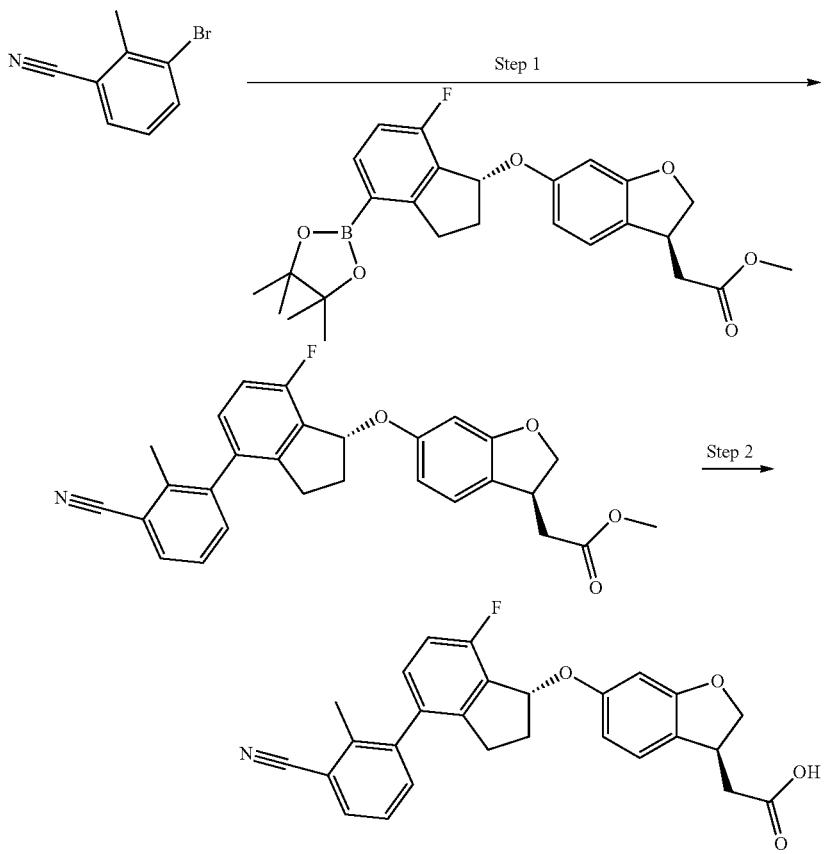

LC (method 19): $t_R$=1.24 min; Mass spectrum: m/z=386 [M+NH$_4$]$^+$.

Step 3: Methyl 2-((S)-6-((R)-4-(2,6-dimethyl-4-(3-(methylsulfonyl)propoxy)phenyl)-7-fluoro-2,3-dihydro-1H-inden-1-yloxy)-2,3-dihydrobenzofuran-3-yl) acetate Methyl 2-((S)-6-((R)-4-bromo-7-fluoro-2,3-dihydro-1H-inden-1-yloxy)-2,3-dihydrobenzofuran-3-yl)acetate [intermediate 1, step 3] (32 mg), 2-(2,6-dimethyl-4-(3-(methylsulfonyl)propoxy)phenyl)-4,4,5,5-tetramethyl-1,3,2-dioxaborolane (42 mg), [1,1'-bis(diphenylphosphino)-ferrocene]-dichloropalladium-(II) (6 mg), 1,1'-bis (diphenylphosphino)-ferrocene (4 mg) and caesium carbonate (50 mg) are suspended in toluene (2 mL) and degassed for 5 minutes with a flow of nitrogen. The mixture is heated under microwave irradiation for 90 minutes at 120° C. The mixture is diluted with ethyl acetate, washed with water, the organic phase dried and the solvent removed under Step 1: Methyl 2-((3S)-6-((1R)-4-(3-cyano-2-methylphenyl)-7-fluoro-2,3-dihydro-1H-inden-1-yloxy)-2,3-dihydrobenzofuran-3-yl)acetate In a microwave vial, methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (200 mg), 3-bromo-2-methylbenzonitrile (169 mg), K$_3$PO$_4$ (274 mg), Palladium-(II)-acetate (10 mg) and dicyclohexyl(2',6'-dimethoxybiphenyl-2-yl)phosphine (S-Phos) (18 mg) are suspended in toluene (10 mL) and water (2 mL) and purged for 10 minutes with argon. The vial is sealed and the mixture is stirred at 100° C. for 4 hours. After cooling to ambient temperature the mixture is partitioned between ethyl acetate and water. The organic phase is dried (MgSO$_4$) and concentrated. The residue is chromatographed on silica gel (cyclohexane/ethyl acetate 90:10) to give the title compound. Yield: 124 mg; LC (method 20): $t_R$=8.09 min; Mass spectrum (ESI$^+$): m/z=558 [M+−H]$^+$.

Step 2: 2-((3S)-6-(((1R)-4-(3-Cyano-2-methylphenyl)-7-fluoro-2,3-dihydro-1H-inden-1-yloxy)-2,3-dihydrobenzofuran-3-yl)acetic acid LiOH×H$_2$O (131 mg) is added to a solution of methyl 2-((3S)-6-(((1R)-4-(3-cyano-2-methylphenyl)-7-fluoro-2,3-dihydro-1H-inden-1-yloxy)-2,3-dihydrobenzofuran-3-yl)acetate (119 mg) in tetrahydrofuran (1 mL), water (1 mL) and methanol (1 mL) at room temperature. The mixture is stirred at room temperature for 12 hours. The mixture is concentrated, cooled to 0° C., diluted with water and acidified with 4 M aqueous HCl solution. The resulting mixture is extracted with dichloromethane. The organic phase is dried (MgSO$_4$). The solvent is evaporated to give the title compound. Yield: 103 mg; LC (method 20): $t_R$=6.30 min; Mass spectrum (ESI$^-$): m/z=442 [M−H]$^-$.

Intermediate 31

2-((S)-6-((R)-4-(4-Cyano-2,6-dimethylphenyl)-7-fluoro-2,3-dihydro-1H-inden-1-yloxy)-2,3-dihydrobenzofuran-3-yl)acetic acid

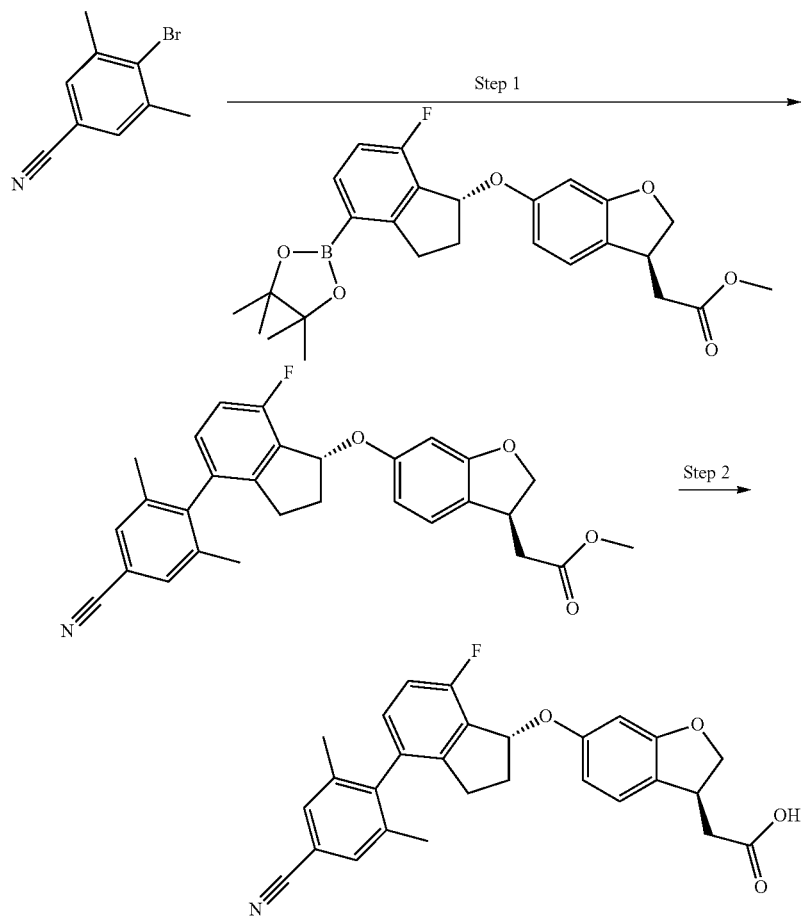

Step 1: Methyl 2-((S)-6-((R)-4-(4-cyano-2,6-dimethylphenyl)-7-fluoro-2,3-dihydro-1H-inden-1-yloxy)-2,3-dihydrobenzofuran-3-yl)acetate In a microwave vial, methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (200 mg), 4-bromo-3,5-dimethylbenzonitrile (90 mg), K$_3$PO$_4$ (273 mg), Palladium-(II)-acetate (10 mg) and dicyclohexyl (2',6'-dimethoxybiphenyl-2-yl)phosphine (S-Phos) (17 mg) are suspended in toluene (10 mL) and water (2 mL) and purged for 10 minutes with argon. The vial is sealed and the mixture is stirred at 100° C. for 4 hours. After cooling to ambient temperature the mixture is partitioned between ethyl acetate and water. The organic phase is dried (MgSO$_4$) and concentrated. The residue is chromatographed on silica gel (cyclohexane/ethyl acetate 90:10) to give the title compound. Yield: 85 mg; LC (method 19): $t_R$=1.52 min; Mass spectrum (ESI$^+$): m/z=471 [M+−H]$^+$.

Step 2: 2-((S)-6-((R)-4-(4-Cyano-2,6-dimethylphenyl)-7-fluoro-2,3-dihydro-1H-inden-1-yloxy)-2,3-dihydrobenzofuran-3-yl)acetic acid LiOH×H$_2$O (38 mg) is added to a solution of methyl 2-((S)-6-((R)-4-(4-cyano-2,6-dimethylphenyl)-7-fluoro-2,3-dihydro-1H-inden-1-yloxy)-2,3-dihydrobenzofuran-3-yl)acetate (85 mg) in tetrahydrofuran (1 mL), water (1 mL) and methanol (1 mL) at room temperature. The mixture is stirred at room temperature for 12 hours. The mixture is concentrated, cooled to 0° C., diluted with water and acidified with 4 M aqueous HCl solution. The resulting mixture is extracted with dichloromethane. The organic phase is dried (MgSO$_4$). The solvent is evaporated and the residue is chromatographed on silica gel (dichloromethane/methanol/acetic acid 9:0.05:0.05) to give the title compound. Yield: 41 mg; LC (method 20): $t_R$=6.91 min; Mass spectrum (ESI⁻): m/z=456 [M−H]⁻.

Intermediate 32

Methyl 2-((S)-6-((R)-4-(4-(dimethylcarbamoyl)-2,6-dimethylphenyl)-7-fluoro-2,3-dihydro-1H-inden-1-yloxy)-2,3-dihydrobenzofuran-3-yl)acetate

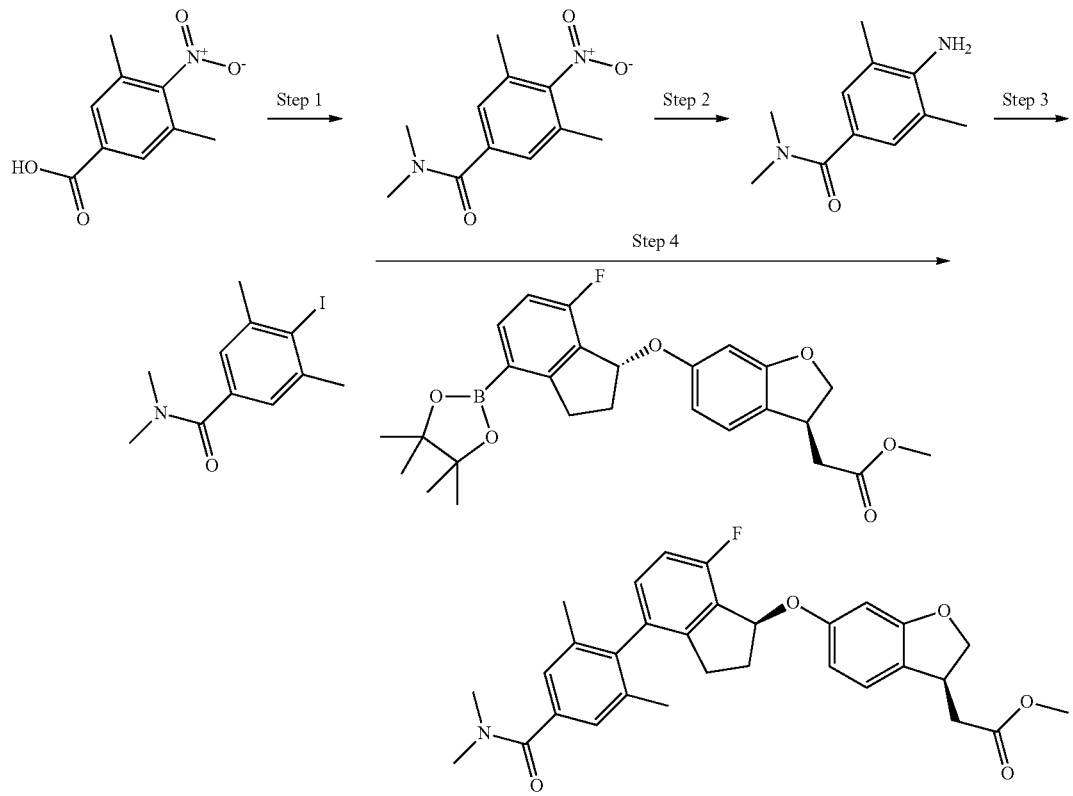

Step 1: N,N,3,5-Tetramethyl-4-nitrobenzamide 1,1'-Carbonyldiimidazole (914 mg) is added to a solution of 3,5-dimethyl-4-nitrobenzoic acid (1 g) in tetrahydrofuran (10 mL). The mixture is stirred for 3 hours at room temperature, dimethylamine (7.7 mL, 2 M in tetrahydrofuran) is added and the mixture is stirred for further 30 minutes. After concentration the mixture is diluted with ethyl acetate and washed with hydrochloric acid (0.2 M), saturated aqueous NaHCO₃ solution and brine. The organic phase is dried (Na₂SO₄) and concentrated to give the title compound. Yield: 1 g; LC (method 20): $t_R$=5.11 min; Mass spectrum (ESI⁺): m/z=223 [M+H]⁺.

Step 2: 4-Amino-N,N,3,5-tetramethylbenzamide

10% Palladium on carbon (100 mg) is added to a solution of N,N,3,5-tetramethyl-4-nitrobenzamide (1 g) in methanol (10 mL) and the mixture is hydrogenated for 3 hours under 2 bar hydrogen pressure. Then the catalyst is filtered off and washed with methanol. The combined mother liquors are concentrated to give the title compound. Yield: 1 g; LC (method 20): $t_R$=2.75 min; Mass spectrum (ESI⁺): m/z=193 [M+H]⁺.

Step 3: 4-Iodo-N,N,3,5-tetramethylbenzamide

4-Amino-N,N,3,5-tetramethylbenzamide (500 mg) is dissolved in concentrated hydrochloric acid (2 mL), cooled to 0° C. and treated dropwise with a solution of NaNO₂ (269 mg) in water (0.5 mL). The mixture is stirred for 1 hour and a solution of KI (1.3 g) in water (1.5 mL) is added dropwise. The mixture is stirred for 15 minutes, allowed to warm to room temperature and then partitioned between dichloromethane and water. The organic phase is washed with 10% aqueous solution of Na₂S₂O₃, dried (MgSO₄) and concentrated. The residue is chromatographed on silica gel (cyclohexane/ethyl acetate 100:0→50:50) to give the title compound. Yield: 300 mg; LC (method 20): $t_R$=6.32 min; Mass spectrum (ESI⁺): m/z=304 [M+H]⁺.

Step 4: Methyl 2-((S)-6-((R)-4-(4-(dimethylcarbamoyl)-2,6-dimethylphenyl)-7-fluoro-2,3-dihydro-1H-inden-1-yloxy)-2,3-dihydrobenzofuran-3-yl)acetate In a microwave vial, methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (75 mg), 4-iodo-N,N,3,5-tetramethylbenzamide (97 mg), K₃PO₄ (102 mg) and dicyclohexyl(2',6'-dimethoxybiphenyl-2-yl)phosphine (S-Phos) (7 mg) are suspended in toluene (2 mL) and water (0.2 mL) and purged for 10 minutes with argon. Palladium-(II)-acetate (4 mg) are added, the vial is sealed and the mixture is stirred at 120° C. for 5 hours. After cooling to ambient temperature the mixture is partitioned between ethyl acetate and water. The organic phase is dried (MgSO₄) and concentrated. The residue is chromatographed on silica gel (cyclohexane/ethyl acetate 100:0→80:20) to give the title compound. Yield: 70 mg; LC (method 25): $t_R$=1.41 min; Mass spectrum (ESI⁺): m/z=518 [M+H]⁺.

Intermediate 33

Methyl 2-((S)-6-((R)-4-(2,6-dimethyl-4-(methylcarbamoyl)phenyl)-7-fluoro-2,3-dihydro-1H-inden-1-yloxy)-2,3-dihydrobenzofuran-3-yl)acetate washed with methanol. The combined mother liquors are concentrated to give the title compound. Yield: 850 mg; LC (method 21): $t_R$=6.02; Mass spectrum (ESI⁺): m/z=179 [M+H]⁺.

Step 3: 4-Iodo-N,3,5-trimethylbenzamide

4-Amino-N,3,5-trimethylbenzamide (850 mg) is dissolved in concentrated hydrochloric acid (2 mL), cooled to 0° C. and treated dropwise with a solution of NaNO₂ (580 mg) in water (0.5 mL). The mixture is stirred for 1 hour and a solution of KI (2.8 g) in water (1.5 mL) is added dropwise. The mixture is stirred for 15 minutes, allowed to warm to room temperature

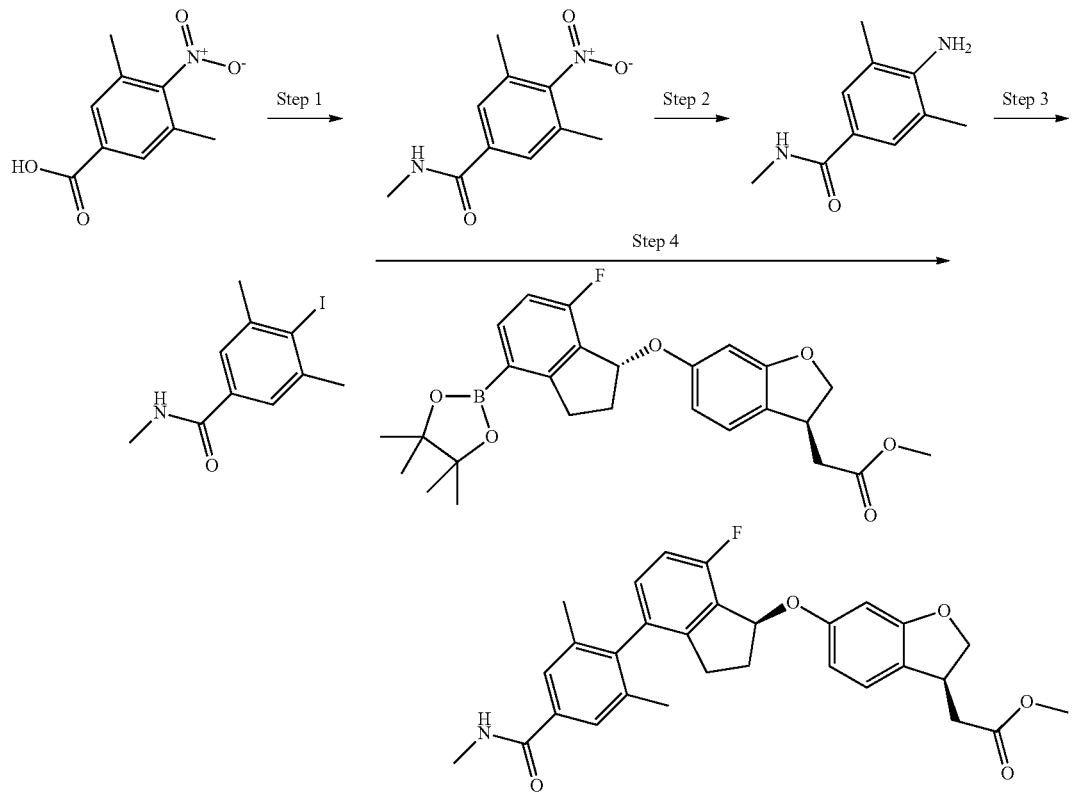

Step 1: N,3,5-Trimethyl-4-nitrobenzamide 1,1'-Carbonyldiimidazole (914 mg) is added to a suspension of 3,5-dimethyl-4-nitrobenzoic acid (1 g) in tetrahydrofuran (10 mL). The mixture is stirred for 3 hours at room temperature, methylamine (7.7 mL, 2 M in tetrahydrofuran) is added and the mixture is stirred for further 30 minutes. After concentration the mixture is diluted with ethyl acetate and washed with hydrochloric acid (0.2 M), saturated aqueous NaHCO₃ solution and brine. The organic phase is dried (Na₂SO₄) and concentrated to give the title compound. Yield: 1 g; LC (method 20): $t_R$=4.82 min; Mass spectrum (ESI⁺): m/z=209 [M+H]⁺.

Step 2: 4-Amino-N,3,5-trimethylbenzamide

10% Palladium on carbon (100 mg) is added to a solution of N,3,5-trimethyl-4-nitrobenzamide (1 g) in methanol (10 mL) and the mixture is hydrogenated for 3 hours under 3 bar hydrogen pressure. Then the catalyst is filtered off and and then partitioned between dichloromethane and water. The organic phase is washed with 10% aqueous solution of Na₂S₂O₃, dried (MgSO₄) and concentrated. The residue is chromatographed on silica gel (cyclohexane/ethyl acetate 100:0→50:50) to give the title compound. Yield: 850 mg; LC (method 20): $t_R$=5.88 min; Mass spectrum (ESI⁺): m/z=290 [M+H]⁺.

Step 4: Methyl 2-((S)-6-((R)-4-(2,6-dimethyl-4-(methylcarbamoyl)phenyl)-7-fluoro-2,3-dihydro-1H-inden-1-yloxy)-2,3-dihydrobenzofuran-3-yl)acetate In a microwave vial, methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (75 mg), 4-iodo-N,3,5-trimethylbenzamide (93 mg), K₃PO₄ (102 mg) and dicyclohexyl(2',6'-dimethoxybiphenyl-2-yl)phosphine (S-Phos) (7 mg) are suspended in toluene (1.8 mL) and water (0.2 mL) and purged for 10 minutes with argon. Palladium-(II)-acetate (4 mg) is added, the vial is sealed and the mixture is stirred at 120° C. for 5 hours. After cooling to ambient temperature the mixture is partitioned between ethyl acetate and water. The organic phase is dried (MgSO$_4$) and concentrated. The residue is chromatographed on silica gel (cyclohexane/ethyl acetate 100:0→80:20) to give the title compound. Yield: 16 mg; LC (method 25): t$_R$=1.32 min; Mass spectrum (ESI$^+$): m/z=504 [M+H]$^+$.

Intermediate 34

Methyl 2-((S)-6-((R)-4-(2,6-dimethyl-4-(morpholine-4-carbonyl)phenyl)-7-fluoro-2,3-dihydro-1H-inden-1-yloxy)-2,3-dihydrobenzofuran-3-yl)acetate

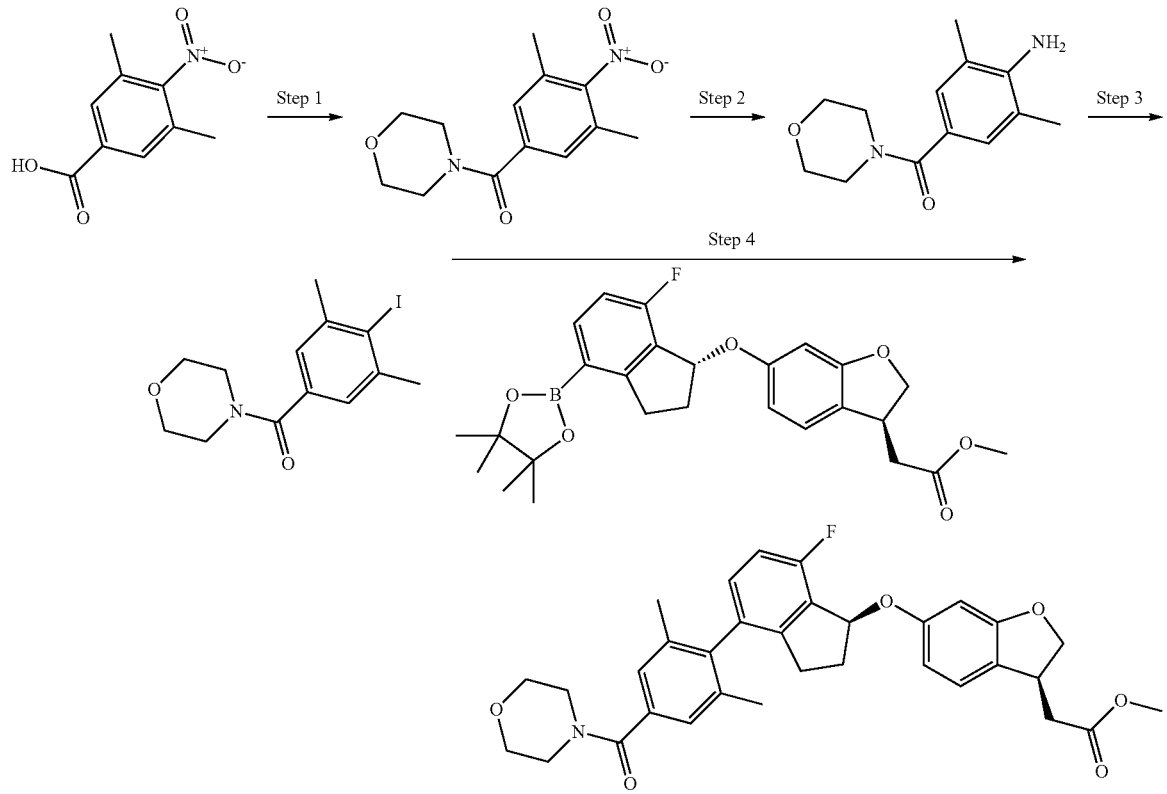

Step 1:
(3,5-Dimethyl-4-nitrophenyl)(morpholino)methanone 1,1'-Carbonyldiimidazole (1.66 g) is added to a solution of 3,5-dimethyl-4-nitrobenzoic acid (1 g) in tetrahydrofuran (10 mL). The mixture is stirred for 3 hours at room temperature, morpholine (0.9 mL) is added and the mixture is stirred for further 30 minutes. After concentration the mixture is diluted with ethyl acetate and washed with hydrochloric acid (0.2 M), saturated aqueous NaHCO$_3$ solution and brine. The organic phase is dried (Na$_2$SO$_4$) and concentrated to give the title compound. Yield: 1.3 g; LC (method 20): t$_R$=5.10 min; Mass spectrum (ESI$^+$): m/z=265 [M+H]$^+$.

Step 2:
(4-Amino-3,5-dimethylphenyl)(morpholino)methanone

10% Palladium on carbon (100 mg) is added to a solution of (3,5-dimethyl-4-nitrophenyl)(morpholino)methanone (1.3 g) in methanol (10 mL) and the mixture is hydrogenated for 3 hours under 2 bar hydrogen pressure. Then the catalyst is filtered off and washed with methanol. The combined mother liquors are concentrated to give the title compound. Yield: 1.1 g; LC (method 20): t$_R$=1.94; Mass spectrum (ESI$^+$): m/z=235 [M+H]$^+$.

Step 3:
(4-Iodo-3,5-dimethylphenyl)(morpholino)methanone (4-Amino-3,5-dimethylphenyl)(morpholino)methanone (1.2 g) is dissolved in concentrated hydrochloric acid (2 mL), cooled to 0° C. and treated dropwise with a solution of NaNO$_2$ (530 mg) in water (0.5 mL). The mixture is stirred for 1 hour and a solution of KI (2.6 g) in water (1.5 mL) is added dropwise. The mixture is stirred for 15 minutes at 0° C. and for 12 hours at room temperature and is then partitioned between dichloromethane and water. The organic phase is washed with 10% aqueous solution of Na$_2$S$_2$O$_3$, dried (MgSO$_4$) and concentrated. The residue is chromatographed on silica gel (cyclohexane/ethyl acetate 100:0→50:50) to give the title compound. Yield: 1.1 g; LC (method 20): t$_R$=6.13 min; Mass spectrum (ESI$^+$): m/z=346 [M+H]$^+$.

Step 4: Methyl 2-((S)-6-((R)-4-(2,6-dimethyl-4-(morpholine-4-carbonyl)phenyl)-7-fluoro-2,3-dihydro-1H-inden-1-yloxy)-2,3-dihydrobenzofuran-3-yl)acetate In a microwave vial, methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (75 mg), (4-iodo-3,5-dimethylphenyl)(morpholino)methanone (110 mg), K₃PO₄ (102 mg) and dicyclohexyl(2',6'-dimethoxybiphenyl-2-yl)phosphine (S-Phos) (7 mg) are suspended in toluene (2 mL) and water (0.2 mL) and purged for 10 minutes with argon. Palladium-(II)-acetate (4 mg) are added, the vial is sealed and the mixture is stirred at 120° C. for 5 hours. After cooling to ambient temperature the mixture is partitioned between ethyl acetate and water. The organic phase is dried (MgSO₄) and concentrated. The residue is chromatographed on silica gel (cyclohexane/ethyl acetate 100:0→80:20) to give the title compound. Yield: 55 mg; LC (method 25): $t_R$=1.38 min; Mass spectrum (ESI⁺): m/z=560 [M+H]⁺.

Intermediate 35

((S)-6-{(R)-7-Fluoro-4-[4-(2-hydroxy-2-methyl-propylcarbamoyl)-2,6-dimethyl-phenyl]-indan-1-yloxy}-2,3-dihydro-benzofuran-3-yl)-acetic acid methyl ester Step 1: N-(2-Hydroxy-2-methyl-propyl)-3,5-dimethyl-4-nitro-benzamide The title compound is prepared following a procedure analogous to that described in Step 1 in the preparation of Intermediate 34, starting from 1-amino-2-methyl-propan-2-ol (Kasai, Shizuo et al. Journal of Medicinal Chemistry, 2012, vol. 55, #9 p. 4336-4351).

Step 2: 4-Amino-N-(2-hydroxy-2-methyl-propyl)-3,5-dimethyl-benzamide

The title compound is prepared following a procedure analogous to that described in Step 2 in the preparation of Intermediate 27-20, starting from N-(2-hydroxy-2-methyl-propyl)-3,5-dimethyl-4-nitro-benzamide.

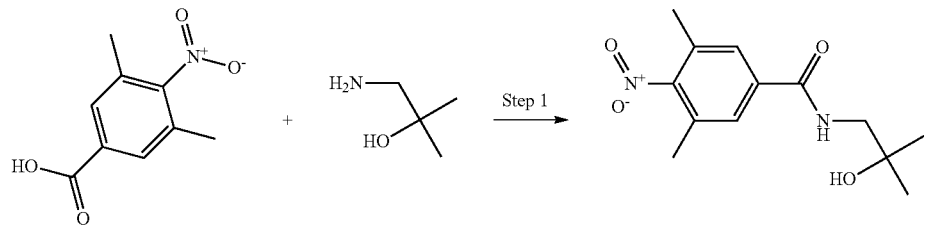

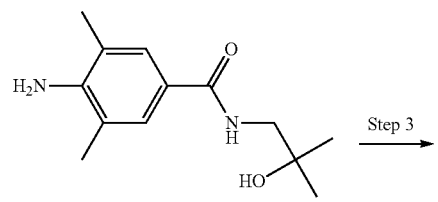

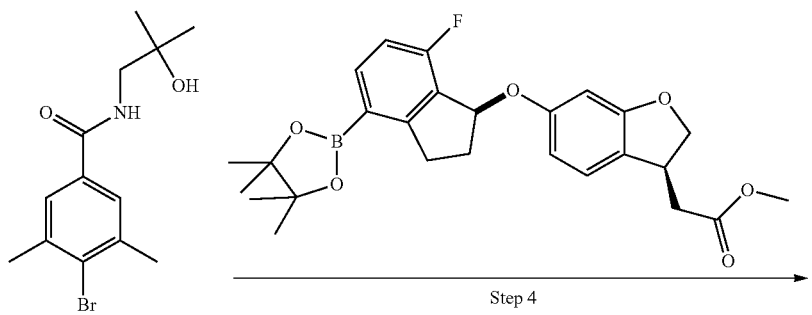

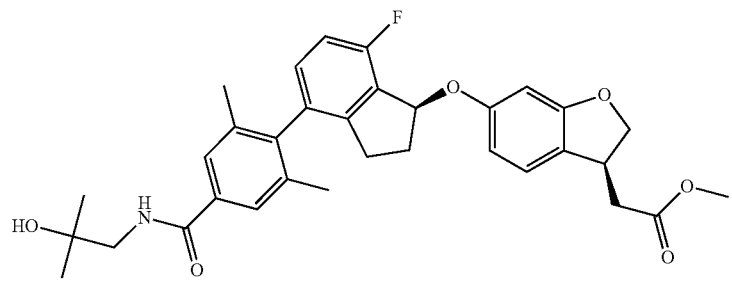

Step 3: 4-Bromo-N-(2-hydroxy-2-methyl-propyl)-3,5-dimethyl-benzamide

The title compound is prepared following a procedure analogous to that described in Step 3 in the preparation of Intermediate 27-20, starting from 4-amino-N-(2-hydroxy-2-methyl-propyl)-3,5-dimethyl-benzamide.

Step 4: ((S)-6-{(R)-7-Fluoro-4-[4-(2-hydroxy-2-methyl-propylcarbamoyl)-2,6-dimethyl-phenyl]indan-1-yloxy}-2,3-dihydro-benzofuran-3-yl)-acetic acid methyl ester The title compound is prepared following a procedure analogous to that described in Step 5 in the preparation of Intermediate 1, starting from 4-bromo-N-(2-hydroxy-2-methyl-propyl)-3,5-dimethyl-benzamide.

Intermediate 36

Methyl 2-((S)-6-((R)-4-(4-(2-cyano-2-methylpropoxy)-2,6-dimethylphenyl)-7-fluoro-2,3-dihydro-1H-inden-1-yloxy)-2,3-dihydrobenzofuran-3-yl)acetate

Step 1: 2-Cyano-2-methylpropyl 4-methylbenzenesulfonate

To a solution of 3-hydroxy-2,2-dimethylpropanenitrile (0.5 g) in dichloromethane (8 mL) and pyridine (1.5 mL) is added at 0° C. p-toluene-sulfonylchloride (1.0 g) in portions. The mixture is stirred for 12 hours at room temperature, diluted with diethylether and washed with 1 M aqueous HCl solution and brine. After drying (MgSO$_4$) the solvent is evaporated and the residue is chromatographed on silica gel (petrole ether/ethyl acetate 90:10→50:50) to give the title compound. Yield: 770 mg; Mass spectrum (ESI$^+$): m/z=254 [M+H]$^+$.

Step 2: 3-(4-Bromo-3,5-dimethylphenoxy)-2,2-dimethylpropanenitrile

To a solution of 2-cyano-2-methylpropyl 4-methylbenzenesulfonate (760 mg) and 4-bromo-3,5-dimethylphenol (500 mg) in N,N-dimethylformamide (8 mL) is added Cs$_2$CO$_3$ (2.0 g). The mixture is stirred for 12 hours at 80° C., diluted with diethylether and washed with water and brine. After drying (MgSO$_4$) the solvent is evaporated and the residue is chromatographed on silica gel (petrole ether/ethyl acetate

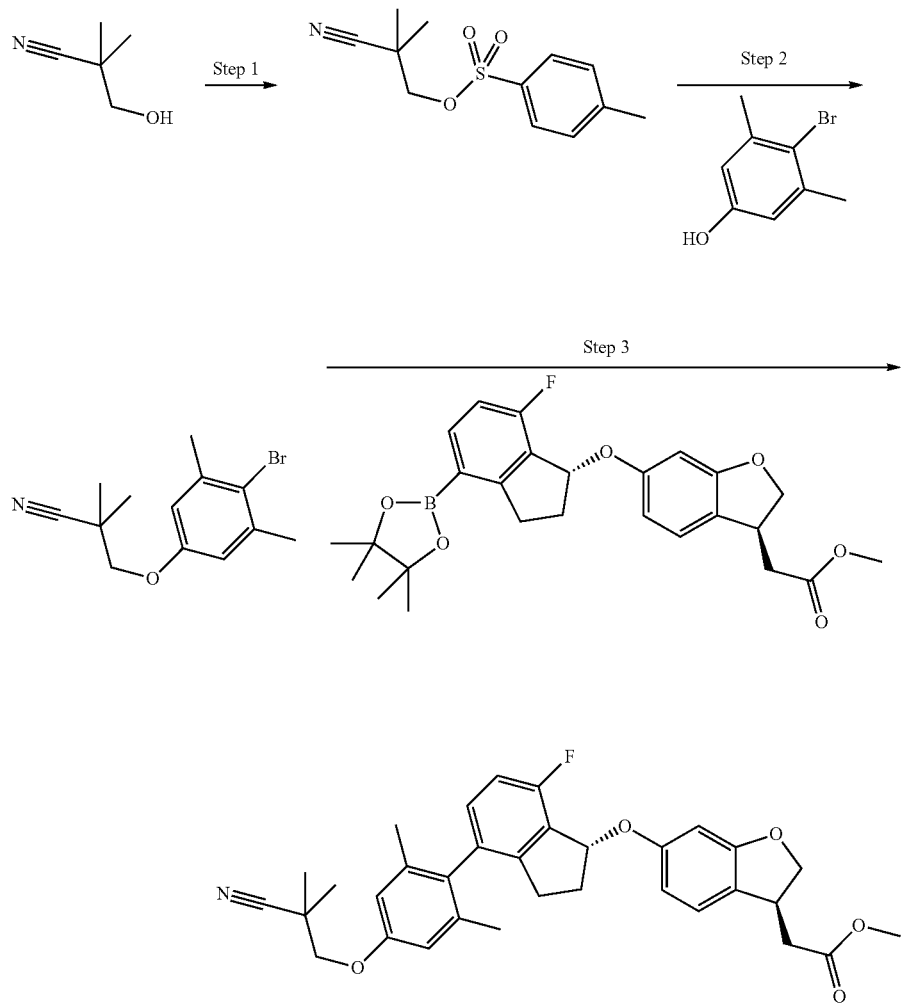

90:10→60:40) to give the title compound. Yield: 572 mg; Mass spectrum (ESI+): m/z=282 [M+H]+.

Step 3: Methyl 2-((S)-6-((R)-4-(4-(2-cyano-2-methylpropoxy)-2,6-dimethylphenyl)-7-fluoro-2,3-dihydro-1H-inden-1-yloxy)-2,3-dihydrobenzofuran-3-yl) acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and 3-(4-bromo-3,5-dimethylphenoxy)-2,2-dimethylpropanenitrile following a procedure analogous to that described in Step 5 of Intermediate 1. LC (method 8): $t_R$=0.89 min; Mass spectrum (ESI+): m/z=544 [M+H]+.

Intermediate 37

Methyl 2-((S)-6-((R)-4-(4-(2-(tert-butoxycarbonylamino)ethoxy)-2,6-dimethylphenyl)-7-fluoro-2,3-dihydro-1H-inden-1-yloxy)-2,3-dihydrobenzofuran-3-yl)acetate ethylcarbamate (270 mg) and $Cs_2CO_3$ (810 mg). The mixture is stirred for 20 hours at room temperature. tert-Butyl 2-bromoethylcarbamate (110 mg) and $Cs_2CO_3$ (325 mg) are added and the mixture is stirred for 4 hours. Again tert-butyl 2-bromoethylcarbamate (110 mg) and $Cs_2CO_3$ (325 mg) are added and the mixture is stirred for 12 hours. The mixture is partitioned between water and diethylether. The organic phase is washed with brine and dried ($MgSO_4$). The solvent is evaporated and the residue is chromatographed on silica gel (cyclohexane/ethyl acetate 99:1→80:20) to give the title compound. Yield: 320 mg; LC (method 8): $t_R$=0.66 min; Mass spectrum (ESI+): m/z=344 [M+H]+.

Step 2: Methyl 2-((S)-6-((R)-4-(4-(2-(tert-butoxycarbonylamino)ethoxy)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,

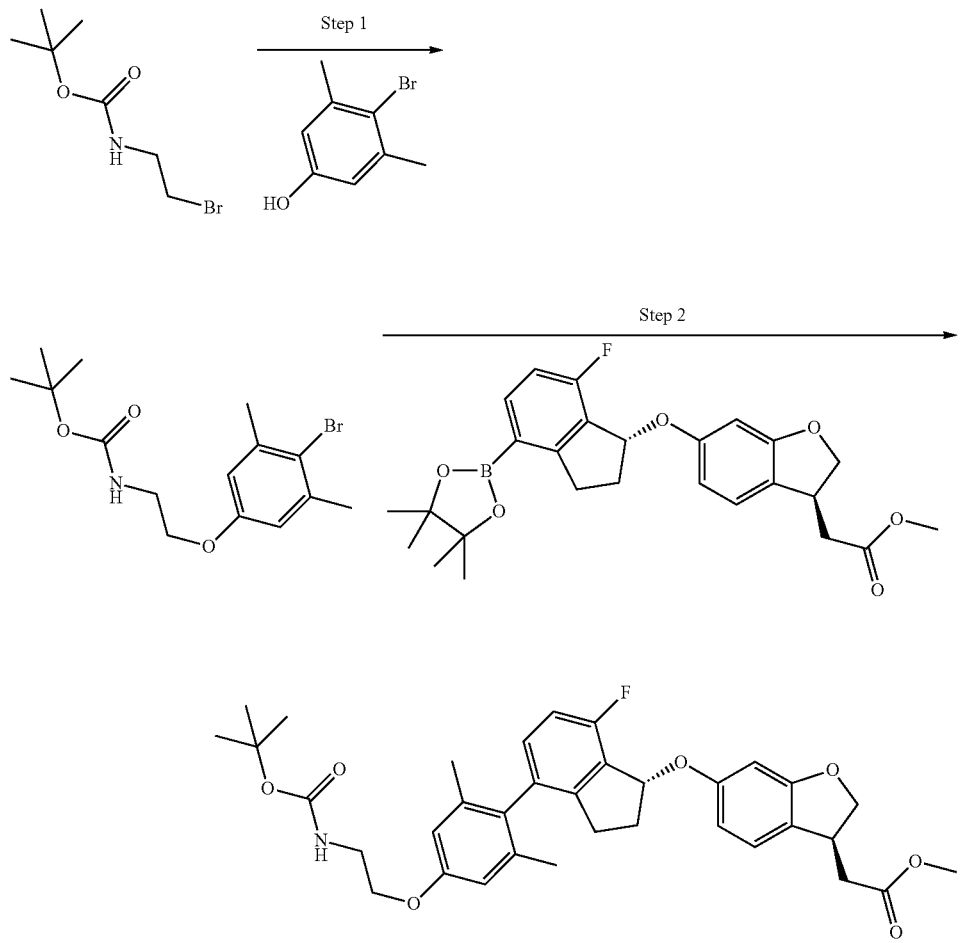

Step 1: tert-Butyl 2-(4-bromo-3,5-dimethylphenoxy)ethylcarbamate

To a solution of 4-bromo-3,5-dimethylphenol (200 mg) in N,N-dimethylformamide (5 mL) is added tert-butyl 2-bromo- 3-dihydro-1H-inden-1-yloxy)-2,3-dihydrobenzofuran-3-yl) acetate and tert-butyl 2-(4-bromo-3,5-dimethylphenoxy)ethylcarbamate following a procedure analogous to that described in Step 5 of Intermediate 1. LC (method 8): $t_R$=0.92 min; Mass spectrum (ESI+): m/z=606 [M+H]+.

Intermediate 38

Methyl 2-((S)-6-((R)-7-fluoro-4-(4-((4-hydroxytetrahydro-2H-pyran-4-yl)methoxy)-2,6-dimethylphenyl)-2,3-dihydro-1H-inden-1-yloxy)-2,3-dihydrobenzofuran-3-yl)acetate

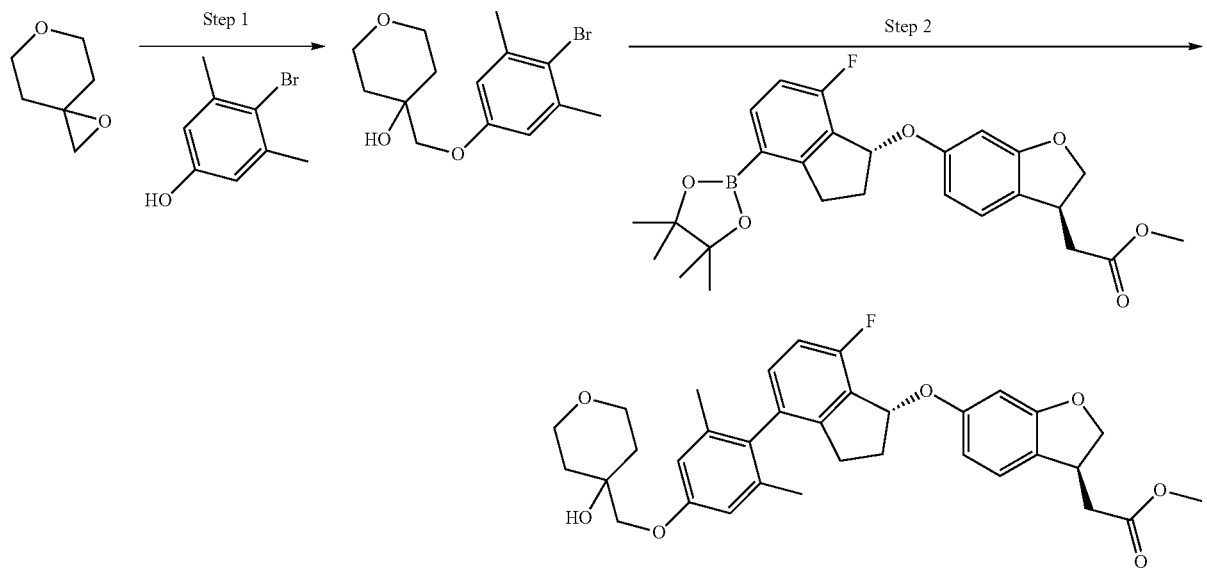

Step 1: 4-((4-Bromo-3,5-dimethylphenoxy)methyl)tetrahydro-2H-pyran-4-ol

The title compound is prepared from 4-bromo-3,5-dimethylphenol and 1,6-dioxaspiro[2.5]octane following a procedure analogous to that described in Step 3 of Intermediate 2. LC (method 7): $t_R$=1.04 min; Mass spectrum (ESI$^-$): m/z=313 [M−H]$^-$.

Step 2: Methyl 2-((S)-6-((R)-7-fluoro-4-(4-((4-hydroxytetrahydro-2H-pyran-4-yl)methoxy)-2,6-dimethylphenyl)-2,3-dihydro-1H-inden-1-yloxy)-2,3-dihydrobenzofuran-3-yl)acetate The title compound is prepared from methyl methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 4-((4-bromo-3,5-dimethylphenoxy)methyl)tetrahydro-2H-pyran-4-ol following a procedure analogous to that described in Step 5 of Intermediate 1. The product is purified by HPLC on reversed phase. LC (method 7): $t_R$=1.17 min; Mass spectrum (ESI$^+$): m/z=577 [M+H]$^+$.

Intermediate 39

Methyl 2-((S)-6-((R)-7-fluoro-4-(4-(3-hydroxy-3-methylbutyl)-2,6-dimethylphenyl)-2,3-dihydro-1H-inden-1-yloxy)-2,3-dihydrobenzofuran-3-yl)acetate

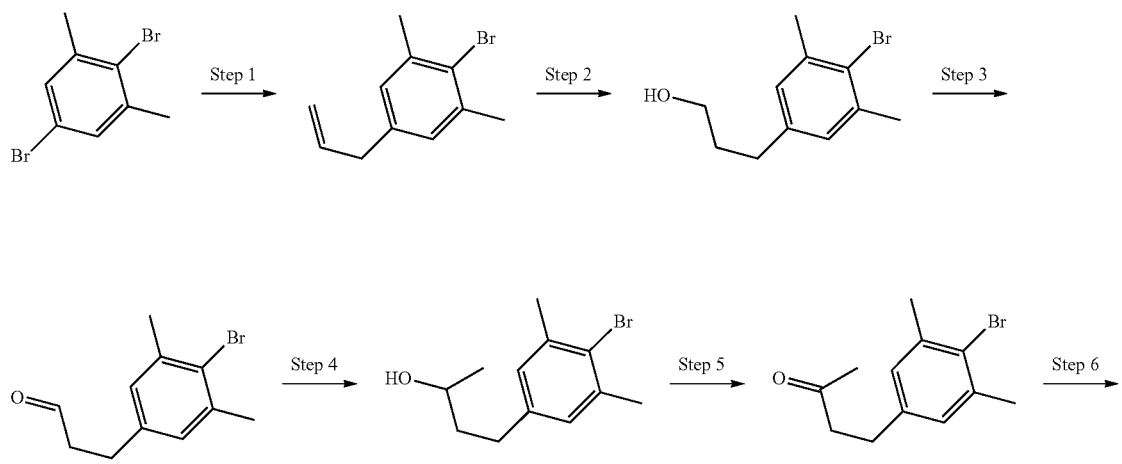

Step 7

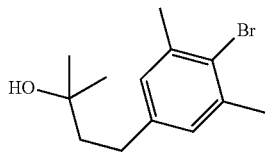 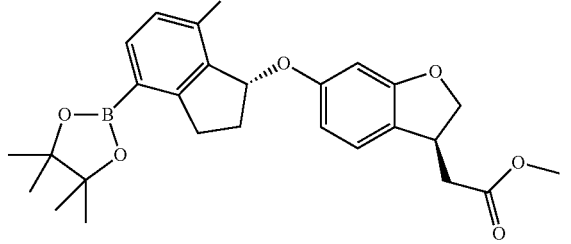

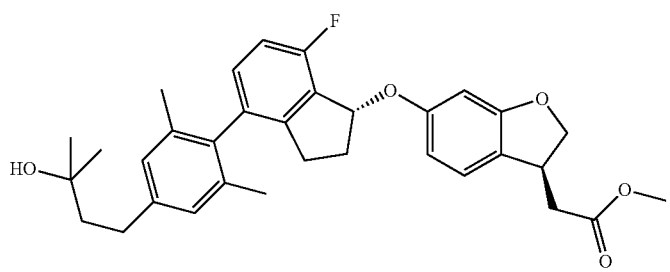

Step 1: 5-Allyl-2-bromo-1,3-dimethylbenzene

To a solution of isopropylmagnesium chloride (6.15 mL of a 2 M solution in tetrahydrofurane) in tetrahydrofurane (75 mL) is added dropwise at 0° C. n-butyllithium (15.4 mL of a 1.6 M solution in n-hexane). The mixture is stirred for 10 minutes, a solution of 2,5-dibromo-1,3-dimethylbenzene (5 g) in tetrahydrofurane (75 mL) is added within 10 minutes. The mixture is stirred for 2 hours, cooled to −40° C. and then CuCN×LiCl (5.5 mL of a 1 M solution in tetrahydrofurane) is added dropwise. After stirring for 5 minutes 3-bromopropene (6.6 mL) is added dropwise, the mixture is stirred for 1 hour, warmed to room temperature and stirred for further 12 hours. Then the reaction is quenched by addition of saturated aqueous $NH_4Cl$ solution. The mixture is extracted with diethylether, the organic phase is dried ($MgSO_4$) and concentrated. The residue is chromatographed on silica gel (dichloromethane) to give the title compound. Yield: 3.76 g; LC (method 8): $t_R$=0.83 min; Mass spectrum (ESI$^+$): m/z=225 [M+H]$^+$.

Step 2: 3-(4-Bromo-3,5-dimethylphenyl)propan-1-ol

A solution of 5-allyl-2-bromo-1,3-dimethylbenzene (1.0 g) is cooled to 0° C., 9-borabicyclo[3.3.1]nonane (9-BBN, 26 mL of a 0.5 M solution in tetrahydrofurane) is added dropwise and the mixture is stirred for 2 hours at room temperature. After cooling to 0° C. NaOH (6.7 mL, 4 M) and $H_2O_2$ (6.7 mL, 35%) are added dropwise. The mixture is stirred for 12 hours while warming to room temperature. Then the mixture is partitioned between brine and diethylether. The organic phase is dried ($MgSO_4$) and concentrated. The residue is chromatographed on silica gel (cyclohexane/ethyl acetate 95:5→70:30) to give the title compound. Yield: 750 mg; LC (method 8): $t_R$=0.28 min; Mass spectrum (ESI$^+$): m/z=260 [M+NH$_4$]$^+$.

Step 3: 3-(4-Bromo-3,5-dimethylphenyl)propanal

To a solution of 3-(4-bromo-3,5-dimethylphenyl)propan-1-ol (250 mg) in dichloromethane (5 mL) is added at 0° C. 1,1-dihydro-1,1,1-triacetoxy-1,2-benziodoxol-3(1H)-on (Dess-Martin periodinan, 2.7 mL of a 15% solution in dichloromethane). The mixture is stirred for 12 hours at room temperature, cooled to 0° C. and 1,1-dihydro-1,1,1-triacetoxy-1,2-benziodoxol-3(1H)-on (Dess-Martin periodinan, 1.6 mL of a 15% solution in dichloromethane) is added. After stirring for 4 hours isopropanol (5 mL) is added, the mixture is stirred for 15 minutes and the solvents are evaporated in vacuo. The residue is chromatographed on silica gel (cyclohexane/ethyl acetate 99:1→70:30) to give the title compound. Yield: 120 mg; LC (method 8): $t_R$=0.38 min; Mass spectrum (ESI$^-$): m/z=239 [M−H]$^-$.

Step 4: 4-(4-Bromo-3,5-dimethylphenyl)butan-2-ol

To a solution of 3-(4-bromo-3,5-dimethylphenyl)propanal (120 mg) in tetrahydrofurane (2 mL) is added at 0° C. methylmagnesium bromide (800 µL of a 1.4 M solution in tetrahydrofurane/toluene 1:3). After stirring for 30 minutes the mixture is partitioned between saturated aqueous $NH_4Cl$ solution and diethylether. The organic phase is dried ($MgSO_4$) and concentrated. The residue is chromatographed on silica gel (cyclohexane/ethyl acetate 99:1→70:30) to give the title compound. Yield: 130 mg; LC (method 8): $t_R$=0.37 min; Mass spectrum (ESI$^+$): m/z=274 [M+NH$_4$]$^+$.

Step 5: 4-(4-Bromo-3,5-dimethylphenyl)butan-2-one

To a solution of 4-(4-bromo-3,5-dimethylphenyl)butan-2-ol (130 mg) in dichloromethane (8 mL) is added at 0° C. 1,1-dihydro-1,1,1-triacetoxy-1,2-benziodoxol-3(1H)-on (Dess-Martin periodinan, 1.4 mL of a 15% solution in dichloromethane). The mixture is stirred for 12 hours at room temperature. The solvents are evaporated in vacuo. The residue is chromatographed on silica gel (cyclohexane/ethyl acetate 99:1→70:30) to give the title compound. Yield: 100 mg; LC (method 8): $t_R$=0.44 min; Mass spectrum (ESI$^+$): m/z=255 [M+H]$^+$.

Step 6: 4-(4-Bromo-3,5-dimethylphenyl)-2-methylbutan-2-ol

To a solution of 4-(4-bromo-3,5-dimethylphenyl)butan-2-one (100 mg) in tetrahydrofurane (2 mL) is added at 0° C. methylmagnesium bromide (840 µL of a 1.4 M solution in tetrahydrofurane/toluene 1:3). The mixture is stirred for 2 hours while warming to room temperature and then partitioned between saturated aqueous NH$_4$Cl solution and diethylether. The organic phase is dried (MgSO$_4$) and concentrated to give the title compound. Yield: 105 mg; LC (method 8): $t_R$=0.47 min; Mass spectrum (ESI$^+$): m/z=271 [M+H]$^+$.

Step 7: Methyl 2-((S)-6-((R)-7-fluoro-4-(4-(3-hydroxy-3-methylbutyl)-2,6-dimethylphenyl)-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 4-(4-bromo-3,5-dimethylphenyl)-2-methylbutan-2-ol following a procedure analogous to that described in Step 5 of Intermediate 1. LC (method 8): $t_R$=0.83 min; Mass spectrum (ESI$^+$): m/z=533 [M+H]$^+$.

Intermediate 40

1-Oxa-6-thiaspiro[2.5]octane

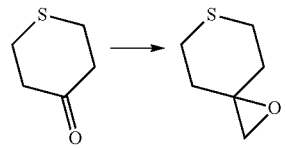 [SMILES: O=C1CCSCC1 ; C1CC2(CCS1)CO2]

To a suspension of trimethylsulfoxonium iodide (2 g) in dimethylsulfoxide (15 mL) is added portionwise NaH (820 mg of a 60% dispersion in mineral oil). The mixture is stirred for 1 hour and a solution of dihydro-2H-thiopyran-4(3H)-one (2 g) in dimethylsulfoxide (2 mL) is added dropwise. The mixture is stirred for 12 hours, diluted with ethylacetate and washed twice with water and brine. The organic phase is dried (MgSO$_4$) and concentrated. The residue is chromatographed on silica gel (cyclohexane/ethyl acetate 99:1→70:30) to give the title compound. Yield: 742 mg; LC (method 7): $t_R$=0.64 min; Mass spectrum (ESI$^+$): m/z=131 [M+H]$^+$.

Intermediate 41

Methyl 2-((S)-6-((R)-7-Fluoro-4-(4-((1,1-dioxo-4-hydroxytetrahydro-2H-thiopyran-4-yl)methoxy)-2,6-dimethylphenyl)-2,3-dihydro-1H-inden-1-yloxy)-2,3-dihydrobenzofuran-3-yl)acetate

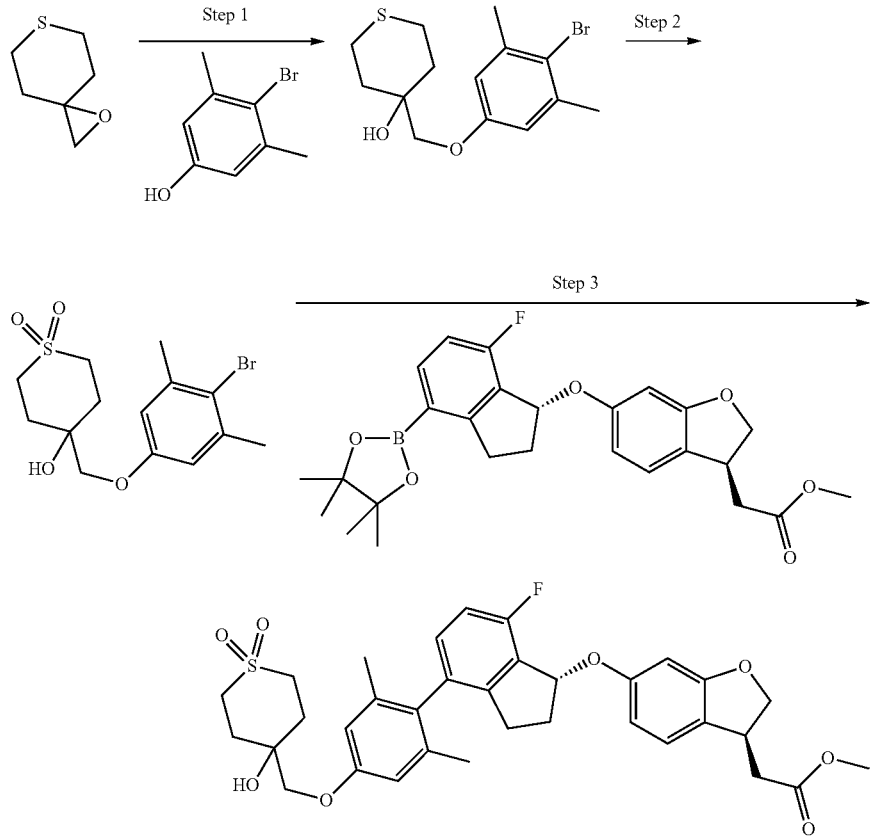

Step 1: 4-((4-Bromo-3,5-dimethylphenoxy)methyl)tetrahydro-2H-thiopyran-4-ol

To a solution of 4-bromo-3,5-dimethylphenol (700 mg) in N,N-dimethylformamide (7 mL) is added $Cs_2CO_3$ (1.7 g) and 1-oxa-6-thiaspiro[2.5]octane (586 mg). The mixture is stirred for 12 hour at 100° C. The mixture is diluted with water and extracted twice with ethyl acetate. The combined organic phases are washed with water and brine, dried ($MgSO_4$) and concentrated. The residue is chromatographed on silica gel (cyclohexane/ethyl acetate 99:1→60:40) to give the title compound. Yield: 986 mg; LC (method 7): $t_R$=1.14 min; Mass spectrum (ESI$^+$): m/z=348 [M+NH$_4$]$^+$.

Step 2: 1,1-Dioxo-4-((4-bromo-3,5-dimethylphenoxy)methyl)tetrahydro-2H-thiopyran-4-ol To a solution of 4-((4-bromo-3,5-dimethylphenoxy)methyl)tetrahydro-2H-thiopyran-4-ol (175 mg) in dichloromethane (3 mL) is added at −10° C. meta-chloro-perbenzoic acid (MCPBA, 270 mg, 70%). The mixture is stirred for 12 hour while warming to room temperature. The mixture is diluted with dichloromethane and washed with 1 M aqueous NaOH solution. The organic phase is dried ($MgSO_4$) and concentrated. The residue is chromatographed on silica gel (petrole ether/ethyl acetate 70:30→0:100) to give the title compound. Yield: 152 mg; Mass spectrum (ESI$^+$): m/z=380 [M+NH$_4$]$^+$.

Step 3: Methyl 2-((S)-6-((R)-7-fluoro-4-(4-((1,1-dioxo-4-hydroxytetrahydro-2H-thiopyran-4-yl)methoxy)-2,6-dimethylphenyl)-2,3-dihydro-1H-inden-1-yloxy)-2,3-dihydrobenzofuran-3-yl)acetate In a microwave vial methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (190 mg), 1,1-dioxo-4-((4-bromo-3,5-dimethylphenoxy)methyl)tetrahydro-2H-thiopyran-4-ol (150 mg), $K_3PO_4$ (250 mg) and dicyclohexyl(2',6'-dimethoxybiphenyl-2-yl)phosphine (S-Phos) (21 mg) are suspended in N,N-dimethylformamide (2 mL) and water (100 µL). The mixture is purged for 10 minutes with argon. Palladium-(II)-acetate (6 mg) is added, the vial is sealed and the mixture is stirred at 110° C. for 3 hours. After cooling to room temperature the mixture is partitioned between diethylether and saturated aqueous NH$_4$Cl solution. The organic phase is dried ($MgSO_4$) and concentrated. The residue is chromatographed on silica gel (petrole ether/ethyl acetate 50:50→0:100) to give the title compound. Yield: 90 mg; LC (method 8): $t_R$=0.53 min; Mass spectrum (ESI$^+$): m/z=625 [M+H]$^+$.

Intermediate 42

Methyl 2-((S)-6-((R)-4-(2,6-dimethyl-4-(3-(methylsulfonyl)propyl)phenyl)-7-fluoro-2,3-dihydro-1H-inden-1-yloxy)-2,3-dihydrobenzofuran-3-yl)acetate

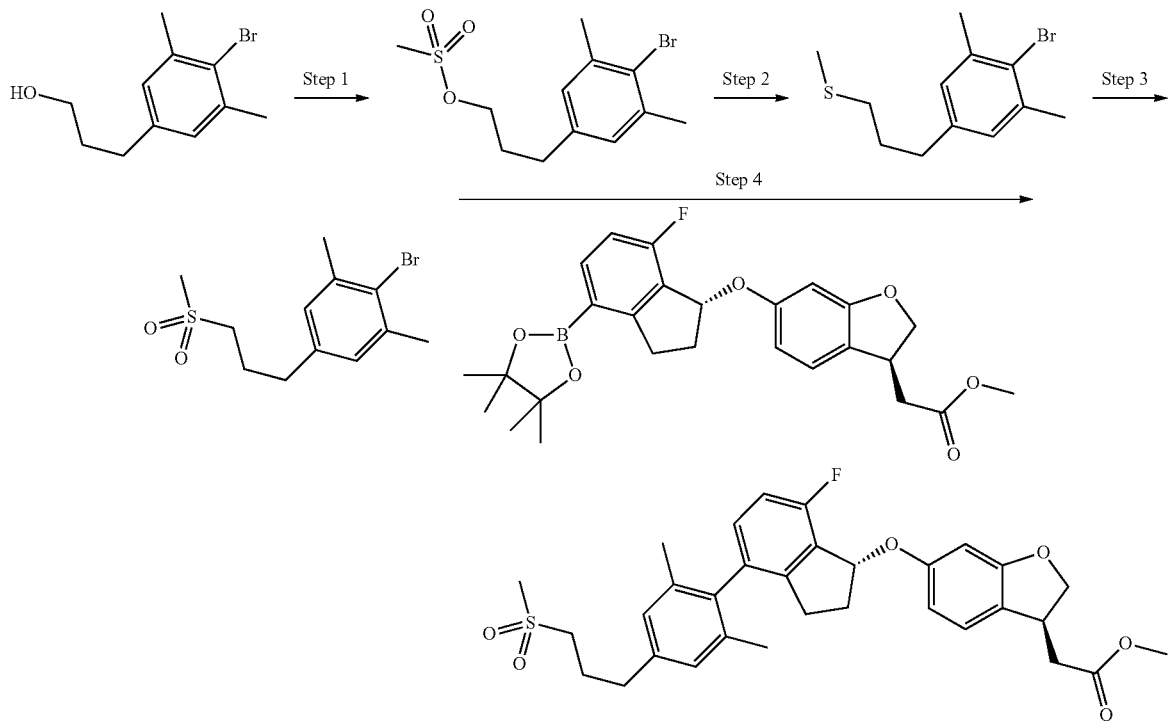

Step 1: 3-(4-Bromo-3,5-dimethylphenyl)propyl methanesulfonate

To a cooled (0° C.) solution of 3-(4-bromo-3,5-dimethylphenyl)propan-1-ol (250 mg) and triethylamine (160 µL) in dichloromethane (2 mL) is added methanesulfonyl chloride (850 µL). The mixture is stirred for 12 hours at room temperature. The mixture is partitioned between dichloromethane and saturated aqueous NaHCO$_3$ solution and stirred vigorously for 30 minutes. The organic phase is separated, washed with brine and dried ($MgSO_4$). The solvent is evaporated and the residue is chromatographed on silica gel (cyclohexane/ethyl acetate 80:20→50:50) to give the title compound. Yield: 235 mg; LC (method 8): $t_R$=0.44 min; Mass spectrum (ESI$^+$): m/z=343 [M+Na]$^+$.

Step 2: (3-(4-Bromo-3,5-dimethylphenyl)propyl) (methyl)sulfane

NaSMe (65 mg) is added to a solution of 3-(4-bromo-3,5-dimethylphenyl)propyl methanesulfonate (230 mg) in N,N-dimethylformamide (5 mL). The mixture is stirred for 12 hours. NaSMe (25 mg) is added and the mixture is stirred for 1 hour. Then the mixture is partitioned between water and diethylether. The organic phase is dried (MgSO$_4$) and concentrated. The residue is chromatographed on silica gel (cyclohexane/ethyl acetate 99:1→80:20) to give the title compound. Yield: 145 mg; LC (method 8): $t_R$=0.88 min.

Step 3: 2-bromo-1,3-dimethyl-5-(3-(methylsulfonyl) propyl)benzene

The title compound is prepared from (3-(4-bromo-3,5-dimethylphenyl)propyl)(methyl)sulfane following a procedure analogous to that described in Step 2 of Intermediate 41. LC (method 7): $t_R$=1.04 min; Mass spectrum (ESI$^+$): m/z=305 [M+H]$^+$.

Step 4: Methyl 2-((S)-6-((R)-4-(2,6-dimethyl-4-(3-(methylsulfonyl)propyl)phenyl)-7-fluoro-2,3-dihydro-1H-inden-1-yloxy)-2,3-dihydrobenzofuran-3-yl) acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and 2-bromo-1,3-dimethyl-5-(3-(methylsulfonyl) propyl)benzene following a procedure analogous to that described in Step 5 of Intermediate 1. LC (method 8): $t_R$=0.66 min; Mass spectrum (ESI$^+$): m/z=567 [M+H]$^+$.

Intermediate 43

Methyl 2-((S)-6-((R)-4-(2,6-dimethyl-4-(2-(methylsulfonamido)ethoxy)phenyl)-7-fluoro-2,3-dihydro-1H-inden-1-yloxy)-2,3-dihydrobenzofuran-3-yl) acetate

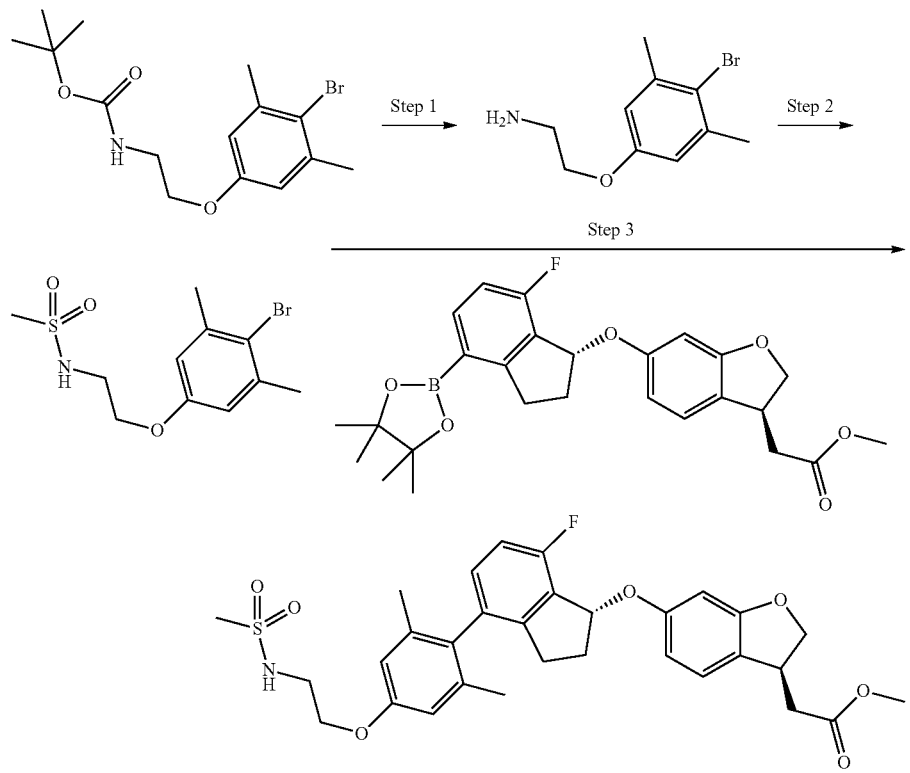

Step 1: 2-(4-Bromo-3,5-dimethylphenoxy)ethanamine

To a solution of tert-butyl 2-(4-bromo-3,5-dimethylphenoxy)ethylcarbamate (310 mg) in dichloromethane (8 mL) is added trifluoroacetic acid (700 μL). The mixture is stirred for 12 hours at room temperature. Then saturated aqueous K$_2$CO$_3$ solution is added, the mixture is stirred for 30 minutes and the phases are separated. The organic phase is washed with saturated aqueous K$_2$CO$_3$ solution and dried (MgSO$_4$). The solvent is evaporated to give the title compound. Yield: 200 mg; LC (method 7): $t_R$=0.83 min; Mass spectrum (ESI$^+$): m/z=244 [M+H]$^+$.

Step 2: N-(2-(4-bromo-3,5-dimethylphenoxy)ethyl)methanesulfonamide

To a cooled (0° C.) solution of 2-(4-bromo-3,5-dimethylphenoxy)ethanamine (100 mg) and triethylamine (63 μL) in dichloromethane (2 mL) is added methanesulfonyl chloride (32 μL). The mixture is stirred for 2 hours at 0° C. Then the mixture is partitioned between dichloromethane and water. The organic phase is separated, washed with brine and dried (MgSO$_4$). The solvent is evaporated and the residue is purified by HPLC on reversed phase to give the title compound. Yield: 90 mg; LC (method 7): t$_R$=1.01 min; Mass spectrum (ESI$^+$): m/z=322 [M+H]$^+$.

Step 3: Methyl 2-((S)-6-((R)-4-(2,6-dimethyl-4-(2-(methylsulfonamido)ethoxy)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and N-(2-(4-bromo-3,5-dimethylphenoxy)ethyl)methanesulfonamide following a procedure analogous to that described in Step 5 of Intermediate 1. LC (method 8): t$_R$=0.59 min; Mass spectrum (ESI$^+$): m/z=584 [M+H]$^+$.

Intermediate 44

Methyl 2-((S)-6-((R)-4-(4-(2-acetamidoethyl)-2,6-dimethylphenyl)-7-fluoro-2,3-dihydro-1H-inden-1-yloxy)-2,3-dihydrobenzofuran-3-yl)acetate

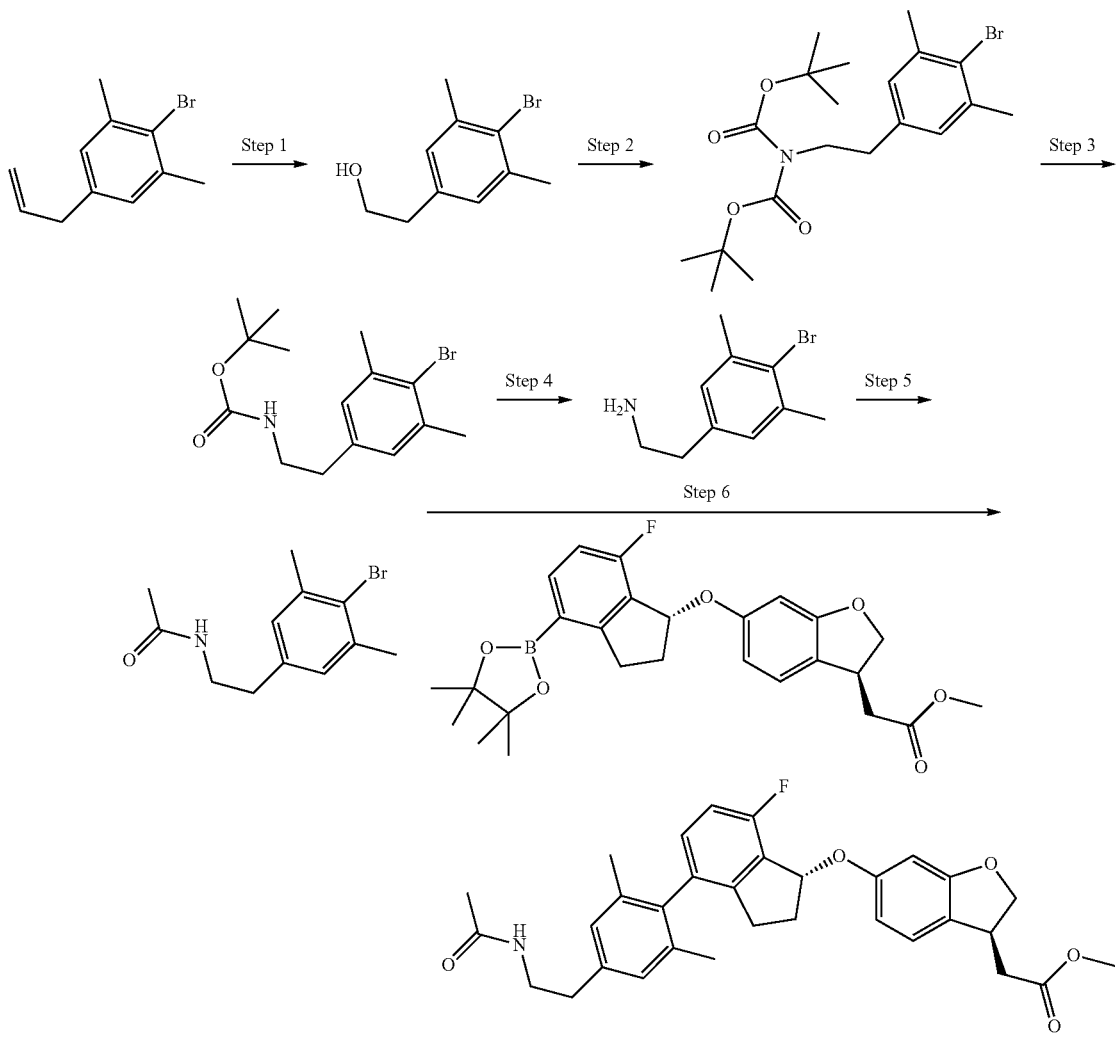

Step 1: 2-(4-Bromo-3,5-dimethylphenyl)ethanol

O$_3$ is bubbled through a cooled (−78° C.) solution of 5-allyl-2-bromo-1,3-dimethylbenzene (2 g) in dichloromethane (70 mL) until a light blue color is observed. Then O$_2$ is bubbled through the solution until the color disappears. Afterwards methanol (70 mL) and NaBH$_4$ (1.45 g) are added and the mixture is stirred for 12 hours while warming to room temperature. The mixture is then partitioned between 1 M aqueous HCl solution and diethylether. The organic phase is dried (MgSO$_4$) and concentrated. The residue is chromatographed on silica gel (cyclohexane/ethyl acetate 95:5→70:

30) to give the title compound. Yield: 390 mg; LC (method 8): $t_R$=0.22 min; Mass spectrum (ESI$^+$): m/z=211 [M+H—H$_2$O]$^+$.

Step 2: N,N-Di-tert.-butoxycarbonyl-2-(4-bromo-3,5-dimethylphenyl)ethanamine

A solution of di-tert.-butyl azodicarboxylate (2.85 g) in dichloromethane (10 mL) is added dropwise over 15 minutes to a solution of 2-(4-bromo-3,5-dimethylphenyl)ethanol (950 mg), di-tert.butyl-iminodicarboxylate (3.75 g) and tributylphosphine (4.4 mL) in dichloromethane (40 mL) at −10° C. The resulting solution is stirred for 2 hours while warming to room temperature and then partitioned between saturated aqueous NaHCO$_3$ solution and dichloromethane. The aqueous phase is extracted with dichloromethane. The combined organic phases are dried (MgSO$_4$) and concentrated. The residue is chromatographed on silica gel (cyclohexane/ethyl acetate 99:1→70:30) to give the title compound. Yield: 1.19 g; LC (method 8): $t_R$=1.06 min; Mass spectrum (ESI$^+$): m/z=451 [M+Na]$^+$.

Step 3: tert-Butyl 4-bromo-3,5-dimethylphenethylcarbamate

To a solution of N,N-di-tert.-butoxycarbonyl-2-(4-bromo-3,5-dimethylphenyl)ethanamine (1.19 g) in dichloromethane (25 mL) is added trifluoroacetic acid (320 µL). The mixture is stirred for 12 hours at room temperature. Then the mixture is partitioned between saturated aqueous NaHCO$_3$ solution and dichloromethane. The organic phase is dried (MgSO$_4$), the solvent is evaporated and the residue is chromatographed on silica gel (cyclohexane/ethyl acetate 99:1→70:30) to give the title compound. Yield: 550 mg; LC (method 8): $t_R$=0.68 min; Mass spectrum (ESI$^+$): m/z=328 [M+H]$^+$.

Step 4: 2-(4-Bromo-3,5-dimethylphenyl)ethanamine

The title compound is prepared from tert-butyl 4-bromo-3,5-dimethylphenethylcarbamate following a procedure analogous to that described in Step 1 of Intermediate 43. LC (method 7): $t_R$=0.83 min; Mass spectrum (ESI$^+$): m/z=228 [M+H]$^+$.

Step 5: N-(4-Bromo-3,5-dimethylphenethyl)acetamide

To a cooled (0° C.) solution of 2-(4-bromo-3,5-dimethylphenyl)ethanamine (100 mg) and triethylamine (68 µL) in dichloromethane (3 mL) is added acetyl chloride (31 µL). The mixture is stirred for 2 hours at 0° C. Then the mixture is partitioned between dichloromethane and water. The organic phase is separated and dried (MgSO$_4$). The solvent is evaporated and the residue is purified by HPLC on reversed phase to give the title compound. Yield: 25 mg; LC (method 7): $t_R$=0.98 min; Mass spectrum (ESI$^+$): m/z=270 [M+H]$^+$.

Step 6: Methyl 2-((S)-6-((R)-4-(4-(2-acetamidoethyl)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and N-(4-bromo-3,5-dimethylphenethyl)acetamide following a procedure analogous to that described in Step 5 of Intermediate 1. LC (method 8): $t_R$=0.53 min; Mass spectrum (ESI$^+$): m/z=532 [M+H]$^+$.

Intermediate 45

Methyl 2-((S)-6-((R)-4-(4-(2-acetamidoethoxy)-2,6-dimethylphenyl)-7-fluoro-2,3-dihydro-1H-inden-1-yloxy)-2,3-dihydrobenzofuran-3-yl)acetate

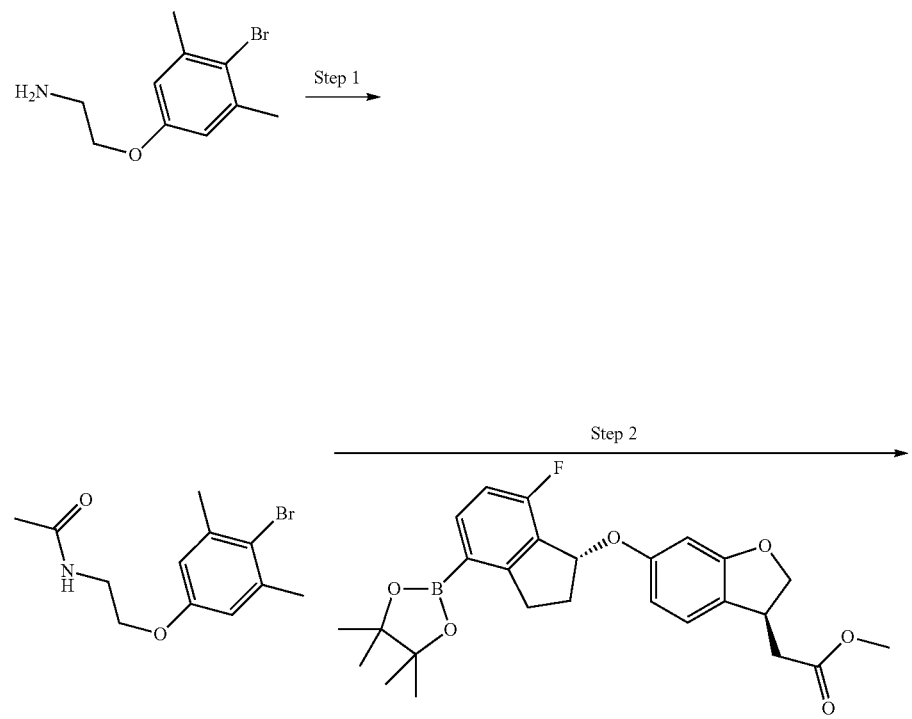

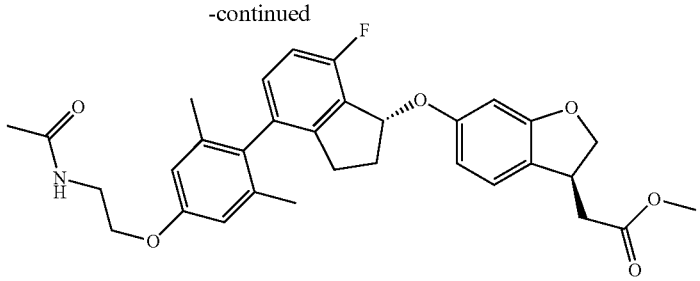

Step 1: N-(2-(4-Bromo-3,5-dimethylphenoxy)ethyl)acetamide

The title compound is prepared from 2-(4-bromo-3,5-dimethylphenoxy)ethanamine following a procedure analogous to that described in Step 5 of Intermediate 44. LC (method 7): $t_R$=0.97 min; Mass spectrum (ESI$^+$): m/z=286 [M+H]$^+$.

Step 2: Methyl 2-((S)-6-((R)-4-(4-(2-acetamidoethoxy)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and N-(2-(4-bromo-3,5-dimethylphenoxy)ethyl)acetamide following a procedure analogous to that described in Step 5 of Intermediate 1. LC (method 8): $t_R$=0.50 min; Mass spectrum (ESI$^+$): m/z=548 [M+H]$^+$.

Intermediate 46

Methyl 2-((S)-6-((R)-4-(2,6-dimethyl-4-(2-(methylsulfonamido)ethyl)phenyl)-7-fluoro-2,3-dihydro-1H-inden-1-yloxy)-2,3-dihydrobenzofuran-3-yl)acetate

Step 1 →

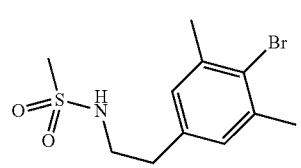

Step 2 →

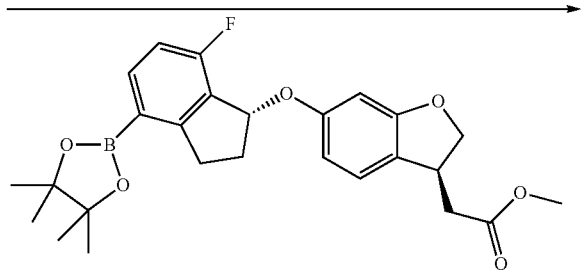

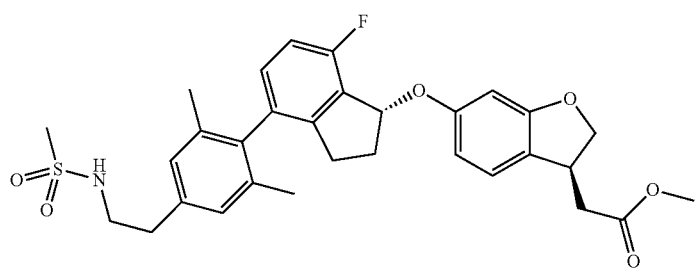

Step 1: N-(4-Bromo-3,5-dimethylphenethyl)methanesulfonamide

The title compound is prepared from 2-(4-bromo-3,5-dimethylphenyl)ethanamine following a procedure analogous to that described in Step 2 of Intermediate 43. LC (method 7): $t_R$=1.02 min; Mass spectrum (ESI$^+$): m/z=306 [M+H]$^+$.

Step 2: Methyl 2-((S)-6-((R)-4-(2,6-dimethyl-4-(2-(methylsulfonamido)ethyl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and N-(4-bromo-3,5-dimethylphenethyl)methanesulfonamide following a procedure analogous to that described in Step 5 of Intermediate 1. LC (method 8): $t_R$=0.58 min; Mass spectrum (ESI$^+$): m/z=568 [M+H]$^+$.

Intermediate 47

Methyl 2-((3S)-6-((1R)-4-(2,6-dimethyl-4-(1-methyl-2-oxopyrrolidin-3-yloxy)phenyl)-7-fluoro-2,3-dihydro-1H-inden-1-yloxy)-2,3-dihydrobenzofuran-3-yl)acetate

Step 1: 3-(4-Bromo-3,5-dimethylphenoxy)-1-methylpyrrolidin-2-one

To a solution of 4-bromo-3,5-dimethylphenol (100 mg) in N,N-dimethylformamide (2 mL) is added 3-bromo-1-methylpyrrolidin-2-one (100 mg) and K$_2$CO$_3$ (105 mg). The mixture is stirred for 12 hours at room temperature. Then the mixture is partitioned between water and diethylether. The organic phase is dried (MgSO$_4$) and concentrated. The residue is chromatographed on silica gel (cyclohexane/ethyl acetate 80:20→50:50) to give the title compound. Yield: 65 mg; LC (method 7): $t_R$=1.0 min; Mass spectrum (ESI$^+$): m/z=298 [M+H]$^+$.

Step 2: Methyl 2-((3S)-6-((1R)-4-(2,6-dimethyl-4-(1-methyl-2-oxopyrrolidin-3-yloxy)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 3-(4-bromo-3,5-dimethylphenoxy)-1-methylpyrrolidin-2-one following a procedure analogous to that described in Step 5 of Intermediate 1. LC (method 8): $t_R$=0.60 min; Mass spectrum (ESI$^+$): m/z=560 [M+H]$^+$.

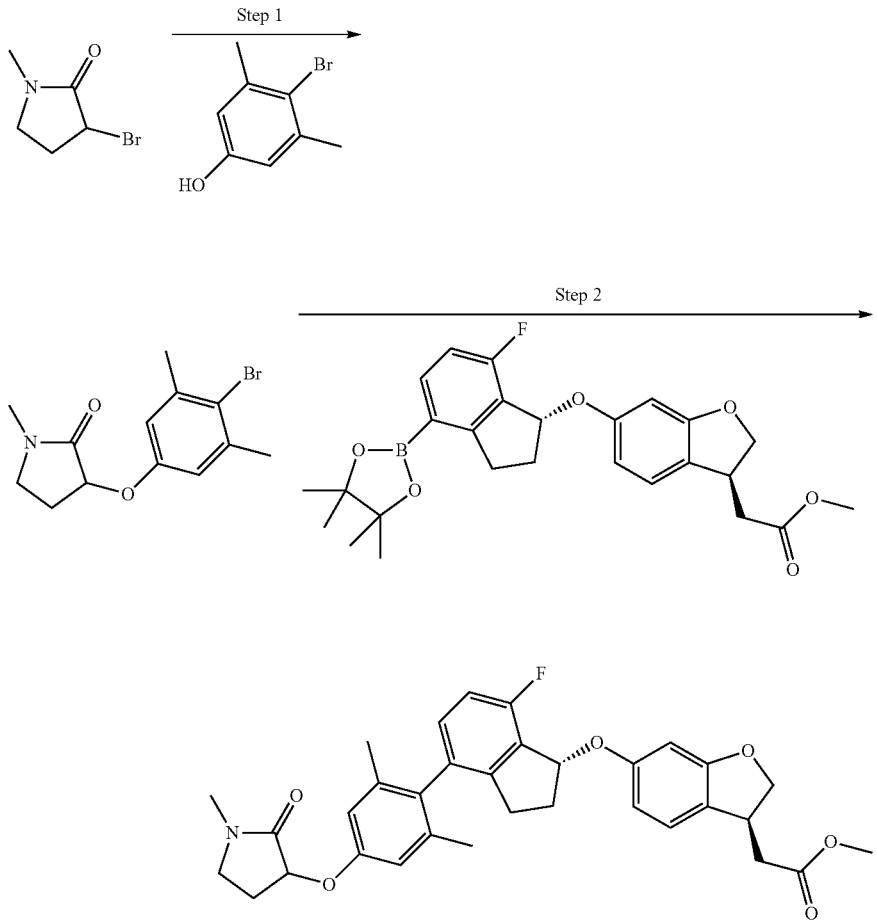

Intermediate 48

Methyl 2-((S)-6-((R)-4-(4-(2,2-dimethyl-3-(methylsulfonyl)propoxy)-2,6-dimethylphenyl)-7-fluoro-2,3-dihydro-1H-inden-1-yloxy)-2,3-dihydrobenzofuran-3-yl)acetate

Step 2: 3-(4-Bromo-3,5-dimethylphenoxy)-2,2-dimethylpropan-1-ol

To a mixture of 4-bromo-3,5-dimethylphenol (625 mg) and $Cs_2CO_3$ (5 g) in N,N-dimethylformamide (10 mL) is added 5,5-dimethyl-[1,3,2]dioxathiane-2-oxide (467 mg). The mixture is stirred for 12 hours at 100° C. and then partitioned

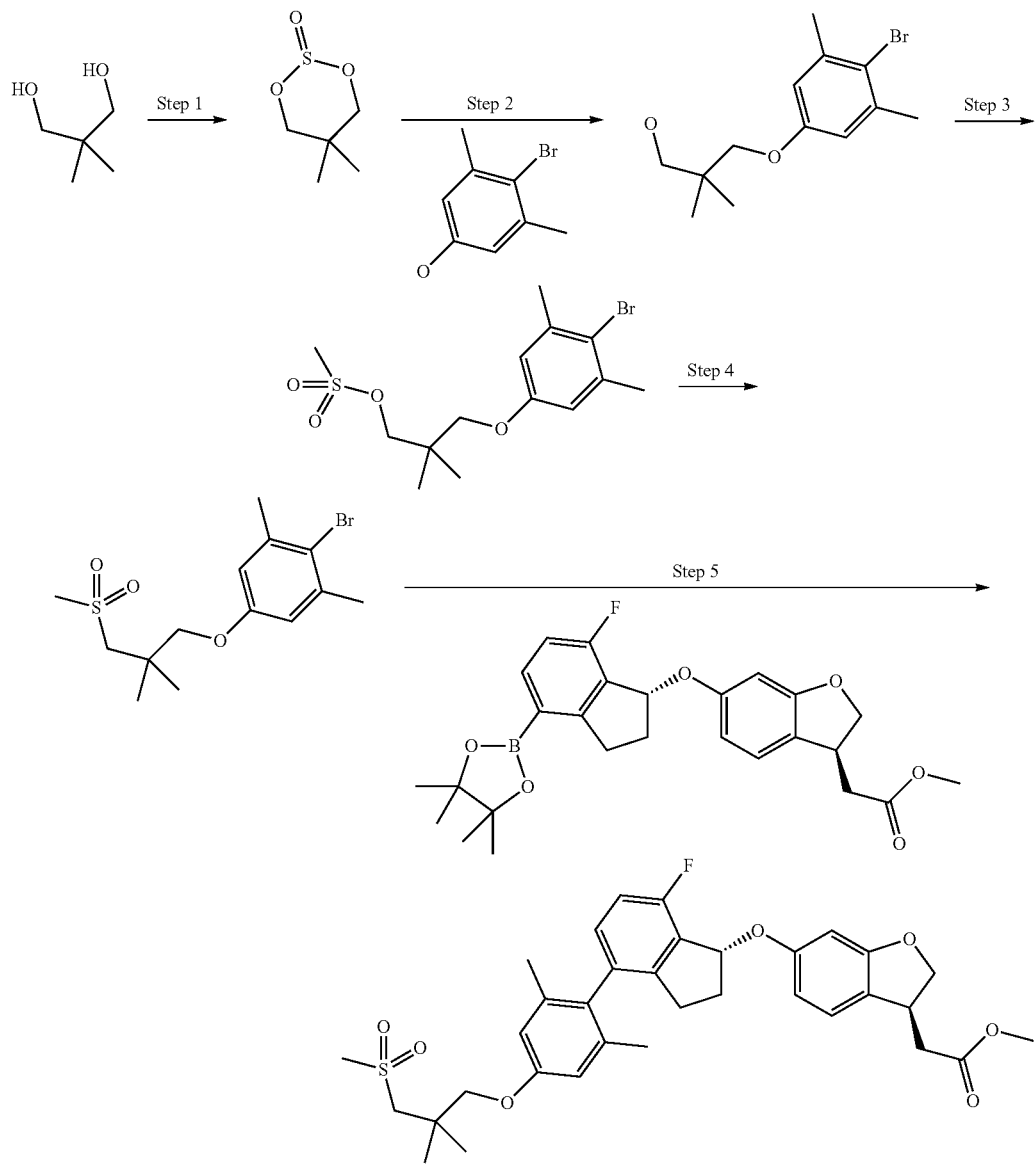

Step 1: 5,5-Dimethyl-[1,3,2]dioxathiane-2-oxide

To a solution of 2,2-dimethyl-propane-1,3-diol (1 g) in dichloromethane (5 mL) is added dropwise at 0° C. thionylchloride (735 µL). The mixture is stirred for 3 hours at 40° C. and then partitioned between saturated aqueous $NaHCO_3$ solution and dichloromethane. The organic phase is washed with brine and dried ($MgSO_4$). The solvent is evaporated to give the title compound. Yield: 1 g; TLC: $r_f$=0.65 (silicagel, cyclohexane/ethyl acetate 3:1).

between water and ethyl acetate. The organic phase is washed with brine and dried ($MgSO_4$). The solvent is evaporated and the residue is purified by HPLC on reversed phase to give the title compound. Yield: 251 mg; LC (method 7): $t_R$=1.16 min; Mass spectrum ($ESI^+$): m/z=287 $[M+H]^+$.

Step 3: 3-(4-Bromo-3,5-dimethylphenoxy)-2,2-dimethylpropyl methanesulfonate

To a cooled (0° C.) solution of 3-(4-bromo-3,5-dimethylphenoxy)-2,2-dimethylpropan-1-ol (251 mg) and triethylamine (160 µL) in dichloromethane (3 mL) is added methanesulfonyl chloride (75 µL). The mixture is stirred for 2 days while warming to room temperature. Then the mixture is diluted with dichloromethane, washed with saturated aqueous NaHCO$_3$ solution and dried (MgSO$_4$). The solvent is evaporated and the residue is chromatographed on silica gel (cyclohexane/ethyl acetate 99:1→50:50) to give the title compound. Yield: 271 mg; LC (method 7): t$_R$=1.18 min; Mass spectrum (ESI$^+$): m/z=365 [M+H]$^+$.

Step 4: 2-Bromo-5-(2,2-dimethyl-3-(methylsulfonyl) propoxy)-1,3-dimethylbenzene

In a microwave vial sodium methanesulfinate (720 mg) is added to a solution of 3-(4-bromo-3,5-dimethylphenoxy)-2,2-dimethylpropyl methanesulfonate (271 mg) in N-methyl-2-pyrrolidinon (NMP) (8 mL). The mixture is heated to 180° C. for 30 minutes. Then the mixture is diluted with diethylether, washed with water and brine and dried (MgSO$_4$). The solvent is evaporated and the residue is purified by HPLC on reversed phase to give the title compound. Yield: 32 mg; LC (method 8): t$_R$=0.47 min; Mass spectrum (ESI$^+$): m/z=349 [M+H]$^+$.

Step 5: Methyl 2-((S)-6-((R)-4-(4-(2,2-dimethyl-3-(methylsulfonyl)propoxy)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 2-bromo-5-(2,2-dimethyl-3-(methylsulfonyl)propoxy)-1,3-dimethylbenzene following a procedure analogous to that described in Step 5 of Intermediate 1. LC (method 8): t$_R$=0.81 min; Mass spectrum (ESI$^+$): m/z=611 [M+H]$^+$.

Intermediate 49

3-(4-Bromo-3,5-dimethylphenoxy)-1-methylcyclopentanol (Enantiomer 1 and Enantiomer 2)

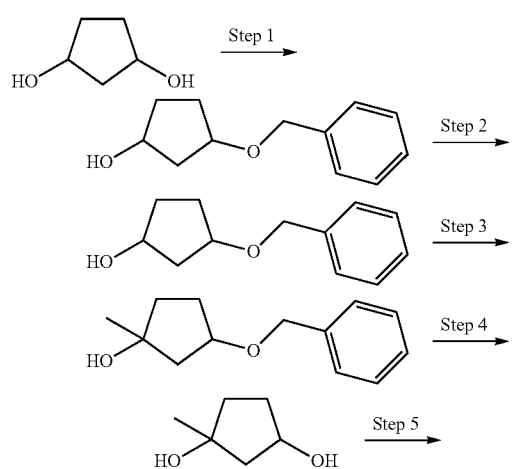

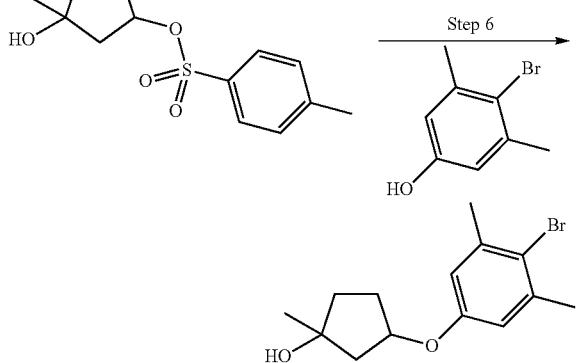

Step 1: 3-(Benzyloxy)cyclopentanol

Under argon NaH (60% dispersion in mineral oil; 2.85 g) is added to a cold (0° C.) solution of cyclopentane-1,3-diol (3.6 g) in N,N-dimethylformamide (40 mL). The mixture is stirred for 12 hours, followed by dropwise addition of (4.2 mL) and stirring for 12 hours at room temperature. Afterwards the mixture is partitioned between saturated aqueous NH$_4$Cl solution and diethylether. The organic phase is washed with water, dried (MgSO$_4$) and concentrated. The residue is chromatographed on silica gel (petrole ether/ethyl acetate 50:50→20:80) to give the title compound. Yield: 540 mg; LC (method 7): t$_R$=0.85 min; Mass spectrum (ESI$^+$): m/z=193 [M+H]$^+$.

Step 2: 3-(Benzyloxy)cyclopentanone

To a solution of 3-(benzyloxy)cyclopentanol (530 mg) in dichloromethane (8 mL) is added at 0° C. 1,1-dihydro-1,1,1-triacetoxy-1,2-benziodoxol-3(1H)-on (Dess-Martin periodinan, 8 mL of a 15% solution in dichloromethane). The mixture is stirred for 3 hours, diluted with dichloromethane, washed with 1 M aqueous NaOH solution and dried (MgSO$_4$). The solvents are evaporated in vacuo and the residue is chromatographed on silica gel (petrole ether/ethyl acetate 90:10→40:60) to give the title compound. Yield: 430 mg; LC (method 7): t$_R$=0.90 min; Mass spectrum (ESI$^+$): m/z=191 [M+H]$^+$.

Step 3: 3-(Benzyloxy)-1-methylcyclopentanol

Methylmagnesium bromide (4.8 mL, 1.4 M solution in toluene/tetrahydrofurane 3:1) is added dropwise under argon to a solution of 3-(benzyloxy)cyclopentanone (420 mg) in tetrahydrofurane (10 mL) at −78° C. The mixture is stirred for 12 hours while warming to room temperature and partitioned between 1 M aqueous HCl solution and ethyl acetate. The aqueous phase is extracted with ethyl acetate. The combined organic phases are washed with brine and dried (MgSO$_4$). The solvents are evaporated in vacuo to give the title compound. Yield: 400 mg; LC (method 7): t$_R$=0.93 min; Mass spectrum (ESI$^+$): m/z=229 [M+Na]$^+$.

Step 4: 1-Methylcyclopentane-1,3-diol

To a solution of 3-(benzyloxy)-1-methylcyclopentanol (390 mg) in methanol (15 mL) is added 10% palladium on activated carbon (100 mg) and the mixture is hydrogenated at a pressure of 2 bar for 12 hours. The catalyst is filtered off and washed with methanol. The combined mother liquors are concentrated to give the title compound. Yield: 125 mg; TLC: $r_f$=0.18 (silicagel, petrole ether/ethyl acetate 1:1).

Step 5: 3-Hydroxy-3-methylcyclopentyl 4-methylbenzenesulfonate

The title compound is prepared from 1-methylcyclopentane-1,3-diol following a procedure analogous to that described in Step 1 of Intermediate 23. TLC: $r_f$=0.48 (silicagel, petrole ether/ethyl acetate 1:1).

Step 6: 3-(4-Bromo-3,5-dimethylphenoxy)-1-methylcyclopentanol (Enantiomer 1 and Enantiomer 2)

To a mixture of 4-bromo-3,5-dimethylphenol (300 mg) and $Cs_2CO_3$ (600 mg) in N,N-dimethylformamide (3 mL) is added 3-hydroxy-3-methylcyclopentyl 4-methylbenzenesulfonate (275 mg). The mixture is stirred for 12 hours at 50° C. and then partitioned between water and diethylether. The organic phase is dried ($MgSO_4$) and concentrated. The residue is chromatographed on silica gel (petrole ether/ethyl acetate 90:10→30:70). The enantiomers are separated by SFC on chiral phase (column: Daicel IA, 5 μm, 250 mm×10 mm; eluent: $scCO_2$/(methanol+0.2% diethylamine) 85:15, 10 mL/min):

Enantiomer 1: $t_R$=4.7 min; Yield: 31 mg; LC (method 8): $t_R$=0.47 min; Mass spectrum ($ESI^+$): m/z=299 $[M+H]^+$.

Enantiomer 2: $t_R$=5.7 min; Yield: 42 mg; LC (method 8): $t_R$=0.47 min; Mass spectrum ($ESI^+$): m/z=299 $[M+H]^+$.

Intermediate 50

Methyl 2-((3S)-6-((1R)-7-fluoro-4-(4-(3-hydroxy-3-methylcyclopentyloxy)-2,6-dimethylphenyl)-2,3-dihydro-1H-inden-1-yloxy)-2,3-dihydrobenzofuran-3-yl)acetate (Diastereomer 1)

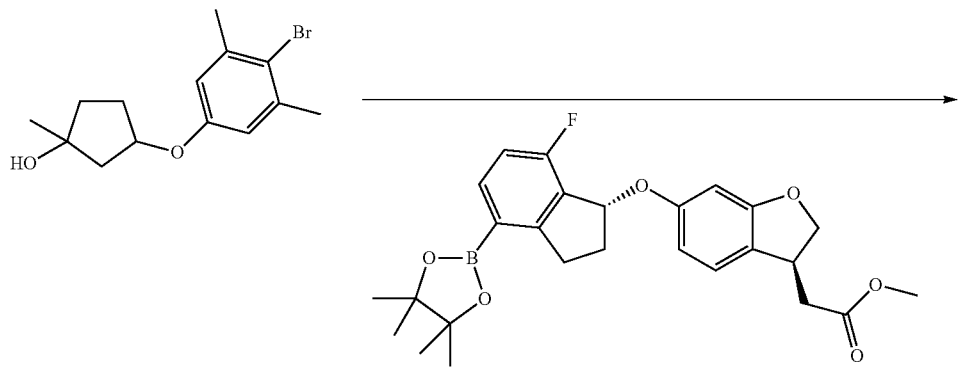

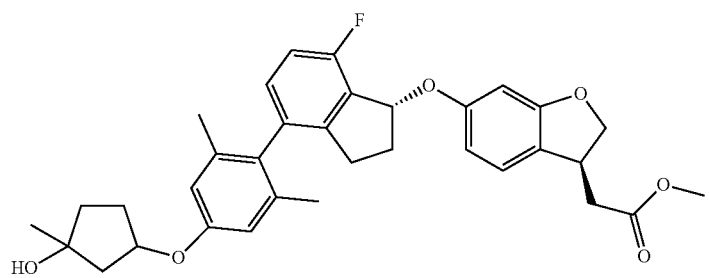

The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate and 3-(4-bromo-3,5-dimethylphenoxy)-1-methylcyclopentanol (enantiomer 1) following a procedure analogous to that described in Step 5 of Intermediate 1. LC (method 8): $t_R$=0.81 min.

Intermediate 51

Methyl 2-((3S)-6-((1R)-7-fluoro-4-(4-(3-hydroxy-3-methylcyclopentyloxy)-2,6-dimethylphenyl)-2,3-dihydro-1H-inden-1-yloxy)-2,3-dihydrobenzofuran-3-yl)acetate (Diastereomer 2)

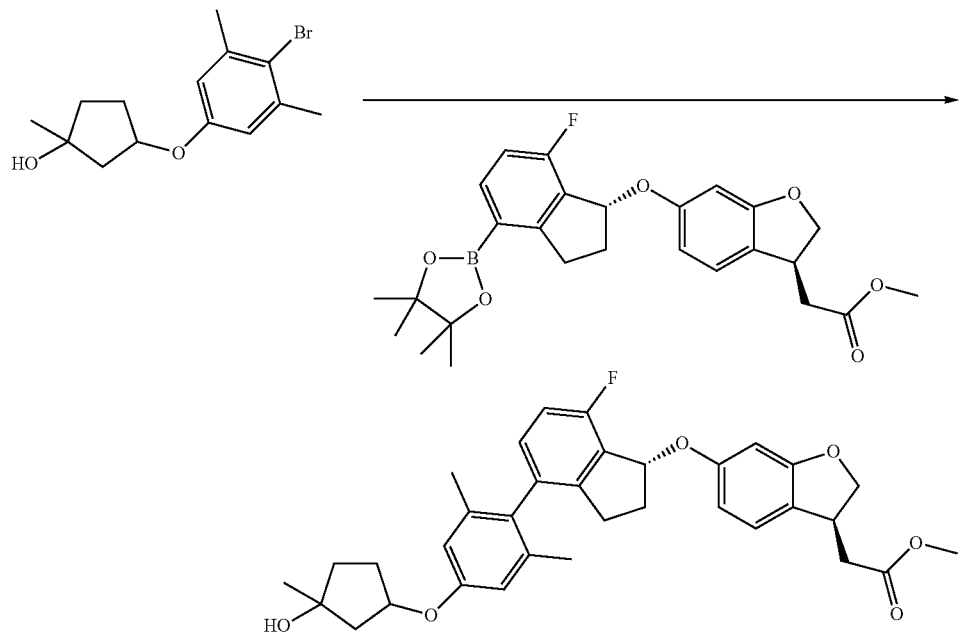

The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate and 3-(4-bromo-3,5-dimethylphenoxy)-1-methylcyclopentanol (enantiomer 2) following a procedure analogous to that described in Step 5 of Intermediate 1. LC (method 8): $t_R$=0.81 min.

Intermediate 52

4-(4-(3,6-dihydro-2H-pyran-4-yl)-2,6-dimethylphenyl)-7-fluoro-2,3-dihydro-1H-inden-1-one and 4-(4-(7-fluoro-1-oxo-2,3-dihydro-1H-inden-4-yl)-3,5-dimethylphenyl)-5,6-dihydro-2H-pyran-2-one

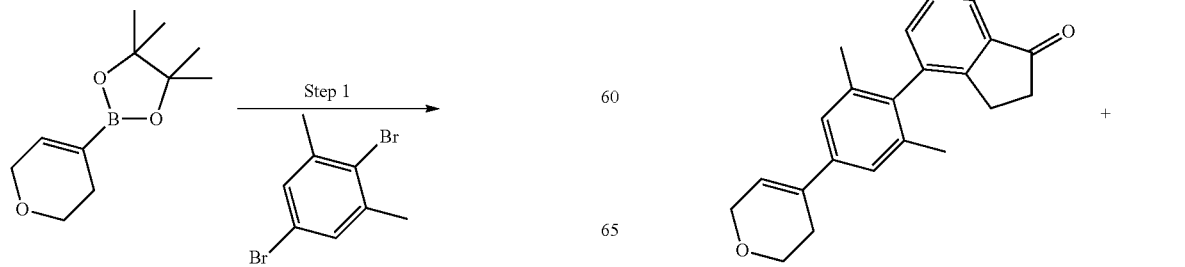

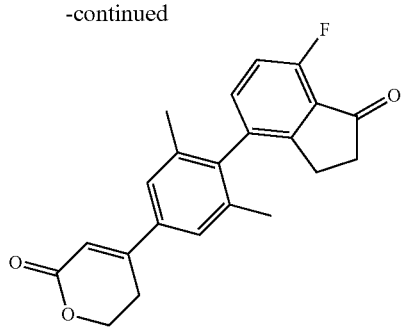

Step 1: 4-(4-Bromo-3,5-dimethylphenyl)-3,6-dihydro-2H-pyran

In a microwave vial 2,5-dibromo-1,3-dimethylbenzene (800 mg), 2-(3,6-dihydro-2H-pyran-4-yl)-4,4,5,5-tetramethyl-1,3,2-dioxaborolane (640 mg) and $K_3PO_4$ (1.3 g) are suspended in toluene (12 mL) and water (1.2 mL) and purged for 10 minutes with argon. [1,1'-Bis(diphenylphosphino)-ferrocene]-dichloropalladium-(II) (100 mg) is added, the vial is sealed and the mixture is stirred at 60° C. for 12 hours. After cooling to room temperature the mixture is diluted with diethylether and washed with saturated aqueous $NH_4Cl$ solution. The organic phase is dried ($MgSO_4$) and concentrated. The residue is chromatographed on silica gel (cyclohexane/ethyl acetate 99:1→60:40) to give the title compound. Yield: 404 mg.

Step 2: 4-(4-(3,6-dihydro-2H-pyran-4-yl)-2,6-dimethylphenyl)-7-fluoro-2,3-dihydro-1H-inden-1-one and 4-(4-(7-fluoro-1-oxo-2,3-dihydro-1H-inden-4-yl)-3,5-dimethylphenyl)-5,6-dihydro-2H-pyran-2-one In a microwave vial 7-fluoro-4-(4,4,5,5-tetramethyl-1,3,2-dioxaborolan-2-yl)-2,3-dihydro-1H-inden-1-one (200 mg), 4-(4-bromo-3,5-dimethylphenyl)-3,6-dihydro-2H-pyran (200 mg), $K_3PO_4$ (310 mg) and dicyclohexyl(2',6'-dimethoxybiphenyl-2-yl)phosphine (S-Phos) (25 mg) are suspended in toluene (2 mL), 1,4-dioxane (2 mL) and water (250 µL) and purged for 10 minutes with argon. Palladium-(II)-acetate (7 mg) is added, the vial is sealed and the mixture is stirred at 110° C. for 3 hours. After cooling to room temperature the mixture is partitioned between diethylether and saturated aqueous $NH_4Cl$ solution. The organic phase is dried ($MgSO_4$) and concentrated. The residue is chromatographed on silica gel (petrole ether/ethyl acetate 90:10→50:50) to give the title compounds.

4-(4-(3,6-dihydro-2H-pyran-4-yl)-2,6-dimethylphenyl)-7-fluoro-2,3-dihydro-1H-inden-1-one: Yield: 100 mg; LC (method 7): $t_R$=1.10 min; Mass spectrum (ESI$^+$): m/z=337 [M+H]$^+$.

4-(4-(7-fluoro-1-oxo-2,3-dihydro-1H-inden-4-yl)-3,5-dimethylphenyl)-5,6-dihydro-2H-pyran-2-one: Yield: 48 mg; LC (method 7): $t_R$=0.99 min; Mass spectrum (ESI$^+$): m/z=351 [M+H]$^+$.

Intermediate 53

Methyl 2-((S)-6-((R)-4-(2,6-dimethyl-4-(tetrahydro-2H-pyran-4-yl)phenyl)-7-fluoro-2,3-dihydro-1H-inden-1-yloxy)-2,3-dihydrobenzofuran-3-yl)acetate

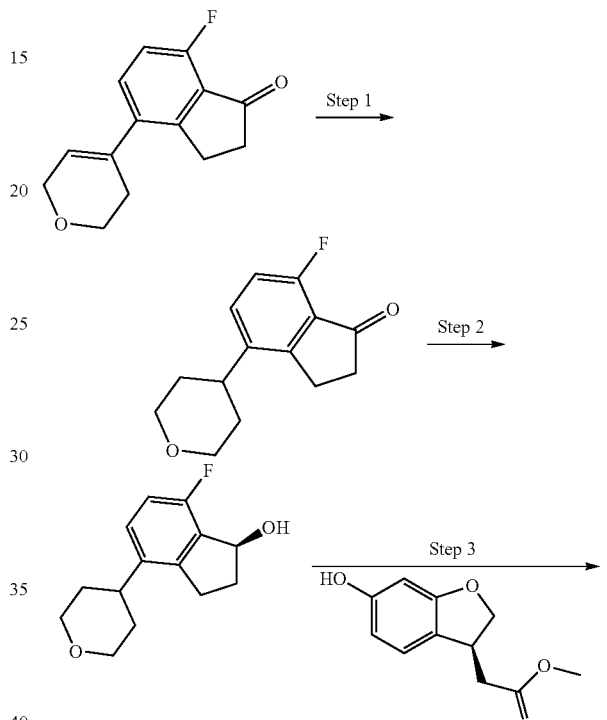

Step 1: 7-Fluoro-4-(tetrahydro-2H-pyran-4-yl)-2,3-dihydro-1H-inden-1-one

To a solution of 4-(3,6-dihydro-2H-pyran-4-yl)-7-fluoro-2,3-dihydro-1H-inden-1-one (100 mg) in tetrahydrofurane (10 mL) is added 10% palladium on activated carbon (30 mg) and the mixture is hydrogenated at a pressure of 2 bar for 12 hours. The catalyst is filtered off and washed with methanol. The combined mother liquors are concentrated and the residue is chromatographed on silica gel (petrole ether/ethyl acetate 80:20→50:50) to give the title compound. Yield: 55 mg; LC (method 8): $t_R$=0.36 min; Mass spectrum (ESI$^+$): m/z=339 [M+H]$^+$.

Step 2: (S)-7-Fluoro-4-(tetrahydro-2H-pyran-4-yl)-2,3-dihydro-1H-inden-1-ol

The title compound is prepared from 7-fluoro-4-(tetrahydro-2H-pyran-4-yl)-2,3-dihydro-1H-inden-1-one following a procedure analogous to that described in Step 2 of Intermediate 1. Mass spectrum (ESI$^+$): m/z=363 [M+Na]$^+$.

Step 3: Methyl 2-((S)-6-((R)-4-(2,6-dimethyl-4-(tetrahydro-2H-pyran-4-yl)phenyl)-7-fluoro-2,3-dihydro-1H-inden-1-yloxy)-2,3-dihydrobenzofuran-3-yl)acetate The title compound is prepared from (S)-7-fluoro-4-(tetrahydro-2H-pyran-4-yl)-2,3-dihydro-1H-inden-1-ol and (S)-methyl 2-(6-hydroxy-2,3-dihydrobenzofuran-3-yl)acetate following a procedure analogous to that described in Step 3 of Intermediate 1. LC (method 26): $t_R$=0.95 min; Mass spectrum (ESI$^+$): m/z=531 [M+H]$^+$.

Intermediate 54

Methyl 2-((S)-6-((R)-4-(2,6-dimethyl-4-(6-oxo-3,6-dihydro-2H-pyran-4-yl)phenyl)-7-fluoro-2,3-dihydro-1H-inden-1-yloxy)-2,3-dihydrobenzofuran-3-yl)acetate

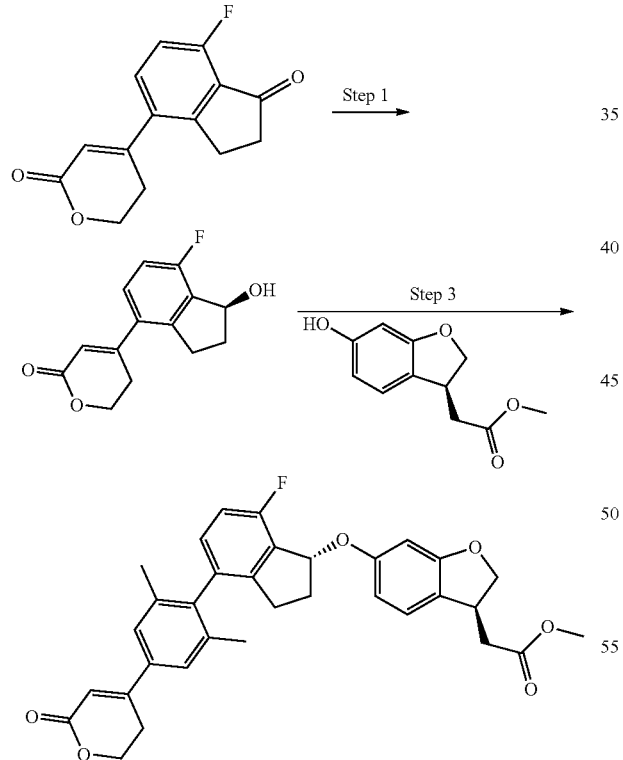

Step 1: (S)-4-(7-Fluoro-1-hydroxy-2,3-dihydro-1H-inden-4-yl)-5,6-dihydro-2H-pyran-2-one The title compound is prepared from 4-(7-fluoro-1-oxo-2,3-dihydro-1H-inden-4-yl)-5,6-dihydro-2H-pyran-2-one following a procedure analogous to that described in Step 1 of Intermediate 2. LC (method 7): $t_R$=0.97 min; Mass spectrum (ESI$^+$): m/z=353 [M+H]$^+$.

Step 2: Methyl 2-((S)-6-((R)-4-(2,6-dimethyl-4-(6-oxo-3,6-dihydro-2H-pyran-4-yl)phenyl)-7-fluoro-2,3-dihydro-1H-inden-1-yloxy)-2,3-dihydrobenzofuran-3-yl)acetate The title compound is prepared from (S)-4-(7-fluoro-1-hydroxy-2,3-dihydro-1H-inden-4-yl)-5,6-dihydro-2H-pyran-2-one and (S)-methyl 2-(6-hydroxy-2,3-dihydrobenzofuran-3-yl)acetate following a procedure analogous to that described in Step 3 of Intermediate 1. LC (method 7): $t_R$=1.18 min; Mass spectrum (ESI$^+$): m/z=543 [M+H]$^+$.

Intermediate 55

Methyl 2-((S)-6-((R)-4-(2,6-bis(methoxymethyl)-4-((3-methyloxetan-3-yl)methoxy)phenyl)-7-fluoro-2,3-dihydro-1H-inden-1-yloxy)-2,3-dihydrobenzofuran-3-yl)acetate

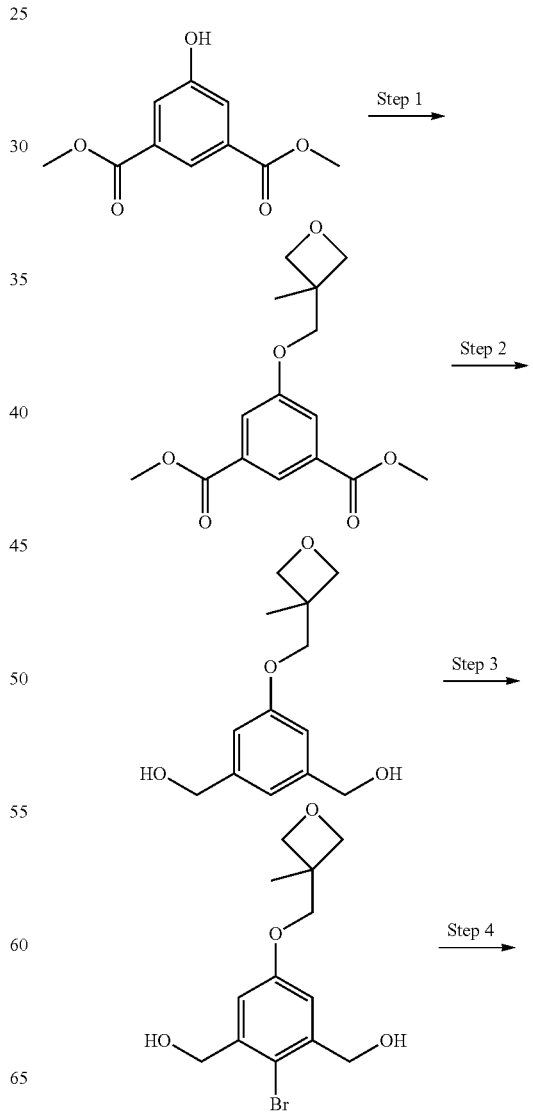

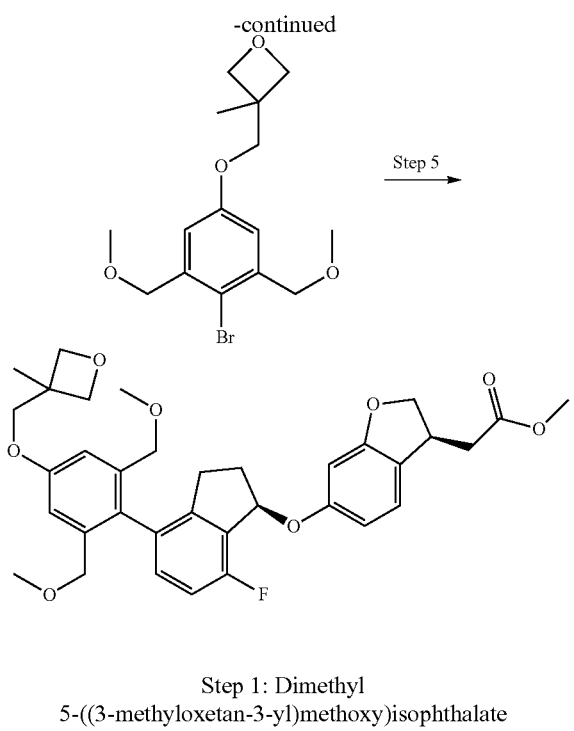

Step 1: Dimethyl 5-((3-methyloxetan-3-yl)methoxy)isophthalate

A mixture of dimethyl 5-hydroxyisophthalate (500 mg), (3-methyloxetan-3-yl)methyl 4-methylbenzenesulfonate (915 mg), and potassium carbonate (850 mg) in N,N-dimethylformamide (3 mL) is stirred at 50° C. for 5 h. The reaction mixture is diluted with water and the precipitate is filtered off, washed with water, and dried to give the title compound. LC (method 7): $t_R$=0.97 min; Mass spectrum (ESI$^+$): m/z=295 [M+H]$^+$.

Step 2: (5-((3-Methyloxetan-3-yl)methoxy)-1,3-phenylene)dimethanol

The title compound is prepared from dimethyl 5-((3-methyloxetan-3-yl)methoxy)isophthalate by reduction with lithium aluminum hydride in tetrahydrofuran. LC (method 7): $t_R$=0.69 min; Mass spectrum (ESI$^+$): m/z=239 [M+H]$^+$.

Step 3: (2-Bromo-5-((3-methyloxetan-3-yl)methoxy)-1,3-phenylene)dimethanol

NBS (212 mg) is added to ((5-((3-Methyloxetan-3-yl)methoxy)-1,3-phenylene)dimethanol (270 mg) in acetonitrile (5 mL) and the resulting mixture is stirred at room temperature for 3 h. The solvent is evaporated in vacuo and the residue is chromatographed on silica gel (cyclohexane/ethyl acetate 50:50→0:100) to give the title compound. LC (method 7): $t_R$=0.76 min; Mass spectrum (ESI$^-$): m/z=315 [M–H]$^-$.

Step 4: 3-((4-Bromo-3,5-bis(methoxymethyl)phenoxy)methyl)-3-methyloxetane

Sodium hydride (50% in mineral oil; 150 mg) is to (2-bromo-5-((3-methyloxetan-3-yl)methoxy)-1,3-phenylene)dimethanol (370 mg) in tetrahydrofuran (10 mL ander an argon atmosphere. The resulting mixture is stirred for 20 min at room temperature prior to the addition of methyl iodide (546 mg). The reaction mixture is stirred for 3 h at room temperature. More sodium hydride (50% in mineral oil; 110 mg) and methyl iodide (200 μL) are added and the mixture is stirred over night at room temperature. The reaction mixture is quenched with ice water and extracted with ethyl acetate. The combined extracts are washed with water, dried over MgSO$_4$ and concentrated in vacuo. The residue is chromatographed on silica gel (cyclohexane/ethyl acetate 90:10→60:40) to give the title compound. LC (method 7): $t_R$=1.05 min; Mass spectrum (ESI$^+$): m/z=362 [M+NH$_4$]$^+$.

Step 5: Methyl 2-((S)-6-((R)-4-(2,6-bis(methoxymethyl)-4-((3-methyloxetan-3-yl)methoxy)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydro-benzofuran-3-yl)acetate and 3-((4-bromo-3,5-bis(methoxymethyl)phenoxy)methyl)-3-methyloxetane following a procedure analogous to that described in Step 5 of Intermediate 1. LC (method 8): $t_R$=0.72 min; Mass spectrum (ESI$^+$): m/z=607 [M+H]$^+$.

Intermediate 56

Methyl 2-((S)-6-((R)-7-fluoro-4-(4-(1-(2-hydroxy-2-methylpropyl)-1H-pyrazol-4-yl)-2,6-dimethylphenyl)-2,3-dihydro-1H-inden-1-yloxy)-2,3-dihydrobenzofuran-3-yl)acetate

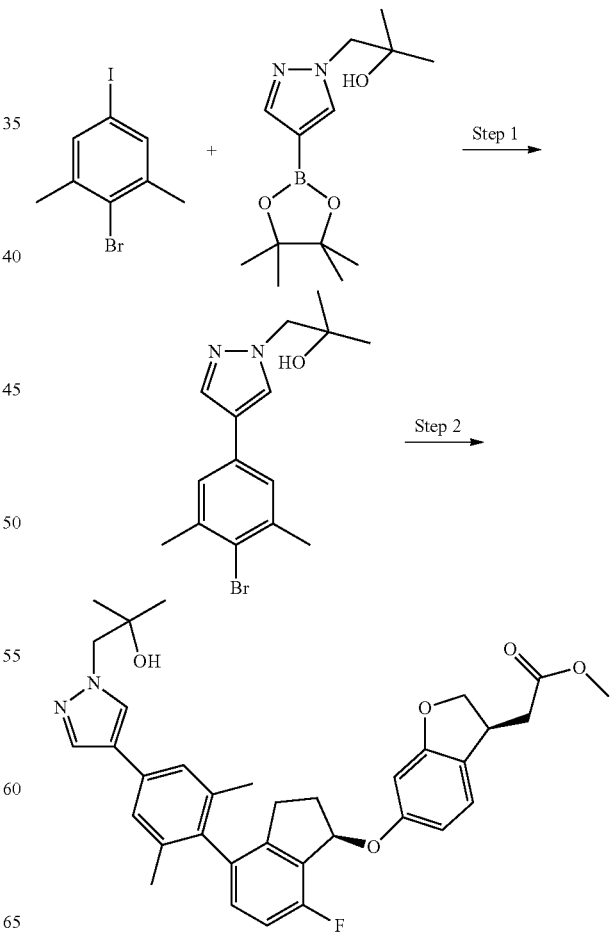

Step 1: 1-(4-(4-Bromo-3,5-dimethylphenyl)-1H-pyrazol-1-yl)-2-methylpropan-2-ol A mixture of 2-bromo-5-iodo-1,3-dimethylbenzene (1.00 g), 2-methyl-1-(4-(4,4,5,5-tetramethyl-1,3,2-dioxaborolan-2-yl)-1H-pyrazol-1-yl)propan-2-ol (1.11 g), and 2 M aqueous $Na_2CO_3$ solution (4.0 mL) in N,N-dimethylformamide is purged with argon for 3 min. [1,1'-Bis(diphenylphosphino)-ferrocene]-dichloropalladium dichloromethane complex (85 mg) is added and the mixture is stirred at 60° C. for 3 h. After cooling to room temperature the mixture is diluted with water and ethyl acetate. The organic phase is washed with brine, dried over $MgSO_4$ and concentrated in vacuo. The residue is purified by HPLC on reversed phase to give the title compound. LC (method 11): $t_R$=1.12 min; Mass spectrum (ESI$^+$): m/z=323, 325 [M+H]$^+$.

Step 2: Methyl 2-((S)-6-((R)-7-fluoro-4-(4-(1-(2-hydroxy-2-methylpropyl)-1H-pyrazol-4-yl)-2,6-dimethylphenyl)-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydro-benzofuran-3-yl)acetate and 1-(4-(4-bromo-3,5-dimethylphenyl)-1H-pyrazol-1-yl)-2-methylpropan-2-ol following a procedure analogous to that described in Step 5 of Intermediate 1. LC (method 11): $t_R$=1.23 min; Mass spectrum (ESI$^+$): m/z=585 [M+H]$^+$.

Intermediate 57

Methyl 2-((S)-6-((R)-4-(2,6-dimethyl-4-(1-methyl-2-oxo-1,2-dihydropyridin-4-yl)phenyl)-7-fluoro-2,3-dihydro-1H-inden-1-yloxy)-2,3-dihydrobenzofuran-3-yl)acetate

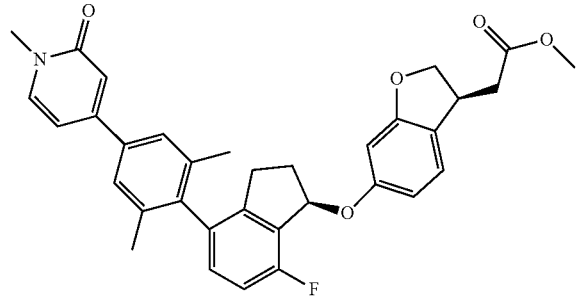

Step 1: 4-(4-Bromo-3,5-dimethylphenyl)-1-methylpyridin-2(1H)-one

The title compound is prepared from 2-bromo-5-iodo-1,3-dimethylbenzene and 1-methyl-2-oxo-1,2-dihydropyridin-4-ylboronic acid following a procedure analogous to that described in Step 1 of Intermediate 56. LC (method 11): $t_R$=1.04 min; Mass spectrum (ESI$^+$): m/z=292, 294 [M+H]$^+$.

Step 2: Methyl 2-((S)-6-((R)-4-(2,6-dimethyl-4-(1-methyl-2-oxo-1,2-dihydropyridin-4-yl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydro-benzofuran-3-yl)acetate and 4-(4-bromo-3,5-dimethylphenyl)-1-methylpyridin-2(1H)-one following a procedure analogous to that described in Step 5 of Intermediate 1. LC (method 11): $t_R$=1.19 min; Mass spectrum (ESI$^+$): m/z=554 [M+H]$^+$.

Intermediate 58

Methyl 2-((S)-6-((R)-4-(2,6-dimethyl-4-(1-methyl-6-oxo-1,6-dihydropyridin-3-yl)phenyl)-7-fluoro-2,3-dihydro-1H-inden-1-yloxy)-2,3-dihydrobenzofuran-3-yl)acetate

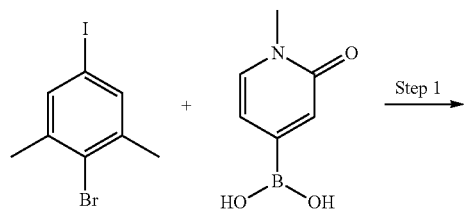

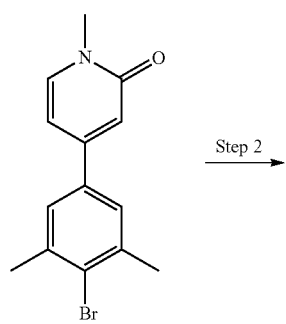

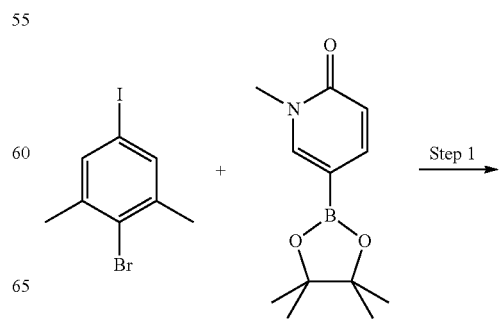

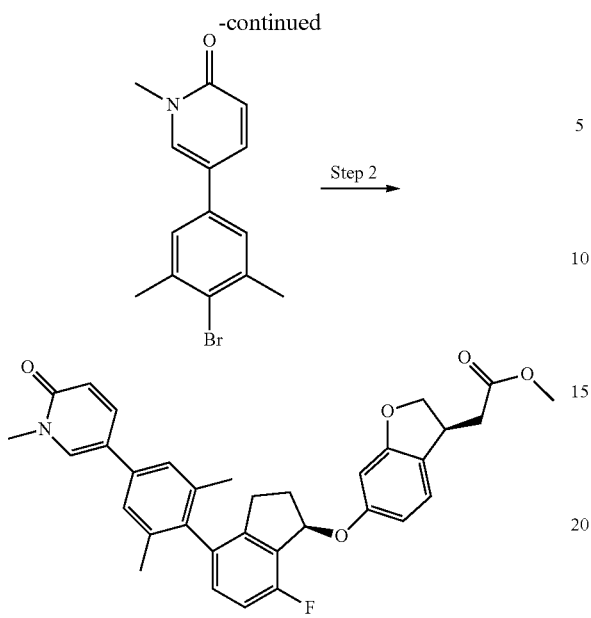

Step 1: 5-(4-Bromo-3,5-dimethylphenyl)-1-methylpyridin-2(1H)-one

The title compound is prepared from 2-bromo-5-iodo-1,3-dimethylbenzene and 1-methyl-5-(4,4,5,5-tetramethyl-1,3,2-dioxaborolan-2-yl)pyridin-2(1H)-one following a procedure analogous to that described in Step 1 of Intermediate 56. LC (method 11): $t_R$=1.05 min; Mass spectrum (ESI⁺): m/z=292, 294 [M+H]⁺.

Step 2: Methyl 2-((S)-6-((R)-4-(2,6-dimethyl-4-(1-methyl-6-oxo-1,6-dihydropyridin-3-yl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydro-benzofuran-3-yl)acetate and 5-(4-bromo-3,5-dimethylphenyl)-1-methylpyridin-2(1H)-one following a procedure analogous to that described in Step 5 of Intermediate 1. LC (method 11): $t_R$=1.19 min; Mass spectrum (ESI⁺): m/z=554 [M+H]⁺.

Intermediate 59

Methyl 2-((S)-6-((R)-4-(2,6-dimethyl-4-(1H-1,2,4-triazol-1-yl)phenyl)-7-fluoro-2,3-dihydro-1H-inden-1-yloxy)-2,3-dihydrobenzofuran-3-yl)acetate

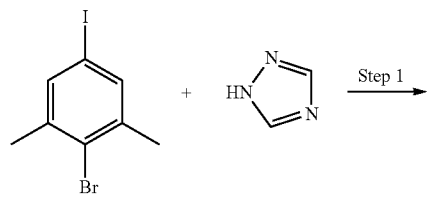

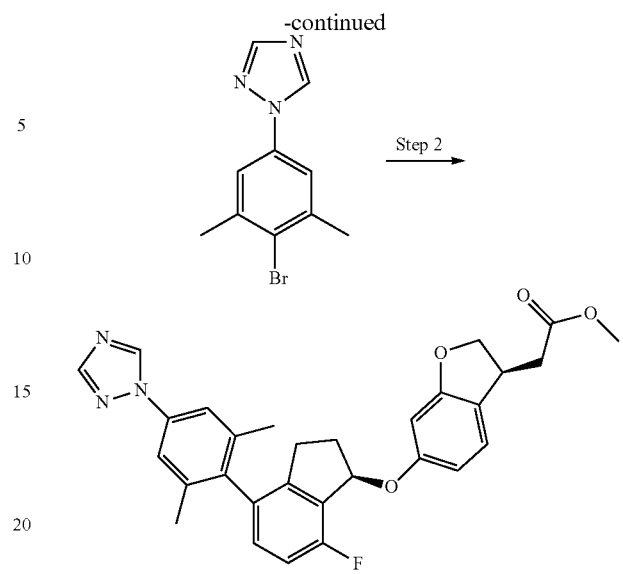

Step 1: 1-(4-Bromo-3,5-dimethylphenyl)-1H-1,2,4-triazole

A mixture of 2-bromo-5-iodo-1,3-dimethylbenzene (500 mg), 1,2,4-triazole (340 mg), potassium carbonate (770 mg), and copper(I) iodide (232 mg) in N-methyl-2-pyrrolidinone is stirred at 130° C. over night. More potassium carbonate (770 mg) and copper(I) iodide (232 mg) are added and the mixture is heated to 150° C. for 4 h. After cooling to room temperature the mixture is diluted with tetrahydrofuran and filtered. The filtrate is concentrated in vacuo and purified by HPLC on reversed phase to give the title compound. LC (method 7): $t_R$=0.99 min; Mass spectrum (ESI⁺): m/z=252, 254 [M+H]⁺.

Step 2: Methyl 2-((S)-6-((R)-4-(2,6-dimethyl-4-(1H-1,2,4-triazol-1-yl)phenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydro-benzofuran-3-yl)acetate and 1-(4-bromo-3,5-dimethylphenyl)-1H-1,2,4-triazole following a procedure analogous to that described in Step 5 of Intermediate 1. LC (method 7): $t_R$=1.16 min; Mass spectrum (ESI⁺): m/z=514 [M+H]⁺.

Intermediate 60

2-((S)-6-((R)-4-(4-(2,5-Di hydrofuran-3-yl)-2,6-dimethylphenyl)-7-fluoro-2,3-dihydro-1H-inden-1-yloxy)-2,3-dihydrobenzofuran-3-yl)acetic acid

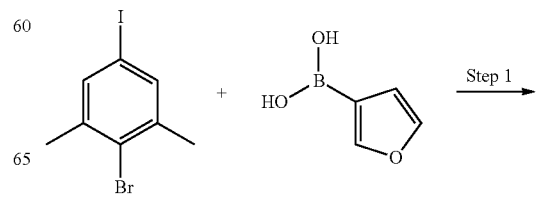

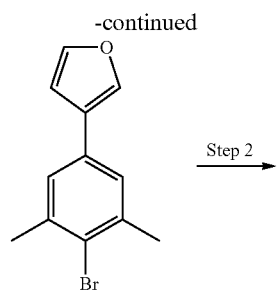

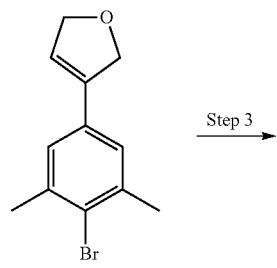

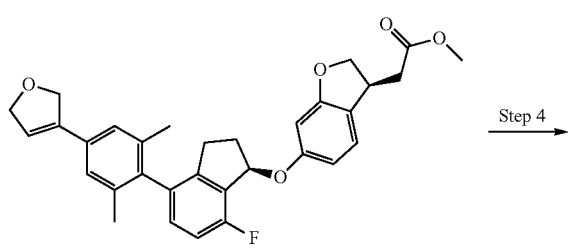

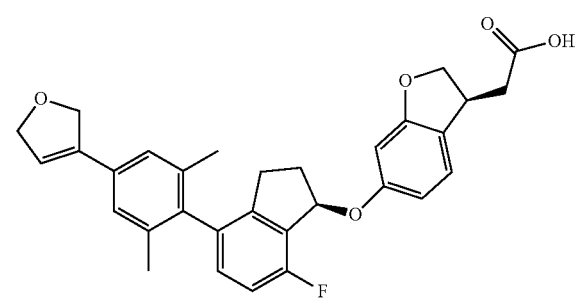

Step 1: 3-(4-Bromo-3,5-dimethylphenyl)furan

A mixture of 2,5-dibromo-1,3-dimethylbenzene (2.00 g), 1-furan-3-ylboronic acid (856 mg), and 2 M aqueous Na₂CO₃ solution (11 mL) in 1,4-dioxane (40 mL) is purged with argon for 5 min. Tetrakis-triphenylphosphine-palladium-(0) (270 mg) is added and the mixture is stirred at 100° C. over night. More tetrakis-triphenylphosphine-palladium-(0) (50 mg) is added and the mixture is stirred for another 5 h at 100° C. After cooling to room temperature the mixture is diluted with ethyl acetate and aqueous NH₄Cl solution. The aqueous phase is extracted with ethyl acetate and the combined extracts are washed with brine, dried over MgSO₄ and concentrated in vacuo. The residue is chromatographed on silica gel (cyclohexane/ethyl acetate 100:0→90:10) to give the title compound. LC (method 7): $t_R$=1.22 min; Mass spectrum (EI⁺): m/z=250 [M]⁺.

Step 2: 3-(4-Bromo-3,5-dimethylphenyl)-2,5-dihydrofuran

Triethylsilane (3.67 mL) is added dropwise to a solution of 3-(4-bromo-3,5-dimethylphenyl)furan (580 mg) in trifluoroacetic acid and the resulting mixture is stirred at room temperature for 3 h. Saturated aqueous NaHCO₃ solution is added and the aqueous phase is separated and extracted with ethyl acetate. The combined extracts are washed with brine, dried over MgSO₄ and concentrated in vacuo. The residue is chromatographed on silica gel (cyclohexane/ethyl acetate 95:5) to give the title compound. LC (method 9): $t_R$=1.16 min; Mass spectrum (ESI⁺): m/z=251, 253 [M+H]⁺.

Step 3: Methyl 2-((S)-6-((R)-4-(4-(2,5-dihydrofuran-3-yl)-2,6-dimethylphenyl)-7-fluoro-2,3-dihydro-1H-inden-1-yloxy)-2,3-dihydrobenzofuran-3-yl)acetate The title compound is prepared from methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydro-benzofuran-3-yl)acetate and 3-(4-bromo-3,5-dimethylphenyl)-2,5-dihydrofuran following a procedure analogous to that described in Step 5 of Intermediate 1. LC (method 9): $t_R$=1.26 min; Mass spectrum (ESI⁺): m/z=515 [M+H]⁺.

Step 4: 2-((S)-6-((R)-4-(4-(2,5-Dihydrofuran-3-yl)-2,6-dimethylphenyl)-7-fluoro-2,3-dihydro-1H-inden-1-yloxy)-2,3-dihydrobenzofuran-3-yl)acetic acid The title compound is prepared from methyl 2-((S)-6-((R)-4-(4-(2,5-dihydrofuran-3-yl)-2,6-dimethylphenyl)-7-fluoro-2,3-dihydro-1H-inden-1-yloxy)-2,3-dihydrobenzofuran-3-yl)acetate following a procedure analogous to that described in Step 2 of Intermediate 30 using NaOH instead of LiOH× H₂O. LC (method 9): $t_R$=0.16 min; Mass spectrum (ESI⁺): m/z=501 [M+H]⁺.

Intermediate 61

2,6-Dimethyl-4-(4,4,5,5-tetramethyl-1,3,2-dioxaborolan-2-yl)aniline

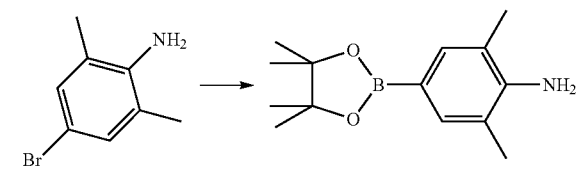

The title compound is prepared from 4-bromo-2,6-dimethylaniline following a procedure analogous to that described in Step 4 of Intermediate 1. LC (method 7): $t_R$=0.99 min; Mass spectrum (ESI⁺): m/z=248 [M+H]⁺.

Intermediate 62

Methyl 2-((S)-6-((R)-4-(2,6-dimethyl-4-(1-methyl-6-oxo-1,6-dihydropyrimidin-4-yl)phenyl)-7-fluoro-2,3-dihydro-1H-inden-1-yloxy)-2,3-dihydrobenzofuran-3-yl)acetate

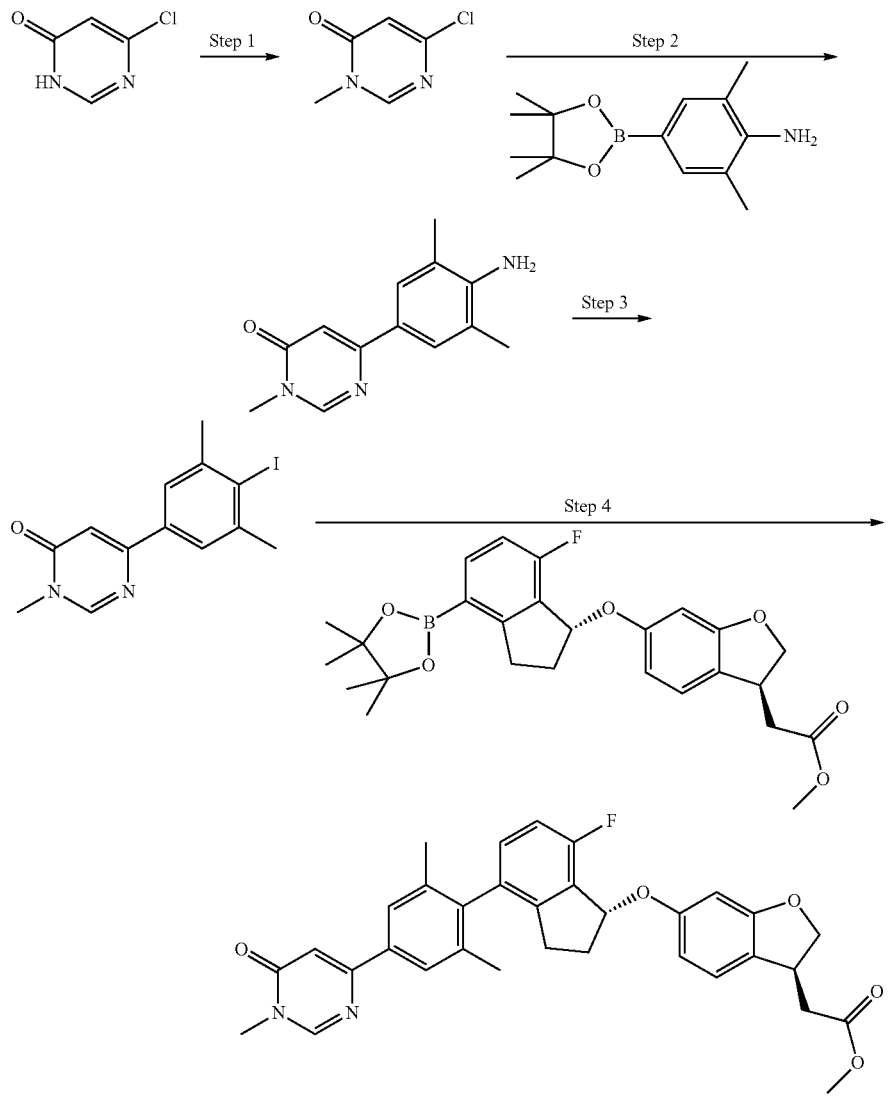

Step 1: 6-Chloro-3-methylpyrimidin-4(3H)-one

A mixture of 6-chloropyrimidin-4(3H)-one (5 g), methyliodide (2.6 mL) and K₂CO₃ (10.6 g) in acetone (100 mL) is stirred at room temperature over night. The mixture is partitioned between water and ethyl acetate. The organic phase is washed with brine, dried (MgSO₄) and concentrated. The residue is triturated with diisopropylether to give the title compound. Yield: 5.1 g; LC (method 11): $t_R$=0.25 min; Mass spectrum (ESI⁺): m/z=145 [M+H]⁺.

Step 2: 6-(4-Amino-3,5-dimethylphenyl)-3-methylpyrimidin-4(3H)-one

In a microwave vial 2,6-dimethyl-4-(4,4,5,5-tetramethyl-1,3,2-dioxaborolan-2-yl)aniline (5.6 g) and 6-chloro-3-methylpyrimidin-4(3H)-one (3 g) are suspended in N,N-dimethylformamide (30 mL) and Na₂CO₃ (26 mL of a 2M aqueous solution). The mixture is purged for 5 minutes with argon. [1,1'-Bis(diphenylphosphino)-ferrocene]-dichloropalladium dichloromethane complex (508 mg) is added, the vial is sealed and the mixture is stirred at 65° C. for 12 hours. After cooling to room temperature the mixture is Partitioned between water and ethyl acetate. The aqueous phase is extracted twice with ethyl acetate and the combined organic phases are washed with brine and dried (MgSO₄). The solvents are evaporated to give the title compound. Yield: 2.6 g; LC (method 11): $t_R$=0.71 min; Mass spectrum (ESI⁺): m/z=230 [M+H]⁺.

Step 3: 6-(4-Iodo-3,5-dimethylphenyl)-3-methylpyrimidin-4(3H)-one

To a solution of 6-(4-amino-3,5-dimethylphenyl)-3-methylpyrimidin-4(3H)-one (2.6 g) and p-toluenesulfonic acid monohydrate (6.5 g) in tert.-butanol (30 mL) is added dropwise at 10-15° C. a solution of NaNO₃ (1.6 g) and KI (4.7 g) in water (10 mL). The mixture is stirred for 20 minutes at 15°

C. and 3 hours at room temperature. Thereafter the mixture is treated with water (50 mL), saturated aqueous NaHCO$_3$ solution (20 mL) and 10% aqueous solution of Na$_2$S$_2$O$_3$ (20 mL). The mixture is extracted 4 times with ethyl acetate. The combined organic phases are washed with 10% aqueous solution of Na$_2$S$_2$O$_3$ and brine. After drying (MgSO$_4$) the solvents are evaporated. The crude product is used directly in the next step.

Step 4: Methyl 2-((S)-6-((R)-4-(2,6-dimethyl-4-(1-methyl-6-oxo-1,6-dihydropyrimidin-4-yl)phenyl)-7-fluoro-2,3-dihydro-1H-inden-1-yloxy)-2,3-dihydrobenzofuran-3-yl)acetate The title compound is prepared from 6-(4-iodo-3,5-dimethylphenyl)-3-methylpyrimidin-4(3H)-one and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 11): t$_R$=1.19 min; Mass spectrum (ESI$^+$): m/z=555 [M+H]$^+$.

Intermediate 63

Methyl 2-((S)-6-((R)-4-(2,6-dimethyl-4-(1-methyl-2-oxo-1,2-dihydropyrimidin-5-yl)phenyl)-7-fluoro-2,3-dihydro-1H-inden-1-yloxy)-2,3-dihydrobenzofuran-3-yl)acetate

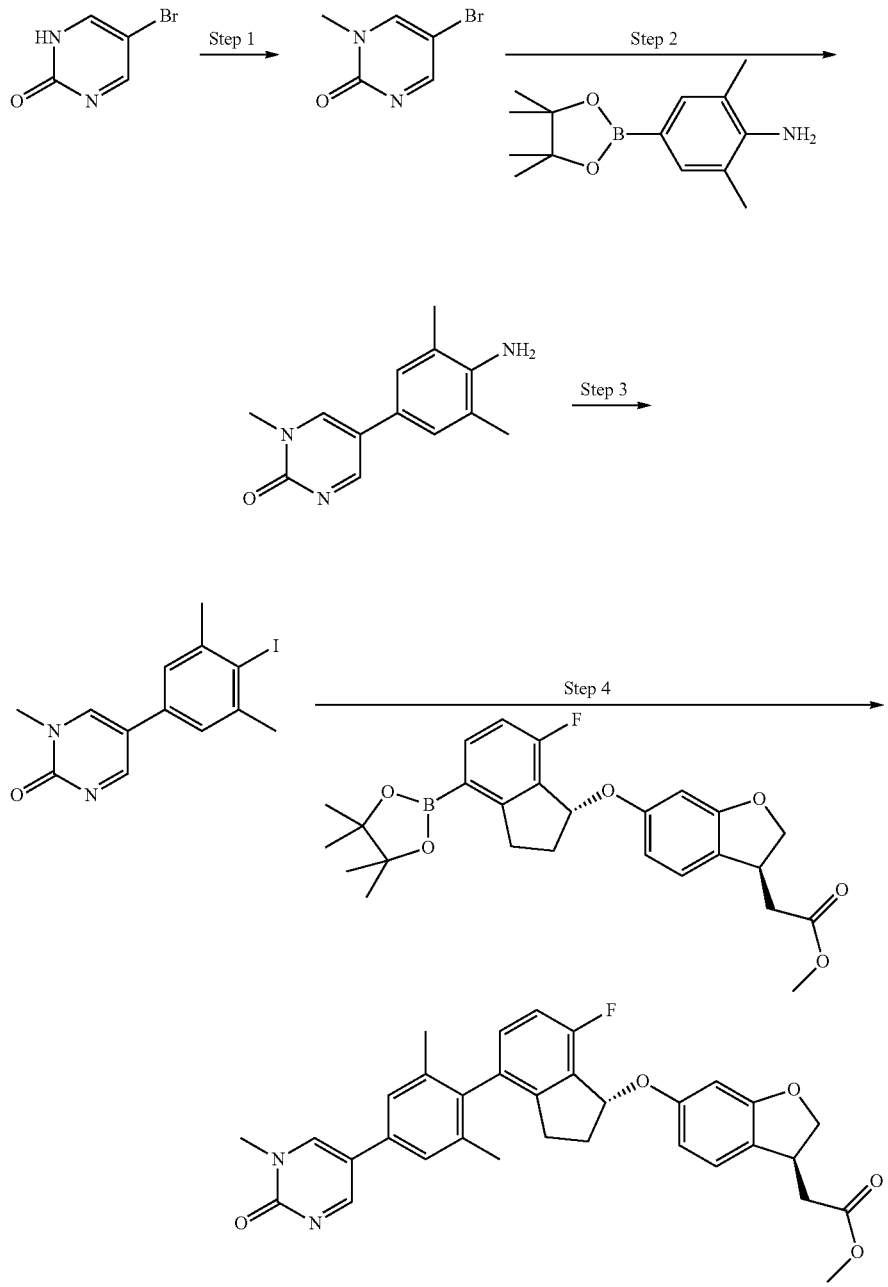

Step 1: 5-Bromo-1-methylpyrimidin-2(1H)-one

A mixture of 5-bromopyrimidin-2(1H)-one (3 g), methyliodide (1.1 mL) and $K_2CO_3$ (2.4 g) in N,N-dimethylformamide (60 mL) is stirred for 5 hours at room temperature. The mixture is filtered and the mother liquor is concentrated. The residue is partitioned between water and dichloromethane. The organic phase is washed with brine, dried ($MgSO_4$) and concentrated to give the title compound. Yield: 385 mg; LC (method 9): $t_R$=0.25 min; Mass spectrum (ESI$^+$): m/z=189 [M+H]$^+$.

Step 2: 5-(4-Amino-3,5-dimethylphenyl)-1-methylpyrimidin-2(1H)-one

The title compound is prepared from 5-bromo-1-methylpyrimidin-2(1H)-one and 2,6-dimethyl-4-(4,4,5,5-tetramethyl-1,3,2-dioxaborolan-2-yl)aniline following a procedure analogous to that described in Step 2 of Intermediate 62. The mixture is stirred for 12 hours at 70° C. LC (method 9): $t_R$=0.63 min; Mass spectrum (ESI$^+$): m/z=230 [M+H]$^+$.

Step 3: 5-(4-Iodo-3,5-dimethylphenyl)-1-methylpyrimidin-2(1H)-one

The title compound is prepared from 5-(4-amino-3,5-dimethylphenyl)-1-methylpyrimidin-2(1H)-one following a procedure analogous to that described in Step 3 of Intermediate 62. LC (method 9): $t_R$=0.96 min; Mass spectrum (ESI$^+$): m/z=341 [M+H]$^+$.

Step 4: Methyl 2-((S)-6-((R)-4-(2,6-dimethyl-4-(1-methyl-2-oxo-1,2-dihydropyrimidin-5-yl)phenyl)-7-fluoro-2,3-dihydro-1H-inden-1-yloxy)-2,3-dihydrobenzofuran-3-yl)acetate The title compound is prepared from 5-(4-iodo-3,5-dimethylphenyl)-1-methylpyrimidin-2(1H)-one and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 14): $t_R$=1.08 min; Mass spectrum (ESI$^+$): m/z=555 [M+H]$^+$.

Intermediate 64

Methyl 2-((S)-6-((R)-4-(2,6-dimethyl-4-(pyridazin-4-yl)phenyl)-7-fluoro-2,3-dihydro-1H-inden-1-yloxy)-2,3-dihydrobenzofuran-3-yl)acetate

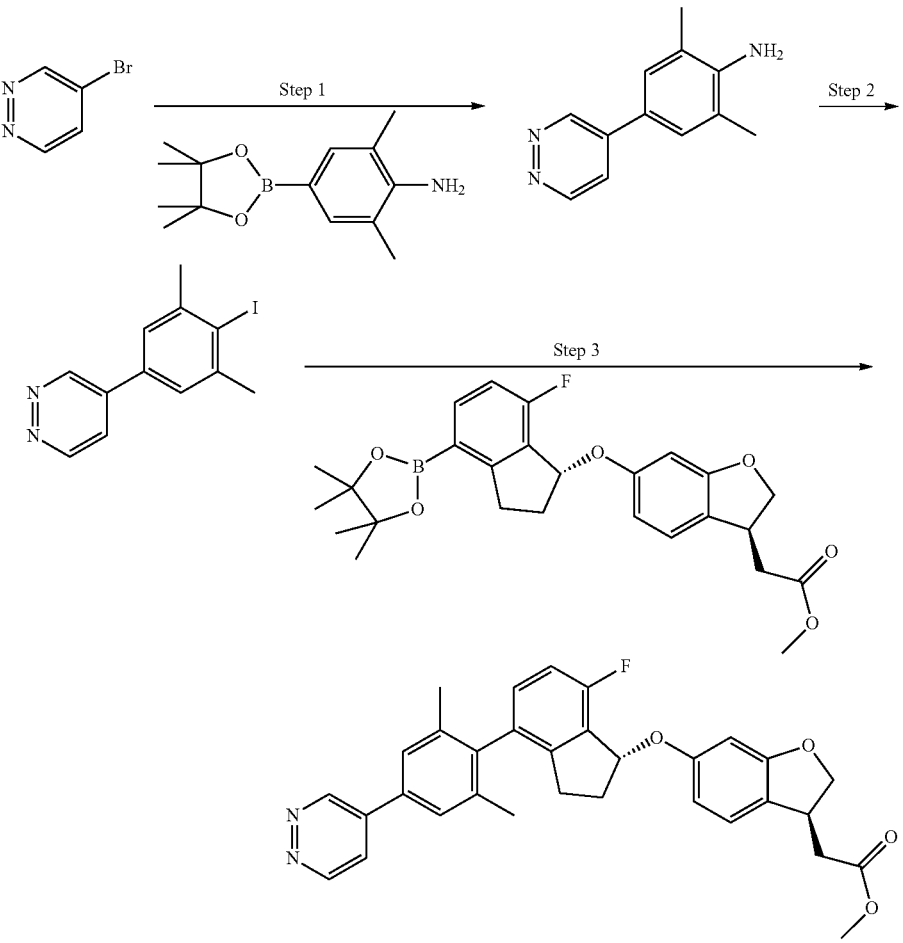

Step 1: 2,6-Dimethyl-4-(pyridazin-4-yl)aniline

The title compound is prepared from 4-bromopyridazine hydrobromide and 2,6-dimethyl-4-(4,4,5,5-tetramethyl-1,3,2-dioxaborolan-2-yl)aniline following a procedure analogous to that described in Step 2 of Intermediate 62. The mixture is stirred for 12 hours at 70° C. LC (method 9): $t_R$=0.66 min; Mass spectrum (ESI$^+$): m/z=200 [M+H]$^+$.

Step 2: 4-(4-Iodo-3,5-dimethylphenyl)pyridazine

The title compound is prepared from 2,6-dimethyl-4-(pyridazin-4-yl)aniline following a procedure analogous to that described in Step 3 of Intermediate 62. LC (method 9): $t_R$=1.02 min; Mass spectrum (ESI$^+$): m/z=311 [M+H]$^+$.

Step 3: Methyl 2-((S)-6-((R)-4-(2,6-dimethyl-4-(pyridazin-4-yl)phenyl)-7-fluoro-2,3-dihydro-1H-inden-1-yloxy)-2,3-dihydrobenzofuran-3-yl)acetate The title compound is prepared from 4-(4-iodo-3,5-dimethylphenyl)pyridazine and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 15): $t_R$=1.20 min; Mass spectrum (ESI$^+$): m/z=525 [M+H]$^+$.

Intermediate 65

Methyl 2-((S)-6-((R)-4-(2,6-dimethyl-4-(pyrimidin-4-yl)phenyl)-7-fluoro-2,3-dihydro-1H-inden-1-yloxy)-2,3-dihydrobenzofuran-3-yl)acetate

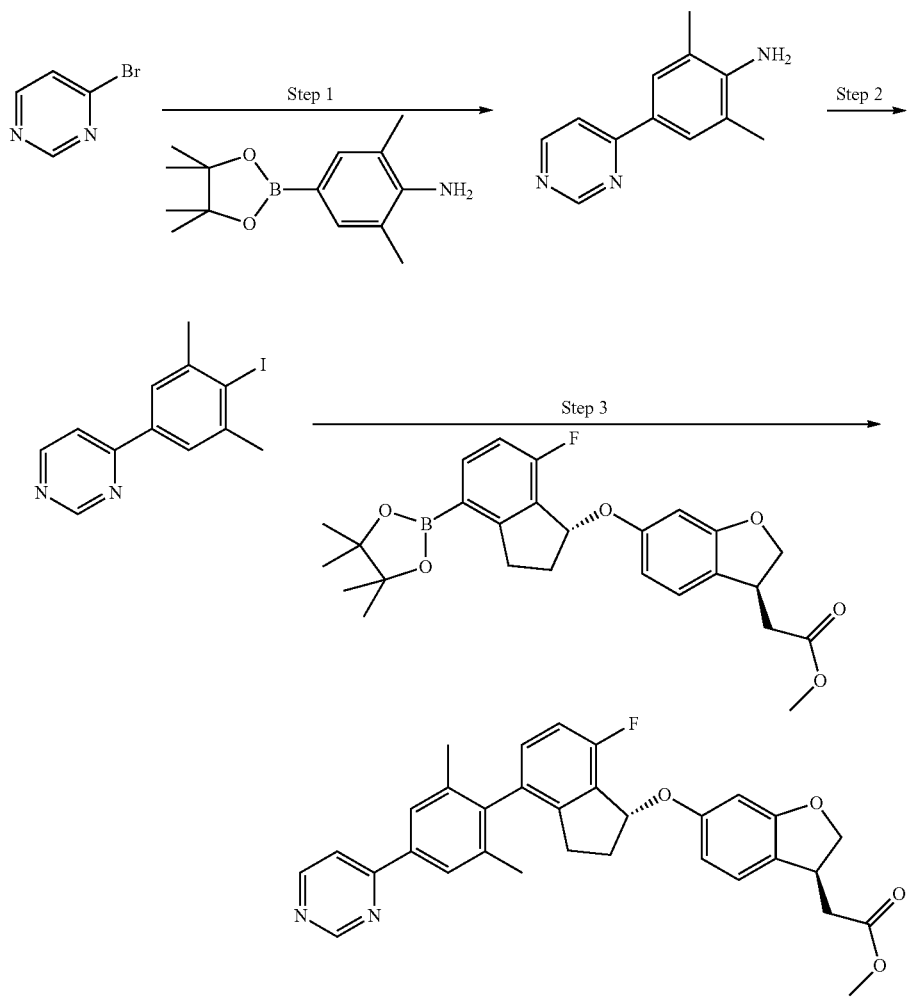

Step 1: 2,6-Dimethyl-4-(pyrimidin-4-yl)aniline

The title compound is prepared from 4-bromopyrimidine hydrochloride and 2,6-dimethyl-4-(4,4,5,5-tetramethyl-1,3,2-dioxaborolan-2-yl)aniline following a procedure analogous to that described in Step 2 of Intermediate 62. The mixture is stirred for 12 hours at 70° C. LC (method 9): $t_R$=0.74 min; Mass spectrum (ESI⁺): m/z=200 [M+H]⁺.

Step 2: 4-(4-Iodo-3,5-dimethylphenyl)pyrimidine

The title compound is prepared from 2,6-dimethyl-4-(pyrimidin-4-yl)aniline following a procedure analogous to that described in Step 3 of Intermediate 62. LC (method 9): $t_R$=1.10 min; Mass spectrum (ESI⁺): m/z=311 [M+H]⁺.

Step 3: Methyl 2-((S)-6-((R)-4-(2,6-dimethyl-4-(pyrimidin-4-yl)phenyl)-7-fluoro-2,3-dihydro-1H-inden-1-yloxy)-2,3-dihydrobenzofuran-3-yl)acetate The title compound is prepared from 4-(4-iodo-3,5-dimethylphenyl)pyrimidine and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 15): $t_R$=1.26 min.

Intermediate 66

Methyl 2-((S)-6-((R)-4-(2,6-dimethyl-4-(1-methyl-6-oxo-1,6-dihydropyridazin-4-yl)phenyl)-7-fluoro-2,3-dihydro-1H-inden-1-yloxy)-2,3-dihydrobenzofuran-3-yl)acetate

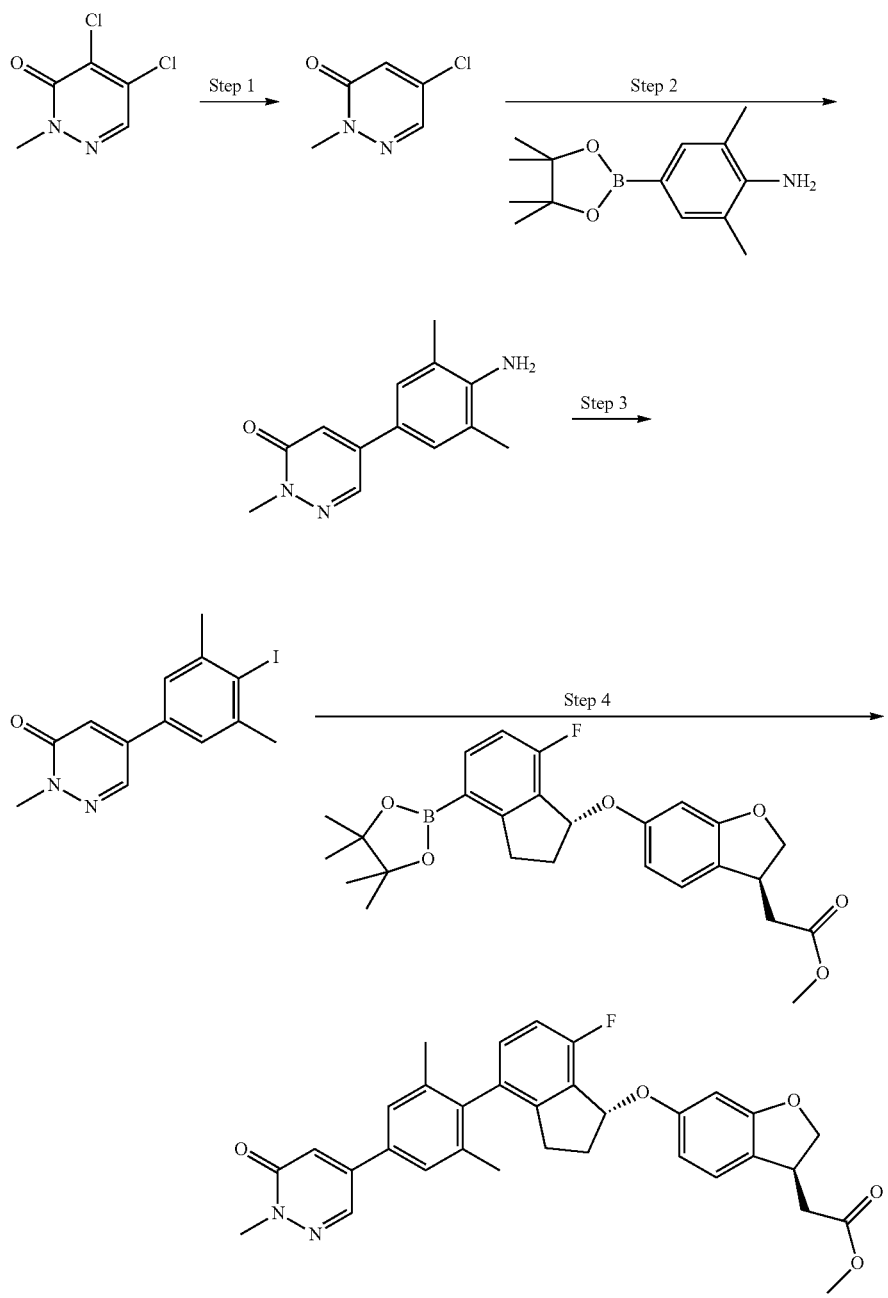

Step 1: 5-Chloro-2-methylpyridazin-3(2H)-one 4,5-Dichloro-2-methylpyridazin-3(2H)-one (1 g) is dissolved in aqueous HI solution (57%, 8.5 mL) and the mixture is heated to reflux for 12 hours. After cooling to room temperature the mixture is treated with aqueous $Na_2S_2O_3$ solution (30%, 100 mL) and stirred for 1 hour. The mixture is then extracted three times with dichloromethane. The combined organic phases are washed with brine, dried ($MgSO_4$) and concentrated. The residue is triturated with diisopropylether. Yield: 414 mg; Mass spectrum ($ESI^+$): m/z=145 $[M+H]^+$.

Step 2: 5-(4-Amino-3,5-dimethylphenyl)-2-methylpyridazin-3(2H)-one

The title compound is prepared from 5-chloro-2-methylpyridazin-3(2H)-one and 2,6-dimethyl-4-(4,4,5,5-tetramethyl-1,3,2-dioxaborolan-2-yl)aniline following a procedure analogous to that described in Step 2 of Intermediate 62. The mixture is stirred for 12 hours at 60° C. LC (method 9): $t_R$=0.79 min; Mass spectrum ($ESI^+$): m/z=230 $[M+H]^+$.

Step 3: 5-(4-Iodo-3,5-dimethylphenyl)-2-methylpyridazin-3(2H)-one

The title compound is prepared from 5-(4-amino-3,5-dimethylphenyl)-2-methylpyridazin-3(2H)-one following a procedure analogous to that described in Step 3 of Intermediate 62. LC (method 9): $t_R$=1.06 min; Mass spectrum ($ESI^+$): m/z=341 $[M+H]^+$.

Step 4: Methyl 2-((S)-6-((R)-4-(2,6-dimethyl-4-(1-methyl-6-oxo-1,6-dihydropyridazin-4-yl)phenyl)-7-fluoro-2,3-dihydro-1H-inden-1-yloxy)-2,3-dihydrobenzofuran-3-yl)acetate The title compound is prepared from 5-(4-iodo-3,5-dimethylphenyl)-2-methylpyridazin-3(2H)-one and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 14): $t_R$=1.18 min; Mass spectrum ($ESI^+$): m/z=555 $[M+H]^+$.

Intermediate 67

Methyl 2-((S)-6-((R)-7-fluoro-4-(4-(2-methoxypyrimidin-4-yl)-2,6-dimethylphenyl)-2,3-dihydro-1H-inden-1-yloxy)-2,3-dihydrobenzofuran-3-yl)acetate

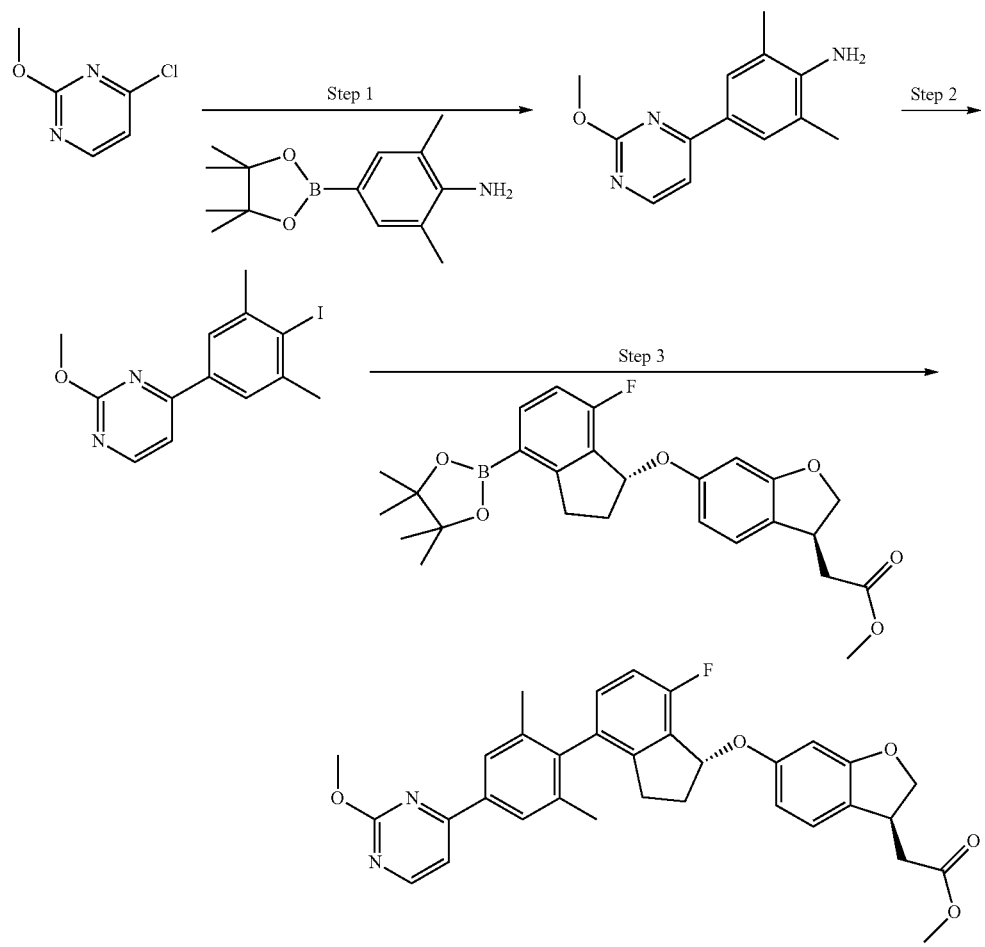

Step 1:
4-(2-Methoxypyrimidin-4-yl)-2,6-dimethylaniline

The title compound is prepared from 4-chloro-2-methoxypyrimidine and 2,6-dimethyl-4-(4,4,5,5-tetramethyl-1,3,2-dioxaborolan-2-yl)aniline following a procedure analogous to that described in Step 2 of Intermediate 62. The mixture is stirred for 12 hours at 60° C. LC (method 14): $t_R$=0.89 min; Mass spectrum (ESI$^+$): m/z=230 [M+H]$^+$.

Step 2:
4-(4-Iodo-3,5-dimethylphenyl)-2-methoxypyrimidine

The title compound is prepared from 5-(4-amino-3,5-dimethylphenyl)-2-methylpyridazin-3(2H)-one following a procedure analogous to that described in Step 3 of Intermediate 62. LC (method 14): $t_R$=1.18 min; Mass spectrum (ESI$^+$): m/z=341 [M+H]$^+$.

Step 3: Methyl 2-((S)-6-((R)-7-fluoro-4-(4-(2-methoxypyrimidin-4-yl)-2,6-dimethylphenyl)-2,3-dihydro-1H-inden-1-yloxy)-2,3-dihydrobenzofuran-3-yl) acetate The title compound is prepared from 4-(4-iodo-3,5-dimethylphenyl)-2-methoxypyrimidine and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 8): $t_R$=0.82 min; Mass spectrum (ESI$^+$): m/z=555 [M+H]$^+$.

Intermediate 68

Methyl 2-((S)-6-((R)-4-(2,6-dimethyl-4-(1H-tetrazol-5-yl)phenyl)-7-fluoro-2,3-dihydro-1H-inden-1-yloxy)-2,3-dihydrobenzofuran-3-yl)acetate

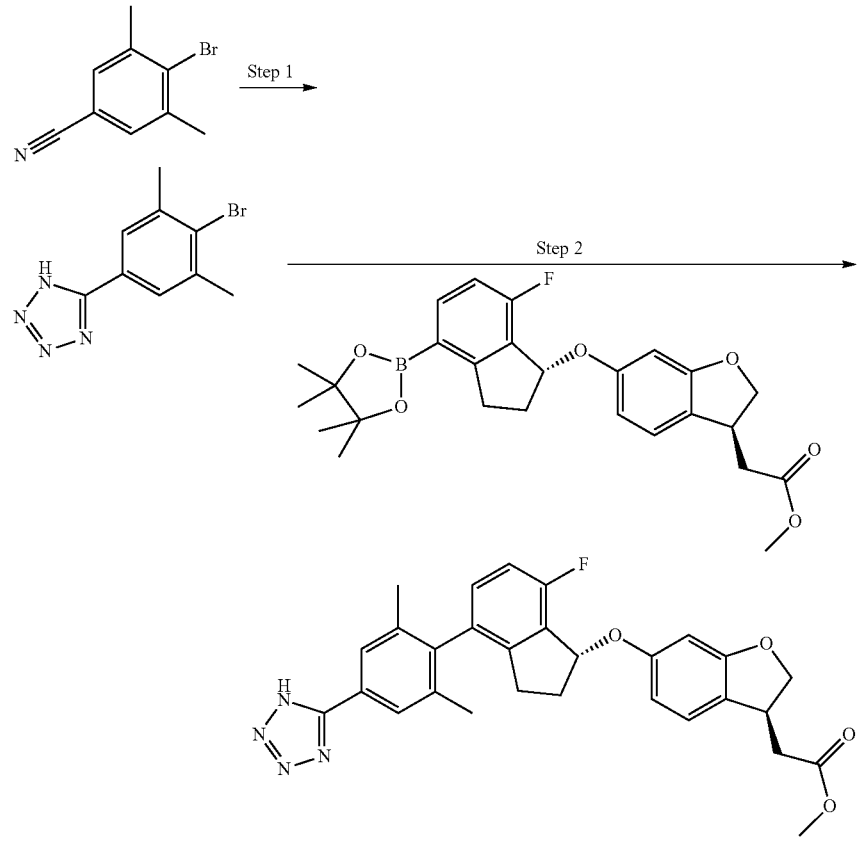

Step 1:
5-(4-Bromo-3,5-dimethylphenyl)-1H-tetrazole

To a solution of 4-bromo-3,5-dimethylbenzonitrile (1 g) in N,N-dimethylformamide (10 mL) is added NH$_4$Cl (770 mg) and NaN$_3$ (800 mg) and the mixture is heated to 100° C. for 12 hours. After cooling to room temperature the mixture is diluted with water. The formed precipitate is filtered off, washed with water and dried to give the title compound. Yield: 650 mg; Mass spectrum (ESI$^+$): m/z=253 [M+H]$^+$.

Step 2: Methyl 2-((S)-6-((R)-4-(2,6-dimethyl-4-(1H-tetrazol-5-yl)phenyl)-7-fluoro-2,3-dihydro-1H-inden-1-yloxy)-2,3-dihydrobenzofuran-3-yl)acetate The title compound is prepared from 5-(4-bromo-3,5-dimethylphenyl)-1H-tetrazole and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl) acetate following a procedure analogous to that described in Step 5 of Intermediate 1. LC (method 11): $t_R$=1.05 min; Mass spectrum (ESI⁺): m/z=515 [M+H]⁺.

Intermediate 69

5-(4-Bromo-3,5-dimethylphenyl)-2-methyl-2H-tetrazole and 5-(4-bromo-3,5-dimethylphenyl)-1-methyl-1H-tetrazole

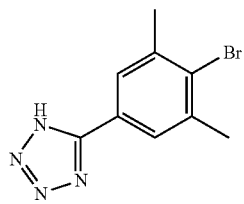

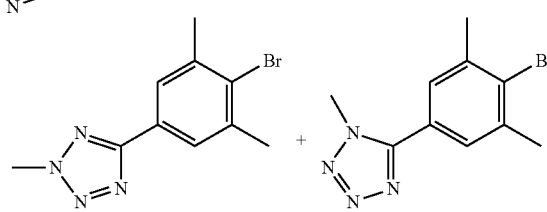

To a solution of 5-(4-bromo-3,5-dimethylphenyl)-1H-tetrazole (780 mg) in N,N-dimethylformamide (12 mL) is added KOH (432 mg) and MeI (210 μL) and the mixture is stirred for 4 hours at room temperature. Then the mixture is diluted with water and extracted 3 times with dichloromethane. The combined organic phases are washed with water, dried (MgSO₄) and concentrated. The residue is chromatographed on silica gel (cyclohexane/ethyl acetate 95:5→70:30) to give the title compounds.

5-(4-bromo-3,5-dimethylphenyl)-1-methyl-1H-tetrazole: Yield: 135 mg; LC (method 11): $t_R$=1.03 min; Mass spectrum (ESI⁺): m/z=267 [M+H]⁺.

5-(4-bromo-3,5-dimethylphenyl)-2-methyl-2H-tetrazole: Yield: 660 mg; LC (method 11): $t_R$=1.16 min; Mass spectrum (ESI⁺): m/z=267 [M+H]⁺.

Intermediate 70

Methyl 2-((S)-6-((R)-4-(2,6-dimethyl-4-(2-methyl-2H-tetrazol-5-yl)phenyl)-7-fluoro-2,3-dihydro-1H-inden-1-yloxy)-2,3-dihydrobenzofuran-3-yl)acetate

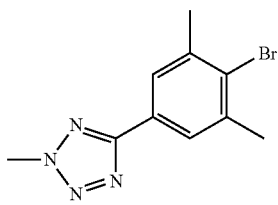

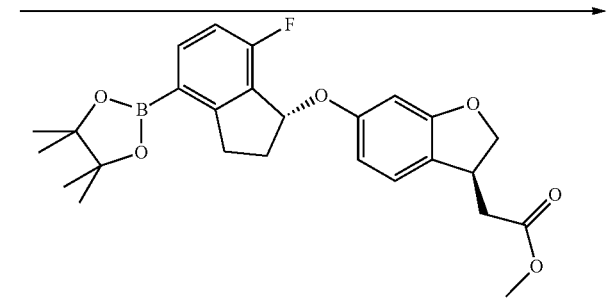

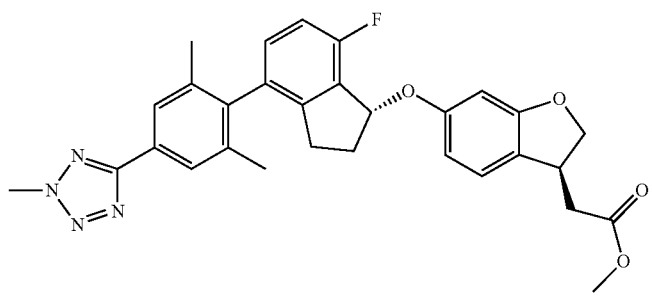

The title compound is prepared from 5-(4-bromo-3,5-dimethylphenyl)-2-methyl-2H-tetrazole and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 11): $t_R$=1.26 min; Mass spectrum (ESI⁺): m/z=529 [M+H]⁺.

Intermediate 71

Methyl 2-((S)-6-((R)-4-(2,6-dimethyl-4-(1-methyl-1H-tetrazol-5-yl)phenyl)-7-fluoro-2,3-dihydro-1H-inden-1-yloxy)-2,3-dihydrobenzofuran-3-yl)acetate

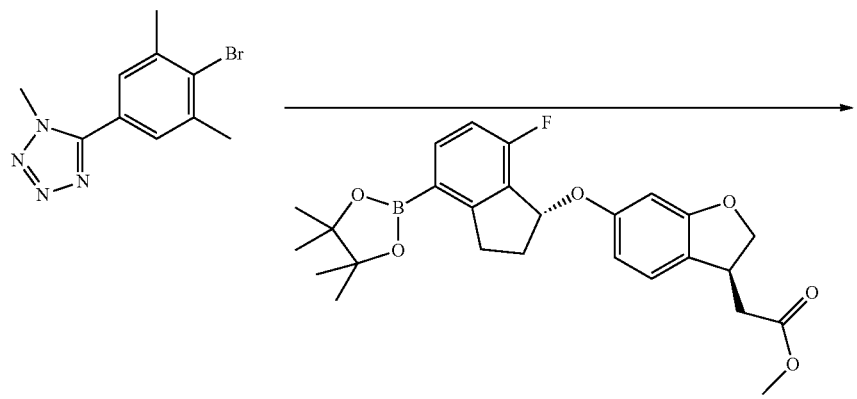

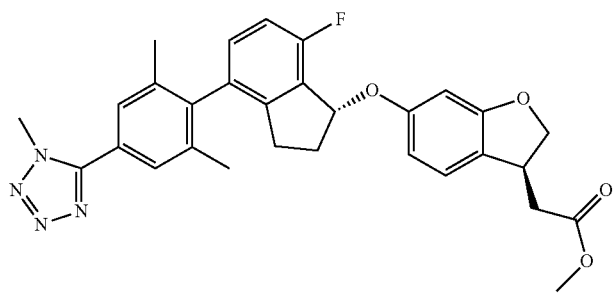

The title compound is prepared from 5-(4-bromo-3,5-dimethylphenyl)-1-methyl-1H-tetrazole and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 11): $t_R$=1.20 min; Mass spectrum (ESI⁺): m/z=529 [M+H]⁺.

Intermediate 72

Methyl 2-((S)-6-((R)-4-(2,6-dimethyl-4-(1-methyl-2-oxo-1,2-dihydropyrimidin-4-yl)phenyl)-7-fluoro-2,3-dihydro-1H-inden-1-yloxy)-2,3-dihydrobenzofuran-3-yl)acetate

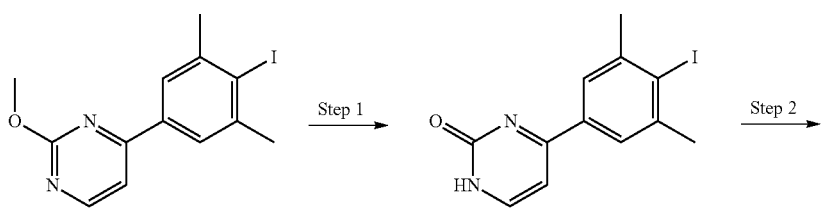

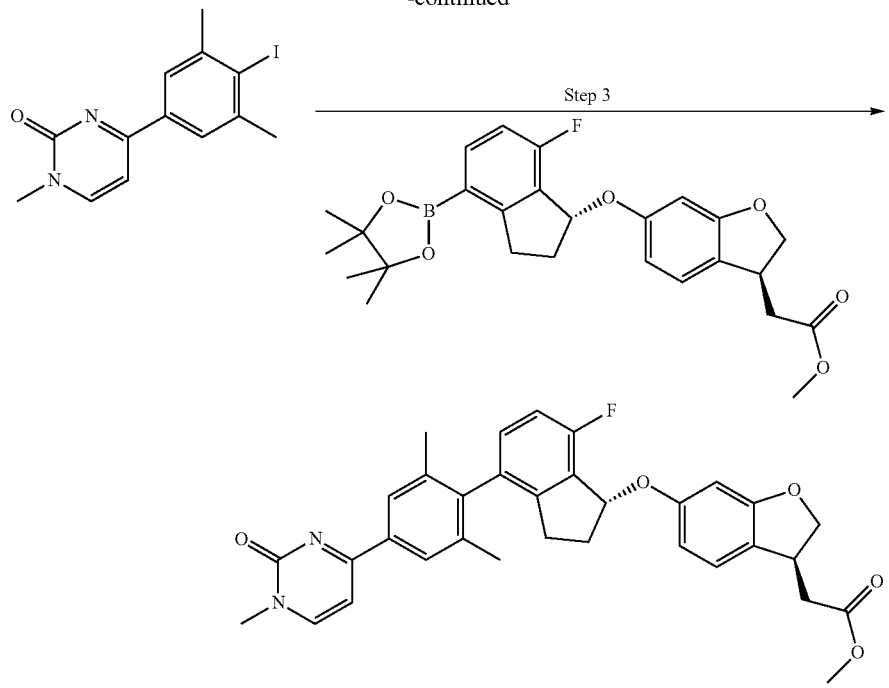

Step 1:
4-(4-Iodo-3,5-dimethylphenyl)pyrimidin-2(1H)-one 4-(4-Iodo-3,5-dimethylphenyl)-2-methoxypyrimidine is dissolved in 33% solution of HBr in acetic acid (7.7 mL) and the mixture is stirred for 12 hours at room temperature. Then the mixture is diluted with water. The formed precipitate is filtered off, washed with acetone and dried. Yield: 1 g; LC (method 11): $t_R$=0.92 min; Mass spectrum (ESI$^+$): m/z=327 [M+H]$^+$.

Step 2: 4-(4-Iodo-3,5-dimethylphenyl)-1-methylpyrimidin-2(1H)-one

A mixture of 4-(4-iodo-3,5-dimethylphenyl)pyrimidin-2(1H)-one (500 mg), methyliodide (165 μL) and $K_2CO_3$ (254 mg) in N,N-dimethylformamide (10 mL) is stirred for 12 hours at room temperature. Then the mixture is partitioned between water and dichloromethane. The aqueous phase is extracted twice with dichloromethane and the combined organic phases are washed with brine. After drying ($MgSO_4$) the solvents are evaporated. The residue is triturated with diethylether. The solid is filtered off and dried to give the title compound. Yield: 380 mg; LC (method 11): $t_R$=0.96 min; Mass spectrum (ESI$^+$): m/z=341 [M+H]$^+$.

Step 3: Methyl 2-((S)-6-((R)-4-(2,6-dimethyl-4-(1-methyl-2-oxo-1,2-dihydropyrimidin-4-yl)phenyl)-7-fluoro-2,3-dihydro-1H-inden-1-yloxy)-2,3-dihydrobenzofuran-3-yl)acetate The title compound is prepared from 4-(4-iodo-3,5-dimethylphenyl)-1-methylpyrimidin-2(1H)-one and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 15): $t_R$=1.14 min; Mass spectrum (ESI$^+$): m/z=555 [M+H]$^+$.

Intermediate 73

1-(5-(4-Bromo-3,5-dimethylphenyl)-2H-tetrazol-2-yl)-2-methylpropan-2-ol and 2-(5-(4-bromo-3,5-dimethylphenyl)-2H-tetrazol-2-yl)-2-methylpropan-1-ol

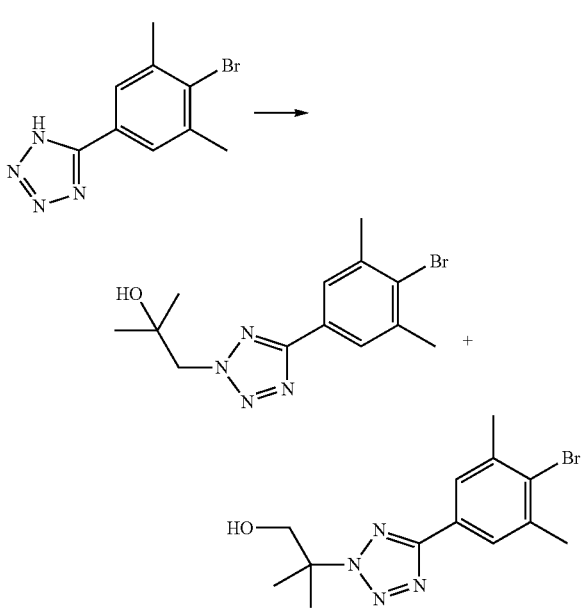

To a solution of 5-(4-bromo-3,5-dimethylphenyl)-1H-tetrazole (500 mg) in methanol (5 mL) is added $Cs_2CO_3$ (645 mg) and 1,1-dimethyloxirane (450 μL). The vial is sealed and the mixture is heated to 60° C. for 3 hours. Cs$_2$CO$_3$ (400 mg) and 1,1-dimethyloxirane (300 μL) are added and the mixture is heated to 60° C. for 12 hours. After addition of 1,1-dimethyloxirane (450 μL) the mixture is heated to 80° C. for 6 hours. Then the solvents are evaporated and the residue is partitioned between water and ethyl acetate. The aqueous phase is extracted twice with ethyl acetate and the combined organic phases are dried (MgSO$_4$). After concentration the residue is purified by HPLC on reversed phase to give the title compounds.

1-(5-(4-bromo-3,5-dimethylphenyl)-2H-tetrazol-2-yl)-2-methylpropan-2-ol: Yield: 310 mg; LC (method 11): t$_R$=1.14 min; Mass spectrum (ESI$^+$): m/z=325 [M+H]$^+$.

2-(5-(4-bromo-3,5-dimethylphenyl)-2H-tetrazol-2-yl)-2-methylpropan-1-ol: Yield: 40 mg; LC (method 11): t$_R$=1.16 min; Mass spectrum (ESI$^+$): m/z=325 [M+H]$^+$.

Intermediate 74

Methyl 2-((S)-6-((R)-7-fluoro-4-(4-(2-(2-hydroxy-2-methylpropyl)-2H-tetrazol-5-yl)-2,6-dimethylphenyl)-2,3-dihydro-1H-inden-1-yloxy)-2,3-dihydrobenzofuran-3-yl)acetate

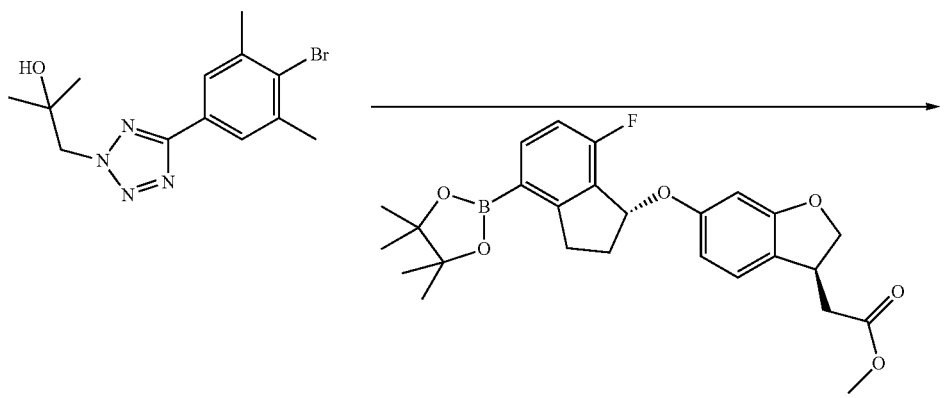

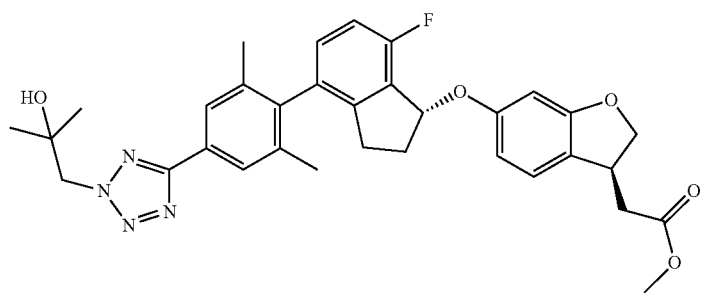

The title compound is prepared from 1-(5-(4-bromo-3,5-dimethylphenyl)-2H-tetrazol-2-yl)-2-methylpropan-2-ol and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 15): t$_R$=1.24 min; Mass spectrum (ESI$^+$): m/z=587 [M+H]$^+$.

Intermediate 75

Methyl 2-((S)-6-((R)-7-fluoro-4-(4-(2-(1-hydroxy-2-methylpropan-2-yl)-2H-tetrazol-5-yl)-2,6-dimethylphenyl)-2,3-dihydro-1H-inden-1-yloxy)-2,3-dihydrobenzofuran-3-yl)acetate

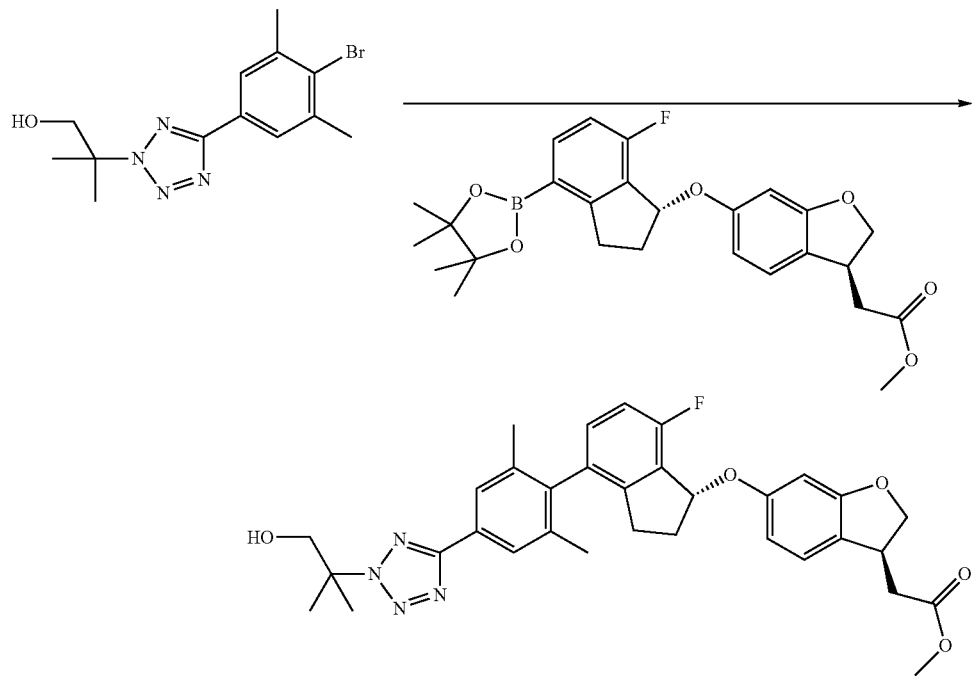

The title compound is prepared from 2-(5-(4-bromo-3,5-dimethylphenyl)-2H-tetrazol-2-yl)-2-methylpropan-1-ol and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 15): $t_R$=1.25 min; Mass spectrum (ESI$^+$): m/z=587 [M+H]$^+$.

Intermediate 76

Methyl 2-((3S)-6-((1R)-7-fluoro-4-(2-(neopentyloxy)pyridin-3-yl)-2,3-dihydro-1H-inden-1-yloxy)-2,3-dihydrobenzofuran-3-yl)acetate

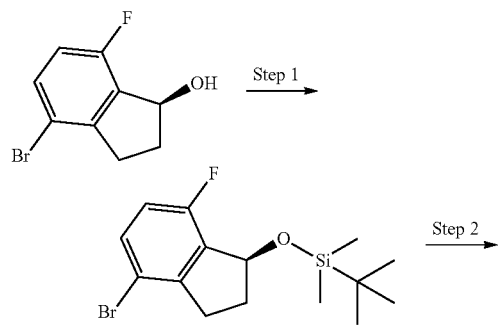

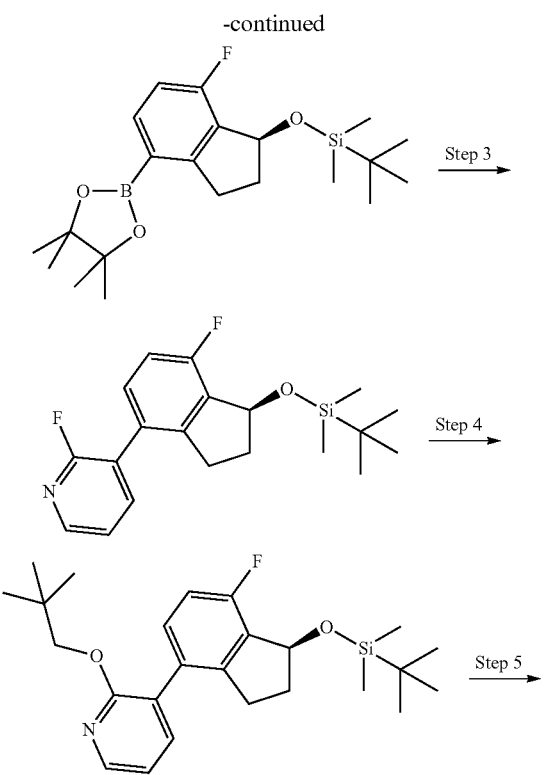

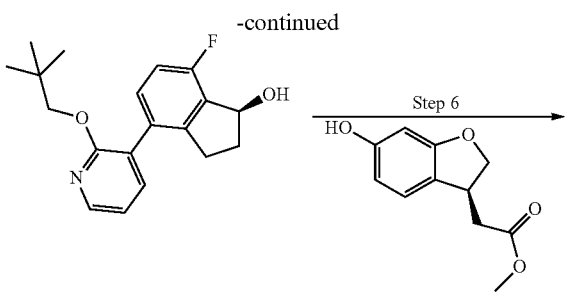

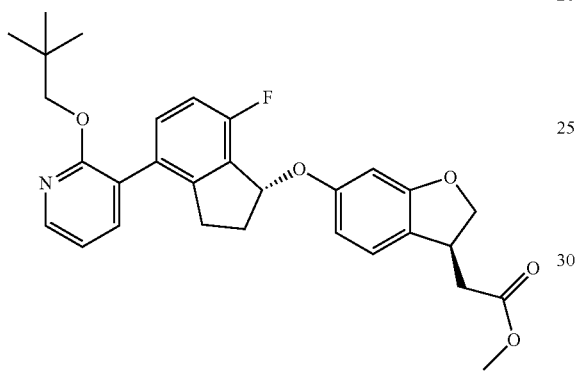

Step 1: (S)-(4-Bromo-7-fluoro-2,3-dihydro-1H-inden-1-yloxy)(tert-butyl)dimethyl-silane (S)-4-bromo-7-fluoro-2,3-dihydro-1H-inden-1-ol (6.8 g) and imidazol (5 g) are dissolved at 0° C. in N,N-dimethylformamide (NMP, 25 mL), treated with tert.-butyldimethylchlorosilane (6.3 g) and stirred for 2 hours at room temperature. Water is added and the mixture is stirred for 10 minutes. Then the mixture is partitioned between 1 M hydrochloric acid and ethyl acetate. The organic phase is dried (MgSO₄) and concentrated to give the title compound. Yield: 9.25 g.

Step 2: (S)-tert-Butyl(7-fluoro-4-(4,4,5,5-tetramethyl-1,3,2-dioxaborolan-2-yl)-2,3-dihydro-1H-inden-1-yloxy)dimethylsilane The title compound is prepared from (S)-(4-bromo-7-fluoro-2,3-dihydro-1H-inden-1-yloxy)(tert-butyl)dimethyl-silane following a procedure analogous to that described in Step 4 of Intermediate 1. LC (method 26): $t_R$=1.30 min.; Mass spectrum (ESI⁺): m/z=410 [M+NH₄]⁺.

Step 3: 3-((1S)-1-(tert-Butyldimethylsilyloxy)-7-fluoro-2,3-dihydro-1H-inden-4-yl)-2-fluoropyridine The title compound is prepared from (S)-tert-butyl(7-fluoro-4-(4,4,5,5-tetramethyl-1,3,2-dioxaborolan-2-yl)-2,3-dihydro-1H-inden-1-yloxy)dimethylsilane and 3-bromo-2-fluoropyridine following a procedure analogous to that described in Step 5 of Intermediate 1. LC (method 7): $t_R$=1.31 min.; Mass spectrum (ESI⁺): m/z=362 [M+H]⁺.

Step 4: 3-((1S)-1-(tert-Butyldimethylsilyloxy)-7-fluoro-2,3-dihydro-1H-inden-4-yl)-2-(neopentyloxy)pyridine 2,2-Dimethylpropan-1-ol (59 mg) is dissolved at 0° C. in N-methylpyrrolidone (NMP, 2 mL), treated with NaH (27 mg, 55% dispersion in mineral oil) and stirred for 15 minutes. The mixture is warmed to room temperature, treated with a solution of 3-((1S)-1-(tert-butyldimethylsilyloxy)-7-fluoro-2,3-dihydro-1H-inden-4-yl)-2-fluoropyridine (200 mg) in N-methylpyrrolidone (NMP, 1 mL) and stirred for 12 hours at 75° C. 2,2-Dimethylpropan-1-ol (59 mg) and NaH (27 mg, 55% dispersion in mineral oil) are added and the mixture is stirred for 4 hours at 80° C. The mixture thus obtained is directly used in the next step.

Step 5: (1S)-7-Fluoro-4-(2-(neopentyloxy)pyridin-3-yl)-2,3-dihydro-1H-inden-1-ol The title compound is prepared from 3-((1S)-1-(tert-butyldimethylsilyloxy)-7-fluoro-2,3-dihydro-1H-inden-4-yl)-2-(neopentyloxy)pyridine following a procedure analogous to that described in Step 2 of Intermediate 6. LC (method 7): $t_R$=1.11 min.

Step 6: Methyl 2-((3S)-6-((1R)-7-fluoro-4-(2-(neopentyloxy)pyridin-3-yl)-2,3-dihydro-1H-inden-1-yloxy)-2,3-dihydrobenzofuran-3-yl)acetate The title compound is prepared from (1S)-7-fluoro-4-(2-(neopentyloxy)pyridin-3-yl)-2,3-dihydro-1H-inden-1-ol and (S)-methyl 2-(6-hydroxy-2,3-dihydrobenzofuran-3-yl)acetate following a procedure analogous to that described in Step 3 of Intermediate 1. LC (method 15): $t_R$=1.32 min.

Intermediate 77

Methyl 2-((S)-6-((R)-4-(2,6-dimethyl-4-(1-methyl-6-oxo-1,6-dihydropyridazin-3-yl)phenyl)-7-fluoro-2,3-dihydro-1H-inden-1-yloxy)-2,3-dihydrobenzofuran-3-yl)acetate

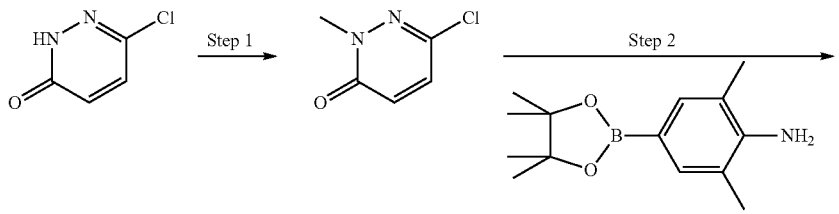

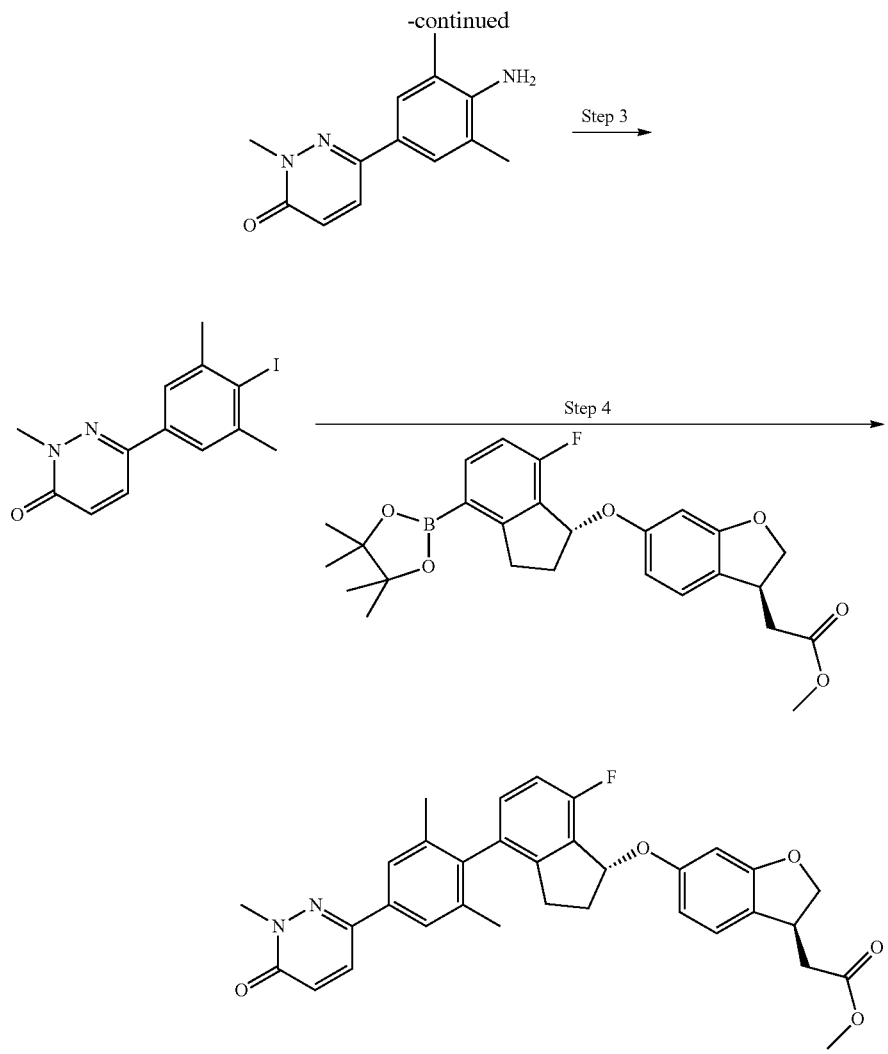

Step 1: 6-Chloro-2-methylpyridazin-3(2H)-one

The title compound is prepared from 6-chloropyridazin-3(2H)-one following a procedure analogous to that described in Step 1 of Intermediate 63.

Step 2: 6-(4-Amino-3,5-dimethylphenyl)-2-methylpyridazin-3(2H)-one

The title compound is prepared from 6-chloro-2-methylpyridazin-3(2H)-one and 2,6-dimethyl-4-(4,4,5,5-tetramethyl-1,3,2-dioxaborolan-2-yl)aniline following a procedure analogous to that described in Step 2 of Intermediate 62. The mixture is stirred for 12 hours at 60° C. LC (method 9): $t_R$=0.78 min; Mass spectrum (ESI$^+$): m/z=230 [M+H]$^+$.

Step 3: 6-(4-Iodo-3,5-dimethylphenyl)-2-methylpyridazin-3(2H)-one

The title compound is prepared from 6-(4-amino-3,5-dimethylphenyl)-2-methylpyridazin-3(2H)-one following a procedure analogous to that described in Step 3 of Intermediate 62. LC (method 7): $t_R$=1.08 min; Mass spectrum (ESI$^+$): m/z=341 [M+H]$^+$.

Step 4: Methyl 2-((S)-6-((R)-4-(2,6-dimethyl-4-(1-methyl-6-oxo-1,6-dihydropyridazin-3-yl)phenyl)-7-fluoro-2,3-dihydro-1H-inden-1-yloxy)-2,3-dihydrobenzofuran-3-yl)acetate The title compound is prepared from 6-(4-iodo-3,5-dimethylphenyl)-2-methylpyridazin-3(2H)-one and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 9): $t_R$=1.18 min; Mass spectrum (ESI$^+$): m/z=555 [M+H]$^+$.

Intermediate 78

Methyl 2-((3S)-6-(((1R)-4-(2-(dimethylcarbamoyl)phenyl)-7-fluoro-2,3-dihydro-1H-inden-1-yloxy)-2,3-dihydrobenzofuran-3-yl)acetate

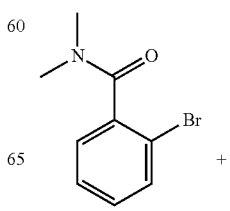

+

-continued

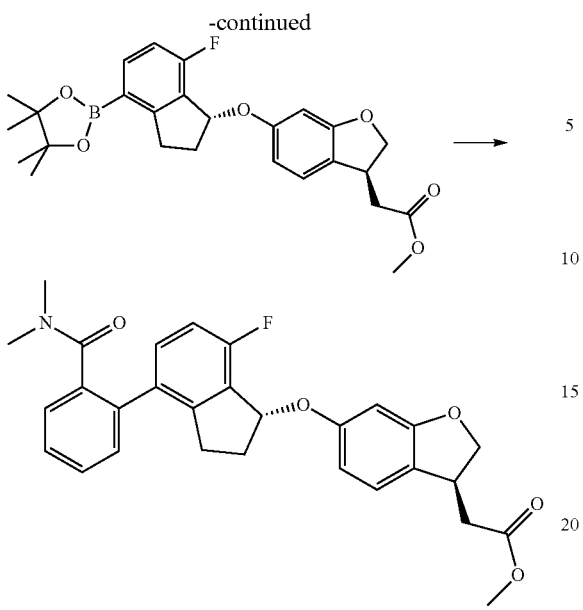

The title compound is prepared from 2-bromo-N,N-dimethylbenzamide and methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate following a procedure analogous to that described in Step 5 of Intermediate 1. LC (method 9): $t_R$=1.14 min; Mass spectrum (ESI$^+$): m/z=490 [M+H]$^+$.

Intermediate 79

5-(2-Fluoro-6-iodophenyl)-1-methyl-1H-tetrazole and 5-(2-fluoro-6-iodophenyl)-2-methyl-2H-tetrazole

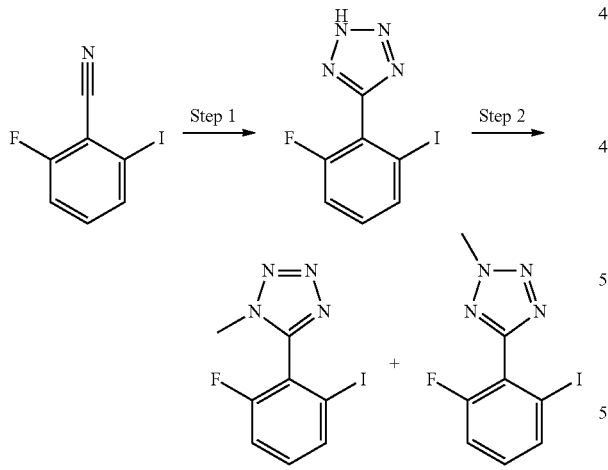

Step 1: 5-(2-Fluoro-6-iodophenyl)-2H-tetrazole

In a microwave vial 2-fluoro-6-iodobenzonitrile (1 g) and azidotributyltin (1.12 mL) are dissolved in toluene (8.4 mL). The vial is sealed and the mixture is heated to 125° C. for 72 hours. After cooling to room temperature the solvent is evaporated and the residue is purified by HPLC on reversed phase. Yield: 494 mg; Mass spectrum (ESI$^+$): m/z=291 [M+H]$^+$.

Step 2: 5-(2-Fluoro-6-iodophenyl)-1-methyl-1H-tetrazole and 5-(2-fluoro-6-iodophenyl)-2-methyl-2H-tetrazole To a solution of 5-(2-fluoro-6-iodophenyl)-2H-tetrazole (986 mg) in N,N-dimethylformamide (3.4 mL) is added K$_2$CO$_3$ (530 mg) and MeI (295 µL) and the mixture is stirred for 12 hours at room temperature. Then the solvent is evaporated and the residue is partitioned between water and ethyl acetate. The aqueous phase is twice extracted with ethyl acetate and the combined organic phases are washed with brine, dried (Na$_2$SO$_4$). After concentration the residue is purified by HPLC on reversed phase to give the title compounds.

5-(2-fluoro-6-iodophenyl)-1-methyl-1H-tetrazole: Yield: 547 mg; Mass spectrum (ESI$^+$): m/z=305 [M+H]$^+$.

5-(2-fluoro-6-iodophenyl)-2-methyl-2H-tetrazole: Yield: 457 mg; Mass spectrum (ESI$^+$): m/z=305 [M+H]$^+$.

Intermediate 80

Methyl 2-((3S)-6-((1R)-7-fluoro-4-(3-fluoro-2-(1-methyl-1H-tetrazol-5-yl)phenyl)-2,3-dihydro-1H-inden-1-yloxy)-2,3-dihydrobenzofuran-3-yl)acetate

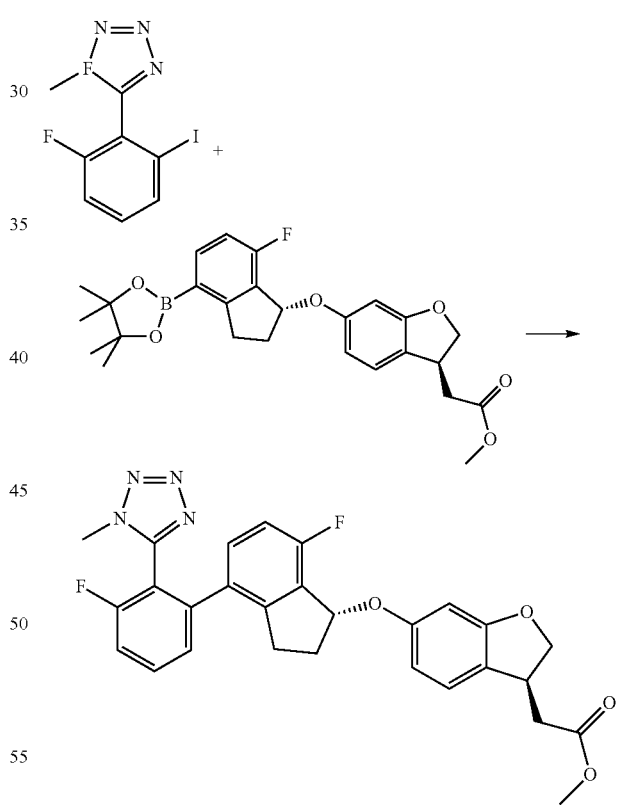

In a microwave vial methyl 2-((S)-6-((R)-7-fluoro-4-(4,4,5,5-tetramethyl-1,3,2-dioxaborolan-2-yl)-2,3-dihydro-1H-inden-1-yloxy)-2,3-dihydrobenzofuran-3-yl)acetate (100 mg), 5-(2-fluoro-6-iodophenyl)-1-methyl-1H-tetrazole (78 mg), K$_3$PO$_4$ (136 mg) are suspended in 1,4-dioxane (3 mL) and purged for 10 minutes with argon. [1,3-Bis(2,6-di-3-pentylphenyl)inidazol-2-ylidene](3-chloropyridyl)palladium(II) dichloride (8.5 mg) is added, the vial is sealed and the mixture is stirred at 100° C. for 12 hours. After cooling to room temperature the solvents are evaporated and the product thus obtained is used directly in the next step.

Intermediate 81

4-(4-Bromo-3,5-dimethyl-phenyl)-pyridine

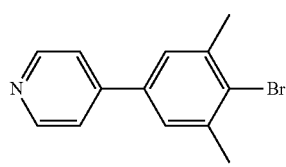

The title compound is prepared from 4-(4,4,5,5-tetramethyl-[1,3,2]dioxaborolan-2-yl)-pyridine and 2-bromo-5-iodo-1,3-dimethyl-benzene following a procedure analogous to that described in Step 1 of Intermediate 56. LC (method 9): $t_R$=0.90 min; Mass spectrum (ESI$^+$): m/z=262/264 (Br) [M+H]$^+$.

Intermediate 82

{(S)-6-[(R)-4-(2,6-Dimethyl-4-pyridin-4-yl-phenyl)-7-fluoro-indan-1-yloxy]-2,3-dihydro-benzofuran-3-yl}-acetic acid methyl ester

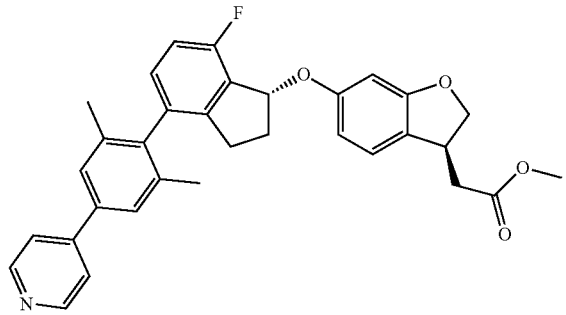 [SMILES: COC(=O)C[C@@H]1COc2cc(O[C@@H]3CCc4c(-c5c(C)cc(-c6ccncc6)cc5C)ccc(F)c43)ccc21]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-bromo-3,5-dimethyl-phenyl)-pyridine following a procedure analogous to that described in Step 5 of Intermediate 1. LC (method 9): $t_R$=1.08 min; Mass spectrum (ESI$^+$): m/z=524 [M+H]$^+$.

Intermediate 83

{(S)-6-[(R)-4-(2-Bromo-pyridin-3-yl)-7-fluoro-indan-1-yloxy]-2,3-dihydro-benzofuran-3-yl}-acetic acid methyl ester The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-bromo-3-iodo-pyridine following a procedure analogous to that described in Step 1 of Intermediate 56. LC (method 9): $t_R$=1.15 min; Mass spectrum (ESI$^+$): m/z=498/500 (Br) [M+H]$^+$.

Intermediate 84

{(S)-6-[(R)-7-Fluoro-4-(2-furan-3-yl-pyridin-3-yl)-indan-1-yloxy]-2,3-dihydro-benzofuran-3-yl}-acetic acid methyl ester The title compound is prepared from {(S)-6-[(R)-4-(2-bromo-pyridin-3-yl)-7-fluoro-indan-1-yloxy]-2,3-dihydro-benzofuran-3-yl}-acetic acid methyl ester and furan-3-boronic acid following a procedure analogous to that described

Intermediate 85

{(S)-6-[(R)-7-Fluoro-4-(2-phenyl-pyridin-3-yl)-indan-1-yloxy]-2,3-dihydro-benzofuran-3-yl}-acetic acid methyl ester

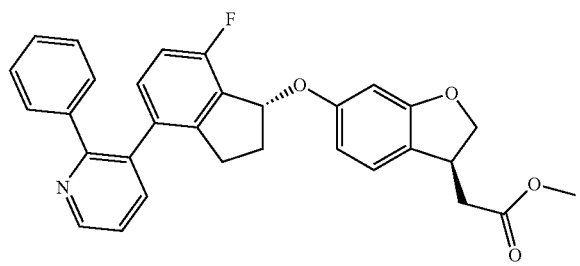 [SMILES: COC(=O)C[C@@H]1COc2cc(O[C@@H]3CCc4c(-c5cccnc5-c5ccccc5)ccc(F)c43)ccc21]

The title compound is prepared from {(S)-6-[(R)-4-(2-bromo-pyridin-3-yl)-7-fluoro-indan-1-yloxy]-2,3-dihydro-benzofuran-3-yl}-acetic acid methyl ester and phenylboronic acid following a procedure analogous to that described in Step 1 of Intermediate 56. LC (method 9): $t_R$=1.15 min; Mass spectrum (ESI$^+$): m/z=496 [M+H]$^+$.

Intermediate 86

4-(4-Bromo-3,5-dimethyl-phenyl)-2-methyl-pyridine

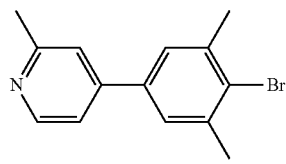 [SMILES: Cc1cc(-c2cc(C)c(Br)c(C)c2)ccn1]

The title compound is prepared from 2-methyl-4-(4,4,5,5-tetramethyl-[1,3,2]dioxaborolan-2-yl)-pyridine and 2-bromo-5-iodo-1,3-dimethyl-benzene following a procedure analogous to that described in Step 1 of Intermediate 56. LC (method 9): $t_R$=0.87 min; Mass spectrum (ESI$^+$): m/z=276/278 (Br) [M+H]$^+$.

Intermediate 87

4-(4-Bromo-3,5-dimethyl-phenyl)-1,3,5-trimethyl-pyrazole

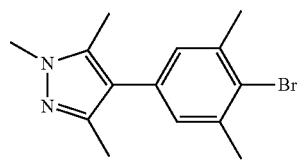 [SMILES: Cc1cc(-c2c(C)nn(C)c2C)cc(C)c1Br]

The title compound is prepared from 4-(4,4,5,5-tetramethyl-[1,3,2]dioxaborolan-2-yl)-1,3,5-trimethyl-pyrazole and 2-bromo-5-iodo-1,3-dimethyl-benzene following a procedure analogous to that described in Step 1 of Intermediate 56. LC (method 7): $t_R$=1.09 min; Mass spectrum (ESI$^+$): m/z=293/295 (Br) [M+H]$^+$.

Intermediate 88

{(S)-6-[(R)-4-(2,6-Dimethyl-4-(1,3,5-trimethyl-pyrazol-4-yl)-phenyl)-7-fluoro-indan-1-yloxy]-2,3-dihydro-benzofuran-3-yl}-acetic acid methyl ester

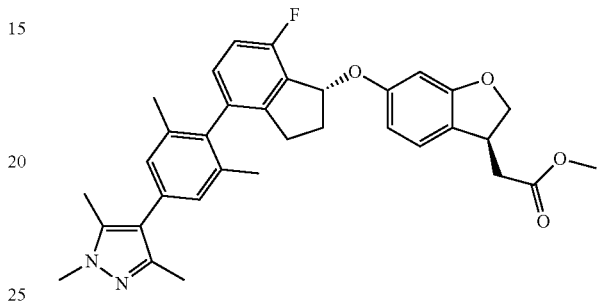

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-bromo-3,5-dimethyl-phenyl)-1,3,5-trimethyl-pyrazole following a procedure analogous to that described in Step 5 of Intermediate 1. LC (method 9): $t_R$=1.24 min; Mass spectrum (ESI$^+$): m/z=555 [M+H]$^+$.

Intermediate 89

{(S)-6-[(R)-7-Fluoro-4-(2-(3,6-dihydropyran-4-yl)-pyridin-3-yl)-indan-1-yloxy]-2,3-dihydro-benzofuran-3-yl}-acetic acid

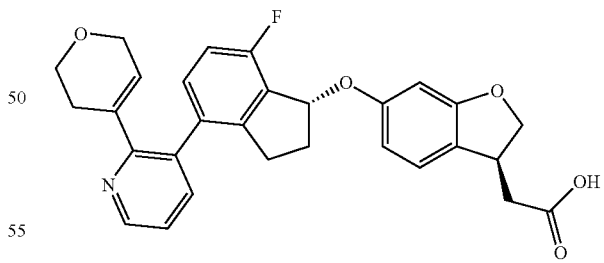

The methyl ester of the title compound is prepared from {(S)-6-[(R)-4-(2-bromo-pyridin-3-yl)-7-fluoro-indan-1-yloxy]-2,3-dihydro-benzofuran-3-yl}-acetic acid methyl ester and 4-(4,4,5,5-tetramethyl-[1,3,2]dioxaborolan-2-yl)-3,6-dihydropyran following a procedure analogous to that described in Step 1 of Intermediate 56. Saponification of the methyl ester, {(S)-6-[(R)-7-fluoro-4-(3,6-dihydropyran-4-yl-pyridin-3-yl)-indan-1-yloxy]-2,3-dihydro-benzofuran-3-yl}-acetic acid methyl ester, gives the title compound following a procedure analogous to that described for Example 4. LC (method 9): $t_R$=0.93 min; Mass spectrum (ESI⁺): m/z=488 [M+H]⁺.

Intermediate 90

3-(4-Bromo-3,5-dimethyl-phenyl)-5-methyl-pyridine

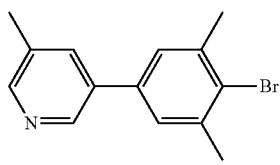

The title compound is prepared from 5-methyl-pyridine-3-boronic acid and 2-bromo-5-iodo-1,3-dimethyl-benzene following a procedure analogous to that described in Step 1 of Intermediate 56. LC (method 9): $t_R$=0.93 min; Mass spectrum (ESI⁺): m/z=276/278 (Br) [M+H]⁺.

Intermediate 91

{(S)-6-[(R)-4-(2,6-Dimethyl-4-(5-methyl-pyridin-3-yl)-phenyl)-7-fluoro-indan-1-yloxy]-2,3-dihydro-benzofuran-3-yl}-acetic acid methyl ester

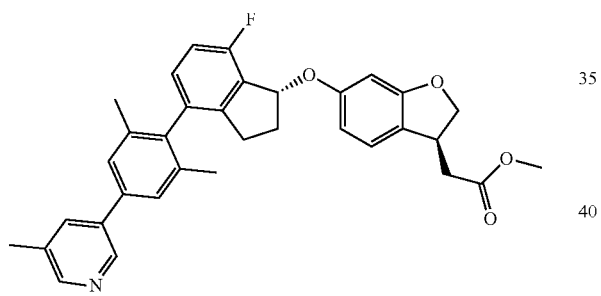

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-bromo-3,5-dimethyl-phenyl)-5-methyl-pyridine following a procedure analogous to that described in Step 5 of Intermediate 1.

Intermediate 92

3-(4-Bromo-3,5-dimethyl-phenyl)-pyridine

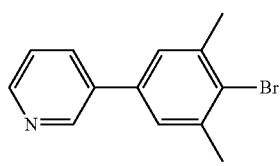

The title compound is prepared from pyridine-3-boronic acid and 2-bromo-5-iodo-1,3-dimethyl-benzene following a procedure analogous to that described in Step 1 of Intermediate 56. LC (method 9): $t_R$=0.99 min; Mass spectrum (ESI⁺): m/z=262/264 (Br) [M+H]⁺.

Intermediate 93

{(S)-6-[(R)-4-(2,6-Dimethyl-4-pyridin-3-yl-phenyl)-7-fluoro-indan-1-yloxy]-2,3-dihydro-benzofuran-3-yl}-acetic acid methyl ester

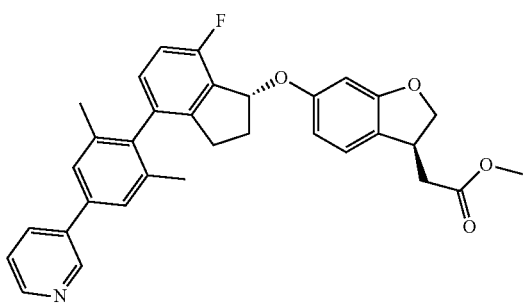 [SMILES: COC(=O)C[C@@H]1COc2cc(O[C@@H]3CCc4c(-c5c(C)cc(-c6cccnc6)cc5C)ccc(F)c43)ccc21]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-bromo-3,5-dimethyl-phenyl)-pyridine following a procedure analogous to that described in Step 5 of Intermediate 1. Mass spectrum (ESI⁺): m/z=524 [M+H]⁺.

Intermediate 94

2-(4-Bromo-3,5-dimethyl-phenyl)-5-methyl-pyrimidine

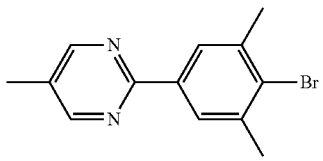 [SMILES: Cc1cnc(-c2cc(C)c(Br)c(C)c2)nc1]

The title compound is prepared from 2-bromo-1,3-dimethyl-5-(4,4,5,5-tetramethyl-[1,3,2]dioxaborolan-2-yl)-benzene and 2-bromo-5-methyl-pyrimidine following a procedure analogous to that described in Step 1 of Intermediate 56. LC (method 7): $t_R$=1.20 min; Mass spectrum (ESI⁺): m/z=277/279 (Br) [M+H]⁺.

Intermediate 95

{(S)-6-[(R)-4-(2,6-Dimethyl-4-(5-methyl-pyrimidin-2-yl)-phenyl)-7-fluoro-indan-1-yloxy]-2,3-dihydro-benzofuran-3-yl}-acetic acid methyl ester

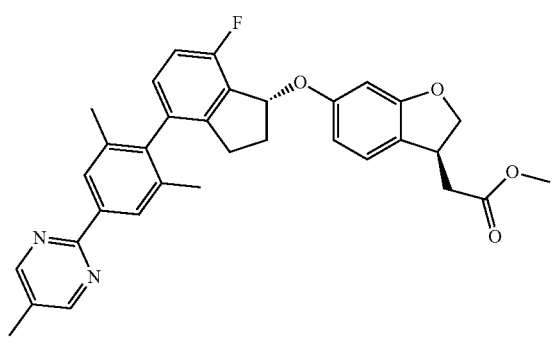

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-5-methyl-pyrimidine following a procedure analogous to that described in Step 5 of Intermediate 1. LC (method 9): $t_R$=1.27 min; Mass spectrum (ESI$^+$): m/z=539 [M+H]$^+$.

Intermediate 96

2-(4-Bromo-3,5-dimethyl-phenyl)-5-methyl-pyrazine

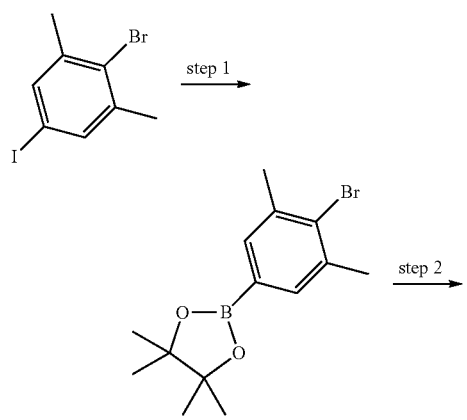

Step 1: 2-bromo-1,3-dimethyl-5-(4,4,5,5-tetramethyl-[1,3,2]dioxaborolan-2-yl)-benzene A flask charged with a stir bar, 2-bromo-5-iodo-1,3-dimethyl-benzene (1.0 g), bis-(pinacolato)-diboron (1.0 g), potassium acetate (1.1 g) and dimethyl sulfoxide (10 mL) is purged with argon for 5 min. [1,1'-Bis(diphenylphosphino)-ferrocene]-dichloropalladium(II) (0.26 g) is added at room temperature, and the mixture is stirred at 90° C. for 3 h. After cooling to room temperature, water is added and the resulting mixture is extracted with ethyl acetate. The combined extracts are dried (MgSO$_4$) and concentrated. The residue is chromatographed on reversed phase (HPLC; acetonitrile/water) to give the title compound. LC (method 9): $t_R$=1.30 min; Mass spectrum (ESI$^+$): m/z=311/313 (Br) [M+H]$^+$.

Step 2: 2-(4-bromo-3,5-dimethyl-phenyl)-5-methyl-pyrazine

The title compound is prepared from 2-bromo-1,3-dimethyl-5-(4,4,5,5-tetramethyl-[1,3,2]dioxaborolan-2-yl)-benzene and 2-bromo-5-methyl-pyrazine following a procedure analogous to that described in Step 1 of Intermediate 56. Mass spectrum (ESI$^+$): m/z=277/279 (Br) [M+H]$^+$.

Intermediate 97

{(S)-6-[(R)-4-(2,6-Dimethyl-4-(5-methyl-pyrazin-2-yl)-phenyl)-7-fluoro-indan-1-yloxy]-2,3-dihydro-benzofuran-3-yl}-acetic acid methyl ester

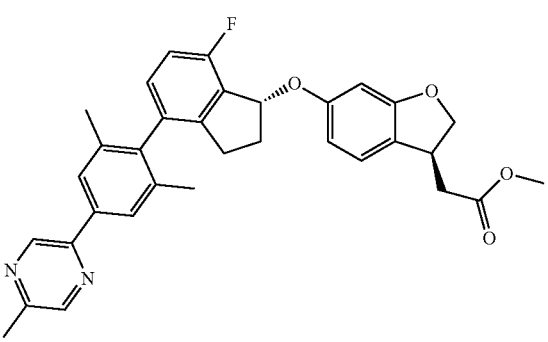

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-5-methyl-pyrazine following a procedure analogous to that described in Step 5 of Intermediate 1.

Intermediate 98

4-(4-Bromo-3,5-dimethyl-phenyl)-2,6-dimethyl-pyrimidine

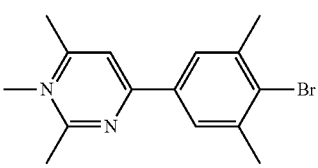

The title compound is prepared from 2-bromo-1,3-dimethyl-5-(4,4,5,5-tetramethyl-[1,3,2]dioxaborolan-2-yl)-benzene and 4-bromo-2,6-dimethyl-pyrimidine following a procedure analogous to that described in Step 1 of Intermediate 56. LC (method 7): $t_R$=1.01 min; Mass spectrum (ESI$^+$): m/z=291/293 (Br) [M+H]$^+$.

Intermediate 99

{(S)-6-[(R)-4-(2,6-Dimethyl-4-(2,6-dimethyl-pyrimidin-4-yl)-phenyl)-7-fluoro-indan-1-yloxy]-2,3-dihydro-benzofuran-3-yl}-acetic acid methyl ester

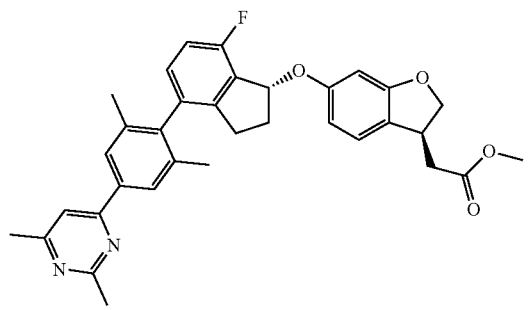

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-bromo-3,5-dimethyl-phenyl)-2,6-dimethyl-pyrimidine following a procedure analogous to that described in Step 5 of Intermediate 1. LC (method 9): $t_R$=1.24 min; Mass spectrum (ESI$^+$): m/z=553 [M+H]$^+$.

Intermediate 100

4-(4-Bromo-3,5-dimethyl-phenyl)-2-methoxy-pyridine

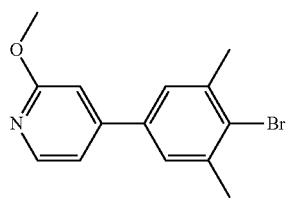 [SMILES: COc1cc(-c2cc(C)c(Br)c(C)c2)ccn1]

The title compound is prepared from 2-methoxy-pyridine-4-boronic acid and 2-bromo-5-iodo-1,3-dimethyl-benzene following a procedure analogous to that described in Step 1 of Intermediate 56. LC (method 9): $t_R$=1.24 min; Mass spectrum (ESI$^+$): m/z=293/295 (Br) [M+H]$^+$.

Intermediate 101

{(S)-6-[(R)-4-(2,6-Dimethyl-4-(2-methoxy-pyridin-4-yl)-phenyl)-7-fluoro-indan-1-yloxy]-2,3-dihydro-benzofuran-3-yl}-acetic acid methyl ester

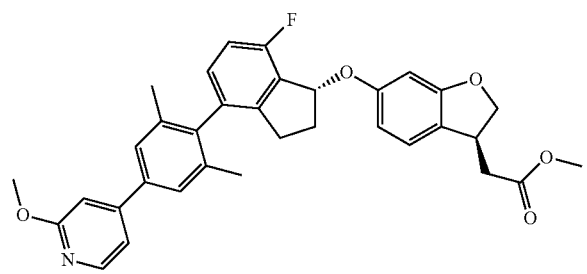

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-bromo-3,5-dimethyl-phenyl)-2-methoxy-pyridine following a procedure analogous to that described in Step 5 of Intermediate 1. LC (method 9): $t_R$=1.30 min; Mass spectrum (ESI$^+$): m/z=554 [M+H]$^+$.

Intermediate 102

5-(4-Bromo-3,5-dimethyl-phenyl)-2-methyl-pyridine

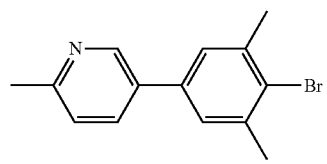 [SMILES: Cc1ccc(-c2cc(C)c(Br)c(C)c2)cn1]

The title compound is prepared from 2-methyl-pyridine-5-boronic acid and 2-bromo-5-iodo-1,3-dimethyl-benzene following a procedure analogous to that described in Step 1 of Intermediate 56. LC (method 9): $t_R$=0.93 min; Mass spectrum (ESI$^+$): m/z=276/278 (Br) [M+H]$^+$.

Intermediate 103

{(S)-6-[(R)-4-(2,6-Dimethyl-4-(6-methyl-pyridin-3-yl)-phenyl)-7-fluoro-indan-1-yloxy]-2,3-dihydro-benzofuran-3-yl}-acetic acid methyl ester

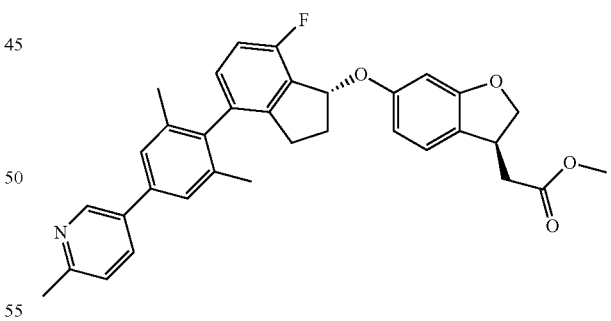

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 5-(4-bromo-3,5-dimethyl-phenyl)-2-methyl-pyridine following a procedure analogous to that described in Step 5 of Intermediate 1. LC (method 9): $t_R$=1.12 min; Mass spectrum (ESI⁺): m/z=538 [M+H]⁺.

Intermediate 104

2-(4-Bromo-3,5-dimethyl-phenyl)-6-methyl-pyrazine

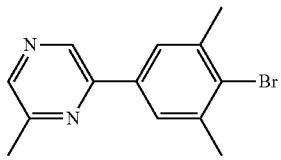 [SMILES: Cc1cncc(-c2cc(C)c(Br)c(C)c2)n1]

The title compound is prepared from 2-bromo-1,3-dimethyl-5-(4,4,5,5-tetramethyl-[1,3,2]dioxaborolan-2-yl)-benzene and 2-bromo-6-methyl-pyrazine following a procedure analogous to that described in Step 1 of Intermediate 56. LC (method 9): $t_R$=1.04 min; Mass spectrum (ESI⁺): m/z=277/279 (Br) [M+H]⁺.

Intermediate 105

{(S)-6-[(R)-4-(2,6-Dimethyl-4-(6-methyl-pyrazin-2-yl)-phenyl)-7-fluoro-indan-1-yloxy]-2,3-dihydro-benzofuran-3-yl}-acetic acid methyl ester

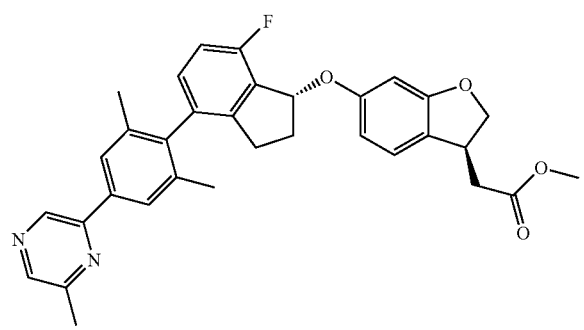 [SMILES: COC(=O)C[C@@H]1COc2cc(O[C@@H]3CCc4c(-c5c(C)cc(-c6cncc(C)n6)cc5C)ccc(F)c43)ccc21]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-6-methyl-pyrazine following a procedure analogous to that described in Step 5 of Intermediate 1. LC (method 26): $t_R$=0.93 min; Mass spectrum (ESI⁺): m/z=539 [M+H]⁺.

Intermediate 106

2-(4-Bromo-3,5-dimethyl-phenyl)-4-methyl-pyrimidine

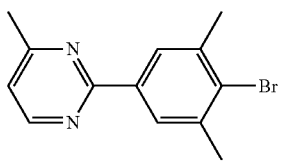 [SMILES: Cc1ccnc(-c2cc(C)c(Br)c(C)c2)n1]

The title compound is prepared from 2-bromo-1,3-dimethyl-5-(4,4,5,5-tetramethyl-[1,3,2]dioxaborolan-2-yl)-benzene and 2-bromo-4-methyl-pyrimidine following a procedure analogous to that described in Step 1 of Intermediate 56. LC (method 9): $t_R$=1.08 min; Mass spectrum (ESI⁺): m/z=277/279 (Br) [M+H]⁺.

Intermediate 107

{(S)-6-[(R)-4-(2,6-Dimethyl-4-(4-methyl-pyrimidin-2-yl)-phenyl)-7-fluoro-indan-1-yloxy]-2,3-dihydro-benzofuran-3-yl}-acetic acid methyl ester

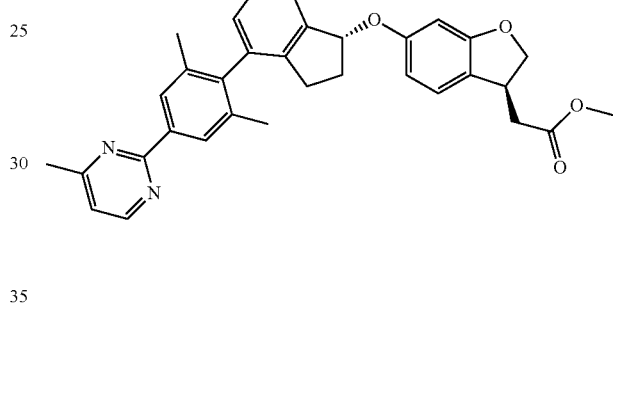

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-4-methyl-pyrimidine following a procedure analogous to that described in Step 5 of Intermediate 1. LC (method 26): $t_R$=0.96 min; Mass spectrum (ESI⁺): m/z=539 [M+H]⁺.

Intermediate 108

3-(4-Bromo-3,5-dimethyl-phenyl)-6-methyl-pyridazine

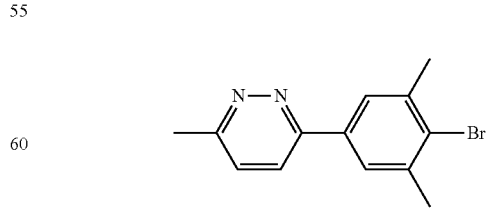

The title compound is prepared from 2-bromo-1,3-dimethyl-5-(4,4,5,5-tetramethyl-[1,3,2]dioxaborolan-2-yl)-benzene and 3-bromo-6-methyl-pyridazine following a procedure analogous to that described in Step 1 of Intermediate 56. LC (method 9): $t_R$=1.11 min; Mass spectrum (ESI$^+$): m/z=277/279 (Br) [M+H]$^+$.

Intermediate 109

{(S)-6-[(R)-4-(2,6-Dimethyl-4-(6-methyl-pyridazin-3-yl)-phenyl)-7-fluoro-indan-1-yloxy]-2,3-dihydro-benzofuran-3-yl}-acetic acid methyl ester

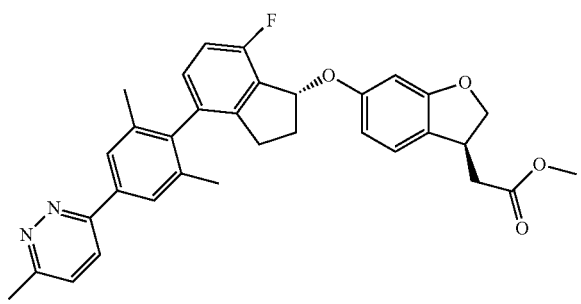

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-bromo-3,5-dimethyl-phenyl)-6-methyl-pyridazine following a procedure analogous to that described in Step 5 of Intermediate 1. LC (method 26): $t_R$=0.75 min; Mass spectrum (ESI$^+$): m/z=539 [M+H]$^+$.

Intermediate 110

4-(4-Chloro-3,5-dimethyl-phenyl)-2,6-dimethyl-pyridine

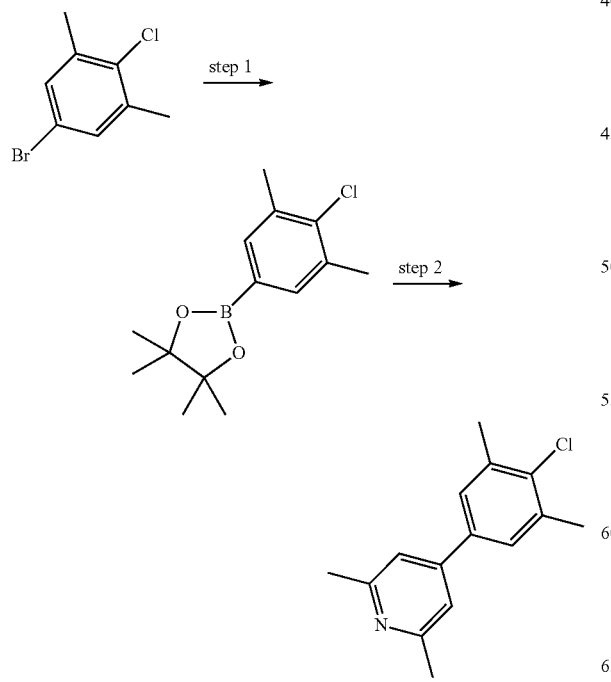

Step 1: 2-chloro-1,3-dimethyl-5-(4,4,5,5-tetramethyl-[1,3,2]dioxaborolan-2-yl)-benzene The title compound is prepared from 5-bromo-2-chloro-1,3-dimethyl-benzene and bis-(pinacolato)-diboron following a procedure analogous to that described in Step 1 of Intermediate 96. LC (method 7): $t_R$=1.10 min; Mass spectrum (ESI$^+$): m/z=552 [M+H]$^+$.

Step 2: 4-(4-chloro-3,5-dimethyl-phenyl)-2,6-dimethyl-pyridine

The title compound is prepared from 2-chloro-1,3-dimethyl-5-(4,4,5,5-tetramethyl-[1,3,2]dioxaborolan-2-yl)-benzene and 4-bromo-2,6-dimethyl-pyridine following a procedure analogous to that described in Step 1 of Intermediate 56. Mass spectrum (ESI$^+$): m/z=246/248 (Cl) [M+H]$^+$.

Intermediate 111

{(S)-6-[(R)-4-(2,6-Dimethyl-4-(2,6-dimethyl-pyridin-4-yl)-phenyl)-7-fluoro-indan-1-yloxy]-2,3-dihydro-benzofuran-3-yl}-acetic acid methyl ester

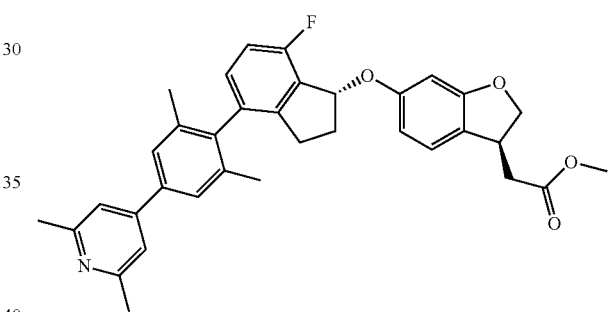

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-chloro-3,5-dimethyl-phenyl)-2,6-dimethyl-pyridine following a procedure analogous to that described in Step 5 of Intermediate 1. LC (method 7): $t_R$=1.10 min; Mass spectrum (ESI$^+$): m/z=552 [M+H]$^+$.

Intermediate 112

2-(4-Bromo-3,5-dimethyl-phenyl)-pyrazine

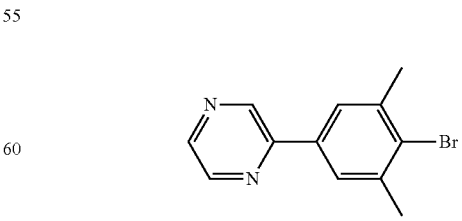

The title compound is prepared from 2-bromo-1,3-dimethyl-5-(4,4,5,5-tetramethyl-[1,3,2]dioxaborolan-2-yl)-benzene and 2-iodo-pyrazine following a procedure analogous to that described in Step 1 of Intermediate 56. LC (method 9): $t_R$=1.12 min; Mass spectrum (ESI$^+$): m/z=263/265 (Br) [M+H]$^+$.

Intermediate 113

{(S)-6-[(R)-4-(2,6-Dimethyl-4-pyrazin-2-yl-phenyl)-7-fluoro-indan-1-yloxy]-2,3-dihydro-benzofuran-3-yl}-acetic acid methyl ester

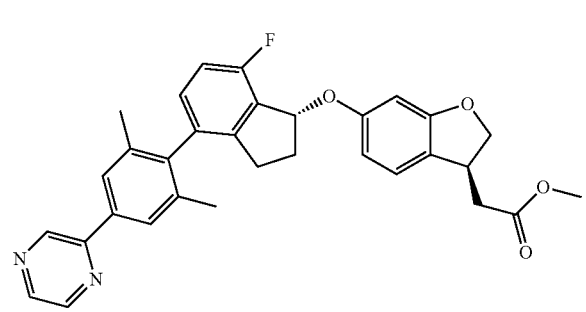 [SMILES: COC(=O)C[C@@H]1COc2cc(O[C@@H]3CCc4c(-c5c(C)cc(-c6cnccn6)cc5C)ccc(F)c43)ccc21]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-pyrazine following a procedure analogous to that described in Step 5 of Intermediate 1. LC (method 9): $t_R$=1.31 min; Mass spectrum (ESI$^+$): m/z=525 [M+H]$^+$.

Intermediate 114

2-(4-Chloro-3,5-dimethyl-phenyl)-5-cyclopropyl-pyrazine

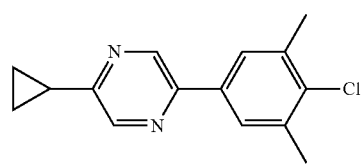 [SMILES: Cc1cc(-c2cnc(C3CC3)cn2)cc(C)c1Cl]

The title compound is prepared from 2-chloro-1,3-dimethyl-5-(4,4,5,5-tetramethyl-[1,3,2]dioxaborolan-2-yl)-benzene and 2-bromo-5-cyclopropyl-pyrazine following a procedure analogous to that described in Step 1 of Intermediate 56. LC (method 11): $t_R$=1.28 min; Mass spectrum (ESI$^+$): m/z=259/261 (Cl) [M+H]$^+$.

Intermediate 115

{(S)-6-[(R)-4-(2,6-Dimethyl-4-(5-cyclopropyl-pyrazin-2-yl)-phenyl)-7-fluoro-indan-1-yloxy]-2,3-dihydro-benzofuran-3-yl}-acetic acid methyl ester

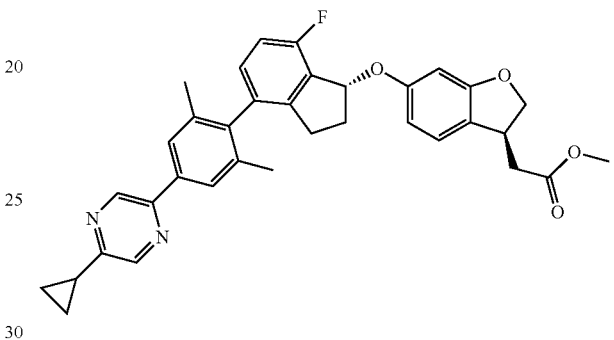

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-chloro-3,5-dimethyl-phenyl)-5-cyclopropyl-pyrazine following a procedure analogous to that described in Step 5 of Intermediate 1. LC (method 7): $t_R$=1.31 min; Mass spectrum (ESI$^+$): m/z=565 [M+H]$^+$.

Intermediate 116

{(S)-6-[(R)-7-Fluoro-4-(2-(2,6-dimethyl-phenyl)-pyridin-3-yl)-indan-1-yloxy]-2,3-dihydro-benzofuran-3-yl}-acetic acid methyl ester

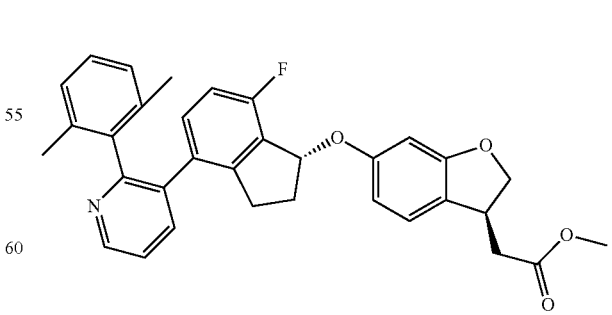

The title compound is prepared from {(S)-6-[(R)-4-(2-bromo-pyridin-3-yl)-7-fluoro-indan-1-yloxy]-2,3-dihydro-benzofuran-3-yl}-acetic acid methyl ester and 2,6-dimethylphenylboronic acid following a procedure analogous to that described in Step 5 of Intermediate 1.

Intermediate 117

3-(4-Chloro-3,5-dimethyl-phenyl)-6-ethyl-pyridazine

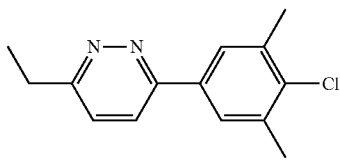 [SMILES: CCc1ccc(-c2cc(C)c(Cl)c(C)c2)nn1]

The title compound is prepared from 2-cloro-1,3-dimethyl-5-(4,4,5,5-tetramethyl-[1,3,2]dioxaborolan-2-yl)-benzene and 3-bromo-6-ethyl-pyridazine following a procedure analogous to that described in Step 1 of Intermediate 56. LC (method 11): $t_R$=1.00 min; Mass spectrum (ESI$^+$): m/z=247/249 (Cl) [M+H]$^+$.

Intermediate 118

{(S)-6-[(R)-4-(2,6-Dimethyl-4-(6-ethyl-pyridazin-3-yl)-phenyl)-7-fluoro-indan-1-yloxy]-2,3-dihydro-benzofuran-3-yl}-acetic acid methyl ester

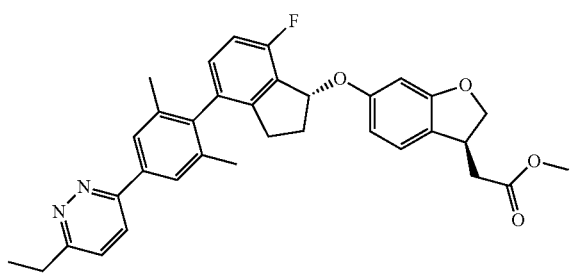 [SMILES: CCc1ccc(-c2cc(C)c(-c3ccc(F)c4c3CC[C@H]4Oc3ccc4c(c3)OC[C@H]4CC(=O)OC)c(C)c2)nn1]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-chloro-3,5-dimethyl-phenyl)-6-ethyl-pyridazine following a procedure analogous to that described in Step 5 of Intermediate 1. LC (method 7): $t_R$=1.14 min; Mass spectrum (ESI$^+$): m/z=553 [M+H]$^+$.

Intermediate 119

5-(4-Chloro-3,5-dimethyl-phenyl)-2-methoxy-pyridine

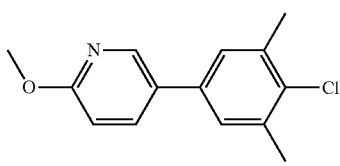 [SMILES: COc1ccc(-c2cc(C)c(Cl)c(C)c2)cn1]

The title compound is prepared from 2-methoxy-pyridine-5-boronic acid and 5-bromo-2-chloro-1,3-dimethyl-benzene following a procedure analogous to that described in Step 1 of Intermediate 56. LC (method 7): $t_R$=1.21 min; Mass spectrum (ESI$^+$): m/z=248/250 (Cl) [M+H]$^+$.

Intermediate 120

{(S)-6-[((R)-4-(2,6-Dimethyl-4-(6-methoxy-pyridin-3-yl)-phenyl)-7-fluoro-indan-1-yloxy]-2,3-dihydro-benzofuran-3-yl}-acetic acid methyl ester

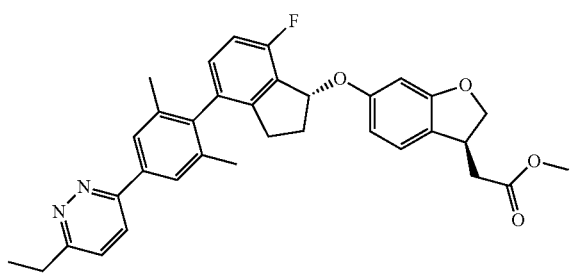 [SMILES: CCc1ccc(-c2cc(C)c(-c3ccc(F)c4c3CC[C@H]4Oc3ccc4c(c3)OC[C@H]4CC(=O)OC)c(C)c2)nn1]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 5-(4-chloro-3,5-dimethyl-phenyl)-2-methoxy-pyridine following a procedure analogous to that described in Step 5 of Intermediate 1. LC (method 7): $t_R$=1.29 min; Mass spectrum (ESI$^+$): m/z=554 [M+H]$^+$.

Intermediate 121

3-(4-Chloro-3,5-dimethyl-phenyl)-5-methoxy-pyridazine

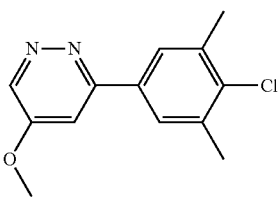 [SMILES: COc1cnnc(-c2cc(C)c(Cl)c(C)c2)c1]

The title compound is prepared from 2-chloro-1,3-dimethyl-5-(4,4,5,5-tetramethyl-[1,3,2]dioxaborolan-2-yl)-benzene and 3-chloro-5-methoxy-pyridazine following a procedure analogous to that described in Step 1 of Intermediate 56. LC (method 11): $t_R$=0.93 min; Mass spectrum (ESI⁺): m/z=249/251 (Cl) [M+H]⁺.

Intermediate 122

{(S)-6-[(R)-4-(2,6-Dimethyl-4-(5-methoxy-pyridazin-3-yl)-phenyl)-7-fluoro-indan-1-yloxy]-2,3-dihydro-benzofuran-3-yl}-acetic acid methyl ester

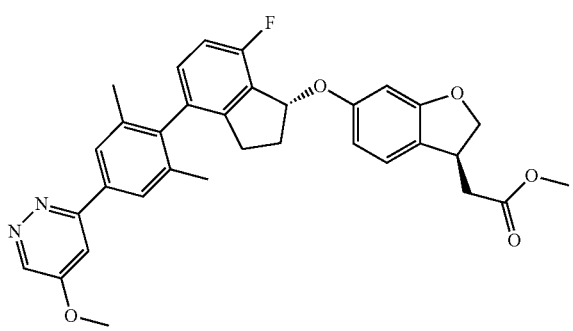 [SMILES: COC(=O)C[C@@H]1COc2cc(O[C@@H]3CCc4c(-c5c(C)cc(-c6cc(OC)cnn6)cc5C)ccc(F)c43)ccc21]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-chloro-3,5-dimethyl-phenyl)-5-methoxy-pyridazine following a procedure analogous to that described in Step 5 of Intermediate 1. LC (method 11): $t_R$=1.10 min; Mass spectrum (ESI⁺): m/z=555 [M+H]⁺.

Intermediate 123

5-(4-Chloro-3,5-dimethyl-phenyl)-3-methyl-pyridazine

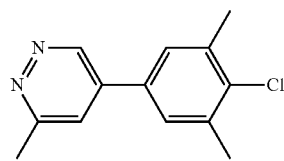 [SMILES: Cc1cc(-c2cc(C)c(Cl)c(C)c2)cnn1]

The title compound is prepared from 3-methyl-5-(4,4,5,5-tetramethyl-[1,3,2]dioxaborolan-2-yl)-pyridazine and 5-bromo-2-chloro-1,3-dimethyl-benzene following a procedure analogous to that described in Step 1 of Intermediate 56. LC (method 11): $t_R$=0.91 min; Mass spectrum (ESI⁺): m/z=233/235 (Cl) [M+H]⁺.

Intermediate 124

{(S)-6-[(R)-4-(2,6-Dimethyl-4-(6-methyl-pyridazin-4-yl)-phenyl)-7-fluoro-indan-1-yloxy]-2,3-dihydro-benzofuran-3-yl}-acetic acid methyl ester

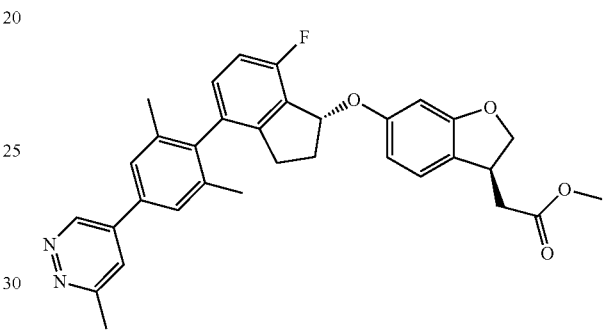

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 5-(4-chloro-3,5-dimethyl-phenyl)-3-methyl-pyridazine following a procedure analogous to that described in Step 5 of Intermediate 1. LC (method 11): $t_R$=1.09 min; Mass spectrum (ESI⁺): m/z=539 [M+H]⁺.

Intermediate 125

4-(4-Chloro-3,5-dimethyl-phenyl)-1,2-dimethyl-imidazole

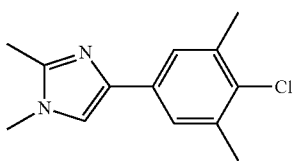 [SMILES: Cc1cc(-c2cn(C)c(C)n2)cc(C)c1Cl]

The title compound is prepared from 2-chloro-1,3-dimethyl-5-(4,4,5,5-tetramethyl-[1,3,2]dioxaborolan-2-yl)-benzene and 4-bromo-1,2-dimethyl-imidazole following a procedure analogous to that described in Step 1 of Intermediate 56.

Intermediate 126

{(S)-6-[(R)-4-(2,6-Dimethyl-4-(1,2-dimethyl-imidazol-4-yl)-phenyl)-7-fluoro-indan-1-yloxy]-2,3-dihydro-benzofuran-3-yl}-acetic acid methyl ester

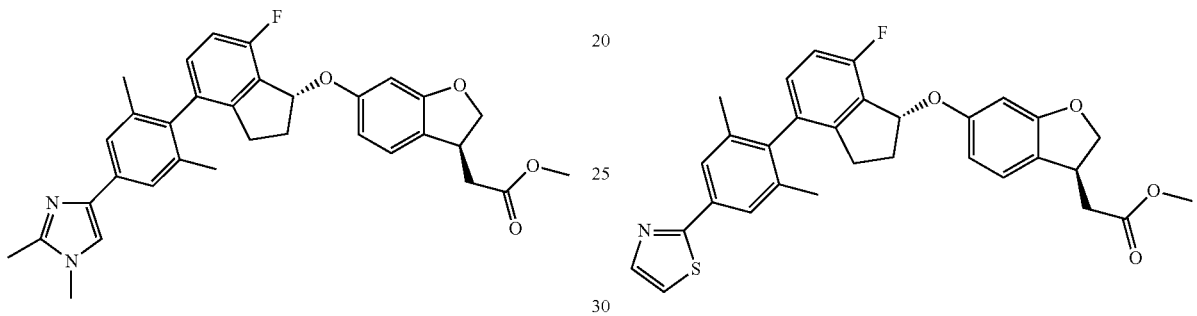

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-chloro-3,5-dimethyl-phenyl)-1,2-dimethyl-imidazole following a procedure analogous to that described in Step 5 of Intermediate 1. LC (method 7): $t_R$=1.06 min; Mass spectrum (ESI$^+$): m/z=541 [M+H]$^+$.

Intermediate 127

2-(4-Bromo-3,5-dimethyl-phenyl)-thiazole

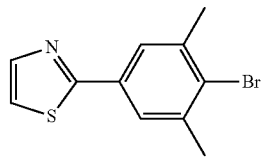

A mixture of 2-bromo-5-iodo-1,3-dimethyl-benzene (0.28 g), 2-thiazolylzinc bromide (0.5 mol/L in tetrahydrofuran; 1.9 mL), tetrakis(triphenylphosphine)palladium(0) (52 mg), and tetrahydrofuran (5 mL) under argon atmosphere is stirred at 100° C. for 3 h. After cooling to room temperature, water is added and the resulting mixture is extracted with ethyl acetate. The solvent is evaporated and the residue is chromatographed on silica gel (cyclohexane/ethyl acetate) to give the title compound. LC (method 9): $t_R$=1.19 min; Mass spectrum (ESI$^+$): m/z=268/270 (Br) [M+H]$^+$.

Intermediate 128

{(S)-6-[(R)-4-(2,6-Dimethyl-4-thiazol-2-yl-phenyl)-7-fluoro-indan-1-yloxy]-2,3-dihydro-benzofuran-3-yl}-acetic acid methyl ester

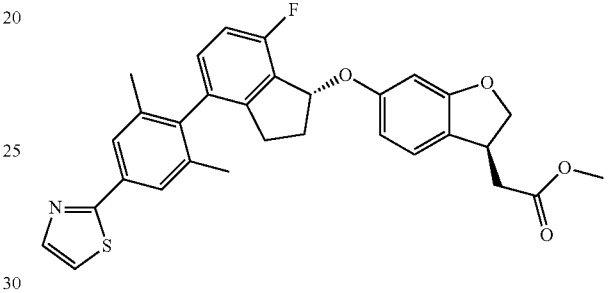

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-thiazole following a procedure analogous to that described in Step 5 of Intermediate 1. LC (method 7): $t_R$=1.29 min; Mass spectrum (ESI$^+$): m/z=530 [M+H]$^+$.

Intermediate 129

4-(4-Chloro-3,5-dimethyl-phenyl)-1-methyl-imidazole

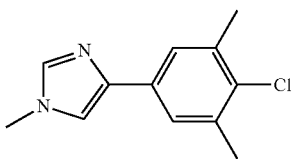

The title compound is prepared from 5-bromo-2-chloro-1,3-dimethyl-benzene and 1-methyl-4-(4,4,5,5-tetramethyl-[1,3,2]dioxaborolan-2-yl)-imidazole following a procedure analogous to that described in Step 1 of Intermediate 56.

Intermediate 130

{(S)-6-[(R)-4-(2,6-Dimethyl-4-(1-methyl-imidazol-4-yl)-phenyl)-7-fluoro-indan-1-yloxy]-2,3-dihydro-benzofuran-3-yl}-acetic acid methyl ester

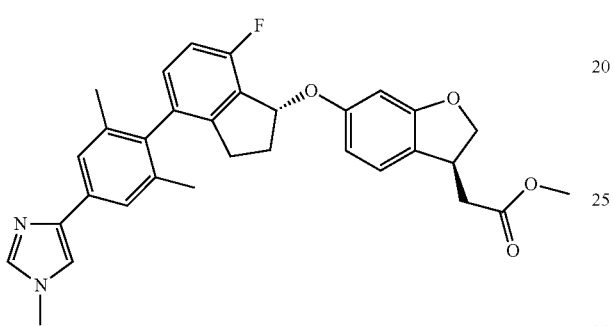

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-chloro-3,5-dimethyl-phenyl)-1-methyl-imidazole following a procedure analogous to that described in Step 5 of Intermediate 1.

Intermediate 131

4-Bromo-N-hydroxy-3,5-dimethyl-benzamidine

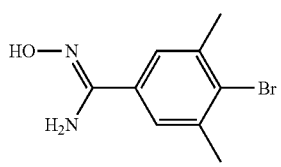

A mixture of 4-bromo-3,5-dimethyl-benzonitrile (1.50 g), hydroxylamine hydrochloride (0.90 g), triethylamine (1.8 mL) and ethanol (30 mL) is stirred at reflux temperature for 4 h. After cooling to room temperature, the mixture is concentrated, the residue is taken up in water, and the resulting mixture is extracted with ethyl acetate. The combined extract is washed with brine, dried (Na$_2$SO$_4$), and concentrated. The residue is chromatographed on silica gel (cyclohexane/ethyl acetate 7:3→3:7) to give the title compound. LC (method 11): t$_R$=0.73 min; Mass spectrum (ESI$^+$): m/z=243/245 (Br) [M+H]$^+$.

Intermediate 132

3-(4-Bromo-3,5-dimethyl-phenyl)-5-methyl-[1,2,4]oxadiazole

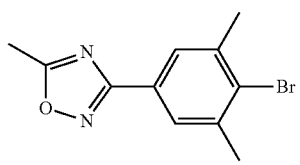

Acetic anhydride (0.35 mL) is added to a solution of 4-bromo-N-hydroxy-3,5-dimethyl-benzamidine (0.30 g) in collidine (3 mL) at room temperature. The solution is stirred at room temperature for 1 h and then at 120° C. for 3 h. After cooling to room temperature, the mixture is concentrated, the residue is taken up in water and acetonitrile, and the resulting mixture is filtered. The filtrate is chromatographed on reversed phase (HPLC; acetonitrile/water/trifluoroacetic acid) to give the title compound. LC (method 11): t$_R$=1.20 min; Mass spectrum (ESI$^+$): m/z=267/269 (Br) [M+H]$^+$.

Intermediate 133

{(S)-6-[(R)-4-(2,6-Dimethyl-4-(5-methyl-[1,2,4]oxadiazol-3-yl)-phenyl)-7-fluoro-indan-1-yloxy]-2,3-dihydro-benzofuran-3-yl}-acetic acid methyl ester

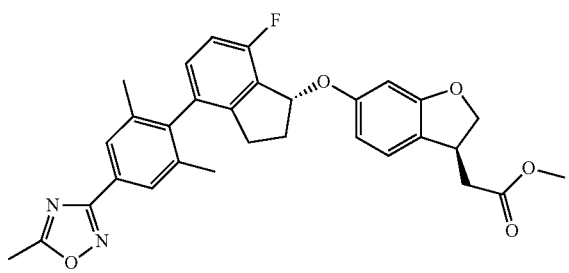

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-bromo-3,5-dimethyl-phenyl)-5-methyl-[1,2,4]oxadiazole following a procedure analogous to that described in Step 5 of Intermediate 1. LC (method 11): $t_R$=1.28 min; Mass spectrum (ESI$^+$): m/z=551 [M+Na]$^+$.

Intermediate 134

2-(4-Bromo-3,5-dimethyl-phenyl)-5-methoxy-pyridine

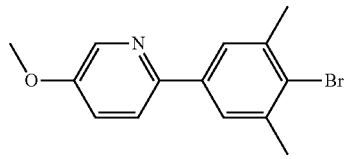 [SMILES: COc1ccc(-c2cc(C)c(Br)c(C)c2)nc1]

The title compound is prepared from potassium 5-methoxy-pyridine-2-trifluoroborate and 2-bromo-5-iodo-1,3-dimethyl-benzene following a procedure analogous to that described in Step 1 of Intermediate 56. LC (method 8): $t_R$=0.72 min; Mass spectrum (ESI$^+$): m/z=292/294 (Br) [M+H]$^+$.

Intermediate 135

{(S)-6-[(R)-4-(2,6-Dimethyl-4-(5-methoxy-pyridin-2-yl)-phenyl)-7-fluoro-indan-1-yloxy]-2,3-dihydro-benzofuran-3-yl}-acetic acid methyl ester

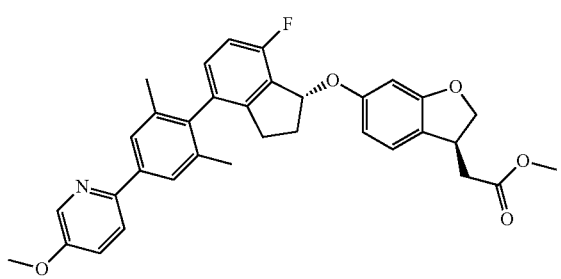

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-5-methoxy-pyridine following a procedure analogous to that described in Step 5 of Intermediate 1. LC (method 8): $t_R$=0.98 min; Mass spectrum (ESI$^+$): m/z=554 [M+H]$^+$.

Intermediate 136

3-(4-Bromo-3,5-dimethyl-phenyl)-5-(2-hydroxy-prop-2-yl)-[1,2,4]oxadiazole

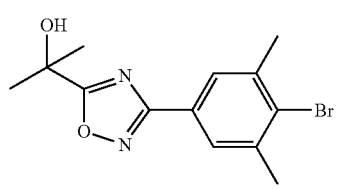 [SMILES: Cc1cc(-c2noc(C(C)(C)O)n2)cc(C)c1Br]

2-(Benzotriazol-1-yl)-1,1,3,3-tetramethyluronium tetrafluoroborate (TBTU; 0.55 g) is added to a solution of 2-hydroxy-isobutyric acid (0.18 g) and N,N-diisopropyl-ethylamine (1.4 mL) in N,N-dimethylformamide (5 mL) at room temperature. The solution is stirred at room temperature for 10 min prior to the addition of 4-bromo-N-hydroxy-3,5-dimethyl-benzamidine (0.40 g). The solution is stirred at room temperature for another 10 min and then at 110° C. overnight. After cooling to room temperature, water is added and the resulting mixture is extracted with ethyl acetate. The combined extract is washed with brine, dried (MgSO$_4$), and concentrated. The residue is chromatographed on reversed phase (HPLC; acetonitrile/water/trifluoroacetic acid) to give the title compound. LC (method 11): $t_R$=1.16 min; Mass spectrum (ESI$^+$): m/z=313/315 (Br) [M+H]$^+$.

Intermediate 137

{(S)-6-[(R)-4-(2,6-Dimethyl-4-(5-[2-hydroxy-prop-2-yl]-[1,2,4]oxadiazol-3-yl)-phenyl)-7-fluoro-indan-1-yloxy]-2,3-dihydro-benzofuran-3-yl}-acetic acid methyl ester

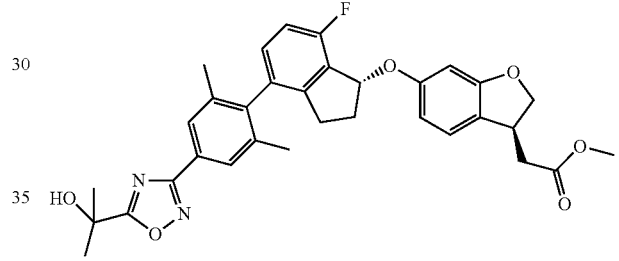

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 3-(4-bromo-3,5-dimethyl-phenyl)-5-(2-hydroxy-prop-2-yl)-[1,2,4]oxadiazole following a procedure analogous to that described in Step 5 of Intermediate 1. LC (method 11): $t_R$=1.25 min; Mass spectrum (ESI$^+$): m/z=573 [M+H]$^+$.

Intermediate 138

2-(4-Bromo-3,5-dimethyl-phenyl)-pyridine

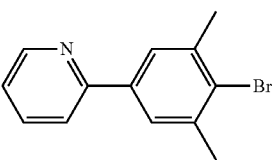

The title compound is prepared from 2-bromo-1,3-dimethyl-5-(4,4,5,5-tetramethyl-[1,3,2]dioxaborolan-2-yl)-benzene and 2-bromo-pyridine following a procedure analogous to that described in Step 1 of Intermediate 56. LC (method 7): t_R=0.91 min; Mass spectrum (ESI⁺): m/z=262/264 (Br) [M+H]⁺.

Intermediate 139

{(S)-6-[(R)-4-(2,6-Dimethyl-4-pyridin-2-yl-phenyl)-7-fluoro-indan-1-yloxy]-2,3-dihydro-benzofuran-3-yl}-acetic acid methyl ester

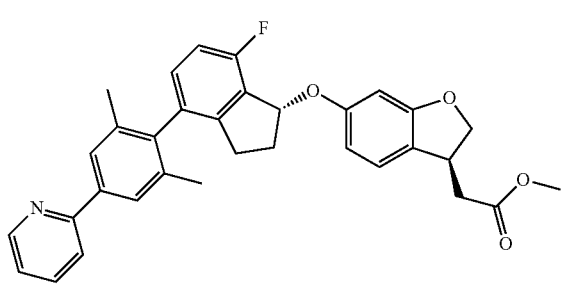 [SMILES: COC(=O)C[C@@H]1COc2cc(O[C@@H]3CCc4c(-c5c(C)cc(-c6ccccn6)cc5C)ccc(F)c43)ccc21]

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-pyridine following a procedure analogous to that described in Step 5 of Intermediate 1. LC (method 7): $t_R$=1.09 min; Mass spectrum (ESI⁺): m/z=524 [M+H]⁺.

Intermediate 140

2-(4-Bromo-3,5-dimethyl-phenyl)-3-methyl-pyridine

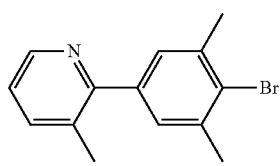 [SMILES: Cc1cccnc1-c1cc(C)c(Br)c(C)c1]

The title compound is prepared from 2-bromo-1,3-dimethyl-5-(4,4,5,5-tetramethyl-[1,3,2]dioxaborolan-2-yl)-benzene and 2-bromo-3-methyl-pyridine following a procedure analogous to that described in Step 1 of Intermediate 56. LC (method 7): $t_R$=0.88 min; Mass spectrum (ESI⁺): m/z=276/278 (Br) [M+H]⁺.

Intermediate 141

{(S)-6-[(R)-4-(2,6-Dimethyl-4-(3-methyl-pyridin-2-yl)-phenyl)-7-fluoro-indan-1-yloxy]-2,3-dihydro-benzofuran-3-yl}-acetic acid methyl ester

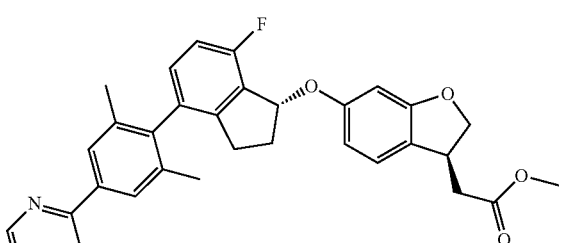

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-3-methyl-pyridine following a procedure analogous to that described in Step 5 of Intermediate 1. LC (method 7): $t_R$=1.07 min; Mass spectrum (ESI⁺): m/z=538 [M+H]⁺.

Intermediate 142

2-(4-Bromo-3,5-dimethyl-phenyl)-6-methyl-pyridine

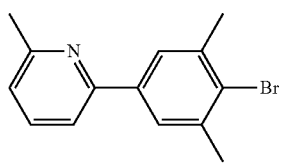 [SMILES: Cc1cccc(-c2cc(C)c(Br)c(C)c2)n1]

The title compound is prepared from 2-bromo-1,3-dimethyl-5-(4,4,5,5-tetramethyl-[1,3,2]dioxaborolan-2-yl)-benzene and 2-bromo-6-methyl-pyridine following a procedure analogous to that described in Step 1 of Intermediate 56. LC (method 7): $t_R$=0.88 min; Mass spectrum (ESI⁺): m/z=276/278 (Br) [M+H]⁺.

Intermediate 143

{(S)-6-[(R)-4-(2,6-Dimethyl-4-(6-methyl-pyridin-2-yl)-phenyl)-7-fluoro-indan-1-yloxy]-2,3-dihydro-benzofuran-3-yl}-acetic acid methyl ester analogous to that described in Step 1 of Intermediate 56. LC (method 7): $t_R$=0.90 min; Mass spectrum (ESI⁺): m/z=276/278 (Br) [M+H]⁺.

Intermediate 145

{(S)-6-[(R)-4-(2,6-Dimethyl-4-(4-methyl-pyridin-2-yl)-phenyl)-7-fluoro-indan-1-yloxy]-2,3-dihydro-benzofuran-3-yl}-acetic acid methyl ester

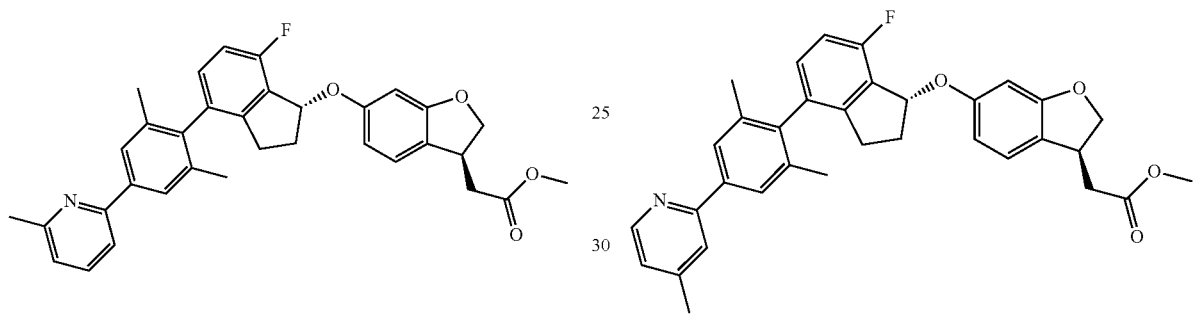

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-6-methyl-pyridine following a procedure analogous to that described in Step 5 of Intermediate 1. LC (method 7): $t_R$=1.07 min; Mass spectrum (ESI⁺): m/z=538 [M+H]⁺.

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-bromo-3,5-dimethyl-phenyl)-4-methyl-pyridine following a procedure analogous to that described in Step 5 of Intermediate 1. LC (method 7): $t_R$=1.07 min; Mass spectrum (ESI⁺): m/z=538 [M+H]⁺.

Intermediate 144

2-(4-Bromo-3,5-dimethyl-phenyl)-4-methyl-pyridine

Intermediate 146

2-(4-Chloro-3,5-dimethyl-phenyl)-4,6-dimethyl-pyridine

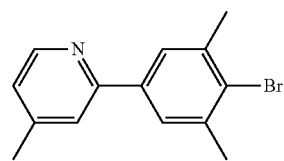 [SMILES: Cc1ccnc(-c2cc(C)c(Br)c(C)c2)c1]

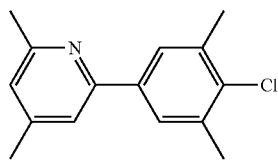 [SMILES: Cc1cc(C)nc(-c2cc(C)c(Cl)c(C)c2)c1]

The title compound is prepared from 2-bromo-1,3-dimethyl-5-(4,4,5,5-tetramethyl-[1,3,2]dioxaborolan-2-yl)-benzene and 2-bromo-4-methyl-pyridine following a procedure The title compound is prepared from 2-chloro-1,3-dimethyl-5-(4,4,5,5-tetramethyl-[1,3,2]dioxaborolan-2-yl)-benzene and 2-bromo-4,6-dimethyl-pyridine following a procedure analogous to that described in Step 1 of Intermediate 56. LC (method 7): $t_R$=0.89 min; Mass spectrum (ESI$^+$): m/z=246/248 (Cl) [M+H]$^+$.

Intermediate 147

{(S)-6-[(R)-4-(2,6-Dimethyl-4-(4,6-dimethyl-pyridin-2-yl)-phenyl)-7-fluoro-indan-1-yloxy]-2,3-dihydro-benzofuran-3-yl}-acetic acid methyl ester

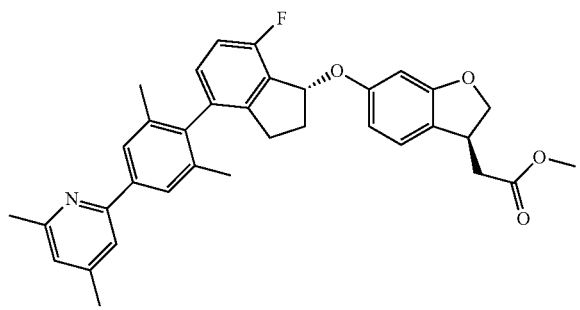

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-chloro-3,5-dimethyl-phenyl)-4,6-methyl-pyridine following a procedure analogous to that described in Step 5 of Intermediate 1. LC (method 7): $t_R$=1.02 min; Mass spectrum (ESI$^+$): m/z=552 [M+H]$^+$.

Intermediate 148

2-(4-Chloro-3,5-dimethyl-phenyl)-1,4-dimethyl-imidazole

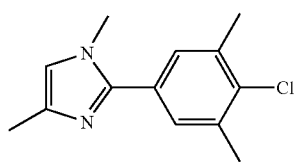 [SMILES: Cc1cn(C)c(-c2cc(C)c(Cl)c(C)c2)n1]

The title compound is prepared from 2-chloro-1,3-dimethyl-5-(4,4,5,5-tetramethyl-[1,3,2]dioxaborolan-2-yl)-benzene and 2-bromo-1,4-dimethyl-imidazole following a procedure analogous to that described in Step 1 of Intermediate 56. LC (method 7): $t_R$=0.82 min; Mass spectrum (ESI$^+$): m/z=235/237 (Cl) [M+H]$^+$.

Intermediate 149

{(S)-6-[(R)-4-(2,6-Dimethyl-4-(1,4-dimethyl-imidazol-2-yl)-phenyl)-7-fluoro-indan-1-yloxy]-2,3-dihydro-benzofuran-3-yl}-acetic acid methyl ester

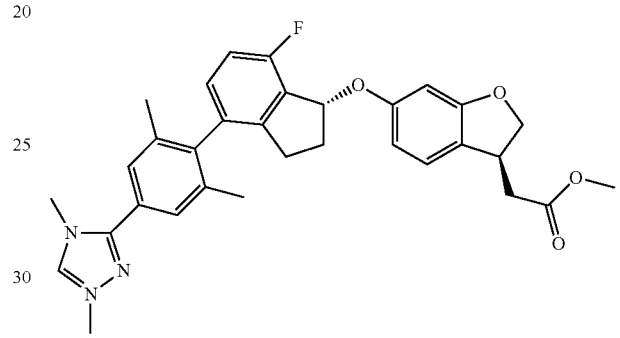

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-chloro-3,5-dimethyl-phenyl)-1,4-dimethyl-imidazole following a procedure analogous to that described in Step 5 of Intermediate 1. LC (method 7): $t_R$=0.98 min; Mass spectrum (ESI$^+$): m/z=541 [M+H]$^+$.

Intermediate 150

2-(4-Chloro-3,5-dimethyl-phenyl)-5-methyl-pyridine

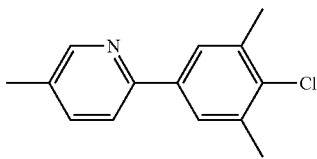 [SMILES: Cc1ccc(-c2cc(C)c(Cl)c(C)c2)nc1]

The title compound is prepared from 2-chloro-1,3-dimethyl-5-(4,4,5,5-tetramethyl-[1,3,2]dioxaborolan-2-yl)-benzene and 2-bromo-5-methyl-pyridine following a procedure analogous to that described in Step 1 of Intermediate 56. LC (method 7): $t_R$=0.90 min; Mass spectrum (ESI⁺): m/z=232/234 (Cl) [M+H]⁺.

Intermediate 151

{(S)-6-[(R)-4-(2,6-Dimethyl-4-(5-methyl-pyridin-2-yl)-phenyl)-7-fluoro-indan-1-yloxy]-2,3-dihydro-benzofuran-3-yl}-acetic acid methyl ester

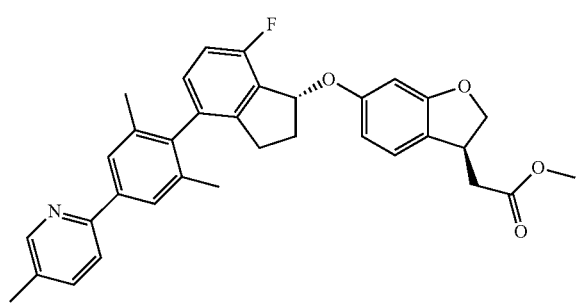

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-chloro-3,5-dimethyl-phenyl)-5-methyl-pyridine following a procedure analogous to that described in Step 5 of Intermediate 1. LC (method 7): $t_R$=1.08 min; Mass spectrum (ESI⁺): m/z=538 [M+H]⁺.

Intermediate 152

2-(4-Chloro-3,5-dimethyl-phenyl)-1-methyl-imidazole

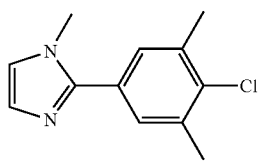

The title compound is prepared from 2-chloro-1,3-dimethyl-5-(4,4,5,5-tetramethyl-[1,3,2]dioxaborolan-2-yl)-benzene and 2-iodo-1-methyl-imidazole following a procedure analogous to that described in Step 1 of Intermediate 56. LC (method 7): $t_R$=0.80 min; Mass spectrum (ESI⁺): m/z=221/223 (Cl) [M+H]⁺.

Intermediate 153

{(S)-6-[(R)-4-(2,6-Dimethyl-4-(1-methyl-imidazol-2-yl)-phenyl)-7-fluoro-indan-1-yloxy]-2,3-dihydro-benzofuran-3-yl}-acetic acid methyl ester

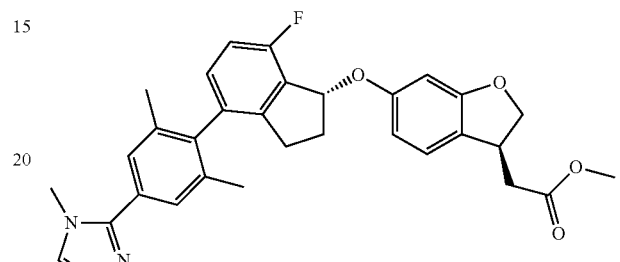

The title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 2-(4-chloro-3,5-dimethyl-phenyl)-1-methyl-imidazole following a procedure analogous to that described in Step 5 of Intermediate 1. LC (method 7): $t_R$=1.02 min; Mass spectrum (ESI⁺): m/z=527 [M+H]⁺.

Intermediate 154

Methyl 2-((S)-6-((R)-4-(2,6-dimethyl-4-((1-methyl-1H-pyrazol-3-yl)methoxy)phenyl)-7-fluoro-2,3-dihydro-1H-inden-1-yloxy)-2,3-dihydrobenzofuran-3-yl)acetate

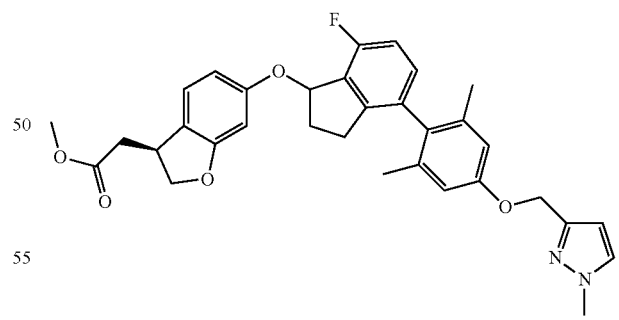

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 3-(chloromethyl)-1-methyl-1H-pyrazole (39.2 mg) were suspended in dimethylformamide (1.8 mL) and potassium carbonate (62 mg) was added. The reaction mixture was shaken for 24 h at 60° C. and than directly chromatographed by HPLC on reversed phase. The product fractions are collected and lyophilized to give the title compound. Yield: 44.5 mg; LC (method 23): $t_R$=2.09 min; Mass spectrum (ESI$^+$): m/z=557 [M+H]$^+$.

Intermediate 155

Methyl 2-((S)-6-((R)-4-(2,6-dimethyl-4-((1-methyl-2-oxo-1,2-dihydropyridin-4-yl)methoxy)phenyl)-7-fluoro-2,3-dihydro-1H-inden-1-yloxy)-2,3-dihydrobenzofuran-3-yl)acetate

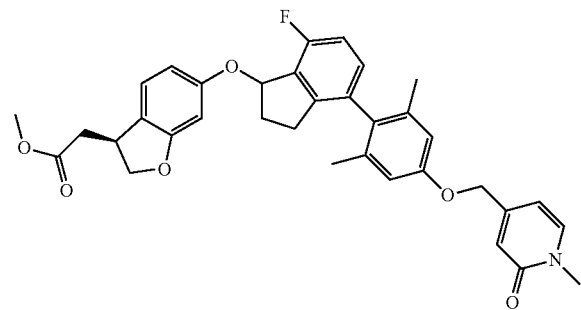

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 4-(chloromethyl)-1-methylpyridin-2(1H)-one (47.3 mg) were suspended in dimethylformamide (1.8 mL) and potassium carbonate (62 mg) was added. The reaction mixture was shaken for 24 h at 60° C. and than directly chromatographed by HPLC on reversed phase. The product fractions are collected and lyophilized to give the title compound. Yield: 49.6 mg; LC (method 23): $t_R$=1.96 min; Mass spectrum (ESI$^+$): m/z=584 [M+H]$^+$.

Intermediate 156

Methyl 2-((S)-6-((R)-7-fluoro-4-(4-((2-methoxypyridin-4-yl)methoxy)-2,6-dimethylphenyl)-2,3-dihydro-1H-inden-1-yloxy)-2,3-dihydrobenzofuran-3-yl)acetate

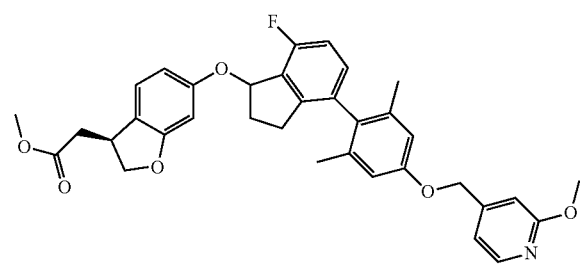

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 4-(chloromethyl)-2-methoxypyridine hydrochloride (58.2 mg) were suspended in dimethylformamide (1.8 mL) and potassium carbonate (62 mg) was added. The reaction mixture was shaken for 24 h at 60° C. and than directly chromatographed by HPLC on reversed phase. The product fractions are collected and lyophilized to give the title compound. Yield: 42 mg; LC (method 23): $t_R$=2.21 min; Mass spectrum (ESI$^+$): m/z=584 [M+H]$^+$.

Intermediate 157

Methyl 2-((S)-6-((R)-4-(2,6-dimethyl-4-(oxazol-2-ylmethoxy)phenyl)-7-fluoro-2,3-dihydro-1H-inden-1-yloxy)-2,3-dihydrobenzofuran-3-yl)acetate

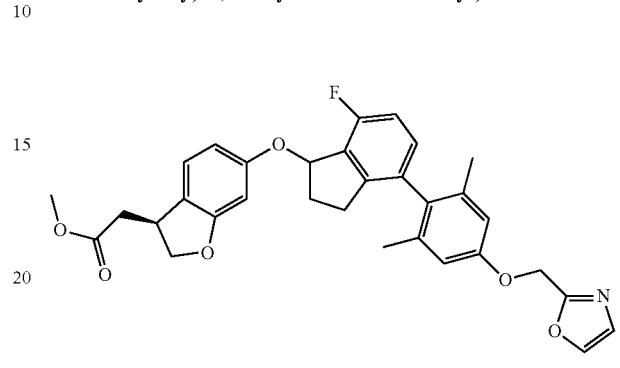

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 2-(chloromethyl)oxazole (25.3 mg) were suspended in dimethylformamide (2.0 mL) and potassium carbonate (62 mg) was added. The reaction mixture was shaken for 24 h at 60° C. Another portion of 2-(chloromethyl)oxazole (25.3 mg) and potassium carbonate (62 mg) was added and the mixture was shaken again for 24 h at 60° C. and than directly chromatographed by HPLC on reversed phase. The product fractions are collected and lyophilized to give the title compound. Yield: 30.9 mg; LC (method 23): $t_R$=2.09 min; Mass spectrum (ESI$^+$): m/z=544 [M+H]$^+$.

Intermediate 158

Methyl 2-((S)-6-((R)-4-(2,6-dimethyl-4-((1-methyl-1H-imidazol-2-yl)methoxy)phenyl)-7-fluoro-2,3-dihydro-1H-inden-1-yloxy)-2,3-dihydrobenzofuran-3-yl)acetate

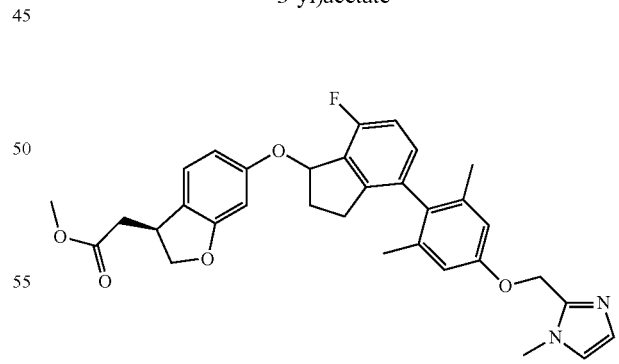

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 2-(chloromethyl)-1-methyl-1H-imidazole (39.2 mg) were suspended in dimethylformamide (1.8 mL) and potassium carbonate (62 mg) was added. The reaction mixture was shaken for 24 h at 60° C. Another portion of 2-(chloromethyl)-1-methyl-1H-imidazole (39.2 mg) and potassium carbonate (62 mg) was added and the mixture was shaken again for 24 h at 60° C. and than directly chromatographed by HPLC on reversed phase. The product fractions are collected and lyophilized to give the title compound. Yield: 31.5 mg; LC (method 23): $t_R$=1.54 min; Mass spectrum (ESI$^+$): m/z=557 [M+H]$^+$.

Intermediate 159

Methyl 2-((S)-6-((R)-4-(2,6-dimethyl-4-((tetrahydro-2H-pyran-4-yl)methoxy)phenyl)-7-fluoro-2,3-dihydro-1H-inden-1-yloxy)-2,3-dihydrobenzofuran-3-yl)acetate

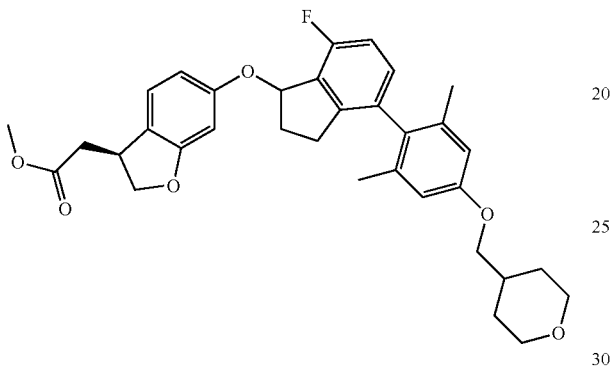

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (138 mg) and 4-(bromomethyl)tetrahydro-2H-pyran (160.3 mg) were suspended in dimethylformamide (5 mL) and potassium carbonate (185.7 mg) was added. The reaction mixture was shaken for 48 h at 60° C. and than directly chromatographed by HPLC on reversed phase. The product fractions are collected and lyophilized to give the title compound. Yield: 117 mg; LC (method 23): $t_R$=2.26 min; Mass spectrum (ESI$^+$): m/z=561 [M+H]$^+$.

Intermediate 160

Methyl 2-((S)-6-((R)-4-(2,6-dimethyl-4-((1-methyl-1H-pyrazol-5-yl)methoxy)phenyl)-7-fluoro-2,3-dihydro-1H-inden-1-yloxy)-2,3-dihydrobenzofuran-3-yl)acetate

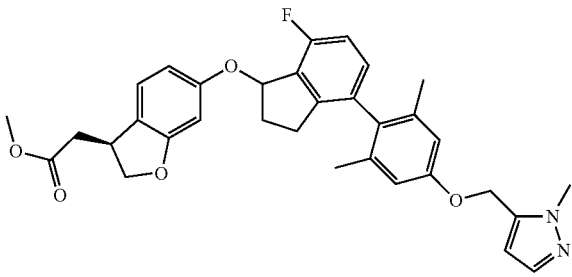

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 5-(chloromethyl)-1-methyl-1H-pyrazole hydrochloride (50.1 mg) were suspended in dimethylformamide (1.8 mL) and potassium carbonate (62 mg) was added. The reaction mixture was shaken for 24 h at 60° C. Another portion of 5-(chloromethyl)-1-methyl-1H-pyrazole hydrochloride (50.1 mg) and potassium carbonate (62 mg) was added and the mixture was shaken again for 24 h at 60° C. and than directly chromatographed by HPLC on reversed phase. The product fractions are collected and lyophilized to give the title compound. Yield: 27.8 mg; LC (method 11): $t_R$=1.13 min; Mass spectrum (ESI$^+$): m/z=557 [M+H]$^+$.

Intermediate 161

Methyl 2-((S)-6-((R)-4-(2,6-dimethyl-4-((1-methyl-1H-pyrazol-4-yl)methoxy)phenyl)-7-fluoro-2,3-dihydro-1H-inden-1-yloxy)-2,3-dihydrobenzofuran-3-yl)acetate

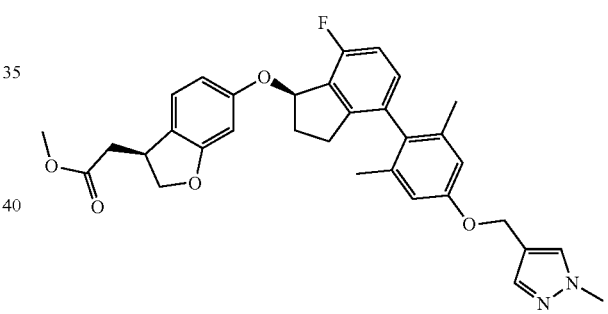

Methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (Intermediate 28-29) (46.3 mg) and 4-(chloromethyl)-1-methyl-1H-pyrazole dihydrochloride (61.1 mg) were suspended in dimethylformamide (1.8 mL) and potassium carbonate (124.4 mg) was added. The reaction mixture was shaken for 24 h at 60° C. and 72 h at 70° C. Another portion of 4-(chloromethyl)-1-methyl-1H-pyrazole dihydrochloride (124.4 mg) and potassium carbonate (124.4 mg) was added and the mixture was shaken again for 24 h at 120° C. and than directly chromatographed by HPLC on reversed phase. The product fractions are collected and lyophilized to give the title compound. Yield: 10.1 mg; LC (method 23): $t_R$=2.06 min; Mass spectrum (ESI$^+$): m/z=557 [M+H]$^+$.

Example 1

2-((S)-6-((R)-4-(2,6-dimethyl-4-((3-methyloxetan-3-yl)methoxy)phenyl)-7-fluoro-2,3-dihydro-1H-inden-1-yloxy)-2,3-dihydrobenzofuran-3-yl)acetic acid

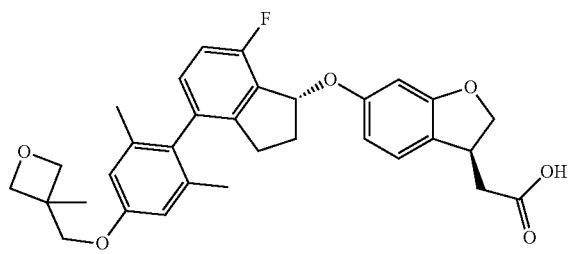 [SMILES: Cc1cc(OCC2(C)COC2)cc(C)c1-c1ccc(F)c2c1CC[C@H]2Oc1ccc2c(c1)OC[C@H]2CC(=O)O]

1 M aqueous NaOH solution (1.15 mL) is added to a solution of methyl 2-((S)-6-((R)-4-(2,6-dimethyl-4-((3-methyloxetan-3-yl)methoxy)phenyl)-7-fluoro-2,3-dihydro-1H-inden-1-yloxy)-2,3-dihydrobenzofuran-3-yl)acetate (420 mg) in methanol (12 mL) at room temperature. The mixture is stirred at room temperature for 48 hours. The mixture is diluted with water and neutralized with 1 M aqueous HCl solution (1.15 mL). The resulting mixture is extracted with ethyl acetate, and the combined extract is washed with brine and dried (MgSO$_4$). The solvent is evaporated and the residue is chromatographed on silica gel (cyclohexane/ethyl acetate 70:30→20:80). The product thus obtained is dissolved in acetonitrile/water (1:1) and lyophilized to give the title compound. Yield: 265 mg; LC (method 4): $t_R$=1.87 min; Mass spectrum (ESI$^+$): m/z=533 [M+H]$^+$.

Example 2

2-((3S)-6-((1R)-4-(2,6-dimethyl-4-((tetrahydrofuran-3-yl)methoxy)phenyl)-7-fluoro-2,3-dihydro-1H-inden-1-yloxy)-2,3-dihydrobenzofuran-3-yl)acetic acid

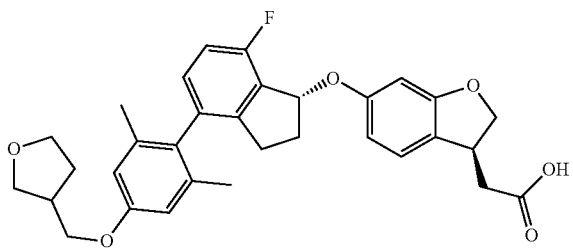 [SMILES: Cc1cc(OCC2CCOC2)cc(C)c1-c1ccc(F)c2c1CC[C@H]2Oc1ccc2c(c1)OC[C@H]2CC(=O)O]

The title compound is prepared from methyl 2-((3S)-6-((1R)-4-(2,6-dimethyl-4-((tetrahydrofuran-3-yl)methoxy)phenyl)-7-fluoro-2,3-dihydro-1H-inden-1-yloxy)-2,3-dihydrobenzofuran-3-yl)acetate following a procedure analogous to that described in example 1. Isopropanol is used instead of methanol. LC (method 1): $t_R$=1.42 min; Mass spectrum (ESI$^+$): m/z=533 [M+H]$^+$.

Example 3

2-((3S)-6-((1R)-4-(2,6-dimethyl-4-((tetrahydrofuran-2-yl)methoxy)phenyl)-7-fluoro-2,3-dihydro-1H-inden-1-yloxy)-2,3-dihydrobenzofuran-3-yl)acetic acid

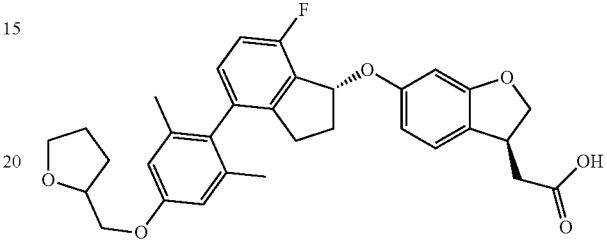

The title compound is prepared from methyl 2-((3S)-6-((1R)-4-(2,6-dimethyl-4-((tetrahydrofuran-2-yl)methoxy)phenyl)-7-fluoro-2,3-dihydro-1H-inden-1-yloxy)-2,3-dihydrobenzofuran-3-yl)acetate following a procedure analogous to that described in example 1. Isopropanol is used instead of methanol. LC (method 1): $t_R$=1.42 min; Mass spectrum (ESI$^+$): m/z=533 [M+H]$^+$.

Example 4

2-((S)-6-((R)-7-Fluoro-4-(4-(3-hydroxy-3-methylbutoxy)-2,6-dimethylphenyl)-2,3-dihydro-1H-inden-1-yloxy)-2,3-dihydrobenzofuran-3-yl)acetic acid

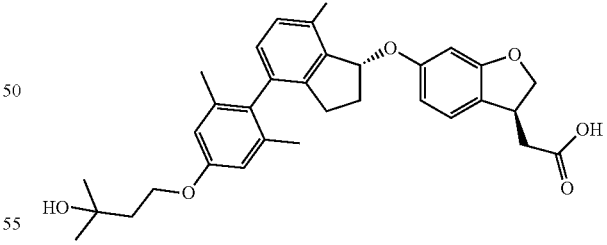

1 M aqueous NaOH solution (420 µL) is added to a solution of methyl 2-((S)-6-((R)-7-fluoro-4-(4-(3-hydroxy-3-methylbutoxy)-2,6-dimethylphenyl)-2,3-dihydro-1H-inden-1-yloxy)-2,3-dihydrobenzofuran-3-yl)acetate (155 mg) in methanol (4 mL) at room temperature. The mixture is stirred at room temperature for 12 hours. The organic solvents are evaporated in vacuo. The residue is diluted with water and neutralized with 1 M aqueous HCl solution (420 µL). The mixture is stirred for 1 hour. The precipitate formed is filtered off, washed with water and dried in vacuo to give the title

Example 5

2-((3S)-6-((1R)-4-(2,6-Dimethyl-4-(2-(methylsulfinyl)ethoxy)phenyl)-7-fluoro-2,3-dihydro-1H-inden-1-yloxy)-2,3-dihydrobenzofuran-3-yl)acetic acid

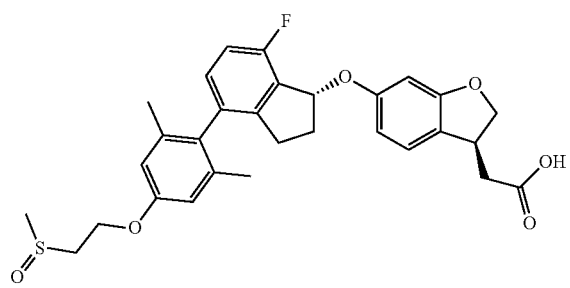 [SMILES: Cc1cc(OCCS(C)=O)cc(C)c1-c1ccc(F)c2c1CC[C@H]2Oc1ccc2c(c1)OC[C@H]2CC(=O)O]

1 M aqueous NaOH solution (480 μL) is added to a solution of methyl 2-((3S)-6-((1R)-4-(2,6-dimethyl-4-(2-(methylsulfinyl)ethoxy)phenyl)-7-fluoro-2,3-dihydro-1H-inden-1-yloxy)-2,3-dihydrobenzofuran-3-yl)acetate (180 mg) in methanol (5 mL) at room temperature. The mixture is stirred at room temperature for 12 hours. The mixture is neutralized with 1 M aqueous HCl solution and partitioned between diethylether and brine. The organic phase is dried (MgSO$_4$) and concentrated. The residue is chromatographed on silica gel (cyclohexane/ethyl acetate 60:40→10:90) to give the title compound. Yield: 80 mg; LC (method 4): $t_R$=1.71 min; Mass spectrum (ESI$^+$): m/z=539 [M+NH$_4$]$^+$.

Example 6

2-((S)-6-((R)-4-(2,6-Dimethyl-4-(2-(methylsulfonyl)ethoxy)phenyl)-7-fluoro-2,3-dihydro-1H-inden-1-yloxy)-2,3-dihydrobenzofuran-3-yl)acetic acid

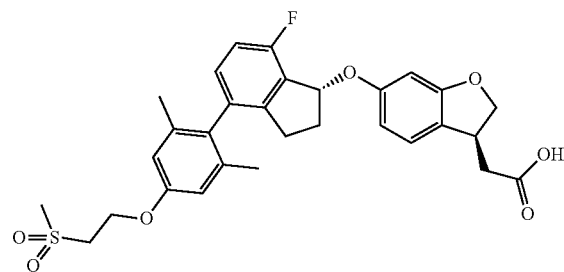 [SMILES: Cc1cc(OCCS(C)(=O)=O)cc(C)c1-c1ccc(F)c2c1CC[C@H]2Oc1ccc2c(c1)OC[C@H]2CC(=O)O]

To a solution of 2-((3S)-6-((1R)-4-(2,6-dimethyl-4-(2-(methylsulfinyl)ethoxy)phenyl)-7-fluoro-2,3-dihydro-1H-inden-1-yloxy)-2,3-dihydrobenzofuran-3-yl)acetic acid (70 mg) in methanol (1.5 mL) and water (0.75 mL) is added potassium peroxomonoslufate (Oxone®) (150 mg). The mixture is stirred for 3 hour at room temperature and then potassium peroxomonoslufate (Oxone®) (80 mg) is added. After stirring for 12 hours at room temperature the mixture is partitioned between ethyl acetate and water. The organic phase is dried (MgSO$_4$) and concentrated. The residue is chromatographed on silica gel (cyclohexane/ethyl acetate 50:50→0: 100). The product thus obtained is dissolved in acetonitrile/water (1:1) and lyophilized to give the title compound. Yield: 7 mg; LC (method 4): $t_R$=1.71 min; Mass spectrum (ESI$^+$): m/z=555 [M+H]$^+$.

Example 7

2-((S)-6-((R)-4-(2,6-Dimethyl-4-(tetrahydro-2H-pyran-4-yloxy)phenyl)-7-fluoro-2,3-dihydro-1H-inden-1-yloxy)-2,3-dihydrobenzofuran-3-yl)acetic acid

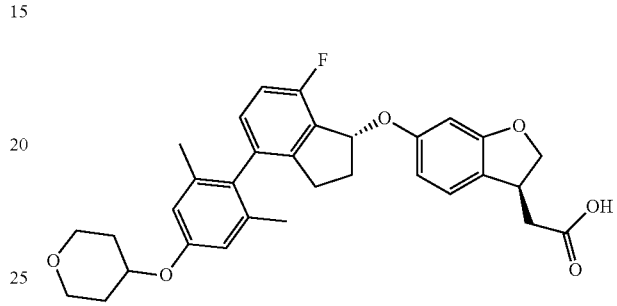

The title compound is prepared from methyl 2-((S)-6-((R)-4-(2,6-dimethyl-4-(tetrahydro-2H-pyran-4-yloxy)phenyl)-7-fluoro-2,3-dihydro-1H-inden-1-yloxy)-2,3-dihydrobenzofuran-3-yl)acetate following a procedure analogous to that described in example 1. LC (method 4): $t_R$=1.90 min; Mass spectrum (ESI$^+$): m/z=533 [M+H]$^+$.

Example 8

2-((S)-6-((R)-4-(2,6-Dimethyl-4-((S)-tetrahydrofuran-3-yloxy)phenyl)-7-fluoro-2,3-dihydro-1H-inden-1-yloxy)-2,3-dihydrobenzofuran-3-yl)acetic acid

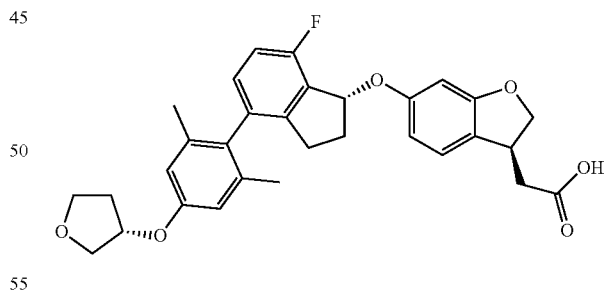

1 M aqueous NaOH solution (585 μL) is added to a solution of methyl 2-((S)-6-((R)-4-(2,6-dimethyl-4-((S)-tetrahydrofuran-3-yloxy)phenyl)-7-fluoro-2,3-dihydro-1H-inden-1-yloxy)-2,3-dihydrobenzofuran-3-yl)acetate (125 mg) in methanol (3 mL). The mixture is stirred at 40° C. for 12 hours. After addition of 1 N hydrochloric acid (585 μL) the mixture is diluted with diethylether and washed with water and brine. The organic phase is dried (MgSO$_4$). The solvent is evaporated and the residue is chromatographed on silica gel (cyclohexane/ethyl acetate 70:30→20:80). The product thus obtained is dissolved in acetonitrile/water (1:1) and lyophilized to give the title compound. Yield: 55 mg; LC (method 4): $t_R$=1.82 min; Mass spectrum (ESI$^+$): m/z=519 [M+H]$^+$.

Example 9

2-((S)-6-((R)-4-(2,6-Dimethyl-4-((R)-tetrahydrofuran-3-yloxy)phenyl)-7-fluoro-2,3-dihydro-1H-inden-1-yloxy)-2,3-dihydrobenzofuran-3-yl)acetic acid

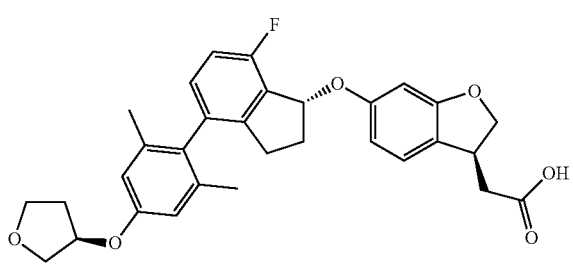 [SMILES: Cc1cc(O[C@@H]2CCOC2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-((R)-tetrahydrofuran-3-yloxy)phenyl)-7-fluoro-2,3-dihydro-1H-inden-1-yloxy)-2,3-dihydrobenzofuran-3-yl)acetate following a procedure analogous to that described in example 8. LC (method 4): $t_R$=1.82 min; Mass spectrum (ESI$^+$): m/z=519 [M+H]$^+$.

Example 10

2-((S)-6-((R)-7-Fluoro-4-(4-(2-hydroxy-2-methylpropoxy)-2,6-dimethylphenyl)-2,3-dihydro-1H-inden-1-yloxy)-2,3-dihydrobenzofuran-3-yl)acetic acid

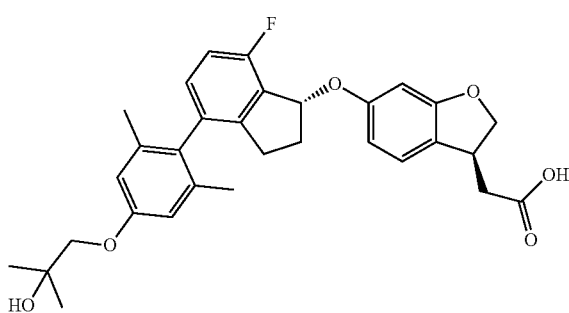 [SMILES: Cc1cc(OCC(C)(C)O)cc(C)c1-c1ccc(F)c2c1CC[C@H]2Oc1ccc2c(c1)OC[C@H]2CC(=O)O]

The title compound is prepared from methyl 2-((S)-6-((R)-7-fluoro-4-(4-(2-hydroxy-2-methylpropoxy)-2,6-dimethylphenyl)-2,3-dihydro-1H-inden-1-yloxy)-2,3-dihydrobenzofuran-3-yl)acetate following a procedure analogous to that described in example 4. LC (method 8): $t_R$=0.50 min; Mass spectrum (ESI$^+$): m/z=521 [M+H]$^+$.

Example 11

2-((3S)-6-((1R)-7-Fluoro-4-(4-(3-hydroxycyclopentyloxy)-2,6-dimethylphenyl)-2,3-dihydro-1H-inden-1-yloxy)-2,3-dihydrobenzofuran-3-yl)acetic acid

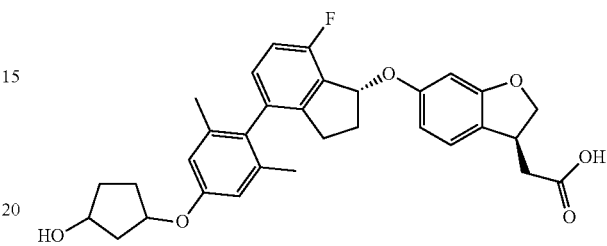

The title compound is prepared from methyl 2-((3S)-6-((1R)-7-fluoro-4-(4-(3-hydroxycyclopentyloxy)-2,6-dimethylphenyl)-2,3-dihydro-1H-inden-1-yloxy)-2,3-dihydrobenzofuran-3-yl)acetate following a procedure analogous to that described in example 4. The product is purified by chromatography on silica gel (petrole ether/ethyl acetate 50:50→0:10) to give the title compound. LC (method 8): $t_R$=0.41 min; Mass spectrum (ESI$^+$): m/z=533 [M+H]$^+$.

Example 12

2-((S)-6-((R)-4-(2,6-Dimethyl-4-(2-(methylamino)-2-oxoethoxy)phenyl)-7-fluoro-2,3-dihydro-1H-inden-1-yloxy)-2,3-dihydrobenzofuran-3-yl)acetic acid In a microwave vial 2-((S)-6-((R)-7-fluoro-4-(4-(2-methoxy-2-oxoethoxy)-2,6-dimethylphenyl)-2,3-dihydro-1H-inden-1-yloxy)-2,3-dihydrobenzofuran-3-yl)acetic acid (15 mg) is dissolved in a 2 M solution of methylamin in tetrahydrofuran (1 mL). The vial is sealed and the mixture is heated to 80° C. for 12 hours. The mixture is concentrated and the residue is purified by HPLC on reversed phase. Yield: 8 mg; LC (method 9): $t_R$=1.03 min; Mass spectrum (ESI$^+$): m/z=520 [M+H]$^+$.

Example 13

2-((S)-6-((R)-4-(4-(2-(Dimethylamino)-2-oxoethoxy)-2,6-dimethylphenyl)-7-fluoro-2,3-dihydro-1H-inden-1-yloxy)-2,3-dihydrobenzofuran-3-yl)acetic acid

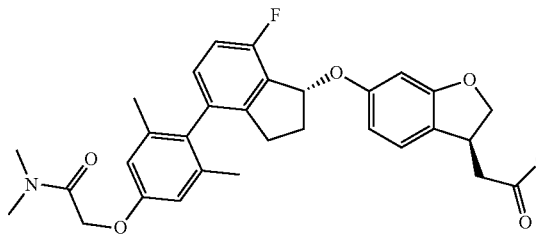

The title compound is prepared from 2-((S)-6-((R)-7-fluoro-4-(4-(2-methoxy-2-oxoethoxy)-2,6-dimethylphenyl)-2,3-dihydro-1H-inden-1-yloxy)-2,3-dihydrobenzofuran-3-yl)acetic acid and 2 M solution of dimethylamin in tetrahydrofuran following a procedure analogous to that described in example 12. LC (method 9): $t_R$=1.06 min; Mass spectrum (ESI$^+$): m/z=534 [M+H]$^+$.

Example 14

2-((S)-6-((R)-4-(4-(2-Amino-2-oxoethoxy)-2,6-dimethylphenyl)-7-fluoro-2,3-dihydro-1H-inden-1-yloxy)-2,3-dihydrobenzofuran-3-yl)acetic acid

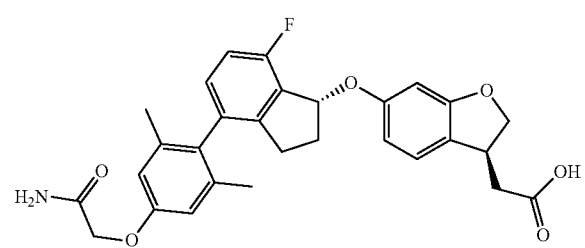 [SMILES: Cc1cc(OCC(N)=O)cc(C)c1-c1ccc(F)c2c1CC[C@H]2Oc1ccc2c(c1)OC[C@H]2CC(=O)O]

The title compound is prepared from 2-((S)-6-((R)-7-fluoro-4-(4-(2-methoxy-2-oxoethoxy)-2,6-dimethylphenyl)-2,3-dihydro-1H-inden-1-yloxy)-2,3-dihydrobenzofuran-3-yl)acetic acid and 0.5 M solution of ammonia in 1,4-dioxane following a procedure analogous to that described in example 12. LC (method 9): $t_R$=1.01 min; Mass spectrum (ESI$^+$): m/z=506 [M+H]$^+$.

Example 15

2-((S)-6-((R)-7-Fluoro-4-(4-(3-hydroxy-2,2-dimethylpropoxy)-2,6-dimethylphenyl)-2,3-dihydro-1H-inden-1-yloxy)-2,3-dihydrobenzofuran-3-yl)acetic acid

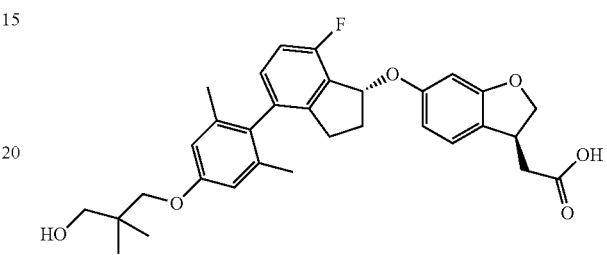

The title compound is prepared from methyl 2-((S)-6-((R)-7-fluoro-4-(4-(3-hydroxy-2,2-dimethylpropoxy)-2,6-dimethylphenyl)-2,3-dihydro-1H-inden-1-yloxy)-2,3-dihydrobenzofuran-3-yl)acetate following a procedure analogous to that described in example 8. LC (method 8): $t_R$=0.67 min; Mass spectrum (ESI$^+$): m/z=535 [M+H]$^+$.

Example 16

2-((S)-6-((R)-7-Fluoro-4-(4-(3-methoxy-2,2-dimethylpropoxy)-2,6-dimethylphenyl)-2,3-dihydro-1H-inden-1-yloxy)-2,3-dihydrobenzofuran-3-yl)acetic acid

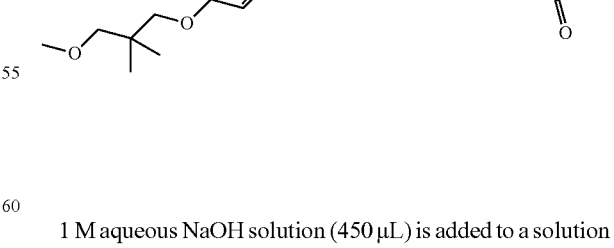

1 M aqueous NaOH solution (450 μL) is added to a solution of methyl 2-((S)-6-((R)-7-fluoro-4-(4-(3-methoxy-2,2-dimethylpropoxy)-2,6-dimethylphenyl)-2,3-dihydro-1H-inden-1-yloxy)-2,3-dihydrobenzofuran-3-yl)acetate (82 mg) in methanol (2 mL). The mixture is stirred at room temperature for 12 hours. 1 N Hydrochloric acid (450 μL) is added and the residue is purified by HPLC on reversed phase to give the title compound. Yield: 39 mg; LC (method 8): $t_R$=0.97 min; Mass spectrum (ESI⁺): m/z=549 [M+H]⁺.

Example 17

2-((S)-6-((R)-4-(2,6-Dimethyl-4-(pyrimidin-5-yl)phenyl)-7-fluoro-2,3-dihydro-1H-inden-1-yloxy)-2,3-dihydrobenzofuran-3-yl)acetic acid

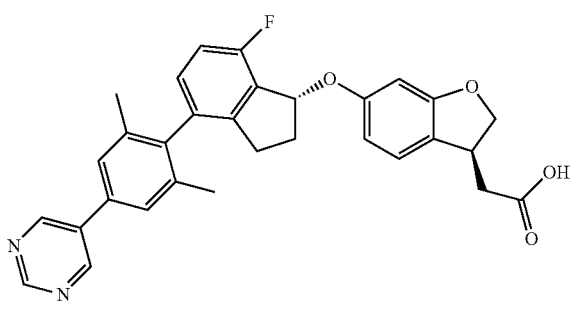 [SMILES: Cc1cc(-c2cncnc2)cc(C)c1-c1ccc(F)c2c1CC[C@H]2Oc1ccc2c(c1)OC[C@H]2CC(=O)O]

1 M aqueous NaOH solution (167 µL) is added to a solution of methyl 2-((S)-6-((R)-4-(2,6-dimethyl-4-(pyrimidin-5-yl)phenyl)-7-fluoro-2,3-dihydro-1H-inden-1-yloxy)-2,3-dihydrobenzofuran-3-yl)acetate (35 mg) in methanol (3 mL). The mixture is stirred at 40° C. for 1 hour. After addition of 1 N hydrochloric acid (167 µL) the mixture is diluted with ethyl acetate and washed with brine. The organic phase is dried (MgSO₄) and concentrated. The product thus obtained is dissolved in 1,4-dioxane and lyophilized to give the title compound. Yield: 29 mg; LC (method 11): $t_R$=1.14 min; Mass spectrum (ESI⁺): m/z=511 [M+H]⁺.

Example 18

2-((S)-6-((R)-4-(2,6-Dimethyl-4-(oxazol-2-yl)phenyl)-7-fluoro-2,3-dihydro-1H-inden-1-yloxy)-2,3-dihydrobenzofuran-3-yl)acetic acid

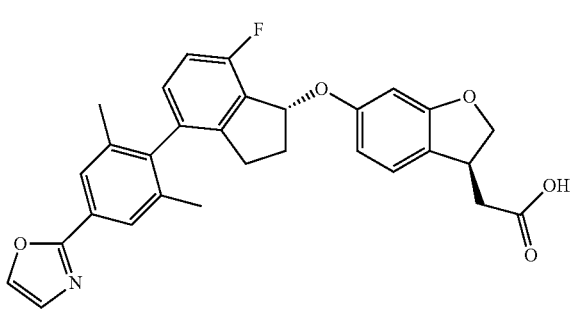 [SMILES: Cc1cc(-c2ncco2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(oxazol-2-yl)phenyl)-7-fluoro-2,3-dihydro-1H-inden-1-yloxy)-2,3-dihydrobenzofuran-3-yl)acetate following a procedure analogous to that described in example 17. LC (method 11): $t_R$=1.19 min; Mass spectrum (ESI⁺): m/z=500 [M+H]⁺.

Example 19

2-((S)-6-((R)-4-(2,6-Dimethyl-4-(1-methyl-1H-pyrazol-4-yl)phenyl)-7-fluoro-2,3-dihydro-1H-inden-1-yloxy)-2,3-dihydrobenzofuran-3-yl)acetic acid

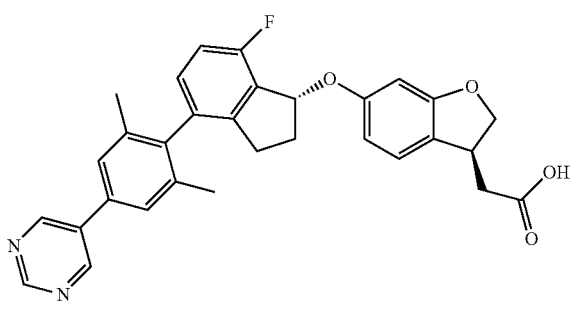 [SMILES: Cc1cc(-c2cncnc2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1-methyl-1H-pyrazol-4-yl)phenyl)-7-fluoro-2,3-dihydro-1H-inden-1-yloxy)-2,3-dihydrobenzofuran-3-yl)acetate following a procedure analogous to that described in example 17. LC (method 11): $t_R$=1.15 min; Mass spectrum (ESI⁺): m/z=513 [M+H]⁺.

Example 20

2-((S)-6-((R)-4-(2,6-Dimethyl-4-(1-methyl-1H-pyrazol-5-yl)phenyl)-7-fluoro-2,3-dihydro-1H-inden-1-yloxy)-2,3-dihydrobenzofuran-3-yl)acetic acid

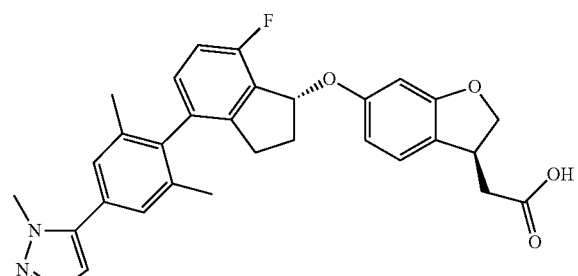

The title compound is prepared from methyl 2-((S)-6-((R)-4-(2,6-dimethyl-4-(1-methyl-1H-pyrazol-5-yl)phenyl)-7-fluoro-2,3-dihydro-1H-inden-1-yloxy)-2,3-dihydrobenzofuran-3-yl)acetate following a procedure analogous to that described in example 17. LC (method 11): $t_R$=1.16 min; Mass spectrum (ESI⁺): m/z=513 [M+H]⁺.

Example 21

2-((S)-6-((R)-4-(4-(2-Cyanopropan-2-yloxy)-2,6-dimethylphenyl)-7-fluoro-2,3-dihydro-1H-inden-1-yloxy)-2,3-dihydrobenzofuran-3-yl)acetic acid

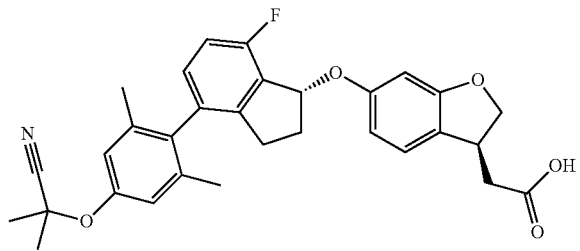 [SMILES: Cc1cc(OC(C)(C)C#N)cc(C)c1-c1ccc(F)c2c1CC[C@H]2Oc1ccc2c(c1)OC[C@H]2CC(=O)O]

1 M aqueous LiOH solution (500 µL) is added to a solution of methyl 2-((S)-6-((R)-4-(4-(2-cyanopropan-2-yloxy)-2,6-dimethylphenyl)-7-fluoro-2,3-dihydro-1H-inden-1-yloxy)-2,3-dihydrobenzofuran-3-yl)acetate (130 mg) in tetrahydrofuran (2 mL). The mixture is stirred at room temperature for 48 hours. 1 N Hydrochloric acid (500 µL) is added and the residue is purified by HPLC on reversed phase. The product thus obtained is chromatographed on silica gel (petrole ether/ethyl acetate 80:20→20:80) to give the title compound. Yield: 23 mg; LC (method 12): $t_R$=0.67 min; Mass spectrum (ESI⁺): m/z=516 [M+H]⁺.

Example 22

2-((S)-6-((R)-4-(4-(3-(Dimethylamino)-2,2-dimethylpropoxy)-2,6-dimethylphenyl)-7-fluoro-2,3-dihydro-1H-inden-1-yloxy)-2,3-dihydrobenzofuran-3-yl)acetic acid

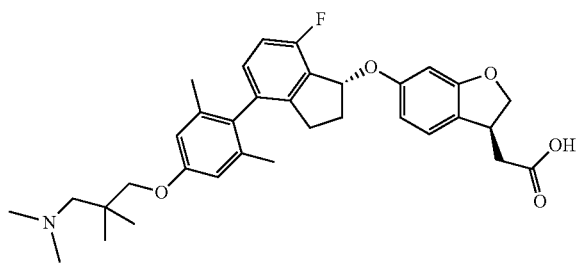 [SMILES: Cc1cc(OCC(C)(C)CN(C)C)cc(C)c1-c1ccc(F)c2c1CC[C@H]2Oc1ccc2c(c1)OC[C@H]2CC(=O)O]

1 M Aqueous NaOH solution (70 µL) is added to a solution of methyl 2-((S)-6-((R)-4-(4-(3-(dimethylamino)-2,2-dimethylpropoxy)-2,6-dimethylphenyl)-7-fluoro-2,3-dihydro-1H-inden-1-yloxy)-2,3-dihydrobenzofuran-3-yl)acetate (20 mg) in methanol (2 mL) at room temperature. The mixture is stirred at room temperature for 48 hours, treated with 1 M aqueous NaOH solution (70 µL) and heated for 4 hours at 50° C. The mixture is neutralized by addition of 1 N aqueous HCl solution and purified by HPLC on reversed phase to give the title compound. Yield: 11 mg; LC (method 14): $t_R$=0.95 min; Mass spectrum (ESI⁺): m/z=562 [M+H]⁺.

Example 23

2-((S)-6-((R)-4-(2,6-Dimethyl-4-(2-(2-oxopyrrolidin-1-yl)ethoxy)phenyl)-7-fluoro-2,3-dihydro-1H-inden-1-yloxy)-2,3-dihydrobenzofuran-3-yl)acetic acid

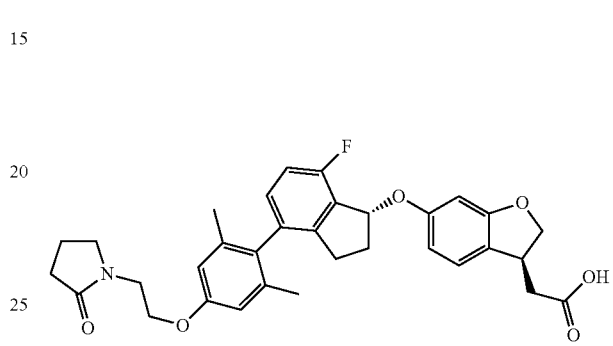

The title compound is prepared from methyl 2-((S)-6-((R)-4-(2,6-dimethyl-4-(2-(2-oxopyrrolidin-1-yl)ethoxy)phenyl)-7-fluoro-2,3-dihydro-1H-inden-1-yloxy)-2,3-dihydrobenzofuran-3-yl)acetate following a procedure analogous to that described in example 4. LC (method 8): $t_R$=0.35 min; Mass spectrum (ESI⁺): m/z=560 [M+H]⁺.

Example 24

2-((S)-6-((R)-4-(4-(3,6-dihydro-2H-pyran-4-yl)-2,6-dimethylphenyl)-7-fluoro-2,3-dihydro-1H-inden-1-yloxy)-2,3-dihydrobenzofuran-3-yl)acetic acid

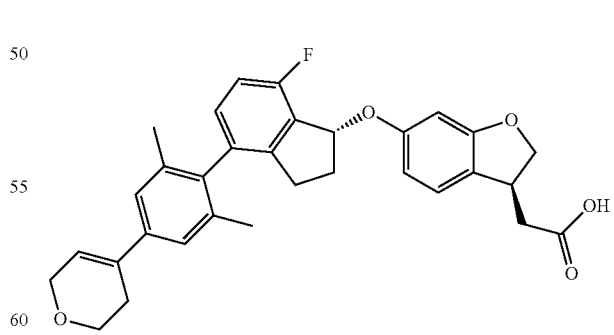

The title compound is prepared from methyl 2-((S)-6-((R)-4-(4-(3,6-dihydro-2H-pyran-4-yl)-2,6-dimethylphenyl)-7-fluoro-2,3-dihydro-1H-inden-1-yloxy)-2,3-dihydrobenzofuran-3-yl)acetate following a procedure analogous to that described in example 4. The reaction is run for 12 hours at room temperature and for 3 hours at 50° C. LC (method 8): $t_R$=0.71 min; Mass spectrum (ESI⁺): m/z=515 [M+H]⁺.

Example 25

2-((S)-6-((R)-4-(2,6-dimethyl-4-(1-(methylsulfonyl)-1,2,3,6-tetrahydropyridin-4-yl)phenyl)-7-fluoro-2,3-dihydro-1H-inden-1-yloxy)-2,3-dihydrobenzofuran-3-yl)acetic acid

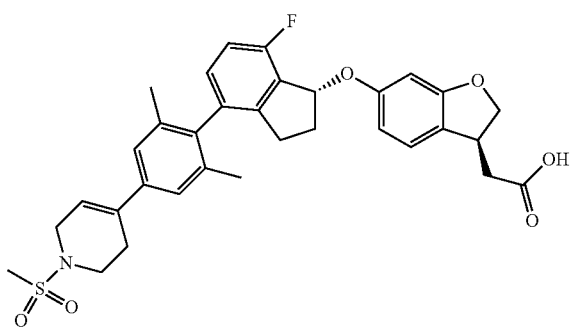 [SMILES: Cc1cc(C2=CCN(S(C)(=O)=O)CC2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1-(methylsulfonyl)-1,2,3,6-tetrahydropyridin-4-yl)phenyl)-7-fluoro-2,3-dihydro-1H-inden-1-yloxy)-2,3-dihydrobenzofuran-3-yl)acetate following a procedure analogous to that described in example 4. The reaction is run for 12 hours at room temperature and for 3 hours at 50° C. LC (method 8): $t_R$=0.51 min; Mass spectrum (ESI⁺): m/z=592 [M+H]⁺.

Example 26

2-((S)-6-((R)-4-(2,6-Dimethyl-4-(1-(methylsulfonyl)azetidin-3-yloxy)phenyl)-7-fluoro-2,3-dihydro-1H-inden-1-yloxy)-2,3-dihydrobenzofuran-3-yl)acetic acid

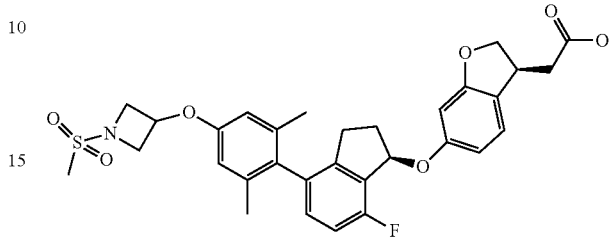

Aqueous NaOH solution (1 M; 39 µL) is added to a solution of methyl 2-((S)-6-((R)-4-(2,6-dimethyl-4-(1-(methylsulfonyl)azetidin-3-yloxy)phenyl)-7-fluoro-2,3-dihydro-1H-inden-1-yloxy)-2,3-dihydrobenzofuran-3-yl)acetate (Intermediate 28-1, 50 mg) in water (0.5 mL) and isopropanol (0.5 mL) at ambient temperature. The mixture is stirred at ambient temperature for 12 hours. The mixture is concentrated and acidified with 10% aqueous citric acid solution. The resulting mixture is extracted with dichloromethane, and the extract dried (MgSO₄). The solvent is evaporated and the residue is chromatographed on silica gel (cyclohexane/ethyl acetate 80:30→0:100) to give the title compound. Yield: 35 mg.

LC (method 20): $t_R$=6.19 min; Mass spectrum (ESI⁻): m/z=580 [M−H]⁻.

The examples in the following table are prepared from the corresponding starting ester intermediates following a procedure analogous to that described for Example 26.

| Ex. No. | Starting intermediate | Structure | Name |
|---|---|---|---|
| 27 | 28-2 | ![structure] | 2-((3S)-6-((1R)-4-(2,6-Dimethyl-4-((1,1-dioxo-tetrahydrothiophen-3-yl)methoxy)phenyl)-7-fluoro-2,3-dihydro-1H-inden-1-yloxy)-2,3-dihydrobenzofuran-3-yl)acetic acid |
| 28 | 28-3 | ![structure] | 2-((S)-6-((R)-4-(2,6-Dimethyl-4-((1,1-dioxo-tetrahydro-2H-thiopyran-4-yl)methoxy)phenyl)-7-fluoro-2,3-dihydro-1H-inden-1-yloxy)-2,3-dihydrobenzofuran-3-yl)acetic acid |

| | | | |
|---|---|---|---|
| 29 | 28-4 | 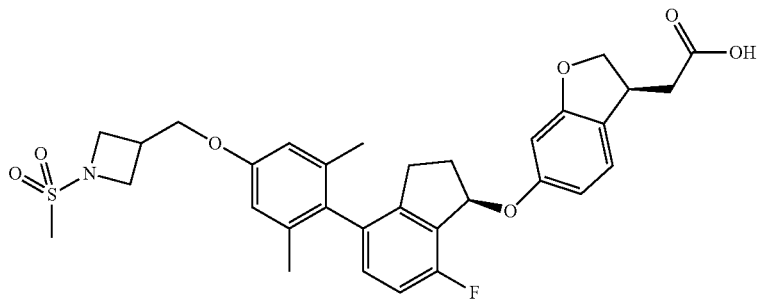 [SMILES: Cc1cc(OCC2CN(S(C)(=O)=O)C2)cc(C)c1-c1ccc(F)c2c1CC[C@H]2Oc1ccc2c(c1)OC[C@H]2CC(=O)O] | 2-((S)-6-((R)-4-(2,6-Dimethyl-4-((1-(methylsulfonyl)azetidin-3-yl)methoxy)phenyl)-7-fluoro-2,3-dihydro-1H-inden-1-yloxy)-2,3-dihydrobenzofuran-3-yl)acetic acid |
| 30 | 28-5 | 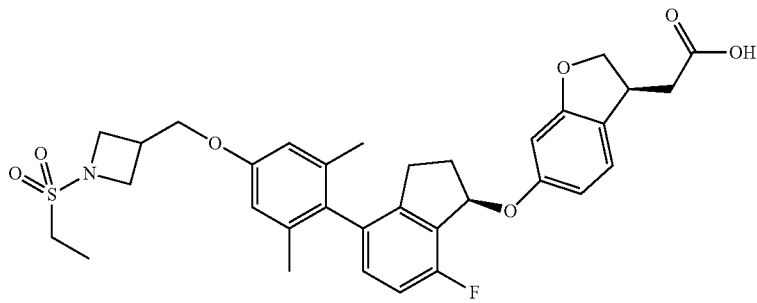 [SMILES: CCS(=O)(=O)N1CC(COc2cc(C)c(-c3ccc(F)c4c3CC[C@H]4Oc3ccc4c(c3)OC[C@H]4CC(=O)O)c(C)c2)C1] | 2-((S)-6-((R)-4-(4-((1-(Ethylsulfonyl)azetidin-3-yl)methoxy)-2,6-dimethylphenyl)-7-fluoro-2,3-dihydro-1H-inden-1-yloxy)-2,3-dihydrobenzofuran-3-yl)acetic acid |
| 31 | 28-6 | 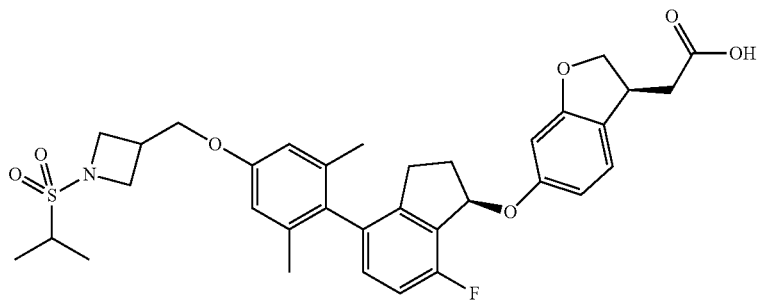 [SMILES: Cc1cc(OCC2CN(S(=O)(=O)C(C)C)C2)cc(C)c1-c1ccc(F)c2c1CC[C@H]2Oc1ccc2c(c1)OC[C@H]2CC(=O)O] | 2-((S)-6-((R)-7-Fluoro-4-(4-((1-(isopropylsulfonyl)azetidin-3-yl)methoxy)-2,6-dimethylphenyl)-2,3-dihydro-1H-inden-1-yloxy)-2,3-dihydrobenzofuran-3-yl)acetic acid |
| 32 | 28-7 | 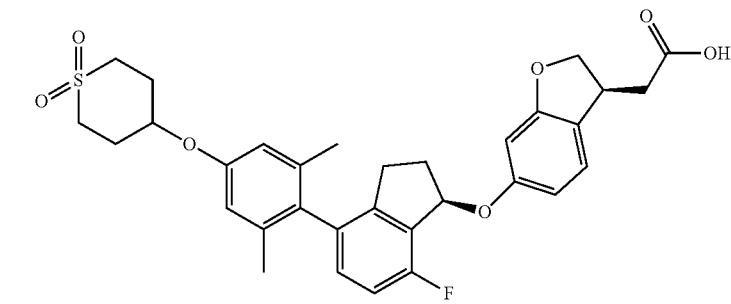 [SMILES: Cc1cc(OC2CCS(=O)(=O)CC2)cc(C)c1-c1ccc(F)c2c1CC[C@H]2Oc1ccc2c(c1)OC[C@H]2CC(=O)O] | 2-((S)-6-((R)-4-(2,6-Dimethyl-4-(1,1-dioxo-tetrahydro-2H-thiopyran-4-yloxy)phenyl)-7-fluoro-2,3-dihydro-1H-inden-1-yloxy)-2,3-dihydrobenzofuran-3-yl)acetic acid |
| 33 | 28-8 | 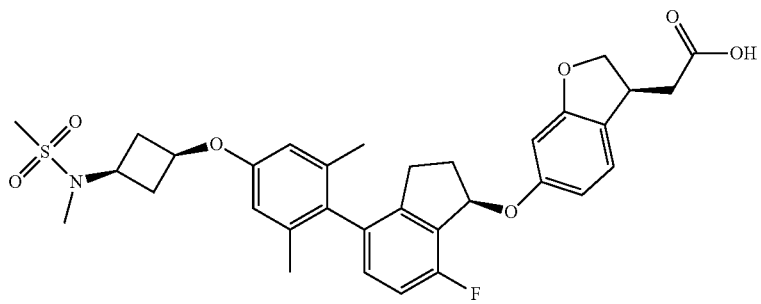 [SMILES: Cc1cc(O[C@H]2C[C@@H](N(C)S(C)(=O)=O)C2)cc(C)c1-c1ccc(F)c2c1CC[C@H]2Oc1ccc2c(c1)OC[C@H]2CC(=O)O] | 2-((S)-6-((R)-4-(2,6-Dimethyl-4-((1s,3S)-3-(N-methylmethylsulfonamido)cyclobutoxy)phenyl)-7-fluoro-2,3-dihydro-1H-inden-1-yloxy)-2,3-dihydrobenzofuran-3-yl)acetic acid |

| | | | |
|---|---|---|---|
| 34 | 28-10 | 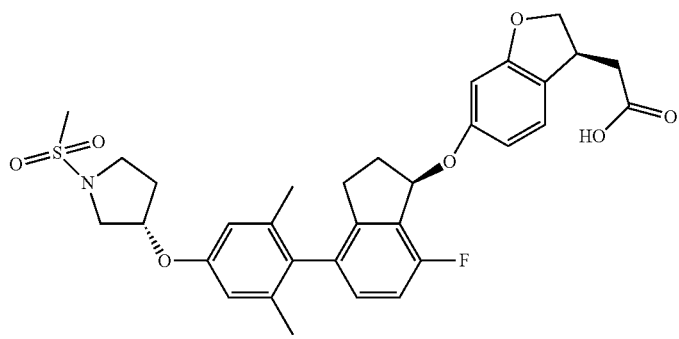 [SMILES: Cc1cc(O[C@H]2CCN(S(C)(=O)=O)C2)cc(C)c1-c1ccc(F)c2c1CC[C@H]2Oc1ccc2c(c1)OC[C@H]2CC(=O)O] | 2-((S)-6-((R)-4-(2,6-Dimethyl-4-((S)-1-(methylsulfonyl)pyrrolidin-3-yloxy)phenyl)-7-fluoro-2,3-dihydro-1H-inden-1-yloxy)-2,3-dihydrobenzofuran-3-yl)acetic acid |
| 35 | 28-11 | 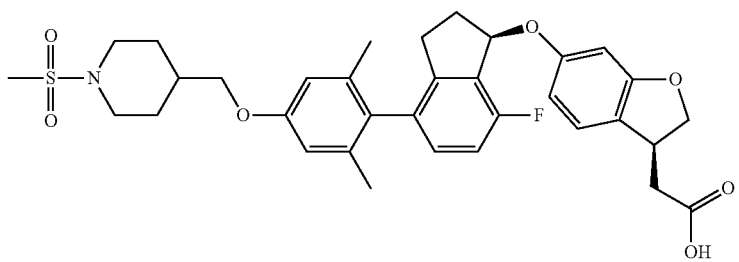 [SMILES: Cc1cc(OCC2CCN(S(C)(=O)=O)CC2)cc(C)c1-c1ccc(F)c2c1CC[C@H]2Oc1ccc2c(c1)OC[C@H]2CC(=O)O] | 2-((S)-6-((R)-4-(2,6-Dimethyl-4-((1-(methylsulfonyl)piperidin-4-yl)methoxy)phenyl)-7-fluoro-2,3-dihydro-1H-inden-1-yloxy)-2,3-dihydrobenzofuran-3-yl)acetic acid |
| 36 | 28-9 | 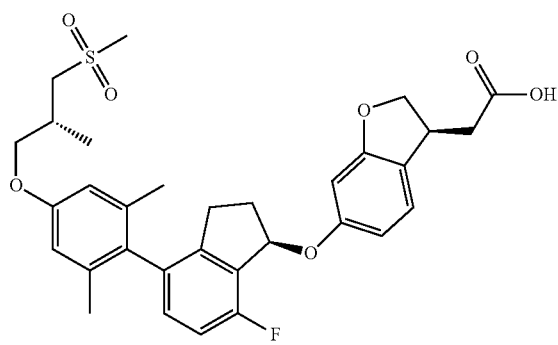 [SMILES: Cc1cc(OC[C@@H](C)CS(C)(=O)=O)cc(C)c1-c1ccc(F)c2c1CC[C@H]2Oc1ccc2c(c1)OC[C@H]2CC(=O)O] | ((S)-6-{(R)-7-Fluoro-4-[4-((R)-3-methanesulfonyl-2-methyl-propoxy)-2,6-dimethyl-phenyl]-indan-1-yloxy}-2,3-dihydro-benzofuran-3-yl)-acetic acid |
| 37 | 28-10 | 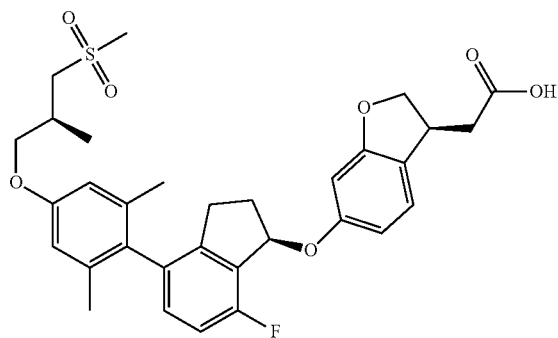 [SMILES: Cc1cc(OC[C@H](C)CS(C)(=O)=O)cc(C)c1-c1ccc(F)c2c1CC[C@H]2Oc1ccc2c(c1)OC[C@H]2CC(=O)O] | ((S)-6-{(R)-7-Fluoro-4-[4-((S)-3-methanesulfonyl-2-methyl-propoxy)-2,6-dimethyl-phenyl]-indan-1-yloxy}-2,3-dihydro-benzofuran-3-yl)-acetic acid |
| 38 | 28-11 | 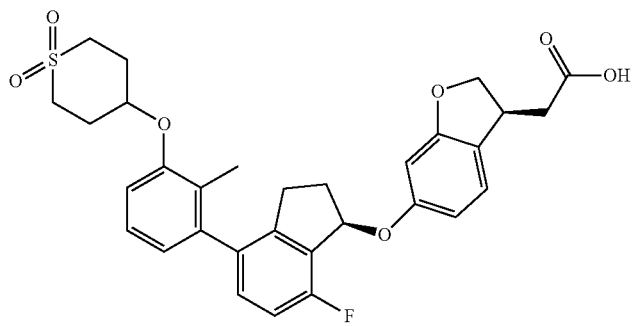 [SMILES: Cc1c(OC2CCS(=O)(=O)CC2)cccc1-c1ccc(F)c2c1CC[C@H]2Oc1ccc2c(c1)OC[C@H]2CC(=O)O] | ((S)-6-{(R)-4-[3-(1,1-Dioxo-hexahydro-1-thiopyran-4-yloxy)-2-methyl-phenyl]-7-fluoro-indan-1-yloxy}-2,3-dihydro-benzofuran-3-yl)-acetic acid |

-continued

| 39 | 28-12 | 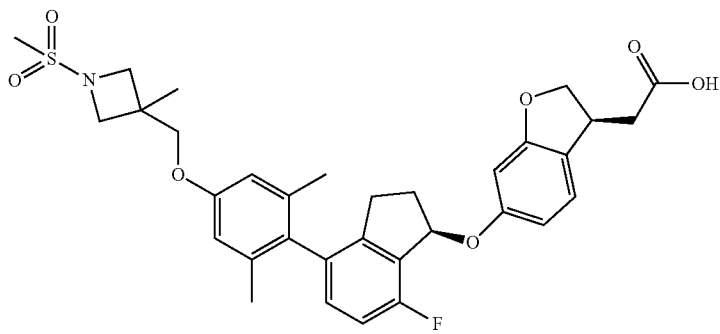 [SMILES: Cc1cc(OCC2(C)CN(S(C)(=O)=O)C2)cc(C)c1-c1ccc(F)c2c1CC[C@H]2Oc1ccc2c(c1)OC[C@H]2CC(=O)O] | ((S)-6-{(R)-7-Fluoro-4-[4-(1-methanesulfonyl-3-methyl-azetidin-3-ylmethoxy)-2,6-dimethyl-phenyl]-indan-1-yloxy}-2,3-dihydro-benzofuran-3-yl)-acetic acid |
| 40 | 28-13 | 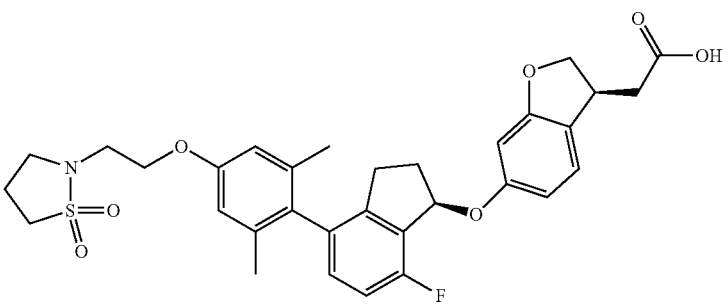 [SMILES: Cc1cc(OCCN2CCCS2(=O)=O)cc(C)c1-c1ccc(F)c2c1CC[C@H]2Oc1ccc2c(c1)OC[C@H]2CC(=O)O] | [(S)-6-((R)-4-{4-[2-(1,1-Dioxo-1-isothiazolidin-2-yl)-ethoxy]-2,6-dimethoxy-phenyl}-7-fluoro-indan-1-yloxy)-2,3-dihydro-benzofuran-3-yl]-acetic acid |
| 41 | 28-14 | 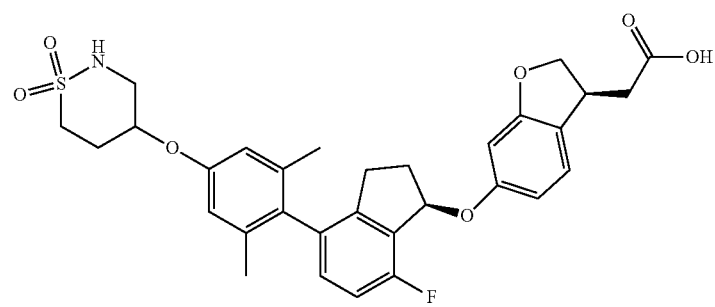 [SMILES: Cc1cc(OC2CCS(=O)(=O)NC2)cc(C)c1-c1ccc(F)c2c1CC[C@H]2Oc1ccc2c(c1)OC[C@H]2CC(=O)O] | ((S)-6-{(R)-4-[4-(1,1-Dioxo-1-[1,2]thiazinan-4-yloxy)-2,6-dimethyl-phenyl]-7-fluoro-indan-1-yloxy}-2,3-dihydro-benzofuran-3-yl)-acetic acid |
| 42 | 28-15 | 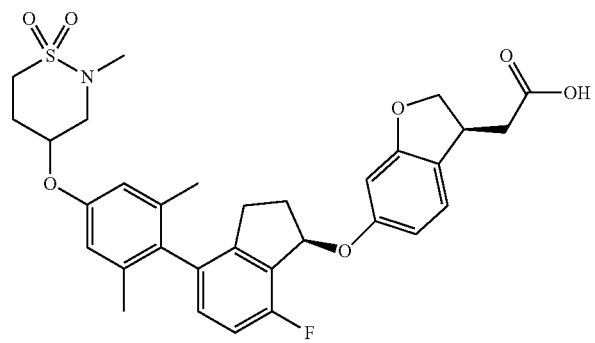 [SMILES: Cc1cc(OC2CCS(=O)(=O)N(C)C2)cc(C)c1-c1ccc(F)c2c1CC[C@H]2Oc1ccc2c(c1)OC[C@H]2CC(=O)O] | ((S)-6-{(R)-4-[2,6-Dimethyl-4-(2-methyl-1,1-dioxo-1-[1,2]thiazinan-4-yloxy)-phenyl]-7-fluoro-indan-1-yloxy}-2,3-dihydro-benzofuran-3-yl)-acetic acid |
| 43 | 28-16 | 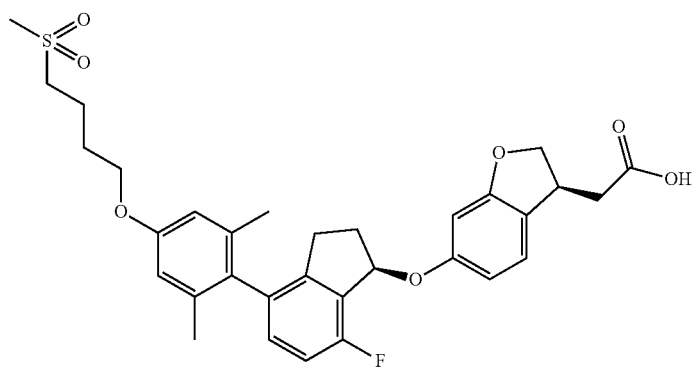 [SMILES: Cc1cc(OCCCCS(C)(=O)=O)cc(C)c1-c1ccc(F)c2c1CC[C@H]2Oc1ccc2c(c1)OC[C@H]2CC(=O)O] | ((S)-6-{(R)-7-Fluoro-4-[4-(4-methanesulfonyl-butoxy)-2,6-dimethyl-phenyl]-indan-1-yloxy}-2,3-dihydro-benzofuran-3-yl)-acetic acid |

| | | | |
|---|---|---|---|
| 44 | 28-17 | 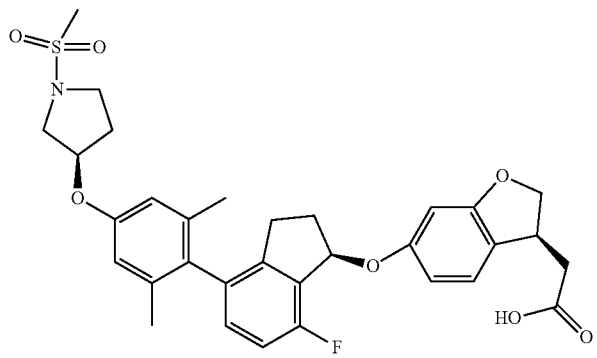 [SMILES: Cc1cc(O[C@@H]2CCN(S(C)(=O)=O)C2)cc(C)c1-c1ccc(F)c2c1CC[C@H]2Oc1ccc2c(c1)OC[C@H]2CC(=O)O] | ((S)-6-{(R)-7-Fluoro-4-[4-((R)-1-methanesulfonyl-pyrrolidin-3-yloxy)-2,6-dimethyl-phenyl]-indan-1-yloxy}-2,3-dihydro-benzofuran-3-yl)-acetic acid |
| 45 | 28-18 | 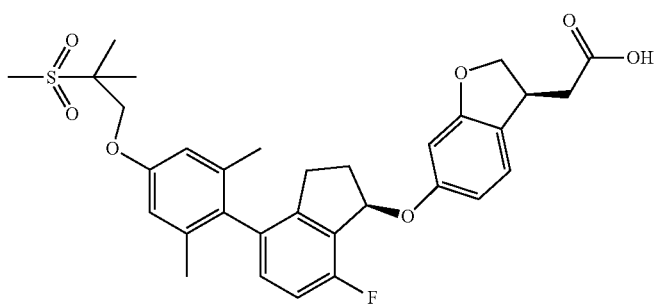 [SMILES: Cc1cc(OCC(C)(C)S(C)(=O)=O)cc(C)c1-c1ccc(F)c2c1CC[C@H]2Oc1ccc2c(c1)OC[C@H]2CC(=O)O] | ((S)-6-{(R)-7-Fluoro-4-[4-(2-methanesulfonyl-2-methyl-propoxy)-2,6-dimethyl-phenyl]-indan-1-yloxy}-2,3-dihydro-benzofuran-3-yl)-acetic acid |
| 46 | 28-19 | 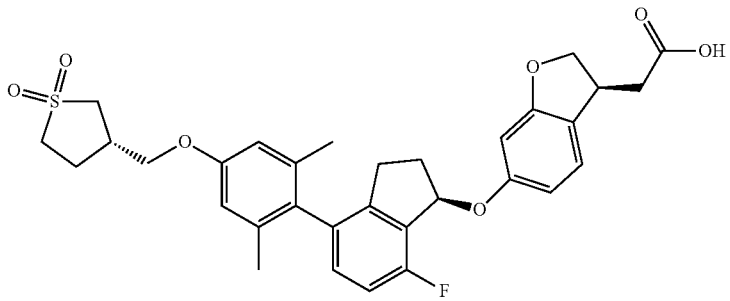 [SMILES: Cc1cc(OC[C@@H]2CCS(=O)(=O)C2)cc(C)c1-c1ccc(F)c2c1CC[C@H]2Oc1ccc2c(c1)OC[C@H]2CC(=O)O] | ((S)-6-{(R)-4-[4-((S)-1,1-Dioxo-tetrahydro-1-thiophen-3-ylmethoxy)-2,6-dimethyl-phenyl]-7-fluoro-indan-1-yloxy}-2,3-dihydro-benzofuran-3-yl)-acetic acid. Absolute configuration unknown |
| 47 | 28-20 | 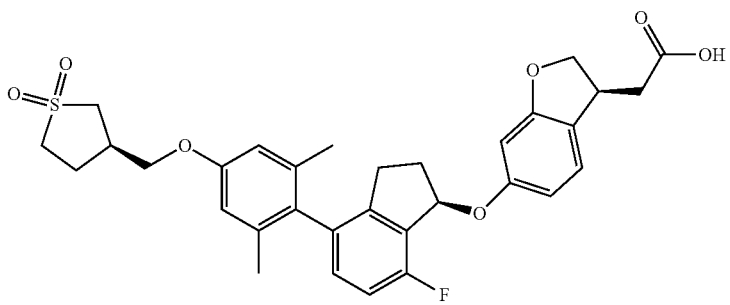 [SMILES: Cc1cc(OC[C@H]2CCS(=O)(=O)C2)cc(C)c1-c1ccc(F)c2c1CC[C@H]2Oc1ccc2c(c1)OC[C@H]2CC(=O)O] | ((S)-6-{(R)-4-[4-((R)-1,1-Dioxo-tetrahydro-1-thiophen-3-ylmethoxy)-2,6-dimethyl-phenyl]-7-fluoro-indan-1-yloxy}-2,3-dihydro-benzofuran-3-yl)-acetic acid Absolute configuration unknown |
| 48 | 28-21 | 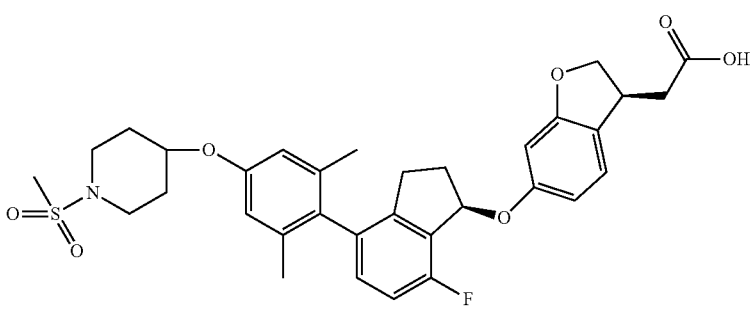 [SMILES: Cc1cc(OC2CCN(S(C)(=O)=O)CC2)cc(C)c1-c1ccc(F)c2c1CC[C@H]2Oc1ccc2c(c1)OC[C@H]2CC(=O)O] | ((S)-6-{(R)-7-Fluoro-4-[4-(1-methanesulfonyl-piperidin-4-yloxy)-2,6-dimethyl-phenyl]-indan-1-yloxy}-2,3-dihydro-benzofuran-3-yl)-acetic acid |

| | | | |
|---|---|---|---|
| 49 | 28-22 | 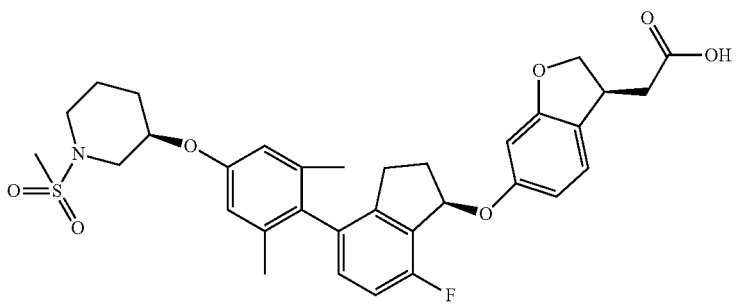 [SMILES: Cc1cc(O[C@@H]2CCCN(S(C)(=O)=O)C2)cc(C)c1-c1ccc(F)c2c1CC[C@H]2Oc1ccc2c(c1)OC[C@H]2CC(=O)O] | ((S)-6-{(R)-7-Fluoro-4-[4-((R)-1-methanesulfonyl-piperidin-3-yloxy)-2,6-dimethyl-phenyl]-indan-1-yloxy}-2,3-dihydro-benzofuran-3-yl)-acetic acid |
| 50 | 28-23 | 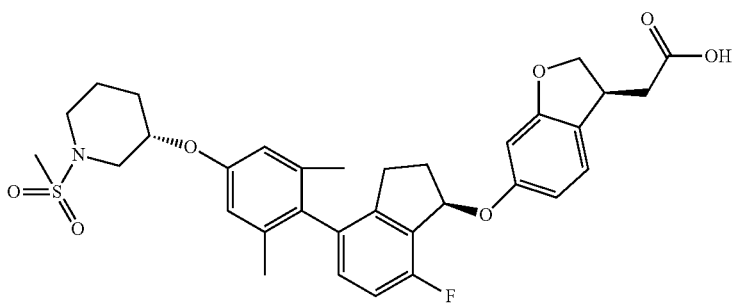 [SMILES: Cc1cc(O[C@H]2CCCN(S(C)(=O)=O)C2)cc(C)c1-c1ccc(F)c2c1CC[C@H]2Oc1ccc2c(c1)OC[C@H]2CC(=O)O] | ((S)-6-{(R)-7-Fluoro-4-[4-((S)-1-methanesulfonyl-piperidin-3-yloxy)-2,6-dimethyl-phenyl]-indan-1-yloxy}-2,3-dihydro-benzofuran-3-yl)-acetic acid |
| 51 | 28-24 | 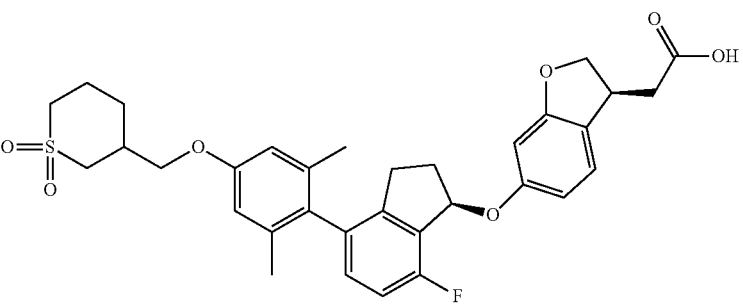 [SMILES: Cc1cc(OCC2CCCS(=O)(=O)C2)cc(C)c1-c1ccc(F)c2c1CC[C@H]2Oc1ccc2c(c1)OC[C@H]2CC(=O)O] | ((S)-6-{(R)-4-[4-(1,1-Dioxo-hexahydro-1-thiopyran-3-ylmethoxy)-2,6-dimethyl-phenyl]-7-fluoro-indan-1-yloxy}-2,3-dihydro-benzofuran-3-yl)-acetic acid |
| 52 | 28-27 | 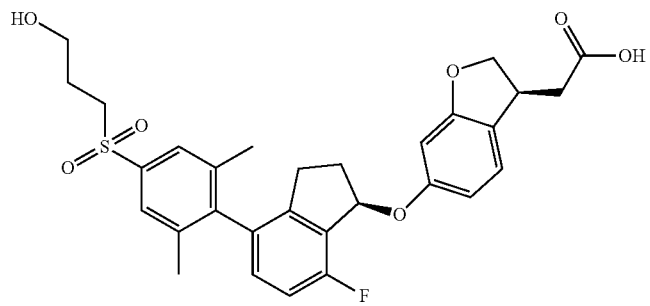 [SMILES: Cc1cc(S(=O)(=O)CCCO)cc(C)c1-c1ccc(F)c2c1CC[C@H]2Oc1ccc2c(c1)OC[C@H]2CC(=O)O] | ((S)-6-{(R)-7-Fluoro-4-[4-(3-hydroxy-propane-1-sulfonyl)-2,6-dimethyl-phenyl]-indan-1-yloxy}-2,3-dihydro-benzofuran-3-yl)-acetic acid |
| 53 | 28-28 | 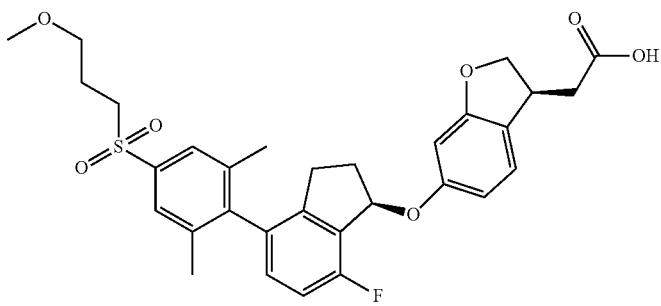 [SMILES: COCCCS(=O)(=O)c1cc(C)c(-c2ccc(F)c3c2CC[C@H]3Oc2ccc3c(c2)OC[C@H]3CC(=O)O)c(C)c1] | ((S)-6-{(R)-7-Fluoro-4-[4-(3-methoxy-propane-1-sulfonyl)-2,6-dimethyl-phenyl]-indan-1-yloxy}-2,3-dihydro-benzofuran-3-yl)-acetic acid |

-continued

| | | | |
|---|---|---|---|
| 54 | 35 | 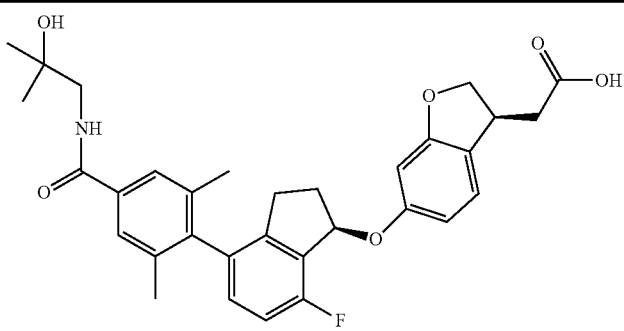 | ((S)-6-{(R)-7-Fluoro-4-[4-(2-hydroxy-2-methyl-propylcarbamoyl)-2,6-dimethyl-phenyl]-indan-1-yloxy}-2,3-dihydro-benzofuran-3-yl)-acetic acid |
| 55 | 28-25 | 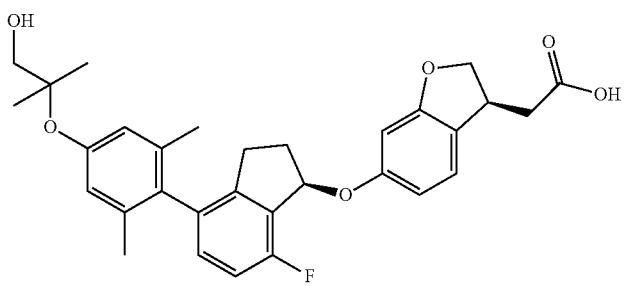 [SMILES: Cc1cc(OC(C)(C)CO)cc(C)c1-c1ccc(F)c2c1CC[C@H]2Oc1ccc2c(c1)OC[C@H]2CC(=O)O] | ((S)-6-{(R)-7-Fluoro-4-[4-(2-hydroxy-1,1-dimethyl-ethoxy)-2,6-dimethyl-phenyl]-indan-1-yloxy}-2,3-dihydro-benzofuran-3-yl)-acetic acid |
| 56 | 28-26 | 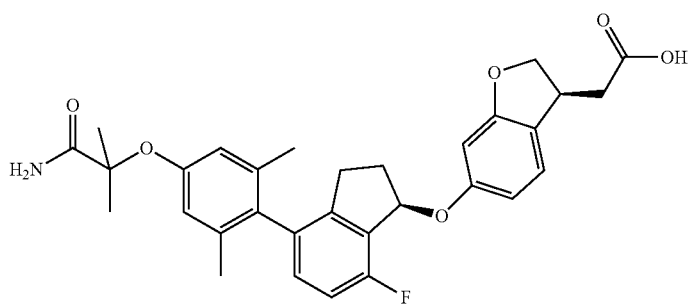 [SMILES: Cc1cc(OC(C)(C)C(N)=O)cc(C)c1-c1ccc(F)c2c1CC[C@H]2Oc1ccc2c(c1)OC[C@H]2CC(=O)O] | ((S)-6-{(R)-4-[4-(1-Carbamoyl-1-methyl-ethoxy)-2,6-dimethyl-phenyl]-7-fluoro-indan-1-yloxy}-2,3-dihydro-benzofuran-3-yl)-acetic acid |

| Example No. | $t_R$ [Min] | LC method No | (ESI$^+$) or (ESI$^-$): m/z |
|---|---|---|---|
| 27 | 6.44 | 20 | 579 [M − H]$^-$ |
| 28 | 6.52 | 20 | 593 [M − H]$^-$ |
| 29 | 6.45 | 20 | 596 [M + H]$^+$ |
| 30 | 6.67 | 20 | 608 [M − H]$^-$ |
| 31 | 13.48 | 21 | 624 [M + H]$^+$ |
| 32 | 6.33 | 20 | 579 [M − H]$^-$ |
| 33 | 6.93 | 20 | 610 [M + H]$^+$ |
| 34 | 12.8 | 21 | 596 [M + H]$^+$ |
| 35 | 6.93 | 20 | 624 [M + H]$^+$ |
| 36 | 6.88 | 20 | 583 [M + H]+ |
| 37 | 6.92 | 20 | 583 [M + H]+ |
| 38 | 8.73 | 20A | 567 [M + H]+ |
| 39 | 7.07 | 20 | 608 [M − H]− |
| 40 | 6.33 | 20 | 596 [M + H]+ |
| 41 | 6.35 | 20 | 580 [M − H]− |
| 42 | 6.81 | 20 | 594 [M − H]− |
| 43 | 6.84 | 20 | 583 [M + H]+ |
| 44 | 6.47 | 20 | 596 [M + H]+ |
| 45 | 6.53 | 20 | 583 [M + H]+ |
| 46 | 6.73 | 20 | 579 [M − H]− |
| 47 | 6.83 | 20 | 579 [M + H]+ |
| 48 | 7.20 | 20 | 608 [M − H]− |
| 49 | 7.10 | 20 | 610 [M + H]+ |
| 50 | 7.18 | 20 | 610 [M + H]+ |
| 51 | 7.04 | 20 | 593 [M − H]− |
| 52 | 5.66 | 20 | 533 [M − H]− |
| 53 | 6.50 | 20 | 569 [M − H]− |
| 54 | 7.78 | 20A | 548 [M − H]− |
| 55 | 6.88 | 20 | 519 [M − H]− |
| 56 | 6.57 | 20 | 532 [M − H]− |

Example 57

2-((S)-6-((R)-4-(2,6-Dimethyl-4-(3-(methylsulfonyl)propoxy)phenyl)-7-fluoro-2,3-dihydro-1H-inden-1-yloxy)-2,3-dihydrobenzofuran-3-yl)acetic acid

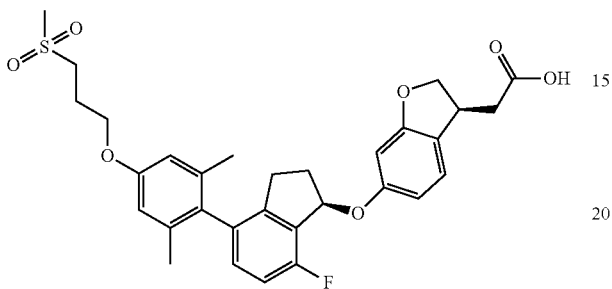

Methyl 2-((S)-6-((R)-4-(2,6-dimethyl-4-(3-(methylsulfonyl)propoxy)phenyl)-7-fluoro-2,3-dihydro-1H-inden-1-yloxy)-2,3-dihydrobenzofuran-3-yl)acetate (Intermediate 29; 9 mg) is suspended in ethanol (1 mL) and aqueous NaOH (1 M; 0.2 mL) is added. The mixture is stirred for 1 hour then concentrated under vacuum, acidified with aqueous HCl (1 M) and extracted twice with dichloromethane. The combined organic extracts are dried and the solvent is removed to give the title compound (8.5 mg). LC (method 20): $t_R$=6.37 min; Mass spectrum (ESI⁻): m/z=567 [M–H]⁻.

Example 58

2-((3S)-6-((1R)-7-Fluoro-4-(2-methyl-3-(3-(methylsulfonyl)propoxy)phenyl)-2,3-dihydro-1H-inden-1-yloxy)-2,3-dihydrobenzofuran-3-yl)acetic acid

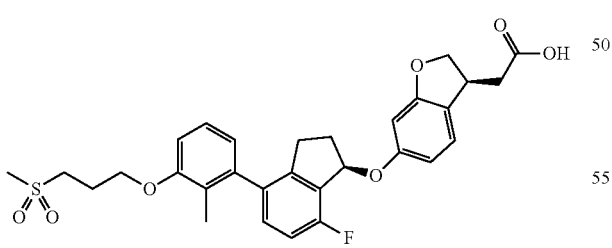

Methyl 2-((3S)-6-((1R)-7-fluoro-4-(2-methyl-3-(3-(methylsulfonyl)propoxy)phenyl)-2,3-dihydro-1H-inden-1-yloxy)-2,3-dihydrobenzofuran-3-yl)acetate (Intermediate 28-32; 64 mg) in methanol (3 mL) and aqueous NaOH (1 M; 0.5 mL) is stirred for 16 hours, concentrated under vacuum, acidified with aqueous HCl (1 M) and extracted with diethyl ether. A precipitate that forms is collected by filtration, washed with some n-hexane, dried and subsequently triturated with a mixture of n-hexane and diethyl ether to give the title compound (30 mg). LC (method 20): $t_R$=6.15 min; Mass spectrum: m/z=555 [M+H]⁺.

Example 59

2-((3S)-6-((1R)-4-(3-Carbamoyl-2-methylphenyl)-7-fluoro-2,3-dihydro-1H-inden-1-yloxy)-2,3-dihydrobenzofuran-3-yl)acetic acid

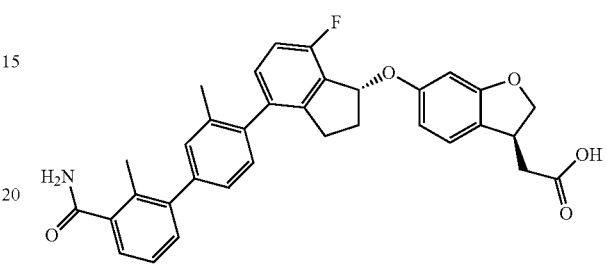

30% Aqueous NH₃ solution (4.2 mL) and 35% aqueous H₂O₂ solution (1.4 ml) are added at 0° C. to a solution of 2-((3S)-6-((1R)-4-(3-cyano-2-methylphenyl)-7-fluoro-2,3-dihydro-1H-inden-1-yloxy)-2,3-dihydrobenzofuran-3-yl)acetic acid (30 mg) in ethanol (5 mL). The mixture is stirred at room temperature for 12 hours, while warming to room temperature. The mixture is concentrated, diluted with water and neutralized with 4 M aqueous HCl solution. The resulting mixture is extracted with dichloromethane. The organic phase is dried (MgSO₄). The solvent is evaporated to give the title compound. Yield: 29 mg; LC (method 20): $t_R$=5.02 min; Mass spectrum (ESI⁺): m/z=462 [M+H]⁺.

Example 60

2-((S)-6-((R)-4-(4-Carbamoyl-2,6-dimethylphenyl)-7-fluoro-2,3-dihydro-1H-inden-1-yloxy)-2,3-dihydrobenzofuran-3-yl)acetic acid

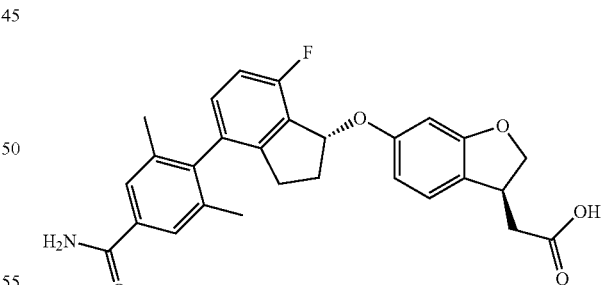

30% Aqueous NH₃ solution (250 µL) and 35% aqueous H₂O₂ solution (83 µl) are added at 0° C. to a solution of 2-((S)-6-((R)-4-(4-cyano-2,6-dimethylphenyl)-7-fluoro-2,3-dihydro-1H-inden-1-yloxy)-2,3-dihydrobenzofuran-3-yl)acetic acid (19 mg) in ethanol (2 mL). The mixture is stirred at room temperature for 12 hours, while warming to room temperature. The mixture is concentrated, diluted with water and neutralized with 4 M aqueous HCl solution. The resulting mixture is extracted with dichloromethane. The organic phase is dried (MgSO₄). The solvent is evaporated to give the title compound. Yield: 19 mg; LC (method 20): $t_R$=5.33 min; Mass spectrum (ESI⁺): m/z=476 [M+H]⁺.

Example 61

2-((S)-6-((R)-4-(4-(Dimethylcarbamoyl)-2,6-dimethylphenyl)-7-fluoro-2,3-dihydro-1H-inden-1-yloxy)-2,3-dihydrobenzofuran-3-yl)acetic acid

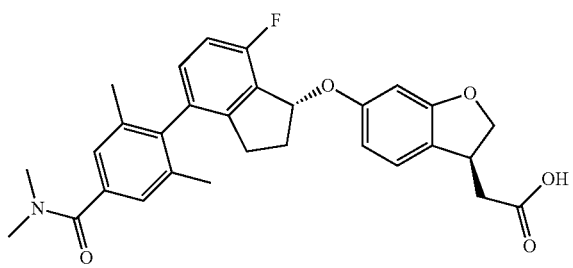 [SMILES: Cc1cc(C(=O)N(C)C)cc(C)c1-c1ccc(F)c2c1CC[C@H]2Oc1ccc2c(c1)OC[C@H]2CC(=O)O]

LiOH×H₂O (11 mg) is added to a solution of methyl 2-((S)-6-((R)-4-(4-(dimethylcarbamoyl)-2,6-dimethylphenyl)-7-fluoro-2,3-dihydro-1H-inden-1-yloxy)-2,3-dihydrobenzofuran-3-yl)acetate (70 mg) in ethanol (2.6 mL) and water (0.5 mL) and the mixture is stirred for 24 hours at room temperature. After concentration the mixture is diluted with water, acidified with aqueous citric acid solution and extracted with dichloromethane. After concentration the mixture is partitioned between dichloromethane and citric acid. The organic phase is dried (MgSO₄) and concentrated to give the title compound. Yield 21 mg, LC (method 20): $t_R$=5.87 min; Mass spectrum (ESI⁺): m/z=504 [M+H]⁺.

Example 62

2-((S)-6-((R)-4-(2,6-Dimethyl-4-(methylcarbamoyl)phenyl)-7-fluoro-2,3-dihydro-1H-inden-1-yloxy)-2,3-dihydrobenzofuran-3-yl)acetic acid

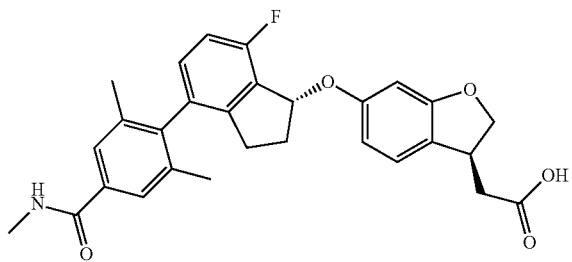 [SMILES: CNC(=O)c1cc(C)c(-c2ccc(F)c3c2CC[C@H]3Oc2ccc3c(c2)OC[C@H]3CC(=O)O)c(C)c1]

LiOH×H₂O (3 mg) is added to a solution of methyl 2-((S)-6-((R)-4-(2,6-dimethyl-4-(methylcarbamoyl)phenyl)-7-fluoro-2,3-dihydro-1H-inden-1-yloxy)-2,3-dihydrobenzofuran-3-yl)acetate (20 mg) in ethanol (0.77 mL) and water (0.5 mL) and the mixture is stirred for 24 hours at room temperature. After concentration the mixture is diluted with water, acidified with aqueous citric acid solution and extracted with dichloromethane. The organic phase is dried (MgSO₄) and the residue chromatographed on silica gel (cyclohexane/ethyl acetate 100:0→60:40) to give the title compound. Yield 11 mg, LC (method 20): $t_R$=5.54 min; Mass spectrum (ESI⁺): m/z=490 [M+H]⁺.

Example 63

2-((S)-6-((R)-4-(2,6-Dimethyl-4-(morpholine-4-carbonyl)phenyl)-7-fluoro-2,3-dihydro-1H-inden-1-yloxy)-2,3-dihydrobenzofuran-3-yl)acetic acid

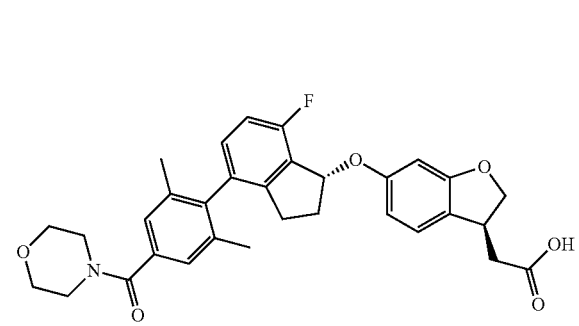 [SMILES: Cc1cc(C(=O)N2CCOCC2)cc(C)c1-c1ccc(F)c2c1CC[C@H]2Oc1ccc2c(c1)OC[C@H]2CC(=O)O]

LiOH×H₂O (4.1 mg) is added to a solution of methyl 2-((S)-6-((R)-4-(2,6-dimethyl-4-(morpholine-4-carbonyl)phenyl)-7-fluoro-2,3-dihydro-1H-inden-1-yloxy)-2,3-dihydrobenzofuran-3-yl)acetate (55 mg) in ethanol (1.9 mL) and water (0.5 mL) and the mixture is stirred for 24 hours at room temperature. After concentration the mixture is diluted with water, acidified with aqueous citric acid solution and extracted with dichloromethane. The organic phase is dried (MgSO₄) and concentrated. The residue is chromatographed on silica gel (cyclohexane/ethyl acetate 50:50) to give the title compound. Yield 10 mg, LC (method 20): $t_R$=5.73 min; Mass spectrum (ESI⁺): m/z=546 [M+H]⁺.

Example 64

2-((S)-6-((R)-4-(4-(2-Cyano-2-methylpropoxy)-2,6-dimethylphenyl)-7-fluoro-2,3-dihydro-1H-inden-1-yloxy)-2,3-dihydrobenzofuran-3-yl)acetic acid

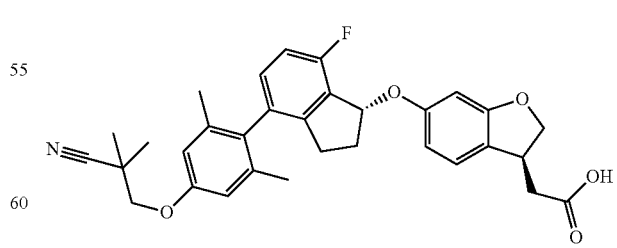

The title compound is prepared from methyl 2-((S)-6-((R)-4-(4-(2-cyano-2-methylpropoxy)-2,6-dimethylphenyl)-7-fluoro-2,3-dihydro-1H-inden-1-yloxy)-2,3-dihydrobenzofuran-3-yl)acetate following a procedure analogous to that described in example 4. LC (method 8): $t_R$=0.70 min; Mass spectrum (ESI$^+$): m/z=530 [M+H]$^+$.

Example 65

2-((S)-6-((R)-4-(4-(2-(tert-Butoxycarbonylamino)ethoxy)-2,6-dimethylphenyl)-7-fluoro-2,3-dihydro-1H-inden-1-yloxy)-2,3-dihydrobenzofuran-3-yl)acetic acid

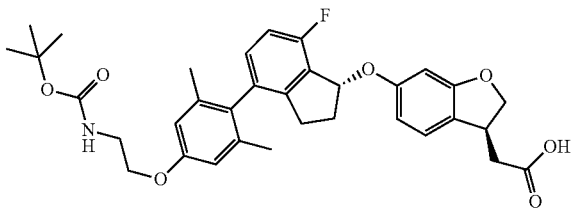 [SMILES: Cc1cc(OCCNC(=O)OC(C)(C)C)cc(C)c1-c1ccc(F)c2c1CC[C@H]2Oc1ccc2c(c1)OC[C@H]2CC(=O)O]

The title compound is prepared from methyl 2-((S)-6-((R)-4-(4-(2-(tert-butoxycarbonylamino)ethoxy)-2,6-dimethylphenyl)-7-fluoro-2,3-dihydro-1H-inden-1-yloxy)-2,3-dihydrobenzofuran-3-yl)acetate following a procedure analogous to that described in example 4. The mixture is stirred for 2 days at 50° C. The product is purified by HPLC on reversed phase. LC (method 8): $t_R$=0.73 min; Mass spectrum (ESI$^+$): m/z=592 [M+H]$^+$.

Example 66

2-((S)-6-((R)-7-Fluoro-4-(4-((4-hydroxytetrahydro-2H-pyran-4-yl)methoxy)-2,6-dimethylphenyl)-2,3-dihydro-1H-inden-1-yloxy)-2,3-dihydrobenzofuran-3-yl)acetic acid

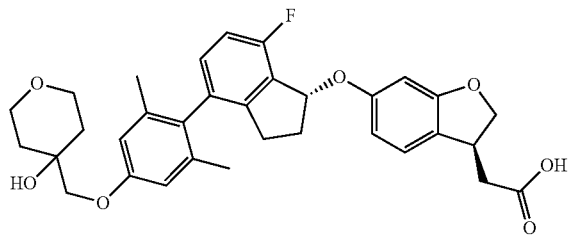 [SMILES: Cc1cc(OCC2(O)CCSCC2)cc(C)c1-c1ccc(F)c2c1CC[C@H]2Oc1ccc2c(c1)OC[C@H]2CC(=O)O]

The title compound is prepared from methyl 2-((S)-6-((R)-7-fluoro-4-(4-((4-hydroxytetrahydro-2H-pyran-4-yl)methoxy)-2,6-dimethylphenyl)-2,3-dihydro-1H-inden-1-yloxy)-2,3-dihydrobenzofuran-3-yl)acetate following a procedure analogous to that described in example 4. TLC: $r_f$=0.2 (silicagel, ethyl acetate); Mass spectrum (ESI$^+$): m/z=563 [M+H]$^+$.

Example 67

2-((S)-6-((R)-7-Fluoro-4-(4-(3-hydroxy-3-methylbutyl)-2,6-dimethylphenyl)-2,3-dihydro-1H-inden-1-yloxy)-2,3-dihydrobenzofuran-3-yl)acetic acid 1 M aqueous NaOH solution (310 µL) is added to a solution of methyl 2-((S)-6-((R)-7-fluoro-4-(4-(3-hydroxy-3-methyl-butyl)-2,6-dimethylphenyl)-2,3-dihydro-1H-inden-1-yloxy)-2,3-dihydrobenzofuran-3-yl)acetate (110 mg) in methanol (4 mL). The mixture is stirred at room temperature for 12 hours and at 50° C. for 2 days. 1 M aqueous NaOH solution (100 µL) is added and the mixture is stirred at 50° C. for 1 hour. Methanol is evaporated in vacuo, the residue is diluted with water and neutralized with 1 M aqueous HCl. The resulting mixture is extracted with ethyl acetate, and the combined organic phases are washed with brine and dried (MgSO$_4$). The solvent is evaporated to give the title compound. Yield: 80 mg; LC (method 8): $t_R$=0.59 min; Mass spectrum (ESI$^+$): m/z=519 [M+H]$^+$.

Example 68

2-((S)-6-((R)-7-Fluoro-4-(4-((4-hydroxytetrahydro-2H-thiopyran-4-yl)methoxy)-2,6-dimethylphenyl)-2,3-dihydro-1H-inden-1-yloxy)-2,3-dihydrobenzofuran-3-yl)acetic acid To a solution of methyl 2-((S)-6-((R)-7-fluoro-4-(4-hydroxy-2,6-dimethylphenyl)-2,3-dihydro-1H-inden-1-yloxy)-2,3-dihydrobenzofuran-3-yl)acetate (100 mg) in N,N-dimethylformamide (2 mL) is added Cs$_2$CO$_3$ (106 mg) and 1-oxa-6-thiaspiro[2.5]octane (37 mg). The mixture is stirred for 12 hour at 100° C. The mixture is diluted with water, acidified with 1 M aqueous HCl solution and extracted twice with ethyl acetate. The combined organic phases are washed with water and brine, dried (MgSO$_4$) and concentrated. The residue is chromatographed on silica gel (cyclo-

Example 69

2-((S)-6-((R)-7-Fluoro-4-(4-((1,1-dioxo-4-hydroxytetrahydro-2H-thiopyran-4-yl)methoxy)-2,6-dimethylphenyl)-2,3-dihydro-1H-inden-1-yloxy)-2,3-dihydrobenzofuran-3-yl)acetic acid

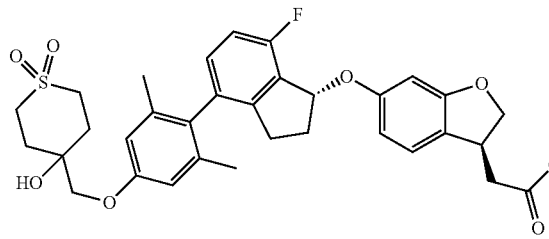

1 M aqueous NaOH solution (250 μL) is added to a solution of methyl 2-((S)-6-((R)-7-fluoro-4-(4-((1,1-dioxo-4-hydroxytetrahydro-2H-thiopyran-4-yl)methoxy)-2,6-dimethylphenyl)-2,3-dihydro-1H-inden-1-yloxy)-2,3-dihydrobenzofuran-3-yl)acetate (85 mg) in tetrahydrofurane (4 mL). The mixture is stirred at room temperature for 12 hours. Then the mixture is diluted with ethyl acetate and neutralized with 1 M aqueous HCl solution. The resulting mixture is diluted with saturated aqueous NaCl solution and the phases are separated. The organic phase is dried (MgSO$_4$) and concentrated to give the title compound. Yield: 80 mg; LC (method 7): $t_R$=1.04 min; Mass spectrum (ESI$^+$): m/z=611 [M+H]$^+$.

Example 70

2-((S)-6-((R)-4-(2,6-Dimethyl-4-(3-(methylsulfonyl)propyl)phenyl)-7-fluoro-2,3-dihydro-1H-inden-1-yloxy)-2,3-dihydrobenzofuran-3-yl)acetic acid

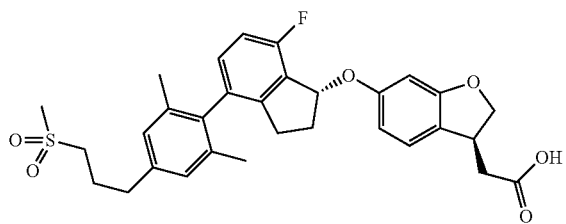 [SMILES: Cc1cc(CCCS(C)(=O)=O)cc(C)c1-c1ccc(F)c2c1CC[C@H]2Oc1ccc2c(c1)OC[C@H]2CC(=O)O]

1 M aqueous NaOH solution (50 μL) is added to a solution of methyl 2-((S)-6-((R)-4-(2,6-dimethyl-4-(3-(methylsulfonyl)propyl)phenyl)-7-fluoro-2,3-dihydro-1H-inden-1-yloxy)-2,3-dihydrobenzofuran-3-yl)acetate (20 mg) in methanol (2 mL). The mixture is stirred at room temperature for 12 hours and at 50° C. for 2 days. 1 M aqueous NaOH solution (18 μL) is added and the mixture is stirred at 50° C. for 2 hours. Methanol is evaporated in vacuo, the residue is diluted with water and neutralized with 1 M aqueous HCl. The resulting mixture is extracted with ethyl acetate, and the organic phase is dried (MgSO$_4$). The solvent is evaporated and the residue is purified by HPLC on reversed phase to give the title compound. Yield: 7 mg; LC (method 8): $t_R$=0.34 min; Mass spectrum (ESI$^+$): m/z=553 [M+H]$^+$.

Example 71

2-((S)-6-((R)-4-(2,6-Dimethyl-4-(2-(methylsulfonamido)ethoxy)phenyl)-7-fluoro-2,3-dihydro-1H-inden-1-yloxy)-2,3-dihydrobenzofuran-3-yl)acetic acid

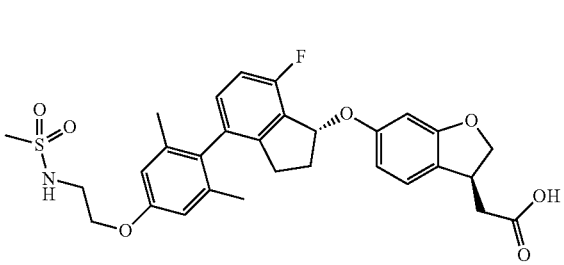 [SMILES: Cc1cc(OCCNS(C)(=O)=O)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(2-(methylsulfonamido)ethoxy)phenyl)-7-fluoro-2,3-dihydro-1H-inden-1-yloxy)-2,3-dihydrobenzofuran-3-yl)acetate following a procedure analogous to that described in example 4. The mixture is stirred for 2 days at 50° C. The product is purified by HPLC on reversed phase. LC (method 7): $t_R$=1.05 min; Mass spectrum (ESI$^+$): m/z=570 [M+H]$^+$.

Example 72

2-((S)-6-((R)-4-(4-(2-Acetamidoethyl)-2,6-dimethylphenyl)-7-fluoro-2,3-dihydro-1H-inden-1-yloxy)-2,3-dihydrobenzofuran-3-yl)acetic acid

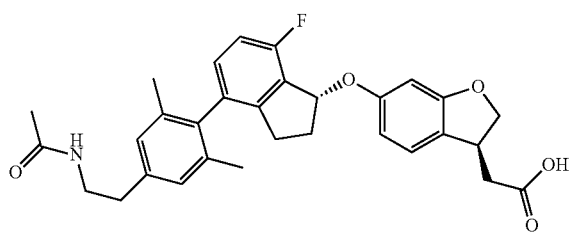 [SMILES: CC(=O)NCCc1cc(C)c(-c2ccc(F)c3c2CC[C@H]3Oc2ccc3c(c2)OC[C@H]3CC(=O)O)c(C)c1]

The title compound is prepared from methyl 2-((S)-6-((R)-4-(4-(2-acetamidoethyl)-2,6-dimethylphenyl)-7-fluoro-2,3-dihydro-1H-inden-1-yloxy)-2,3-dihydrobenzofuran-3-yl)acetate following a procedure analogous to that described in example 4. The mixture is stirred for 12 hours at 50° C. The product is purified by HPLC on reversed phase. LC (method 7): $t_R$=1.04 min; Mass spectrum (ESI$^+$): m/z=518 [M+H]$^+$.

Example 73

2-((S)-6-((R)-4-(4-(2-Acetamidoethoxy)-2,6-dimethylphenyl)-7-fluoro-2,3-dihydro-1H-inden-1-yloxy)-2,3-dihydrobenzofuran-3-yl)acetic acid

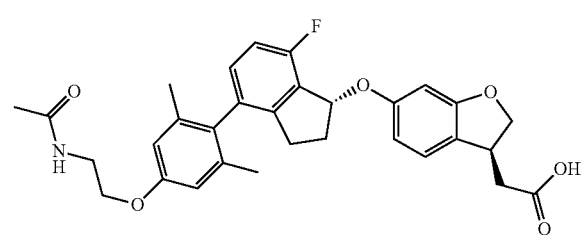 [SMILES: CC(=O)NCCOc1cc(C)c(-c2ccc(F)c3c2CC[C@H]3Oc2ccc3c(c2)OC[C@H]3CC(=O)O)c(C)c1]

The title compound is prepared from methyl 2-((S)-6-((R)-4-(4-(2-acetamidoethoxy)-2,6-dimethylphenyl)-7-fluoro-2,3-dihydro-1H-inden-1-yloxy)-2,3-dihydrobenzofuran-3-yl)acetate following a procedure analogous to that described in example 4. The mixture is stirred for 5 hours at 50° C. The product is purified by HPLC on reversed phase. LC (method 7): $t_R$=1.03 min; Mass spectrum (ESI$^+$): m/z=534 [M+H]$^+$.

Example 74

2-((S)-6-((R)-4-(2,6-dimethyl-4-(2-(methylsulfonamido)ethyl)phenyl)-7-fluoro-2,3-dihydro-1H-inden-1-yloxy)-2,3-dihydrobenzofuran-3-yl)acetic acid

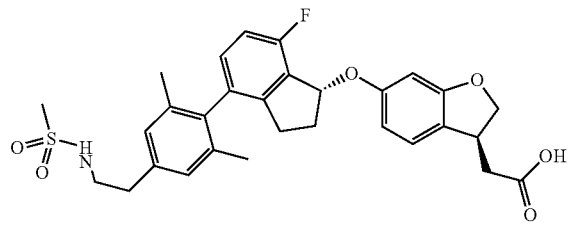 [SMILES: Cc1cc(CCNS(C)(=O)=O)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(2-(methylsulfonamido)ethyl)phenyl)-7-fluoro-2,3-dihydro-1H-inden-1-yloxy)-2,3-dihydrobenzofuran-3-yl)acetate following a procedure analogous to that described in example 4. The mixture is stirred for 20 hours at 50° C. The product is purified by HPLC on reversed phase. LC (method 7): $t_R$=1.06 min; Mass spectrum (ESI$^+$): m/z=554 [M+H]$^+$.

Example 75

2-((S)-6-((R)-7-Fluoro-4-(4-((1-hydroxycyclopropyl)methoxy)-2,6-dimethylphenyl)-2,3-dihydro-1H-inden-1-yloxy)-2,3-dihydrobenzofuran-3-yl)acetic acid

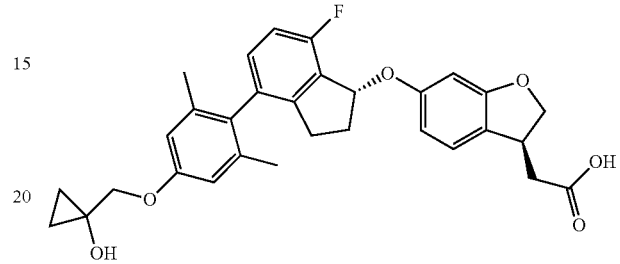

Ethylmagnesium chloride (380 µL of a 1 M solution in tetrahydrofurane) is added dropwise under argon to a solution of 2-((S)-6-((R)-7-fluoro-4-(4-(2-methoxy-2-oxoethoxy)-2,6-dimethylphenyl)-2,3-dihydro-1H-inden-1-yloxy)-2,3-dihydrobenzofuran-3-yl)acetic acid in tetrahydrofurane (4 mL). The mixture is stirred at room temperature for 30 minutes. Ti(OiPr)$_4$ (120 µL) is added dropwise and after stirring for 30 minutes ethylmagnesium chloride (1.15 mL of a 1 M solution in tetrahydrofurane) is added dropwise. The mixture is stirred for 2 hours, partitioned between ethylacetate and saturated aqueous NH$_4$Cl solution and stirred vigorously for 30 minutes. After filtering over celite the phases are separated, the aqueous phase is extracted with diethylether and the combined organic phases are washed with brine and dried (MgSO$_4$). The solvents are evaporated and the residue is purified by HPLC on reversed phase. Yield: 38 mg; LC (method 8): $t_R$=0.38 min; Mass spectrum (ESI$^+$): m/z=519 [M+H]$^+$.

Example 76

2-((3S)-6-((1R)-4-(2,6-Dimethyl-4-(1-methyl-2-oxopyrrolidin-3-yloxy)phenyl)-7-fluoro-2,3-dihydro-1H-inden-1-yloxy)-2,3-dihydrobenzofuran-3-yl)acetic acid

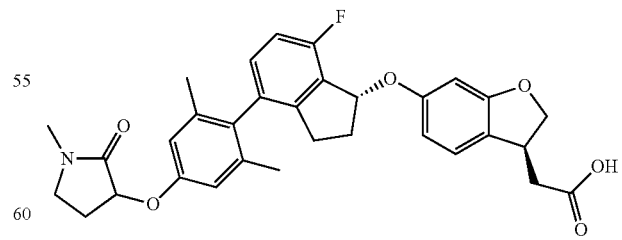

The title compound is prepared from methyl 2-((3S)-6-((1R)-4-(2,6-dimethyl-4-(1-methyl-2-oxopyrrolidin-3-yloxy)phenyl)-7-fluoro-2,3-dihydro-1H-inden-1-yloxy)-2,3-dihydrobenzofuran-3-yl)acetate following a procedure analogous to that described in example 4. The mixture is stirred for 12 hours at 50° C. The product is purified by HPLC on reversed phase. LC (method 7): $t_R$=1.06 min; Mass spectrum (ESI$^+$): m/z=546 [M+H]$^+$.

Example 77

2-((S)-6-((R)-4-(4-(2,2-Dimethyl-3-(methylsulfonyl)propoxy)-2,6-dimethylphenyl)-7-fluoro-2,3-dihydro-1H-inden-1-yloxy)-2,3-dihydrobenzofuran-3-yl)acetic acid

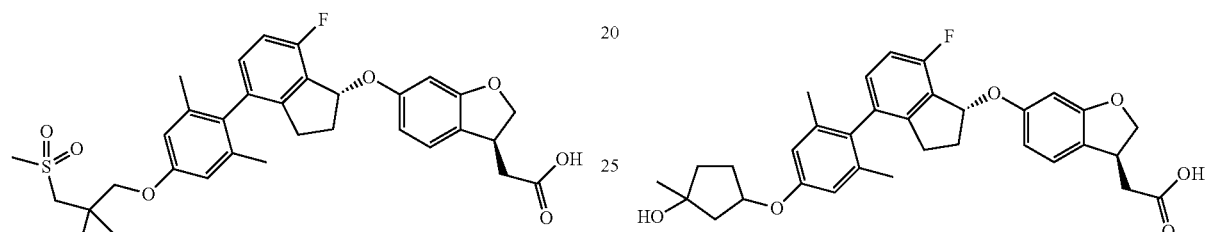

The title compound is prepared from methyl 2-((S)-6-((R)-4-(4-(2,2-dimethyl-3-(methylsulfonyl)propoxy)-2,6-dimethylphenyl)-7-fluoro-2,3-dihydro-1H-inden-1-yloxy)-2,3-dihydrobenzofuran-3-yl)acetate following a procedure analogous to that described in example 4. The mixture is stirred for 3 hours at 50° C. The product is purified by HPLC on reversed phase. LC (method 7): $t_R$=1.14 min; Mass spectrum (ESI$^+$): m/z=597 [M+H]$^+$.

Example 78

2-((3S)-6-((1R)-7-Fluoro-4-(4-(3-hydroxy-3-methylcyclopentyloxy)-2,6-dimethylphenyl)-2,3-dihydro-1H-inden-1-yloxy)-2,3-dihydrobenzofuran-3-yl)acetic acid (Diastereomer 1)

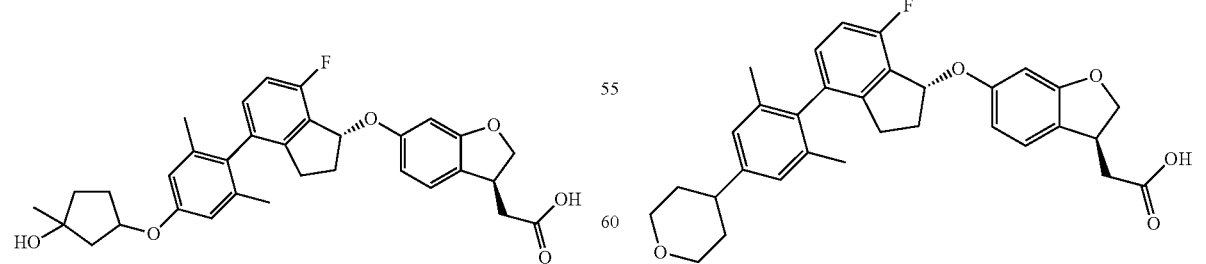

The title compound is prepared from methyl 2-((3S)-6-((1R)-7-fluoro-4-(4-(3-hydroxy-3-methylcyclopentyloxy)-2,6-dimethylphenyl)-2,3-dihydro-1H-inden-1-yloxy)-2,3-dihydrobenzofuran-3-yl)acetate (diastereomer 1) following a procedure analogous to that described in example 1. LC (method 8): $t_R$=0.54 min; Mass spectrum (ESI$^+$): m/z=547 [M+H]$^+$.

Example 79

2-((3S)-6-((1R)-7-Fluoro-4-(4-(3-hydroxy-3-methylcyclopentyloxy)-2,6-dimethylphenyl)-2,3-dihydro-1H-inden-1-yloxy)-2,3-dihydrobenzofuran-3-yl)acetic acid (Diastereomer 2)

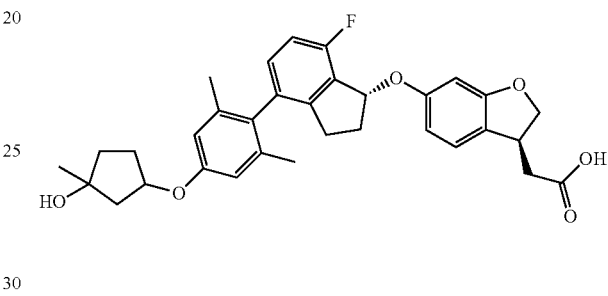

The title compound is prepared from methyl 2-((3S)-6-((1R)-7-fluoro-4-(4-(3-hydroxy-3-methylcyclopentyloxy)-2,6-dimethylphenyl)-2,3-dihydro-1H-inden-1-yloxy)-2,3-dihydrobenzofuran-3-yl)acetate (diastereomer 2) following a procedure analogous to that described in example 1. LC (method 8): $t_R$=0.56 min; Mass spectrum (ESI$^+$): m/z=547 [M+H]$^+$.

Example 80

2-((S)-6-((R)-4-(2,6-Dimethyl-4-(tetrahydro-2H-pyran-4-yl)phenyl)-7-fluoro-2,3-dihydro-1H-inden-1-yloxy)-2,3-dihydrobenzofuran-3-yl)acetic acid

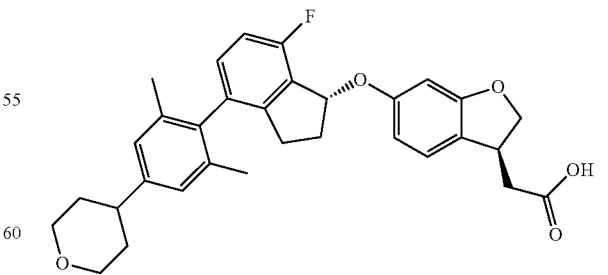

The title compound is prepared from methyl 2-((S)-6-((R)-4-(2,6-dimethyl-4-(tetrahydro-2H-pyran-4-yl)phenyl)-7-fluoro-2,3-dihydro-1H-inden-1-yloxy)-2,3-dihydrobenzofuran-3-yl)acetate following a procedure analogous to that

Example 81

2-((S)-6-((R)-4-(2,6-Dimethyl-4-(6-oxo-3,6-dihydro-2H-pyran-4-yl)phenyl)-7-fluoro-2,3-dihydro-1H-inden-1-yloxy)-2,3-dihydrobenzofuran-3-yl)acetic acid

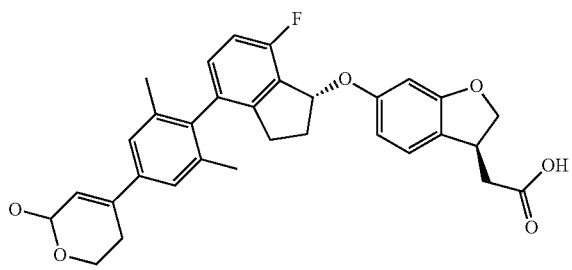 [SMILES: Cc1cc(C2=CC(O)OCC2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(6-oxo-3,6-dihydro-2H-pyran-4-yl)phenyl)-7-fluoro-2,3-dihydro-1H-inden-1-yloxy)-2,3-dihydrobenzofuran-3-yl)acetate following a procedure analogous to that described in example 1. The product is purified by HPLC on reversed phase. LC (method 9): $t_R$=0.96 min; Mass spectrum (ESI$^+$): m/z=529 [M+H]$^+$.

Example 82

2-((S)-6-((R)-4-(2,6-Bis(methoxymethyl)-4-((3-methyloxetan-3-yl)methoxy)phenyl)-7-fluoro-2,3-dihydro-1H-inden-1-yloxy)-2,3-dihydrobenzofuran-3-yl)acetic acid

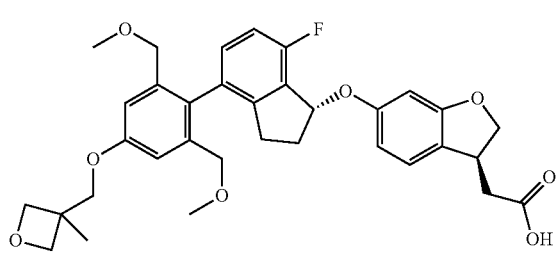 [SMILES: COCc1cc(OCC2(C)COC2)cc(COC)c1-c1ccc(F)c2c1CC[C@H]2Oc1ccc2c(c1)OC[C@H]2CC(=O)O]

The title compound is prepared from methyl 2-((S)-6-((R)-4-(2,6-bis(methoxymethyl)-4-((3-methyloxetan-3-yl)methoxy)phenyl)-7-fluoro-2,3-dihydro-1H-inden-1-yloxy)-2,3-dihydrobenzofuran-3-yl)acetate following a procedure described in example 1. LC (method 26): $t_R$=0.79 min; Mass spectrum (ESI$^+$): m/z=517 [M+H]$^+$.

Example 83

2-((S)-6-((R)-7-Fluoro-4-(4-(1-(2-hydroxy-2-methylpropyl)-1H-pyrazol-4-yl)-2,6-dimethylphenyl)-2,3-dihydro-1H-inden-1-yloxy)-2,3-dihydrobenzofuran-3-yl)acetic acid

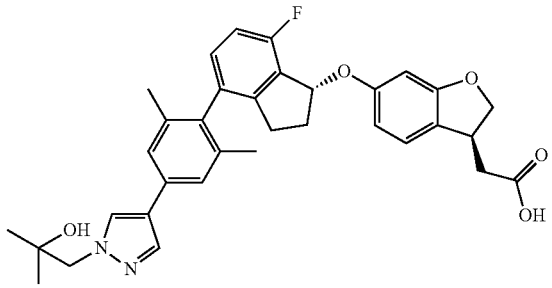 [SMILES: Cc1cc(-c2cnn(CC(C)(C)O)c2)cc(C)c1-c1ccc(F)c2c1CC[C@H]2Oc1ccc2c(c1)OC[C@H]2CC(=O)O]

The title compound is prepared from methyl 2-((S)-6-((R)-7-fluoro-4-(4-(1-(2-hydroxy-2-methylpropyl)-1H-pyrazol-4-yl)-2,6-dimethylphenyl)-2,3-dihydro-1H-inden-1-yloxy)-2,3-dihydrobenzofuran-3-yl)acetate following a procedure analogous to that described in example 4. LC (method 11): $t_R$=1.13 min; Mass spectrum (ESI$^+$): m/z=571 [M+H]$^+$.

Example 84

2-((S)-6-((R)-4-(2,6-Dimethyl-4-(1-methyl-2-oxo-1,2-dihydropyridin-4-yl)phenyl)-7-fluoro-2,3-dihydro-1H-inden-1-yloxy)-2,3-dihydrobenzofuran-3-yl)acetic acid

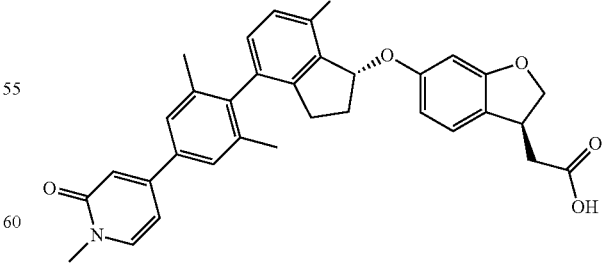

The title compound is prepared from methyl 2-((S)-6-((R)-4-(2,6-dimethyl-4-(1-methyl-2-oxo-1,2-dihydropyridin-4-yl)phenyl)-7-fluoro-2,3-dihydro-1H-inden-1-yloxy)-2,3-dihydrobenzofuran-3-yl)acetate following a procedure analogous to that described in example 4. LC (method 8): $t_R$=0.43 min; Mass spectrum (ESI$^+$): m/z=593 [M+H]$^+$.

analogous to that described in example 4. LC (method 11): $t_R$=1.09 min; Mass spectrum (ESI⁺): m/z=540 [M+H]⁺.

Example 85

2-((S)-6-((R)-4-(2,6-Dimethyl-4-(1-methyl-6-oxo-1,6-dihydropyridin-3-yl)phenyl)-7-fluoro-2,3-dihydro-1H-inden-1-yloxy)-2,3-dihydrobenzofuran-3-yl)acetic acid

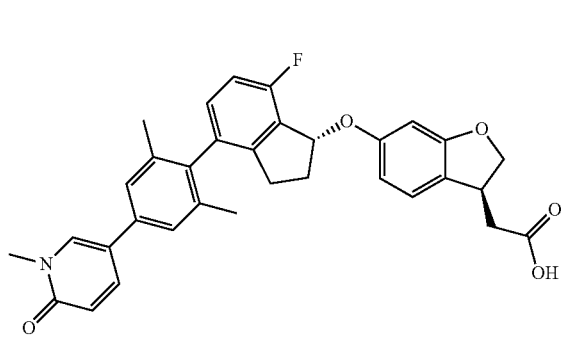 [SMILES: Cc1cc(-c2ccc(=O)n(C)c2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1-methyl-6-oxo-1,6-dihydropyridin-3-yl)phenyl)-7-fluoro-2,3-dihydro-1H-inden-1-yloxy)-2,3-dihydrobenzofuran-3-yl)acetate following a procedure analogous to that described in example 4. LC (method 11): $t_R$=1.09 min; Mass spectrum (ESI⁺): m/z=540 [M+H]⁺.

Example 86

2-((S)-6-((R)-4-(2,6-Dimethyl-4-(1H-1,2,4-triazol-1-yl)phenyl)-7-fluoro-2,3-dihydro-1H-inden-1-yloxy)-2,3-dihydrobenzofuran-3-yl)acetic acid

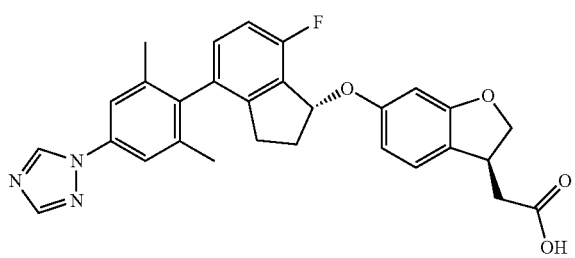 [SMILES: Cc1cc(-n2cncn2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1H-1,2,4-triazol-1-yl)phenyl)-7-fluoro-2,3-dihydro-1H-inden-1-yloxy)-2,3-dihydrobenzofuran-3-yl)acetate following a procedure analogous to that described in example 4. LC (method 7): $t_R$=1.06 min; Mass spectrum (ESI⁺): m/z=500 [M+H]⁺.

Example 87

2-((3S)-6-((1R)-4-(2,6-Dimethyl-4-(tetrahydrofuran-3-yl)phenyl)-7-fluoro-2,3-dihydro-1H-inden-1-yloxy)-2,3-dihydrobenzofuran-3-yl)acetic acid

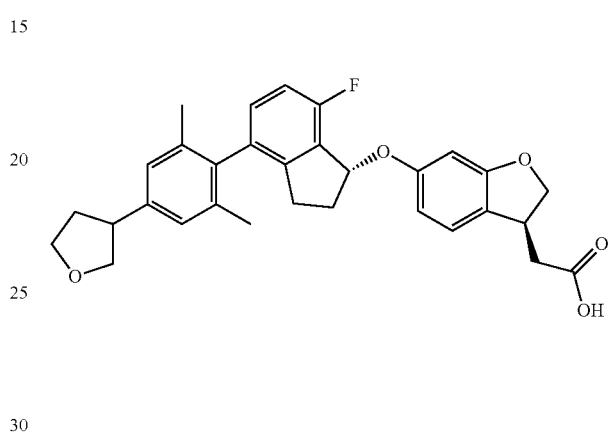

The title compound is prepared from 2-((S)-6-((R)-4-(4-(2,5-dihydrofuran-3-yl)-2,6-dimethylphenyl)-7-fluoro-2,3-dihydro-1H-inden-1-yloxy)-2,3-dihydrobenzofuran-3-yl) acetic acid by hydrogenation in the presence of palladium (10% on carbon) in ethyl acetate at room temperature. LC (method 9): $t_R$=1.17 min; Mass spectrum (ESI⁺): m/z=503 [M+H]⁺.

Example 88

2-((S)-6-((R)-4-(2,6-Dimethyl-4-(1-methyl-6-oxo-1,6-dihydropyrimidin-4-yl)phenyl)-7-fluoro-2,3-dihydro-1H-inden-1-yloxy)-2,3-dihydrobenzofuran-3-yl)acetic acid

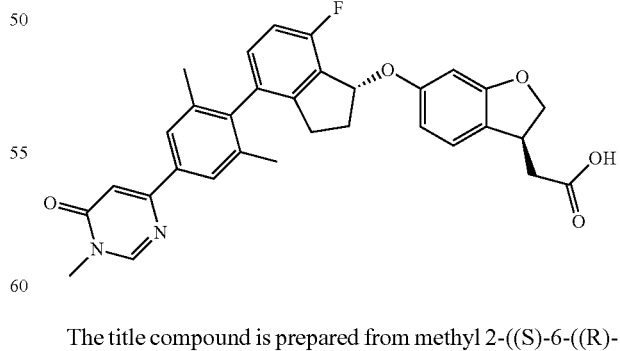

The title compound is prepared from methyl 2-((S)-6-((R)-5-cyano-4-(2,6-dimethyl-4-(1-methyl-2-oxo-1,2-dihydropyridin-4-yl)phenyl)-2,3-dihydro-1H-inden-1-yloxy)-2,3-dihydrobenzofuran-3-yl)acetate following a procedure analogous to that described in example 1. The mixture is stirred for 1 hour at 40° C. The product is purified by HPLC

Example 89

2-((S)-6-((R)-4-(2,6-Dimethyl-4-(1-methyl-2-oxo-1,2-dihydropyrimidin-5-yl)phenyl)-7-fluoro-2,3-dihydro-1H-inden-1-yloxy)-2,3-dihydrobenzofuran-3-yl)acetic acid

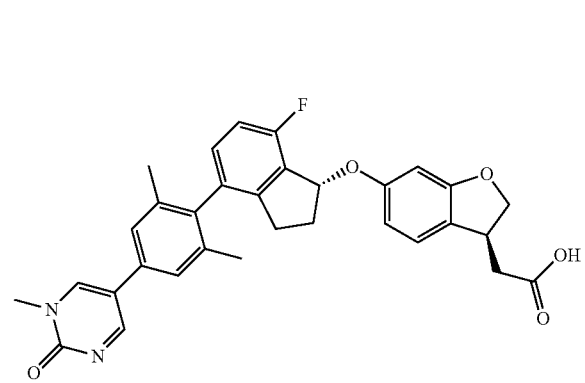 [SMILES: Cc1cc(-c2cnc(=O)n(C)c2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1-methyl-2-oxo-1,2-dihydropyrimidin-5-yl)phenyl)-7-fluoro-2,3-dihydro-1H-inden-1-yloxy)-2,3-dihydrobenzofuran-3-yl)acetate following a procedure analogous to that described in example 1. The mixture is stirred for 2 hours at 40° C. LC (method 15): $t_R$=1.05 min; Mass spectrum (ESI$^+$): m/z=541 [M+H]$^+$.

Example 90

2-((S)-6-((R)-4-(2,6-Dimethyl-4-(pyridazin-4-yl)phenyl)-7-fluoro-2,3-dihydro-1H-inden-1-yloxy)-2,3-dihydrobenzofuran-3-yl)acetic acid

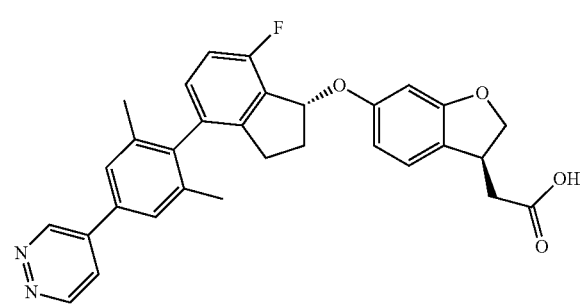

The title compound is prepared from methyl 2-((S)-6-((R)-4-(2,6-dimethyl-4-(pyridazin-4-yl)phenyl)-7-fluoro-2,3-dihydro-1H-inden-1-yloxy)-2,3-dihydrobenzofuran-3-yl)acetate following a procedure analogous to that described in example 1. The mixture is stirred for 4 hours at 40° C. LC (method 15): $t_R$=1.10 min; Mass spectrum (ESI$^+$): m/z=511 [M+H]$^+$.

Example 91

2-((S)-6-((R)-4-(2,6-Dimethyl-4-(pyrimidin-4-yl)phenyl)-7-fluoro-2,3-dihydro-1H-inden-1-yloxy)-2,3-dihydrobenzofuran-3-yl)acetic acid

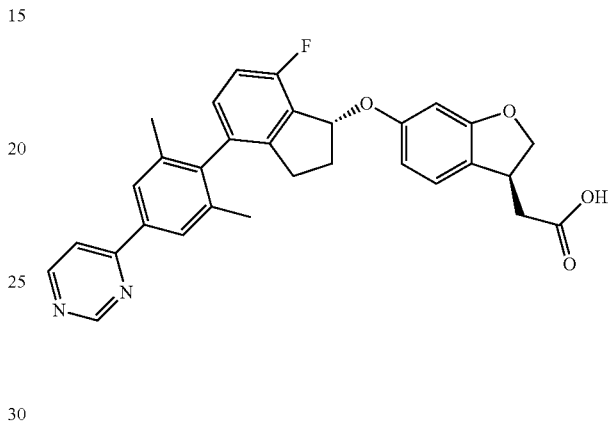

The title compound is prepared from methyl 2-((S)-6-((R)-4-(2,6-dimethyl-4-(pyrimidin-4-yl)phenyl)-7-fluoro-2,3-dihydro-1H-inden-1-yloxy)-2,3-dihydrobenzofuran-3-yl)acetate following a procedure analogous to that described in example 1. The mixture is stirred for 2 hours at 40° C. LC (method 15): $t_R$=1.18 min; Mass spectrum (ESI$^+$): m/z=511 [M+H]$^+$.

Example 92

2-((S)-6-((R)-4-(2,6-Dimethyl-4-(1-methyl-6-oxo-1,6-dihydropyridazin-4-yl)phenyl)-7-fluoro-2,3-dihydro-1H-inden-1-yloxy)-2,3-dihydrobenzofuran-3-yl)acetic acid

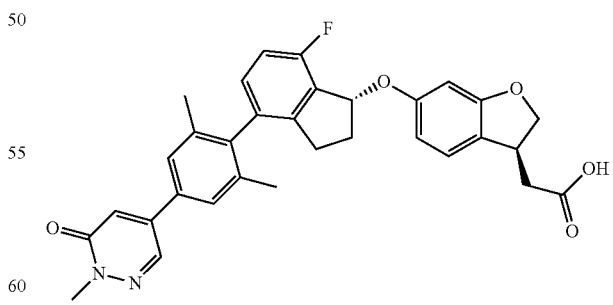

The title compound is prepared from methyl 2-((S)-6-((R)-4-(2,6-dimethyl-4-(1-methyl-6-oxo-1,6-dihydropyridazin-4-yl)phenyl)-7-fluoro-2,3-dihydro-1H-inden-1-yloxy)-2,3-dihydrobenzofuran-3-yl)acetate following a procedure analogous to that described in example 1. The mixture is stirred for 2 days at room temperature. LC (method 14): $t_R$=0.82 min; Mass spectrum (ESI$^+$): m/z=541 [M+H]$^+$.

Example 93

Methyl 2-((S)-6-((R)-7-fluoro-4-(4-(2-methoxypyrimidin-4-yl)-2,6-dimethylphenyl)-2,3-dihydro-1H-inden-1-yloxy)-2,3-dihydrobenzofuran-3-yl)acetate

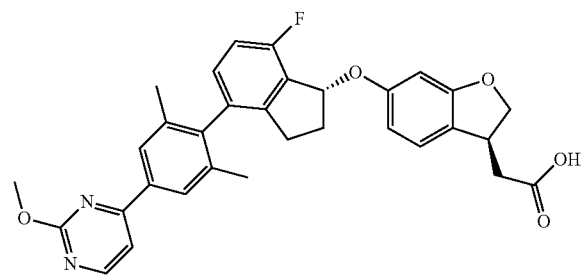 [SMILES: COc1nccc(-c2cc(C)c(-c3ccc(F)c4c3CC[C@H]4Oc3ccc4c(c3)OC[C@H]4CC(=O)O)c(C)c2)n1]

The title compound is prepared from methyl 2-((S)-6-((R)-7-fluoro-4-(4-(2-methoxypyrimidin-4-yl)-2,6-dimethylphenyl)-2,3-dihydro-1H-inden-1-yloxy)-2,3-dihydrobenzofuran-3-yl)acetate following a procedure analogous to that described in example 1. The mixture is stirred for 4 hours at room temperature. LC (method 8): $t_R$=0.60 min; Mass spectrum (ESI$^+$): m/z=541 [M+H]$^+$.

Example 94

2-((S)-6-((R)-4-(2,6-Dimethyl-4-(1H-tetrazol-5-yl)phenyl)-7-fluoro-2,3-dihydro-1H-inden-1-yloxy)-2,3-dihydrobenzofuran-3-yl)acetic acid

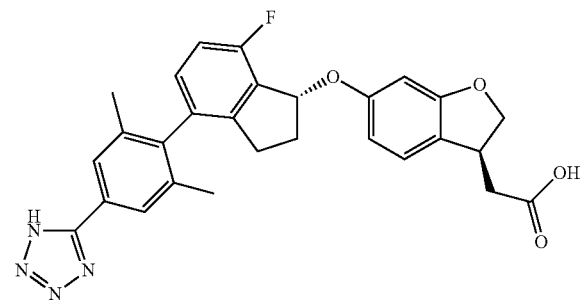 [SMILES: Cc1cc(-c2nnn[nH]2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1H-tetrazol-5-yl)phenyl)-7-fluoro-2,3-dihydro-1H-inden-1-yloxy)-2,3-dihydrobenzofuran-3-yl)acetate following a procedure analogous to that described in example 1. The mixture is stirred for 2 hours at 40° C. The product is purified by HPLC on reversed phase. LC (method 11): $t_R$=1.05 min; Mass spectrum (ESI$^+$): m/z=501 [M+H]$^+$.

Example 95

2-((S)-6-((R)-4-(2,6-Dimethyl-4-(2-methyl-2H-tetrazol-5-yl)phenyl)-7-fluoro-2,3-dihydro-1H-inden-1-yloxy)-2,3-dihydrobenzofuran-3-yl)acetic acid

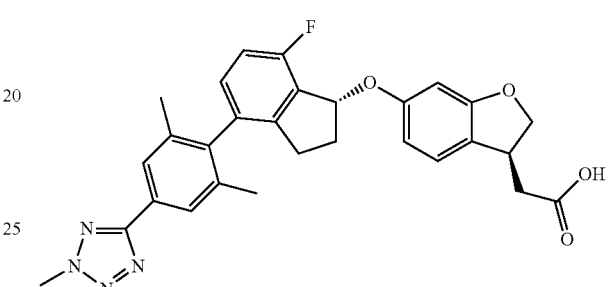

The title compound is prepared from methyl 2-((S)-6-((R)-4-(2,6-dimethyl-4-(2-methyl-2H-tetrazol-5-yl)phenyl)-7-fluoro-2,3-dihydro-1H-inden-1-yloxy)-2,3-dihydrobenzofuran-3-yl)acetate following a procedure analogous to that described in example 1. The mixture is stirred for 3 hours at 40° C. LC (method 11): $t_R$=1.17 min; Mass spectrum (ESI$^+$): m/z=515 [M+H]$^+$.

Example 96

2-((S)-6-((R)-4-(2,6-Dimethyl-4-(1-methyl-1H-tetrazol-5-yl)phenyl)-7-fluoro-2,3-dihydro-1H-inden-1-yloxy)-2,3-dihydrobenzofuran-3-yl)acetic acid

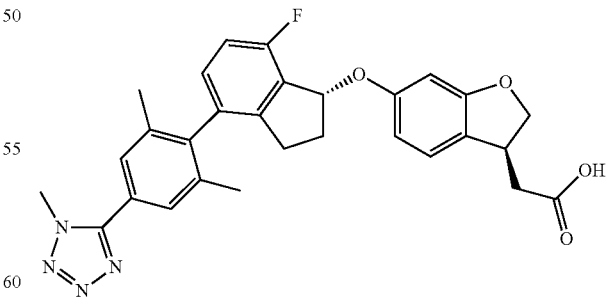

The title compound is prepared from methyl 2-((S)-6-((R)-4-(2,6-dimethyl-4-(1-methyl-1H-tetrazol-5-yl)phenyl)-7-fluoro-2,3-dihydro-1H-inden-1-yloxy)-2,3-dihydrobenzofuran-3-yl)acetate following a procedure analogous to that described in example 1. The mixture is stirred for 2 hours at 40° C. The product is purified by HPLC on reversed phase. LC (method 11): $t_R$=1.10 min; Mass spectrum (ESI$^+$): m/z=515 [M+H]$^+$.

Example 97

2-((S)-6-((R)-4-(2,6-Dimethyl-4-(1-methyl-2-oxo-1,2-dihydropyrimidin-4-yl)phenyl)-7-fluoro-2,3-dihydro-1H-inden-1-yloxy)-2,3-dihydrobenzofuran-3-yl)acetic acid

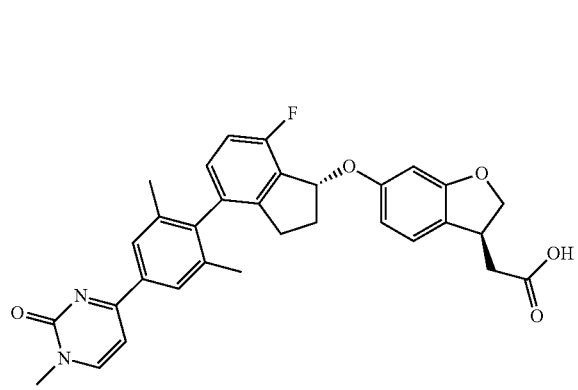 [SMILES: Cc1cc(-c2ccn(C)c(=O)n2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1-methyl-2-oxo-1,2-dihydropyrimidin-4-yl)phenyl)-7-fluoro-2,3-dihydro-1H-inden-1-yloxy)-2,3-dihydrobenzofuran-3-yl)acetate following a procedure analogous to that described in example 1. The mixture is stirred for 6 hours at room temperature. LC (method 11): $t_R$=1.01 min; Mass spectrum (ESI$^+$): m/z=541 [M+H]$^+$.

Example 98

2-((S)-6-((R)-7-Fluoro-4-(4-(2-(2-hydroxy-2-methylpropyl)-2H-tetrazol-5-yl)-2,6-dimethylphenyl)-2,3-dihydro-1H-inden-1-yloxy)-2,3-dihydrobenzofuran-3-yl)acetic acid

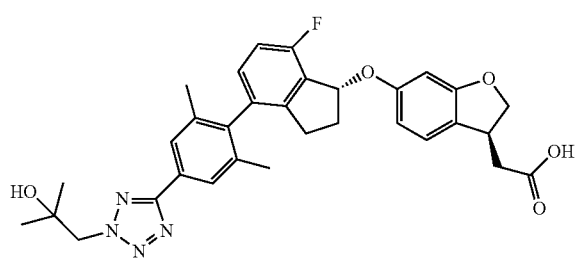 [SMILES: Cc1cc(-c2nnn(CC(C)(C)O)n2)cc(C)c1-c1ccc(F)c2c1CC[C@H]2Oc1ccc2c(c1)OC[C@H]2CC(=O)O]

The title compound is prepared from methyl 2-((S)-6-((R)-7-fluoro-4-(4-(2-(2-hydroxy-2-methylpropyl)-2H-tetrazol-5-yl)-2,6-dimethylphenyl)-2,3-dihydro-1H-inden-1-yloxy)-2,3-dihydrobenzofuran-3-yl)acetate following a procedure analogous to that described in example 1. The mixture is stirred for 2 hours at 40° C. LC (method 11): $t_R$=1.15 min; Mass spectrum (ESI$^+$): m/z=573 [M+H]$^+$.

Example 99

2-((S)-6-((R)-7-Fluoro-4-(4-(2-(1-hydroxy-2-methylpropan-2-yl)-2H-tetrazol-5-yl)-2,6-dimethylphenyl)-2,3-dihydro-1H-inden-1-yloxy)-2,3-dihydrobenzofuran-3-yl)acetic acid

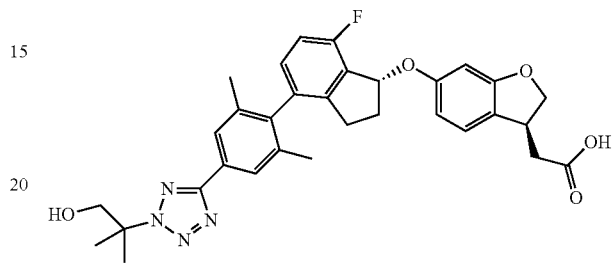

The title compound is prepared from methyl 2-((S)-6-((R)-7-fluoro-4-(4-(2-(1-hydroxy-2-methylpropan-2-yl)-2H-tetrazol-5-yl)-2,6-dimethylphenyl)-2,3-dihydro-1H-inden-1-yloxy)-2,3-dihydrobenzofuran-3-yl)acetate following a procedure analogous to that described in example 1. The mixture is stirred for 2 hours at 40° C. LC (method 11): $t_R$=1.16 min; Mass spectrum (ESI$^+$): m/z=573 [M+H]$^+$.

Example 100

2-((3S)-6-((1R)-4-(2-(Neopentyloxy)pyridin-3-yl)-2,3-dihydro-1H-inden-1-yloxy)-2,3-dihydrobenzofuran-3-yl)acetic acid

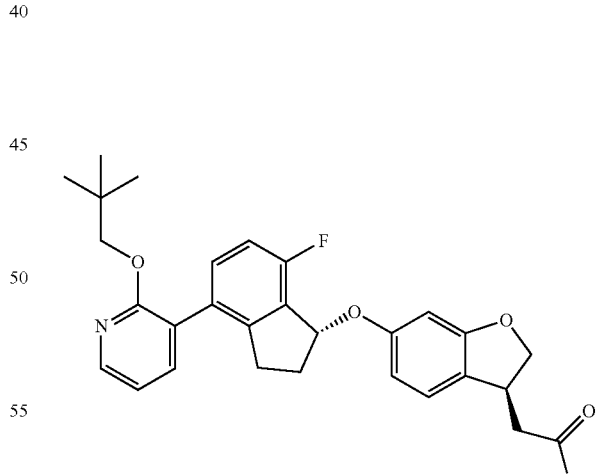

The title compound is prepared from methyl 2-((3S)-6-((1R)-4-(2-(neopentyloxy)pyridin-3-yl)-2,3-dihydro-1H-inden-1-yloxy)-2,3-dihydrobenzofuran-3-yl)acetate following a procedure analogous to that described in example 1. The product is purified by HPLC on reversed phase. LC (method 15): $t_R$=1.26 min; Mass spectrum (ESI$^+$): m/z=492 [M+H]$^+$.

Example 101

2-((S)-6-((R)-4-(2,6-Dimethyl-4-(1-methyl-6-oxo-1,6-dihydropyridazin-3-yl)phenyl)-7-fluoro-2,3-dihydro-1H-inden-1-yloxy)-2,3-dihydrobenzofuran-3-yl)acetic acid

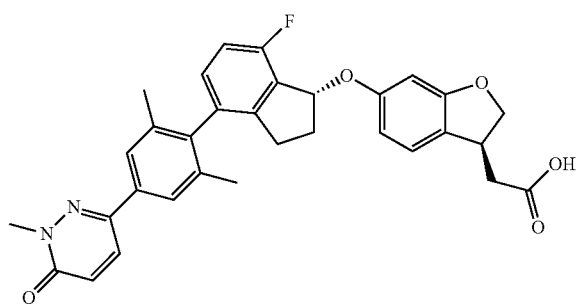 [SMILES: Cc1cc(-c2ccc(=O)n(C)n2)cc(C)c1-c1ccc(F)c2c1CC[C@H]2Oc1ccc2c(c1)OC[C@H]2CC(=O)O]

The title compound is prepared from methyl 2-((S)-6-((R)-4-(2,6-dimethyl-4-(1-methyl-6-oxo-1,6-dihydropyridazin-3-yl)phenyl)-7-fluoro-2,3-dihydro-1H-inden-1-yloxy)-2,3-dihydrobenzofuran-3-yl)acetate following a procedure analogous to that described in example 1. LC (method 7): $t_R$=1.09 min; Mass spectrum (ESI$^+$): m/z=541 [M+H]$^+$.

Example 102

2-((3S)-6-((1R)-4-(2-(Dimethylcarbamoyl)phenyl)-7-fluoro-2,3-dihydro-1H-inden-1-yloxy)-2,3-dihydrobenzofuran-3-yl)acetic acid

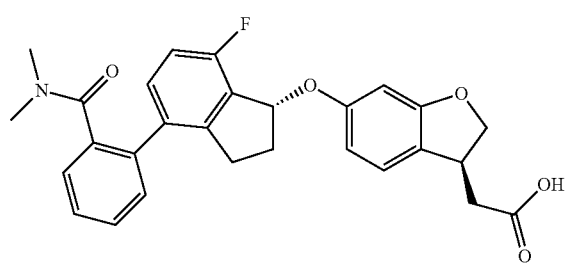 [SMILES: CN(C)C(=O)c1ccccc1-c1ccc(F)c2c1CC[C@H]2Oc1ccc2c(c1)OC[C@H]2CC(=O)O]

The title compound is prepared from methyl 2-((3S)-6-((1R)-4-(2-(dimethylcarbamoyl)phenyl)-7-fluoro-2,3-dihydro-1H-inden-1-yloxy)-2,3-dihydrobenzofuran-3-yl)acetate following a procedure analogous to that described in example 1. The product is purified by HPLC on reversed phase. LC (method 9): $t_R$=1.01 min; Mass spectrum (ESI$^+$): m/z=476 [M+H]$^+$.

Example 103

2-((3S)-6-((1R)-7-Fluoro-4-(3-fluoro-2-(1-methyl-1H-tetrazol-5-yl)phenyl)-2,3-dihydro-1H-inden-1-yloxy)-2,3-dihydrobenzofuran-3-yl)acetic acid

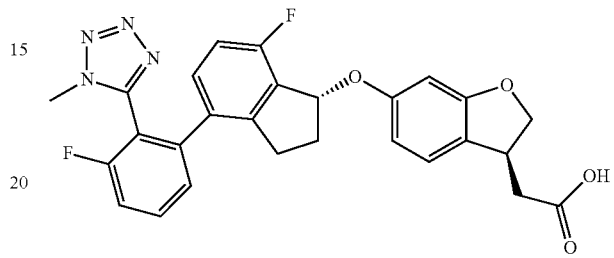

The title compound is prepared from methyl 2-((3S)-6-((1S)-7-fluoro-4-(3-fluoro-2-(1-methyl-1H-tetrazol-5-yl)phenyl)-2,3-dihydro-1H-inden-1-yloxy)-2,3-dihydrobenzofuran-3-yl)acetate following a procedure analogous to that described in example 1. The product is purified by HPLC on reversed phase. LC (method 9): $t_R$=1.01 min; Mass spectrum (ESI$^+$): m/z=505 [M+H]$^+$.

Example 104

{(S)-6-[(R)-4-(2,6-Dimethyl-4-pyridin-4-yl-phenyl)-7-fluoro-indan-1-yloxy]-2,3-dihydro-benzofuran-3-yl}-acetic acid

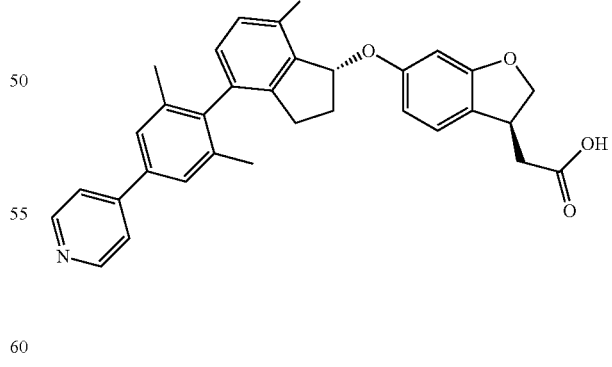

The title compound is prepared from {(S)-6-[(R)-4-(2,6-dimethyl-4-pyridin-4-yl-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=0.98 min; Mass spectrum (ESI$^+$): m/z=510 [M+H]$^+$.

Example 105

{(S)-6-[(R)-7-Fluoro-4-(2-furan-3-yl-pyridin-3-yl)-indan-1-yloxy]-2,3-dihydro-benzofuran-3-yl}-acetic acid

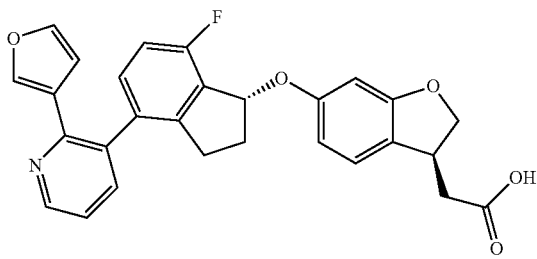 [SMILES: O=C(O)C[C@@H]1COc2cc(O[C@@H]3CCc4c(-c5cccnc5-c5ccoc5)ccc(F)c43)ccc21]

The title compound is prepared from {(S)-6-[(R)-7-fluoro-4-(2-furan-3-yl-pyridin-3-yl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.04 min; Mass spectrum (ESI$^+$): m/z=472 [M+H]$^+$.

Example 106

{(S)-6-[(R)-7-Fluoro-4-(2-phenyl-pyridin-3-yl)-indan-1-yloxy]-2,3-dihydro-benzofuran-3-yl}-acetic acid

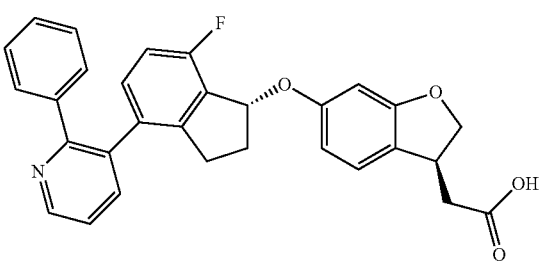 [SMILES: O=C(O)C[C@@H]1COc2cc(O[C@@H]3CCc4c(-c5cccnc5-c5ccccc5)ccc(F)c43)ccc21]

The title compound is prepared from {(S)-6-[(R)-7-fluoro-4-(2-phenyl-pyridin-3-yl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.04 min; Mass spectrum (ESI$^+$): m/z=482 [M+H]$^+$.

Example 107

{(S)-6-[(R)-4-(2,6-Dimethyl-4-(2-methyl-pyridin-4-yl)-phenyl)-7-fluoro-indan-1-yloxy]-2,3-dihydro-benzofuran-3-yl}-acetic acid

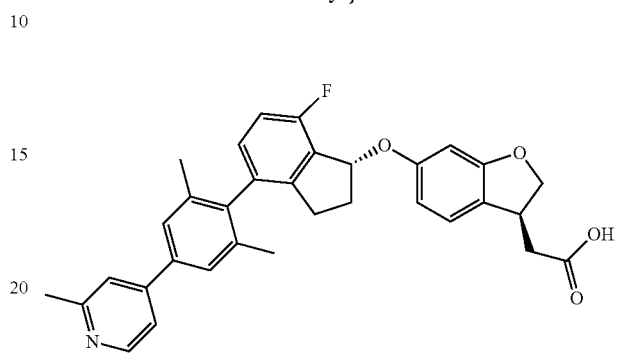

The methyl ester of the title compound is prepared from {(S)-6-[(R)-7-fluoro-4-(4,4,5,5-tetramethyl-[1,3,2]dioxaborolan-2-yl)-indan-1-yloxy]-2,3-dihydro-benzofuran-3-yl}-acetic acid methyl ester and 4-(4-bromo-3,5-dimethyl-phenyl)-2-methyl-pyridine following a procedure analogous to that described in Step 5 of Intermediate 1. Saponification of the methyl ester following a procedure analogous to that described for Example 4 gives the title compound; if the title compound does not precipitate from the aqueous solution, the crude title compound is purified by HPLC. LC (method 9): $t_R$=0.95 min; Mass spectrum (ESI$^+$): m/z=524 [M+H]$^+$.

Example 108

{(S)-6-[(R)-7-Fluoro-4-[2-(1,3,5-trimethyl-pyrazol-4-yl)-pyridin-3-yl]-indan-1-yloxy]-2,3-dihydro-benzofuran-3-yl}-acetic acid

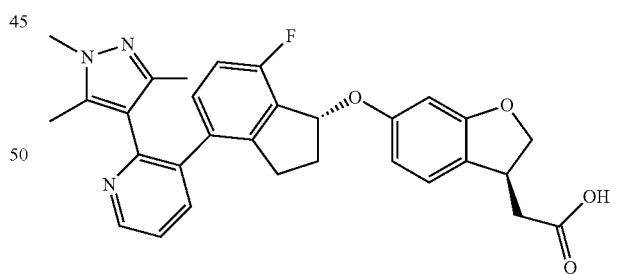

The methyl ester of the title compound is prepared from {(S)-6-[(R)-4-(2-bromo-pyridin-3-yl)-7-fluoro-indan-1-yloxy]-2,3-dihydro-benzofuran-3-yl}-acetic acid methyl ester and 1,3,5-trimethyl-4-(4,4,5,5-tetramethyl-[1,3,2]dioxaborolan-2-yl)-pyrazole following a procedure analogous to that described in Step 5 of Intermediate 1. Saponification of the methyl ester, {(S)-6-[(R)-7-fluoro-4-[2-(1,3,5-trimethyl-1H-pyrazol-4-yl)-pyridin-3-yl]-indan-1-yloxy]-2,3-dihydro-benzofuran-3-yl}-acetic acid methyl ester, following a procedure analogous to that described for Example 4 gives the title compound; if the title compound does not precipitate from the aqueous solution, the crude title compound is purified by HPLC. LC (method 9): $t_R$=0.88 min; Mass spectrum (ESI$^+$): m/z=514 [M+H]$^+$.

Example 109

{(S)-6-[(R)-4-(2,6-Dimethyl-4-(1,3,5-trimethyl-pyrazol-4-yl)-phenyl)-7-fluoro-indan-1-yloxy]-2,3-dihydro-benzofuran-3-yl}-acetic acid

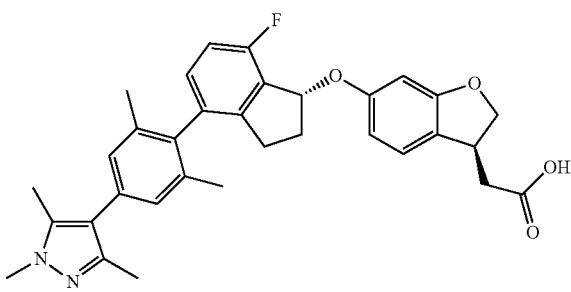 [SMILES: Cc1cc(-c2c(C)nn(C)c2C)cc(C)c1-c1ccc(F)c2c1CC[C@H]2Oc1ccc2c(c1)OC[C@H]2CC(=O)O]

The title compound is prepared from {(S)-6-[(R)-7-fluoro-4-(2,6-dimethyl-4-(1,3,5-trimethyl-pyrazol-4-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.13 min; Mass spectrum (ESI$^+$): m/z=541 [M+H]$^+$.

Example 110

{(S)-6-[(R)-7-Fluoro-4-(2-tetrahydropyran-4-yl-pyridin-3-yl)-indan-1-yloxy]-2,3-dihydro-benzofuran-3-yl}-acetic acid

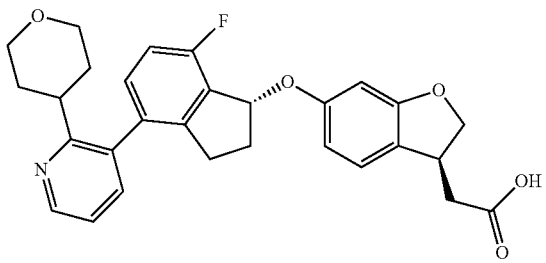

A mixture of {(S)-6-[(R)-7-fluoro-4-(2-(3,6-dihydro-pyran-4-yl)-pyridin-3-yl)-indan-1-yloxy]-2,3-dihydro-benzofuran-3-yl}-acetic acid (30 mg), 10% palladium on carbon (10 mg) and methanol (3 mL) is shaken under hydrogen atmosphere (3 bar) at room temperature for 12 h. The mixture is filtered over Celite and the filtrate is concentrated to give the title compound. LC (method 9): $t_R$=0.96 min; Mass spectrum (ESI$^+$): m/z=490 [M+H]$^+$.

Example 111

{(S)-6-[(R)-4-(2,6-Dimethyl-4-(5-methyl-pyridin-3-yl)-phenyl)-7-fluoro-indan-1-yloxy]-2,3-dihydro-benzofuran-3-yl}-acetic acid

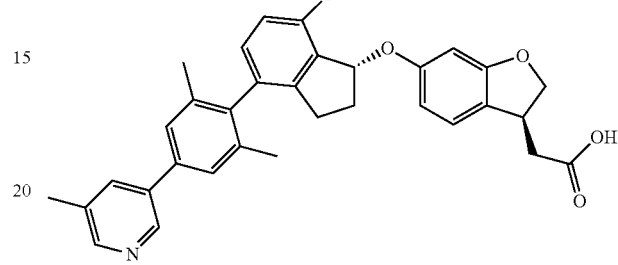

The title compound is prepared from {(S)-6-[(R)-4-(2,6-dimethyl-4-(5-methyl-pyridin-3-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.06 min; Mass spectrum (ESI$^+$): m/z=524 [M+H]$^+$.

Example 112

{(S)-6-[(R)-4-(2,6-Dimethyl-4-pyridin-3-yl-phenyl)-7-fluoro-indan-1-yloxy]-2,3-dihydro-benzofuran-3-yl}-acetic acid

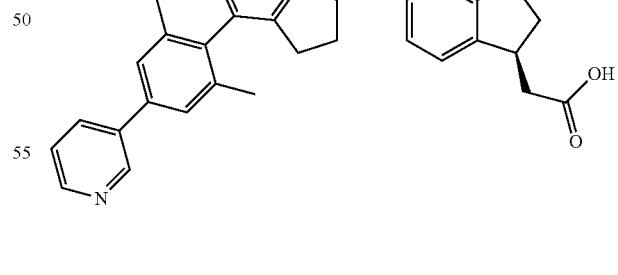

The title compound is prepared from {(S)-6-[(R)-4-(2,6-dimethyl-4-pyridin-3-yl-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.06 min; Mass spectrum (ESI⁺): m/z=510 [M+H]⁺.

Example 113

{(S)-6-[(R)-4-(2,6-Dimethyl-4-(5-methyl-pyrimidin-2-yl)-phenyl)-7-fluoro-indan-1-yloxy]-2,3-dihydro-benzofuran-3-yl}-acetic acid

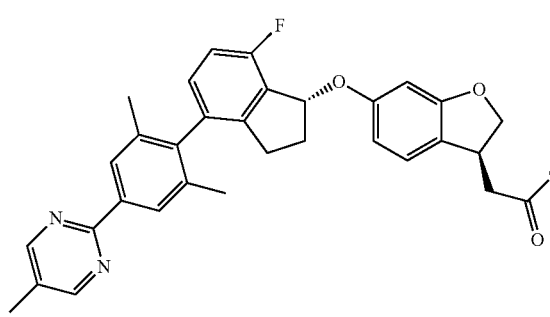

The title compound is prepared from {(S)-6-[(R)-4-(2,6-dimethyl-4-(5-methyl-pyrimidin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=1.19 min; Mass spectrum (ESI⁻): m/z=523 [M−H]⁻.

Example 114

{(S)-6-[(R)-4-(2,6-Dimethyl-4-(5-methyl-pyrazin-2-yl)-phenyl)-7-fluoro-indan-1-yloxy]-2,3-dihydro-benzofuran-3-yl}-acetic acid

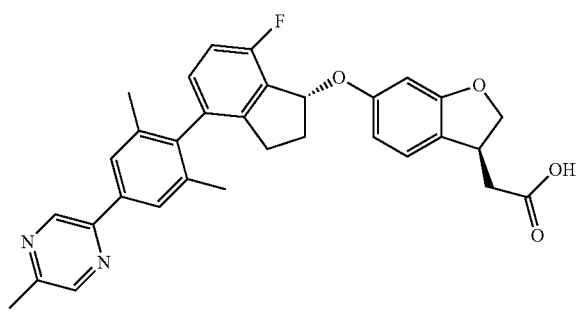

The title compound is prepared from {(S)-6-[(R)-4-(2,6-dimethyl-4-(5-methyl-pyrazin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=1.05 min; Mass spectrum (ESI⁺): m/z=525 [M+H]⁺.

Example 115

{(S)-6-[(R)-4-(2,6-Dimethyl-4-(2,6-dimethyl-pyrimidin-4-yl)-phenyl)-7-fluoro-indan-1-yloxy]-2,3-dihydro-benzofuran-3-yl}-acetic acid

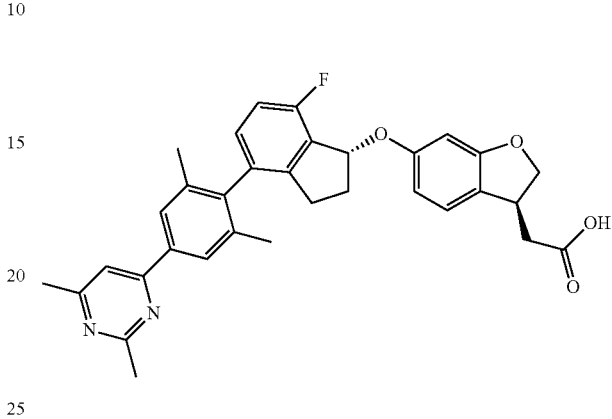

The title compound is prepared from {(S)-6-[(R)-4-(2,6-dimethyl-4-(2,6-dimethyl-pyrimidin-4-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=1.15 min; Mass spectrum (ESI⁻): m/z=537 [M−H]⁻.

Example 116

{(S)-6-[(R)-4-(2,6-Dimethyl-4-(2-methoxy-pyridin-4-yl)-phenyl)-7-fluoro-indan-1-yloxy]-2,3-dihydro-benzofuran-3-yl}-acetic acid

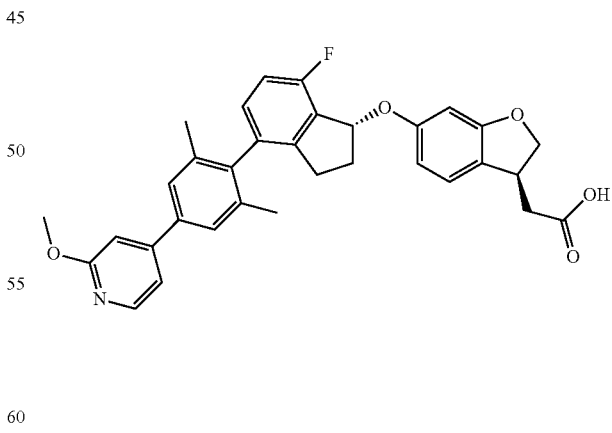

The title compound is prepared from {(S)-6-[(R)-4-(2,6-dimethyl-4-(2-methoxy-pyridin-4-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title com-

Example 117

{(S)-6-[(R)-4-(2,6-Dimethyl-4-(6-methyl-pyridin-3-yl)-phenyl)-7-fluoro-indan-1-yloxy]-2,3-dihydro-benzofuran-3-yl}-acetic acid

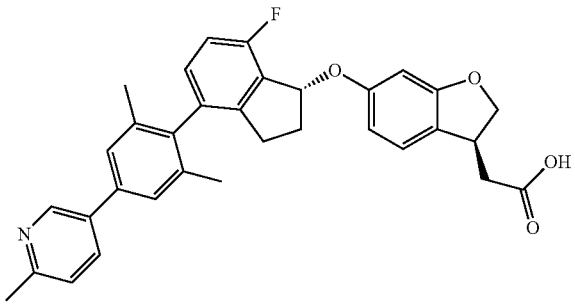 [SMILES: Cc1ccc(-c2cc(C)c(-c3ccc(F)c4c3CC[C@H]4Oc3ccc4c(c3)OC[C@H]4CC(=O)O)c(C)c2)cn1]

The title compound is prepared from {(S)-6-[(R)-4-(2,6-dimethyl-4-(6-methyl-pyridin-3-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.84 min; Mass spectrum (ESI$^+$): m/z=524 [M+H]$^+$.

Example 118

{(S)-6-[(R)-4-(2,6-Dimethyl-4-(6-methyl-pyrazin-2-yl)-phenyl)-7-fluoro-indan-1-yloxy]-2,3-dihydro-benzofuran-3-yl}-acetic acid

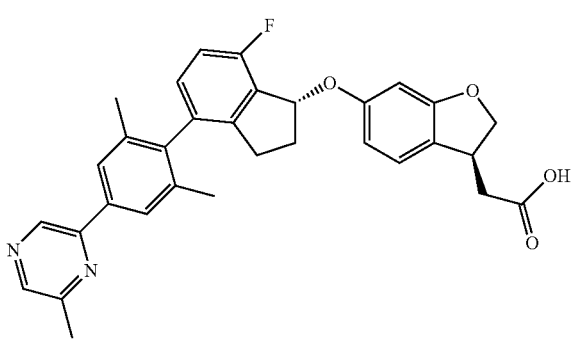 [SMILES: Cc1cncc(-c2cc(C)c(-c3ccc(F)c4c3CC[C@H]4Oc3ccc4c(c3)OC[C@H]4CC(=O)O)c(C)c2)n1]

The title compound is prepared from {(S)-6-[(R)-4-(2,6-dimethyl-4-(6-methyl-pyrazin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.23 min; Mass spectrum (ESI$^+$): m/z=540 [M+H]$^+$.

Example 119

{(S)-6-[(R)-4-(2,6-Dimethyl-4-(4-methyl-pyrimidin-2-yl)-phenyl)-7-fluoro-indan-1-yloxy]-2,3-dihydro-benzofuran-3-yl}-acetic acid

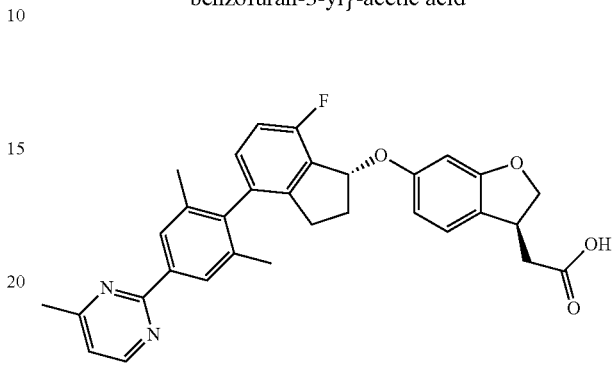

The title compound is prepared from {(S)-6-[(R)-4-(2,6-dimethyl-4-(4-methyl-pyrimidin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.20 min; Mass spectrum (ESI$^-$): m/z=523 [M−H]$^-$.

Example 120

{(S)-6-[(R)-4-(2,6-Dimethyl-4-(6-methyl-pyridazin-3-yl)-phenyl)-7-fluoro-indan-1-yloxy]-2,3-dihydro-benzofuran-3-yl}-acetic acid

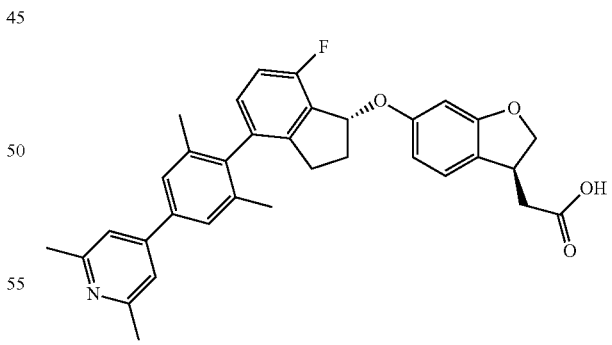

The title compound is prepared from {(S)-6-[(R)-4-(2,6-dimethyl-4-(6-methyl-pyridazin-3-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.18 min; Mass spectrum (ESI$^+$): m/z=525 [M+H]$^+$.

pound is purified by HPLC. LC (method 9): $t_R$=1.08 min; Mass spectrum (ESI⁺): m/z=525 [M+H]⁺.

Example 121

{(S)-6-[(R)-4-(2,6-Dimethyl-4-(2,6-dimethyl-pyridin-4-yl)-phenyl)-7-fluoro-indan-1-yloxy]-2,3-dihydro-benzofuran-3-yl}-acetic acid

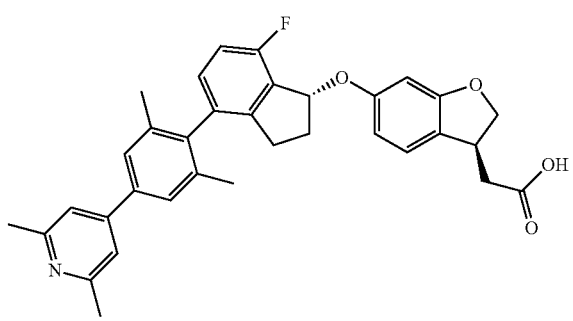 [SMILES: Cc1cc(-c2cc(C)c(-c3ccc(F)c4c3CC[C@H]4Oc3ccc4c(c3)OC[C@H]4CC(=O)O)c(C)c2)cc(C)n1]

The title compound is prepared from {(S)-6-[(R)-4-(2,6-dimethyl-4-(2,6-dimethyl-pyridin-4-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.99 min; Mass spectrum (ESI⁺): m/z=538 [M+H]⁺.

Example 122

{(S)-6-[(R)-4-(2,6-Dimethyl-4-pyrazin-2-yl-phenyl)-7-fluoro-indan-1-yloxy]-2,3-dihydro-benzofuran-3-yl}-acetic acid

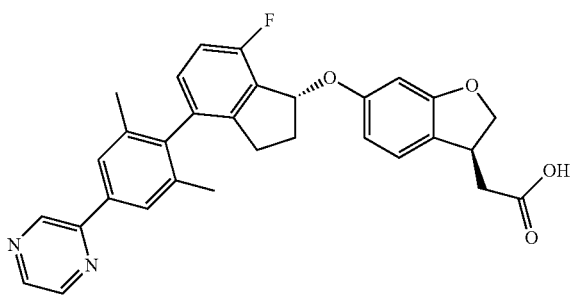 [SMILES: Cc1cc(-c2cnccn2)cc(C)c1-c1ccc(F)c2c1CC[C@H]2Oc1ccc2c(c1)OC[C@H]2CC(=O)O]

The title compound is prepared from {(S)-6-[(R)-4-(2,6-dimethyl-4-pyrazin-2-yl-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=1.14 min; Mass spectrum (ESI⁺): m/z=511 [M+H]⁺.

Example 123

{(S)-6-[(R)-4-(2,6-Dimethyl-4-(5-cyclopropyl-pyrazin-2-yl)-phenyl)-7-fluoro-indan-1-yloxy]-2,3-dihydro-benzofuran-3-yl}-acetic acid

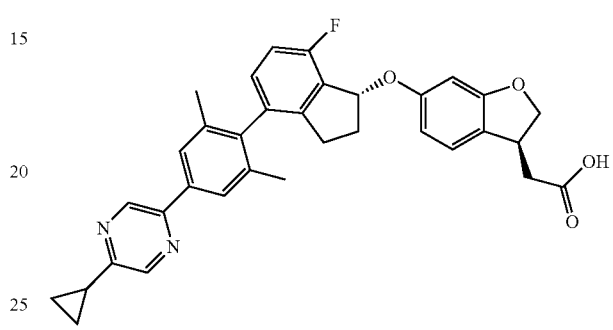

The title compound is prepared from {(S)-6-[(R)-4-(2,6-dimethyl-4-(5-cyclopropyl-pyrazin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 11): $t_R$=1.27 min; Mass spectrum (ESI⁺): m/z=551 [M+H]⁺.

Example 124

{(S)-6-[(R)-4-(2-(2,6-Dimethyl-phenyl)-pyridin-3-yl)-7-fluoro-indan-1-yloxy]-2,3-dihydro-benzofuran-3-yl}-acetic acid

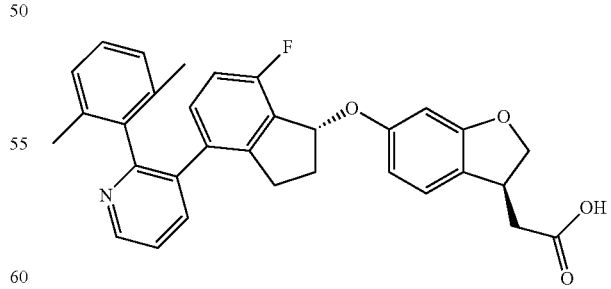

The title compound is prepared from {(S)-6-[(R)-4-(2-(2,6-dimethyl-phenyl)-pyridin-3-yl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.80 min; Mass spectrum (ESI$^+$): m/z=510 [M+H]$^+$.

Example 125

{(S)-6-[(R)-4-(2,6-Dimethyl-4-(6-ethyl-pyridazin-3-yl)-phenyl)-7-fluoro-indan-1-yloxy]-2,3-dihydro-benzofuran-3-yl}-acetic acid

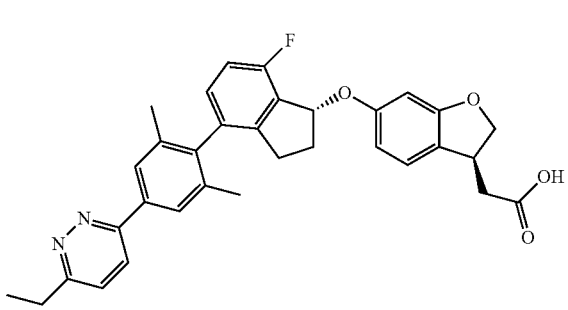 [SMILES: CCc1ccc(-c2cc(C)c(-c3ccc(F)c4c3CC[C@H]4Oc3ccc4c(c3)OC[C@H]4CC(=O)O)c(C)c2)nn1]

The title compound is prepared from {(S)-6-[(R)-4-(2,6-dimethyl-4-(6-ethyl-pyridazin-3-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 11): $t_R$=1.06 min; Mass spectrum (ESI$^+$): m/z=539 [M+H]$^+$.

Example 126

{(S)-6-[(R)-4-(2,6-Dimethyl-4-(6-methoxy-pyridin-3-yl)-phenyl)-7-fluoro-indan-1-yloxy]-2,3-dihydro-benzofuran-3-yl}-acetic acid

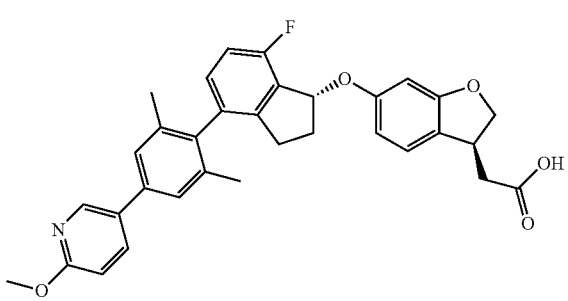 [SMILES: COc1ccc(-c2cc(C)c(-c3ccc(F)c4c3CC[C@H]4Oc3ccc4c(c3)OC[C@H]4CC(=O)O)c(C)c2)cn1]

The title compound is prepared from {(S)-6-[(R)-4-(2,6-dimethyl-4-(6-methoxy-pyridin-3-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 11): $t_R$=1.24 min; Mass spectrum (ESI$^+$): m/z=540 [M+H]$^+$.

Example 127

{(S)-6-[(R)-7-Fluoro-4-(2-[1,4]oxazepan-4-yl-pyridin-3-yl)-indan-1-yloxy]-2,3-dihydro-benzofuran-3-yl}-acetic acid

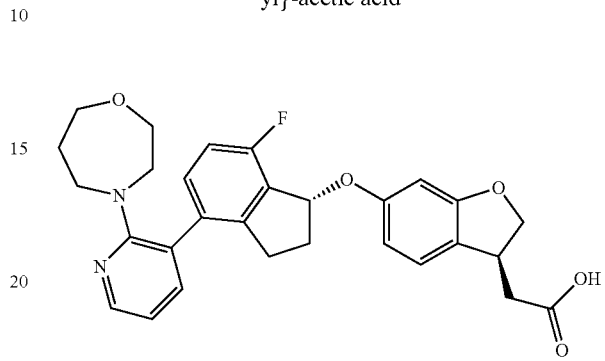

The title compound is prepared from {(S)-6-[(R)-7-fluoro-4-(2-fluoro-pyridin-3-yl)-indan-1-yloxy]-2,3-dihydro-benzofuran-3-yl}-acetic acid methyl ester and [1,4]oxazepane following a procedure analogous to that described for Example 128. LC (method 9): $t_R$=0.87 min; Mass spectrum (ESI$^+$): m/z=505 [M+H]$^+$.

Example 128

{(S)-6-[(R)-7-Fluoro-4-(2-morpholin-4-yl-pyridin-3-yl)-indan-1-yloxy]-2,3-dihydro-benzofuran-3-yl}-acetic acid

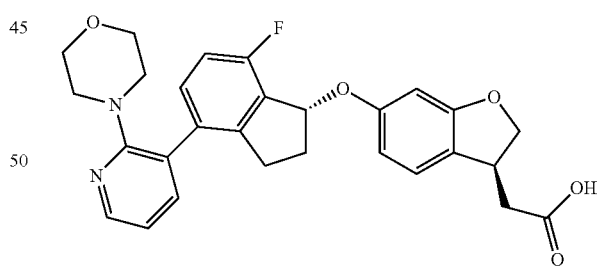

A mixture of {(S)-6-[(R)-7-fluoro-4-(2-fluoro-pyridin-3-yl)-indan-1-yloxy]-2,3-dihydro-benzofuran-3-yl}-acetic acid methyl ester (0.10 g), morpholine (0.10 g) and N-methyl-pyrrolidone (2 mL) is stirred at 180° C. for 48 h. After cooling to room temperature, 2 N aqueous NaOH solution (0.5 mL) is added, and the resulting mixture is stirred at 40° C. for 2 h. The mixture is neutralized with 1 N aqueous HCl solution and concentrated. The residue is chromatographed on reversed

Example 129

{(S)-6-[(R)-4-(2,6-Dimethyl-4-(5-methoxy-pyridazin-3-yl)-phenyl)-7-fluoro-indan-1-yloxy]-2,3-dihydro-benzofuran-3-yl}-acetic acid

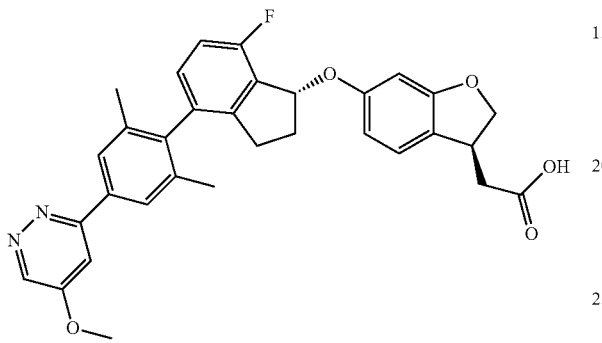

The title compound is prepared from {(S)-6-[(R)-4-(2,6-dimethyl-4-(5-methoxy-pyridazin-3-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 11): $t_R$=1.10 min; Mass spectrum (ESI$^+$): m/z=541 [M+H]$^+$.

Example 130

{(S)-6-[(R)-4-(2,6-Dimethyl-4-(6-methyl-pyridazin-4-yl)-phenyl)-7-fluoro-indan-1-yloxy]-2,3-dihydro-benzofuran-3-yl}-acetic acid

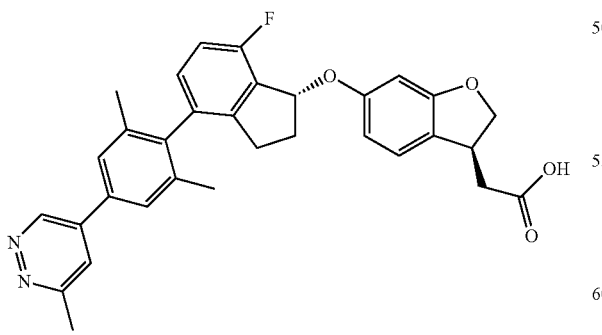

The title compound is prepared from {(S)-6-[(R)-4-(2,6-dimethyl-4-(6-methyl-pyridazin-4-yl)-phenyl)-7-fluoro-indan-1-yloxy]-2,3-dihydro-benzofuran-3-yl}-acetic acid methyl ester following a procedure analogous to that described for Example 4. LC (method 11): $t_R$=1.00 min; Mass spectrum (ESI$^+$): m/z=525 [M+H]$^+$.

Example 131

{(S)-6-[(R)-4-(2,6-Dimethyl-4-(1,2-dimethyl-imidazol-4-yl)-phenyl)-7-fluoro-indan-1-yloxy]-2,3-dihydro-benzofuran-3-yl}-acetic acid

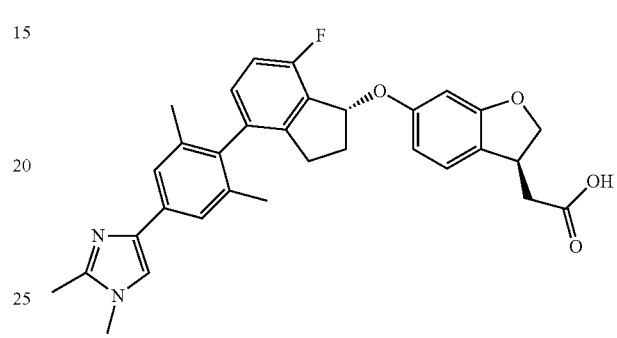

The title compound is prepared from {(S)-6-[(R)-7-fluoro-4-(2,6-dimethyl-4-(1,2-dimethyl-imidazol-4-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=0.88 min; Mass spectrum (ESI$^+$): m/z=527 [M+H]$^+$.

Example 132

{(S)-6-[(R)-4-(2,6-Dimethyl-4-thiazol-2-yl-phenyl)-7-fluoro-indan-1-yloxy]-2,3-dihydro-benzofuran-3-yl}-acetic acid

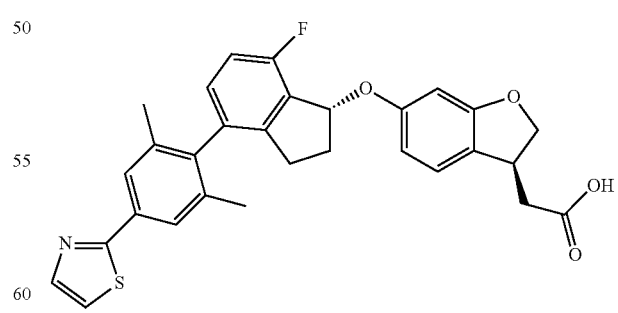

The title compound is prepared from {(S)-6-[(R)-7-fluoro-4-(2,6-dimethyl-4-thiazol-2-yl-phenyl)-indan-1-yloxy]-2,3-dihydro-benzofuran-3-yl}-acetic acid methyl ester following a procedure analogous to that described for Example 4; if the title compound does not precipitate from the aqueous solu-

Example 133

{(S)-6-[(R)-4-(2,6-Dimethyl-4-(1-methyl-imidazol-4-yl)-phenyl)-7-fluoro-indan-1-yloxy]-2,3-dihydro-benzofuran-3-yl}-acetic acid

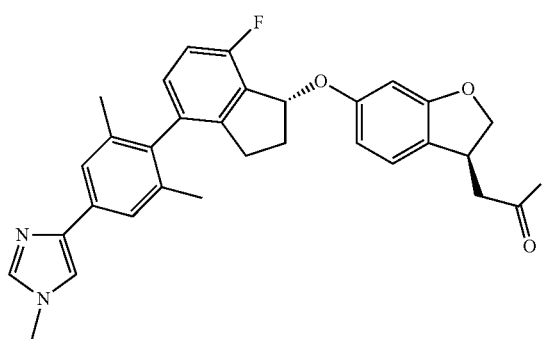

The title compound is prepared from {(S)-6-[(R)-7-fluoro-4-(2,6-dimethyl-4-(1-methyl-imidazol-4-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 9): $t_R$=0.89 min; Mass spectrum (ESI$^+$): m/z=513 [M+H]$^+$.

Example 134

{(S)-6-[(R)-4-(2,6-Dimethyl-4-(5-methyl-[1,2,4]oxadiazol-3-yl)-phenyl)-7-fluoro-indan-1-yloxy]-2,3-dihydro-benzofuran-3-yl}-acetic acid

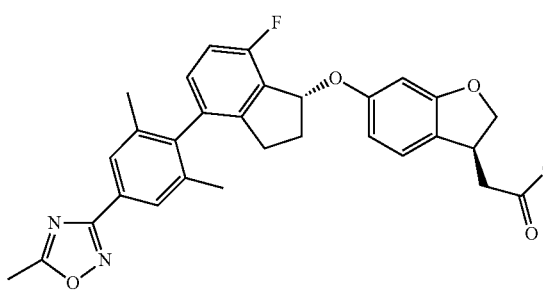

The title compound is prepared from {(S)-6-[(R)-7-fluoro-4-(2,6-dimethyl-4-(5-methyl-[1,2,4]oxadiazol-3-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 11): $t_R$=1.20 min; Mass spectrum (ESI$^+$): m/z=515 [M+H]$^+$.

Example 135

{(S)-6-[(R)-4-(2,6-Dimethyl-4-(5-methoxy-pyridin-2-yl)-phenyl)-7-fluoro-indan-1-yloxy]-2,3-dihydro-benzofuran-3-yl}-acetic acid

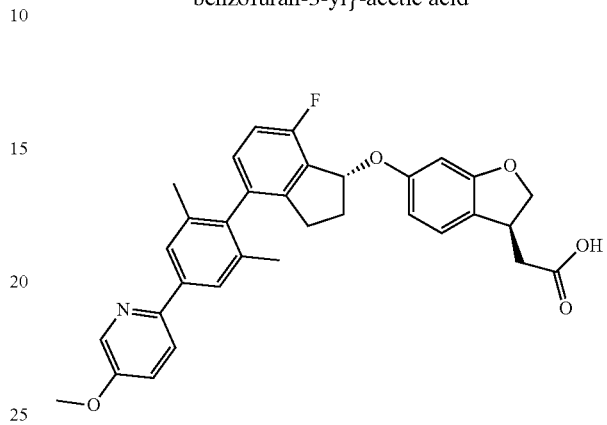

The title compound is prepared from {(S)-6-[(R)-4-(2,6-dimethyl-4-(5-methoxy-pyridin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 8): $t_R$=0.79 min; Mass spectrum (ESI$^+$): m/z=540 [M+H]$^+$.

Example 136

{(S)-6-[(R)-4-(2,6-Dimethyl-4-(5-[2-hydroxy-prop-2-yl]-[1,2,4]oxadiazol-3-yl)-phenyl)-7-fluoro-indan-1-yloxy]-2,3-dihydro-benzofuran-3-yl}-acetic acid

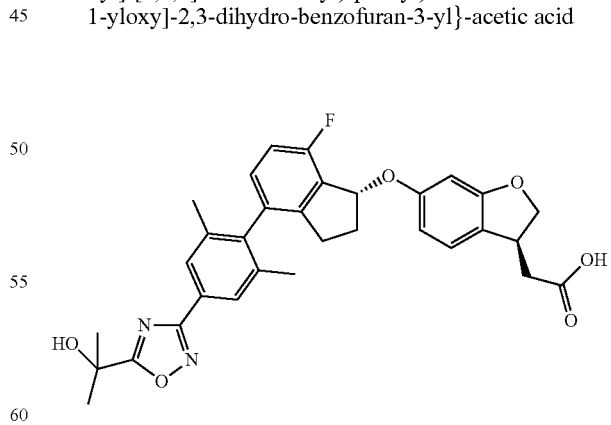

The title compound is prepared from {(S)-6-[(R)-7-fluoro-4-(2,6-dimethyl-4-(5-[2-hydroxy-prop-2-yl]-[1,2,4]oxadiazol-3-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 11): $t_R$=1.16 min; Mass spectrum (ESI⁺): m/z=559 [M+H]⁺.

Example 137

{(S)-6-[(R)-4-(2,6-Dimethyl-4-pyridin-2-yl-phenyl)-7-fluoro-indan-1-yloxy]-2,3-dihydro-benzofuran-3-yl}-acetic acid

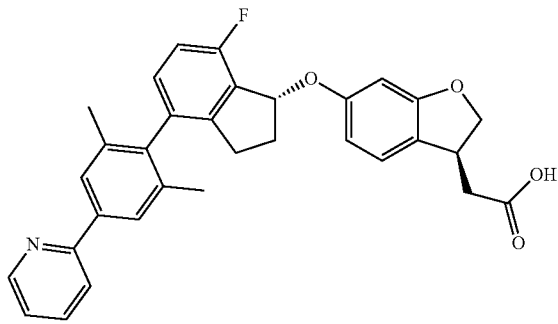 [SMILES: Cc1cc(-c2ccccn2)cc(C)c1-c1ccc(F)c2c1CC[C@H]2Oc1ccc2c(c1)OC[C@H]2CC(=O)O]

The title compound is prepared from {(S)-6-[(R)-4-(2,6-dimethyl-4-pyridin-2-yl-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.99 min; Mass spectrum (ESI⁺): m/z=510 [M+H]⁺.

Example 138

{(S)-6-[(R)-4-(2,6-Dimethyl-4-(3-methyl-pyridin-2-yl)-phenyl)-7-fluoro-indan-1-yloxy]-2,3-dihydro-benzofuran-3-yl}-acetic acid

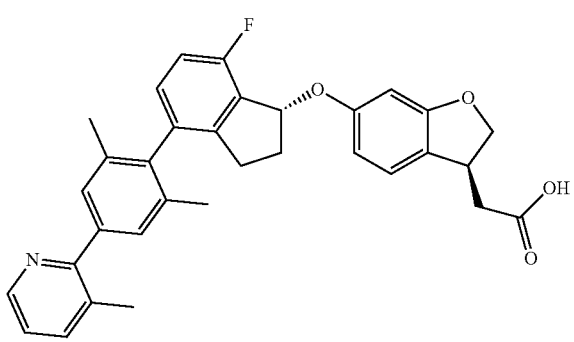 [SMILES: Cc1cccnc1-c1cc(C)c(-c2ccc(F)c3c2CC[C@H]3Oc2ccc3c(c2)OC[C@H]3CC(=O)O)c(C)c1]

The title compound is prepared from {(S)-6-[(R)-4-(2,6-dimethyl-4-(3-methyl-pyridin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.97 min; Mass spectrum (ESI⁺): m/z=524 [M+H]⁺.

Example 139

{(S)-6-[(R)-4-(2,6-Dimethyl-4-(6-methyl-pyridin-2-yl)-phenyl)-7-fluoro-indan-1-yloxy]-2,3-dihydro-benzofuran-3-yl}-acetic acid

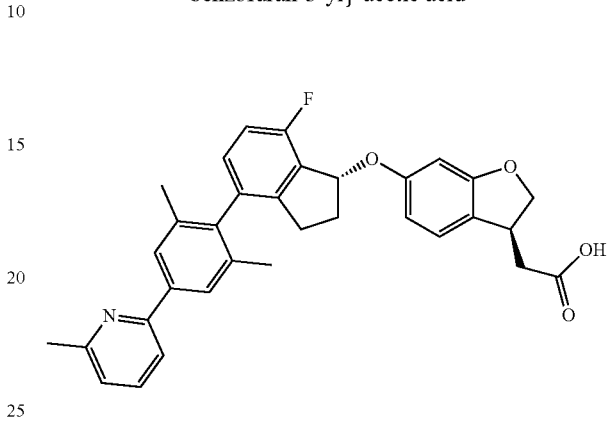

The title compound is prepared from {(S)-6-[(R)-4-(2,6-dimethyl-4-(6-methyl-pyridin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.99 min; Mass spectrum (ESI⁺): m/z=524 [M+H]⁺.

Example 140

{(S)-6-[(R)-4-(2,6-Dimethyl-4-(4-methyl-pyridin-2-yl)-phenyl)-7-fluoro-indan-1-yloxy]-2,3-dihydro-benzofuran-3-yl}-acetic acid

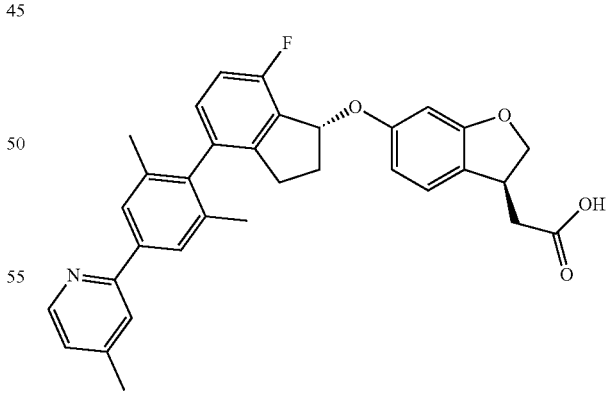

The title compound is prepared from {(S)-6-[(R)-4-(2,6-dimethyl-4-(4-methyl-pyridin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.98 min; Mass spectrum (ESI⁺): m/z=524 [M+H]⁺.

Example 141

{(S)-6-[(R)-4-(2,6-Dimethyl-4-(4,6-dimethyl-pyridin-2-yl)-phenyl)-7-fluoro-indan-1-yloxy]-2,3-dihydro-benzofuran-3-yl}-acetic acid

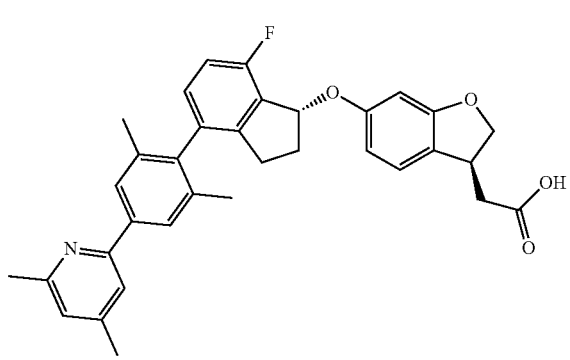 [SMILES: Cc1cc(C)nc(-c2cc(C)c(-c3ccc(F)c4c3CC[C@H]4Oc3ccc4c(c3)OC[C@H]4CC(=O)O)c(C)c2)c1]

The title compound is prepared from {(S)-6-[(R)-4-(2,6-dimethyl-4-(4,6-dimethyl-pyridin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.99 min; Mass spectrum (ESI⁺): m/z=538 [M+H]⁺.

Example 142

{(S)-6-[(R)-4-(2,6-Dimethyl-4-(1,4-dimethyl-imidazol-2-yl)-phenyl)-7-fluoro-indan-1-yloxy]-2,3-dihydro-benzofuran-3-yl}-acetic acid

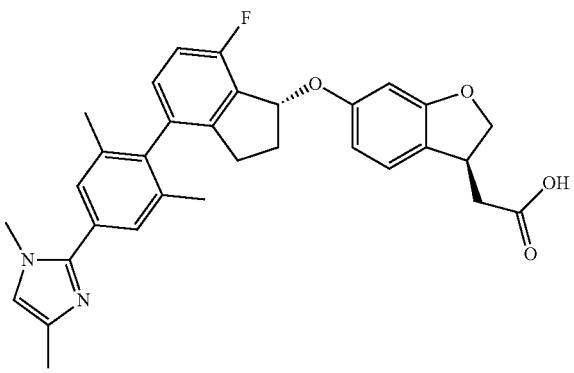 [SMILES: Cc1cn(C)c(-c2cc(C)c(-c3ccc(F)c4c3CC[C@H]4Oc3ccc4c(c3)OC[C@H]4CC(=O)O)c(C)c2)n1]

The title compound is prepared from {(S)-6-[(R)-7-fluoro-4-(2,6-dimethyl-4-(1,4-dimethyl-imidazol-2-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.95 min; Mass spectrum (ESI⁺): m/z=527 [M+H]⁺.

Example 143

{(S)-6-[(R)-4-(2,6-Dimethyl-4-(5-methyl-pyridin-2-yl)-phenyl)-7-fluoro-indan-1-yloxy]-2,3-dihydro-benzofuran-3-yl}-acetic acid

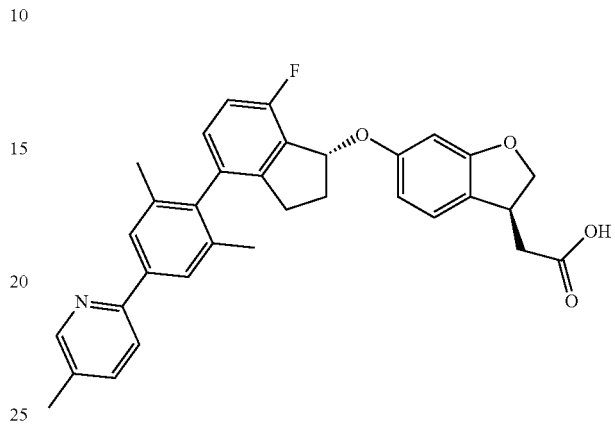

The title compound is prepared from {(S)-6-[(R)-4-(2,6-dimethyl-4-(5-methyl-pyridin-2-yl)-phenyl)-7-fluoro-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.99 min; Mass spectrum (ESI⁺): m/z=524 [M+H]⁺.

Example 144

{(S)-6-[(R)-4-(2,6-Dimethyl-4-(1-methyl-imidazol-2-yl)-phenyl)-7-fluoro-indan-1-yloxy]-2,3-dihydro-benzofuran-3-yl}-acetic acid

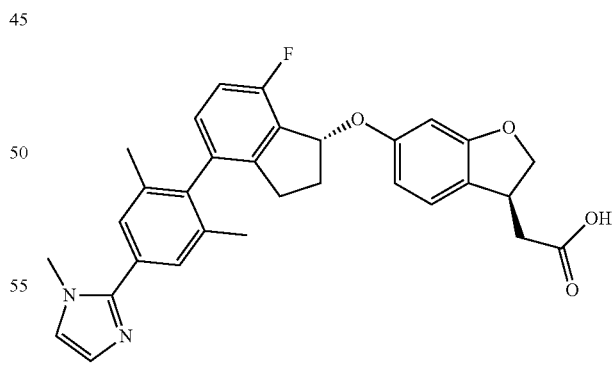

The title compound is prepared from {(S)-6-[(R)-7-fluoro-4-(2,6-dimethyl-4-(1-methyl-imidazol-2-yl)-phenyl)-indan-1-yloxy]-2,3-dihydro-benzofuran-3-yl}-acetic acid methyl ester following a procedure analogous to that described for Example 4; if the title compound does not precipitate from the aqueous solution, the crude title compound is purified by HPLC. LC (method 7): $t_R$=0.94 min; Mass spectrum (ESI⁺): m/z=513 [M+H]⁺.

Example 145

2-((S)-6-((R)-4-(2,6-dimethyl-4-((1-methyl-1H-pyrazol-3-yl)methoxy)phenyl)-7-fluoro-2,3-dihydro-1H-inden-1-yloxy)-2,3-dihydrobenzofuran-3-yl)acetic acid

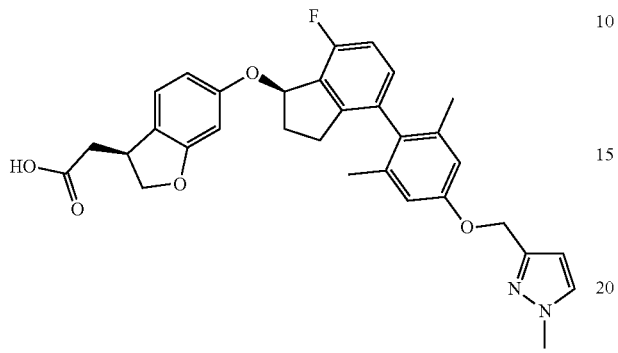

Methyl 2-((S)-6-((R)-4-(2,6-dimethyl-4-((1-methyl-1H-pyrazol-3-yl)methoxy)phenyl)-7-fluoro-2,3-dihydro-1H-inden-1-yloxy)-2,3-dihydrobenzofuran-3-yl)acetate is dissolved in methanol (1 mL) and tetrahydrofuran (1 mL) and aqueous NaOH solution (0.2 mL, 1 Mol/L) was added. The reaction mixture is shaken for 72 hours at room temperature. Aqueous hydrochloric acid (0.2 mL, 1 Mol/L) and dimethylformamide (1 mL) are added and the product is purified by HPLC on reversed phase. The product fractions are collected and lyophilized to give the title compound. LC (method 14): $t_R$=0.69 min; Mass spectrum (ESI$^+$): m/z=543 [M+H]$^+$.

Saponification of the Esters in the Following Table was Performed in Analogy to Example 145

| Example No | Structure | Name |
|---|---|---|
| 146 | 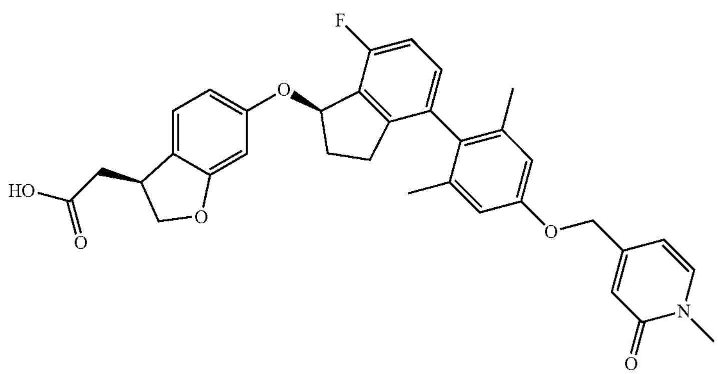 [SMILES: Cc1cc(OCc2ccn(C)c(=O)c2)cc(C)c1-c1ccc(F)c2c1CC[C@H]2Oc1ccc2c(c1)OC[C@H]2CC(=O)O] | 2-((S)-6-((R)-4-(2,6-dimethyl-4-((1-methyl-2-oxo-1,2-dihydropyridin-4-yl)methoxy)phenyl)-7-fluoro-2,3-dihydro-1H-inden-1-yloxy)-2,3-dihydrobenzofuran-3-yl)acetic acid |
| 147 | 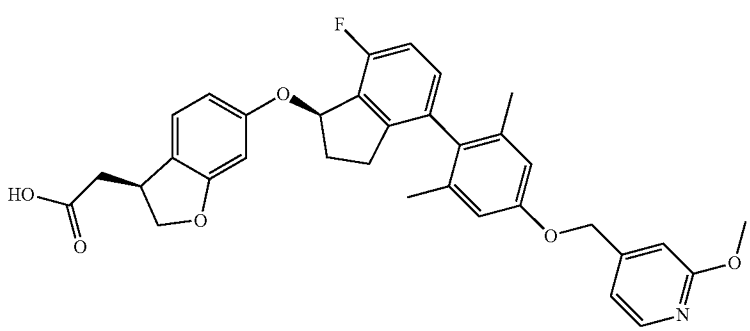 [SMILES: COc1cc(COc2cc(C)c(-c3ccc(F)c4c3CC[C@H]4Oc3ccc4c(c3)OC[C@H]4CC(=O)O)c(C)c2)ccn1] | 2-((S)-6-((R)-7-fluoro-4-(4-((2-methoxypyridin-4-yl)methoxy)-2,6-dimethylphenyl)-2,3-dihydro-1H-inden-1-yloxy)-2,3-dihydrobenzofuran-3-yl)acetic acid |

| | | |
|---|---|---|
| 148 | 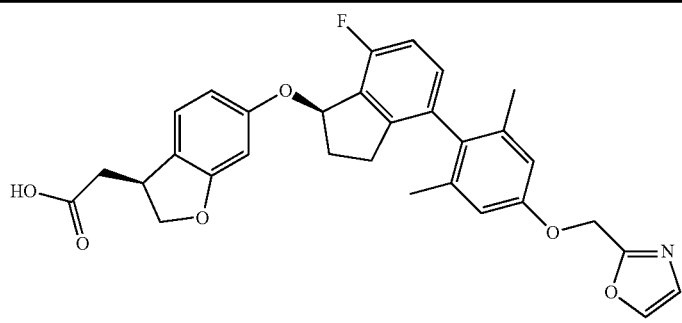 | 2-((S)-6-((R)-4-(2,6-dimethyl-4-(oxazol-2-ylmethoxy)phenyl)-7-fluoro-2,3-dihydro-1H-inden-1-yloxy)-2,3-dihydrobenzofuran-3-yl)acetic acid |
| 149 | 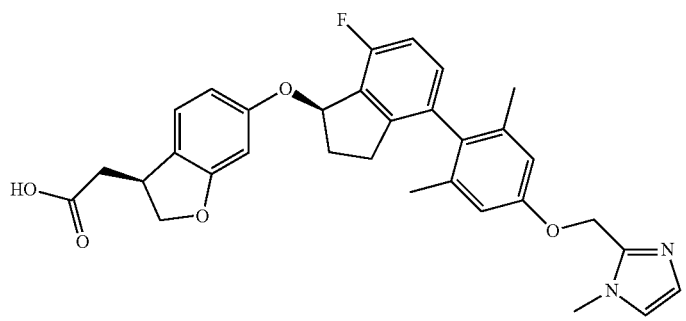 [SMILES: Cc1cc(OCc2nccn2C)cc(C)c1-c1ccc(F)c2c1CC[C@H]2Oc1ccc2c(c1)OC[C@H]2CC(=O)O] | 2-((S)-6-((R)-4-(2,6-dimethyl-4-((1-methyl-1H-imidazol-2-yl)methoxy)phenyl)-7-fluoro-2,3-dihydro-1H-inden-1-yloxy)-2,3-dihydrobenzofuran-3-yl)acetic acid |
| 150 | 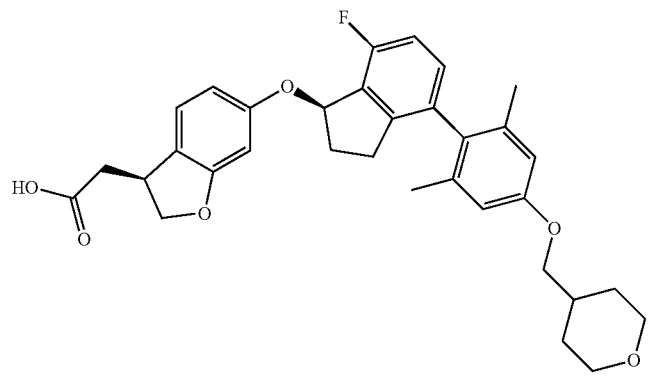 [SMILES: Cc1cc(OCC2CCOCC2)cc(C)c1-c1ccc(F)c2c1CC[C@H]2Oc1ccc2c(c1)OC[C@H]2CC(=O)O] | 2-((S)-6-((R)-4-(2,6-dimethyl-4-((tetrahydro-2H-pyran-4-yl)methoxy)phenyl)-7-fluoro-2,3-dihydro-1H-inden-1-yloxy)-2,3-dihydrobenzofuran-3-yl)acetic acid |
| 151 | 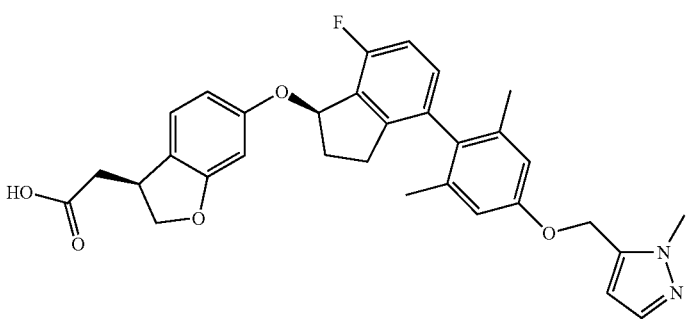 [SMILES: Cc1cc(OCc2ccnn2C)cc(C)c1-c1ccc(F)c2c1CC[C@H]2Oc1ccc2c(c1)OC[C@H]2CC(=O)O] | 2-((S)-6-((R)-4-(2,6-dimethyl-4-((1-methyl-1H-pyrazol-5-yl)methoxy)phenyl)-7-fluoro-2,3-dihydro-1H-inden-1-yloxy)-2,3-dihydrobenzofuran-3-yl)acetic acid |
| 152 | 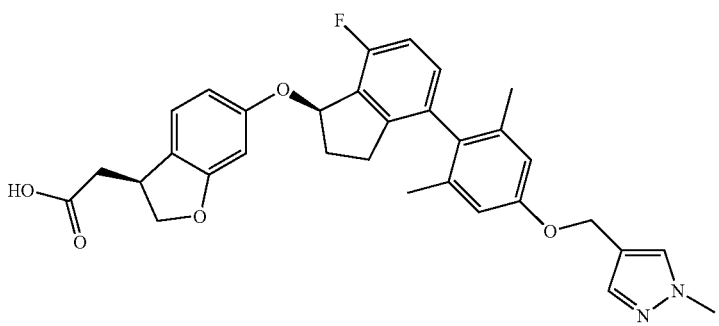 [SMILES: Cc1cc(OCc2cnn(C)c2)cc(C)c1-c1ccc(F)c2c1CC[C@H]2Oc1ccc2c(c1)OC[C@H]2CC(=O)O] | 2-((S)-6-((R)-4-(2,6-dimethyl-4-((1-methyl-1H-pyrazol-4-yl)methoxy)phenyl)-7-fluoro-2,3-dihydro-1H-inden-1-yloxy)-2,3-dihydrobenzofuran-3-yl)acetic acid |

| Example No. | $t_R$ [Min] | LC method No | (ESI$^+$): m/z |
|---|---|---|---|
| 146 | 0.66 | 14 | 570 [M + H]$^+$. |
| 147 | 0.74 | 14 | 570 [M + H]$^+$. |
| 148 | 0.68 | 14 | 530 [M + H]$^+$. |
| 149 | 0.66 | 14 | 543 [M + H]$^+$. |
| 150 | 0.74 | 14 | 547 [M + H]$^+$. |
| 151 | 1.04 | 11 | 543 [M + H]$^+$. |
| 152 | 1.87 | 23 | 543 [M + H]$^+$. |

The invention claimed is:

1. A compound of formula (I)

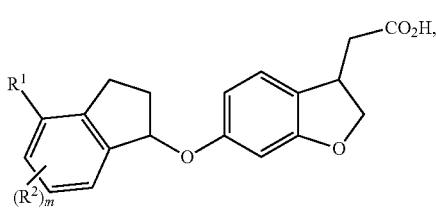

wherein:

$R^1$ is selected from the group consisting of a phenyl ring, a tetrazolyl ring, and a 5- or 6-membered heteroaromatic ring which contains 1, 2, or 3 heteroatoms independently selected from =N—, —NH—, —O—, and —S—, wherein optionally a second ring is annulated to the phenyl or heteroaromatic ring, wherein the second ring is 5- or 6-membered, unsaturated or aromatic and optionally contains 1, 2, or 3 heteroatoms independently selected from =N—, —NH—, —O—, and —S—, with the proviso that only up to two of the heteroatoms are O and S and no O—O, S—S, or S—O bond is formed, and in the second ring independently 1 or 2 $CH_2$ groups are optionally replaced by —C(=O)—, —S(=O)—, or —S(=O)$_2$—, and the phenyl ring, tetrazolyl ring, heteroaromatic ring, annulated phenyl ring, and annulated heteroaromatic ring are substituted with one group $R^3$; each of the phenyl ring, tetrazolyl ring, heteroaromatic ring, annulated phenyl ring, and annulated heteroaromatic ring is optionally additionally substituted with 1 to 4 groups independently selected from $R^4$; and in the heteroaromatic ring and/or the second ring the H-atom in one or more NH groups, if present, is replaced by $R^N$ or $R^3$;

$R^2$ is F, Cl, Br, I, $C_{1-4}$-alkyl, $C_{3-6}$-cycloalkyl, NC—, $H_2N$—C(=O)—, $C_{1-4}$-alkyl-NR$^N$—C(=O)—, HO—C(=O)—, $C_{1-4}$-alkyl-O—C(=O)—, $C_{1-4}$-alkyloxy, or $C_{1-4}$-alkyl-S(=O)$_2$—, wherein any alkyl and cycloalkyl group or sub-group within the groups mentioned is optionally substituted with one or more F atoms, and wherein multiple $R^2$ are identical or different, if m is 2 or 3;

$R^3$ is selected from the group consisting of $C_{1-6}$-alkyl, $C_{2-6}$-alkenyl, $C_{2-6}$-alkinyl, $C_{3-6}$-cycloalkyl-, $C_{1-4}$-alkyl-NH—, ($C_{1-4}$-alkyl)$_2$N—, $C_{1-6}$-alkyl-O—, $C_{3-6}$-cycloalkyl-O—, $C_{1-4}$-alkyl-S—, $C_{1-4}$-alkyl-S(=O)—, and $C_{1-4}$-alkyl-S(=O)$_2$, wherein each alkyl and cycloalkyl group and each alkyl and cycloalkyl sub-group within the groups mentioned is substituted with 1 to 3 groups independently selected from $R^5$ and optionally substituted with 1 or more F atoms; or selected from $C_{1-4}$-alkyl-C(=O)—, heterocyclyl-C(=O)—, HNR$^N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO$_2$C—, $C_{1-4}$-alkyl-O—C(=O)—, $C_{3-6}$-cycloalkyl-O—C(=O)—, heterocyclyl-O—C(=O)—, —NHR$^N$, $C_{1-4}$-alkyl-C(=O)NR$^N$—, $C_{3-6}$-cycloalkyl-C(=O)NR$^N$—, heterocyclyl-C(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, heterocyclyl-O—, phenyl-O—, heteroaryl-O—, $C_{3-6}$-cycloalkyl-S—, heterocyclyl-S—, phenyl-S—, heteroaryl-S—, $C_{3-6}$-cycloalkyl-S(=O)—, heterocyclyl-S(=O)—, phenyl-S(=O)—, heteroaryl-S(=O)—, $C_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, $C_{1-4}$-alkyl-NR$^N$—S(=O)$_2$—, heterocyclyl, phenyl, and heteroaryl, wherein each alkyl, cycloalkyl, and heterocyclyl group or sub-group within the groups mentioned is optionally substituted with 1 to 3 groups independently selected from $R^5$ and optionally substituted with 1 or more F atoms; and wherein each phenyl and heteroaryl group is optionally substituted with 1 to 5 substituents independently selected from $R^6$; heterocyclyl is selected from a cyclobutyl group wherein 1 $CH_2$ group is replaced by —NH— or —O—, a saturated or partially unsaturated $C_{5-7}$-cycloalkyl group wherein 1 $CH_2$ group is replaced by —C(=O)—, —NH—, —O—, —S(=O)—, or —S(=O)$_2$—, and/or 1 CH group is replaced by N; a saturated or partially unsaturated $C_{5-7}$-cycloalkyl group wherein a first $CH_2$ group is replaced by —NH— or —O—, a second $CH_2$ group is replaced by —NH—, —C(=O)—, —S(=O)—, or —S(=O)$_2$—, and/or 1 CH group is replaced by N; and a saturated or partially unsaturated $C_{5-7}$-cycloalkyl group wherein 2 $CH_2$ groups are replaced by —NH—, or a first $CH_2$ group is replaced by —NH—, a second $CH_2$ group is replaced by —O—, and a third $CH_2$ group by —C(=O)—, —S(=O)—, or —S(=O)$_2$— and/or 1 CH group is replaced by N; wherein heteroaryl is selected from a tetrazolyl ring, and a 5- or 6-membered heteroaromatic ring which contains 1, 2, or 3 heteroatoms independently selected from =N—, —NH—, —O—, and —S—, wherein in heteroaromatic groups containing a —HC=N— unit this group is optionally replaced by —NH—C(=O)—; wherein in heteroaryl and heterocyclyl rings with one or more NH groups each of them is replaced by NR$^N$ or NR$^5$; with the proviso that $R^3$ in total cannot be $C_{1-4}$-alkyl-, $C_{1-4}$-alkyl-O—$C_{1-4}$-alkyl, HO—$C_{1-4}$-alkyl, $C_{3-4}$-alkenyl, $C_{1-4}$-alkyl-NH—, ($C_{1-4}$-alkyl)$_2$N—, $C_{1-4}$-alkyl-S—, $C_{1-4}$-alkyl-S(=O)—, and $C_{1-4}$-alkyl-S(=O)$_2$;

$R^4$ is F, Cl, Br, I, CN, —OH, $C_{1-4}$-alkyl, $C_{3-6}$-cycloalkyl-, HO—$C_{1-4}$-alkyl, $C_{1-4}$-alkyl-O—$C_{1-4}$-alkyl, —NR$^N$H, $C_{1-4}$-alkyl-NR$^N$—, $C_{1-4}$-alkyl-O—, $C_{3-6}$-cycloalkyl-O—, $C_{1-4}$-alkyl-S—, $C_{1-4}$-alkyl-S(=O)—, or $C_{1-4}$-alkyl-S(=O)$_2$—, wherein any alkyl and cycloalkyl group or sub-group within the groups mentioned is optionally substituted with 1 or more F atoms;

$R^5$ is selected from the group consisting of Cl, Br, I, $C_{1-4}$-alkyl-, CN, $C_{3-6}$-cycloalkyl-, heterocyclyl-C(=O)—, $H_2N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO—C(=O)—, $C_{1-4}$-alkyl-O—C(=O)—, —NHR$^N$, NR$^N$C$_{1-4}$-alkyl-C(=O)NR$^N$—, $C_{3-6}$-cycloalkyl-C(=O)NR$^N$—, heterocyclyl-C(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, —OH, $C_{1-4}$-alkyl-O—$C_{1-4}$-alkyl-O—, $C_{3-6}$-cycloalkyl-O—, heterocyclyl-O—, phenyl-O—, heteroaryl-O—, $C_{3-6}$-cycloalkyl-S—, heterocyclyl-S—, phenyl-S—, heteroaryl-S—, $C_{1-4}$-alkyl-S(=O)—, $C_{3-6}$-cycloalkyl-S(=O)—, heterocyclyl-S(=O)—, phenyl-S(=O)—, heteroaryl-S(=O)—, $C_{1-4}$-alkyl-S(=O)$_2$, $C_{3-6}$-cycloalkyl-S(=O)$_2$—, heterocyclyl-S(=O)$_2$—, phenyl-S(=O)$_2$—, heteroaryl-S(=O)$_2$—, $H_2N$—S(=O)$_2$—, $C_{1-4}$-alkyl-NR$^N$—S(=O)$_2$—, heterocyclyl, phenyl, and heteroaryl, wherein any alkyl, cycloalkyl, and heterocyclyl group or sub-group within the groups mentioned is optionally substituted with 1 or more F atoms and optionally substituted with 1 or 2 groups independently selected from $H_3C$—, HO—, $H_3C$—O—, and —CN; wherein heterocyclyl is selected from a cyclobutyl group wherein 1 $CH_2$ group is replaced by —NR$^N$— or —O—, a saturated or partially unsaturated $C_{5-7}$-cycloalkyl group wherein 1 $CH_2$ group is replaced by —C(=O)—, —NR$^N$—, —O—, —S(=O)—, or —S(=O)$_2$—, and/or 1 CH group is replaced by N; a saturated or partially unsaturated $C_{5-7}$-cycloalkyl group wherein a first $CH_2$ group is replaced by —NR$^N$—, or —O—, a second $CH_2$ group is replaced by —NR$^N$—, —C(=O)—, —S(=O)—, or —S(=O)$_2$— and/or 1 CH group is replaced by N; and a saturated or partially unsaturated $C_{5-7}$-cycloalkyl group wherein 2 $CH_2$ groups are replaced by —NR$^N$—, or a first $CH_2$ group is replaced by —NR$^N$—, a second $CH_2$ group is replaced by —O—, and a third $CH_2$ group is replaced by —C(=O)—, —S(=O)—, or —S(=O)$_2$—, and/or 1 CH group is replaced by N; and wherein heteroaryl is selected from a tetrazolyl ring, and a 5- or 6-membered heteroaromatic ring which contains 1, 2, or 3 heteroatoms independently from =N—, —NH—, —O—, and —S—, wherein in heteroaromatic groups containing a —HC=N— unit this group is optionally replaced by —NR$^N$—C(=O)—, and wherein in heteroaromatic rings with one or more NH groups each of them is replaced by NR$^N$, and each heteroaryl group is optionally substituted with 1 to 3 substituents independently selected from F, Cl, —CH$_3$, —CN, and —O—CH$_3$;

$R^6$ is F, Cl, Br, I, CN, $C_{1-4}$-alkyl, $C_{3-6}$-cycloalkyl-, HO—$C_{1-4}$-alkyl-, $C_{1-4}$-alkyl-O—$C_{1-4}$-alkyl-, R$^N$HN—, $C_{1-4}$-alkyl-O—, —S(=O)—$C_{1-4}$-alkyl, or S(=O)$_2$—$C_{1-4}$-alkyl, wherein any alkyl and cycloalkyl group or sub-group within the groups mentioned is optionally substituted with one or more F atoms;

$R^N$ is independently selected from the group consisting of H, $C_{1-4}$-alkyl, $C_{1-4}$-alkyl-C(=O)—, $C_{1-4}$-alkyl-NH—C(=O)—, $C_{1-4}$-alkyl-N($C_{1-4}$-alkyl)-C(=O)—, $C_{1-4}$-alkyl-O—C(=O)—, and $C_{1-4}$-alkyl-S(=O)$_2$—; and m is 0, 1, 2, or 3;

wherein in any definition mentioned hereinbefore and if not specified otherwise, any alkyl group or sub-group are straight-chained or branched, or a salt thereof.

2. The compound according to claim 1, wherein:

$R^1$ is selected from the group consisting of a phenyl ring, a tetrazolyl ring, a 5-membered heteroaromatic ring which contains 2 or 3 heteroatoms independently selected from =N—, —NH—, —O—, and —S— with the proviso that not more than one heteroatom is —O— or —S—, and a 6-membered heteroaromatic ring which contains 1 or 2=N— atoms; wherein optionally a second ring is annulated to the phenyl ring and 5- and 6-membered heteroaromatic rings, wherein the second ring is 5- or 6-membered, unsaturated or aromatic and optionally contains 1 or 2 heteroatoms independently selected from =N—, —NH—, —O—,and —S— with the proviso that no O—O, S—S, S—O bond is formed, and in the second ring independently 1 or 2 —CH$_2$— groups are optionally replaced by —C(=O)— or —S(=O)$_2$—, in the heteroaromatic ring and/or the second ring the H-atom in one or more NH groups, if present, is replaced by R$^N$ or R$^3$, and each of the phenyl ring, tetrazolyl ring, heteroaromatic rings, annulated phenyl ring, and annulated heteroaromatic rings is substituted with one group $R^3$ and optionally additionally substituted with 1 or 2 substituents independently selected from $R^4$;

$R^2$ is F, Cl, Br, $H_3C$—, $H_2FC$—, $F_3C$—, cyclopropyl, NC—, $F_2HC$—O—, $F_3C$—O—, or $H_3C$—S(=O)$_2$—, $R^3$ is selected from the group consisting of $C_{1-4}$-alkyl, $C_{3-6}$-cycloalkyl-, $C_{1-4}$-alkyl-O—, $C_{3-6}$-cycloalkyl-O—, $C_{1-4}$-alkyl-S(=O)—, and $C_{1-4}$-alkyl-S(=O)$_2$—, wherein each alkyl and cycloalkyl group and each alkyl and cycloalkyl sub-group within the groups mentioned is substituted with 1 to 3 groups independently selected from $R^5$ and optionally substituted with 1 or more F atoms; or from $C_{1-4}$-alkyl-C(=O)—, heterocyclyl-C(=O)—, HNR$^N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, C(=O)NR$^N$C$_{3-6}$-cycloalkyl-C(=O)NR$^N$—, heterocyclyl-C(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, heterocyclyl-O—, phenyl-O—, heteroaryl-O—, $C_{3-6}$-cycloalkyl-S(=O)—, heterocyclyl-S(=O)—, phenyl-S(=O)—, heteroaryl-S(=O)—, $C_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, $C_{1-4}$-alkyl-NR$^N$—S(=O)$_2$—, heterocyclyl, phenyl, and heteroaryl, wherein each alkyl, cycloalkyl, and heterocyclyl group or sub-group within the groups mentioned is optionally substituted with 1 to 3 groups independently selected from $R^5$ and optionally substituted with 1 or more F atoms; and wherein each phenyl and heteroaryl group is optionally substituted with 1 to 3 substituents independently selected from $R^6$; wherein heterocyclyl is selected from a cyclobutyl group wherein 1 $CH_2$ group is replaced by —NH— or —O—, a saturated or mono-unsaturated $C_{5-6}$-cycloalkyl group wherein 1 $CH_2$ group is replaced by —C(=O)—, —NH—, —O—, —S(=O)—, or —S(=O)₂— and/or 1 CH group is replaced by N; a saturated or mono-unsaturated $C_{5-6}$-cycloalkyl group wherein a first CH₂ group is replaced by —NH— or —O—, a second CH₂ group is replaced by —NH—, —C(=O)—, —S(=O)—, or —S(=O)₂—, and/or 1 CH group is replaced by N; and a saturated or mono-unsaturated $C_{5-6}$-cycloalkyl group wherein 2 CH₂ groups are replaced by —NH—, or a first CH₂ group is replaced by —NH—, a second CH₂ group is replaced by —O—, and a third CH₂ group is replaced by —C(=O)—, —S(=O)—, or —S(=O)₂—, and/or 1 CH group is replaced by N; wherein heteroaryl is selected from a tetrazolyl ring, a pyridin-2-onyl ring, a 5-membered heteroaromatic ring which contains 1, 2, or 3 heteroatoms independently selected from =N—, —NH—, O, and S, and a 6-membered heteroaromatic ring which contains 1 or 2=N— atom, and wherein in heteroaryl and heterocyclyl rings with one or more NH groups each of them is replaced by $NR^N$ or $R^5$, with the proviso that $R^3$ in total cannot be $C_{1-4}$-alkyl-, $C_{1-4}$-alkyl-O—$C_{1-4}$-alkyl, HO—$C_{1-4}$-alkyl, $C_{1-4}$-alkyl-O—, $C_{1-4}$-alkyl-S(=O)—, and $C_{1-4}$-alkyl-S(=O)₂, $R^4$ is F, Cl, Br, CN, $C_{1-3}$-alkyl, $C_{3-4}$-cycloalkyl-, HO—$C_{1-3}$-alkyl, $C_{1-3}$-alkyl-O—$C_{1-3}$-alkyl, —$NR^NH$, $C_{1-4}$-alkyl-O—, $C_{3-5}$-cycloalkyl-O—, $H_3C$—S(=O)—, or $H_3C$—S(=O)₂—, wherein any alkyl and cycloalkyl group is optionally substituted with 1 or more F atoms, $R^5$ is selected from the group consisting of Cl, $C_{1-4}$-alkyl-, —CN, $C_{3-6}$-cycloalkyl-, heterocyclyl-C(=O)—, $H_2N$—C(=O)—, $C_{1-4}$-alkyl-$NR^N$—C(=O)—, $C_{3-6}$-cycloalkyl-$NR^N$—C(=O)—, heterocyclyl-$NR^N$—C(=O)—, heteroaryl-$NR^N$—C(=O)—, —NH₂, $C_{1-4}$-alkyl-$NR^N$—, $C_{1-4}$-alkyl-C(=O)$NR^N$—, $C_{3-6}$-cycloalkyl-C(=O)$NR^N$—, heterocyclyl-C(=O)$NR^N$—, heteroaryl-C(=O)$NR^N$—, $C_{1-4}$-alkyl-S(=O)₂$NR^N$—, —OH, $C_{1-4}$-alkyl-O—, $C_{1-4}$-alkyl-O—$C_{1-4}$-alkyl-O—, $C_{3-6}$-cycloalkyl-O—, heterocyclyl-O—, phenyl-O—, heteroaryl-O—, $C_{1-4}$-alkyl-S(=O)—, $C_{3-6}$-cycloalkyl-S(=O)—, $C_{1-4}$-alkyl-S(=O)₂—, $C_{3-6}$-cycloalkyl-S(=O)₂—, heterocyclyl, and heteroaryl, wherein any alkyl, cycloalkyl, and heterocyclyl group or sub-group within the groups mentioned is optionally substituted with 1 or more F atoms and optionally substituted with 1 or 2 groups independently selected from $H_3C$—, HO—, $H_3C$—O—, and —CN, wherein heterocyclyl is selected from a cyclobutyl group wherein 1 CH₂ group is replaced by —$NR^N$— or —O—; a saturated or partially unsaturated $C_{5-6}$-cycloalkyl group wherein 1 CH₂ group is replaced by —C(=O)—, —$NR^N$—, —O—, —S(=O)—, or —S(=O)₂— and/or 1 CH group is replaced by N; a saturated or partially unsaturated $C_{5-6}$-cycloalkyl group wherein a first CH₂ group is replaced by —$NR^N$— or —O—, a second CH₂ group is replaced by —$NR^N$—, —C(=O)—, —S(=O)—, or —S(=O)₂— and/or 1 CH group is replaced by N; and a saturated or partially unsaturated $C_{5-6}$-cycloalkyl group wherein 2 CH₂ group are replaced by —$NR^N$—, or a first CH₂ group is replaced by —$NR^N$—, a second CH₂ group is replaced by —O—, and a third CH₂ group is replaced by —C(=O)—, —S(=O)—, or —S(=O)₂—, and/or 1 CH group is replaced by N; and wherein heteroaryl is selected from a tetrazolyl ring, a pyridin-2-onyl ring, a 5-membered heteroaromatic ring which contains 1, 2, or 3 heteroatoms independently selected from =N—, —NH—, —O—, and —S—, and a 6-membered heteroaromatic ring which contains 1 or 2=N— atoms, and wherein in heteroaromatic rings with one or more NH groups each of them is replaced by $NR^N$, and each heteroaryl group is optionally substituted with 1 to 3 substituents independently selected from F, Cl, —CH₃, —CN, and —O—CH₃, $R^6$ is F, Cl, —CN, $C_{1-3}$-alkyl, cyclopropyl, HO—$C_{1-3}$-alkyl-, $H_3C$—O—$C_{1-3}$-alkyl-, $H_3C$—O—, —S(=O)CH₃, and or —S(=O)₂—CH₃, wherein any alkyl and cycloalkyl group or sub-group within the groups mentioned is optionally substituted with one or more F atoms;

$R^N$ is H, $C_{1-3}$-alkyl, $H_3C$—C(=O)—, or $C_{1-3}$-alkyl-S(=O)₂—, m is 0, 1, or 2, or a salt thereof.

3. The compound according to claim 2, wherein:

$R^1$ is a consisting of a phenyl ring, a tetrazolyl ring, a 5-membered heteroaromatic ring which contains 2 or 3 heteroatoms independently selected from =N—, —NH—, —O—, and —S—, or a 6-membered heteroaromatic ring which contains 1 or 2=N— atoms; wherein in the 5-membered heteroaromatic ring the H-atom in one or more NH groups are replaced with $R^N$ or $R^3$, and wherein each of the phenyl ring, tetrazolyl ring, and heteroaromatic rings is substituted with one group $R^3$ and optionally additionally substituted with 1 or 2 substituents independently selected from $R^4$; and m is 1 or 2, or a salt thereof.

4. The compound according to claim 2, wherein:

$R^1$ is selected from the group consisting of a phenyl ring, a 5-membered heteroaromatic ring which contains 2 or 3 heteroatoms independently selected from =N—, —NH—, —O— and —S—, and a 6-membered heteroaromatic ring which contains 1 or 2=N— atoms, wherein a second 5- or 6-membered, unsaturated or aromatic ring is annulated to the phenyl ring and 5- and 6-membered heteroaromatic rings, which optionally contains 1 or 2 heteroatoms independently selected from =N—, —NH—, —O—, and —S—, with the proviso that no O—O, S—S, or S—O bond is formed, and in the second ring 1 or 2 —CH₂— groups are optionally replaced by —C(=O)— or —S(=O)₂—, in the heteroaromatic rings and the second rings the H-atom in one or more NH groups, if present, is replaced by $R^N$ or $R^3$, and each annulated phenyl ring and annulated heteroaromatic ring is substituted with one group $R^3$ and optionally additionally substituted with 1 or 2 substituents independently selected from $R^4$; and m is 1 or 2, or a salt thereof.

5. The compound according to claim 1, wherein:

$R^1$ is

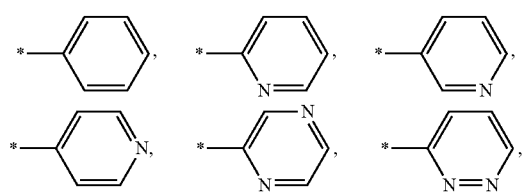

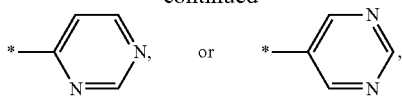

wherein each group is substituted with one group R³ and optionally additionally substituted with 1 or 2 groups independently selected from R⁴;

R² is F, Cl, Br, H₂FC—, F₃C—, NC—, or F₃C—O—;

R³ is selected from the group consisting of C₁₋₄-alkyl, C₃₋₆-cycloalkyl-, C₁₋₄-alkyl-O—, and C₃₋₆-cycloalkyl-O—, wherein each alkyl and cycloalkyl group and each alkyl and cycloalkyl sub-group within the groups mentioned is substituted with 1 to 3 groups independently selected from R⁵ and optionally substituted with 1 or more F atoms; or from H₃C—C(=O)—, heterocyclyl-C(=O)—, H₂N—C(=O)—, C₁₋₃-alkyl-NRᴺ—C(=O)—, C₁₋₄-alkyl-C(=O)NRᴺ—, C₃₋₆-cycloalkyl-C(=O)NRᴺ—, heterocyclyl-C(=O)NRᴺ—, C₁₋₄-alkyl-S(=O)₂NRᴺ—, heterocyclyl-O—, phenyl-O—, heteroaryl-O—, heterocyclyl-S(=O)₂—, H₂N—S(=O)₂—, heterocyclyl, phenyl, and heteroaryl, wherein each alkyl, cycloalkyl, and heterocyclyl group or sub-group within the groups mentioned is optionally substituted with 1 or 2 groups independently selected from R⁵ and optionally substituted with 1 or more F atoms; each phenyl and heteroaryl group is optionally substituted with 1 to 3 substituents independently selected from R⁶; wherein heterocyclyl is selected from a cyclobutyl group wherein 1 CH₂ group is replaced by —NH— or —O—; a saturated or mono-unsaturated C₅₋₆-cycloalkyl group wherein 1 CH₂ group is replaced by —C(=O)—, —NH—, —O— or —S(=O)₂—, and/or 1 CH group is replaced by N; a saturated or mono-unsaturated C₅₋₆-cycloalkyl group wherein a first CH₂ group is replaced by —NH— or —O—, a second CH₂ group is replaced by —C(=O)— or —S(=O)₂—, and/or 1 CH group is replaced by N; and wherein heteroaryl is selected from a pyridin-2-onyl ring, a 5-membered heteroaromatic ring which contains 1, 2, or 3 heteroatoms independently selected from =N—, —NH—, O, and S, and a 6-membered heteroaromatic ring which contains 1 or 2=N— atoms, and wherein in heteroaryl and heterocyclyl rings with one or more NH groups each of them is replaced by NRᴺ or NR⁵; with the proviso that R³ in total cannot be C₁₋₄-alkyl-, C₁₋₄-alkyl-O—C₁₋₄-alkyl, HO—C₁₋₄-alkyl, and C₁₋₄-alkyl-O—;

R⁴ is F, Cl, CN, —CH₃, —CF₃, isopropyl, cyclopropyl, H₃C—O—CH₂—, H₃C—O—, or F₃C—O—;

R⁵ is selected from the group consisting of C₁₋₄-alkyl-, —CN, C₃₋₆-cycloalkyl-, heterocyclyl-C(=O)—, H₂N—C(=O)—, C₁₋₄-alkyl-NRᴺ—C(=O)—, C₁₋₄-alkyl-NRᴺ—, C₁₋₄-alkyl-C(=O)NRᴺ—, C₁₋₄-alkyl-S(=O)₂NRᴺ—, —OH, C₁₋₄-alkyl-O—, C₁₋₄-alkyl-O—C₁₋₄-alkyl-O—, C₃₋₆-cycloalkyl-O—, heterocyclyl-O—, C₁₋₄-alkyl-S(=O)—, C₁₋₄-alkyl-S(=O)₂—, heterocyclyl, and heteroaryl, wherein any alkyl, cycloalkyl, and heterocyclyl group or sub-group within the groups mentioned is optionally substituted with 1 or more F atoms and optionally substituted with 1 or 2 groups independently selected from H₃C—, H₃C—O—, and —CN, wherein heterocyclyl is selected from a cyclobutyl group wherein 1 CH₂ group is replaced by —NRᴺ— or —O—; a saturated or partially unsaturated C₅₋₆-cycloalkyl group wherein 1 CH₂ group is replaced by —C(=O)—, —NRᴺ—, —O—, —S(=O)— or —S(=O)₂— and/or 1 CH group is replaced by N; a saturated or partially unsaturated C₅₋₆-cycloalkyl group wherein 1 CH₂ group is replaced by —NRᴺ— or —O—, a second CH₂ group is replaced by —NRᴺ—, —C(=O)—, —S(=O)— or —S(=O)₂—, and/or 1 CH group is replaced by N; and a saturated or partially unsaturated C₅₋₆-cycloalkyl group wherein 2 CH₂ group are replaced by —NRᴺ—, or a first CH₂ group is replaced by —NRᴺ—, a second CH₂ group is replaced by —O—, and a third CH₂ group is replaced by —C(=O)—, —S(=O)—, or —S(=O)₂—, and/or 1 CH group is replaced by N; and wherein heteroaryl is selected from a pyridin-2-onyl ring, a 5-membered heteroaromatic ring which contains 1 or 2 heteroatoms independently selected from =N—, —NH—, —O—, and —S—, and a 6-membered heteroaromatic ring which contains 1 or 2=N— atoms, and wherein in heteroaromatic rings with one or more NH groups each of them is replaced by NRᴺ, and each heteroaryl group is optionally substituted with 1 or 2 substituents independently selected from F, Cl, —CH₃, —CN, and —O—CH₃;

R⁶ is F, Cl, —CN, —CH₃, —CF₃, —OCH₃, —OCF₃, —S(=O)CH₃, or —S(=O)₂—CH₃;

Rᴺ is H, H₃C—, H₃C—C(=O)—, or C₁₋₃-alkyl-S(=O)₂—; and m is 1 or 2, or a salt thereof.

6. The compound according to claim 1, wherein:

R¹ is

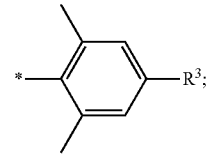

R² is F, Cl, or NC—;

R³ is selected from the group consisting of C₁₋₄-alkyl, C₃₋₆-cycloalkyl-, C₁₋₄-alkyl-O—, and C₃₋₆-cycloalkyl-O—, wherein each alkyl and cycloalkyl group and each alkyl and cycloalkyl sub-group within the groups mentioned is substituted with 1 group selected from R⁵ and optionally substituted with 1 or 2 H₃C— group; or selected from H₃C—C(=O)—, heterocyclyl-C(=O)—, H₂N—C(=O)—, H₃C—NRᴺ—C(=O)—, heterocyclyl-O—, heteroaryl-O—, H₂N—S(=O)₂—, heterocyclyl, phenyl, and heteroaryl, wherein each heterocyclyl group or sub-group within the groups mentioned is optionally substituted with 1 or 2 groups independently selected from R⁵ and optionally substituted with 1 or more F atoms; each phenyl and heteroaryl group is optionally substituted with 1 or 2 substituents independently selected from R⁶; wherein heterocyclyl is selected from a cyclobutyl group wherein 1 CH₂ group is replaced by —NH— or —O—; a saturated or mono-unsaturated C₅₋₆-cycloalkyl group wherein 1 CH₂ group is replaced by —C(=O)—, —NH—, —O— or —S(=O)₂— and/or 1 CH group is replaced by N; a saturated or mono-unsaturated C₅₋₆-cycloalkyl group wherein a first CH₂ group is replaced by —NH— or —O—, a second CH₂ group is replaced by —NH—, —C(=O)— or —S(=O)₂— and/or 1 CH group is replaced by N; and wherein heteroaryl is selected from a 5-membered heteroaromatic ring which contains 1 or 2 heteroatoms independently of each other selected from =N—, —NH—, —O—, and —S—, and a 6-membered heteroaromatic ring which contains 1 or 2=N— atoms, and wherein in heteroaryl and heterocyclyl rings with one or more NH group each of them is replaced with $NR^N$ or $NR^5$; with the proviso that $R^3$ in total cannot be $C_{1-4}$-alkyl-, $C_{1-4}$-alkyl-O—$C_{1-4}$-alkyl, HO—$C_{1-4}$-alkyl, and $C_{1-4}$-alkyl-O—;

$R^5$ is selected from the group consisting of $C_{1-4}$-alkyl-, —CN, $C_{3-6}$-cycloalkyl-, heterocyclyl-C(=O)—, $H_2N$—C(=O)—, $C_{1-4}$-alkyl-$NR^N$—C(=O)—, $C_{1-4}$-alkyl-$NR^N$—, $C_{1-4}$-alkyl-S(=O)$_2NR^N$—, —OH, $C_{1-4}$-alkyl-O—, $C_{3-6}$-cycloalkyl-O—, heterocyclyl-O—, $C_{1-4}$-alkyl-S(=O)—, $C_{1-4}$-alkyl-S(=O)$_2$—, heterocyclyl, and heteroaryl, wherein any alkyl, cycloalkyl, and heterocyclyl group or sub-group within the groups mentioned is optionally substituted with 1 or more F atoms and optionally substituted with 1 or 2 groups independently selected from $H_3C$—, $H_3C$—O—, and —CN, wherein heterocyclyl is selected from a cyclobutyl group wherein 1 $CH_2$ group is replaced by —$NR^N$— or —O—; a saturated or partially unsaturated $C_{5-6}$-cycloalkyl group wherein 1 $CH_2$ group is replaced by —C(=O)—, —$NR^N$—, —O—, —S(=O)— or —S(=O)$_2$—, and/or 1 CH group is replaced by N; a saturated or partially unsaturated $C_{5-6}$-cycloalkyl group wherein a first $CH_2$ group is replaced by —$NR^N$—, or —O—, a second $CH_2$ group is replaced by —$NR^N$—, —C(=O)—, —S(=O)—, or —S(=O)$_2$—, and/or 1 CH group is replaced by N; and a saturated or partially unsaturated $C_{5-6}$-cycloalkyl group wherein 2 $CH_2$ groups are replaced by —$NR^N$—, or a first $CH_2$ group is replaced by —$NR^N$—, a second $CH_2$ group is replace by —O—, and a third $CH_2$ group is replaced by —C(=O)—, —S(=O)— or —S(=O)$_2$— and/or 1 CH group is replaced by N; and wherein heteroaryl is selected from a pyridin-2-onyl ring, a 5-membered heteroaromatic ring which contains 1 or 2 heteroatoms independently selected from =N—, —NH—, —O—, and —S—, and a 6-membered heteroaromatic ring which contains 1 or 2=N— atoms, and wherein in heteroaromatic rings with one or more NH group each of them is replaced by $NR^N$, and each heteroaryl group is optionally substituted with 1 or 2 substituents independently selected from F, Cl, —$CH_3$, —CN, and —O—$CH_3$;

$R^6$ is F, $CH_3$, CN, or —$OCH_3$;

$R^N$ is H, $H_3C$—, $H_3C$—C(=O)—, or $C_{1-3}$-alkyl-S(=O)$_2$—; and m is 1 or 2, or a salt thereof.

7. A pharmaceutically acceptable salt of a compound according to claim 1.

8. A pharmaceutical composition comprising the compound according to claim 1 or a pharmaceutically acceptable salts thereof and an inert carrier or diluent.

9. A method for palliatively treating diseases or conditions which are influenced by the modulation of the function of GPR40 in a patient in need thereof, comprising administering a compound according to claim 1 or a pharmaceutically acceptable salt thereof to the patient.

10. The method according to claim 9, wherein the diseases or conditions which are influenced by the modulation of the function of GPR40 in a patient are selected from diabetes, insulin resistance, obesity, cardiovascular disease, and dyslipidemia.

11. The pharmaceutical composition according to claim 8, further comprising an additional therapeutic agent.

12. The pharmaceutical composition according to claim 11, wherein the additional therapeutic agent is an antidiabetic agent, agents for the treatment of overweight and/or obesity, or an agents for the treatment of high blood pressure, heart failure, and/or atherosclerosis.

13. The compound according to claim 1, wherein the compound is 2-((S)-6-((R)-4-(2,6-dimethyl-4-((3-methyloxetan-3-yl)methoxy)phenyl)-7-fluoro-2,3-dihydro-1H-inden-1-yloxy)-2,3-dihydrobenzofuran-3-yl)acetic acid or a salt thereof.

14. The compound according to claim 1, wherein the compound is 2-((S)-6-((R)-7-fluoro-4-(4-(3-hydroxy-3-methylbutoxy)-2,6-dimethylphenyl)-2,3-dihydro-1H-inden-1-yloxy)-2,3-dihydrobenzofuran-3-yl)acetic acid or a salt thereof.

15. The compound according to claim 1, wherein the compound is 2-((S)-6-((R)-4-(2,6-dimethyl-4-(tetrahydro-2H-pyran-4-yloxy)phenyl)-7-fluoro-2,3-dihydro-1H-inden-1-yloxy)-2,3-dihydrobenzofuran-3-yl)acetic acid or a salt thereof.

16. The compound according to claim 1, wherein the compound is 2-((S)-6-((R)-4-(2,6-dimethyl-4-((S)-tetrahydrofuran-3-yloxy)phenyl)-7-fluoro-2,3-dihydro-1H-inden-1-yloxy)-2,3 -dihydrobenzofuran-3-yl)acetic acid or a salt thereof.

17. The compound according to claim 1, wherein the compound is 2((S)-6-((R)-4-(2,6-dimethyl-4-((R)-tetrahydrofuran-3-yloxy)phenyl)-7-fluoro-2,3-dihydro-1H-inden-1-yloxy)-2,3-dihydrobenzofuran-3-yl)acetic acid or a salt thereof.

18. The compound according to claim 1, wherein the compound is 2-((S)-6-((R)-7-fluoro-4-(4-(2-hydroxy-2-methylpropoxy)-2,6-dimethylphenyl)-2,3-dihydro-1H-inden-1-yloxy)-2,3-dihydrobenzofuran-3-yl)acetic acid or a salt thereof.

19. The compound according to claim 1, wherein the compound is 2-((S)-6-(R)-7-fluoro-4-(4-(3 -hydroxy-2,2-dimethylpropoxy)-2,6-dimethylphenyl)-2,3-dihydro-1H-inden-1-yloxy)-2,3 -dihydrobenzofuran-3-yl)acetic acid or a salt thereof.

20. The compound according to claim 1, wherein the compound is 2-((S)-6-((R)-4-(2,6-dimethyl-4-((1,1-dioxotetrahydro-2H-thiopyran-4-yl)methoxy)phenyl)-7-fluoro-2,3-dihydro-1H-inden-1-yloxy)-2,3-dihydrobenzofuran-3-yl) acetic acid or a salt thereof.

21. The compound according to claim 1, wherein the compound is ((S)-6-{(R)-7-fluoro-4-[4-(2-methanesulfonyl-2-methylpropoxy)-2,6-dimethylphenyl]indan-1-yloxy}-2,3 -dihydro-benzofuran-3-yl)acetic acid or a salt thereof.

22. The compound according to claim 1, wherein the compound is 2-((S)-6-((R)-4-(4-(2-cyano-2-methylpropoxy)-2,6-dimethylphenyl)-7-fluoro-2,3-dihydro-1H-inden-1-yloxy)-2,3-dihydrobenzofuran-3-yl)acetic acid or a salt thereof.

23. The compound according to claim 1, wherein the compound is 2-((S)-6((R)-7-fluoro-4-(4-((4-hydroxytetrahydro-2H-pyran-4-yl)methoxy)-2,6-dimethylphenyl)-2,3-dihydro-1H-inden-1-yloxy)-2,3-dihydrobenzofuran-3-yl)acetic acid or a salt thereof.

24. The compound according to claim 1, wherein the compound is 2-((S)-6-((R)-7-fluoro-4-(4-((1,1-dioxo-4-hydroxytetrahydro-2H-thiopyran-4-yl)methoxy)-2,6-dimethylphenyl)-2,3-dihydro-1H-inden-1-yloxy)-2,3-dihydrobenzofuran-3-yl)acetic acid or a salt thereof.

25. The compound according to claim 1, wherein the compound is 2((S)-6((R)-4-(2,6-dimethyl-4-(2-methyl-2H-tetrazol-5-yl)phenyl)-7-fluoro-2,3-dihydro-1H-inden-1-yloxy)-2,3-dihydrobenzofuran-3-yl)acetic acid or a salt thereof.

26. The compound according to claim 1, wherein the compound is 2-((S)-6-((R)-7-fluoro-4-(4-(2-(2-hydroxy-2-methylpropyl)-2H-tetrazol-5-yl)-2,6-dimethylphenyl)-2,3 -dihydro-1H-inden-1-yloxy)-2,3-dihydrobenzofuran-3-yl)acetic acid or a salt thereof.

27. The compound according to claim 1, wherein the compound is {(S)-6-[(R)-4-(2,6-dimethyl-4-(5-methylpyrimidin-2-yl)phenyl)-7-fluoroindan-1-yloxyl -2,3-dihydrobenzofuran-3-yl}acetic acid or a salt thereof.

28. The compound according to claim 1, wherein the compound is {(S)-6[(R)-4-(2,6-dimethyl-4-(6-methylpyridazin-3-yl)phenyl)-7-fluoroindan-1-yloxy]-2,3-dihydrobenzofuran-3-yl}acetic acid or a salt thereof.

29. The compound according to claim 1, wherein the compound is {(S)-6[(R)-4-(2,6-dimethyl-4-(1-methylimidazol-4-yl)phenyl)-7-fluoroindan-1-yloxyl-2,3-dihydrobenzofuran-3-yl}-acetic acid or a salt thereof.

30. The compound according to claim 1, wherein the compound is {(S)-6[(R)-4-(2,6-dimethyl-4-(6-methylpyridin-2-yl)phenyl)-7-fluoroindan-1-yloxyl-2,3-dihydrobenzofuran-3-yl}-acetic acid or a salt thereof.

31. The compound according to claim 1, wherein the compound is {(S)-6-[(R)-4-(2,6)-dimethyl-4-(4-methylpyridin-2-yl)-7-flouroindan-1-yloxy]-2,3-dihydrobenzofuran-3-yl }-acetic acid or a salt thereof.

32. The compound according to claim 1, wherein the compound is 2((S)-6-((R)-4-(2,6-dimethyl-4-((tetrahydro-2H-pyran-4-yl)methoxy)phenyl)-7-fluoro-2,3-dihydro-1H-inden-1-yloxy)-2,3-dihydrobenzofuran-3-yl)acetic acid or a salt thereof.

* * * * *